(12) United States Patent
Stanton, Jr.

(10) Patent No.: US 6,673,908 B1
(45) Date of Patent: Jan. 6, 2004

(54) TUMOR NECROSIS FACTOR RECEPTOR 2

(75) Inventor: Vincent P. Stanton, Jr., Belmont, MA (US)

(73) Assignee: Nuvelo, Inc., Sunnyvale, CA (US)

( * ) Notice: Subject to any disclaimer, the term of this patent is extended or adjusted under 35 U.S.C. 154(b) by 42 days.

(21) Appl. No.: 09/968,455

(22) Filed: Oct. 1, 2001

Related U.S. Application Data

(60) Division of application No. 09/649,035, filed on Aug. 25, 2000, which is a continuation-in-part of application No. 09/590,749, filed on Jun. 8, 2000, now abandoned, which is a continuation-in-part of application No. 09/495,780, filed on Feb. 1, 2000, now abandoned, which is a continuation-in-part of application No. 09/492,712, filed on Jan. 27, 2000, now abandoned, which is a continuation-in-part of application No. PCT/US00/01392, filed on Jan. 20, 2000, application No. 09/968,455, which is a continuation-in-part of application No. 09/451,252, filed on Nov. 29, 1999, now abandoned, which is a continuation-in-part of application No. 09/427,835, filed on Oct. 26, 1999, now abandoned, which is a continuation-in-part of application No. 09/414,330, filed on Oct. 6, 1999, now abandoned, which is a continuation-in-part of application No. 09/389,993, filed on Sep. 3, 1999, now abandoned, and a continuation-in-part of application No. 09/370,841, filed on Aug. 9, 1999, now abandoned, and a continuation-in-part of application No. 09/300,747, filed on Apr. 26, 1999, now abandoned.

(60) Provisional application No. 60/131,334, filed on Apr. 26, 1999, provisional application No. 60/131,191, filed on Apr. 26, 1999, and provisional application No. 60/121,047, filed on Feb. 22, 1999.

(51) Int. Cl.$^7$ ............ C07H 21/04; C12Q 1/68; C12P 19/34

(52) U.S. Cl. ............ 536/22.1; 536/23.1; 536/24.3; 536/24.31; 536/24.33; 435/6; 435/91.1; 435/91.2

(58) Field of Search ............ 435/6, 91.1, 91.2; 536/22.1, 23.1, 24.3, 24.31, 24.33

(56) References Cited

U.S. PATENT DOCUMENTS 6,492,118 B1 * 12/2002 Abrams ............ 435/6
6,492,121 B2 * 12/2002 Kurane ............ 435/6

OTHER PUBLICATIONS

Smith et al., "A receptor for tumor necrosis factor defines an unusual family of cellular and viral proteins", Science, (1990), vol. 248 (4958), pp. 1019–1022.*

* cited by examiner

*Primary Examiner*—Gary Benzion
*Assistant Examiner*—Arun Kr. Chakrabarti
(74) *Attorney, Agent, or Firm*—Fish & Richardson P.C.

(57) ABSTRACT

The present disclosure describes the use of genetic variance information for genes involved in inflammatory or immunologic disease, disorder, or dysfunction. The variance information is indicative of the expected response of a patient to a method of treatment. Methods of determining relevant variance information and additional methods of using such variance information are also described.

10 Claims, No Drawings

SEQUENCE LISTING

<160> NUMBER OF SEQ ID NOS: 1

<210> SEQ ID NO 1
<211> LENGTH: 3683
<212> TYPE: DNA
<213> ORGANISM: Homo sapiens

<400> SEQUENCE: 1

| | | | | | | |
|---|---|---|---|---|---|---|
| gcgagcgcag | cggagcctgg | agagaaggcg | ctgggctgcg | agggcgcgag | ggcgcgaggg | 60 |
| caggggcaa | ccggaccccg | cccgcaccca | tggcgcccgt | cgccgtctgg | gccgcgctgg | 120 |
| ccgtcggact | ggagctctgg | gctgcggcgc | acgccttgcc | cgcccaggtg | gcatttacac | 180 |
| cctacgcccc | ggagcccggg | agcacatgcc | ggctcagaga | atactatgac | cagacagctc | 240 |
| agatgtgctg | cagcaaatgc | tcgccgggcc | aacatgcaaa | agtcttctgt | accaagacct | 300 |
| cggacaccgt | gtgtgactcc | tgtgaggaca | gcacatacac | ccagctctgg | aactgggttc | 360 |
| ccgagtgctt | gagctgtggc | tcccgctgta | gctctgacca | ggtggaaact | caagcctgca | 420 |
| ctcgggaaca | gaaccgcatc | tgcacctgca | ggcccggctg | gtactgcgcg | ctgagcaagc | 480 |
| aggagggggtg | ccggctgtgc | gcgccgctgc | gcaagtgccg | cccgggcttc | ggcgtggcca | 540 |
| gaccaggaac | tgaaacatca | gacgtggtgt | gcaagccctg | tgccccgggg | acgttctcca | 600 |
| acacgacttc | atccacggat | atttgcaggc | cccaccagat | ctgtaacgtg | gtggccatcc | 660 |
| ctgggaatgc | aagcatggat | gcagtctgca | cgtccacgtc | ccccacccgg | agtatggccc | 720 |
| cagggggcagt | acacttaccc | cagccagtgt | ccacacgatc | ccaacacacg | cagccaactc | 780 |
| cagaacccag | cactgctcca | agcacctcct | tcctgctccc | aatgggcccc | agcccccag | 840 |
| ctgaagggag | cactggcgac | ttcgctcttc | cagttggact | gattgtgggt | gtgacagcct | 900 |
| tgggtctact | aataatagga | gtggtgaact | gtgtcatcat | gacccaggtg | aaaaagaagc | 960 |
| ccttgtgcct | gcagagagaa | gccaaggtgc | ctcacttgcc | tgccgataag | gcccggggta | 1020 |
| cacagggccc | cgagcagcag | cacctgctga | tcacagcgcc | gagctccagc | agcagctccc | 1080 |
| tggagagctc | ggccagtgcg | ttggacagaa | gggcgcccac | tcggaaccag | ccacaggcac | 1140 |
| caggcgtgga | ggccagtggg | gccggggagg | cccgggccag | caccgggagc | tcagattctt | 1200 |
| cccctggtgg | ccatgggacc | caggtcaatg | tcacctgcat | cgtgaacgtc | tgtagcagct | 1260 |
| ctgaccacag | ctcacagtgc | tcctcccaag | ccagctccac | aatgggagac | acagattcca | 1320 |
| gcccctcgga | gtccccgaag | gacgagcagg | tcccccttctc | caaggaggaa | tgtgcctttc | 1380 |
| ggtcacagct | ggagacgcca | gagaccctgc | tggggagcac | cgaagagaag | ccctgcccc | 1440 |
| ttggagtgcc | tgatgctggg | atgaagccca | gttaaccagg | ccggtgtggg | ctgtgtcgta | 1500 |
| gccaaggtgg | gctgagccct | ggcaggatga | ccctgcgaag | gggccctggt | ccttccaggc | 1560 |
| ccccaccact | aggactctga | ggctctttct | gggccaagtt | cctctagtgc | cctccacagc | 1620 |
| cgcagcctcc | ctctgacctg | caggccaaga | gcagaggcag | cgagttgggg | aaagcctctg | 1680 |
| ctgccatggt | gtgtccctct | cggaaggctg | gctgggcatg | gacgttcggg | gcatgctggg | 1740 |
| gcaagtccct | gactctctgt | gacctgcccc | gcccagctgc | acctgccagc | ctggcttctg | 1800 |
| gagcccttgg | gttttttgtt | tgtttgtttg | tttgtttgtt | tgtttctccc | cctgggctct | 1860 |
| gcccagctct | ggcttccaga | aaacccagc | atccttttct | gcagggggc | tttctggaga | 1920 |
| ggagggatgc | tgcctgagtc | acccatgaag | acaggacagt | gcttcagcct | gaggctgaga | 1980 |
| ctgcgggatg | gtcctggggc | tctgtgtagg | gaggaggtgg | cagccctgta | gggaacgggg | 2040 |

-continued

```
tccttcaagt tagctcagga ggcttggaaa gcatcacctc aggccaggtg cagtggctca   2100
cgcctatgat cccagcactt tgggaggctg aggcgggtgg atcacctgag gttaggagtt   2160
cgagaccagc ctggccaaca tggtaaaacc ccatctctac taaaaataca gaaattagcc   2220
gggcgtggtg gcgggcacct atagtcccag ctactcagaa gcctgaggct gggaaatcgt   2280
ttgaacccgg gaagcggagg ttgcagggag ccgagatcac gccactgcac tccagcctgg   2340
gcgacagagc gagagtctgt ctcaaagaa aaaaaaaaa gcaccgcctc caaatgctaa    2400 cttgtcctt tgtaccatgg tgtgaaagtc agatgcccag agggcccagg caggccacca    2460
tattcagtgc tgtggcctgg gcaagataac gcacttctaa ctagaaatct gccaattttt   2520
taaaaaagta agtaccactc aggccaacaa gccaacgaca aagccaaact ctgccagcca   2580
catccaaccc cccacctgcc atttgcaccc tccgccttca ctccggtgtg cctgcagccc   2640
cgcgcctcct tccttgctgt cctaggccac accatctcct ttcagggaat ttcaggaact   2700
agagatgact gagtcctcgt agccatctct ctactcctac ctcagcctag accctcctcc   2760
tcccccagag gggtgggttc ctcttcccca ctccccacct tcaattcctg ggccccaaac   2820
gggctgccct gccactttgg tacatggcca gtgtgatccc aagtgccagt cttgtgtctg   2880
cgtctgtgtt gcgtgtcgtg ggtgtgtgta gccaaggtcg gtaagttgaa tggcctgcct   2940
tgaagccact gaagctggga ttcctcccca ttagagtcag ccttcccct cccagggcca   3000 gggccctgca gaggggaaac cagtgtagcc ttgcccggat tctgggagga agcaggttga    3060
ggggctcctg gaaaggctca gtctcaggag catgggdata aaggagaagg catgaaattg   3120
tctagcagag caggggcagg gtgataaatt gttgataaat tccactggac ttgagcttgg   3180
cagctgaact attggagggt gggagagccc agccattacc atggagacaa gaagggtttt    3240
ccaccctgga atcaagatgt cagactggct ggctgcagtg acgtgcacct gtactcagga   3300
ggctgagggg aggatcactg gagcccagga gtttgaggct gcagcgagct atgatcgcgc    3360
cactacactc cagcctgagc aacagagtga gaccctgtct cttaaagaaa aaaaagtca    3420 gactgctggg actggccagg tttctgccca cattggaccc acatgaggac atgatggagc    3480
gcacctgccc cctggtggac agtcctggga gaacctcagg cttccttggc atcacagggc    3540
agagccggga agcgatgaat ttggagactc tgtggggcct tggttccctt gtgtgtgtgt   3600
gttgatccca agacaatgaa agtttgcact gtatgctgga cggcattcct gcttatcaat   3660
aaacctgttt gttttaaaaa aaa                                           3683
```

TUMOR NECROSIS FACTOR RECEPTOR 2

RELATED APPLICATIONS

This application is a divisional of U.S. application Ser. No. 09/649,035, filed Aug. 25, 2000, which is a continuation-in-part of Stanton, U.S. application Ser. No. 09/590,749, filed Jun. 8, 2000, now abandoned, which is a continuation-in-part of Stanton, U.S. application Ser. No. 09/495,780, tiled Feb. 1, 2000, now abandoned, entitled GENE SEQUENCE VARIATIONS WITH UTILITY IN DETERMINING THE TREATMENT OF INFLAMMATORY OR IMMUNOLOGIC DISEASE, which is a continuation-in-part of Stanton, U.S. application Ser. No. 09/492,712, filed Jan. 27, 2000, now abandoned, GENE SEQUENCE VARIATIONS WITH UTILITY IN DETERMINING THE TREATMENT OF INFLAMMATORY OR IMMUNOLOGIC DISEASE, which is a continuation-in-part of Stanton, International application Ser. No. PCT/US00/01392, filed Jan. 20, 2000, entitled GENE SEQUENCE VARIATIONS WITH UTILITY IN DETERMINING THE TREATMENT OF DISEASE. This application is also a continuation-in-part of U.S. application Ser. No. 09/451,252, filed Nov. 29, 1999, now abandoned, which is a continuation-in-part of Stanton, U.S. application Ser. No. 09/427,835, filed Oct. 26, 1999, now abandoned, entitled GENE SEQUENCE VARIATIONS WTTH UTILITY IN DETERMINING THE TREATMENT OF DISEASE, which is a continuation-in-part of U.S. application Ser. No. 09/414,330, filed Oct. 6, 1999, now abandoned, which is a continuation-in-part of U.S. application Ser. No. 09/389,993, Sep. 3, 1999, now abandoned, and a continuation-in-part of U.S application Ser. No. 09/370,841, filed Aug. 9, 1999, now abandoned, and Stanton and Adams, U.S. application Ser. No. 09/300,747, filed Apr. 26, 1999, now abandoned, entitled GENE SEQUENCE VARIATIONS WITH UTILITY IN DETERMINING THE TREATMENT OF DISEASE, and claims the benefit of U.S. Provisional Patent Application, Stanton & Adams, Ser. No. 60/131,334, filed Apr. 26, 1999, and U.S. Provisional Patent Application, Stanton &Adams 60/131,191, filed Apr. 26, 1999, and U.S. Provisional Patent Application, Stanton &Adams 60/121,047, filed Feb. 22, 1999, all of which are entitled GENE SEQUENCE VARIANCES WITH UTILITY IN DETERMINING THE TREATMENT OF DISEASE, which are hereby incorporated by reference in their entireties, including drawings and tables.

BACKGROUND OF THE INVENTION

This application concerns the field of mammalian therapeutics and the selection of therapeutic regimens utilizing host genetic information, including gene sequence variances within the human genome in human populations.

The information provided in the Background of the Invention is not admitted to be prior art to the present invention but is provided solely to assist the understanding of the reader.

Many drugs or treatments have highly variable safety and efficacy effects on different individuals. Due to such variability, a given drug or treatment may be effective in one individual but ineffective or ill tolerated in another individual. Thus, administering such drugs to individuals, who would not benefit from such administration, would result in wasted cost and time. It could also directly worsen the patient's condition and even cause the patient's death.

For some drugs, variances in individual reaction, measured in selected pharmacokinetic parameters, has been shown to be inheritable by over 90%. For a limited number of drugs, variances in DNA sequences of specific genes involved in drug action and metabolism have been identified. These variances have been shown to variably affect safety or efficacy of these drugs in different individuals. As the human genome sequencing is completed and as additional human gene sequence variances are identified, power of genetic methods for predicting drug response will further increase.

In this application, we address the difficulties that arise in treating inflammatory diseases and other diseases in which modulation of immunologic function provides the basis for therapeutic intervention, including for example, diseases treated with antiinflammatory, analgesic or antipyretic drugs as well as autacoids, eicosanoids, interleukins, cytokines or their agonists or antagonists. Diseases or conditions involving the inflammatory response or the immune system constitute a complex and heterogeneous group of diseases, involving all organ systems from the central nervous system and the circulatory system to the viscera and skin. These diseases may be acute or chronic, may progress from an acute stage to a chronic condition, or may exhibit a waxing and waning pattern of flare ups and remissions. Due to their wide anatomical distribution, this group of diseases can (collectively) lead to impairment of a wide range of essential physiological functions. The unifying theme in the treatment of these diseases is the modulation of inflammatory mediators or immune function. The evaluation of long term response to therapy is, for many of these diseases, the most important index of treatment efficacy, due to the progressive nature of inflammatory or immunological diseases. Since it is often difficult to assess the long-term effects of treatment over a short observation period (particularly for diseases with a waxing and waning pattern) there is considerable utility in a genetic test that can predict long term outcomes. Many treatments for diseases with significant inflammatory or immunological components are quite costly. Again, the development of a genetic test that can be used to identify a high responder group may change the economics of treating a population with an expensive therapy. Therapeutics that modulate immunologic or inflammatory responses also frequently pose significant risks for patients. Thus, a test that would allow more judicious use of potentially harmful compounds or biologicals on patients likely to suffer side effects, and/or those patients unlikely to benefit from treatment, would have considerable use both in drug development and in effective use of approved treatments. As healthcare becomes increasingly costly, the ability to allocate healthcare resources effectively becomes more urgent, and methods that lead to safer and more economical use of medicines will contribute to more effective use of healthcare resources.

SUMMARY OF THE INVENTION

The present invention is concerned generally with the field of identifying an appropriate treatment regimen for an inflammatory disease (or a disease in which modulation of the inflammatory response or the immune system is being tested for therapeutic effect) based upon genotype in mammals, particularly in humans. It is further concerned with the genetic basis of inter-patient variation in response to therapy, including drug therapy. Specifically, this invention describes the identification of gene sequence variances useful in the field of therapeutics for optimizing efficacy and safety of drug therapy. This will be accomplished by establishing diagnostic tests for variances and demonstrating their value in the development, marketing, and use of pharmaceutical products in the clinic. Methods for identifying genetic variances and determining their utility in the selection of optimal therapy for specific patients are also described. In general, the invention relates to methods for identifying genetically defined patient subsets that respond to drug therapy differently from other subsets or controls.

The inventors have determined that the identification of gene sequence variances in genes that may affect response to therapeutic interventions directed against diseases in which there is abnormal immune/inflammatory response can be exploited to improve therapeutic outcomes for such diseases. Such variances can be used, for example, to identify patients in whom specific therapeutic interventions are likely to be efficacious, well tolerated, and safe. Methods are described in this application for determining whether genetic variances account for variable drug efficacy and safety and for determining whether a given drug or other therapy may be safe and effective in a class of patients with a particular genotype. Methods are also described for developing diagnostic tests so that pharmacogenetic tests can be used in the care of individual patients. Also provided in this invention are identifications of genes and sequence variances which can be useful in connection with predicting differences in response to treatment and selection of appropriate treatment of a disease or condition. A target gene and variances have utility in pharmacogenetic association studies and diagnostic tests to improve the use of certain drugs or other therapies including, but not limited to, the drug classes and specific drugs identified in the 1999 Physicians' Desk Reference (53rd edition), Medical Economics Data, 1998, or the 1995 United States Pharmacopeia XXIII National Formulary XVIII, Interpharm Press, 1994, Examples 1 through 3 or other sources as described below.

The terms "disease" or "condition" are commonly recognized in the art and designate the presence of signs and/or symptoms in an individual or patient that are generally recognized as abnormal. Diseases or conditions may be diagnosed and categorized based on pathological changes. Signs may include any objective evidence of a disease such as changes that are evident by physical examination of a patient or the results of diagnostic tests which may include, among others, laboratory tests to determine the presence of DNA sequence variances or variant forms of certain genes in a patient. Symptoms are subjective evidence of disease or a patients condition, i.e. the patients perception of an abnormal condition that differs from normal function, sensation, or appearance, which may include, without limitations, physical disabilities, morbidity, pain, and other changes from the normal condition experienced by an individual. Various diseases or conditions include, but are not limited to; those categorized in standard textbooks of medicine including, without limitation, textbooks of nutrition, allopathic, homeopathic, and osteopathic medicine. In certain aspects of this invention, the disease or condition is selected from the group consisting of the types of diseases listed in standard texts such as Harrison's Principles of Internal Medicine (14th Ed) by Anthony S. Fauci, Eugene Braunwald, Kurt J. Isselbacher, et al. (Editors), McGraw Hill, 1997, or Robbins Pathologic Basis of Disease (6th edition) by Ramzi S. Cotran, Vinay Kumar, Tucker Collins & Stanley L. Robbins, W B Saunders Co., 1998, or other texts described below. This application is directed particularly to diseases in which abnormal function of the immune system or the inflammatory response is part of the disease process, or in which modulation of immune or inflammatory function is being tested as a therapeutic intervention.

In connection with the methods of this invention, unless otherwise indicated, the term "suffering from a disease or condition" means that a person is either presently subject to the signs and symptoms, or is more likely to develop such signs and symptoms than a normal person in the population. Thus, for example, a person suffering from a condition can include a developing fetus, a person subject to a treatment or environmental condition which enhances the likelihood of developing the signs or symptoms of a condition, or a person who is being given or will be given a treatment which increase the likelihood of the person developing a particular condition. For example, tardive dyskinesia is associated with long-term use of anti-psychotics;dyskinesias, paranoid ideation, psychotic episodes and depression have been associated with use of L-dopa in Parkinson's disease; and dizziness, diplopia, ataxia, sedation, impaired mentation, weight gain, and other undesired effects have been described for various anticonvulsant therapies. Thus, methods of the present invention which relate to treatments of patients (e.g., methods for selecting a treatment, selecting a patient for a treatment, and methods of treating a disease or condition in a patient) can include primary treatments directed to a presently active disease or condition, secondary treatments which are intended to cause a biological effect relevant to a primary treatment, and prophylactic treatments intended to delay, reduce, or prevent the development of a disease or condition, as well as treatments intended to cause the development of a condition different from that which would have been likely to develop in the absence of the treatment.

The term "therapy" refers to a process which is intended to produce a beneficial change in the condition of a mammal, e.g., a human, often referred to as a patient. A beneficial change can, for example, include one or more of: restoration of function, reduction of symptoms, limitation or retardation of progression of a disease, disorder, or condition or prevention, limitation or retardation of deterioration of a patient's condition, disease or disorder. Such therapy can involve, for example, nutritional modifications, administration of radiation, administration of a drug, behavioral modifications, and combinations of these, among others.

The term "drug" as used herein refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, lipoproteins, and modifications and combinations thereof. A biological product is preferably a monoclonal or polyclonal antibody or fragment thereof such as a variable chain fragment; cells; or an agent or product arising from recombinant technology, such as, without limitation, a recombinant protein, recombinant vaccine, or DNA construct developed for therapeutic, e.g., human therapeutic, use. The term "drug" may include, without limitation, compounds that are approved for sale as pharmaceutical products by government regulatory agencies (e.g., U.S. Food and Drug Administration (USFDA or FDA), European Medicines Evaluation Agency (EMEA), and a world regulatory body governing the International Conference of Harmonization (ICH) rules and guidelines), compounds that do not require approval by government regulatory agencies, food additives or supplements including compounds commonly characterized as vitamins, natural products, and completely or incompletely characterized mixtures of chemical entities including natural compounds or purified or partially purified natural products. The term "drug" as used herein is synonymous with the terms "medicine", "pharmaceutical product", or "product". Most preferably the drug is approved by a government agency for treatment of a specific disease or condition. A "low molecular weight compound" has a molecular weight <5,000 Da, more preferably <2500 Da, still more preferably <1000 Da, and most preferably <700 Da.

Those familiar with drug use in medical practice will recognize that regulatory approval for drug use is commonly limited to approved indications, such as to those patients afflicted with a disease or condition for which the drug has been shown to be likely to produce a beneficial effect in a controlled clinical trial. Unfortunately, it has generally not been possible with current knowledge to predict which patients will have a beneficial response, with the exception of certain diseases such as bacterial infections where suitable laboratory methods have been developed. Likewise, it has generally not been possible to determine in advance whether a drug will be safe in a given patient. Regulatory approval for the use of most drugs is limited to the treatment of selected diseases and conditions. The descriptions of approved drug usage, including the suggested diagnostic studies or monitoring studies, and the allowable parameters of such studies, are commonly described in the "label" or "insert" which is distributed with the drug. Such labels or inserts are preferably required by government agencies as a condition for marketing the drug and are listed in common references such as the Physicians Desk Reference (PDR). These and other limitations or considerations on the use of a drug are also found in medical journals, publications such as pharmacology, pharmacy or medical textbooks including, without limitation, textbooks of nutrition, allopathic, homeopathic, and osteopathic medicine.

Many widely used drugs are effective in a minority of patients receiving the drug, particularly when one controls for the placebo effect. For example, the PDR shows that about 45% of patients receiving Cognex (tacrine hydrochloride) for Alzheimer's disease show no change or minimal worsening of their disease, as do about 68% of controls (including about 5% of controls who were much worse). About 58% of Alzheimer's patients receiving Cognex were minimally improved, compared to about 33% of controls, while about 2% of patients receiving Cognex were much improved compared to about 1% of controls. Thus a tiny fraction of patients had a significant benefit. Response to many cancer chemotherapy drugs is even worse. For example, 5-fluorouracil is standard therapy for advanced colorectal cancer, but only about 20–40% of patients have an objective response to the drug, and, of these, only 1–5% of patients have a complete response (complete tumor disappearance; the remaining patients have only partial tumor shrinkage). Conversely, up to 20–30% of patients receiving 5-FU suffer serious gastrointestinal or hematopoietic toxicity, depending on the regimen.

Thus, in a first aspect, the invention provides a method for selecting a treatment for a patient suffering from a disease or condition by determining whether or not a gene or genes in cells of the patient (in some cases including both normal and disease cells, such as cancer cells) contain at least one sequence variance which is indicative of the effectiveness of the treatment of the disease or condition. The gene or genes are specified herein, in Tables 1, and 3. Preferably the at least one variance includes a plurality of variances which may provide a haplotype or haplotypes. Preferably the joint presence of the plurality of variances is indicative of the potential effectiveness or safety of the treatment in a patient having such plurality of variances. The plurality of variances may each be indicative of the potential effectiveness of the treatment, and the effects of the individual variances may be independent or additive, or the plurality of variances may be indicative of the potential effectiveness if at least 2, 3, 4, or more appear jointly. The plurality of variances may also be combinations of these relationships. The plurality of variances may include variances from one, two, three or more gene loci.

In preferred embodiments of aspects of the invention involving genes relating to inflammatory or immunological conditions the gene product is involved in a function as described in the Background of the Invention or otherwise described herein.

In some cases, the selection of a method of treatment, i.e., a therapeutic regimen, may incorporate selection of one or more from a plurality of medical therapies. Thus, the selection may be the selection of a method or methods which is/are more effective or less effective than certain other therapeutic regimens (with either having varying safety parameters). Likewise or in combination with the preceding selection, the selection may be the selection of a method or methods, which is safer than certain other methods of treatment in the patient.

The selection may involve either positive selection or negative selection or both, meaning that the selection can involve a choice that a particular method would be an appropriate method to use and/or a choice that a particular method would be an inappropriate method to use. Thus, in certain embodiments, the presence of the at least one variance is indicative that the treatment will be effective or otherwise beneficial (or more likely to be beneficial) in the patient. Stating that the treatment will be effective means that the probability of beneficial therapeutic effect is greater than in a person not having the appropriate presence or absence of particular variances. In other embodiments, the presence of the at least one variance is indicative that the treatment will be ineffective or contra-indicated for the patient. For example, a treatment may be contra-indicated if the treatment results, or is more likely to result, in undesirable side effects, or an excessive level of undesirable side effects. A determination of what constitutes excessive side-effects will vary, for example, depending on the disease or condition being treated, the availability of alternatives, the expected or experienced efficacy of the treatment, and the tolerance of the patient. As for an effective treatment, this means that it is more likely that desired effect will result from the treatment administration in a patient with a particular variance or variances than in a patient who has a different variance or variances. Also in preferred embodiments, the presence of the at least one variance is indicative that the treatment is both effective and unlikely to result in undesirable effects or outcomes, or vice versa (is likely to have undesirable side effects but unlikely to produce desired therapeutic effects).

In reference to response to a treatment, the term "tolerance" refers to the ability of a patient to accept a treatment, based, e.g., on deleterious effects and/or effects on lifestyle. Frequently, the term principally concerns the patients perceived magnitude of deleterious effects such as nausea, weakness, dizziness, and diarrhea, among others. Such experienced effects can, for example, be due to general or cell-specific toxicity, activity on non-target cells, cross-reactivity on non-target cellular constituents (non-mechanism based), and/or side effects of activity on the target cellular substituents (mechanism based), or the cause of toxicity may not be understood. In any of these circumstances one may identify an association between the undesirable effects and variances in specific genes.

Adverse responses to drugs constitute a major medical problem, as shown in two recent meta-analyses (Lazarou, J. et al, Incidence of adverse drug reactions in hospitalized patients: a meta-analysis of prospective studies, JAMA 279:1200–1205, 1998; Bonn, Adverse drug reactions remain a major cause of death, Lancet 351:1183, 1998). An estimated 2.2 million hospitalized patients in the United Stated had serious adverse drug reactions in 1994, with an estimated 106,000 deaths (Lazarou et al.). To the extent that some of these adverse events are due to genetically encoded biochemical diversity among patients in pathways that effect drug action, the identification of variances that are predictive of such effects will allow for more effective and safer drug use.

In embodiments of this invention, the variance or variant form or forms of a gene is/are associated with a specific response to a drug. The frequency of a specific variance or variant form of the gene may correspond to the frequency of an efficacious response to administration of a drug. Alternatively, the frequency of a specific variance or variant form of the gene may correspond to the frequency of an adverse event resulting from administration of a drug. Alternatively the frequency of a specific variance or variant form of a gene may not correspond closely with the frequency of a beneficial or adverse response, yet the variance may still be useful for identifying a patient subset with high response or toxicity incidence because the variance may account for only a fraction of the patients with high response or toxicity. In such a case the preferred course of action is identification of a second or third or additional variances that permit identification of the patient groups not usefully identified by the first variance. Preferably, the drug will be effective in more than 20% of individuals with one or more specific variances or variant forms of the gene, more preferably in 40% and most preferably in >60%. In other embodiments, the drug will be toxic or create clinically unacceptable side effects in more than 10% of individuals with one or more variances or variant forms of the gene, more preferably in >30%, more preferably in >50%, and most preferably in >70% or in more than 90%.

Also in other embodiments, the method of selecting a treatment includes eliminating a treatment, where the presence or absence of the at least one variance is indicative that the treatment will be ineffective or contra-indicated, e.g., would result in excessive weight gain. In other preferred embodiments, in cases in which undesirable side-effects may occur or are expected to occur from a particular therapeutic treatment, the selection of a method of treatment can include identifying both a first and second treatment, where the first treatment is effective to treat the disease or condition, and the second treatment reduces a deleterious effect of the first treatment.

The phrase "eliminating a treatment" refers to removing a possible treatment from consideration, e.g., for use with a particular patient based on the presence or absence of a particular variance(s) in one or more genes in cells of that patient, or to stopping the administration of a treatment which was in the course of administration.

Usually, the treatment will involve the administration of a compound preferentially active or safe in patients with a form or forms of a gene, where the gene is one identified herein. The administration may involve a combination of compounds. Thus, in preferred embodiments, the method involves identifying such an active compound or combination of compounds, where the compound is less active or is less safe or both when administered to a patient having a different form of the gene.

Also in preferred embodiments, the method of selecting a treatment involves selecting a method of administration of a compound, combination of compounds, or pharmaceutical composition, for example, selecting a suitable dosage level and/or frequency of administration, and/or mode of administration of a compound. The method of administration can be selected to provide better, preferably maximum therapeutic benefit. In this context, "maximum" refers to an approximate local maximum based on the parameters being considered, not an absolute maximum.

Also in this context, a "suitable dosage level" refers to a dosage level which provides a therapeutically reasonable balance between pharmacological effectiveness and deleterious effects. Often this dosage level is related to the peak or average serum levels resulting from administration of a drug at the particular dosage level.

Similarly, a "frequency of administration" refers to how often in a specified time period a treatment is administered, e.g., once, twice, or three times per day, every other day, once per week, etc. For a drug or drugs, the frequency of administration is generally selected to achieve a pharmacologically effective average or peak serum level without excessive deleterious effects (and preferably while still being able to have reasonable patient compliance for self-administered drugs). Thus, it is desirable to maintain the serum level of the drug within a therapeutic window of concentrations for the greatest percentage of time possible without such deleterious effects as would cause a prudent physician to reduce the frequency of administration for a particular dosage level.

A particular gene or genes can be relevant to the treatment of more than one disease or condition, for example, the gene or genes can have a role in the initiation, development, course, treatment, treatment outcomes, or health-related quality of life outcomes of a number of different diseases, disorders, or conditions. Thus, in preferred embodiments, the disease or condition or treatment of the disease or condition is any which involves a gene from the gene list described herein as Tables 1 and 3.

Determining the presence of a particular variance or plurality of variances in a particular gene in a patient can be performed in a variety of ways. In preferred embodiments, the detection of the presence or absence of at least one variance involves amplifying a segment of nucleic acid including at least one of the at least one variances. Preferably a segment of nucleic acid to be amplified is 500 nucleotides or less in length, more preferably 100 nucleotides or less, and most preferably 45 nucleotides or less. Also, preferably the amplified segment or segments includes a plurality of variances, or a plurality of segments of a gene or of a plurality of genes.

In another aspect determining the presence of a set of variances in a specific gene related to treatment of inflammation or immune disease disease or other related genes, or genes listed in Tables 1 and 3, may entail a haplotyping test that requires allele specific amplification of a large DNA segment of no greater than 25,000 nucleotides, preferably no greater than 10,000 nucleotides and most preferably no greater than 5,000 nucleotides. Alternatively one allele may be enriched by methods other than amplification prior to determining genotypes at specific variant positions on the enriched allele as a way of determining haplotypes. Preferably the determination of the presence or absence of a haplotype involves determining the sequence of the variant sites by methods such as chain terminating DNA sequencing or minisequencing, or by oligonucleotide hybridization or by mass spectrometry.

The term "genotype" in the context of this invention refers to the alleles present in DNA from a subject or patient, where an allele can be defined by the particular nucleotide(s) present in a nucleic acid sequence at a particular site(s). Often a genotype is the nucleotide(s) present at a single polymorphic site known to vary in the human population.

In preferred embodiments, the detection of the presence or absence of the at least one variance involves contacting a nucleic acid sequence corresponding to one of the genes identified above or a product of such a gene with a probe. The probe is able to distinguish a particular form of the gene or gene product or the presence or a particular variance or variances, e.g., by differential binding or hybridization. Thus, exemplary probes include nucleic acid hybridization probes, peptide nucleic acid probes, nucleotide-containing probes which also contain at least one nucleotide analog, and antibodies, e.g., monoclonal antibodies, and other probes as discussed herein. Those skilled in the art are familiar with the preparation of probes with particular specificities. Those skilled in the art will recognize that a variety of variables can be adjusted to optimize the discrimination between two variant forms of a gene, including changes in salt concentration, temperature, pH and addition of various compounds that affect the differential affinity of GC vs. AT base pairs, such as tetramethyl ammonium chloride. (See Current Protocols in Molecular Biology by F. M. Ausubel, R. Brent, R. E. Kngston, D. D. Moore, J. D. Seidman, K. Struhl, and V. B. Chanda (editors, John Wiley & Sons.)

In other preferred embodiments, determining the presence or absence of the at least one variance involves sequencing at least one nucleic acid sample. The sequencing involves sequencing of a portion or portions of a gene and/or portions of a plurality of genes which includes at least one variance site, and may include a plurality of such sites. Preferably, the portion is 500 nucleotides or less in length, more preferably 100 nucleotides or less, and most preferably 45 nucleotides or less in length. Such sequencing can be carried out by various methods recognized by those skilled in the art, including use of dideoxy termination methods (e.g., using dye-labeled dideoxy nucleotides) and the use of mass spectrometric methods. In addition, mass spectrometric methods may be used to determine the nucleotide present at a variance site. In preferred embodiments in which a plurality of variances is determined, the plurality of variances can constitute a haplotype or collection of haplotypes. Preferably the methods for determining genotypes or haplotypes are designed to be sensitive to all the common genotypes or haplotypes present in the population being studied (for example, a clinical trial population).

The terms "variant form of a gene", "form of a gene", or "allele" refer to one specific form of a gene in a population, the specific form differing from other forms of the same gene in the sequence of at least one, and frequently more than one, variant sites within the sequence of the gene. The sequences at these variant sites that differ between different alleles of the gene are termed "gene sequence variances" or "variances" or "variants". The term "alternative form" refers to an allele that can be distinguished from other alleles by having distinct variances at least one, and frequently more than one, variant sites within the gene sequence. Other terms known in the art to be equivalent include mutation and polymorphism, although mutation is often used to refer to an allele associated with a deleterious phenotype. In preferred aspects of this invention, the variances are selected from the group consisting of the variances listed in the variance tables herein or in a patent or patent application referenced and incorporated by reference in this disclosure. In the methods utilizing variance presence or absence, reference to the presence of a variance or variances means particular variances, i.e., particular nucleotides at particular polymorphic sites, rather than just the presence of any variance in the gene.

Variances occur in the human genome at approximately one in every 500–1,000 bases within the human genome when two alleles are compared. When multiple alleles from unrelated individuals are compared the density of variant sites increases as different individuals, when compared to a reference sequence, will often have sequence variances at different sites. At most variant sites there are only two alternative nucleotides involving the substitution of one base for another or the insertion/deletion of one or more nucleotides. Within a gene there may be several variant sites. Variant forms of the gene or alternative alleles can be distinguished by the presence of alternative variances at a single variant site, or a combination of several different variances at different sites (haplotypes).

It is estimated that there are 3,300,000,000 bases in the sequence of a single haploid human genome. All human cells except germ cells are normally diploid. Each gene in the genome may span 100–10,000,000 bases of DNA sequence or 100–20,000 bases of mRNA. It is estimated that there are between 60,000 and 150,000 genes in the human genome. The "identification" of genetic variances or variant forms of a gene involves the discovery of variances that are present in a population. The identification of variances is needed for development of a diagnostic test to determine whether a patient has a variant form of a gene that is known to be associated with a disease, condition, or predisposition or with the efficacy or safety of the drug. Identification of previously undiscovered genetic variances is distinct from the process of "determining" the status of known variances by a diagnostic test (often referred to as genotyping). The present invention provides exemplary variances in genes listed in the gene tables, as well as methods for discovering additional variances in those genes and a comprehensive written description of such additional possible variances. Also described are methods for DNA diagnostic tests to determine the DNA sequence at a particular variant site or sites.

The process of "identifying" or discovering new variances involves comparing the sequence of at least two alleles of a gene, more preferably at least 10 alleles and most preferably at least 50 alleles (keeping in mind that each somatic cell has two alleles). The analysis of large numbers of individuals to discover variances in the gene sequence between individuals in a population will result in detection of a greater fraction of all the variances in the population. Preferably the process of identifying reveals whether there is a variance within the gene; more preferably identifying reveals the location of the variance within the gene; more preferably identifying provides knowledge of the sequence of the nucleic acid sequence of the variance, and most preferably identifying provides knowledge of the combination of different variances that comprise specific variant forms of the gene or alleles (referred to as alleles). In identifying new variances it is often useful to screen different population groups based on racial, ethnic, gender, and/or geographic origin because particular variances may differ in frequency between such groups. It may also be useful to screen DNA from individuals with a particular disease or condition of interest because they may have a higher frequency of certain variances than the general population.

The process of genotyping involves using diagnostic tests for specific variances that have already been identified. It will be apparent that such diagnostic tests can only be performed after variances and variant forms of the gene have been identified. Identification of new variances can be accomplished by a variety of methods, alone or in combination, including, for example, DNA sequencing, SSCP, heteroduplex analysis, denaturing gradient gel electrophoresis (DGGE), heteroduplex cleavage (either enzymatic as with T4 Endonuclease 7, or chemical as with osmium tetroxide and hydroxylamine), computational methods (described herein), and other methods described herein as well as others known to those skilled in the art. (See, for example: Cotton, R. G. H., Slowly but surely towards better scanning for mutations, Trends in Genetics 13(2): 43–6, 1997 or Current Protocols in Human Genetics by N. C. Dracoli, J. L. Haines, B. R. Korf, D. T. Moir, C. C. Morton, C. E. Seidman, D. R. Smith, and A. Boyle (editors), John Wiley & Sons.)

In the context of this invention, the term "analyzing a sequence" refers to determining at least some sequence information about the sequence, e.g., determining the nucleotides present at a particular site or sites in the sequence, particularly sites that are known to vary in a population, or determining the base sequence of all or of a portion of the particular sequence.

In the context of this invention, the term "haplotype" refers to a cis arrangement of two or more polymorphic nucleotides, i.e., variances, on a particular chromosome, e.g., in a particular gene. The haplotype preserves information about the phase of the polymorphic nucleotides—that is, which set of variances were inherited from one parent, and which from the other. A genotyping test does not provide information about phase. For example, an individual heterozygous at nucleotide 25 of a gene (both A and C are present) and also at nucleotide 100 (both G and T are present) could have haplotypes 25A–100G and 25C–100T, or alternatively 25A–100T and 25C–100G. Only a haplotyping test can discriminate these two cases definitively.

The terms "variances", "variants" and "polymorphisms", as used herein, may also refer to a set of variances, haplotypes or a mixture of the two. Further, the term variance, variant or polymorphism (singular), as used herein, also encompasses a haplotype. This usage is intended to minimize the need for cumbersome phrases such as: "... measure correlation between drug response and a *variance, variances, haplotype, haplotypes or a combination of variances and haplotypes* ... ", throughout the application. Instead, the italicized text in the foregoing sentence can be represented by the word "variance", "variant" or "polymorphism". Similarly, the term genotype, as used herein, means a procedure for determining the status of one or more variances in a gene, including a set of variances comprising a haplotype. Thus phrases such as "... genotype a patient ..." refer to determining the status of one or more variances, including a set of variances for which phase is known (i.e. a haplotype).

In preferred embodiments of this invention, the frequency of the variance or variant form of the gene in a population is known. Measures of frequency known in the art include "allele frequency", namely the fraction of genes in a population that have one specific variance or set of variances. The allele frequencies for any gene should sum to 1. Another measure of frequency known in the art is the "heterozygote frequency" namely, the fraction of individuals in a population who carry two alleles, or two forms of a particular variance or variant form of a gene, one inherited from each parent. Alternatively, the number of individuals who are homozygous for a particular form of a gene may be a useful measure. The relationship between allele frequency, heterozygote frequency, and homozygote frequency is described for many genes by the Hardy-Weinberg equation, which provides the relationship between allele frequency, heterozygote frequency and homozygote frequency in a freely breeding population at equilibrium. Most human variances are substantially in Hardy-Weinberg equilibrium. In a preferred aspect of this invention, the allele frequency, heterozygote frequency, and homozygote frequencies are determined experimentally. Preferably a variance has an allele frequency of at least 0.01, more preferably at least 0.05, still more preferably at least 0.10. However, the allele may have a frequency as low as 0.001 if the associated phenotype is, for example, a rare form of toxic reaction to a treatment or drug. Beneficial responses may also be rare.

In this regard, "population" refers to a defined group of individuals or a group of individuals with a particular disease or condition or individuals that may be treated with a specific drug identified by, but not limited to geographic, ethnic, race, gender, and/or cultural indices. In most cases a population will preferably encompass at least ten thousand, one hundred thousand, one million, ten million, or more individuals, with the larger numbers being more preferable. In a preferred aspect of this invention, the population refers to individuals with a specific disease or condition that may be treated with a specific drug. In an aspect of this invention, the allele frequency, heterozygote frequency, or homozygote frequency of a specific variance or variant form of a gene is known. In preferred embodiments of this invention, the frequency of one or more variances that may predict response to a treatment is determined in one or more populations using a diagnostic test.

It should be emphasized that it is currently not generally practical to study an entire population to establish the association between a specific disease or condition or response to a treatment and a specific variance or variant form of a gene. Such studies are preferably performed in controlled clinical trials using a limited number of patients that are considered to be representative of the population with the disease. Since drug development programs are generally targeted at the largest possible population, the study population will generally comprise men and women, as well as members of various racial and ethnic groups, depending on where the clinical trial is being performed. This is important to establish the efficacy of the treatment in all segments of the population.

In the context of this invention, the term "probe" refers to a molecule which detectably distinguishes between target molecules differing in structure. Detection can be accomplished in a variety of different ways depending on the type of probe used and the type of target molecule. Thus, for example, detection may be based on discrimination of activity levels of the target molecule, but preferably is based on detection of specific binding. Examples of such specific binding include antibody binding and nucleic acid probe hybridization. Thus, for example, probes can include enzyme substrates, antibodies and antibody fragments, and nucleic acid hybridization probes. Thus, in preferred embodiments, the detection of the presence or absence of the at least one variance involves contacting a nucleic acid sequence which includes a variance site with a probe, preferably a nucleic acid probe, where the probe preferentially hybridizes with a form of the nucleic acid sequence containing a complementary base at the variance site as compared to hybridization to a form of the nucleic acid sequence having a non-complementary base at the variance site, where the hybridization is carried out under selective hybridization conditions. Such a nucleic acid hybridization probe may span two or more variance sites. Unless otherwise specified, a nucleic acid probe can include one or more nucleic acid analogs, labels or other substituents or moieties so long as the base-pairing function is retained.

As is generally understood, administration of a particular treatment, e.g., administration of a therapeutic compound or combination of compounds, is chosen depending on the disease or condition which is to be treated. Thus, in certain preferred embodiments, the disease or condition is one for which administration of a treatment is expected to provide a therapeutic benefit; in certain embodiments, the compound is a compound identified herein, e.g., in a drug table (Tables 5–13, 16, 17, 18).

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the presence of one or more sequence variances or alleles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition.

Effectiveness is measured in a particular population. In conventional drug development the population is generally every subject who meets the enrollment criteria (i.e. has the particular form of the disease or condition being treated). It is an aspect of the present invention that segmentation of a study population by genetic criteria can provide the basis for identifying a subpopulation in which a drug is effective against the disease or condition being treated.

The term "deleterious effects" refers to physical effects in a patient caused by administration of a treatment which are regarded as medically undesirable. Thus, for example, deleterious effects can include a wide spectrum of toxic effects injurious to health such as death of normally functioning cells when only death of diseased cells is desired, nausea, fever, inability to retain food, dehydration, damage to critical organs such as arrythmias, renal tubular necrosis, fatty liver, or pulmonary fibrosis leading to coronary, renal, hepatic, or pulmonary insufficiency among many others. In this regard, the term "contra-indicated" means that a treatment results in deleterious effects such that a prudent medical doctor treating such a patient would regard the treatment as unsuitable for administration. Major factors in such a determination can include, for example, availability and relative advantages of alternative treatments, consequences of non-treatment, and permanency of deleterious effects of the treatment.

It is recognized that many treatment methods, e.g., administration of certain compounds or combinations of compounds, may produce side-effects or other deleterious effects in patients. Such effects can limit or even preclude use of the treatment method in particular patients, or may even result in irreversible injury, dysfunction, or death of the patient. Thus, in certain embodiments, the variance information is used to select both a first method of treatment and a second method of treatment. Usually the first treatment is a primary treatment which provides a physiological effect directed against the disease or condition or its symptoms. The second method is directed to reducing or eliminating one or more deleterious effects of the first treatment, e.g., to reduce a general toxicity or to reduce a side effect of the primary treatment. Thus, for example, the second method can be used to allow use of a greater dose or duration of the first treatment, or to allow use of the first treatment in patients for whom the first treatment would not be tolerated or would be contra-indicated in the absence of a second method to reduce deleterious effects or to potentiate the effectiveness of the first treatment.

In a related aspect, the invention provides a method for selecting a method of treatment for a patient suffering from a disease or condition by comparing at least one variance in at least one gene in the patient, with a list of variances in the gene from Tables 1 and 3, or other gene related to inflammatory or immunological disease, which are indicative of the effectiveness of at least one method of treatment. Preferably the comparison involves a plurality of variances or a haplotype indicative of the effectiveness of at least one method of treatment. Also, preferably the list of variances includes a plurality of variances.

Similar to the above aspect, in preferred embodiments the at least one method of treatment involves the administration of a compound effective in at least some patients with a disease or condition; the presence or absence of the at least one variance is indicative that the treatment will be effective in the patient; and/or the presence or absence of the at least one variance is indicative that the treatment will be ineffective or contra-indicated in the patient; and/or the treatment is a first treatment and the presence or absence of the at least one variance is indicative that a second treatment will be beneficial to reduce a deleterious effect of or potentiate the effectiveness of the first treatment; and/or the at least one treatment is a plurality of methods of treatment. For a plurality of treatments, preferably the selecting involves determining whether any of the methods of treatment will be more effective than at least one other of the plurality of methods of treatment. Yet other embodiments are provided as described for the preceding aspect in connection with methods of treatment using administration of a compound; treatment of various diseases, and variances in particular genes.

In the context of variance information in the methods of this invention, the term "list" refers to one or more variances which have been identified for a gene of potential importance in accounting for inter-individual variation in treatment response. Preferably there is a plurality of variances for the gene, preferably a plurality of variances for the particular gene. Preferably, the list is recorded in written or electronic form. For example, identified variances of identified genes are recorded for some of the genes in Tables 1 and 3, additional variances for genes in Table 1 are provided in Table 1 of Stanton & Adams, U.S. Application Ser. No. 09/300,747, supra, and additional gene variance identification tables are provided in a form which allows comparison with other variance information. The possible additional variances in the identified genes are provided in Table 3 in Stanton & Adams, U.S. application Ser. No. 09/300,747, supra.

In addition to the basic method of treatment, often the mode of administration of a given compound as a treatment for a disease or condition in a patient is significant in determining the course and/or outcome of the treatment for the patient. Thus, the invention also provides a method for selecting a method of administration of a compound to a patient suffering from a disease or condition, by determining the presence or absence of at least one variance in cells of the patient in at least one identified gene from Tables 1 and 3, where such presence or absence is indicative of an appropriate method of administration of the compound. Preferably, the selection of a method of treatment (a treatment regimen) involves selecting a dosage level or frequency of administration or route of administration of the compound or combinations of those parameters. In preferred embodiments, two or more compounds are to be administered, and the selecting involves selecting a method of administration for one, two, or more than two of the compounds, jointly, concurrently, or separately. As understood by those skilled in the art, such plurality of compounds may be used in combination therapy, and thus may be formulated in a single drug, or may be separate drugs administered concurrently, serially, or separately. Other embodiments are as indicated above for selection of second treatment methods, methods of identifying variances, and methods of treatment as described for aspects above.

In another aspect, the invention provides a method for selecting a patient for administration of a method of treatment for a disease or condition, or of selecting a patient for a method of administration of a treatment, by comparing the presence or absence of at least one variance in a gene as identified above in cells of a patient, with a list of variances in the gene, where the presence or absence of the at least one variance is indicative that the treatment or method of administration will be effective in the patient. If the at least one variance is present in the patient's cells, then the patient is selected for administration of the treatment.

In preferred embodiments, the disease or the method of treatment is as described in aspects above, specifically including, for example, those described for selecting a method of treatment.

In another aspect, the invention provides a method for identifying a subset of patients with enhanced or diminished response or tolerance to a treatment method or a method of administration of a treatment where the treatment is for a disease or condition in the patient. The method involves correlating one or more variances in one or more genes as identified in aspects above in a plurality of patients with response to a treatment or a method of administration of a treatment. The correlation may be performed by determining the one or more variances in the one or more genes in the plurality of patients and correlating the presence or absence of each of the variances (alone or in various combinations) with the patient's response to treatment. The variances may be previously known to exist or may also be determined in the present method or combinations of prior information and newly determined information may be used. The enhanced or diminished response should be statistically significant, preferably such that p=0.10 or less, more preferably 0.05 or less, and most preferably 0.02 or less. A positive correlation between the presence of one or more variances and an enhanced response to treatment is indicative that the treatment is particularly effective in the group of patients having those variances. A positive correlation of the presence of the one or more variances with a diminished response to the treatment is indicative that the treatment will be less effective in the group of patients having those variances. Such information is useful, for example, for selecting or de-selecting patients for a particular treatment or method of administration of a treatment, or for demonstrating that a group of patients exists for which the treatment or method of treatment would be particularly beneficial or contraindicated. Such demonstration can be beneficial, for example, for obtaining government regulatory approval for a new drug or a new use of a drug In preferred embodiments, the variances are in at least one of the identified genes listed on Tables 1 and 3, or are particular variances described herein. Also, preferred embodiments include drugs, treatments, variance identification or determination, determination of effectiveness, and/or diseases as described for aspects above or otherwise described herein.

In preferred embodiments, the correlation of patient responses to therapy according to patient genotype is carried out in a clinical trial, e.g., as described herein according to any of the variations described. Detailed description of methods for associating variances with clinical outcomes using clinical trials are provided below. Further, in preferred embodiments the correlation of pharmacological effect (positive or negative) to treatment response according to genotype or haplotype in such a clinical trial is part of a regulatory submission to a government agency leading to approval of the drug. Most preferably the compound or compounds would not be approvable in the absence of the genetic information allowing identification of an optimal responder population.

As indicated above, in aspects of this invention involving selection of a patient for a treatment, selection of a method or mode of administration of a treatment, and selection of a patient for a treatment or a method of treatment, the selection may be positive selection or negative selection. Thus, the methods can include eliminating a treatment for a patient, eliminating a method or mode of administration of a treatment to a patient, or elimination of a patient for a treatment or method of treatment.

Also, in methods involving identification and/or comparison of variances present in a gene of a patient, the methods can involve such identification or comparison for a plurality of genes. Preferably, the genes are functionally related to the same disease or condition, or to the aspect of disease pathophysiology that is being subjected to pharmacological manipulation by the treatment (e.g., a drug), or to the activation or inactivation or elimination of the drug, and more preferably the genes are involved in the same biochemical process or pathway.

In another aspect, the invention provides a method for identifying the forms of a gene in an individual, where the gene is one specified as for aspects above, by determining the presence or absence of at least one variance in the gene. In preferred embodiments, the at least one variance includes at least one variance selected from the group of variances identified in variance tables herein. Preferably, the presence or absence of the at least one variance is indicative of the effectiveness of a therapeutic treatment in a patient suffering from a disease or condition and having cells containing the at least one variance.

The presence or absence of the variances can be determined in any of a variety of ways as recognized by those skilled in the art. For example, the nucleotide sequence of at least one nucleic acid sequence which includes at least one variance site (or a complementary sequence) can be determined, such as by chain termination methods, hybridization methods or by mass spectrometric methods. Likewise, in preferred embodiments, the determining involves contacting a nucleic acid sequence or a gene product of one of one of the genes with a probe which specifically identifies the presence or absence of a form of the gene. For example, a probe, e.g., a nucleic acid probe, can be used which specifically binds, e.g., hybridizes, to a nucleic acid sequence corresponding to a portion of the gene and which includes at least one variance site under selective binding conditions. As described for other aspects, determining the presence or absence of at least two variances and their relationship on the two gene copies present in a patient can constitute determining a haplotype or haplotypes.

Other preferred embodiments involve variances related to types of treatment, drug responses, diseases, nucleic acid sequences, and other items related to variances and variance determination as described for aspects above.

In yet another aspect, the invention provides a pharmaceutical composition which includes a compound which has a differential effect in patients having at least one copy, or alternatively, two copies of a form of a gene as identified for aspects above and a pharmaceutically acceptable carrier, excipient, or diluent. The composition is adapted to be preferentially effective to treat a patient with cells containing the one, two, or more copies of the form of the gene.

In preferred embodiments of aspects involving pharmaceutical compositions, active compounds, or drugs, the material is subject to a regulatory limitation or restriction on approved uses or indications or is subject to a recommendation, e.g., by the U.S. Food and Drug Administration (FDA), limiting approved use of the composition to patients having at least one copy of the particular form of the gene which contains at least one variance. Alternatively, the composition is subject to a regulatory limitation or restriction on approved uses, or a recommendation to limit use, indicating that the composition is not approved for use or should not be used in patients having at least one copy of a form of the gene including at least one variance. Also in preferred embodiments, the composition is packaged, and the packaging includes a label or insert indicating or suggesting beneficial therapeutic approved use of the composition in patients having one or two copies of a form of the gene including at least one variance. Alternatively, the label or insert limits approved use, or recommends limiting use, of the composition to patients having zero or one or two copies of a form of the gene including at least one variance. The latter embodiment would be likely where the presence of the at least one variance in one or two copies in cells of a patient means that the composition would be ineffective or deleterious to the patient. Also in preferred embodiments, the composition is indicated for use in treatment of a disease or condition which is one of those identified for aspects above. Also in preferred embodiments, the at least one variance includes at least one variance from those identified herein.

The term "packaged" means that the drug, compound, or composition is prepared in a manner suitable for distribution or shipping with a box, vial, pouch, bubble pack, or other protective container, which may also be used in combination. The packaging may have printing on it and/or printed material may be included in the packaging.

In preferred embodiments, the drug is selected from the drug classes or specific exemplary drugs identified in an example, in a table herein, and is subject to a regulatory limitation or suggestion or warning as described above that limits or suggests limiting approved use to patients having specific variances or variant forms of a gene identified in Examples or in the gene list provided below in order to achieve maximal benefit and avoid toxicity or other deleterious effect.

A pharmaceutical composition can be adapted to be preferentially effective in a variety of ways. In some cases, an active compound is selected which was not previously known to be differentially active, or which was not previously recognized as a therapeutic compound. Alternatively the compound was previously known as a therapeutic compound, but the composition is formulated in a manner appropriate for administration for treatment of a disease or condition for which a gene of this invention is involved in treatment response, and the active compound had not been formulated appropriately for such use before. For example, a compound may previously have been formulated for topical treatment of a skin condition, but is found to be effective in IV or other internal treatment of a disease identified for this invention. For compounds that are differentially effective on the gene, such alternative alternative formulations are adapted to be preferentially effective. In some cases, the concentration of an active compound which has differential activity can be adjusted such that the composition is appropriate for administration to a patient with the specified variances. For example, the presence of a specified variance may allow or require the administration of a much larger dose, which would not be practical with a previously utilized composition. Conversely, a patient may require a much lower dose, such that administration of such a dose with a prior composition would be impractical or inaccurate. Thus, the composition may be prepared in a higher or lower unit dose form, or prepared in a higher or lower concentration of the active compound or compounds. In yet other cases, the composition can include additional compounds needed to enable administration of a particular active compound in a patient with the specified variances, which was not in previous compositions, e.g., because the majority of patients did not require or benefit from the added component.

The term "differential" or "differentially" generally refers to a statistically significant different level in the specified property or effect. Preferably, the difference is also functionally significant. Thus, "differential binding or hybridization" is sufficient difference in binding or hybridization to allow discrimination using an appropriate detection technique. Likewise, "differential effect" or "differentially active" in connection with a therapeutic treatment or drug refers to a difference in the level of the effect or activity which is distinguishable using relevant parameters and techniques for measuring the effect or activity being considered. Preferably the difference in effect or activity is also sufficient to be clinically significant, such that a corresponding difference in the course of treatment or treatment outcome would be expected, at least on a statistical basis.

Also usefully provided in the present invention are probes which specifically recognize a nucleic acid sequence corresponding to a variance or variances in a gene as identified in aspects above or a product expressed from the gene, and are able to distinguish a variant form of the sequence or gene or gene product from one or more other variant forms of that sequence, gene, or gene product under selective conditions. Those skilled in the art recognize and understand the identification or determination of selective conditions for particular probes or types of probes. An exemplary type of probe is a nucleic acid hybridization probe, which will selectively bind under selective binding conditions to a nucleic acid sequence or a gene product corresponding to one or the genes identified for aspects above. Another type of probe is a peptide or protein, e.g., an antibody or antibody fragment which specifically or preferentially binds to a polypeptide expressed from a particular form of a gene as characterized by the presence or absence of at least one variance. Thus, in another aspect, the invention concerns such probes. In the context of this invention, a "probe" is a molecule, commonly a nucleic acid, though also potentially a protein, carbohydrate, polymer, or small molecule, that is capable of binding to one variance or variant form of the gene to a greater extent than to a form of the gene having a different base at one or more variance sites, such that the presence of the variance or variant form of the gene can be determined. Preferably the probe distinguishes at least one variance identified in Examples, tables or lists below or in Tables 1 or 3 of Stanton & Adams, U.S. application Ser. No. 09/300,747, supra.

In preferred embodiments, the probe is a nucleic acid probe at least 15, preferably at least 17 nucleotides in length, more preferably at least 20 or 22 or 25, preferably 500 or fewer nucleotides in length, more preferably 200 or 100 or fewer, still more preferably 50 or fewer, and most preferably 30 or fewer. In preferred embodiments, the probe has a length in a range between from any one of the above lengths to any other of the above lengths (including endpoints). The probe specifically hybridizes under selective hybridization conditions to a nucleic acid sequence corresponding to a portion of one of the genes identified in connection with above aspects. The nucleic acid sequence includes at least one and preferably two or more variance sites. Also in preferred embodiments, the probe has a detectable label, preferably a fluorescent label. A variety of other detectable labels are known to those skilled in the art. Such a nucleic acid probe can also include one or more nucleic acid analogs.

In preferred embodiments, the probe is an antibody or antibody fragment which specifically binds to a gene product expressed from a form of one of the above genes, where the form of the gene has at least one specific variance with a particular base at the variance site, and preferably a plurality of such variances.

In connection with nucleic acid probe hybridization, the term "specifically hybridizes" indicates that the probe hybridizes to a sufficiently greater degree to the target sequence than to a sequence having a mismatched base at least one variance site to allow distinguishing such hybridization. The term "specifically hybridizes" thus means that the probe hybridizes to the target sequence, and not to non-target sequences, at a level which allows ready identification of probe/target sequence hybridization under selective hybridization conditions. Thus, "selective hybridization conditions" refer to conditions which allow such differential binding. Similarly, the terms "specifically binds" and "selective binding conditions" refer to such differential binding of any type of probe, e.g., antibody probes, and to the conditions which allow such differential binding. Typically hybridization reactions to determine the status of variant sites in patient samples are carried out with two different probes, one specific for each of the (usually two) possible variant nucleotides. The complementary information derived from the two separate hybridization reactions is useful in corroborating the results.

Likewise, the invention provides an isolated, purified or enriched nucleic acid sequence of 15 to 500 nucleotides in length, preferably 15 to 100 nucleotides in length, more preferably 15 to 50 nucleotides in length, and most preferably 15 to 30 nucleotides in length, which has a sequence which corresponds to a portion of one of the genes identified for aspects above. Preferably the lower limit for the preceding ranges is 17, 20, 22, or 25 nucleotides in length. In other embodiments, the nucleic acid sequence is 30 to 300 nucleotides in length, or 45 to 200 nucleotides in length, or 45 to 100 nucleotides in length. The nucleic acid sequence includes at least one variance site. Such sequences can, for example, be amplification products of a sequence which spans or includes a variance site in a gene identified herein. Likewise, such a sequence can be a primer, or amplification nucleotide which is able to bind to or extend through a variance site in such a gene. Yet another example is a nucleic acid hybridization probe comprised of such a sequence. In such probes, primers, and amplification products, the nucleotide sequence can contain a sequence or site corresponding to a variance site or sites, for example, a variance site identified herein. Preferably the presence or absence of a particular variant form in the heterozygous or homozygous state is indicative of the effectiveness of a method of treatment in a patient.

Likewise, the invention provides a set of primers or amplification oligonucleutides (e.g., 2,3,4,6,8,10 or even more) adapted for binding to or extending through at least one gene identified herein. In preferred embodiments the set includes primers or amplifications oligonucleotides adapted to bind to or extend through a plurality of sequence variances in a gene(s) identified herein. The plurality of variances preferably provides a haplotype. Those skilled in the art are familiar with the use of amplification oligonucleotides (e.g., PCR primers) and the appropriate location, testing and use of such oligonucleotides. In certain embodiments, the oligonucleotides are designed and selected to provide variance-specific amplification.

In reference to nucleic acid sequences which "correspond" to a gene, the term "correspond" refers to a nucleotide sequence relationship, such that the nucleotide sequence has a nucleotide sequence which is the same as the reference gene or an indicated portion thereof, or has a nucleotide sequence which is exactly complementary in normal Watson-Crick base pairing, or is an RNA equivalent of such a sequence, e.g., an mRNA, or is a cDNA derived from an mRNA of the gene.

In another aspect, the invention provides a method for determining a genotype of an individual in relation to one or more variances in one or more of the genes identified in above aspects by using mass spectrometric determination of a nucleic acid sequence which is a portion of a gene identified for other aspects of this invention or a complementary sequence. Such mass spectrometric methods are known to those skilled in the art. In preferred embodiments, the method involves determining the presence or absence of a variance in a gene; determining the nucleotide sequence of the nucleic acid sequence; the nucleotide sequence is 100 nucleotides or less in length, preferably 50 or less, more preferably 30 or less, and still more preferably 20 nucleotides or less. In general, such a nucleotide sequence includes at least one variance site, preferably a variance site which is informative with respect to the expected response of a patient to a treatment as described for above aspects.

As indicated above, many therapeutic compounds or combinations of compounds or pharmaceutical compositions show variable efficacy and/or safety in various patients in whom the compound or compounds is administered. Thus, it is beneficial to identify variances in relevant genes, e.g., genes related to the action or toxicity of the compound or compounds. Thus, in a further aspect, the invention provides a method for determining whether a compound has a differential effect due to the presence or absence of at least one variance in a gene or a variant form of a gene, where the gene is a gene identified for aspects above.

The method involves identifying a first patient or set of patients suffering from a disease or condition whose response to a treatment differs from the response (to the same treatment) of a second patient or set of patients suffering from the same disease or condition, and then determining whether the occurrence or frequency of occurrence of at least one variance in at least one gene differs between the first patient or set of patients and the second patient or set of patients. A correlation between the presence or absence of the variance or variances and the response of the patient or patients to the treatment indicates that the variance provides information about variable patient response. In general, the method will involve identifying at least one variance in at least one gene. An alternative approach is to identify a first patient or set of patients suffering from a disease or condition and having a particular genotype, haplotype or combination of genotypes or haplotypes, and a second patient or set of patients suffering from the same disease or condition that have a genotype or haplotype or sets of genotypes or haplotypes that differ in a specific way from those of the first set of patients. Subsequently the extent and magnitude of clinical response can be compared between the first patient or set of patients and the second patient or set of patients. A correlation between the presence or absence of a variance or variances or haplotypes and the response of the patient or patients to the treatment indicates that the variance provides information about variable patient response and is useful for the present invention.

The method can utilize a variety of different informative comparisons to identify correlations. For example a plurality of pairwise comparisons of treatment response and the presence or absence of at least one variance can be performed for a plurality of patients. Likewise, the method can involve comparing the response of at least one patient homozygous for at least one variance with at least one patient homozygous for the alternative form of that variance or variances. The method can also involve comparing the response of at least one patient heterozygous for at least one variance with the response of at least one patient homozygous for the at least one variance. Preferably the heterozygous patient response is compared to both alternative homozygous forms, or the response of heterozygous patients is grouped with the response of one class of homozygous patients and said group is compared to the response of the alternative homozygous group.

Such methods can utilize either retrospective or prospective information concerning treatment response variability. Thus, in a preferred embodiment, it is previously known that patient response to the method of treatment is variable.

Also in preferred embodiments, the disease or condition is as for other aspects of this invention; for example, the treatment involves administration of a compound or pharmaceutical composition.

In preferred embodiments, the method involves a clinical trial, e.g., as described herein. Such a trial can be arranged, for example, in any of the ways described herein, e.g., in the Detailed Description.

The present invention also provides methods of treatment of a disease or condition, preferably a disease or condition related to an inflammatory or immunological disease or other inflammatory or immunological clinical symptomology. Such methods combine identification of the presence or absence of particular variances, preferably in a gene or genes from Tables 1 and 3, with the administration of a compound; identification of the presence of particular variances with selection of a method of treatment and administration of the treatment; and identification of the presence or absence of particular variances with elimination of a method of treatment based on the variance information indicating that the treatment is likely to be ineffective or contra-indicated, and thus selecting and administering an alternative treatment effective against the disease or condition. Thus, preferred embodiments of these methods incorporate preferred embodiments of such methods as described for such sub-aspects.

As used herein, a "gene" is a sequence of DNA present in a cell that directs the expression of a "biologically active" molecule or "gene product", most commonly by transcription to produce RNA and translation to produce protein. The "gene product" is most commonly a RNA molecule or protein or a RNA or protein that is subsequently modified by reacting with, or combining with, other constituents of the cell. Such modifications may include, without limitation, modification of proteins to form glycoproteins, lipoproteins, and phosphoproteins, or other modifications known in the art. RNA may be modified without limitation by polyadenylation, splicing, capping or export from the nucleus or by covalent or noncovalent interactions with proteins. The term "gene product" refers to any product directly resulting from transcription of a gene. In particular this includes partial, precursor, and mature transcription products (i.e., pre-mRNA and mRNA), and translation products with or without further processing including, without limitation, lipidation, phosphorylation, glycosylation, or combinations of such processing The term "gene involved in the origin or pathogenesis of a disease or condition" refers to a gene that harbors mutations or polymorphisms that contribute to the cause of disease, or variances that affect the progression of the disease or expression of specific characteristics of the disease. The term also applies to genes involved in the synthesis, accumulation, or elimination of products that are involved in the origin or pathogenesis of a disease or condition including, without limitation, proteins, lipids, carbohydrates, hormones, or small molecules.

By "pathway" or "gene pathway" is meant the group of biologically relevant genes involved in a pharmacodynamic or pharmacokinetic mechanism of drug, agent, or candidate therapeutic intervention. These mechanisms may further include any physiologic effect the drug or candidate therapeutic intervention renders.

The term "gene involved in the action of a drug" refers to any gene whose gene product affects the efficacy or safety of the drug or affects the disease process being treated by the drug, and includes, without limitation, genes that encode gene products that are targets for drug action, gene products that are involved in the metabolism, activation or degradation of the drug, gene products that are involved in the bioavailability or elimination of the drug to the target, gene products that affect biological pathways that, in turn, affect the action of the drug such as the synthesis or degradation of competitive substrates or allosteric effectors or rate-limiting reaction, or, alternatively, gene products that affect the pathophysiology of the disease process via pathways related or unrelated to those altered by the presence of the drug compound. (Particular variances in the latter category of genes may be associated with patient groups in whom disease etiology is more or less susceptible to amelioration by the drug. For example, there are several pathophysiological mechanisms in hypertension, and depending on the dominant mechanism in a given patient, that patient may be more or less likely than the average hypertensive patient to respond to a drug that primarily targets one pathophysiological mechanism. The relative importance of different pathophysiological mechanisms in individual patients is likely to be affected by variances in genes associated with the disease pathophysiology.) The "action" of a drug refers to its effect on biological products within the body. The action of a drug also refers to its effects on the signs or symptoms of a disease or condition, or effects of the drug that are unrelated to the disease or condition leading to unanticipated effects on other processes. Such unanticipated processes often lead to adverse events or toxic effects. The terms "adverse event" or "toxic" event" are known in the art and include, without limitation, those listed in the FDA reference system for adverse events.

In accordance with the aspects above and the Detailed Description below, there is also described for this invention an approach for developing drugs that are explicitly indicated for, and/or for which approved use is restricted to individuals in the population with specific variances or combinations of variances, as determined by diagnostic tests for variances or variant forms of certain genes involved in the disease or condition or involved in the action or metabolism or transport of the drug. Such drugs may provide more effective treatment for a disease or condition in a population identified or characterized with the use of a diagnostic test for a specific variance or variant form of the gene if the gene is involved in the action of the drug or in determining a characteristic of the disease or condition. Such drugs may be developed using the diagnostic tests for specific variances or variant forms of a gene to determine the inclusion of patients in a clinical trial.

Thus, the invention also provides a method for producing a pharmaceutical composition by identifying a compound which has differential activity or effectiveness against a disease or condition in patients having at least one variance in a gene, preferably in a gene from Tables 1 and 3, compounding the pharmaceutical composition by combining the compound with a pharmaceutically acceptable carrier, excipient, or diluent such that the composition is preferentially effective in patients who have at least one copy of the variance or variances. In some cases, the patient has two copies of the variance or variances. In preferred embodiments, the active component of the pharmaceutical composition is a compound listed in the compound tables below (Tables 5–13, 16, 17, 18), or a compound chemically related to one of the listed compounds.

Similarly, the invention provides a method for producing a pharmaceutical agent by identifying a compound which has differential activity against a disease or condition in patients having at least one copy of a form of a gene, preferably a gene from Tables 1 and 3, having at least one variance and synthesizing the compound in an amount sufficient to provide a pharmaceutical effect in a patient suffering from the disease or condition. The compound can be identified by conventional screening methods and its activity confirmed. For example, compound libraries can be screened to identify compounds which differentially bind to products of variant forms of a particular gene product, or which differentially affect expression of variant forms of the particular gene, or which differentially affect the activity of a product expressed from such gene. Alternatively, the design of a compound can exploit knowledge of the variances provided herein to avoid significant allele specific effects, in order to reduce the likelihood of significant pharmacogenetic effects durign the clinical development process. Preferred embodiments are as for the preceding aspect.

In another aspect, the invention provides a method of treating a disease or condition in a patient by selecting a patient whose cells have an allele of an identified gene, preferably a gene selected from the genes listed in Tables 1 and 3. The allele contains at least one variance correlated with more effective response to a treatment of said disease or condition. The method also includes altering the level of activity in cells of the patient of a product of the allele, where the altering provides a therapeutic effect.

Preferably the allele contains a variance as shown in Tables 1 and 3 or other variance table herein, or in Table1 or 3 of Stanton & Adams, U.S. application Ser. No. 09/300,747, supra. Also preferably, the altering involves administering to the patient a compound preferentially active on at least one but less than all alleles of the gene.

Preferred embodiments include those as described above for other aspects of treating a disease or condition.

As recognized by those skilled in the art, all the methods of treating described herein include administration of the treatment to a patient.

In a further aspect, the invention provides a method for determining a method of treatment effective to treat a disease or condition by altering the level of activity of a product of an allele of a gene selected from the genes listed in Tables 1 and 3, and determining whether that alteration provides a differential effect (with respect to reducing or alleviating a disease or condition, or with respect to variation in toxicity or tolerance to a treatment) in patients with at least one copy of at least one allele of the gene as compared to patients with at least one copy of one alternative allele., The presence of such a differential effect indicates that altering the level or activity of the gene provides at least part of an effective treatment for the disease or condition.

Preferably the method for determining a method of treatment is carried out in a clinical trial, e.g., as described above and/or in the Detailed Description below.

In still another aspect, the invention provides a method for performing a clinical trial or study, which includes selecting or stratifying subjects in the trial or study using a variance or variances or haplotypes from one or more genes specified in Tables 1 and 3. Preferably the differential efficacy, tolerance, or safety of a treatment in a subset of patients who have a particular variance, variances, or haplotype in a gene or genes from Tables 1 and 3 is determined by conducting a clinical trial and using a statistical test to assess whether a relationship exists between efficacy, tolerance, or safety and the presence or absence of any of the variances or haplotype in one or more of the genes. Rresults of the clinical trial or study are indicative of whether a higher or lower efficacy, tolerance, or safety of the treatment in a subset of patients is associated with any of the variance or variances or haplotype in one or more of the genes. In preferred embodiments, the clinical trial or study is a Phase I, II, III, or IV trial or study. Preferred embodiments include the stratifications and/or statistical analyses as described below in the Detailed Description.

In preferred embodiments, normal subjects or patients are prospectively stratified by genotype in different genotype-defined groups, including the use of genotype as a enrollment criterion, using a variance, variances or haplotypes from Tables 1 and 3, and subsequently a biological or clinical response variable is compared between the different genotype-defined groups. In preferred embodiments, normal subjects or patients in a clinical trial or study are stratified by a biological or clinical response variable in different biologically or clinically-defined groups, and subsequently the frequency of a variance, variances or haplotypes from Tables 1 and 3 is measured in the different biologically or clinically defined groups.

In preferred embodiments, e.g., of the above two analyses (and in other aspects of this invention involving patient or normal subject stratification), the normal subjects or patients in a clinical trial or study are stratified by at least one demographic characteristic selected from the goup consisting of sex, age, racial origin, ethnic origin, or geographic origin.

Generally the method will involve assigning patients or subjects to a group to receive the method of treatment or to a control group.

In yet another aspect, the invention provides experimental methods for finding additional variances in a gene provided in Tables 1 and 3. A number of experimental methods can also beneficially be used to identify variances. Thus, the invention provides methods for producing cDNA (Example 4) and detecting additional variances in the genes provided in Tables 1 or 3 using the single strand conformation polymorphism (SSCP) method (Example 5), the T4 Endonuclease VII method (Example 6) or DNA sequencing (Example 7) or other methods pointed out below. The application of these methods to the identified genes will provide identification of additional variances that can affect inter-individual variation in drug or other treatment response. One skilled in the art will recognize that many methods for experimental variance detection have been described (in addition to the exemplary methods of examples 5, 6, and 7) and can be utilized. These additional methods include chemical cleavage of mismatches (see, e.g., Ellis TP, et al., Chemical cleavage of mismatch: a new look at an established method. Human Mutation 11(5):345–53, 1998), denaturing gradient gel electrophoresis (see, e.g., Van Orsouw NJ, et al., Design and application of 2-D DGGE-based gene mutational scanning tests. Genet Anal. 14(5–6):205–13, 1999) and heteroduplex analysis (see, e.g., Ganguly A, et al., Conformation-sensitive gel electrophoresis for rapid detection of single-base differences in double-stranded PCR products and DNA fragments: evidence for solvent-induced bends in DNA heteroduplexes. Proc Natl Acad Sci U S A. 90 (21):10325–9, 1993). Table 3 of Stanton & Adams, U.S. application Ser. No. 09/300,747, supra, provides a description of the additional possible variances that could be detected by one skilled in the art by testing an identified.gene in Tables 1 and 3 using the variance detection methods described or other methods which are known or are developed.

The present invention provides a method for treating a patient at risk for an inflammatory or immunologic disease or condition (for example to prevent or delay the onset of frank disease) or a patient already diagnosed with inflammatory or immunologic disease or a disease associated with said disease. The methods include identifying such a patient and determining the patient's genotype or haplotype for an identified gene or genes. The patient identification can, for example, be based on clinical evaluation using conventional clinical metrics and/or on evaluation of a genetic variance or variances in one or more genes, preferably a gene or genes from Table 1. The invention provides a method for using the patient's genotype status to determine a treatment protocol which includes a prediction of the efficacy and/or safety of a therapy.

In an another related aspect, the invention provides a method for identifying a patient for participation in a clinical trial of a therapy for the treatment of a disease inflammatory or immunologic disease or an associated inflammatory or immunopathological condition. The method involves determining the genotype or haplotype of a patient with (or at risk for) an inflammatory or immunological disease. Preferably the genotype is for a variance in a gene from Table 1. Patients with eligible genotypes are then assigned to a treatment or placebo group, preferably by a blinded randomization procedure. In preferred embodiments, the selected patients have no copies, one copy or two copies of a specificallele of a gene or genes identified in Table 1. Alternatively, patients selected for the clinical trial may have zero, one or two copies of an allele belonging to a set of alleles, where the set of alleles comprise a group of related alleles. One procedure for rigorously defining a set of alleles is by applying phylogenetic methods to the analysis of haplotypes. (See, for example: Templeton A. R., Crandall K. A. and C. F. Sing A cladistic analysis of phenotypic associations with haplotypes inferred from restriction endonuclease mapping and DNA sequence data. III. Cladogram estimation. Genetics 1992 Oct;132(2):619–33.) Regardless of the specific tools used to group alleles, the trial would then test the hypothesis that a statistically significant difference in response to a treatment can be demonstrated between two groups of patients each defined by the presence of zero, one or two alleles (or allele groups) at a gene or genes. Said response may be a desired or an undesired response. In a preferred embodiment, the treatment protocol involves a comparison of placebo vs. treatment response rates in two or more genotype-defined groups. For example a group with no copies of an allele may be compared to a group with two copies, or a group with no copies may be compared to a group consisting of those with one or two copies. In this manner different genetic models (dominant, co-dominant, recessive) for the transmission of a treatment response trait can be tested. Alternatively, statistical methods that do not posit a specific genetic model, such as contingency tables, can be used to measure the effects of an allele on treatment response.

In another preferred embodiment, patients in a clinical trial can be grouped (at the end of the trial) according to treatment response, and statistical methods can be used to compare allele (or genotype or haplotype) frequencies in two groups. For example responders can be compared to nonresponders, or patients suffering adverse events can be compared to those not experiencing such effects. Alternatively response data can be treated as a continuous variable and the ability of genotype to predict response can be measured. In a preferred embodiments patients who exhibit extreme phenotypes are compared with all other patients or with a group of patients who exhibit a divergent extreme phenotype. For example if there is a continuous or semi-continuous measure of treatment response (for example the Alzheimer's Disease Assessment Scale, the Mini-Mental State Examination or the Hamilton Depression Rating Scale) then the 10% of patients with the most favorable responses could be compared to the 10% with the least favorable, or the patients one standard deviation above the mean score could be compared to the remainder, or to those one standard deviation below the mean score. One useful way to select the threshold for defining a response is to examine the distribution of responses in a placebo group. If the upper end of the range of placebo responses is used as a lower threshold for an 'outlier response' then the outlier response group should be almost free of placebo responders. This is a useful threshold because the inclusion of placebo responders in a 'true' reponse group decreases the ability of statistical methods to detect a genetic difference between responders and nonresponders.

In an another related aspect, the invention provides a method for identifying a patient for participation in a clinical trial of a therapy for the treatment of inflammatory or immunological disease or an associated dysfunction or disorder. The method involves characterizing a patient with a disease risk and determining the patient's genotype, allele status, for an identified gene, preferably a gene from Tables 1 and 3. In preferred embodiments, the method further involves determining the patient's allele status and selecting those patients having at least one wild type allele, preferably having two wild type alleles for an identified gene, as candidates likely to develop inflammatory or immunological disease or associated pathological disease, disorder or dysfunction.

In a related aspect, the invention provides a method for developing a disease management protocol that entails diagnosing a patient with a disease or a disease susceptibility, determining the genotype of the patient at a gene or genes correlated with treatment response and then selecting an optimal treatment based on the disease and the genotype (or genotypes or haplotypes). The disease management protocol may be useful in an education program for physicians, other caregivers or pharmacists; may constitute part of a drug label; or may be useful in a marketing campaign.

By "disease mangement protocol" or "treatment protocol" is meant a means for devising a therapeutic plan for a patient using laboratory, clinical and genetic data, including the patient's diagnosis and genotype. The protocol clarifies therapeutic options and provides information about probable prognoses with different treatments. The treatment protocol may provide an estimate of the likelihood that a patient will respond positively or negatively to a therapeutic intervention. The treatment protocol may also provide guidance regarding optimal drug dose and administration and likely timing of recovery or rehabilitation. A "disease mangement protocol" or "treatment protocol" may also be formulated for asymptomatic and healthy subjects in order to forecast furniture disease risks based on laboratory, clinical and genetic variables. In this setting the protocol specifies optimal preventive or prophylactic interventions, including use of compounds, changes in diet or behavior, or other measures. The treatment protocol may include the use of a computer program.

In a preferred embodiment, the treatment protocol involves a comparison of the allele status of a patient with a control population and a responder population. This comparison allows for a statistical calculation of a patient's likelihood of responding to a therapy, e.g., a calculation of the correlation between a particular allele status and treatment response. In the context of this aspect, the term "wild-type allele" refers to an allele of a gene which produces a product having a level of activity which is most common in the general population. Two different alleles may both be wild-type alleles for this purpose if both have essentially the same level of activity (e.g., specific activity and numbers of active molecules).

In preferred embodiments of above aspects involving prediction of drug efficacy, the prediction of drug efficacy involves candidate therapeutic interventions that are known or have been identified to be metabolized in hepatic tissues. Preferably the candidate therapeutic intervention will be effective in patients with the genotype of a least one allele, and preferably two alleles from Tables 1 and 3, but have a risk to develop inflammatory or immunological disease.

In particular applications of the invention, wherein the above aspects involving a gene variance evaluation or treatment selection or patient selection or method of treatment, the method includes a determination of the genotypic allele status of the patient. Determination of the patient's allele status as being heterozygous or homozygous is predictive of the patient having a poor response to a candidate therapeutic intervention and development of inflammatory or immunological disease or similar inflammatory or immunological dysftnction. In preferred embodiments, the above methods are used for or include identification of inflammatory or immunological disease and/or the likelihood of occurrence and/or severity of such disease. In preferred embodiments, the invention is suitable for identifying a patient with inflammatory or immunological disease but with inflammatory or immunological dysfunction. The method preferably involves determination of the allele status or variance presence or absence determination for at least one gene from Tables1 and 3.

In another aspect, the invention provides a method for treating a patient at risk for an inflammatory or immunological disease or condition by a) identifying a patient with such a risk, b) determining the genotypic allele status of the patient, and c) converting the data obtained in step b) into a treatment protocol that includes a comparison of the genotypic allele status determination with the allele frequency of a control population. This comparison allows for a statistical calculation of the patient's risk for having an inflammatory or immunological disease or condition, e.g., based on correlation of the allele frequencies for a population with response or disease occurrence and/or severity. In preferred embodiments, the method provides a treatment protocol that predicts a patient being heterozygous or homozygous for an identified allele to exhibit signs and or symptoms of inflammatory or immunological disease or condition, whereas a patient who is wild-type homozygous for the said allele, as responding favorably to these therapies.

In a related aspect, the invention provides a method for treating a patient at risk for or diagnosed with an inflammatory or immunological disease or condition using the methods of the above aspect and conducting a step c) which involves determining the gene allele load status of the patient. This method further involves converting the data obtained in steps b) and c) into a treatment protocol that includes a comparison of the allele status determinations of these steps with the allele frequency of a control population. This affords a statistical calculation of the patient's risk for having inflammatory or immunological disease or inflammatory or immunological dysfunction. In a preferred embodiment, the method is useful for identifying inflammatory or immunological disase or dysfunction. In addition, in related embodiments, the methods provide a treatment protocol that predicts a patient to be at high risk for an inflammatory or immunological disease responding by exhibiting signs and symptoms of inflammatory or immunological dysfunction if the patient is determined as having a genotype or allelic difference in the identified gene or genes. Such patients are preferably given alternative therapies.

The invention also provides a method for improving the safety of candidate therapies for the identification of an inflammatory or immunological disease or dysfunction. The method includes the step of comparing the relative safety of the candidate therapeutic intervention in patients having different alleles in one or more than one of the genes listed in Tables 1 and 3. Preferably, administration of the drug is preferentially provided to those patients with an allele type associated with increased efficacy. In a preferred embodiment, the alleles of identified gene or genes used are wild-type and those associated with reduced biological activity.

As used herein, by "therapy associated with inflammatory or immunological disease" is meant any therapy resulting in dysfunction or signs and symptoms of an inflammatory or immunologic condition or dysfunction, or those associated with the pathophysiological manifestations of a clinically diagnosed inflammatory or immunologic disorder or syndrome. A suitable therapy can be a pharmacological agent or drug that may enhance or inhibit metabolic pathways identified to affect the molecular structure or function of the parent candidate therapeutic intervention thereby affecting inflammatory or immunological disease progression of any of these inflammatory or immunological dysfunctions.

By "inflammatory or immunological dysfunction" is meant a disease or syndrome in which symptomology is similar to an inflammatory or immunological disease. Specifically included are: arthritis, asthma, chronic obstructive pulmonary disease, autoimmune disease, inflammatory bowel disease, immunosuppression related to transplantation, pain associated with inflammation, psoriasis, atherosclerosis, and hepatitis.

By "drug efficacy" is meant the determination of an appropriate drug, drug dosage, administration schedule, and prediction of therapeutic utility.

By "allele load" is meant the relative ratio of identified gene alleles in the patient's chromosomal DNA.

By "identified allele" is meant a particular gene isoform that can be distinguished from other identified gene isoforms using the methods of the invention.

By "PCR, PT-PCR, or ligase chain reaction amplification" is meant subjecting a DNA sample to a Polymerase Chain Reaction step or ligase-mediated chain reaction step, or RNA to a RT-PCR step, such that, in the presence of appropriately designed primers, a nucleic acid fragment is synthesized or fails to be synthesized and thereby reveals the allele status of a patient. The nucleic acid may be further analyzed by DNA sequencing using techniques known in the art.

By "gene allele status" is meant a determination of the relative ratio of wild type identified alleles compared to an allelic variant that may encode a gene product of reduced catalytic activity. This may be accomplished by nucleic acid sequencing, RT-PCR, PCR, examination of the identified gene translated protein, a determination of the identified protein activity, or by other methods available to those skilled in the art.

By "treatment protocol" is meant a therapy plan for a patient using genetic and diagnostic data, including the patient's diagnosis and genotype. The protocol enhances therapeutic options and clarifies prognoses. The treatment protocol may include an indication of whether or not the patient is likely to respond positively to a candidate therapeutic intervention that is known to affect inflammatory or immunological function. The treatment protocol may also include an indication of appropriate drug dose, recovery time, age of disease onset, rehabilitation time, symptomology of attacks, and risk for future disease. A treatment protocol, including any of the above aspects, may also be formulated for asymptomatic and healthy subjects in order to forecast future disease risks an determine what preventive therapies should be considered or invoked in order to lessen these disease risks. The treatment protocol may include the use of a computer software program to analyze patient data.

By "patient at risk for a disease" or "patient with high risk for a disease" is meant a patient identified or diagnosed as having inflammatory or immunological disease or inflammatory or immunological dysfunction or having a genetic predisposition or risk for acquiring inflammatory or immunological disease or inflammatory or immunological dysfunction, where the predisposition or risk is higher than average for the general population or is sufficiently higher than for other individuals as to be clinically relevant. Such risk can be evaluated, for example, using the methods of the invention and techniques available to those skilled in the art.

By "converting" is meant compiling genotype determinations to predict either prognosis, drug efficacy, or suitability of the patient for participating in clinical trials of a candidate therapeutic intervention with known propensity of inflammatory or immunological disease or dysfunction. For example, the genotype may be compiled with other patient parameters such as age, sex, disease diagnosis, and known allelic frequency of a representative control population. The converting step may provide a determination of the statistical probability of the patient having a particular disease risk, drug response, or patient outcome.

By "prediction of patient outcome" is meant a forecast of the patient's likely health status. This may include a prediction of the patient's response to therapy, rehabilitation time, recovery time, cure rate, rate of disease progression, predisposition for future disease, or risk of having relapse.

By "therapy for the treatment of a disease" is meant any pharmacological agent or drug with the property of healing, curing, or ameliorating any symptom or disease mechanism associated with inflammatory or immunological disease or inflammatory or immunological conditions, or dysfunction.

By "responder population" is meant a patient or patients that respond favorably to a given therapy.

In another aspect, the invention provides a kit containing at least one probe or at least one primer (or other amplification oligonucleotide) or both (e.g., as described above) corresponding to a gene or genes listed in Tables1 and 3 or other gene related to an immunological or inflammatory disease or condition. The kit is preferably adapted and configured to be suitable for identification of the presence or absence of a particular variance or variances, which can include or comprise a nucleic acid sequence corresponding to a portion of a gene. A plurality of variances may comprise a haplotype of haplotypes. The kit may also contain a plurality of either or both of such probes and/or primers, e.g., 2, 3, 4, 5, 6, or more of such probes and/or primers. Preferably the plurality of probes and/or primers are adapted to provide detection of a plurality of different sequence variances in a gene or plurality of genes, e.g., in 2, 3, 4, 5, or more genes or to amplify and/or sequence a nucleic acid sequence including at least one variance site in a gene or genes. Preferably one or more of the variance or variances to be detected are correlated with variability in a treatment response or tolerance, and are preferably indicative of an effective response to a treatment. In preferred embodiments, the kit contains components (e.g., probes and/or primers) adapted or useful for detection of a plurality of variances (which may be in one or more genes) indicative of the effectiveness of at least one treatment, preferably a plurality of different treatments for a particular disease or condition. It may also be desirable to provide a kit containing components adapted or useful to allow detection of a plurality of variances indicative of the effectiveness of a treatment or treatment against a plurality of diseases. The kit may also optionally contain other components, preferably other components adapted for identifying the presence of a particular variance or variances. Such additional components can, for example, independently include a buffer or buffers, e.g., amplification buffers and hybridization buffers, which may be in liquid or dry form, a DNA polymerase, e.g., a polymerase suitable for carrying out PCR (e.g., a thermostable DNA polymerase), and deoxy nucleotide triphosphates (dNTPs). Preferably a probe includes a detectable label, e.g., a fluorescent label, enzyme label, light scattering label, or other label. Preferably the kit includes a nucleic acid or polypeptide array on a solid phase substrate. The array may, for example, include a plurality of different antibodies, and/or a plurality of different nucleic acid sequences. Sites in the array can allow capture and/or detection of nucleic acid sequences or gene products corresponding to different variances in one or more different genes. Preferably the array is arranged to provide variance detection for a plurality of variances in one or more genes which correlate with the effectiveness of one or more treatments of one or more diseases, which is preferably a variance as described herein.

The kit may also optionally contain instructions for use, which can include a listing of the variances correlating with a particular treatment or treatments for a disease or diseases and/or a statement or listing of the diseases for which a particular variance or variances correlates with a treatment efficacy and/or safety.

Preferably the kit components are selected to allow detection of a variance described herein, and/or detection of a variance indicative of a treatment, e.g., administration of a drug, pointed out herein.

Additional configurations for kits of this invention will be apparent to those skilled in the art.

The invention also includes the use of such a kit to determine the genotype(s) of one or more individuals with respect to one or more variance sites in one or more genes identified herein. Such use can include providing a result or report indicating the presence and/or absence of one or more variant forms or a gene or genes which are indicative of the effectiveness of a treatment or treatments.

In another aspect, the invention provides a method for determining whether there is a genetic component to intersubject variation in a surrogate treatment response. The method involves administering the treatment to a group of related (preferably normal) subjects and a group of unrelated (preferably normal) subjects, measuring a surrogate pharmacodynamic or pharmacokinetic drug response variable in the subjects, performing a statistical test measuring the variation in response in the group of related subjects and, separately in the group of unrelated subjects, comparing the magnitude or pattern of variation in response or both between the groups to determine if the responses of the groups are different, using a predetermined statistical measure of difference. A difference in response between the groups is indicative that there is a genetic component to intersubject variation in the surrogate treatment response.

In preferred embodiments, the size of the related and unrelated groups is set in order to achieve a predetermined degree of statistical power.

In another aspect, the invention provides a method for evaluating the combined contribution of two or more variances to a surrogate drug response phenotype in subjects (preferably normal subjects) by a. genotyping a set of unrelated subjects participating in a clinical trial or study, e.g., a Phase I trial, of a compound. The genotyping is for two or more variances (which can be a haplotype), thereby identifying subjects with specific genotypes, where the two or more specific genotypes define two or more genotype-defined groups. A drug is administered to subjects with two or more of said specific genotypes, and a surrogate pharmacodynamic or pharmacokinetic drug response variable is measured in the subjects. A statistical test or tests is performed to measure response in the groups separately, where the statistical tests provide a measurement of variation in response with each group. The magnitude or pattern of variation in response or both is compared between the groups to determine if the groups are different using a predetermined statistical measure of difference.

In preferred embodiments, the specific genotypes are homozygous genotypes for two variances. In preferred embodiments, the comparison is between groups of subjects differing in three or more variances, e.g., 3, 4, 5, 6, or even more variances.

In another aspect, the invention provides a method for providing contract research services to clients (preferably in the pharmaceutical and biotechnology industries), by enrolling subjects (e.g., normal and/or patient subjects) in a clinical drug trial or study unit (preferably a Phase I drug trial or study unit) for the purpose of genotyping the subjects in order to assess the contribution of genetic variation to variation in drug response, genotyping the subjects to determine the status of one or more variances in the subjects, administering a compound to the subjects and measuring a surrogate drug response variable, comparing responses between two or more genotype-defined groups of subjects to determine whether there is a genetic component to the interperson variability in response to said compound; and reporting the results of the Phase I drug trial to a contracting entity. Clearly, intermediate results, e.g., response data and/or statistical analysis of response or variation in reponse can also be reported.

In preferred embodiments, at least some of the subjects have disclosed that they are related to each other and the genetic analysis includes comparison of groups of related individuals. To encourage participation of sufficient numbers of related individuals, it can be advantageous to offer or provide compensation to one or more of the related individuals based on the number of subjects related to them who participate in the clinical trial, or on whether at least a minimum number of related subjects participate, e.g., at least 3, 5, 10, 20, or more.

In a related aspect, the invention provides a method for recruiting a clinical trial population for studies of the influence of genetic variation on drug response, by soliciting subjects to participate in the clinical trial, obtaining consent of each of a set of subjects for participation in the clinical trial, obtaining additional related subjects for participation in the clinical trial by compensating one or more of the related subjects for participation of their related subjects at a level based on the number of related subjects participating or based on participation of at least a minimum specified number of related subjects, e.g., at minimum levels as specified in the preceding aspect.

In the various aspects of this invention, a gene is a gene as identified in Tables 1 or 3, or is a gene in a pathway as identified in Table 1, preferably a gene having a function as identified in Table 1. Some such additional genes, and exemplary variances are provided in a parent application.

In the various aspects of this invention, the drug is preferably a drug as identified in a drug table herein, or is a drug in the same chemical class.

By "pathway" or "gene pathway" is meant the goup of biologically relevant genes involved in a pharmacodynamic or pharmacokinetic mechanism of drug, agent, or candidate therapeutic intervention. These mechanisms may further include any physiologic effect the drug or candidate therapeutic intervention renders. Included in this are "biochemical pathways" which is used in its usual sense to refer to a series of related biochemical processes (and the corresponding genes and gene products) involved in carrying out a reaction or series of reactions. Generally in a cell, a pathway performs a significant process in the cell.

By "pharmacological activity" used herein is meant a biochemical or physiological effect of drugs, compounds, agents, or candidate therapeutic interventions upon administration and the mechanism of action of that effect.

The pharmacological activity is then determined by interactions of drugs, compounds, agents, or candidate therapeutic interventions, or their mechanism of action, on their target proteins or macromolecular components. By "agonist" or "mimetic" or "activators" is meant a drug, agent, or compound that activate physiologic components and mimic the effects of endogenous regulatory compounds. By "antagonists", "blockers" or "inhibitors" is meant drugs, agents, or compounds that bind to physiologic components and do not mimic endogenous regulatory compounds, or interfere with the action of endogenous regulatory compounds at physiologic components. These inhibitory compounds do not have intrinsic regulatory activity, but prevent the action of agonists. By "partial agonist" or "partial antagonist" is meant an agonist or antagonist, respectively, with limited or partial activity. By "negative agonist" or "inverse antagonists" is meant that a drug, compound, or agent that can interact with a physiologic target protein or macromolecular component and stabilizes the protein or component such that agonist-dependent conformational changes of the component do not occur and agonist mediated mechanism of physiological action is prevented. By "modulators" or "factors" is meant a drug, agent, or compound that interacts with a target protein or macromolecular component and modifies the physiological effect of an agonist.

As used herein the term "chemical class" refers to a group of compounds that share a common chemical scaffold but which differ in respect to the substituent groups linked to the scaffold. Examples of chemical classes of drugs include, for example, phenothiazines, piperidines, benzodiazepines and aminoglycosides. Members of the phenothiazine class include, for example, compounds such as chlorpromazine hydrochoride, mesoridazine besylate, thioridazine hydrochloride, acetophenazine maleate trifluoperazine hydrochloride and others, all of which share a phenothiazine backbone. Members of the piperidine class include, for example, compounds such as meperidine, diphenoxylate and loperamide, as well as phenylpiperidines such as fentanyl, sufentanil and alfentanil, all of which share the piperidine backbone. Chemical classes and their members are recognized by those skilled in the art of medicinal chemistry.

As used herein the term "surrogate marker" refers to a biological or clinical parameter that is measured in place of the biologically definitive or clinically most meaningful parameter. In comparison to definitive markers, surrogate markers are generally either more convenient, less expensive, provide earlier information or provide pharmacological or physiological information not directly obtainable with definitive markers. Examples of surrogate biological parameters: (i) testing erythrocye membrane acetylcholinesterase levels in subjects treated with an acetylcholinesterase inhibitor intended for use in Alzheimer's disease patients (where inhibition of brain acetylcholinesterase would be the definitive biological parameter); (ii) measuring levels of CD4 positive lymphocytes as a surrogate marker for response to a treatment for aquired immune deficiency syndrome (AIDS). Examples of surrogate clinical parameters: (i) performing a psychometric test on normal subjects treated for a short period of time with a candidate Alzheimer's compound in order to determine if there is a measurable effect on cognitive function. The definitive clinical test would entail measurring cognitive function in a clinical trial in Alzheimer's disease patients. (ii) Measuring blood pressure as a surrogate marker for myocardial infarction. The measurement of a surrogate marker or parameter may be an endpoint in a clinical study or clinical trial, hence "surrogate endpoint".

As used herein the term "related" when used with respect to human subjects indicates that the subjects are known to share a common line of descent; that is, the subjects have a known ancestor in common. Examples of preferred related subjects include sibs (brothers and sisters), parents, grandparents, children, grandchildren, aunts, uncles, cousins, second cousins and third cousins. Subjects less closely related than third cousins are not sufficiently related to be useful as "related" subjects for the methods of this invention, even if they share a known ancestor, unless some related individuals that lie between the distantly related subjects are also included. Thus, for a group of related indivuals, each subject shares a known ancestor within three generations or less with at least one other subject in the group, and preferably with all other subjects in the group or has at least that degree of consanguinity due to multiple known common ancestors. More preferably, subjects share a common ancestor within two generations or less, or otherwise have equivalent level of consanguinity. Conversely, as used herein the term "unrelated", when used in respect to human subjects, refers to subjects who do not share a known ancestor within 3 generations or less, or otherwise have known relatedness at that degree.

As used herein the term "pedigree" refers to a group of related individuals, usually comprising at least two generations, such as parents and their children, but often comprising three generations (that is, including grandparents or grandchildren as well). The relation between all the subjects in the pedigree is known and can be represented in a genealogical chart.

As used herein the term "hybridization", when used with respect to DNA fragments or polynucleotides encompasses methods including both natural polynucleotides, non-natural polynucleotides or a combination of both. Natural polynucleotides are those that are polymers of the four natural deoxynucleotides (deoxyadenosine triphosphate [dA], deoxycytosine triphosphate [dC], deoxyguanine triphosphate [dG] or deoxythymidine triphosphate [dT], usually designated simply thymidine triphosphate [T]) or polymers of the four natural ribonucleotides (adenosine triphosphate [A], cytosine triphosphate [C], guanine triphosphate [G] or uridine triphosphate [U]). Non-natural polynucleotides are made up in part or entirely of nucleotides that are not natural nucleotides; that is, they have one or more modifications. Also included among non-natural polynucleotides are molecules related to nucleic acids, such as peptide nucleic acid [PNA]). Non-natural polynucleotides may be polymers of non-natural nucleotides, polymers of natural and non-natural nucleotides (in which there is at least one non-natural nucleotide), or otherwise modified polynucleotides. Non-natural polynucleotides may be useful because their hybridization properties differ from those of natural polynucleotides. As used herein the term "complementary", when used in respect to DNA fragments, refers to the base pairing rules established by Watson and Crick: A pairs with T or U; G pairs with C. Complementary DNA fragments have sequences that, when aligned in antiparallel orientation, conform to the Watson-Crick base pairing rules at all positions or at all positions except one. As used herein, complementary DNA fragments may be natural polynucleotides, non-natural polynucleotides, or a mixture of natural and non-natural polynucleotides.

As used herein "amplify" when used with respect to DNA refers to a family of methods for increasing the number of copies of a starting DNA fragment. Amplification of DNA is often performed to simplify subsequent determination of DNA sequence, including genotyping or haplotyping. Amplification methods include the polymerase chain reaction (PCR), the ligase chain reaction (LCR) and methods using Q beta replicase, as well as transcription-based amplification systems such as the isothermal amplification procedure known as self-sustained sequence replication (3SR, developed by T. R. Gingeras and colleagues), strand displacement amplification (SDA, developed by G. T. Walker and colleagues) and the rolling circle amplification method (developed by P. Lizardi and D. Ward).

As used herein "contract research services for a client" refers to a business arrangement wherein a client entity pays for services comprising in part or in whole of work performed using the methods described herein. The client entity may include a commercial or non-profit organization whose primary business is in the pharmaceutical, biotechnology, diagnostics, medical device or contract research organization (CRO) sector, or any combination of those sectors. Services provided to such a client may include any of the methods described herein, particularly including clinical trial services, and especially the services described in the Detailed Description relating to a Pharmacogenetic Phase I Unit. Such services are intended to allow the earliest possible assessment of the contribution of a variance or variances or haplotypes, from one or more genes, to variation in a surrogate marker in humans. The surrogate marker is generally selected to provide information on a biological or clinical response, as defined above.

As used herein, "comparing the magnitude or pattern of variation in response" between two or more groups refers to the use of a statistical procedure or procedures to measure the difference between two different distributions. For example, consider two genotype-defined groups, AA and aa, each homozygous for a different variance or haplotype in a gene believed likely to affect response to a drug. The subjects in each group are subjected to treatment with the drug and a treatment response is measured in each subject (for example a surrogate treatment response). One can then construct two distributions: the distribution of responses in the AA group and the distribution of responses in the aa group. These distributions may be compared in many ways, and the significance of any difference qualified as to its significance (often expressed as a p value), using methods known to those skilled in the art. For example, one can compare the means, medians or modes of the two distributions, or one can compare the variance or standard deviations of the two distributions. Or, if the form of the distributions is not known, one can use nonparametric statistical tests to test whether the distributions are different, and whether the difference is significant at a specified level (for example, the $p<0.05$ level, meaning that, by chance, the distributions would differ to the degree measured less than one in 20 similar experiments). The types of comparisons described are similar to the analysis of heritability in quantitative genetics, and would draw on standard methods from quantitative genetics to measure heritability by comparing data from related subjects.

Another type of comparison that can be usefully made is between related and unrelated groups of subjects. That is, the comparison of two or more distributions is of particular interest when one distribution is drawn from a population of related subjects and the other distribution is drawn from a group of unrelated subjects, both subjected to the same treatment. (The related subjects may comprise small groups of related subjects, each compared only to their relatives.) A comparison of the distribution of a drug response variable (e.g. a surrogate marker) between two such groups may provide information on whether the drug response variable is under genetic control. For example, a narrow distribution in the group(s) of related subjects (compared to the unrelated subjects) would tend to indicate that the measured variable is under genetic control (i.e. the related subjects, on account of their genetic homogeneity, are more similar than the unrelated individuals). The degree to which the distribution was narrower in the related individuals (compared to the unrelated individuals) would be proportionate to the degree of genetic control. The narrowness of the distribution could be quantified by, for example, computing variance or standard deviation. In other cases the shape of the distribution may not be known and nonparametric tests may be preferable. Nonparametric tests include methods for comparing medians such as the sign test, the slippage test, or the rank correlation coefficient (the nonparametric equivalent of the ordinary correlation coefficient). Pearson's Chi square test for comparing an observed set of frequencies with an expected set of frequencies can also be useful.

The present invention provides a number of advantages. For example, the methods described herein allow for use of a determination of a patient's genotype for the timely administration of the most suitable therapy for that particular patient. The methods of this invention provide a basis for successfully developing and obtaining regulatory approval for a compound even though efficacy or safety of the compound in an unstratified population is not adequate to justify approval. From the point of view of a pharmaceutical or biotechnology company, the information obtained in pharmacogenetic studies of the type described herein could be the basis of a marketing campaign for a drug. For example, a marketing campaign that emphasized the superior efficacy or safety of a compound in a genotype or haplotype restricted patient population, compared to a similar or competing compound used in an undifferentiated population of all patients with the disease. In this respect a marketing campaign could promote the use of a compound in a genetically defined subpopulation, even though the compound was not intrinsically superior to competing compounds when used in the undifferentiated population with the target disease. In fact even a compound with an inferior profile of action in the undifferentiated disease population could become superior when coupled with the appropriate pharmacogenetic test.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Other features and advantages of the invention will be apparent from the following description of the preferred embodiments thereof, and from the claims.

DETAILED DESCRIPTION OF THE INVENTION

The tables are first briefly described.

Table 1, the Inflammation and Immunology Gene Table, lists genes that may be involved in pharmacological response to inflammation or immunologic therapeutics, or that may define disease subsets with different prognosis and consequent implications for treatment. The table has seven columns. Column 1, headed "Class" provides broad groupings of genes relevant to the pharmacology of antiinflammation drugs or drugs affecting the immune system. Column 2, headed "Pathway", provides a more detailed categorization of the different classes of genes by indicating the overall purpose of large groups of genes. These pathways contain genes implicated in the etiology or treatment response of the various diseases detailed in Table 2. Column 3, headed "Function", further categorizes the pathways listed in column 2. Some categories in column 2 are not further categorized in column 3.

Column 4, headed "Name", lists the genes belonging to the class, pathway and function shown to the left (in columns 1–3). The gene names given are generally those used in the OMIM database or in GenBank, however one skilled in the art will recognize that many genes have more than one name, and that it is a straightforward task to identify synonymous names. For example, many alternate gene names are provided in the OMIM record for a gene.

In column 5, headed "OMIM", the Online Mendelian Inheritance in Man (OMIM) record number is listed for each gene in column 4. This record number can be entered next to the words: "Enter one or more search keywords:" at the OMIM world wide web site. The url is: http://www3.ncbi.nlm.nih.gov/Omim/searchomim.html. An OMIM record exists for most characterized human genes. The record often has useful information on the chromosome location, function, alleles, and human diseases or disorders associated with each gene.

Column 6, headed "GID", provides the GenBank identification number (hence GID) of a genomic, cDNA, or partial sequence of the gene named in column 4. Usually the GID provides the record of a cDNA sequence. Many genes have multiple Genbank accession numbers, representing different versions of a sequence obtained by different research groups, or corrected or updated versions of a sequence. As with the gene name, one skilled in the art will recognize that alternative GenBank records related to the named record can be obtained easily. All other GenBank records listing sequences that are alternate versions of the sequences named in the table are equally suitable for the inventions described in this application. (One straightforward way to obtain additional GenBank records for a gene is on the internet. General instructions can be found at the NCBI web site at: http://www3.ncbi.nlm.nih.gov. More specifically, the GenBank record number in column 6 can be entered at the url: http://www3.ncbi.nlm.nih.gov/Entrez/nucleotide.html.

Once the GenBank record has been retrieved one can click on the "nucleotide neighbors" link and additional GenBank records from the same gene will be listed.

Column 7, headed "locus", provides the chromosome location of the gene listed on the same row. The chromosome location helps confirm the identity of the named gene if there is any ambiguity.

Table 2 is a matrix showing the intersection of genes and therapeutic indications—that is, which categories of genes are most likely to account for interpatient variation in reponse to treatments for which diseases. The Table is displayed on two pages. On each page the first two columns provide a framework for organizing the genes listed in Table 1. Column 1 is similar to the 'Class' column in Table 1, while column 2 is a combination of the 'Pathway' and 'Function' columns in Table 1. It is intended that the summary terms listed in columns 1 and 2 be read as referring to all the genes in the corresponding sections of Table 1. The remaining columns in Table 2 list ten inflammatory or immunologic diseases. The information in the Table lies in the shaded boxes at the intersection of various 'Pathways" (the rows) and treatment indications (the 13 columns) An intersection box is shaded when a a row corresponding to a particular pathway (and by extension all the genes listed in that pathway in Table 1) intersects a column for a specific inflammatory disease or immune disorders such that the pathway and genes are of possible use in explaining interpatient differences in response to treatments for the inflammation or immunologic indication. Thus, the Table enables one skilled in the art to identify therapeutically relevant genes in patients with one of the 13 indications for the purposes of stratification of these patients based upon genotype and subsequent correlation of genotype with drug response. The shaded intersections indicate preferred sets of genes for understanding the basis of interpatient variation in response to therapy of the indicated disease indication, and in that respect are exemplary. Any of the genes in the table may account for interpatient variation in response to treatments for any of the diseases listed. Thus, the shaded boxes indicate the gene pathways that one skilled in the art would first investigate in trying to understand interpatient variation in response to therapy for the listed indications.

Table 3 is a partial list of DNA sequence variances in genes relevant to the methods described in the present invention. These variances were identified by the inventors in studies of selected genes listed in Table 1, and are provided here as useful for the methods of the present invention. The variances in Table 3 were discovered by one or more of the methods described below in the Detailed Description or Examples. Table 3 has eight columns. Column 1, the "Name" column, contains the Human Genome Organization (HUGO) identifier for the gene. Column 2, the "GID" column provides the GenBank accession number of a genomic, cDNA, or partial sequence of a particular gene. Column 3, the "OMIM_ID" column contains the record number corresponding to the Online Mendelian Inheritance in Man database for the gene provided in columns 1 and 2. This record number can be entered at the world wide web site http://www3.ncbi.nlm.nih.gov/Omim/searchomim.html to search the OMIM record on the gene. Column 4, the VGX_Symbol column, provides an internal identifier for the gene. Column 5, the "Description" column provides a descriptive name for the gene, when available. Column 6, the "Variance_Start" column provides the nucleotide location of a variance with respect to the first listed nucleotide in the GenBank accession number provided in column 2. That is, the first nucleotide of the GenBank accession is counted as nucleotide 1 and the variant nucleotide is numbered accordingly. Column 7, the "variance" column provides the nucleotide location of a variance with respect to an ATG codon believed to be the authentic ATG start codon of the gene, where the A of ATG is numbered as one (1) and the immediately preceding nucleotide is numbered as minus one (−1). This reading frame is important because it allows the potential consequence of the variant nucleotide to be interpreted in the context of the gene anatomy (5' untranslated region, protein coding sequence, 3' untranslated region). Column 7 also provides the identity of the two variant nucleotides at the indicated position. For example, in the first entry in Table 3, AB000221, the variance is 364C>T, indicating the presence of a T or a C at nucleotide 427 of GenBank sequence AB000221. Column 8, the "CDS_ Context" column indicates whether the variance is in a coding region but silent (S); in a coding region and results in an amino acid change (e.g., R347C, where the letters are one letter amino acid abbreviations and the number is the amino acid residue in the encoded amino acid sequence which is changed); in a sequence 5' to the coding region (5); or in a sequence 3' to the coding region (3). As indicated above, interpreting the location of the variance in the gene depends on the correct assignment of the initial ATG of the encoded protein (the translation start site). It should be recognized that assignment of the correct ATG may occasionally be incorrect in GenBank, but that one skilled in the art will know how to carry out experiments to definitively identify the correct translation initiation codon (which is not always an ATG). In the event of any potential question concerning the proper identification of a gene or part of a gene, due for example, to an error in recording an identifier or the absence of one or more of the identifiers, the priority for use to resolve the ambiguity is GenBank accession number, OMIM identification number, HUGO identifier, common name identifier.

Tables 5–13, 16, 17, 18 provide lists of exemplary compounds in clinical development for various inflammatory or immunologic diseases. The compounds listed in the tables are exemplary; that is, the methods of the invention will apply to other compounds as well. Each table has four columns. The first column is titled "Product Name", the second column is titled "Chemical Name", the third "Action" and the fourth "Indication". Under these headings are listed rows of compounds. For each compound there is a brief summary of information about the product name, its pharmacological action and potential clinical uses. The first column, "Product Name", provides the generic name and/or alphanumeric designation of the compound, as well as its trade name in some cases (in capital letters). The second column, "Chemical Name" provides the full chemical name of the compound. The listed compounds, or compounds chemically related to those listed (e.g. by modification of one or more chemical moieties of the listed compounds), are suitable for the methods of this invention. The third column, "Action", summarizes in a word or phrase an important pharmacological action of the compound, or what is currently believed to be an important pharmacological action— in most cases additional pharmacological actions are known but not listed to conserve space; alternatively, subsequent studies may reveal additional or alternative pharmacological actions. (Sources listed in the detailed description will help clarify whether additional pharmacological actions have been discovered.) The fourth column, "Indication", provides an exemplary disease or condition for which the compound is currently being, or has already been, developed. In many cases the compound is being, has already been, or will likely be developed for other indications. Again, one skilled in the art will know how to identify additional drug development programs for these compounds. For example, a compound in development for one inflammatory disease is likely to be evaluated in the treatment of other inflammatory diseases.

DETAILED DESCRIPTION OF THE PREFERRED EMBODIMENTS

I. Inflammatory or Immunological Disease, Disorders, or Dysfunctions

Inflammatory or immunological diseases and clinical symptoms include diseases and processes such as: arthritis (including rheumatoid arthritis, osteoarthritis, and other degenerative syndromes of the joints), asthma, chronic obstructive pulmonary disease (including bronchitis, bronchiectasis, emphysema and other pulmonary diseases associated with obstruction to air flow), interstitial or restrictive lung diseases, autoimmune disease (including systemic lupus erythematosus, scleroderma and other diseases characterized by autoantibodies), transplantation (often treated with long term immunosuppressive therapy), pain associated with inflammation, psoriasis and other inflammatory skin diseases, atherosclerosis (for which there is strong data supporting the role of inflammatory pathogenetic mechanisms), and hepatitis, among other diseases. One skilled in the art will recognize that there may be overlap between some of the conditions listed.

Challenges in treating diseases with a significant inflammatory or immunological component include: (i) limited understanding of the pathophysiologic basis of these diseases and conditions, (ii) a complex mix of immune/ inflammatory mediators operating simultaneously, with the primary (initiating) events often unclear and the relative importance of different mediators unknown, and (iii) medical interventions that rarely produce specifical effects or address the underlying pathophysiologic basis of the disease or condition. Thus, medical management of inflammatory or immunologic disorders is empirical in nature. This is associated with multiple undesirable side effects, and thus, disease progression is common. Based upon these clinical realities and the difficulties drug developers face in developing new treatments for diseases with an inflammatory or immunologic component, the use of genotype based stratification to identify populations enriched for responders, nonresponders, and/or those likely to develop undesirable side effects will provide clear commercial and medical benefits. Ultimately, medical practitioners and patients will also benefit from greater choices of medicines with superior safety and efficacy characterisitcs when used in conjunction with genetic diagnostic tests.

Inflammation is a complex process that comprises different cellular and physiologic events that can be initiated by tissue injury, by abnormal immune function. They can also be initiated by a wide variety of other endogenous or exogenous factors, not all of which are understood. The inflammatory process can also escape normal regulatory control and become part of the disease process.

Autoimmunity is one aspect of some diseases associated with abnormal immunologic function. Such diseases are characterized by the presence of autoantibodies and oligoclonal B cell populations. Immunological reactions associated with loss of self tolerance may be localized to a specific tissue or may be systemic. Ultimaltely, in severe cases, the immune system produces life threatening damage to tissues and result in compromised physiological functions. Autoimmunity can be initiated by a variety of endogenous (genetic predisposition and others) and exogenous (chemicals, drugs, microorganisms, and others) factors.

Exemplary diseases characterized by abnormal inflammatory or immunologic responses (also referred to herein as inflammatory or immune diseases or disorders) are described below. These diseases are suitable for application of methods described in this invention for identification of variances in a gene or genes involved in therapeutic response, e.g. efficacy, tolerability or toxicity.

A. Arthritis

Description of Arthritis

Arthritis comprises a variety of diseases characterized by pain, swelling, and limited movement in joints and connective tissues. Arthritis is usually chronic and there are three prevalent forms of the disease: rheumatoid arthritis (RA), osteoarthritis (OA), and fibromyalgia. In RA, the synovial joint lining becomes inflamed as a result of hyperactive immune response. There are an estimated 2.1 million Americans with RA, two thirds being women. In OA, the cartilage that covers the ends of the bones within joints deteriorates and causing pain and loss of movement as bone begins to rub against bone. There are an estimated 20.7 million Americans with OA, the majority being over the age of 45. In fibromyalgia, widespread pain affects muscles, attachments of muscles to bone, and the connective tissues, i.e., the ligaments and tendons. There are an estimated 3.7 million individuals diagnosed with fibromyalgia syndrome. Other serious and common forms of arthritis or related disorders include, among others, gout, systemic lupus erythmatosus, scleroderma, ankylosing spondylitis, and juvenile arthritis.

Rheumatoid arthritis involves the disarthroidal joints and can affect a variety of other organs. The clinical hallmarks of RA include: morning stiffness; swelling of three or more joints; swelling of hand joints (proximal interphalangeal, metacarpophalangeal, or wrist); symmetric swelling; subcutaneous nodules; serum rheumatoid factor; and erosions and or periarticular osteopenia in hand or wrist joints as often observed on radiograph.

Osteoarthritis is a degenerative process in joint tissues that may occur in response to aging, genetic, or environmental factors. Its symptoms include progressive degeneration of cartilage, bone remodeling, and overgrowth of bone. Clinical hallmarks of OA include deep aching pain in the afflicted joints (hands, knees spine, and hips), morning stiffness of short duration, variable joint thickening, and effusion. Pathologically OA is characterized by breakdown of cartilage. Destruction of joint cartilage involves direct physical injury, enzymatic degradation as a result of the injury to chondrocytes, and subchondral bone stiffening as a result of the bone remodeling.

Current Therapies for Arthritis

Agents used to treat RA fall into one of the following four categories: analgesics (NSAIDs, salicylates), disease modifying antirheumatic agents (gold compounds, cytotoxic), hormones (glucocorticoids), and skin and mucosal membrane preparations. Therapies for the treatment of OA focus on decreasing pain (analgesics) and physical therapies to increase joint mobility.

Analgesics: Typically, pain associated with arthritis can be controlled with NSAIDs including but not excluded to, salicylates, para-aminophenol derivatives, indole and indene derivatives, heteroaryl acetic acids, arylproprionic acids, anthranilic acids, enolic acids, or alkanones. Antiinflammatory agents such as cyclooxygenase inhibitors, and lipoxygenase inhibitors, among others, can be used to block the inflammation physiological pathways which mediate pain and progression of the disease. However, because these drugs are limited in their efficacy in advanced or more severe stages of arthritis, these agents are usually add-on therapies.

NSAIDs principally act by inhibiting prostaglandin and leukotriene synthesis. These compounds inhibit key enzymes in the biosynthetic pathway, i.e. cyclooxygenase. There are drugs that selectively inhibit isoforms of cyclooxygenase 1 and 2 (COX-1, COX-2). These drugs enhance patient tolerance due to the prevalence of COX-2 induction occuring in inflammation mediated by cytokines and others.

Further, pyrimidine synthesis inhibitors can be used as an antiinflammatory agent in arthritis, e.g. leflunomide.

Disease-Modifying Antirheumatic Drugs or agents: Agents involved in the modification of clinical disease manifestation, reduction in inflammation, or slowing the disease progression are referred to as disease-modifying antirheumatic drugs (DMARDs). They include gold salts (aurothioglucose, aurothiomalate, auranofin), hypotensives (angiotension converting enzyme inhibitors), anaprox, immunosuppressives (azathioprine, cyclosporine), agents to treat metallic poison (penicillamine), depen, naprosen, immuran, antimalarials (chloroquine, hydroxychloroquine), alkylating agents (cyclophosphamide), absorbable sulfonamides (sulfasalazine), irritants and counter-irritants (capsaicin), antimicrobial agents (tetracyclines), and antimetabolites (methotrexate).

Hormones and Growth Factors: Agents acting at hormone receptors or growth factor receptors include steroids (glucocorticoids), adrenocorticotrophic hormone (corticotropin), and tumor necrosis factor inhibitors (soluble TNF receptors (enbrel) and TNF monoclonal antibody (remicade). The autoimmunity component of the disease is driven primarily by activated T-cells and give rise to cytokines IL-1 and TNF at the rheumatoid synovium. These agents are known to interfere with the actions of these cytokines.

Corticosteroids affect the inflammation within the joints by: decreasing growth and development of mast cells, inducing apoptosis, suppressing lymphocyte generation of IL-5 and other cytokines, inhibiting some mediator release, inhibiting cytokine production, inhibiting the transcription of cytokines (for example IL-8, TNF-α, prototypic antiviral chemokine (regulated-on-activation normal T-expressed and secreted, RANTES), and GM-CSF), and inhibiting nitric oxide synthesis.

Skin and mucosal membrane preparations: Irritants and counter-irritants can be used to treat arthritic joints, such as but not limited to, Capaicin Chlorambucil, cyclosporine, cyclophosphamide are agents that are available for use in the treatment of refractory RA or with severe extraarticular complications such as vasiculitits, comeal perforation or other severe systemic maladies associated with RA.

Limitations of Current Therapies for Arthritis

Low Efficacy Limitations of Therapies for Arthritis

The therapies discussed above are limited to the slowing or retarding the progression of arthritis. As joint degeneration progresses and result in irreversible damage, options become limited. Thus, therapies for arthritis are aimed at reducing manifestation of symptoms by controlling the clinical manifestations of inflammation.

Reduction in clinical symptoms of arthritis following DMARDs therapy is only evident after several weeks to months of therapy. Slow clinical relevance of these therapies limits determination of optimal therapy for individuals with arthritis and makes it diffcult to select optimal therapy for any given stage of the disease.

Toxicity or Undesired Side Effects as Therapeutic Limitations of Arthritis

Toxicity and undesired side effects associated with above current therapies for arthritis require monitoring. Drugs used to treat arthritis may cause death, disability, disease, and pose risks to an unborn child. The undesired side effects or toxicities are listed for each drug category as described above.

Analgesics associated side effects include dyspepsia, gastric or small bowel bleeding, ulceration, renal insufficiency, confusion, rash, headache, hepatic toxicity. NSAIDs also reversibly inhibit platelet aggregation and prolong bleeding time.

Antirheumatic agents (DMARDs) associated side effects include: antimalarials—retinal or macular damage; sulfonamides—hematologic toxicities (leukopenia, thrombocytopenia, hemolysis in patients with glucose 6-phosphate dehydrogenase (G6PD) deficiency); antimetabolites—hepatic compromise including hepatic fibrosis, ascites, esophageal varices, cirrhosis, pneumonitis, myelosuppression; immunosuppressives—myelosuppression, (cyclosporine: renal insufficiency anemia, hypertension); agents to treat metallic poison—rash, stomatitis, dysgeusia or metallic taste, myelosuppression (thrombocytopenia), proteinuria, nephrotic syndrome or renal failure, and induction of autoimmune syndromes (systemic lupus erythmatosus, myesthenia gravis, polymyocytis, Goodpasture's syndrome), gold preparations: hematologic, renal, pulmonary, and proteinuria; and chlorambucil—myelosuppression, myeloproliferative disorders, malignancy, and hemorrhagic cystitis.

Soluble TNF receptors agents have been shown to induce sepsis and predispose patients to serious infections. Further this product was associated with site of injection reactions, infections, and headache.

Glucocorticoid associated side effects include increased appetite, weight gain, fluid retention, acne, ecchymosis, development of cushoid facies, hypertension, hyperkalemia, diabetes, hyperglycemia, hyperosmolar state, hyperlipidemia, hepatic steatosis, atherosclerosis, myopathy, aseptic necrosis, osteoporosis, ulcers, pancreatitis, psuedotumor cerebri, pyschosis, glaucoma, cataract formation, vascular necrosis, increased suseptibility to infection, impairment of the hypothalamus-pituitary axis, decreased thyroid hormone serum binding protiens, and impaired wound healing.

Since the majority of RA patients are women in their reproductive years, the level and extent the agents used to treat RA affects or has a potential to affect mothers during pregnancy or the developing fetus, either across the placenta or through beast milk. Clinical medical therapeutic decisions should weigh the use of all of the above current therapies for RA against known capacity of these agents to affect both the mother and the child.

Description of Mechanism of Action Hypotheses for Future Drug Development for Arthritis Rheumatoid arthritis has been thought to be the result of host genetic factors, immunoregulatory abnormalities and autoimmunity, and triggering or persistent microbial infection.

Host genetic factors. The HLA-DR4 antigen (HLA, human leukocyte antigen) is significantly increased in RA patients. Recent studies show that a subtype of the HLA-DR4 share similar epitope among several MHC class II molecules and predispose to RA.

Autoimmune component. In over 80% of RA patients autoantibodies to the Fc portion of IgG (rheumatoid factors, RF) are present and can be used to determine diagnosis. The higher the titer of RFs, joint disease and extrarticular manifestations are more severe.

Related to the autoimmune component of the disease, ICAM-1 inhibitors, or other agents to reduce adhesion have been developed.

Microbial Infections. Of all the examined pathogens, only the Epstein-Barr virus (EBV) has remained unproven as a cause of RA. EBV has been shown to share a similar epitope as the HLA-DR4 epitopes, but EBV is ubiquitous and has yet to be a proven cause of RA.

A gene, genes, or gene pathway involved in the etiology of arthritis or associated disorders or potential sites for targeted drug therapy of arthritis are depicted in Table 2 with the specific gene list in Table 1. Current candidate therapeutic interventions in development for the treatment of arthritis are listed in Table 5.

B. Chronic Obstructive Pulmonary Disease

Description of Chronic Obstructive Pulmonary Disease

Chronic obstructive pulmonary disease (COPD) is an imperfect term that refers to four pulmonary disorders including simple chronic bronchitis, asthmatic bronchitis, chronic obstructive bronchitis, and emphysema. A common characteristic of the disease is airway obstruction. Airways obstruction denotes the slowing of forced expiration. A decrease in the forced expiratory volume in 1 second (FEV1) to forced vital capacity (FVC) indicates that airflow is impaired. Forced expiration is determined primarily by intrinsic resistance of the airways, compressibility of the airways, and lung elastic recoil. Reduced maximal expiratory flow results from high airway resistance, reduced lung recoil, or excessive airways collapsibility. The overall cost of these illnesses to society is enormous due to the extent of the number of individuals afflicted with COPD. Approximately 15 million Americans are afflicted, and COPD is currently the fourth-leading cause of mortality. The high morbidity and mortality rates associated with COPD are linked to the failure to identify at-risk patients for intervention. Large reserves of pulmonary function in lungs and the slow progressive nature of the disease can often delay the clinical diagnosis and therapeutic intervention.

Simple chronic bronchitis is predominantly characterized by chronic productive cough and is usually the result of low-grade exposure to bronchial irritants. This syndrome is associated with enhanced mucous secretion, reduced ciliary activity, and impaired resistance to bronchial infection. Bronchitis patients range from those who experience sporadic cough producing mucous to those with a severe, disabling condition manifested by one or more of the following symptoms of increased resistance to airflow, hypoxia, hypercapnia, and irreversible narrowing of the small airways such as bronchioles and bronchi.

Repeated exposure to bronchiole irritants in individuals with hyperactive or sensitive airways can lead to bronchospasm, i.e. bronchial smooth muscle constriction, that is frequently accompanied by excess mucous production and edema of the bronchial walls. Episodic bronchospasm in individuals with chronic bronchitis is termed asthmatic bronchitis and is applied to those individuals with chronic airway constriction, chronic productive cough, and episodic bronchospasm.

Emphysema is characterized by abnormal, excessive, permanent enlargement of airway spaces distal to the terminal bronchioles, and is accompanied by destruction of their walls and may or may not be associated with fibrotic tissue. These changes result in a reduction of elastic recoil permitting excessive airway collapse upon expiration and leads to irreversible airway flow obstruction. Emphysema is strongly related to and correlated to inhalation of tobacco smoke such as cigarette or cigar smoking.

In emphysema, there is a loss of elastic recoil leading to pulmonary hyperinflation. The hyperinflation reaches a limit when the diaphragm is pushed flat and no longer functions effectively. The chest wall is expanded to the point that it pushes inward rather than exerting its normal outward force. These anatomical changes alter inspiration to the point that exertion is nearly impossible.

A deficiency in alpha 1-antitrypsin can predispose individuals to signs and symptoms of COPD. In these individuals there is a marked alveolar wall destruction with a non-uniform pattern of air space enlargement. In these patients there may be excessive formation of thick mucous and is often accompanied by persistent cough.

Complications of COPD include hypoxemia, cor pulmonale, hypercapnia, and dyspnea. Sustained chronic hypoxemia is a condition that leads to pulmonary vasoconstriction that with time becomes irreversible and leads to cor pulmonale.

Current therapies for COPD

Current therapies for treatment of COPD are aimed at: reducing the airway obstruction reversibly, controlling the persistent cough and sputum production, reducing or eliminate airway infections, increasing exercise tolerance to the maximum allowable at the individual's level of physiological deficit, controlling the remedial disease complications, i.e. cardiovascular dysfunction and arterial hypoxemia, and relieving anxiety and depression or other psychiatric symptoms that accompany patients attempts to cope with the debilitating clinical manifestations. Lastly, all treatment regimens include education and supportive therapy to encourage subjects with COPD to cease behaviors that may exacerbate symptoms such as inhalation of pulmonary irritants, i.e. smoking and others, and substance abuse, i.e. narcotics and sedatives.

Bronchodilators

Bronchodilators can be inhaled or administered by oral, subcutaneous, or intravenous routes.

Beta-adrenergic agonists or other sympathomimetic agents are used to produce rapid acute bronchodilation.

Anticholinergics agents are used to produce sustained bronchodilation. Nebulized atropine has been supplanted with the advent of a quaternary ammonium salt, ipratropium bromide, which undergoes minimal systemic absorption and thus has limited anticholinergic toxicity. Ipratropium has been shown to be effective in patients that have not responded to β-adrenergic agonists and can reduce sputum volume without altering viscosity.

Anticholinergics and beta-adrenergic agonist combinations have been used with some success. Such combinations reduce the need to administer high doses, due to additive effects, and therefore reduce the likelihood for adverse effects or toxic side effects.

Theophylline is a methylxanthine bronchodilator. Theophylline improves airway flow, decreases dyspnea, reduces pulmonary arterial pressure, increases arterial oxygen tension, improves diaphragmatic strength and endurance, increases right ventricular function (pulmonary vasodilator and cardiac inotropic effects), and may produce antiinflammatory effects.

Expectorants

Expectorants can be used to increase secretion clearance in patients with COPD. Although this therapy has not been demonstrated to render clinical benefit, it is an add-on therapy that enables the patient to experience an enhanced productive cough.

Anti-Inflammatory agents

Prolonged use of corticosteroids have been used to retard the rate of decline in FEV1 in COPD subjects. However, it has been determined that systemic corticosteroids are beneficial for acute exacerbations of COPD but are not used for long-term treatment and have not been proven to retard the progression of the disease. Corticosteroids affect the decline of FEV1 in the airways by: decreasing growth and development of mast cells, inducing apoptosis; suppressing lymphocyte generation of IL-5 and other cytokines; inhibiting some mediator release; inhibiting cytokine production; inhibiting the transcription of cytokines (for example IL-8, TNF-α, prototypic antiviral chemokine (regulated-on-activation normal T-expressed and secreted, RANTES), and GM-CSF); and inhibiting nitric oxide synthesis.

Antiproteases and antioxidants

Alpha1-protease inhibitor deficiency as a cause of early development of emphysema has increased the awareness of the role of protease-antiprotease and oxidant-antioxidant imbalances in COPD. Intravenous delivery of alpha 1-protease inhibitor can provide the appropriate levels for individuals with a genetic deficiency and individuals with acquired deficiency.

Mucolytics and secretion clearance agents can be used to assist in the removal of secretions during productive cough. These agents can thin secretions in patients with chronic bronchitis.

Supplemental oxygen therapy is used to treat deleterious effects of sustained chronic hypoxemia and hypercapnia. Correction of this condition is one of the treatments shown to have a positive effect on the survival rate in patients with COPD.

Treatment of cases of cor pulmonale includes the use of diuretics and positive inotropic agents such as digitalis. Careful monitoring is needed in these patients due to a development of marked right ventricular hypertrophy.

Dyspnea may be severely disabling despite aggressive therapy. Judicious use of opiates to control dyspnea and increase exercise tolerance have been proven beeneficial. Unfortunately, opiates can have a respiratory depressant effect and care should be taken to deliver the appropriate therapeutic dose.

Many patients with COPD find themselves anxious or depressed or both. Appropriate use of psychoactive agents can be used to control the signs and symptoms of anxiety and depression.

Surgical procedures can be performed to attempt to restore pulmonary capacity and function. Lung volume reduction surgery is useful to remove a portion of emphysematous lung tissue so that the diaphragm can return to its normal dome shape and the chest wall can reassume its normal configuration, mechanics, and physiology. Bullectomy is a procedure in which large bullae and surrounding lung tissue are removed. This allows for the remaining tissue to expand and once again function normally. Another procedure is lung transplantation. This expensive and aggressive approach is usually reserved for younger patients, particularly those who are alpha 1-antitrypsin deficient.

Limitations of Current Therapies for COPD

The most common limitations for the use of bronchodilators is the mistaken use of inhalants and inadequate patient education.

Beta adrenergic therapy is limited by three factors: 1) the density of β2 receptors in the airways decreases with age, 2) despite the selectivity of the β2 receptor agonists, there is cross reactivity to β1 receptors and may affect the myocardium and other peripheral tissues, and 3) there is β-adrenergic receptor desensitization. Most of the recommended doses of beta adrenergic agonists provide less than maximal bronchodilation. Beta-adrenergic agonists can cause tremor, reflex tachycardia, tachyphylaxis, cardiomyopathy, and other cardiac toxic effects. Tachycardia is particularly problematic in the elderly or for those individuals who are at cardiac risk. Further, β-adrenergic agonists have been shown to cause hyperkalemia. The majority of patients with COPD are current or former smokers, all of whom are may have coexisting coronary artery disease, thus in the compendium of therapies it is desirable to have alternatives to β-adrenergic agonists.

Anticholinergics as bronchodilators have been associated with systemic side effects. In particular, systemic anticholinergic side effects include bradycardia (if pronounced, includes compensatory tachycardia), dry mouth, inhibition of sweating, dilatation of the pupils, and visual blurring. Ipratropium has a slow onset of action and a longer duration of action than β-adrenergic agonists which can be deleterious for acute bronchodilation because patients continue to administer the drug without effect and overdose.

Theophylline continues to be a controversial treatment due to misconceptions of its role as a bronchodilator, drug delivery problems, and conflicting results of comparative studies during acute exacerbations. Further, theophylline has a limited therapeutic window, i.e. the dose needed to achieve bronchodilation is close to the dose associated with undesirable or adverse side effects including convulsions, cardiac arrhythmias, tachycardia, vasodilation, and diuresis. Further complicating therapy with theophylline is the intra-patient variability in efficacious response.

Long-term use of corticosteroids can be useful for patients in which continued symptoms or severe airflow limitations exist despite therapy with other agents. Only 20–30% of these patients experience therapeutic benefit for long-term use and indiscriminate use often leads to adverse effects without benefits. Unfortunately there have not been identified predictors of responders or nonresponders to long term steroid use in patients with COPD. Therefore, only those patients that attempt long-tem steroid use and have documented clinical improvement should continue steroid therapy. Unfortunately, those patients in which long-term steroid use results in no benefit are subjected to potential adverse effects or toxicities. Glucocorticoid associated side effects include: increased appetite, weight gain, fluid retention, acne, ecchymosis, development of cushoid facies, hypertension, hyperkalemia, diabetes, hyperglycemia, hyperosmolar state, hyperlipidemia, hepatic steatosis, atherosclerosis, myopathy, aseptic necrosis, osteoporosis, ulcers, pancreatitis, psuedotumor cerebri, pyschosis, glaucoma, cataract formation, vascular necrosis, increased suseptibility to infection, impairment of the hypothalamus-pituitary axis, decreased thyroid hormone serum binding protiens, and impaired wound healing.

Mucolytic and secretion clearance agents have been shown to improve thinning secretions. So far, there is little evidence to suggest that these agents render clinical improvement. Further cough suppressants may impair secretion clearance and possibly increase risk of pulmonary infection.

Description of Mechanism of Action Hypotheses for Future Drug Development of Candidate Therapeutic Interventions of COPD Since the predominant category of patients with COPD were or are current smokers, smoking cessation programs and agents used to help patients quit smoking will be a valuable addition to therapeutic regimens. Nicotine replacement therapies such as nicotine patches (transdermal), gum, and transnasal formulations as well as bupropion (an antidepressant or other in this category) should be considered.

Other therapies to be considered are novel bronchodilators for inhalation therapy without the use of chorofluorohydrocarbons (CFCs), next generation anticholinergic therapies, alpha 1 antiproteinase augmentation therapies, and refinement of surgical procedures.

A gene, genes, or gene pathway involved in the etiology of COPD or associated disorders or potential sites for targeted drug therapy of COPD are depicted in Table 2 with the specific gene list in Table 1. Current candidate therapeutic interventions in development for the treatment of COPD are listed in Table 6.

C. Autoimmune Disease

Description of Autoimmune disease

An immune response to "self" antigens, or autoimmunity, can vary from minimal to severe depending on the extent of the loss of self tolerance and to localization of antigens. There is a distinction between autoimmune response, which may or may not be pathologic, and autoimmune disease, which does lead to pathologic conditions. In autoimmune disease there is a combination of the following types of evidence: 1) identification of the target antigens, 2) identification and isolation of self-reactive autoantibodies or self-reactive lymphocytes, 3) identification of clinical evidence, i.e. familial hereditary data, lymphocyte infiltration, MHC association and clinical symptomatic improvement with immunosuppressive agents. Initiation of auotimmune disease is thought to require one or more of the following: genetic predisposition to loss of tolerance, environmental factors that stimulate aberrant immune response, or loss or dysfunction of cellular or organ physiological processes leading to pathological immune response. Since many autoreactive clones of T and B cells exist and are normally regulated by homeostatic mechanisms, loss or breakdown of this system of checks and balances can lead to activation or enhancement of these autoreactive clones and ultimately lead to autoimmune disease.

There are few autoimmune disease indications wherein inflammation and immune response gene pathways should be considered in the stratification or therapeutic choice of patient groups based upon genotype. There are multiple examples of autoimmune diseases or diseases that have an autoimmune component. They include: amyotrophic lateral sclerosis, anti-phospholipid syndrome, aplastic anemia, autoimmune hemolytic anemia, diabetes mellitus type 1, Guillan-Barre syndrome, idiopathic thromobocytopenic purpura, Grave's disease, myasthenia gravis, polymyositis, rheumatoid arthritis, Hashimoto's thyroiditis, uveitis, Wegener granulomatosis, periarteritis nodosa, ocular pemphigoid, pemphigus vulgaris, psoriasis, Goodpasture's syndrome, Churg-Strauss vasiculitis, poly-dermatomyositis, Cogan syndrome-autoimmune inner ear disease, hemolytic uremic syndrome, idiopathic glomerulonephritis, inflammatory bowel disease, Crohn's disease, microscopic polyarteritis, and multifocal motorneuron neuropathy. Here we discuss four specific diseases that represent larger patient populations and are representative of diseases in which therapy can be aimed at suppressing the hyperactivity of the immune system. These include multiple sclerosis, systemic lupus erythmatosus, scleroderma, diabetes mellitus type I, sarcoidosis, and nephritis.

Multiple Sclerosis

Multiple sclerosis (MS) is a disorder of multifocal sites of myelin sheath destruction, perivascular-lymphocytic cuffing and variable degree of oligodendroglial loss. In profound cases, there is gliosis, axonal transection, and neuronal and axonal loss. There are an estimated 300,000 Americans diagnosed with MS. The estimated cost of MS is $5 billion dollars.

Clinically, MS begins with a relapsing illness with episodes of neurological dysfunction lasting several weeks, followed by substantial or complete improvement. This is identified as the relapsing-remitting stage of the disease found to be predominantly in females (1.6:1). There are some patients that remain in this stage of the disease for decades; others may rapidly progress to the next stage. As time progresses, and repeated relapses occur, recovery becomes less and less complete or as substantial. In these cases, a gradual relapse independent clinical progression develops and is termed secondary progressive MS. Further, a nonrelapsing-nonremitting form is characterized by a gradual progression and steady worsening of neurological function without any recovery or improvement. A steady but gradual neurological decline, predominately identified in males, characterizes the primary progressive form of MS. Clarity in understanding the significance of these varying disease patterns and diagnosis is dependent on quality neurological examination overtime.

Systemic Lupus Erythmatosus

Systemic lupus erythmatosus (SLE) is a disease characterized by inflammation in many different organ systems associated with the production of antibodies to reactive to nuclear, cytoplasmic, and cell membrane antigens. Clinical manifestations of the disease include reddish rash on the cheeks, fatigue, anemia, rashes, sun sensitivity, alopecia, arthritis, pericarditis, pleurisy, vasiculitis, nephritis, and central nervous system disease. The immune hypereactivity appears to derive from immune hypereactivity and loss of self-tolerance. In these patients antibodies are produced against several nuclear components, notably antinuclear antibodies to native double stranded DNA, single stranded DNA, or nucleohistones.

Scleroderma

Scleroderma is a chronic disease marked by increases of fibrotic tissue involving the circulatory system, connective tissue (in particular the skin), visceral organs, and the immune system. There are approximately 500–700,000 Americans diagnosed with scleroderma. There are two types of scleroderma, localized and systemic. In localized scleroderma (linear and morphea) the disorder of the connective tissue is limited to the skin, the tissues just beneath the skin, and muscle. Internal organs are not affected. In systemic scleroderma (sclerosis) vascular, digestive, pulmonary, renal, muscle and joints may be affected. Raynaud's syndrome (frequent spasms of small arteries induced by temperature changes and emotion resulting in deprivation of blood supply to peripheral tissues), CREST syndrome (calcium deposits, Reynaud's syndrome, loss of muscular control of the esophagus, sclerodactylia, and telangiectasia), and Sjogren's syndrome (inflammation of the conductive, cornea, tear, and salivary glands with progressive destruction by lymphocytes and plasma cells) are both subcategories of scleroderma.

The clinical manifestations of scleroderma include the following symptoms: fatigue, swelling and numbness of the hands and feet, shiny skin and disappearance of skin folds, ulcers on the fingers, calcium deposits on the fingers, joint inflammation, joints tightening into bend position, muscle weakness, itchy skin, difficulty in swallowing, shortness of breath, fatty diarrhea or constipation, and loss of body hair. Although ultimately renal impairment and failure is a common endpoint, therapy affecting the hypertensive phase or renal involvement has changed the mortality rate.

Diabetes Mellitus type I

This form of diabetes involves the chronic inflammatory destruction of the insulin-producing islet cells of the pancreas. Although this form of diabetes is treated similarly to the type II form (which is not linked to autoimmunity), i.e. insulin replacement therapy, early identification of type I versus type II individuals may be useful to thwart the autoimmune destruction of the β-cells. There are an estimated 500,000 to 1 million Americans that have type I diabetes, it is the seventh leading cause of death, and the following is a list of the progressive complications that are associated with the unregulated carbohydrate balance in tissues: retinopathy leading to blindness, nephropathy (diabetic nephropathy is the leading cause of end-stage renal disease), coronary and cardiovascular disease, neuropathy (severe forms can lead to amputation), impotence (diabetic neuropathy and cardiovascular disease can lead to impotence), and stroke.

Sarcoidosis

Sarcoidosis is a granulomatous disorder characterized by enhanced cellular immune response at one or more involved sites. The prevalence of sarcoidosis is 5 in 100,000, so approximately 13,000 patients have been diagnosed. Between 80–90% of patients with sarcoidosis have pulmonary involvement, however, any organ can be affected. Pulmonary involvement includes dyspnea with or without exertion, persistent dry cough, and atypical chest pain. Cor pulmonale can develop as a complication of pulmonary dysfunction and further progress to right atria dilatation and right ventricular hypertrophy. Ocular involvement includes disturbance in visual acuity, and in chronic cases may lead to glaucoma, cataract formation and retinal neovascularization. In 80% of the cases, sarcoidosis is self-limiting and results in minimal symptomology, discomfort, or debilitation. However in the remaining 20%, sarcoidosis patients face potenitally serious debilitation, disfigurement, and can be life threatening. Misdiagnosis is frequent and can limit appropriate therapeutic intervention.

Nephritis

Inflammation of the kidneys results in impaired renal function. Nephritis can be either interstitial or glomerular. In either case, mononuclear cells infiltrate in the interstitium of the renal cortex. Eosinophils, and in some cases, polymorphonuclear leukocytes are found in a similar compartment. The infiltrate may be diffuse or patchy and may be accompanied by fibrotic tissue. Membranous nephropathy may develop and lead to impairment of glomerular filtration rate. There is evidence to suggest both cytotoxic T cells and T-cell mediate delayed hypersensitivity are involved. Nephritis is a component of the clinical manifestation of systemic lupus erythmatosis, scleroderma, and other autoimmune diseases and disorders.

Current therapy for Autoimmune Diseases and Disorders

Agents used to treat autoimmune disease fall into one of the following four categories: analgesics (NSAIDs, salicylates), immunosuppressive agents, hormones (glucocorticoids), and skin and mucosal membrane preparations Analgesics: Typically, pain associated with autoimmune disease can be controlled with NSAIDs including but not excluded to, salicylates, para-aminophenol derivatives, indole and indene derivatives, heteroaryl acetic acids, arylproprionic acids, anthranilic acids, enolic acids, or alkanones. Antiinflammatory agents such as cyclooxygenase inhibitors, lipoxygenase inhibitors, and others can be used to block the inflammation physiological pathway which mediate pain. However, because these drugs are limited in their efficacy in advanced or more severe stages of autoimmune disease, these agents are add-on therapies.

NSAIDs derive their principle mechanism of action by the inhibition of prostaglandin and leukotriene synthesis. These compounds inhibit key enzymes in the biosynthetic pathway, i.e. cyclooxygenase. There are drugs that selectively inhibit isoforms of cyclooxygenase 1 and 2 (COX-1, COX-2) which enhances patient tolerance due to the prevalence of COX-2 induction occurs in inflammation mediated by cytokines and others.

Immunosuppressive drugs or agents: Agents involved in the modification of the immune system for the treatment of autoimmune disease are immunosuppressive agents. Immunosuppressives include azathioprine, cyclosporine, penicillamine, antimalarials (chloroquine, hydroxychloroquine), alkylating agents (cyclophosphamide), and antimetabolites (methotrexate).

Hormones and Growth Factors: Agents acting at hormone receptors or growth factor receptors include steroids (glucocorticoids), adrenocorticotrophic hormone (corticotropin), and tumor necrosis factor inhibitors (soluble TNF receptors (enbrel) and TNF monoclonal antibody (remicade). Since the autoimmunity component of the disease is driven primarily by activated T-cells, which give rise to cytokines IL-1 and TNF at the affected areas. These agents are known to interfere with the actions of these cytokines.

Corticosteroids affect the immune response by: decreasing growth and development of mast cells, inducing apoptosis, suppressing lymphocyte generation of IL-5 and other cytokines, inhibiting some mediator release, inhibiting cytokine production, inhibiting the transcription of cytokines (for example IL-8, TNF-α, prototypic antiviral chemokine (regulated-on-activation normal T-expressed and secreted, RANTES), and GM-CSF), and inhibiting nitric oxide synthesis.

Plasma Exchange: A useful technique for the removal of autoantibodies is a process called plasmaphoresis or plasma exchange. In this process, antibodies are removed that mediate humoral immune response to the autoantigen.

Antioxidants: Many of the therapies in use for these auotimmune diseases are aimed at reducing the level and extent of tissue damage mediated by T-cell immune response. For example, dimethyl sulfoxide, dimethyl sulfone, para-aminobenzoic acid, and vitamin E are included in this category.

Limitations of Current Therapies for Autoimmune Disease
Limitations Current Therapies for Autoimmune Disease based upon Low efficacy The therapies discussed above are related to the slowing or retarding the progression of autoimmune disease. As immune response tissue damage occurs, degeneration of the function progresses, irreversible damage occurs, and therapeutic options become limited. Thus, therapies for autoimmune disease are aimed at reduction of manifestation of symptoms by controlling the clinical manifestations of inflammation and the hypersensitive immune response.

The reduction of clinical symptoms of autoimmune disease following immunosuppressive therapy by one of the agents listed above is only evident after several weeks to months after therapy. The slow clinical relevance of these therapies limits the clinician to determine optimal therapy for individuals with autoimmune disease, and provides a risk for selection of optimal therapy for any given stage of the disease. Furthermore, there may be delays in identifying those patients that have an autoimmune hyperreactivity, and this can delay therapeutic intervention.

Limitations Current Therapies for Autoimmune Disease based upon Toxicity or Undesired side effects There are toxicities and undesired side effects associated with the above current therapies for autoimmune disease that require monitoring. Drugs used to treat autoimmune disease may cause death, disability, disease, and place an unborn child at risk. The undesired side effects or toxicities are listed for each drug category as described above.

Analgesics associated side effects include dyspepsia, gastric or small bowel bleeding, ulceration, renal insufficiency, confusion, rash, headache, hepatic toxicity. NSAIDs also reversibly inhibit platelet aggregation and prolong bleeding time.

Immunosuppressive therapies have associated side effects including—antimalarials: retinal or macular damage; sulfonamides: hematologic toxicities (leukopenia, thrombocytopenia, hemolysis in patients with glucose 6-phosphate dehydrogenase (G6PD) deficiency); antimetabolites: hepatic compromise including hepatic fibrosis, ascites, esopageal varices, cirrhosis, pneumonitis, myelosuppression; immunosuppressives: myelosuppression, (cyclosporine: renal insufficiency anemia, hypertension); penicillamine: rash, stomatitis, dysgeusia or metallic taste, myelosuppression (thrombocytopenia), proteinuria, nephrotic syndrome or renal failure, and induction of autoimmune syndromes (systemic lupus erythmatosus, myesthenia gravis, polymyocytis, Goodpasture's syndrome).

Glucocorticoid associated side effects include: increased appetite, weight gain, fluid retention, acne, ecchymosis, development of cushoid facies, hypertension, hyperkalemia, diabetes, hyperglycemia, hyperosmolar state, hyperlipidemia, hepatic steatosis, atherosclerosis, myopathy, aseptic necrosis, osteoporosis, ulcers, pancreatitis, psuedotumor cerebri, pyschosis, glaucoma, cataract formation, vascular necrosis, increased suseptibility to infection, impairment of the hypothalamus-pituitary axis, decreased thyroid hormone serum binding protiens, and impaired wound healing.

Since the majority of autoimmune disease patients are women in their reproductive years, the level and extent the agents used to treat autoimmune disease affects or has a potential to affect the mother during pregnancy, cross the placenta, affect the developing fetus, or be excreted in breast milk during lactation are important issues facing the skilled practitioner. Clinical medical therapeutic decisions should weigh the use of all of the above current therapies for autoimmune disease against known capacity of these agents to affect both the mother and the child.

Description of Mechanism of Action Hypotheses for Future Drug Development for the Treatment of Autoimmune Disease Autoimmune disease has been thought to be the result of host genetic factors, immunoregulatory abnormalities and autoimmunity, and triggering or persistent microbial infection.

A gene, genes, or gene pathway involved in the etiology of atuoimmune diseases or disorders or associated disorders or potential sites for targeted drug therapy of autoimmunity are depicted in Table 2 with the specific gene list in Table 1. Current candidate therapeutic interventions in development are listed for the treatment of autoimmune disease or disorder, Tables 7 and 9, and for systemic lupus erythmatosus, Table 8.

D. Immunosuppression-Transplantation
Description of Transplantation

There are many different conditions in which medical or surgical therapy is unable to halt, retard, or treat the underlying disease, disorder, or dysfunction. Although many refractory diseases, disorders, or dysfunctions do not lead to severe cases, there are some in which the progression leads to conditions in which the remaining therapeutic alternative is replacement of the diseased tissue with normal donated tissue by transplantation. These end stage conditions include both primary disease or complications from a disease. For example whole organ transplantation is an end-stage therapuetic alternative in the following indications, end-stage cardiomyopathy, end-stage renal disease, pulmonary disease, cirrhosis of the liver, as well as other end-stage diseases affecting whole organ function.

Besides whole, or partial organ transplantation there are programs aimed at replacing cells in specific tissues to enable or restore physiologic function. For example, cellular transplantation includes, but are not excluded to, grafting bone marrow cells in patients with hematopoeitic or lymphocytic cancers, dopaminergic producing cells in brains of patients with Parkinson's disease, striated muscle cells in patient's with Duchenne's muscular dystrophy, myocytes or cardiomyocytes in patient's with ischemic heart disease or cardiomyopathy, and replacement of neurons or astrocytes or glial cells in neurodegenerative disease including but not excluded to Alzheimer's disease, amyotrophic lateral sclerosis, multiple sclerosis, Huntington's disease, refractory pain, epilepsy, and stroke.

In this way, transplantation includes autografts, isografts, allografts or xenografts and can involve whole organ or cellular grafts. With the exception of autologous transplantation, all other transplantation procedures include pre- and post-surgical immunosuppression to blunt graft rejection or graft versus host disease. Successful immunosuppression in this setting includes an appropriate balance between the need to prevent the process of graft rejection and the risk of suppressing the recipient's immune system to the extent that they become vulnerable to infection or other complications.

Transplantation is immunologically mediated. Both T cells and circulating antibodies are induced against allografts or xenografts. While the antibodies are responsible for rejection of erythrocytes, T-cells are mainly responsible for the rejection of most other type of tissue. The antigens found on grafted tissue which initiate the rapid rejection of an allograft are found on most cell membranes and are encoded by genes in the major histocompatibility complex (MHC) which are called the HLA. The structures encoded in these genes, MHC class I and class II molecules, are involved in the determining the discrimination between self and non-self. The degree of the histocompatibility betwee donor and recipient can be determined serologically, by genotyping, or by a mixed lymphocyte reaction. Survival of HLA nonmatched allografts is prolonged by anti-inflammatory agents, cytotoxic agents, antimetabolites, and other modalities aimed at immunosuppressing the recipient. These approaches have proven clinical success in terms of graft survival and clinical symptomology.

Rejection can occur at any time, and is either hyperacute, acute or delayed. The rate, extent, and underlying mechanism of transplantation rejection varies dramatically from individual to individual. Physiological factors include patency of blood circulation, lymphatic drainage, expression of antigens on the graft, and others that can influence the rejection rate.

In hyperacute rejection, preexisting host antibodies to antigens found on the grafted tissue mount an immune response. These antibodies activate complement, followed by platelet activation and deposition causing swelling and interstitial hemorrhage in a whole organ graft, or specific cell targeting in a cellular transplant. Cell mediated immunity is not activated in the hyperacute response.

In acute rejection, infiltration of lymphocytes and macrophages recognize the foreign antigen on the graft cells, and initiate a cascade of intragraft events that ultimately leads to host cellular and humoral mediated destruction of the grafted tissue and if unchecked will result in irreversible loss of the graft. This acute process occurs rapidly and does not in the first stages affect the vital structures of a whole organ graft, which allows for identification of the process and implementation of therapy. In many cases, an acute rejection episode can be reversed, and approximately 30–50% of whole organ graft recipients undergo one or more of these episodes in the early transplant period.

Delayed or chronic rejection occurs in a slower process than acute rejection and ultimately leads to a gradual loss of function in the grafted tissues. In chronic or delayed rejection, both cell mediated immunity and humoral immunity is activated. Chronic rejection is characterized by arteriosclerosis, in which the smooth muscle cells lining the arteries in the graft organ proliferate to create lesions and lead to fibrosis, with a result of constricting blood flow. As a result of the chronic immune rejection, there is slow and progressive destruction of the grafted organ or cells. If damage to the tissue is extensive, very little can be done to save the graft.

Current Immunosuppressive Therapies

The goal of clinical immunosuppression in the transplantation setting is to control allograft rejection. Clinical immunosuppression involves the non-specific suppression of both cell-mediated and humoral immune reactivity to the grafted tissue. Although a number of methods have been proposed, successful prolongation of graft survival has been attained through the use of a combination of therapies that suppress both the lymphocytic interaction and proliferation and therapies that deplete the pool of available lymphocytes.

Antiproliferative agents

These agents are useful to blunt the proliferative phase of lymphocyte activation of the immune response.

Purine analogs

Azathioprine acts to inhibit the proliferation of T cells. Azathioprine is cleaved to 6-mercaptopurine and it is this active compound that serves to suppress the T-cell mediated antigenic determination and engraftment. Azathioprone is a relatively non-selective immunosuppressive agent. Other agents in the same class as azathioprine, i.e. antimetabolites, include but are not excluded to, mercaptopurine, chlorambucil, and cyclophosphamide.

Pyrimidine analogs

These agents (cytosine arabinoside) inhibit DNA synthesis and therefore have their greatest effect on the immune response during the proliferative phase of lymphocyte activation. These agents inhibit primary antibody response and have minimal effects on the cell-mediated immunity.

Folic acid analogs

These agents (methotrexate, aminopterin) inhibit dihydrofolate reductase preventing the conversion of folic acid to tetrahydrofolic acid. This conversion is necessary for the production of DNA and RNA.

Alkylating Agents

These agents (nitrogen mustard, phenylalanine mustard, busulfan, cyclophosphamide) alter the structure of the DNA and RNA. These agents have reactive ring structures which combine with electron rich groups such as tertiary nitrogen in purines or pyrimidines, or —NH2, —COOH, —SH, —PO3H2 groups. These reactions alter the composition of the DNA, and if not repaired, chromosomal replication will be altered in acitvated proliferating cells. The use of alkylating agents in the setting of transplantation is time dependent and is effective just before or during the activation of the immune system by antigen. Cyclophosphamide has been shown to have a greater effect on B-cells rather than T-cells, thereby inhibiting the humoral response to a greater degree.

Antibiotics

These agents (actinomycin D, mitomycin C, puramycin, chloramphenicol) inhibit either nucleic acid or protein synthesis.

Cyclosporin acts by inhibiting the production of IL-2, which results in an inhibition of the proliferation of T and B lymphocytes. Cyclosporin is widely prescribed for transplantation patients due to the clinical advantage of potent immunosuppression with limited myelosuppression.

FK-506 (Tacrolimus) is an agent that acts by inhibiting the production of IL-2 which prevents the proliferation of T and B lymphocytes.

Mycophenolate mofetil is rapidly converted to mycophenolic acid which selectively inhibits T and B cell proliferation. Mycophenolate mofetil has an advantage over azathiprine because it does not damage chromosomes.

Lymphocyte Depletion agents

Antilymphocytic globulin (ALG) is an agent that binds to circulating T-lymphocytes and the cells coated with the ALG are lysed and cleared by the reticuloendothelial system. ALG is more commonly used for renal transplantation, showing little to no benefit for liver or bone marrow transplantation.

Radiation

Total lymphoid irradiation or total body irradiation is based upon the immunosuppression observed after this procedure was used in patients with Hodgkin's lymphoma. The radiation causes breakdown in the nucleic acid structure, and the effect is time dependent since there are systems within all cells for the repair of DNA. Since the radiation affects those cells in M or G2 phase, those cells in G1 or S phase are resistant.

Monoclonal antibodies

A murine monoclonal antibody is available to deplete the circulating CD3 lymphocytes. This antibody reacts with the T3 recognition site of the T-lymphocytes and blocks the recognition of the Class I and II antigens. This leads to prevention of the activation of the effector lymphocytes. This antibody has been useful in the treatment of rejection of renal, pancreatic, hepatic, cardiac, and pulmonary whole organ transplantations.

Steroids—such as the glucocorticoids are widely used in transplantation in combination with other drugs. As well as providing antiinflammatory therapy, corticosteroids suppress immune function by inhibiting the activation of T cells. Corticosteroids affect the inflammation within the airways by: decreasing growth and development of mast cells, inducing apoptosis, suppressing lymphocyte generation of IL-5 and other cytokines, inhibiting some mediator release, inhibiting cytokine production, inhibiting the transcription of cytokines (for example IL-8, TNF-α, prototypic antiviral chemokine (regulated-on-activation normal T-expressed and secreted, RANTES), and GM-CSF), and inhibiting nitric oxide synthesis. Steroids are highly effective in the early induction and maintenance regimens and are first line therapy in acute allograft rejection.

Blood transfusions can be used to cause allosensitzation if the recipient is exposed to donor antigens in the presence of azathioprine. In this way, induction of a specific degree of hyporeactivity against graft antigens can result by a potential suppressor cell phenomena.

Limitations of Immunosuppressive therapies

Limitations of Immunosuppressive Therapies due to Lack of Efficacy

As suggested, the efficacy of immunosuppression is a balance between prevention of graft rejection or graft versus host disease and subjecting a patient unnecessarily to blunted immune defenses to ward off infections. All too often, this balance is not achieved and on one end the patient succumbs to infections or on the other the graft is rejected. It has been estimated that 30% of the transplantation patients are in this category.

Limitations of Immunosuppressive Therapies due to Toxicities or Undesired Side Effects Antiproliferative Agents Azathioprine is associated with suppression of bone marrow production, and blood disorders including anemia, thrombocytopenia, and leukopenia. Hepatotoxicty ocurrs in a dose-independent manner, and is irreversible. Azathioprine is associated with chromosome damage and therefore is mutagenic.

Methotrexate and aminopterin are associated with bone marrow suppression, mucosal breakdown, gastrointestinal bleeding, megaloblastic hematopoiesis.

Alkylating Agents are associated with stomatitis, nausea, vomiting, diarrhea, skin rash, anemia, and alopecia. Specifically, cyclophosphamide has been associated with fluid retention, hemorrhagic cystitis, and cardiac toxicity.

Cyclosporin is associated with gingival hyperplasia, hirsutism, tremor, hypertension, hyperkalemia, hepatotoxicity, hyperglycemia, hypomagnesiumemia, hypercholesterolemia, hypertriglyceridemia, and hyperuricemia, nausea and gastrointestinal irregularities, and renal dysfunction. Nephrotoxicity associated with cyclosporin manifests as tubular necrosis, interstitial fibrosis, and tubular atrophy.

FK506 is associated with neurotoxicity, nephrotoxicity, and disturbances of glucose metabolism. The major neurotoxic symptoms are reversible and dose dependent and include headache, tremors, parasthesias, insomnia, increased sensitivity to light, mood changes, aphasia, and seizures. There has been a suggested association of FK-506 with cardiomyopathy and it is contraindicated in pregnancy.

Lymphocyte Depletion Agents

ALGs are associated with anemia, thrombocytopenia, and allergic reactions including urticaria, anaphylactoid reactions, serum sickness, joint pain, fever, and malaise.

Radiation is associated with higher incidence of infections and chromosomal breakage and mutations.

Monoclonal antibody therapy has been associated with the production of human anti-mouse antibodies (HAMA) in 80% of the treated patients and the sensitization rate is 15–40% thus limiting retreatment rates. Side effects are fever, chills, nausea, vomiting, headache, dyspnea, wheezing, pulmonary edema, tachycardia, hypotension, aseptic menigitis, seizures, and coma. These symptoms are related to the inordinate release of cytokines TNF, IL-1, and interferon-gamma. Although these symptoms can be reduced by pretreatment with steroids, acetominophen, or diphenhydramine the HAMA response precludes repeated use.

Steroids-Glucocorticoid associated side effects include: increased appetite, weight gain, fluid retention, acne, ecchymosis, development of cushoid facies, hypertension, hyperkalemia, diabetes, hyperglycemia, hyperosmolar state, hyperlipidemia, hepatic steatosis, atherosclerosis, myopathy, aseptic necrosis, osteoporosis, ulcers, pancreatitis, psuedotumor cerebri, pyschosis, glaucoma, cataract formation, vascular necrosis, increased suseptibility to infection, impairment of the hypothalamus-pituitary axis, decreased thyroid hormone serum binding protiens, and impaired wound healing.

Complications of Immunosuppression

In addition to the above listed toxicities and undesirable side effects, potent immunosuppression as required in the transplantation setting leads to prolonged immune compromise and predisposes the patient to infections (80% of the patients) and cancer (ranging between 10–40% of the patients). This risk has been proposed to result from impaired immune surveillance mechanisms, chronic antigenic stimulation, reactivation of latent oncogenic viruses and the direct oncogenic effects of the immunosuppressive agents.

Moreover, 40% of the deaths of transplant patients are attributable to the complications of infections or a combination of infection and graft rejection. The infections experienced by transplant patients are 50% bacterial, 30% viral, 15% fungal. Some of the common bacterial infections are Staphylococcus aureus, Staphylococcus epidermidis, and gram-negative rods in line sepsis. Urinary tract infections, pneumonias, wound infections, and surgical infections (including cholecystitis, appendicitis, diverticular disease, ulcer, etc.). Common viral infections include cytomegalovirus, Epstein-Barr virus, Herpes Simplex. Virus, and varicella zoster virus. Further, common fungal or protozoan infections include Candida albicans, Asperigillus flavus, Cryptococcus neoformans, Coccidiodes immitis, Histoplasma capsulatum, Norcardia asteroides, and Pneumocystis carinii.

Description of Mechanism of Action Hypotheses for Future Immunosuppressive Drug Development The majority of the hypotheses for future therapeutic interventions for graft rejection and graft immunoreactivity are based upon the understanding the immunologic mechanisms that cause and perpetuate the rejection within the graft.

A gene, genes, or gene pathway involved in the etiology of transplantation or immunosuppression or associated disorders or potential sites for targeted drug therapy of transplantation are depicted in Table 2 with the specific gene list in Table 1. Current candidate therapeutic interventions in development for the treatment of anemia are listed in Tables 9 and 10.

E. Pain Associated with Inflammation

Description of Pain Associated with Inflammation

Pain associated with inflammation can be caused by pathologic processes in somatic structures or viscera, or by prolonged dysfunction of parts the peripheral nervous system. Pain associated with inflammation may be the result of recurrent injuries, trauma, headache, arthritis, chronic obstructive pulmonary disease, psoriasis, or other pathologies. Pain associated with inflammation may be acute or chronic depending on the level and extent of the inflammation.

Current therapies for Pain Associated with Inflammation

Therapeutic management of pain resulting from inflammation includes a three step ladder approach: non-opioid analgesics are stepwise prescribed in combination with moderate to potent opiates. The guidelines call for a determination by the patient and the physician of pain relief. Broadly speaking, the guidelines are as follows: mild pain is treated with non-opioid analgesics, moderate or persisting pain is treated with a weak opioid plus non-opioid analgesics, and severe pain that persists or increases is treated with a potent opioid plus non-opioid analgesics.

Analgesics: Typically, pain associated with inflammation can be controlled with NSAIDs including but not excluded to, salicylates, para-aminophenol derivatives, indole and indene derivatives, heteroaryl acetic acids, arylproprionic acids, anthranilic acids, enolic acids, or alkanones. Antiinflammatory agents such as cyclooxygenase inhibitors, lipoxygenase inhibitors, and others can be used to block the inflammation physiological pathway which mediate pain and the progression of the disease. However, because these drugs are limited in their efficacy in advanced or more severe stages of arthritis, these agents are add-on therapies.

NSAIDs derive their principle mechanism of action by the inhibition of prostaglandin and leukotriene synthesis. These compounds inhibit key enzymes in the biosynthetic pathway, i.e. cyclooxygenase. There are drugs that selectively inhibit isoforms of cyclooxygenase 1 and 2 (COX-1, COX-2) which enhances patient tolerance due to the prevalence of COX-2 induction occurs in inflammation mediated by cytokines and others.

Further, pyrimidine synthesis inhibitors can be used as an antiinflammatory agent in arthritis, e.g. leflunomide.

Limitations of Current Therapies for Pain Associated with Inflammation

Limitation of Therapies for Pain Associated with Inflammation due to Low efficacy The therapies discussed above are limited to the slowing or retarding the progression of arthritis. As degeneration of the joints progresses, and irreversible damage occurs, the options become limited. Thus, therapies for arthritis are aimed at reduction of manifestation of symptoms by controlling the clinical manifestations of inflammation.

Limitations of Therapies of Pain Associated with Inflammation due too Toxicity or Undesired side effects Analgesics associated side effects include dyspepsia, gastric or small bowel bleeding, ulceration, renal insufficiency, confusion, rash, headache, hepatic toxicity. NSAIDs also reversibly inhibit platelet aggregation and prolong bleeding time.

Description of Mechanism of Action Hypotheses for Future Pain Associated with Inflammation Drug Development The persistence of pain most likely involves a cascade of pathological neurochemical events that lead to abnormal sensory hyperexcitability and excitotoxicity. The genes listed in FIG. 1 are part of a pathway are all involved in producing prostaglandins or leukotrienes, which are two potent mediators of inflammation. Inordinate levels of prostaglandins have been implicated in pain associated with inflammation, and several drugs target this branch of the pathway, to inhibit the action of leukotrienes. When a cell receives a pro-inflammatory stimulus, such as tumor necrosis factor, membrane phosphlipids, or interleukin-1, as shown in the figure, membrane phospholipases are activated, and arachidonic acid is released from membrane phospholipids into the cell. The liberated arachidonic acid is then metabolized either by the cyclooxgenase enzymes, which leads to the production of prostaglandins, or the lipoxgenase family of enzymes, which leads to the production of leukotrienes. There are several types of prostaglandins and leukotrienes, and many of the enzymes listed here function to convert one form into another.

The presence of leukotrienes and prostaglandins can lead to a persistence of neural hyperexcitability involving a sequence of neuroplastic events.

A gene, genes, or gene pathway involved in the etiology of pain or associated disorders or potential sites for targeted drug therapy of pain are depicted in Table 2 with the specific gene list in Table 1. Current candidate therapeutic interventions in development for the treatment of pain associated with inflammation are listed in Table 11.

F. Psoriasis

Description of Psoriasis

Papulosquamous skin disorders have diverse etiologies and include psoriasis, Reiter's syndrome, pityriasis rosea, lichen planus, oityriasis rubra pilaris, secondary syphilis, mycosis fungoides, and ichthyosiform eruptions.

Psoriasis is a genetically determined, chronic epidermal proliferative disease with an unpredictable course. Psoriasis appears as erythematous plaques with silvery, mica-like scales, and is usually nonpruritic. The plaques appear anywhere on the body and almost never involves the mucous membranes. There are variations of psoriasis including guttate psoriasis, inverse psoriasis, pustular psoriasis, erythroderma, and psoriatic arthritis. There is an increased prevalence of psoriasis in subjects with the HLA antigens BW17, B13, and BW37. Further, 30% of cases have a family history of psoriasis. The Koebner phenomena is a hallmark characteristic of psoriasis, e.g. intense trauma (scratches or surgical incisions) to the skin induces new linear papulosquamous lesions.

This multifactorial disease is characterized by an accelerated cell cycle in an increased number of dividing cells that results in rapid epidermal cell proliferation. It is estimated that 4–5 million Americans have psoriasis, 100,000 have severe cases, and 1 in 20 have psoriatric arthritis.

Current Therapies for Psoriasis

The goals of the therapeutic regimens is to limit the epidermal proliferation underlying the dermal inflammation. There are both topical and systemic treatments available, however in either category the treatment suppresses the condition for only as long as is administered. The treatment of psoriasis entails a stepwise increase of extent of the therapy ranging from topical applications to phototherapy to systemic interventions to prevent the epidermal proliferation.

In the first step topical treatments include corticosteroid ointments, vitamin D containing ointments, preparations containing coal tar or anthralin, salicylic acid containing ointments, and various other moisturizers and bath solutions. These steps are aimed at reducing the itching, scaling, and progression of the lesions.

In the second step, phototherapy other than natural sunlight can be used to thwart the epidermal cell proliferation. In these cases, ultarviolet light is administered to affected areas or uniformly to the body. In phototherapy, light delivered to the skin activates porphyrin molecules. These activated molecules transfer their energy to form cytotoxic singlet oxygen leading to lethal alteration of cellular membranes and subsequent tissue destruction. In UVB therapy, UVB light is administered alone or with ointments containing coal tar, anthralin, or salicylic acid. UVA light is administered with psoralen.

In the third step of therapeutic regimens for psoriasis, systemic agents are administered to those cases refractory to the previously described first two steps. These compounds include retinoids, methotrexate, hydroxyurea, cyclosporin, azthioprine, 5-fluorouracil, cyclophosphamide, vinblastine, dapsone, and sulfasalazine.

Limitations of Current Therapies for Psoriasis

The main limitation of the current therapies for psoriasis is that the drugs are only efficacious during the administration. Further, periods of remission and outbreaks are difficult to impossible to predict. It has been shown that patients should rotate their treatments to retain efficacy. This can lead to missed schedules and requires patient education. Lastly, for all the listed therapies there is unreliable efficacy in their ability to stop proliferation and inflammation of the lesions.

Toxicities of the current therapies include the following: phototherapy can lead to other skin lesions and sunburn. Cytotoxic agents used as immunosuppresive agents including methotrexate, 5-fluorouracil, cyclophospahmide, and vinblastine have associated side effects including hepatic compromise including hepatic fibrosis, ascites, esopageal varices, cirrhosis, pneumonitis, myelosuppression, (cyclosporine: renal insuffienciency anemia, hypertension).

A gene, genes, or gene pathway involved in the etiology of psoriasis or associated disorders or potential sites for targeted drug therapy of psoriasis are depicted in Table 2 with the specific gene list in Table 1. Current candidate therapeutic interventions in development for the treatment of psoriasis are listed in Table 12.

G. Atherosclerosis

Description and Potential Intervention of Atherosclerosis

Atherosclerosis is a complex combination of hyperlipidemia, injury to the endothelium, and inflammation. The interaction of these multiple processes in association with local genetic and hemodynamic influences may promote the formation of atheromatous plaques as a reparative response of the arterial wall. Atherosclerotic plaques are composed of thrombogenic lipid-rich core protected by a fibrous cap comprising smooth muscle cells and inflammatory cells. The inflammatory cells are predominantly macrophages. As atherosclerotic plagues build blood flow is reduced creating ischemia in tissues down stream from the area of the plaque.

In another model, the stenosis created by the plaques may be a part of the resulting ischemic event. Frequently, less obstructive but more vulnerable plaques occur which are characterized by a thinned fibrous cap, marked lipid accumulation, a large number of macrophages, and a smaller amount of smooth muscle cells. It has been proposed that since these plaques are more prone to rupture creating contact with the highly thrombogenic materials of the lipid-rich nucleus of these lesions, thrombosis is stimulated.

Advanced atherosclerotic lesions are caused by a series of cellular and molecular events involving replication of smooth muscle cells and macrophages on the vessel wall. The interaction of these cells with the T lymphocytes can lead to a fibrproliferative response. Large amounts of connective tissue produced by these smooth muscle cells comprise macrophages, T lymphocytes, smooth muscle cells, connective tissue, necrotic residues, and varying amounts of lipids and lipoproteins.

Endothelial cells maintain the vessel surface in a non-thrombogenic state, preventing platelet and leukocyte adhesion, and act in maintaining the vascular tonus by releasing nitric oxide, prostaglandin, and endothelin. These cells also produce growth factors, cytokines, and chemokines to maintain the integrity of the collagen- and proteoglycan-rich basement membrane. Changes in some of these functions may trigger cell interactions with monocytes, platelets, smooth muscle cells, and lymphocytes. Hyperlipidemia and hypercholesterolemia are sufficient to induce dysfunction of the endothelial modulation of the vasoactive reactions and arteriolar tonus.

The inflammatory mechanisms involved in the initial events or atherosclerosis are classic components of a specialized type of chronic inflammatory response that precedes the migration and proliferation of smooth muscle cells of the vessel wall. The foramtion and accumulation of foam cells in the intima leads to the first stage of the atherosclerotic lesion. In this stage, the accumulation of fatty strain comprise a mixture of macrophages, lipids, and T lymphocytes representing a a purely inflammatory response. If the stimulating agent is maintained, i.e. hyperlipidemia, hypercholesterolemia, or other risk factor, then the protective inflammmatory response will also persist and themay become deleterious to the cells lining the arterial wall. This condition may lead to an intermediate lesion that may contain multiple smooth muscle cell layers, macrophages, and T lymphocytes. A fibrous capsule is formed covering the contents of the lesion.

There is evidence to suggest that the inflammatory process and specific immune mechanisms are involved in athergenesis. At sites close to the plaque rupture, inflammatory processes are observed resulting from T cell-dependent autoimmune response. This may lead to an inflammatory reactions participating in the destabilization of the fibrous cap. Immunoglobulins, T lymphocytes, and macrophages are found in the plaques. B lymphocytes and plasmocytes amy aslo be detected in the adventitia adjacent to the plaques. Autoimmune reactions against the oxidized lipoproteins have been observed. The macrophages are transformed into foam cells and in the presence of LDL, form immunocomplexes with the LDL by Fc fragments of the immunoglublins. These LDL immunocomplexes can induce numerous metabolic and functional changes iwhich can directly or indirectly damage the endothelial cells leading to the progressin of the atherosclerotic lesion.

Despite the evidence of the involvement of the immune system in atherogenesis, the complexity of the immune reactions and response impairs the clarification of the involvement of these machanisms at the various stages of athersclerosis. The sequence of immune response event suggests an initial mechanism to respond to injury. However, this protective inflammatory response in the presence of persistant stimulus and the formation of a fibroprliferative response can be amplified.

Attempts to modify the specific cell interactions with growth factor mediators or intracellular signalling molecules has provided a window to the potential prevention or regression of the lesions.

A gene, genes, or gene pathway involved in the etiology of athersclerosis or associated disorders or potential sites for targeted drug therapy of athersclerosis are depicted in Table 2 with the specific gene list in Table 1. Current candidate therapeutic interventions in development for the treatment of athersclerosis are listed in Table 13.

Advantages of Inclusion of Pharmacogenetic Stratification in Clinical Development of Agents for use in Inflammation and Inflammation-Mediated Diseases The advantages of a clinical research and drug development program that includes the use of polymorphic genotyping for the stratification of patients for the appropriate selection of candidate therapeutic intervention includes: 1) identification of patients that may respond earlier and show signs and symptoms of clinical improvement or side effects and toxicities, 2) identification of the primary gene and relevant polymorphic variance that directly affects manifestation of efficacy, safety, toxicity, or undesired side effects, 3) identification of pathophysiologic relevant variance or variances and potential therapies affecting those allelic genotypes or haplotypes, and 4) identification of allelic variances or haplotypes in genes that indirectly affects efficacy, safety or both.

Based upon these advantages, designing and performing a clinical trial, either prospective or retrospective, which includes a genotype stratification arm will incorporate analysis of clinical outcomes and genetic variation associated with those outcomes, and hypothesis testing of the statistically relevant correlation of the genotypic stratification and therapeutic benefits. If statistical relevance is detectable, these studies will be incorporated into regulatory filings. Ultimately, these clinical trial data will be considered during the approval for marketing process, as well as, incorporated into accepted medical management of inflammatory disease.

Impact of Stratification Based Upon Genotype in Drug Development for Drugs, Compounds, or Candidate Therapeutic Interventions for Inflammatory Disease There is evidence to suggest that there are safety response differences to drug therapy in arthritis which may be attributable to genotypic differences between individuals. There is provided in this invention examples of gene pathways that are implicated in the disease process or its therapy and those that potentially cause this variability as described in the Examples. The Detailed Description below demonstrates how identification of a candidate gene or genes and gene pathways, stratification, clinical trial design, and implementation of genotyping for appropriate medical management of a given disease can be used to identify the genetic cause of variations in clinical response to therapy, new diagnostic tests, new therapeutic approaches for treating this disorder, and new pharmacuetical products or formulations for therapy. Gene pathways including, but not limited to, those that are outlined in the gene pathway Table 1, and pathway matrix Table 2 and discussed below are candidates for the genetic analysis and product development using the methods described above.

A sample of therapies approved or in development for preventing or treating the progression of the above described indications currently known in the art are listed in Tables 5 through 13. In these tables, the candidate therapeutics were sorted and listed by mechanism of action. Further, the product name, the pharmacologic mechanism of action, chemical name (if specified), and the indication is listed as well.

Pharmacogenomics studies for these drugs, as well as other agents, drugs, compounds or candidate therapeutic interventions, could be performed by identifying genes that are involved in the function of a drug including, but not limited to is absorption, distribution metabolism, or elimination , the interaction of the drug with its target as well as potential alternative targets, the response of the cell to the binding of a drug to a target, the metabolism (including synthesis, biodistribution or elimination) of natural compounds which may alter the activity of the drug by complementary, competitive or allosteric mechanisms that potentiate or limit the effect of the drug, and genes involved in the etiology of the disease that alter its response to a particular class of therapeutic agents. It will be recognized to those skilled in the art that this broadly includes proteins involved in pharmacokinetics as well as genes involved in pharmacodynamics. This also includes genes that encode proteins homologous to the proteins believed to carry out the above functions, which are also worth evaluation as they may carry out similar functions. Together the foregoing proteins constitute the candidate genes for affecting response of a patient to the therapeutic intervention. Using the methods described above, variances in these genes can be identified, and research and clinical studies can be performed to establish an association between a drug response or toxicity and specific variances.

II. Identification of interpatient variation in response; identification of genes and variances relevant to drug action; development of diagnostic tests; and use of variance status to determine treatment Development of therapeutics in man follows a course from compound discovery and analysis in a laboratory (preclinical development) to testing the candidate therapeutic intervention in human subjects (clinical development). The preclinical development of candidate therapeutic interventions for use in the treatment of human diseases, disorders, or conditions begins at the discovery stage whereby a candidate therapy is tested in vitro to achieve a desired biochemical alteration of a biochemical or physiological event. If successful, the candidate is generally tested in animals to determine toxicity, adsorption, distribution, metabolism and excretion in a living species. Occasionally, there are available animal models that mimic human diseases, disorders, and conditions in which testing the candidate therapeutic intervention can provide supportive data to warrant proceeding to test the compound in humans. It is widely recognized that preclinical data is imperfect in predicting response to a compound in man. Both safety and efficacy have to ultimately be demonstrated in humans. Therefore, given economic constraints, and considering the complexities of human clinical trials, any technical advance that increases the likelihood of successfully developing and registering a compound, or getting new indications for a compound, or marketing a compound successfully against competing compounds or treatment regimens, will find immediate use. Indeed, there has been much written about the potential of pharmacogenetics to change the practice of medicine. In this application we provide descriptions of the methods one skilled in the art would use to advance compounds through clinical trials using genetic stratification as a tool to circumvent some of the difficulties typically encountered in clinical development, such as poor efficacy or toxicity. We also provide specific genes, variation in which may account for interpatient variation in treatment response, and further we provide specific exemplary variances in those genes that may account for variation in treatment response.

The study of sequence variation in genes that mediate and modulate the action of drugs may provide advances at virtually all stages of drug development. For example, identification of amino acid variances in a drug target during preclinical development would allow development of non-allele selective agents. During early clinical development, knowledge of variation in a gene related to drug action could be used to design a clinical trial in which the variances are taken account of by, for example, including secondary endpoints that incorporate an analysis of response rates in genetic subgroups. In later stages of clinical development the goal might be to first establish retrospectively whether a particular problem, such as liver toxicity, can be understood in terms of genetic subgroups, and thereby controlled using a genetic test to screen patients. Thus genetic analysis of drug reponse can aid successful development of therapeutic products at any stage of clinical development. Even after a compound has achieved regulatory approval its commercialization can be aided by the methods of this invention, for example by allowing identification of genetically defined responder subgroups in new indications (for which approval in the entire disease population could not be achieved) or by providing the basis for a marketing campaign that highlights the superior efficacy and/or safety of a compound coupled with a genetic test to identify preferential responders. Thus the methods of this invention will provide medical, economic and marketing advantages for products, and over the longer term increase therapeutic alternatives for patients.

As indicated in the Summary above, certain aspects of the present invention typically involve the following process, which need not occur separately or in the order stated. Not all of these described processes should be present in a particular method, or need be performed by a single entity or organization or person. Additionally, if certain of the information is available from other sources, that information can be utilized in the present invention. The processes are as follows: a) variability between patients in the response to a particular treatment is observed; b) at least a portion of the variable response is correlated with the presence or absence of at least one variance in at least one gene; c) an analytical or diagnostic test is provided to determine the presence or absence of the at least one variance in individual patients; d) the presence or absence of the variance or variances is used to select a patient for a treatment or to select a treatment for a patient, or the variance information is used in other methods described herein.

A. Identification of Interpatient Variability in Response to a Treatment

Interpatient variability is the rule, not the exception, in clinical therapeutics. One of the best sources of information on interpatient variability is the nurses and physicians supervising the clinical trial who accumulate a body of first hand observations of physiological responses to the drug in different normal subjects or patients. Evidence of interpatient variation in response can also be measured statistically, and may be best assessed by descriptive statistical measures that examine variation in response (beneficial or adverse) across a large number of subjects, including in different patient subgroups (men vs. women; whites vs. blacks; Northern Europeans vs. Southern Europeans, etc.).

In accord with the other portions of this description, the present invention concerns DNA sequence variances that can affect one or more of:

i. The susceptibility of individuals to a disease;

ii. The course or natural history of a disease;

iii. The response of a patient with a disease to a medical intervention, such as, for example, a drug, a biologic substance, physical energy such as radiation therapy, or a specific dietary regimen. (The terms 'drug', 'compound' or 'treatment' as used herein may refer to any of the foregoing medical interventions.) The ability to predict either beneficial or detrimental responses is medically useful.

Thus variation in any of these three parameters may constitute the basis for initiating a pharmacogenetic study directed to the identification of the genetic sources of interpatient variation. The effect of a DNA sequence variance or variances on disease susceptibility or natural history (i and ii, above) are of particular interest as the variances can be used to define patient subsets which behave differently in response to medical interventions such as those described in (iii). The methods of this invention are also useful in a clinical development program where there is not yet evidence of interpatient variation (perhaps because the compound is just entering clinical trials) but such variation in response can be reliably anticipated. It is more economical to design pharmacogenetic studies from the beginning of a clinical development program than to start at a later stage when the costs of any delay are likely to be high given the resources typically committed to such a program.

In other words, a variance can be useful for customizing medical therapy at least for either of two reasons. First, the variance may be associated with a specific disease subset that behaves differently with respect to one or more therapeutic interventions (i and ii above); second, the variance may affect response to a specific therapeutic intervention (iii above). Consider for exemplary purposes pharmacological therapeutic interventions. In the first case, there may be no effect of a particular gene sequence variance on the observable pharmacological action of a drug, yet the disease subsets defined by the variance or variances differ in their response to the drug because, for example, the drug acts on a pathway that is more relevant to disease pathophysiology in one variance-defined patient subset than in another variance-defined patient subset. The second type of useful gene sequence variance affects the pharmacological action of a drug or other treatment. Effects on pharmacological responses fall generally into two categories; pharmacokinetic and pharmacodynamic effects. These effects have been defined as follows in Goodman and Gilman's Phamacologic Basis of Therapeutics (ninth edition, McGraw Hill, New York, 1986): "Pharmacokinetics" deals with the absorption, distribution, biotransformations and excretion of drugs. The study of the biochemical and physiological effects of drugs and their mechanisms of action is termed "pharmacodynamics."

Useful gene sequence variances for this invention can be described as variances which partition patients into two or more groups that respond differently to a therapy or that correlate with differences in disease susceptibility or progression, regardless of the reason for the difference, and regardless of whether the reason for the difference is known. The latter is true because it is possible, with genetic methods, to establish reliable associations even in the absence of a pathophysiological hypothesis linking a gene to a phenotype, such as a pharmacological response, disease susceptibility or disease prognosis.

B. Identification of Specific Genes and Correlation of Variances in Those Genes with Response to Treatment of Diseases or Conditions It is useful to identify particular genes which do or are likely to mediate the efficacy or safety of a treatment method for a disease or condition, particularly in view of the large number of genes which have been identified and which continue to be identified in humans. As is further discussed in section C below, this correlation can proceed by different paths. One exemplary method utilizes prior information on the pharmacology or pharmacokinetics or pharmacodynamics of a treatment method, e.g., the action of a drug, which indicates that a particular gene is, or is likely to be, involved in the action of the treatment method, and further suggests that variances in the gene may contribute to variable response to the treatment method. For example if a compound is known to be glucuronidated then a glucuronyltransferase is likely involved. If the compound is a phenol, the likely glucuronyltransferase is UGT1 (either the UGT1*1 or UGT1*6 transcripts, both of which catalyze the conjugation of planar phenols with glucuronic acid). Similar inferences can be made for many other biotransformation reactions.

Alternatively, if such information is not known, variances in a gene can be correlated empirically with treatment response. In this method, variances in a gene which exist in a population can be identified. The presence of the different variances or haplotypes in individuals of a study group, which is preferably representative of a population or populations of known geographic, ethnic and/or racial background, is determined. This variance information is then correlated with treatment response of the various individuals as an indication that genetic variability in the gene is at least partially responsible for differential treatment response. It may be useful to independently analyze variances in the different geographic, ethnic and/or racial groups as the presence of different genetic variances in these groups (i.e. different genetic background) may influence the effect of a specific variance. That is, there may be a gene x gene interaction involving one unstudied gene, however the indicated demographic variables may act as a surrogate for the unstudied allele. Statistical measures known to those skilled in the art are preferably used to measure the fraction of interpatient variation attributable to any one variance, or to measure the response rates in different subgroups defined genetically or defined by some combination of genetic, demographic and clinical criteria.

Useful methods for identifying genes relevant to the pharmacological action of a drug or other treatment are known to those skilled in the art, and include review of the scientific literature combined with inteferential or deductive reasoning that one skilled in the art of molecular pharmacology and molecular biology would be capable of; large scale analysis of gene expression in cells treated with the drug compared to control cells; large scale analysis of the protein expression pattern in treated vs. untreated cells, or the use of techniques for identification of interacting proteins or ligand-protein interactions, such as yeast two-hybrid systems.

C. Development of a Diagnostic Test to Determine Variance Status

In accordance with the description in the Summary above, the present invention generally concerns the identification of variances in genes which are indicative of the effectiveness of a treatment in a patient. The identification of specific variances, in effect, can be used as a diagnostic or prognostic test. Correlation of treatment efficacy and/or toxicity with particular genes and gene families or pathways is provided in Stanton et al., U.S. Provisional Application 60/093,484, filed Jul. 20, 1998, entitled GENE SEQUENCE VARIANCES WITH UTILITY IN DETERMINING THE TREATMENT OF DISEASE (concerns the safety and efficacy of compounds active on folate or pyrimidine metabolism or action) and Stanton, U.S. Provisional Application No. 60/121,047, filed Feb. 22, 1999, entitled GENE SEQUENCE VARIANCES WITH UTILITY IN DETERMINING THE TREATMENT OF DISEASE (concerning Alzheimer's disease and other dementias and cognitive disorders), which are hereby incorporated by reference in their entireties including drawings.

Genes identified in the examples below and in the Tables and Figures can be used in the methods of the present invention. A variety of genes which the inventors realize may account for interpatient variation in response to treatments for inflammatory or immune diseases, conditions, disorders, and/or the development of same are listed in Tables 1 and 3. Gene sequence variances in said genes are particularly useful for aspects of the present invention.

Methods for diagnostic tests are well known in the art. Generally in this invention, the diagnostic test involves determining whether an individual has a variance or variant form of a gene that is involved in the disease or condition or the action of the drug or other treatment or effects of such treatment. Such a variance or variant form of the gene is preferably one of several different variances or forms of the gene that have been identified within the population and are known to be present at a certain frequency. In an exemplary method, the diagnostic test involves determining the sequence of at least one variance in at least one gene after amplifying a segment of said gene using a DNA amplification method such as the polymerase chain reaction (PCR). In this method, DNA for analysis is obtained by amplifying a segment of DNA or RNA (generally after converting the RNA to cDNA) spanning one or more variances in the gene sequence. Preferably, the amplified segment is <500 bases in length, in an alternative embodiment the amplified segment is <100 bases in length, most preferably <45 bases in length.

In some cases it will be desirable to determine a haplotype instead of a genotype. In such a case the diagnostic test is performed by amplifying a segment of DNA or RNA (cDNA) spanning more than one variance in the gene sequence and preferably maintaining the phase of the variances on each allele. The term "phase" refers to the relationship of variances on a single chromosomal copy of the gene, such as the copy transmitted from the mother (maternal copy or maternal allele) or the father (paternal copy or paternal allele). The haplotyping test may take part in two phases, where first genotyping tests at two or more variant sites reveal which sites are heterozygous in each patient or normal subject. Subsequently the phase of the two or more variant sites can be determined. In performing a haplotyping test preferably the amplified segment is >500 bases in length, more preferably it is >1,000 bases in length, and most preferably it is >2,500 bases in length. One way of preserving phase is to amplify one strand in the PCR reaction. This can be done using one or a pair of oligonucleotide primers that terminate (i.e. have a 3' end that stops) opposite the variant site, such that one primer is perfectly complementary to one variant form and the other primer is perfectly complementary to the other variant form. Other than the difference in the 3' most nucleotide the two primers are identical (forming an allelic primer pair). Only one of the allelic primers is used in any PCR reaction, depending on which strand is being amplified. The primer for the opposite strand may also be an allelic primer, or it may prime from a non-polymorphic region of the template. This method exploits the requirement of most polymerases for perfect complementarity at the 3' terminus of the primer in a primer-template complex. See, for example: Lo Y M, Patel P, Newton C R, Markham A F, Fleming K A and J S Wainscoat. (1991) Direct haplotype determination by double ARMS: specificity, sensitivity and genetic applications. *Nucleic Acids Res* July 11;19(13):3561–7.

It is apparent that such diagnostic tests are performed after initial identification of variances within the gene, which allows selection of appropriate allele specific primers.

Diagnostic genetic tests useful for practicing this invention belong to two types: genotyping tests and haplotyping tests. A genotyping test simply provides the status of a variance or variances in a subject or patient. For example suppose nucleotide 150 of hypothetical gene X on an autosomal chromosome is an adenine (A) or a guanine (G) base. The possible genotypes in any individual are AA, AG or GG at nucleotide 150 of gene X.

In a haplotyping test there is at least one additional variance in gene X, say at nucleotide 810, which varies in the population as cytosine (C) or thymine (T). Thus a particular copy of gene X may have any of the following combinations of nucleotides at positions 150 and 810: 150A-810C, 150A-810T, 150G-810C or 150G-810T. Each of the four possibilities is a unique haplotype. If the two nucleotides interact in either RNA or protein, then knowing the haplotype can be important. The point of a haplotyping test is to determine the haplotypes present in a DNA or cDNA sample (e.g. from a patient). In the example provided there are only four possible haplotypes, but, depending on the number of variances in the gene and their distribution in human populations there may be three, four, five, six or more haplotypes at a given gene. The most useful haplotypes for this invention are those which occur commonly in the population being treated for a disease or condition. Preferably such haplotypes occur in at least 5% of the population, more preferably in at least 10%, still more preferably in at least 20% of the population and most preferably in at least 30% or more of the population. Conversely, when the goal of a pharmacogenetic program is to identify a relatively rare population that has an adverse reaction to a treatment, the most useful haplotypes may be rare haplotypes, which may occur in less than 5%, less than 2%, or even in less than 1% of the population. One skilled in the art will recognize that the frequency of the adverse reaction provides a useful guide to the likely frequency of salient causative haplotypes.

Based on the identification of variances or variant forms of a gene, a diagnostic test utilizing methods known in the art can be used to determine whether a particular form of the gene, containing specific variances or haplotypes, or combinations of variances and haplotypes, is present in at least one copy, one copy, or more than one copy in an individual. Such tests are commonly performed using DNA or RNA collected from blood, cells, tissue scrapings or other cellular materials, and can be performed by a variety of methods including, but not limited to, PCR based methods, hybridization with allele-specific probes, enzymatic mutation detection, chemical cleavage of mismatches, mass spectrometry or DNA sequencing, including minisequencing. Methods for haplotyping are described above. In particular embodiments, hybridization with allele specific probes can be conducted in two formats: (1) allele specific oligonucleotides bound to a solid phase (glass, silicon, nylon membranes) and the labelled sample in solution, as in many DNA chip applications, or (2) bound sample (often cloned DNA or PCR amplified DNA) and labelled oligonucleotides in solution (either allele specific or short—e.g. 7 mers or 8 mers—so as to allow sequencing by hybridization). Preferred methods for diagnosing testing of variances are described in four patent applications Stanton et al, entitled A METHOD FOR ANALYZING POLYNUCLEOTIDES, Ser. No. 09/394,467; 09/394,457; 09/394,774; and 09/394,387; all filed Sep. 10, 1999. The application of such diagnostic tests is possible after identification of variances that occur in the population. Diagnostic tests may involve a panel of variances from one or more genes, often on a solid support, which enables the simultaneous determination of more than one variance in one or more genes.

D. Use of Variance Status to Determine Treatment

The present disclosure describes exemplary gene sequence variances in genes identified in a gene table herein (e.g., Table 3), and variant forms of these gene that may be determined using diagnostic tests. As indicated in the Summary, such a variance-based diagnostic test can be used to determine whether or not to administer a specific drug or other treatment to a patient for treatment of a disease or condition. Preferably such diagnostic tests are incorporated in texts such as are described in Clinical Diagnosis and Management by Laboratory Methods (19th Ed) by John B. Henry (Editor) W B Saunders Company, 1996; Clinical Laboratory Medicine : Clinical Application of Laboratory Data, (6th edition) by R. Ravel, Mosby-Year Book, 1995, or other medical textbooks including, without limitation, textbooks of medicine, laboratory medicine, therapeutics, pharmacy, pharmacology, nutrition, allopathic, homeopathic, and osteopathic medicine; preferably such a test is developed as a 'home brew' method by a certified diagnostic laboratory; most preferably such a diagnostic test is approved by regulatory authorities, e.g., by the U.S. Food and Drug Administration, and is incorporated in the label or insert for a therapeutic compound, as well as in the Physicians Desk Reference.

In such cases, the procedure for using the drug is restricted or limited on the basis of a diagnostic test for determining the presence of a variance or variant form of a gene. Alternatively the use of a genetic test may be advised as best medical practice, but not absolutely required, or it may be required in a subset of patients, e.g. those using one or more other drugs, or those with impaired liver or kidney function. The procedure that is dictated or recommended based on genotype may include the route of administration of the drug, the dosage form, dosage, schedule of administration or use with other drugs; any or all of these may require selecting or determination consistent with the results of the diagnostic test or a plurality of such tests. Preferably the use of such diagnostic tests to determine the procedure for administration of a drug is incorporated in a text such as those listed above, or medical textbooks, for example, textbooks of medicine, laboratory medicine, therapeutics, pharmacy, pharmacology, nutrition, allopathic, homeopathic, and osteopathic medicine. As previously stated, preferably such a diagnostic test or tests are required by regulatory authorities and are incorporated in the label or insert as well as the Physicians Desk Reference.

Variances and variant forms of genes useful in conjunction with treatment methods may be associated with the origin or the pathogenesis of a disease or condition. In many useful cases, the variant form of the gene is associated with a specific characteristic of the disease or condition that is the target of a treatment, most preferably response to specific drugs or other treatments. Examples of diseases or conditions ameliorable by the methods of this invention are identified in the Examples and tables below; in general treatment of disease with current methods, particularly drug treatment, always involves some unknown element (involving efficacy or toxicity or both) that can be reduced by appropriate diagnostic methods.

Alternatively, the gene is involved in drug action, and the variant forms of the gene are associated with variability in the action of the drug. For example, in some cases, one variant form of the gene is associated with the action of the drug such that the drug will be effective in an individual who inherits one or two copies of that form of the gene. Alternatively, a variant form of the gene is associated with the action of the drug such that the drug will be toxic or otherwise contra-indicated in an individual who inherits one or two copies of that form of the gene.

In accord with this invention, diagnostic tests for variances and variant forms of genes as described above can be used in clinical trials to demonstrate the safety and efficacy of a drug in a specific population. As a result, in the case of drugs which show variability in patient response correlated with the presence or absence of a variance or variances, it is preferable that such drug is approved for sale or use by regulatory agencies with the recommendation or requirement that a diagnostic test be performed for a specific variance or variant form of a gene which identifies specific populations in which the drug will be safe and/or effective. For example, the drug may be approved for sale or use by regulatory agencies with the specification that a diagnostic test be performed for a specific variance or variant form of a gene which identifies specific populations in which the drug will be toxic. Thus, approved use of the drug, or the procedure for use of the drug, can be limited by a diagnostic test for such variances or variant forms of a gene; or such a diagnostic test may be considered good medical practice, but not absolutely required for use of the drug.

As indicated, diagnostic tests for variances as described in this invention may be used in clinical trials to establish the safety and efficacy of a drug. Methods for such clinical trials are described below and/or are known in the art and are described in standard textbooks. For example, diagnostic tests for a specific variance or variant form of a gene may be incorporated in the clinical trial protocol as inclusion or exclusion criteria for enrollment in the trial, to allocate certain patients to treatment or control groups within the clinical trial or to assign patients to different treatment cohorts. Alternatively, diagnostic tests for specific variances may be performed on all patients within a clinical trial, and statistical analysis performed comparing and contrasting the efficacy or safety of a drug between individuals with different variances or variant forms of the gene or genes. Preferred embodiments involving clinical trials include the genetic stratification strategies, phases, statistical analyses, sizes, and other parameters as described herein.

Similarly, diagnostic tests for variances can be performed on groups of patients known to have efficacious responses to the drug to identify differences in the frequency of variances between responders and non-responders. Likewise, in other cases, diagnostic tests for variance are performed on groups of patients known to have toxic responses to the drug to identify differences in the frequency of the variance between those having adverse events and those not having adverse events. Such outlier analyses may be particularly useful if a limited number of patient samples are available for analysis. It is apparent that such clinical trials can be or are performed after identifying specific variances or variant forms of the gene in the population. In defining outliers it is useful to examine the distribution of responses in the placebo group; outliers should preferably have responses that exceed in magnitude the extreme responses in the placebo group.

The identification and confirmation of genetic variances is described in certain patents and patent applications. The description therein is useful in the identification of variances in the present invention. For example, a strategy for the development of anticancer agents having a high therapeutic index is described in Housman, International Application PCT/US/94 08473 and Housman, INHIBITORS OF ALTERNATIVE ALLELES OF GENES ENCODING PROTEINS VITAL FOR CELL VIABILITY OR CELL GROWTH AS A BASIS FOR CANCER THERAPEUTIC AGENTS, U.S. Pat. No. 5,702,890, issued Dec. 30, 1997, which are hereby incorporated by reference in their entireties. Also, a number of gene targets and associated variances are identified in Housman et al., U.S. Patent Application Ser. No. 09/045,053, entitled TARGET ALLELES FOR ALLELE-SPECIFIC DRUGS, filed Mar. 19, 1998, which is hereby incorporated by reference in its entirety, including drawings.

The described approach and techniques are applicable to a variety of other diseases, conditions, and/or treatments and to genes associated with the etiology and pathogenesis of such other diseases and conditions and the efficacy and safety of such other treatments.

Useful variances for this invention can be described generally as variances which partition patients into two or more groups that respond differently to a therapy (a therapeutic intervention), regardless of the reason for the difference, and regardless of whether the reason for the difference is known.

III. From Variance List to Clinical Trial: Identifying Genes and Gene Variances that Account for Variable Responses to Treatment There are a variety of useful methods for identifying a subset of genes from a large set of candidate genes that should be prioritized for further investigation with respect to their influence on inter-individual variation in disease predisposition or response to a particular drug. These methods include for example, (1) searching the biomedical literature to identify genes relevant to a disease or the action of a drug, (2) screening the genes identified in step 1 for variances. A large set of exemplary variances are provided in Table 3. Other methods include (3) using computational tools to predict the functional effects of variances in specific genes, (4) using in vitro or in vivo experiments to identify genes which may participate in the response to a drug or treatment, and to determine the variances which affect gene, RNA or protein function, and may therefore be important genetic variables affecting disease manifestations or drug response, and (5) retrospective or prospective clinical trials. Computational tools are described in U.S. Patent Application, Stanton et al., Ser. No. 09/330,747, filed Apr. 26, 1999, entitled GENE SEQUENCE VARIANCES WITH UTILITY IN DETERMINING THE TREATMENT OF DISEASE, and in Stanton et al., Ser. No. 09/419,705, filed Oct. 14, 1999, entitled VARIANCE SCANNING METHOD FOR IDENTIFYING GENE SEQUENCE VARIANCES, which are hereby incorporated by reference in their entireties, including drawings. Other methods are considered below in some detail.

(1) To begin, one preferably identifies, for a given treatment, a set of candidate genes that are likely to affect disease phenotype or drug response. This can be accomplished most efficiently by first assembling the relevant medical, pharmacological and biological data from available sources (e.g., public databases and publications). One skilled in the art can review the literature (textbooks, monographs, journal articles) and online sources (databases) to identify genes most relevant to the action of a specific drug or other treatment, particularly with respect to its utility for treating a specific disease, as this beneficially allows the set of genes to be analyzed ultimately in clinical trials to be reduced from an initial large set. Specific strategies for conducting such searches are described below. In some instances the literature may provide adequate information to select genes to be studied in a clinical trial, but in other cases additional experimental investigations of the sort described below will be preferable to maximize the likelihood that the salient genes and variances are moved forward into clinical studies. Specific genes relevant to understanding interpatient variation in response to treatments for major inflammatory and immunologic diseases are listed in Table 1. In Table 2 preferred sets of genes for analysis of variable therapeutic response in specific diseases are highlighted. These genes are exemplary; they do not constitute a complete set of genes that may account for variation in clinical response. Experimental data are also useful in establishing a list of candidate genes, as described below.

(2) Having assembled a list of candidate genes generally the second step is to screen for variances in each candidate gene. Experimental and computational methods for variance detection are described in this invention, and tables of exemplary variances are provided (Table 3) as well as methods for identifying additional variances and a written description of such possible additional variances in the cDNAs of genes that may affect drug action (see Stanton & Adams, Application Ser. No. 09/300,747, filed Apr. 26, 1999, entitled GENE SEQUENCE VARIANCES WITH UTILITY IN DETERMINING THE TREATMENT OF DISEASE, incorporated in its entirety.

(3) Having identified variances in candidate genes the next step is to assess their likely contribution to clinical variation in patient response to therapy, preferably by using informatics-based approaches such as DNA and protein sequence analysis and protein modeling. The literature and informatics-based approaches provide the basis for prioritization of candidate genes, however it may in some cases be desirable to further narrow the list of candidate genes, or to measure experimentally the phenotype associated with specific variances or sets of variances (e.g. haplotypes).

(4) Thus, as a third step in candidate gene analysis, one skilled in the art may elect to perform in vitro or in vivo experiments to assess the functional importance of gene variances, using either biochemical or genetic tests. (Certain kinds of experiments—for example gene expression profiling and proteome analysis—may not only allow refinement of a candidate gene list but may also lead to identification of additional candidate genes.) Combination of two or all of the three above methods will provide sufficient information to narrow and prioritize the set of candidate genes and variances to a number that can be studied in a clinical trial with adequate statistical power.

(5) The fourth step is to design retrospective or prospective human clinical trials to test whether the identified allelic variance, variances, or haplotypes or combination thereof influence the efficacy or toxicity profiles for a given drug or other therapeutic intervention. It should be recognized that this fourth step is the crucial step in producing the type of data that would justify introducing a diagnostic test for at least one variance into clinical use. Thus while each of the above four steps are useful in particular instances of the invention, this final step is indispensable. Further guidance and examples of how to perform these five steps are provided below.

(6) A fifth (optional) step entails methods for using a genotyping test in the promotion and marketing of a treatment method. It is widely appreciated that there is a tendency in the pharmaceutical industry to develop many compounds for well established therapeutic targets. Examples include beta adrenergic blockers, hydroxymethylglutaryl (HMG) CoA reductase inhibitors (statins), dopamine D2 receptor antagonists and serotonin transporter inhibitors. Frequently the pharmacology of these compounds is quite similar in terms of efficacy and side effects. Therefore the marketing of one compound vs. other members of the class is a challenging problem for drug companies, and is reflected in the lesser success that late products typically achieve compared to the first and second approved products. It occurred to the inventors that genetic stratification can provide the basis for identifying a patient population with a superior response rate or improved safety to one member of a class of drugs, and that this information can be the basis for commercialization of that compound. Such a commercialization campaign can be directed at caregivers, particularly physicians, or at patients and their families, or both.

1. Identification of Candidate Genes Relevant to the Action of a Drug

Practice of this invention will often begin with identification of a specific pharmaceutical product, for example a drug, that would benefit from improved efficacy or reduced toxicity or both, and the recognition that pharmacogenetic investigations as described herein provide a basis for achieving such improved characteristics. The question then becomes which genes and variances, such as those provided in this application in Tables 1 and 3, would be most relevant to interpatient variation in response to the drug. As discussed above, the set of relevant genes includes both genes involved in the disease process and genes involved in the interaction of the patient and the treatment—for example genes involved in pharmacokinetic and pharmacodynamic action of a drug. The biological and biomedical literature and online databases provide useful guidance in selecting such genes. Specific guidance in the use of these resources is provided below.

Review the literature and online sources

One way to find genes that affect response to a drug in a particular disease setting is to review the published literature and available online databases regarding the pathophysiology of the disease and the pharmacology of the drug. Literature or online sources can provide specific genes involved in the disease process or drug response, or describe biochemical pathways involving multiple genes, each of which may affect the disease process or drug response.

Alternatively, biochemical or pathological changes characteristic of the disease may be described; such information can be used by one skilled in the art to infer a set of genes that can account for the biochemical or pathologic changes. For example, to understand variation in response to a drug that modulates interleukin-6 (IL-6) levels in a immune disorder associated with altered levels of IL-6 one would preferably study, at a minimum, variances in genes responsible for IL-6 biosynthesis, release from the cell, receptor binding, presynaptic reuptake, and degradation or metabolism. Genes responsible for each of these functions should be examined for variation that may account for interpatient differences in drug response or disease manifestations. As recognized by those skilled in the art, a comprehensive list of such genes can be obtained from textbooks, monographs and the literature.

There are several types of scientific information, described in some detail below, that are valuable for identifying a set of candidate genes to be investigated with respect to a specific disease and therapeutic intervention. First there is the medical literature, which provides basic information on disease pathophysiology and therapeutic interventions. A subset of this literature is devoted to specific description of pathologic conditions. Second there is the pharmacology literature, which will provide additional information on the mechanism of action of a drug (pharmacodynamics) as well as its principal routes of metabolic transformation (pharmacokinetics) and the responsible proteins. Third there is the biomedical literature (principally genetics, physiology, biochemistry and molecular biology), which provides more detailed information on metabolic pathways, protein structure and function and gene structure. Fourth, there are a variety of online databases that provide additional information on metabolic pathways, gene families, protein function and other subjects relevant to selecting a set of genes that are likely to affect the response to a treatment.

Medical Literature

A good starting place for information on molecular pathophysiology of a specific disease is a general medical textbook such as *Harrison's Principles of Internal Medicine*, 14th edition, (2 Vol Set) by A. S. Fauci, E. Braunwald, K. J. Isselbacher, et al. (editors), McGraw Hill, 1997, or *Cecil Textbook of Medicine* (20th Ed) by R. L. Cecil, F. Plum and J. C. Bennett (Editors) W B Saunders Co., 1996. For pediatric diseases texts such as *Nelson Textbook of Pediatrics* (15th edition) by R. E. Behrman, R. M. Kliegman, A. M. Arvin and W. E. Nelson (Editors), W B Saunders Co., 1995 or *Oski's Principles and Practice of Pediatrics* (3rd Edition) by J. A. Mamillan & F. A. Oski Lippincott-Raven, 1999 are useful introductions. For obstetrical and gynecological disorders texts such as *Williams Obstetrics* (20th Ed) by F. G. Cunningham, N. F. Gant, P. C. McDonald et al. (Editors), Appleton & Lange, 1997 provide general information on disease pathophysiology. For psychiatric disorders texts such as the *Comprehensive Textbook of Psychiatry*, VI (2 Vols) by H. I. Kaplan and B. J. Sadock (Editors), Lippincott, Williams & Wilkins, 1995, or *The American Psychiatric Press Textbook of Psychiatry* (3rd edition) by R. E. Hales, S. C. Yudofsky and J. A. Talbott (Editors) Amer Psychiatric Press, 1999 provide an overview of disease nosology, pathophysiological mechanisms and treatment regimens.

In addition to these general texts, there are a variety of more specialized medical texts that provide greater detail about specific disorders which can be utilized in developing a list of candidate genes and variances relevant to interpatient variation in response to a treatment. For example, within the field of medicine there are standard textbooks for each of the subspecialties. Some examples include:

*Heart Disease: A Textbook of Cardiovascular Medicine* (2 Volume set) by E. Braunwald (Editor), W B Saunders Co., 1996.

*Hurst's the Heart, Arteries and Veins* (9th Ed) (2 Vol Set) by R. W. Alexander, R. C. Schlant, V. Fuster, W. Alexander and E. H. Sonnenblick (Editors) McGraw Hill, 1998.

*Principles of Neurology* (6th edition) by R. D. Adams, M. Victor (editors), and A. H. Ropper (Contributor), McGraw Hill, 1996.

*Sleisenger & Fordtran's Gastrointestinal and Liver Disease: Pathophysiology, Diagnosis, Management* (6th edition) by M. Feldman, B. F. Scharschmidt and M. Sleisenger (Editors), W B Saunders Co., 1997.

*Textbook of Rheumatology* (5th edition) by W. N. Kelley, S. Ruddy, E. D. Harris Jr. and C. B. Sledge (Editors) (2 volume set) W B Saunders Co., 1997.

*Williams Textbook of Endocrinology* (9th edition) by J. D. Wilson, D. W. Foster, H. M. Kronenberg and Larsen (Editors), W B Saunders Co., 1998.

*Wintrobe's Clinical Hematology* (10th Ed) by G. R. Lee, J. Foerster (Editor) and J. Lukens (Editors) (2 Volumes) Lippincott, Williams & Wilkins, 1998.

*Cancer: Principles & Practice of Oncology* (5th edition) by V. T. Devita, S. A. Rosenberg and S. Hellman (editors), Lippincott-Raven Publishers, 1997.

*Principles of Pulmonary Medicine* (3rd edition) by S. E. Weinberger & J Fletcher (Editors), W B Saunders Co., 1998.

*Diagnosis and Management of Renal Disease and Hypertension* (2nd edition) by A. K. Mandal & J. C. Jennette (Editors), Carolina Academic Press, 1994.*Massry & Glassock's Textbook of Nephrology* (3rd edition) by S. G. Massry & R. J. Glassock (editors) Williams & Wilkins, 1995.

*The Management of Pain* by J. J. Bonica, Lea and Febiger, 1992

*Ophthalmology* by M. Yanoff & J. S. Duker, Mosby Year Book, 1998

*Clinical Ophthalmology: A Systemic Approach* by J. J. Kanski, Butterworth-Heineman, 1994.*Essential Otolaryngology* by J. K. Lee Appleton and Lange 1998.

In addition to these subspecialty texts there are many textbooks and monographs that concern more restricted disease areas, or specific diseases. Such books provide more extensive coverage of pathophysiologic mechanisms and therapeutic options. The number of such books is too great to provide examples for all but a few diseases, however one skilled in the art will be able to readily identify relevant texts. One simple way to search for relevant titles is to use the search engine of an online bookseller such as http://www.amazon.com or http://www.barnesandnoble.com using the disease or drug (or the group of diseases or drugs to which they belong) as search terms. For example a search for asthma would turn up titles such as *Asthma: Basic Mechanisms and Clinical Management* (3rd edition) by P. J. Barnes, I. W. Rodger and N. C. Thomson (Editors), Academic Press, 1998 and *Airways and Vascular Remodelling in Asthma and Cardiovascular Disease: Implications for Therapeutic Intervention,* by C. Page & J. Black (Editors), Academic Press, 1994.

Pathology Literature

In addition to medical texts there are texts that specifically address disease etiology and pathologic changes associated with disease. A good general pathology text is *Robbins Pathologic Basis of Disease* (6th edition) by R. S. Cotran, V. Kumar, T. Collins and S. L. Robbins, W B Saunders Co., 1998. Specialized pathology texts exist for each organ system and for specific diseases, similar to medical texts. These texts are useful sources of information for one skilled in the art for developing lists of genes that may account for some of the known pathologic changes in disease tissue. Exemplary texts are as follows:

*Bone Marrow Pathology* $2^{nd}$ edition, by B. J. Bain, I. Lampert. & D. Clark, Blackwell Science, 1996

*Atlas of Renal Pathology* by F. G. Silva, W. B. Saunders, 1999.

*Fundamentals of Toxicologic Pathology* by W. M. Haschek and C. G. Rousseaux, Academic Press, 1997.

*Gastrointestinal Pathology* by P. Chandrasoma, Appleton and Lange, 1998.

*Ophthalmic Pathology with Clinical Correlations* by J. Sassani, Lippincott-Raven, 1997.

Pathology of Bone and Joint Disordersby F. McCarthy, F. J. Frassica and A. Ross, W. B. Saunders, 1998.

*Pulmonary Pathology* by M. A. Grippi, Lippicott-Raven, 1995.

*Neuropathology* by D. Ellison, L. Chimelli, B. Harding, S. Love& J. Lowe, Mosby Year Book, 1997.

*Greenfield's Neuropatholgy* $6^{th}$ edition by J. G. Greenfield, P. L. Lantos & D. I. Graham, Edward Arnold, 1997.

Pharmacology, Pharmacogenetics and Pharmacy Literature

There are also both general and specialized texts and monographs on pharmacology that provide data on pharmacokinetics and pharmacodynamics of drugs. The discussion of pharmacodynamics (mechanism of action of the drug) in such texts is often supported by a review of the biochemical pathway or pathways that are affected by the drug. Also, proteins related to the target protein are often listed; it is important to account for variation in such proteins as the related proteins may be involved in drug pharmacology. For example, there are 14 known serotonin receptors. Various pharmacological serotonin agonists or antagonists have different affinities for these different receptors. Variation in a specific receptor may affect the pharmacology not only of drugs targeted to that receptor, but also drugs that are principally agonists or antagonists of different receptors. Such compounds may produce different effects on two allelic forms of a non-targeted receptor; for example on variant form may bind the compound with higher affinity than the other, or a compound that is principally an antagonist for one allele may be a partial agonist for another allele. Thus genes encoding proteins structurally related to the target protein should be screened for variance in order to successfully realize the methods of the present invention. A good general pharmacology text is *Goodman & Gilman's the Pharmacological Basis of Therapeutics* (9th Ed) by J. G. Hardman, L. E. Limbird, P. B. Molinoff, R. W. Ruddon and A. G. Gilman (Editors) McGraw Hill, 1996. There are also texts that focus on the pharmacology of drugs for specific disease areas, or specific classes of drugs (e.g. natural products) or adverse drug interactions, among other subjects. Specific examples include:

*The American Psychiatric Press Textbook of Psychopharmacology* (2nd edition) by A. F. Schatzberg & C. B. Nemeroff (Editors), American Psychiatric Press, 1998.

*Essential Psychopharmacology: Neuroscientific Basis and Practical Applications* by N. Muntner and S. M. Stahl, Cambridge Univ Press, 1996.

There are also texts on pharmacogenetics which are particularly useful for identifying genes which may contribute to variable pharmacokinetic response. In addition there are texts on some of the major xenobiotic metabolizing proteins, such as the cytochrome P450 genes.

*Pharmacogenetics of Drug Metabolism* (International Encyclopedia of Pharmacology and Therapeutics) by Werner Kalow (Editor) Pergamon Press, 1992.

*Genetic Factors in Drug Therapy: Clinical and Molecular Pharmacogenetics* by D. A Price Evans, Cambridge Univ Press, 1993.

*Pharmacogenetics* (Oxford Monographs on Medical Genetics, 32) by W. W. Weber, Oxford Univ Press, 1997.

*Cytochrome P450: Structure. Mechanism, and Biochemistry* by P. R. Ortiz de Montellano (Editor), Plenum Publishing Corp, 1995.

*Appleton & Lange's Review of Pharmacy,* $6^{th}$ edition, (Appleton & Lange's Review Series) by G. D. Hall & B. S. Reiss, Appleton & Lange, 1997.

Genetics, Biochemistry and Molecular Biology Literature

In addition to the medical, pathology, and pharmacology texts listed above there are several information sources that one skilled in the art will turn to for information on the genetic, physiologic, biochemical, and molecular biological aspects of the disease, disorder or condition or the effect of the therapeutic intervention on specific physiologic processes. The biomedical literature may include information on nonhuman organisms that is relevant to understanding the likely disease or pharmacological pathways in man.

Also provided below are illustrative texts which will aid in the identification of a pathway or pathways, and a gene or genes that may be relevant to interindividual variation in response to a therapy. Textbooks of biochemistry, genetics and physiology are often useful sources for such pathway information. In order to ascertain the appropriate methods to analyze the effects of an alleleic variance, variances, or haplotypes in vitro, one skilled in the art will review existing information on molecular biology, cell biology, genetics, biochemistry; and physiology. Such texts are useful sources for general and specific information on the genetic and biochemical processes involved in disease and in drug action, as well as experimental procedures that may be useful in performing in vitro research on an allelic variance, variances, or haplotye.

Texts on gene structure and function and RNA biochemistry will be useful in evaluating the consequences of variances that do not change the coding sequence (silent variances). Such variances may alter the interaction of RNA with proteins or other regulatory molecules affecting RNA processing, polyadenylation, or export.

Molecular and Cellular Biology

*Molecular Cell Biology* by H. Lodish, D. Baltimore, A. Berk, L. Zipurksy & J. Darnell, W H Freeman & Co., 1995.

*Essentials of Molecular Biology,* D. Freifelder and MalacinskiJones and Bartlett, 1993.

*Genes and Genomes: A Changing Perspective,* M. Singer and P. Berg, 1991. University Science Books

*Gene Structure and Expression,* J. D. Hawkins, 1996. Cambridge University Press

*Molecular Biology of the Cell,* 2nd edition, B. Alberts et al., Garland Publishing, 1994.

Molecular Genetics

*The Metabolic and Molecular Bases of Inherited Disease* by C. R. Scriver, A. L. Beaudet, W. S. Sly (Editors), 7th edition, McGraw Hill, 1995

*Genetics and Molecular Biology*, R. Schleif, 1994. 2nd edition, Johns Hopkins University Press

*Genetics*, P. J. Russell, 1996. 4th edition, Harper Collins

*An Introduction to Genetic Analysis*, Griffiths et al.1993. 5th edition, W. H. Freeman and Company

*Understanding Genetics: A molecular approach*, Rothwell, 1993. Wiley-Liss

General Biochemistry

*Biochemistry*, L. Stryer, 1995. W. H. Freeman and Company

*Biochemistry*, D. Voet and J. G. Voet, 1995. John Wiley and Sons

*Principles of Biochemistry*, A. L. Lehninger, D. L. Nelson, and M. M. Cox, 1993. Worth Publishers

*Biochemistry*, G. Zubay, 1998. Wm. C. Brown Communications

*Biochemistry*, C. K. Mathews and K. E. van Holde, 1990. Benjamin/Cummings

Transcription

*Eukaryotic Transcriptiuon Factors*, D. S. Latchman, 1995. Academic Press

*Eukarvotic Gene Transcription*, S. Goodbourn (ed.), 1996. Oxford University Press.

*Transcription Factors and DNA Replication*, D. S. Pederson and N. H. Heintz, 1994. CRC Press/R. G. Landes Company

*Transcriptional Regulation*, S. L. McKnight and K. Yamamoto (eds.), 1992. 2 volumes, Cold Spring Harbor Laboratory Press

RNA

*Control of Messenger RNA Stability*, J. Belasco and G. Brawerman (eds.), 1993. Academic Press

*RNA-Protein Interactions*, Nagai and Mattaj (eds.), 1994. Oxford University Press

*mRNA Metabolism and Post-transcriptional Gene Regulation*, Harford and Morris (eds.), 1997. Wiley-Liss Translation

*Translational Control*, J. W. B. Hershey, M. B. Mathews, and N. Sonenberg (eds.), 1995. Cold Spring Harbor Laboratory Press General Physiology

*Textbook of Medical Physiology* $9^{th}$ Edtion by A. C. Guyton and J. E. Hall W. B. Saunders, 1997

*Review of Medical Physiology*, $18^{th}$ Edition by W. F. Ganong, Appleton and Lange, 1997

Online Databases

Those skilled in the art are familiar with how to search the biomedical literature, such as, e.g., libraries, online PubMed, abstract listings, and online mutation databases. One particularly useful resource is maintained at the web site of the National Center for Biotechnology Information (ncbi):

>   http://www.ncbi.nlm.nih.gov/. From the ncbi site one can access Online Mendelian Inheritance in Man (OMIM),. OMIM can be found at:
>   http://www3.ncbi.nlm.nih.gov/Omim/searchomim.html. OMIM is a medically oriented database of genetic information with entries for thousands of genes. The OMIM record number is provided for many of the genes in Tables 1 and 3 (see column 3), and constitutes an excellent entry point for identification of references that point to the broader literature. Another useful site at NCBI is the Entrez browser, located at http://www3.ncbi.nlm.nih.gov/Entrez/. One can search genomes, polynucleotides, proteins, 3D structures, taxonomy or the biomedical literature (PubMed) via the Entrez site. More generally links to a number of useful sites with biomedical or genetic data are maintained at sites such as Med Web at the Emory University Health Sciences Center Library:
>   htt://WWW.MedWeb.Emory.Edu/MedWeb/; Riken, a Japanese web site at:
>   http://www.rtc.riken.go.jp/othersite.html with links to DNA sequence, structural, molecular biology, bioinformatics, and other databases; at the Oak Ridge National Laboratory web site: http://www.ornl.gov/hgmis/links.html; or at the Yahoo website of Diseases and Conditions:
>   http://dir.yahoo.com/health/diseases and conditions/index.html. Each of the indicated web sites has additional useful links to other sites.

Another type of database with utility in selecting the genes on a biochemical pathway that may affect the response to a drug are databases that provide information on biochemical pathways. Examples of such databases include the Kyoto Encyclopedia of Genes and Genomes (KEGG), which can be found at:

>   http://www.genome.ad.jp/kegg/kegg.html. This site has pictures of many biochemical pathways, as well as links to other metabolic databases such as the well known Boehringer Mannheim biochemical pathways charts:
>   http://www.expasy.ch/cgi-bin/search-biochem-index. The metabolic charts at the latter site are comprehensive, and excellent starting points for working out the salient enzymes on any given pathway.

Each of the web sites mentioned above has links to other useful web sites, which in turn can lead to additional sites with useful information.Research Libraries Those skilled in the art will often require information found only at large libraries. The National Library of Medicine (http://www.nlm.nih.gov/) is the largest medical library in the world and its catalogs can be searched online. Other libraries, such as university or medical school libraries are also useful to conduct searches. Biomedical books such as those referred to above can often be obtained from online bookstores as described above.

Biomedical Literature

To obtain up to date information on drugs and their mechanism of action and biotransformation; disease pathophysiology; biochemical pathways relevant to drug action and disease pathophysiology; and genes that encode proteins relevant to drug action and disease one skilled in the art will consult the biomedical literature . A widely used, publically accessible web site for searching published journal articles is PubMed (http://www.ncbi.nlm.nih.gov/PubMed/). At this site, one can search for the most recent articles (within the last 1–2 months) or oler literature (back to 1966). Many Journals also have their own sites on the world wide web and can be searched online. For example see the IDEAL web site at:

>   http://www.apnet.com/www/ap/aboutid.html. This site is an online library, featuring full text journals from Academic Press and selected journals from W. B. Saunders and Churchill Livingstone. The site provides access (for a fee) to nearly 2000 scientific, technical, and medical journals.

Experimental methods for identification of genes involved in the action of a drug There are a number of experimental methods for identifying genes and gene products that mediate or modulate the effects of a drug or other treatment. They encompass analyses of RNA and protein expression as well as methods for detecting protein—protein interactions and protein—ligand interactions. Two preferred experimental methods for identification of genes that may be involved in the action of a drug are (1) methods for measuring the expression levels of many MRNA transcripts in cells or organisms treated with the drug (2) methods for measuring the expression levels of many proteins in cells or organisms treated with the drug.

RNA transcripts or proteins that are substantially increased or decreased in drug treated cells or tissues relative to control cells or tissues are candidates for mediating the action of the drug. Preferably the level of an MRNA is at least 30% higher or lower in drug treated cells, more preferably at least 50% higher or lower, and most preferably two fold higher or lower than levels in non-drug treated control cells. The analysis of RNA levels can be performed on total RNA or on polyadenylated RNA selected by oligodT affinity. Further, RNA from different cell compartments can be analyzed independently—for example nuclear vs. cytoplasmic RNA. In addition to RNA levels, RNA kinetics can be examined, or the pool of RNAs currently being translated can be analyzed by isolation of RNA from polysomes. Other useful experimental methods include protein interaction methods such as the yeast two hybrid system and variants thereof which facilitate the detection of protein—protein interactions. Preferably one of the interacting proteins is the drug target or another protein strongly implicated in the action of the compound being assessed.

The pool of RNAs expressed in a cell is sometimes referred to as the transcriptome. Methods for measuring the transcriptome, or some part of it, are known in the art. A recent collection of articles summarizing some current methods appeared as a supplement to the journal *Nature Genetics*. (The Chipping Forecast. Nature Genetics supplement, volume 21, January 1999.) A preferred method for measuring expression levels of mRNAs is to spot PCR products corresponding to a large number of specific genes on a nylon membrane such as Hybond N Plus (Amersham-Pharmacia). Total cellular MRNA is then isolated, labelled by random oligonucleotide priming in the presence of a detectable label (e.g. alpha 33P labelled radionucleotides or dye labelled nucleotides), and hybridized with the filter containing the PCR products. The resulting signals can be analyzed by commercially available software, such as can be obtained from Clontech/Molecular Dynamics or Research Genetics, Inc.

Experiments have been described in model systems that demonstrate the utility of measuring changes in the transcriptome before and after changing the growth conditions of cells, for example by changing the nutrient environment. The changes in gene expression help reveal the network of genes that mediate physiological responses to the altered growth condition. Similarly, the addition of a drug to the cellular or in vivo environment, followed by monitoring the changes in gene expression can aid in identification of gene networks that mediate pharmacological responses.

The pool of proteins expressed in a cell is sometimes referred to as the proteome. Studies of the proteome may include not only protein abundance but also protein subcellular localization and protein-protein interaction. Methods for measuring the proteome, or some part of it, are known in the art. One widely used method is to extract total cellular protein and separate it in two dimensions, for example first by size and then by isoelectric point. The resulting protein spots can be stained and quantitated, and individual spots can be excised and analyzed by mass spectrometry to provide definitive identification. The results can be compared from two or more cell lines or tissues, at least one of which has been treated with a drug. The differential up or down modulation of specific proteins in response to drug treatment may indicate their role in mediating the pharmacologic actions of the drug. Another way to identify the network of proteins that mediate the actions of a drug is to exploit methods for identifying interacting proteins. By starting with a protein known to be involved in the action of a drug—for example the drug target—one can use systems such as the yeast two hybrid system and variants thereof (known to those skilled in the art; see Ausubel et al., Current Protocols in Molecular Biology, op. cit.) to identify additional proteins in the network of proteins that mediate drug action. The genes encoding such proteins would be useful for screening for DNA sequence variances, which in turn may be useful for analysis of interpatient variation in response to treatments. For example, the protein 5-lipoxygenase (5LO) is an enzyme which is at the beginning of the leukotriene biosynthetic pathway and is a target for anti-inflammatory drugs used to treat asthma and other diseases. In order to detect proteins that interact with 5-lipoxygenase the two-hybrid system was recently used to isolate three different proteins, none previously known to interact with 5LO. (Provost et al., Interaction of 5-lipoxygenase with cellular proteins. *Proc. Natl. Acad. Sci. U.S.A.* 96: 1881–1885, 1999.) A recent collection of articles summarizing some current methods in proteomics appeared in the August 1998 issue of the journal *Electrophoresis* (volume 19, number 11). Other useful articles include: Blackstock WP, et al.

Proteomics: quantitative and physical mapping of cellular proteins. *Trends Biotechnol.* 17 (3): p. 121–7, 1999, and Patton W. F., Proteome analysis II. Protein subcellular redistribution: linking physiology to genomics via the proteome and separation technologies involved. *J Chromatogr B Biomed Sci App.* 722(1–2):203–23. 1999.

Since many of these methods can also be used to assess whether specific polymorphisms are likely to have biological effects, they are also relevant in section 3, below, concerning methods for assessing the likely contribution of variances in candidate genes to clinical variation in patient responses to therapy.

2. Screen for Variances in Genes that may be Related to Therapeutic Response

Having identified a set of genes that may affect response to a drug the next step is to screen the genes for variances that may account for interindividual variation in response to the drug. There are a variety of levels at which a gene can be screened for variances, and a variety of methods for variance screening. The two main levels of variance screening are genomic DNA screening and cDNA screening. Genomic variance detection may include screening the entire genomic segment spanning the gene from 2 kb to 10 kb upstream of the transcription start site to the polyadenylation site, or 2 to 10 kb beyond the polyadenylation site. Alternatively genomic variance detection may (for intron containing genes) include the exons and some region around them containing the splicing signals, for example, but not all of the intronic sequences. In addition to screening introns and exons for variances it is generally desirable to screen regulatory DNA sequences for variances. Promoter, enhancer and silencer and other regulatory elements have been described in human genes. The promoter is generally proximal to the transcription start site, although there may be several promoters and several transcription start sites. Enhancer, silencer and other regulatory elements may be intragenic or may lie outside the introns and exons, possibly at a considerable distance, such as 100 kb away. Variances in such sequences may affect basal gene expression or regulation of gene expression. In either case such variation may affect the response of an individual patient to a therapeutic intervention, for example a drug, as described in the examples. Thus in practicing the present invention it is useful to screen regulatory sequences as well as transcribed sequences, in order to identify variances that may affect gene transcription. Frequently the genomic sequence of a gene can be found in the sources above, particularly by searching GenBank or Medline (PubMed). The name of the gene can be entered at a site such as Entrez:

http://www.ncbi.nlm.nih.gov/Entrez/nucleotide.html.
Using the genomic sequence and information from the biomedical literature one skilled in the art can perform a variance detection procedure such as those described in examples 15, 16 and 17.

Variance detection is often first performed on the cDNA of a gene for several reasons. First, available data on functional sequence variances suggests that variances in the transcribed portion of a gene may be most likely to have functional consequences as they can affect the interaction of the transcript with a wide variety of cellular factors during the complex processes of RNA transcription, processing and translation, with consequent effects on RNA splicing, stability, translational efficiency or other processes. Second, as a practical matter the cDNA sequence of a gene is often available before the genomic structure is known, although the reverse will be true in the future as the sequence of the human genome is determined. Third, the cDNA is often compact compared to the genomic locus, and can be screened for variances with much less effort. If the genomic structure is not known then only the cDNA seqence can be scanned for variances. Methods for preparing cDNA are described in Example 14. Methods for variance detection on cDNA are described below and in the examples.

In general it is preferable to catalog genetic variation at the genomic DNA level because there are an increasing number of well documented instances of functionally important variances that lie outside of transcribed sequence. Also, to properly use optimal genetic methods to assess the contribution of a candidate gene to variation in a phenotype of interest it is desirable to understand the character of sequence variation in the candidate gene: what is the nature of linkage disequilibrium between different variances in the gene; are there sites of recombination within the gene; what is the extent of homoplasy in the gene (i.e. occurance of two variant sites that are identical by state but not identical by descent because the same variance arose at least twice in human evolutionary history on two different haplotypes); what are the different haplotypes and how can they be grouped to increase the power of genetic analysis?

Methods for variance screening have been described, including DNA sequencing. See for example: U.S. Pat. No. 5,698,400: Detection of mutation by resolvase cleavage; U.S. Pat. No. 5,217,863: Detection of mutations in nucleic acids; and U.S. Pat. No. 5,750,335: Screening for genetic variation, as well as the examples and references cited therein for examples of useful variance detection procedures. Detailed variance detection procedures are also described in examples 15, 16 and 17. One skilled in the art will recognize that depending on the specific aims of a variance detection project (number of genes being screened, number of individuals being screened, total length of DNA being screened) one of the above cited methods may be preferable to the others, or yet another procedure may be optimal. A preferred method of variance detection is chain terminating DNA sequencing using dye labeled primers, cycle sequencing and software for assessing the quality of the DNA sequence as well as specialized software for calling heterozygotes. The use of such procedures has been described by Nickerson and colleagues. See for example: Rieder M. J., et al. Automating the identification of DNA variations using quality-based fluorescence re-sequencing: analysis of the human mitochondrial genome. *Nucleic Acids Res.* 26 (4):967–73, 1998, and: Nickerson D. A., et al. PolyPhred: automating the detection and genotyping of single nucleotide substitutions using fluorescence-based resequencing. *Nucleic Acids Res.* 25 (14):2745–51, 1997.Although the variances provided in Table 3 comprise principally of cDNA variances, it is an aspect of this invention that detection of genomic variances is also a useful method for identification of variances that may account for interpatient variation in response to a therapy.

Another important aspect of variance detection is the use of DNA from a panel of human subjects that represents a known population. For example, if the subjects are being screened for variances relevant to a specific drug development program it is desirable to include both subjects with the target disease and healthy subjects in the panel, because certain variances may occur at different frequencies in the healthy and disease populations and can only be reliably detected by screening both populations. Also, for example, if the drug development program is taking place in Japan, it is important to include Japanese individuals in the screening population. In general, it is always desirable to include subjects of known geographic, racial or ethnic identity in a variance screening experiment so the results can be interpreted appropriately for different patient populations, if necessary. Also, in order to select optimal sets of variances for genetic analysis of a gene locus it is desirable to know which variances have occurred recently—perhaps on multiple different chromosomes—and which are ancient. Inclusion of one or more apes or monkees in the variance screening panel is one way of gaining insight into the evolutionary history of variances. Chimpanzees are preferred subjects for inclusion in a variance screening panel.

3. Assess the Likely Contribution of Variances in Candidate Genes to Clinical Variation in Patient Responses to Therapy Once a set of genes likely to affect disease pathophysiology or drug action has been identified, and those genes have been screened for variances, said variances (e.g., provided in Table 3) can be assessed for their contribution to variation in the pharmacological or toxicological phenotypes of interest. Such studies are useful for reducing a large number of candidate variances to a smaller number of variances to be tested in clinical trials. There are several methods which can be used in the present invention for assessing the medical and pharmaceutical implications of a DNA sequence variance. They range from computational methods to in vitro and/or in vivo experimental methods, to prospective human clinical trials, and also include a variety of other laboratory and clinical measures that can provide evidence of the medical consequences of a variance. In general, human clinical trials constitute the highest standard of proof that a variance or set of variances is useful for selecting a method of treatment, however, computational and in vitro data, or retrospective analysis of human clinical data may provide strong evidence that a particular variance will affect response to a given therapy, often at lower cost and in less time than a prospective clinical trial. Moreover, at an early stage in the analysis when there are many possible hypotheses to explain interpatient variation in treatment response, the use of informatics-based approaches to evaluate the likely functional effects of specific variances is an efficient way to proceed.

Informatics-based approaches to the prediction of the likely functional effects of variances include DNA and protein sequence analysis (phylogenetic approaches and motif searching) and protein modeling (based on coordinates in the protein database, or pdb; see http://www.rcsb.org/pdb/). See, for example: Kawabata et al. The Protein Mutant Database. Nucleic Acids Research 27: 355–357, 1999; also available at: http://pmd.ddbj.nig.ac.jp. Such analyses can be performed quickly and inexpensively, and the results may allow selection of certain genes for more extensive in vitro or in vivo studies or for more variance detection or both.

The three dimensional structure of many medically and pharmaceutically important proteins, or homologs of such proteins in other species, or examples of domains present in such proteins, is known as a result of x-ray crystallography studies and, increasingly, nuclear magnetic resonance studies. Further, there are increasingly powerful tools for modeling the structure of proteins with unsolved structure, particularly if there is a related (homologous) protein with known structure. (For reviews see: Rost et al., Protein fold recognition by prediction-based threading, *J. Mol. Biol.* 270:471–480, 1997; Firestine et al., Threading your way to protein function, *Chem. Biol.* 3:779–783, 1996) There are also powerful methods for identifying conserved domains and vital amino acid residues of proteins of unknown structure by analysis of phylogenetic relationships. (Deleage et al., Protein structure prediction: Implications for the biologist, *Biochimie* 79:681–686, 1997; Taylor et al., Multiple protein structure alignment, *Protein Sci.* 3:1858–1870, 1994) These methods can permit the prediction of functionally important variances, either on the basis of structure or evolutionary conservation. For example, a crystal structure can reveal which amino acids comprise a small molecule binding site. The identification of a polymorphic amino acid variance in the topological neighborhood of such a site, and, in particular, the demonstration that at least one variant form of the protein has a variant amino acid which impinges on (or which may otherwise affect the chemical environment around) the small molecule binding pocket differently from another variant form, provides strong evidence that the variance may affect the function of the protein. From this it follows that the interaction of the protein with a treatment method, such an administered compound, will likely be variable between different patients. One skilled in the art will recognize that the application of computational tools to the identification of functionally consequential variances involves applying the knowledge and tools of medicinal chemistry and physiology to the analysis.

Phylogenetic approaches to understanding sequence variation are also useful. Thus if a sequence variance occurs at a nucleotide or encoded amino acid residue where there is usually little or no variation in homologs of the protein of interest from non-human species, particularly evolutionarily remote species, then the variance is more likely to affect function of the RNA or protein. Computational methods for phylogenetic analysis are known in the art, (see below for citations of some methods).

Computational methods are also useful for analyzing DNA polymorphisms in transcriptional regulatory sequences, including promoters and enhancers. One useful approach is to compare variances in potential or proven transcriptional regulatory sequences to a catalog of all known transcriptional regulatory sequences, including consensus binding domains for all transcription factor binding domains. See, for example, the databases cited in: Burks, C. Molecular Biology Database List. *Nucleic Acids Research* 27: 1–9, 1999, and links to useful databases on the internet at:

http://www.oup.co.uk/nar/Volume 27/issue 01/summary/gkc105 gml.html. In particular see the Transcription Factor Database (Heinemeyer, T., et al. (1999) Expanding the TRANSFAC database towards an expert system of regulatory molecular mechanisms. *Nucleic Acids Res.* 27: 318–322, or on the internet at:

http://193.175.244.40/TRANSFAC/index.html). Any sequence variances in transcriptional regulatory sequences can be assessed for their effects on mRNA levels using standard methods, either by making plasmid constructs with the different allelic forms of the sequence, transfecting them into cells and measuring the output of a reporter transcript, or by assays of cells with different endogenous alleles of variances. One example of a polymorphism in a transcriptional regulatory element that has a pharmacogenetic effect is described by Drazen et al. (1999) Pharmacogenetic association between ALOX5 promoter genotype and the response to anti-asthma treatment. *Nature Genetics* 22: 168–170. Drazen and co-workers found that a polymorphism in an Sp1-transcription factor binding domain, which varied among subjects from 3–6 tandem copies, accounted for varied expression levels of the 5-lipoxygenase gene when assayed in vitro in reporter construct assays. This effect would have been flagged by an informatics analysis that surveyed the 5-lipoxygenase candidate promoter region for transcriptional regulatory sequences (resulting in discovery of polymorphism in the Sp1 motif).

4. Perform in vitro or in vivo Experiments to Assess the Functional Importance of Gene Variances There are two broad types of studies useful for assessing the likely importance of variances: analysis of RNA or protein abundance (as described above in the context of methods for identifying candidate genes for explaining interpatient variation in treatment response) or analysis of functional differences in different variant forms of a gene, MRNA or protein. Studies of functional differences may involve direct measurements of biochemical activity of different variant forms of an MRNA or protein, or may involve assaying the influence of a variance or variances on various cell properties, including both tissue culture and in vivo studies.

The selection of an appropriate experimental program for testing the medical consequences of a variance may differ depending on the nature of the variance, the gene, and the disease. For example if there is already evidence that a protein is involved in the pharmacologic action of a drug, then the in vitro or in vivo demonstration that an amino acid variance in the protein affects its biochemical activity is strong evidence that the variance will have an effect on the pharmacology of the drug in patients, and therefore that patients with different variant forms of the gene may have different responses to the same dose of drug. If the variance is silent with respect to protein coding information, or if it lies in a noncoding portion of the gene (e.g., a promoter, an intron, or a 5'- or 3'-untranslated region) then the appropriate biochemical assay may be to assess MRNA abundance, half life, or translational efficiency. If, on the other hand, there is no substantial evidence that the protein encoded by a particular gene is relevant to drug pharmacology, but instead is a candidate gene on account of its involvement in disease pathophysiology, then the optimal test may be a clinical study addressing whether two patient groups distinguished on the basis of the variance respond differently to a therapeutic intervention. This approach reflects the current reality that biologists do not sufficiently understand gene regulation, gene expression and gene function to consistently make accurate inferences about the consequences of DNA sequence variances for pharmacological responses.

In summary, if there is a plausible hypothesis regarding the effect of a protein on the action of a drug, then in vitro and in vivo approaches, including those described below, will be useful to predict whether a given variance is therapeutically consequential. If, on the other hand, there is no evidence of such an effect, then the preferred test is an empirical clinical measure of the impact to the variance on efficacy or toxicity in vivo (which requires no evidence or assumptions regarding the mechanism by which the variance may exert an effect on a therapeutic response). However, given the expense and statistical constraints of clinical trials, it is preferable to limit clinical testing to variances for which there is at least some experimental or computational evidence of a functional effect.

Experimental Methods: Genomic DNA Analysis

Variances in DNA may affect the basal transcription or regulated transcription of a gene locus. Such variances may be located in any part of the gene but are most likely to be located in the promoter region, the first intron, or in 5' or 3' flanking DNA, where enhancer or silencer elements may be located. Methods for analyzing transcription are well known to those skilled in the art and exemplary methods are briefly described above and in some of the texts cited elsewhere in this application. Transcriptional run off assay is one useful method. Detailed protocols can be found in texts such as: *Current Protocols in Molecular Biology* edited by: F. M. Ausubel, et al. John Wiley & Sons, Inc, 1999, or: *Molecular Cloning: A Laboratory Manual* by J. Sambrook, E. F. Fritsch and T Maniatis. 1989. 3 vols, 2nd edition, Cold Spring Harbor Laboratory Press Experimental Methods: RNA Analysis RNA variances may affect a wide range of processes including RNA splicing, polyadenylation, capping, export from the nucleus, interaction with translation intiation, elongation or termination factors, or the ribosome, or interaction with cellular factors including regulatory proteins, or factors that may affect mRNA half life. However, the effect of most RNA sequence variances on RNA function, if any, should ultimately be measurable as an effect on RNA or protein levels—either basal levels or regulated levels or levels in some abnormal cell state, such as cells from patients with a disease. Therefore, one preferred method for assessing the effect of RNA variances on RNA function is to measure the levels of RNA produced by different alleles in one or more conditions of cell or tissue growth. Said measuring can be done by conventional methods such as Northern blots or RNAase protection assays (kits available from Ambion, Inc.), or by methods such as the Taqman assay (developed by the Applied Biosystems Division of the Perkin Elmer Corporation), or by using arrays of oligonucleotides or arrays of cDNAs attached to solid surfaces. Systems for arraying cDNAs are available commercially from companies such as Nanogen and General Scanning. Complete systems for gene expression analysis are available from companies such as Molecular Dynamics. For recent reviews of systems for high throughput RNA expression analysis see the supplement to volume 21 of Nature Genetics entitled "The Chipping Forecast", especially articles beginning on pages 9, 15, 20 and 25.

Additional methods for analyzing the effect of variances on RNA include secondary structure probing, and direct measurement of half life or turnover. Secondary structure can be determined by techniques such as enzymatic probing (using enzymes such as T1, T2 and S1 nuclease), chemical probing or RNAase H probing using oligonucleotides. Most RNA structural assays are performed in vitro, however some techniques can be performed on cell extracts or even in living cells, using fluorescence resonance energy transfer to monitor the state of RNA probe molecules.

Experimental Methods: Protein Analysis

There are a variety of experimental methods for investigating the effect of an amino acid variance on response of a patient to a treatment. The preferred method will depend on the availability of cells expressing a particular protein, and the feasibility of a cell-based assay vs. assays on cell extracts, on proteins produced in a foreign host, or on proteins prepared by in vitro translation.

For example, the methods and systems listed below can be utilized to demonstrate differential expression, stability and/or activity of different variant forms of a protein, or in phenotype/genotype correlations in a model system.

For the determination of protein levels or protein activity a variety of techniques are available. The in vitro protein activity can be determined by transcription or translation in bacteria, yeast, baculovirus, COS cells (transient), Chinese Hamster Ovary (CHO) cells, or studied directly in human cells, or other cell systems can be used. Further, one can perform pulse chase experiments to determine if there are changes in protein stability (half-life).

One skilled in the art can construct cell based assays of protein function, and then perform the assays in cells with different genotypes or haplotypes. For example, identification of cells with different genotypes, e.g.cell lines established from families and subsequent determination of relevant protein phenotypes (e.g expression levels, post translational modifications, activity assays) may be performed using standard methods.

Assays of protein levels or function can also be performed on cell lines (or extracts from cell lines) derived from pedigrees in order to determine whether there is a genetic component to variation in protein levels or function. The experimental analysis is as above for RNAs, except the assays are different. Experiments can be performed on naive cells or on cells subjected to various treatments, including pharmacological treatments.

In another approach to the study of amino acid variances one can express genes corresponding to different alleles in experimental organisms and examine effects on disease phenotype (if relevant in the animal model), or on response to the presence of a compound. Such experiments may be performed in animals that have disrupted copies of the homologous gene (e.g. gene knockout animals engineered to be deficient in a target gene), or variant forms of the human gene may be introduced into germ cells by transgenic methods, or a combination of approaches may be used. To create animal strains with targeted gene disruptions a DNA construct is created (using DNA sequence information from the host animal) that will undergo homologous recombination when inserted into the nucleus of an embryonic stem cell. The targeted gene is effectively inactivated due to the insertion of non-natural sequence—for example a translation stop codon or a marker gene sequence that interrupts the reading frame. Well known PCR based methods are then used to screen for those cells in which the desired homologous recombination event has occurred. Gene knockouts can be accomplished in worms, drosophila, mice or other organisms. Once the knockout cells are created (in whatever species) the candidate therapeutic intervention can be administered to the animal and pharmacological or biological responses measured, including gene expression levels. If variant forms of the gene are useful in explaining interpatient variation in reponse to the compound in man, then complete absence of the gene in an experimental organism should have a major effect on drug response. As a next step various human forms of the gene can be introduced into the knockout organism (a technique sometimes referred to as a knock-in). Again, pharmacological studies can be performed to assess the impact of different human variances on drug response. Methods relevant to the experimental approaches described above can be found in the following exemplary texts:

General Molecular Biology Methods

*Molecular Biology: A project approach*, S. J. Karcher, Fall 1995. Academic Press

*DNA Cloning: A Practical Approach*, D. M. Glover and B. D. Hayes (eds). 1995. IRL/Oxford University Press. Vol. 1-Core Techniques; Vol 2-Expression Systems; Vol. 3- Complex Genomes; Vol. 4-Mammalian Systems.

*Short Protocols in Molecular Biology*, Ausubel et al. October 1995. 3rd edition, John Wiley and Sons

*Current Protocols in Molecular Biology* Edited by: F. M. Ausubel, R. Brent, R. E. Kingston, D. D. Moore, J. G. Seidman, K. Struhl, (Series Editor: V. B. Chanda), 1988

*Molecular Cloning: A laboratory manual*, J. Sambrook, E. F. Fritsch. 1989. 3 vols, 2nd edition, Cold Spring Harbor Laboratory Press Polymerase chain reaction (PCR)

*PCR Primer: A laboratory manual*, C. W. Diffenbach and G. S. Dveksler (eds.). 1995. Cold Spring Harbor Laboratory Press.

*The Polymerase Chain Reaction*, K. B. Mullis et al. (eds.), 1994. Birkhauser

*PCR Strategies*, M. A. Innis, D. H. Gelf, and J. J. Sninsky (eds.), 1995. Academic Press General procedures for discipline specific studies

*Current Protocols in Neuroscience* Edited by: J. Crawley, C. Gerfen, R. McKay, M. Rogawski, D. Sibley, P. Skolnick, (Series Editor: G. Taylor), 1997.

*Current Protocols in Pharmacology* Edited by: S. J. Enna / M. Williams, J. W. Ferkany, T. Kenakin, R. E. Porsolt, J. P. Sullivan, (Series Editor: G. Taylor),1998.

*Current Protocols in Protein Science* Edited by: J. E. Coligan, B. M. Dunn, H. L. Ploegh, D. W. Speicher, P. T. Wingfield, (Series Editor: Virginia Benson Chanda), 1995.

*Current Protocols in Cell Biology* Edited by: J. S. Bonifacino, M. Dasso, J. Lippincott-Schwartz, J. B. Harford, K. M. Yamada, (Series Editor: K. Morgan) 1999.

*Current Protocols in Cytometry Managing* Editor: J. P. Robinson, Z. Darzynkiewicz (ed) /P. Dean (ed), A. Orfao (ed), P. Rabinovitch (ed), C. Stewart (ed), H. Tanke (ed), L. Wheeless (ed), (Series Editor: J. Paul Robinson), 1997.

*Current Protocols in Human Genetics* Edited by: N. C. Dracopoli, J. L. Haines, B. R. Korf, et al., (Series Editor: A. Boyle), 1994.

*Current Protocols in Immunology* Edited by: J. E. Coligan, A. M. Kruisbeek, D. H. Margulies, E. M. Shevach, W. Strober, (Series Editor: R. Coico), 1991.

IV. Clinical Trials

A clinical trial is the definitive test of the utility of a variance or variances for the selection of optimal therapy. A clinical trial in which an interaction of gene variances and clinical outcomes (desired or undesired) is explored will be referred to herein as a "pharmacogenetic clinical trial". Pharmacogenetic clinical trials require no knowledge of the biological function of the gene containing the variance or variances to be assessed, nor any knowledge of how the therapeutic intervention to be assessed works at a biochemical level. The pharmacogenetics effects of a variance can be addressed at a purely statistical level: either a particular variance or set of variances is consistently associated with a significant difference in a salient drug response parameter (e.g. response rate, effective dose, side effect rate, etc.) or not. On the other hand, if there is information about either the biochemical basis of a therapeutic intervention or the biochemical effects of a variance, then a pharmacogenetic clinical trial can be designed to test a specific hypothesis. In preferred embodiments of the methods of this application the mechanism of action of the compound to be genetically analyzed is at least partially understood.

Methods for performing clinical trials are well known in the art. (see e.g. *Guide to Clinical Trials* by Bert Spilker, Raven Press, 1991; *The Randomized Clinical Trial and Therapeutic Decisions* by Niels Tygstrup (Editor), Marcel Dekker; *Recent Advances in Clinical Trial Design and Analysis* (Cancer Treatment and Research, Ctar 75) by Peter F. Thall (Editor) Kluwer Academic Pub, 1995. *Clinical Trials: A Methodologic Perspective* by Steven Piantadosi, Wiley Series in Probability and Statistics, 1997). However, performing a clinical trial to test the genetic contribution to interpatient variation in drug response entails additional design considerations, including (i) defining the genetic hypothesis or hypotheses, (ii) devising an analytical strategy for testing the hypothesis, including determination of how many patients will need to be enrolled to have adequate statistical power to measure an effect of a specified magnitude (power analysis), (iii) definition of any primary or secondary genetic endpoints, and (iv) definition of methods of statistical genetic analysis, as well as other aspects. In the outline below some of the major types of genetic hypothesis testing, power analysis and statistical testing and their application in different stages of the drug development process are reviewed. One skilled in the art will recognize that certain of the methods will be best suited to specific clinical situations, and that additional methods are known and can be used in particular instances.

A. Performing a Clinical Trial: Overview

As used herein, a "clinical trial" is the testing of a therapeutic intervention in a volunteer human population for the purpose of determining whether it is safe and/or efficacious in the treatment of a disease, disorder, or condition. The present invention describes methods for achieving superior efficacy and/or safety in a genetically defined subgroup defined by the presence or absence of at least one gene sequence variance, compared to the effect that could be obtained in a conventional trial (without genetic stratification).

A "clinical study" is that part of a clinical trial that involves determination of the effect of a candidate therapeutic intervention on human subjects. It includes clinical evaluation of physiologic responses including pharmacokinetic (bioavailability as affected by drug absorption, distribution, metabolism and excretion) and pharmacodynamic (physiologic response and efficacy) parameters. A pharmacogenetic clinical study (or clinical trial) is a clinical study that involves testing of one or more specific hypotheses regarding the interaction of a genetic variance or variances (or set of variances, i.e. haplotype or haplotypes) on response to a therapeutic intervention. Pharmacogenetic hypotheses are formulated before the study, and may be articulated in the study protocol in the form of primary or secondary endpoints. For example an endpoint may be that in a particular genetic subgroup the rate of objectively defined responses exceeds the response rate in a control group (either the entire control group or the subgroup of controls with the same genetic signature as the treatment subgroup they are being compared to) or exceeds that in the whole treatment group (i.e. without genetic stratification) by some predefined relative or absolute amount.

For a clinical study to commence enrollment and proceed to treat subjects at an institution that receives any federal support (most medical institutions in the U.S.), an application that describes in detail the scientific premise for the therapeutic intervention and the procedures involved in the study, including the endpoints and analytical methods to be used in evaluating the data, should be reviewed and accepted by a review panel, often termed an Institutional Review Board (IRB). Similarly any clinical study that will ultimately be evaluated by the FDA as part of a new drug or product application (or other application as described below), should be reviewed and approved by an IRB. The IRB is responsible for determining that the trial protocol is safe, conforms to established ethical principles and guidelines, has risks proportional to any expected benefits, assures equitable selection of patients, provides sufficient information to patients (via a consent form) to insure that they can make an informed decision about participation, and insures the privacy of participants and the confidentiality of any data collected. (See the report of the National Commission for Protection of Human Subjects of Biomedical and Behavioral Research (1978). The Belmont Report: Ethical Principles and Guidelines for the Protection of Human Subjects of Research. Washington, D.C.: DHEW Publication Number (OS) 78-0012. For a recent review see: Coughlin, S. S. (ed.) (1995) Ethics in Epidemiology and Clinical Research. Epidemiology Resources, Newton, Mass.) The European counterpart of the U.S. FDA is the European Medicines Evaluation Agency (EMEA). Similar agencies exist in other countries and are responsible for insuring, via the regulatory process, that clinical trials conform to similar standards as are required in the U.S. The documents reviewed by an IRB include a clinical protocol containing the information described above, and a consent form.

It is also customary, but not required, to prepare an investigator's brochure which describes the scientific hypothesis for the proposed therapeutic intervention, the preclinical data, and the clinical protocol. The brochure is made available to any physician participating in the proposed or ongoing trial.

The supporting preclinical data is a report of all the in vitro, in vivo animal or previous human trial or other data that supports the safety and/or efficacy of a given therapeutic intervention. In a pharmacogenetic clinical trial the preclinical data may also include a description of the effect of a specific genetic variance or variances on biochemical or physiologic experimental variables in vitro or in vivo, or on treatment outcomes, as determined by in vivo studies in animals or humans (for example in an earlier trial), or by retrospective genetic analysis of clinical trial or other medical data (see below) used to formulate or strengthen a pharmacogenetic hypothesis. For example, case reports of unusual pharmacological responses in individuals with rare alleles (e.g. mutant alleles), or the observation of clustering of pharmacological responses in family members may provide the rationale for a pharmacogenetic clinical trial.

The clinical protocol provides the relevant scientific and therapeutic introductory information, describes the inclusion and exclusion criteria for human subject enrollment, including genetic criteria if relevant (e.g. if genotype is to be among the enrollment criteria), describes in detail the exact procedure or procedures for treatment using the candidate therapeutic intervention, describes laboratory analyses to be performed during the study period, and further describes the risks (both known and possible) involving the use of the experimental candidate therapeutic intervention. In a clinical protocol for a pharmacogenetic clinical trial, the clinical protocol will further describe the genetic variance and/or variances hypothesized to account for differential responses in the normal human subjects or patients and supporting preclinical data, if any, a description of the methods for genotyping, genetic data collection and data handling as well as a description of the genetic statistical analysis to be performed to measure the interaction of the variance or variances with treatment response. Further, the clinical protocol for a pharmacogenetic clinical trial will include a description of the genetic study design.

For example patients may be stratified by genotype and the response rates in the different groups compared, or patients may be segregated by response and the genotype frequencies in the different responder or nonresponder groups measured. One or more gene sequence variances or a combination of variances and/or haplotypes may be studied.

The informed consent document is a description of the therapeutic intervention and the clinical protocol in simple language (e.g. third grade level) for the patient to read, understand, and, if willing, agree to participate in the study by signing the document. In a pharmacogenetic clinical study the informed consent document will describe, in simple language, the use of a genetic test or a limited set of genetic tests to determine the subject or patient's genotype at a particular gene variance or variances, and to further ascertain whether, in the study population, particular variances are associated with particular clinical or physiological responses. The consent form should also describe procedures for assuring privacy and confidentiality of genetic information.

The U.S. FDA reviews proposed clinical trials through the process of an Investigational New Drug Application (IND). The IND is composed of the investigator's brochure, the supporting in vitro and in vivo animal or previous human data, the clinical protocol, and the informed consent forms. In each of the sections of the IND, a specific description of a single allelic variance or a number of variances to be tested in the clinical study will be included. For example, in the investigator's brochure a description of the gene or genes hypothesized to account, at least in part, for differential responses will be included as well as a description of a genetic variance or variances in one or more candidate genes. Further, the preclinical data may include a description of in vivo, in vitro or in silico studies of the biochemical or physiologic effects of a variance or variances (e.g., haplotype) in a candidate gene or genes, as well as the predicted effects of the variance or variances on efficacy or toxicology of the candidate therapeutic intervention. The results of retrospective genetic analysis of response data in patients treated with the candidate therapy may be the basis for formulating the genetic hypotheses to be tested in the prospective trial. The U.S. FDA reviews applications with particular attention to safety and toxicological data to ascertain whether candidate compounds should be tested in humans.

The established phases of clinical development are Phase I, II, III, and IV. The fundamental objectives for each phase become increasingly complex as the stages of clinical development progress. In Phase I, safety in humans is the primary focus. In these studies, dose-ranging designs establish whether the candidate therapeutic intervention is safe in the suspected therapeutic concentration range.

However, it is common practice to obtain information about surrogate markers of efficacy even in phase I clinical trials. In a pharmacogenetic clinical trial there may be an analysis of the effect of a variance or variances on Phase I safety or surrogate efficacy parameters. At the same time, evaluation of pharmacokinetic parameters (e.g., adsorption, distribution, metabolism, and excretion) may be a secondary objective; again, in a pharmacogenetic clinical study there may be an analysis of the effect of sequence variation in genes that affect absorbtion, distribution, metabolism and excretion of the candidate compound on pharmacokinetic parameters such as peak blood levels, half life or tissue distribution of the compound. As clinical development stages progress, trial objectives focus on the appropriate dose and method of administration required to elicit a clinically relevant therapeutic response. In a pharmacogenetic clinical trial, there may be a comparison of the effectiveness of several doses of a comp ound in patients with different genotypes, in order to identify interactions between genotype and optimal dose. For this purpose the doses selected for late stage clinical testing may be greater, equal or less than those chosen based upon preclinical safety and efficacy determinations. Data on the function of different alleles of genes affecting pharmacokinetic parameters could provide the basis for selecting an optimal dose or range or doses of a compound or biological. Genes involved in drug metabolism may be particularly useful to study in relation to understanding interpatient variation in optimal dose. Genes involved in drug metabolism include the cytochrome P450s, especially 2D6, 3A4, 2C9, 2E1, 2A6 and 1A1; the glucuronyltransferases; the acetyltransferases; the methyltransferases; the sulfotransferases; the glutathione system; the flavine monooxygenases and other enzymes known in the art.

An additional objective in the latter stages of clinical development is demonstration of the effect of the therapeutic intervention on a broad population. In phase III trials, the number of individuals enrolled is dictated by a power analysis. The number of patients required for a given pharmacogenetic clinical trial will be determined by prior knowledge of variance or haplotype frequency in the study population, likely response rate in the treated population, expected magnitude of pharmacogenetic effect (for example, the ratio of response rates between a genetic subgroup and the unfractionated population, or between two different genetic subgroups); nature of the genetic effect, if known (e.g. dominant effect, codominant effect, recessive effect); and number of genetic hypotheses to be evaluated (including number of genes and/or variances to be studied, number of gene or variance interactions to be studied). Other considerations will likely arise in the design of specific trials.

Clinical trials should be designed to blind both human subjects and study coordinators from biasing that may otherwise occur during the testing of a candidate therapeutic invention. Often the candidate therapeutic intervention is compared to best medical treatment, or a placebo (a compound, agent, device, or procedure that appears identical to the candidate therapeutic intervention but is therapeutically inert). The combination of a placebo group and blind controls for potentially confounding factors such as prejudice on the part of study participants or investigators, insures that real, rather than perceived or expected, effects of the candidate therapeutic intervention are measured in the trials. Ideally blinding extends not only to trial subjects and investigators but also to data review committees, ancillary personnel, statisticians, and clinical trial monitors.

In pharmacogenetic clinical studies, a placebo arm or best medical control group may be required in order to ascertain the effect of the allelic variance or variances on the efficacy or toxicology of the candidate therapeutic intervention as well as placebo or best medical therapy. It will be important to assure that the composition of the control and test populations are matched, to the degree possible, with respect to genetic background and allele frequencies. This is particularly true if the variances being investigated may have an effect on disease manifestations (in addition to a hypothesized effect on response to treatment). It is likely that standard clinical trial procedures such as insuring that treatment and control groups are balanced for race, sex and age composition and other non-genetic factors relevant to disease will be sufficient to assure that genetic background is controlled, however a preferred practice is to explicitly test for genetic stratification between test and control groups. Methods for minimizing the possibility of spurious results attributable to genetic stratification between two comparison groups include the use of surrogate markers of geographic, racial and/or ethnic background, such as have been described by Rannala and coworkers. (See, for example: Rannala B, and JL Mountain. 1997 Detecting immigration by using multilocus genotypes. *Proc Natl Acad Sci USA* Aug. 19, 1994(17):9197–201.) One procedure would be to assure that surrogate markers of genetic background (such as those described by Rannala and Mountain) occur at comparable frequency in two comparison groups.

Open label trials are unblinded; in single blind trials patients are kept unaware of treatment assignments; in double blind trials both patients and investigators are unaware of the treatment groups; a combination of these procedures may be instituted during the trial period. Pharmacogenetic clinical trial design may include one or a combination of open label, single blind, or double blind clinical trial designs. Reduction of biases attributable to the knowledge of either the type of treatment or the genotype of the normal subjects or patients is an important aspect of study design. So, for example, even in a study that is single blind with respect to treatment, it should be possible to keep both patients and caregivers blinded to genotype during the study.

In designing a clinical trial it is important to include termination endpoints such as adverse clinical events, inadequate study participation either in the form of lack of adherence to the clinical protocol or loss to follow up, (e.g. such that adequate power is no longer assured), lack of adherence on the part of trial investigators to the trial protocol, or lack of efficacy or positive response within the test group. In a pharmacogenetic clinical trial these considerations obtain not only in the entire treatment group, but also in the genetically defined subgroups. That is, if a dangerous toxic effect manifests itself predominantly or exclusively in a genetically defined subpopulation of the total treatment population it may be deemed inappropriate to continue treating that genetically defined subgroup. Such decisions are typically made by a data safety monitoring committee, a group of experts not including the investigators, and generally not blinded to the analysis, who review the data from an ongoing trial on a regular basis.

It is important to note that medicine is a conservative field, and clinicians are unlikely to change their behavior on the basis of a single clinical trial. Thus it is likely that, in most instances, two or more clinical trials will be required to convince physicians that they should change their prescribing habits in view of genetic information. Large scale trials represent one approach to providing increased data supporting the utility of a genetic stratification. In such trials the stringent clinical and laboratory data collection characteristic of traditional trials is often relaxed in exchange for a larger patient population. Important goals in large scale pharmacogenetic trials will include establishing whether a pharmacogenetic effect is detectable in all segments of a population. For example, in the North American population one might seek to demonstrate a pharmacogenetic effect in people of African, Asian, European and Hispanic (i.e. Mexican and Puerto Rican) origin, as well as in native American people. (It generally will not be practical to segment patients by geographical origin in a standard clinical trial, due to loss of power.) Another goal of a large scale clinical trial may be to measure more precisely, and with greater confidence, the magnitude of a pharmacogenetic effect first identified in a smaller trial. Yet another undertaking in a large scale clinical trial may be to examine the interaction of an established pharmacogenetic variable (e.g. a variance in gene A, shown to affect treatment response in a smaller trial) with other genetic variances (either in gene A or in other candidate genes). A large scale trial provides the statistical power necessary to test such interactions.

In designing all of the above stages of clinical testing investigators should be attentive to the statistical problems raised by testing multiple different hypotheses, including multiple genetic hypotheses, in subsets of patients. Bonferroni's correction or other suitable statistical methods for taking account of multiple hypothesis testing will need to be judiciously applied. However, in the early stages of clinical testing, when the main goal is to reduce the large number of potential hypotheses that could be tested to a few that will be tested, based on limited data, it may be impractical to rigidly apply the multiple testing correction.

B. Phase I Clinical Trials

1. Introduction

Phase I of clinical development is generally focused on safety, although drug companies are increasingly obtaining information on pharmacokinetics and surrogate pharmacodynamic markers in early trials. Phase I studies are typically performed with a small number (<60) of normal, healthy volunteers usually at single institutions. The primary endpoints in these studies usually relate to pharmacokinetic parameters (i.e. adsorption, distribution, metabolism and bioavailability), and dose-related side effects. In a Phase I pharmacogenetic clinical trial, stratification based upon allelic variance or variances of a candidate gene or genes related to pharmacokinetic parameters may allow early assessment of potential genetic interactions with treatment.

Phase I studies of some diseases (e.g. cancer or other medically intractable diseases for which no effective medical alternative exists) may include patients who satisfy specified inclusion criteria. These safety/limited-efficacy studies can be conducted at multiple institutions to ensure rapid enrollment of patients. In a pharmacogenetic Phase I study that includes patients, or a mixture of patients and normals, the status of a variance or variances suspected to affect the efficacy of the candidate therapeutic intervention may be used as part of the inclusion criteria. Alternatively, analysis of variances or haplotypes in patients with different treatment responses may be among the the endpoints. It is not unusual for such a Phase I study design to include a double-blind, balanced, random-order, crossover sequence (separated by washout periods), with multiple doses on separate occasions and both pharmacokinetic and pharmacodynamic endpoints.

2. Phase I trials with subjects drawn from large populations and/or from related volunteer subjects: the Pharmacogenetic Phase I Unit concept In general it is useful to be able to assess the contribution of genetic variation to treatment response at the earliest possible stage of clinical development. Such an assessment, if accurate, will allow efficient prioritization of candidate compounds for subsequent detailed pharmacogenetic studies; only those treatments where there is early evidence of a significant interaction of genetic variation with treatment response would be advanced to pharmacogenetic studies in later stages of development. In this invention we describe methods for achieving early insight—in Phase I—into the contribution of genetic variation to variation in surrogate treatment response variables. It occurred to the inventors that this can be accomplished by bringing the power of genetic linkage analysis and outlier analysis to Phase I testing via the recruitment of a very large Phase I population including a large number of individuals who have consented in advance to genetic studies (occasionally referred to hereinafter as a Pharmacogenetic Phase I Unit). In one embodiment of a Pharmacogenetic Phase I Unit many of the subjects are related to each other by blood. (Currently Phase I trials are performed in unrelated individuals, and there is no consideration of genetic recruitment criteria, or of genetic analysis of surrogate markers.) There are several novel ways in which a large population, or a population comprised at least in part of related individuals, could be useful in early clinical trials. Some of the most attractive applications depend on the availability of surrogate markers for pharmacodynamic drug action which can be used early in clinical development, preferably in normal subjects in Phase I. Such surrogate markers are increasingly used in Phase I, as drug development companies seek to make early yes/no decisions about compounds.

Recruitment of a population optimized for clinical genetic investigation may entail utilization of methods in statistical genetics to select the size and composition of the population. For example powerful methods for detecting and mapping quantitative trait loci in sibpairs have been developed. These methods can provide some estimate of the statistical power derived from a given number of groups of closely related individuals. Ideally subjects in the pharmacogenetic Phase I unit are of known ethnic/racial/geographic background and willing to participate in Phase I studies, for pay, over a period of years. The population is preferably selected to achieve a specified degree of statistical power for genetic association studies, or is selected in order to be able to reliably identify a certain number of individuals with rare genotypes, as discussed below. Family participation could be encouraged by appropriate incentive compensation. For example, individual subjects might be paid $200 for participation in a study; two sibs participating in the same study might each be paid $300; if they could encourage another sib (or cousin) to participate the three related individuals might each be paid $350, and so forth. This type of compensation would encourage subjects to recruit their relatives to participate in Phase I studies. (It would also increase the cost of studies, however the type of data that can be obtained can not be duplicated with conventional approaches.) The optimal location to establish such a Phase I unit is a city with a stable population, many large families, and a positive attitide about gene technology. The Pharmacogenetic Phase I Unit population can then be used to test for the existence of genetic variation in response to any drug as a first step in deciding whether to proceed with extensive pharmacogenetic studies in later stages of clinical development. Specific uses of a large Phase I unit in which some or all subjects are related include:

a. It should be possible, for virtually any compound, to assess the magnitude of the genetic contribution to variation in drug response (if any) by comparing variation in drug response traits among related vs. non-related individuals. The rationale is as follows: if a surrogate drug response trait (i.e.a surrogate marker of pharmacodynamic effect that can be measured in normal subjects) is under strong genetic control then related individuals, who share 25% (cousins) or 50% (sibs) of their alleles, should have less divergent responses (less intragroup variance) than unrelated individuals, who share a much smaller fraction of alleles. That is, individuals who share alleles at the genes that affect drug response should be more similar to each other (i.e. have a narrower distribution of responses, whether measured by variance, standard deviation or other means) than individuals who, on average, share very few alleles. By using statistical methods known in the art the degree of variation in a set of data from related individuals (each individual would only be compared with his/her relatives, but such comparisons would be performed within each group of relatives and a summary statistic developed) could be compared to the degree of variation in a set of unrelated individuals (the same subjects could be used, but the second comparison would be across related groups). Account would be taken of the degree of similarity expected between related individuals, based on the fraction of the genome they shared by descent. Thus the extent of variation in the surrogate response marker between identical twins should be less than between sibs, which should be less than between first cousins, which should be less than that between second cousins, and so forth, if there is a genetic component to the variation. It is well known from twin studies (in which, for example, variation between identical twins is compared to variation between fraternal twins) that pharmacokinetic variables (e.g. compound half life, peak concentration) are frequently over 90% heritable; the type of study proposed here (comparison of variation within groups of sibs and cousins to variation between unrelated subjects) would also show this genetic effect, without requiring the recruitment of monozygotic twins. For a summary of pharmacokinetic studies in twins see: Propping, Paul (1978) *Pharmacogenetics. Rev. Physiol. Biochem. Pharmacol.* 83: 123–173.

It may be that the pattern of drug responses that distinguishes related individuals from non-related individuals is more complex than, for example, variance or standard deviation. For example, there may be two discrete phenotypes characteristic of intrafamilial variation (a bimodal distribution) that are not a feature of variation between unrelated individuals (where, for example, variation might be more nearly continuous). Such a pattern could be attributable to Mendelian inheritance operating on a restricted set of alleles in a family (or families) with, for example, AA homozygotes giving one phenotype and AB heterozygotes and BB homozygotes giving a second phenotype, all in the context of a relatively homogeneous genetic background. In contrast, variation among non-related subjects would be less discrete due to a greater degree of variation in genetic background and the presence of additional alleles C, D and E at the candidate locus. Statistical measures of the significance of such differences in distribution, including nonparametric methods such as chi square and contingency tables, are known in the art.

The methods described herein for measuring whether pharmacodynamic traits are under genetic control, using surrogate markers of drug efficacy in phase I studies which include groups of related individuals, will be useful in obtaining an early assessment of the extent of genetically determined variation in drug response for a given therapeutic compound. Such information provides an informed basis for either stopping development at the earliest possible stage or, preferably, continuing with development but with a plan for identifying and controlling for genetic variation so as to allow rapid progression through the regulatory approval process.

For example, it is well known that Alzheimers trials are long and expensive, and most drugs are only effective in a fraction of patients. Using surrogate measures of response in normals drawn from a population of related individuals would help to assess the contribution of genetic variation to variation in treatment response. For an acetylcholinesterase inhibitor, relevant surrogate pharmacodynamic measures could include testing erythrocye membrane acetylcholinesterase levels in drug treated normal subjects, or performing psychometric tests that are affected by treatment (and ideally that correlate with clinical efficacy) and measuring the effect of treatment. As another example, antidepressant drugs can produce a variety of effects on mood in normal subjects—or no effect at all. Careful monitoring and measurement of such responses in related vs. unrelated normal subjects, and statistical comparison of the degree of variation in each group, could provide an early readout on whether there is a genetic component to drug response (and hence clinical efficacy). The observation of similar effects in family members, and comparatively dissimilar effects in unrelated subjects would provide compelling evidence of a pharmacogenetic effect and justify the substantial expenditure necessary for a full pharmacogenetic drug development program. Conversely, the absence of any significant family influence on drug response would provide an early termination point for pharmacogenetic studies. Note that the proposed studies do not require any knowledge of candidate genes, nor is DNA collection or genotyping required—simply a reliable surrogate pharmacodynamic assay and small groups of related normal individuals. Refined statistical methods should permit the magnitude of the pharmacogenetic effect to be measured, which could be a further criteria for deciding whether to proceed with pharmacogenetic analysis. The greater the differential in magnitude or pattern of variance between the related and the unrelated subjects, the greater the extent of genetic control of the trait.

Not all drug response traits are under the predominant control of one locus. Many such traits are under the control of multiple genes, and may be referred to as quantitative trait loci. It is then desirable to identify the major loci contributing to variation in the drug response trait. This can be done for example, to map quantitative trait loci in a population of drug treated related normals. Either a candidate gene approach or a genome wide scanning approach can be used. (For review of some relevant methods see: Hsu L, Aragaki C, Quiaoit F. (1999) A genome-wide scan for a simulated data set using two newly developed methods. *Genet Epidemiol* 17 Suppl 1:S621-6; Zhao LP, Aragaki C, Hsu L, Quiaoit F. (1998) Mapping of complex traits by single-nucleotide polymorphisms. *Am J Hum Genet* 63(1):225–40; Stoesz M R, Cohen J C, Mooser V, et al. (1997) Extension of the Haseman-Elston method to multiple alleles and multiple loci: theory and practice for candidate genes. *Ann Hum Genet* 61 (Pt 3):263–74.)) However, this method would require at least 100 patients (preferably 200, and still more preferably>300) to have adequate statistical power, and each patient would have to be genotyped at a few polymorphic loci (candidate gene approach) or hundreds of polymorphic loci (genome scanning approach).

b. With a large Phase I population of normal subjects that need not be related (a second type of Pharmacogenetic Phase I Unit) it is possible to efficiently identify and recruit for any Phase I trial a set of individuals comprising virtually any combination of genotypes present in a population (for example, all common genotypes, or a group of genotypes expected to represent outliers for a drug response trait of interest). This method preferably entails obtaining blood or other tissue (e.g. buccal smear) in advance from a large number of the subjects in the Phase I unit. Ideally consent for genotyping would be obtained at the same time. It would be most efficient if blanket consent for genotyping any polymorphic site or sites could be obtained. Second best would be consent for testing any site relevant to any customer project (not specific at the time of initial consent). Third best would be consent to genotype polymorphic sites relevant to specific disease areas. Another, less desirable, solution would be to obtain consent for genotyping on a project by project basis (for example by mailing out reply cards), after the specific polymorphic sites to be genotyped are known.

One useful way to screen for pharmacogenetic effects in Phase I is to recruit homozygotes for a variance or variances of interest in one or more candidate genes. For example, consider a compound for which there are two genes that are strong candidates for influencing response to treatment. Gene X has alleles A and A', while gene Y has alleles B and B'. If these genes do in fact contribute significantly to response then one would expect that, regardless of the mode of inheritance (recessive, codominant, dominant, polygenic) homozygotes would exhibit the most extreme responses. One would also expect epistatic interactions, if any, to be most extreme in double homozygotes. Thus one would ideally perform a surrogate drug response test in Phase I volunteers doubly homozygous at both X and Y. That is, test AA/BB, A'A'/BB, AA/B'B' and A'A'/B'B' subjects. If the allele frequencies for A and A' are 0.15 and 0.85, and for B and B' 0.2 and 0.8 then the frequency of AA homozygotes is expected to be 2.25% and BB homozygotes 4%. In the absence of any linkage between the genes, the frequency of AA/BB double homozygotes is expected to be $0.0225 \times 0.04 = 0.0009$ or 0.09%, or about 1 subject in 1000. Ideally at least 5 subjects of each genotype are recruited for the Phase I study, and preferably at least 10 subject. Thus, even for variances of moderately low allele frequency (15%, 20%), the identification of potential outliers (i.e. homozygotes) for the candidate genes of interest will require a large population. Preferably the Phase I unit has enrolled at least 1,000 normal individuals, more preferably 2,000, still more preferably 5,000 and most preferably 10,000 or more. In another application of the large, genotyped Phase I population it may be useful to identify individuals with rare variances in candidates genes (either homozygous or heterozygous), in order to determine whether those variances are predisposing to extreme pharmacological responses to the compound. For example, variances occurring at 5% allele frequency are expected to occur in homozygous form in 0.25% of the population ($0.05 \times 0.05$), and therefore may rarely, if ever, be encountered in early clinical development. Yet it may be serious adverse effects occuring in just such a small group that create problems in later stages of drug development. In yet another application of the large genotyped Phase I population, subjects may be selected to represent the known common variances in one or more genes that are candidates for influencing the response to treatment. By insuring that all common genotypes are represented in a Phase I trial the likelihood of misleading results due to genetic stratification (resulting in discrepancy with results of later, larger trials can be reduced.

It would be useful to prospectively genotype the large Phase I population for variances that are commonly the source of interpatient variation in drug response, since demand for genotyped groups of such patients can be anticipated from pharmaceutical companies and contract research organizations (CROs). For example, genotyping might initially focus on common pharmacological targets such as estrogen receptors, adrenergic receptors, or serotonin receptors. The pre-genotyped Phase I population could be part of a package of services (along with genotyping assay development capability, high throughput genotyping capacity and software and expertise in statistical genetics) designed to accelerate pharmacogenetic Phase I studies. Eventually, as the databank of genotypes built up, individuals with virtually any genotype or combination of genotypes could be called in for precisely designed physiological or toxicological studies designed to test for pharmacogenetic effects.

One of the most useful aspects of the Pharmacogenetic Phase I Unit is that subjects with rare genotypes can be pharmacologically assessed in a small study. This addresses a serious limitation of conventional clinical trials with respect to the investigation of polygenic traits or the effect of rare alleles. Unfortunately even Phase III studies, as currently performed, are often barely powered to address simple one variance hypotheses about efficacy or toxicity. The problem, of course, is that each time a new genetic variable is introduced the comparison groups are cut in halves or thirds (or even smaller groups if there are multiple haplotypes at each gene). It is therefore a challenging problem to test the interaction of several genes in determining drug response. Yet the character of drug response data in populations—there is often a continuous distribution of responses among different individuals—suggests that drug responses may often be mediated by several genes. (On the other hand, there are an increasing number of well documented single gene, or even single variance, pharmacogenetic effects in the literature, showing that it is possible to detect the effect of a single variance.) One approach to identifying pharmacogenetic effects is to focus on finding the single gene variances that have the largest effects. This approach can be undertaken within the scale of current clinical trials. However, in order to develop a test which predicts a large fraction of the quantitative variation in a drug response trait it may be desirable to test the effect of multiple genes, including the interaction of variances at different genes, which may be non-additive (referred to as epistasis). The Pharmacogenetic Phase I Unit provides a way to efficiently test for gene interactions or multigene effects by, for example, allowing easy identification of individuals who, on account of being homozygous at several loci of interest, should be outliers for the drug response phenotypes of interest if there is a gene×gene interaction. Testing drug response in a small number of such individuals will provide a quick read on gene interaction. Obtaining genetic data on the pharmacodynamic action of a compound in Phase I should also provide a crude measure of allele affects—which variances or haplotypes increase pharmacological responses and which decrease them. This information is of great value in designing subsequent trials, as it constrains the number of hypotheses to be tested, thereby enabling powerful statistical designs. This is because when the effect of variances on drug response measures is unknown one is forced to statistically test all the possible effects of each allele (e.g. two tailed tests). As the number of genetically defined groups increases (e.g. as a result of multiple variances or haplotypes) there is a loss of statistical power due to multiple testing correction. On the other hand, if the relative phenotypic effect of each allele at a locus is known (or can be hypothesized) from Phase I data then each individual in a subsequent clinical trial contributes useful information—there is a specific prediction of response based on that individuals combination of genotypes or haplotypes, and testing the fit of the actual data to those predictions provides for powerful statistical designs. (It is also possible to measure allele effects biochemically, of course, to establish which alleles have positive and which negative effects, but at considerable cost.)

It is important to note that Phase I trials can provide useful information at almost any stage of clinical development. It is not unusual, for example, for a product in Phase II or even Phase III testing to be remanded to Phase I in order to clarify some aspect of toxicology or physiology. In this context a Pharmacogenetic Phase I Unit would be extremely useful to a drug development company. Phase I studies in defined genetic subgroups drawn from a large genotyped population, or in groups of related individuals, would be the most economical and efficient way to clarify the existence of pharmacogenetic effects, if any, paving the way for future rational development of the product.

C. Phase II Clinical Trials

Phase II studies generally include a limited number of patients (<100) who satisfy a set of predefined inclusion criteria and do not satisfy any predefined exclusion criteria of the trial protocol. Phase II studies can be conducted at single or multiple institutions. Inclusion/exclusion criteria may include historical, clinical and laboratory parameters for a disease, disorder, or condition; age; gender; reproductive status (i.e. pre- or postmenopausal); coexisting medical conditions; psychological, emotional or cognitive state, or other objective measures known to those skilled in the art. In a pharmacogenetic Phase II trial the inclusion/exclusion criteria may include one or more genotypes or haplotypes. Alternatively, genetic analysis may be performed at the end of the trial. The primary goals in Phase II testing may include (i) identification of the optimal medical indication for the compound, (ii) definition of an optimal dose or range or doses, balancing safety and efficacy considerations (dose-finding studies), (iii) extended safety studies (complementing Phase I safety studies), (iv) evaluation of efficacy in patients with the targeted disease or condition, either in comparison to placebo or to current best therapy. To some extent these goals may be achieved by performing multiple trials with different goals. Likewise, Phase II trials may be designed specifically to evaluate pharmacogenetic aspects of the drug candidate. Primary efficacy endpoints typically focus on clinical benefit, while surrogate endpoints may measure treatment response variables such as clinical or laboratory parameters that track the progress or extent of disease, often at lesser time, cost or difficulty than the definitive endpoints. A good surrogate marker should be convincingly associated with the definitive outcome. Examples of surrogate endpoints include tumor size as a surrogate for survival in cancer trials, and cholesterol levels as a surrogate for heart disease (e.g. myocardial infarction) in trials of lipid lowering cardiovascular drugs. Secondary endpoints supplement the primary endpoint and may be selected to help guide further clinical studies.

In a pharmacogenetic Phase II clinical trial, retrospective or prospective design will include the stratification of patients based upon a variance or variances in a gene or genes suspected of affecting treatment response. The gene or genes may be involved in mediating pharmacodynamic or pharmacokinetic response to the candidate therapeutic intervention. The parameters evaluated in the genetically stratified trial population may include primary, secondary or surrogate endpoints. Pharmacokinetic parameters—for example, dosage, absorbtion, toxicity, metabolism, or excretion—may also be evaluated in genetically stratified groups. Other parameters that may be assessed in parallel with genetic stratification include gender, race, ethnic or geographic origin (population history) or other demographic factors.

While it is optimal to initiate pharmacogenetic studies in phase I, as described above, it may be the case that pharmacogenetic studies are not considered until phase II, when problems relating either to efficacy or toxicity are first encountered. It is highly desirable to initiate pharmacogenetic studies no later than Phase II of a clinical development plan because (1) phase III studies tend to be large and expensive—not an optimal setting in which to explore untested pharmacogenetic hypotheses; (2) phase III studies are typically designed to test one fairly narrow hypothesis regarding efficacy of one or a few dose levels in a specific disease or condition. Phase II studies are often numerous, and are intended to provide a broad picture of the pharmacology of the candidate compound. This is a good setting for initial pharmacogenetic studies. Several pharmacogenetic hypotheses may be tested in phase II, with the goal of eliminating all but one or two.

D. Phase III Clinical Trials

Phase III studies are generally designed to measure efficacy of a new treatment in comparision to placebo or to an established treatment method. Phase II studies are often performed at multiple sites. The design of this type of trial includes power analysis to ensure the sufficient data will be gathered to demonstrate the anticipated effect, making assumptions about reponse rate based on earlier trials. As a result Phase III trials frequently include large numbers of patients (up to 5,000). Primary endpoints in Phase III studies may include reduction or arrest of disease progression, improvement of symptoms, increased longevity or increased disease-free longevity, or other clinical measures known in the art. In a pharmacogenetic Phase III clinical study, the endpoints may include determination of efficacy or toxicity in genetically defined subgroups. Preferably the genetic analysis of outcomes will be confined to an assessment of the impact of a small number of variances or haplotypes at a small number of genes, said variances having already been statistically associated with outcomes in earlier trials. Most preferably variances at only one or two genes will be assessed.

After successful completion of one or more Phase III studies, the data and information from all trials conducted to test a new treatment method are compiled into a New Drug Application (NDA) and submitted for review by the U.S. FDA, which has authority to grant marketing approval in the U.S. and its territories. The NDA includes the raw (unanalyzed) clinical data, i.e. the patient by patient measurements of primary and secondary endpoints, a statistical analysis of all of the included data, a document describing in detail any observed side effects, tabulation of all patients who dropped-out of trials and detailed reasons for their termination, and any other available data pertaining to ongoing in vitro or in vivo studies since the submission of the investigational new drug (IND) application. If pharmacoeconomic objectives are a part of the clinical trial design then data supporting cost or economic analyses are included in the NDA. In a pharmacogenetic clinical study, the pharmacoeconomic analyses may include genetically stratified assessment of the candidate therapeutic intervention in a cost benefit analysis, cost of illness study, cost minimization study, or cost utility analysis. The analysis may also be simultaneously stratified by standard criteria such as race/ethnicity/geographic origin, sex, age or other criteria. Data from a genetically stratified analysis may be used to support an application for approval for marketing of the candidate therapeutic intervention.

E. Phase IV Clinical Trials

Phase IV studies occur after a therapeutic intervention has been approved for marketing, and are typically conducted for suveillance of safety, particularly occurance of rare side effects. The other principal reason for Phase IV studies is to produce information and relationships useful for marketing a drug. In this regard pharmacogenetic analysis may be very useful in Phase IV trials. Consider, for example, a drug that is the fourth or fifth member of a drug class (say statins, or thiazidinediones or fluoropyrimidines) to obtain marketing approval, and which does not differ significantly in clinical effects—efficacy or safety—from other members of the drug class. The first, second and third drugs in the class will likely have a dominant market position (based on their earlier introduction into the marketplace) that is difficult to overcome, particularly in the absence of differentiating clinical effects. However, it is possible that the new drug produces a superior clinical effect—for example, higher response rate, greater magnitude of response or fewer side effects—in a genetically defined subgroup. The genetic subgroup with superior response may constitute a larger fraction of the total patient population than the new drug would likely achieve otherwise. In this instance, there is a clear rationale for performing a Phase IV pharmacogenetic trial to identify a variance or variances that mark a patient population with superior clinical response. Subsequently a marketing campaign can be designed to alert patients, physicians, pharmacy managers, managed care organizations and other parties that, with the use of a rapid and inexpensive genetic test to identify eligible patients, the new drug is superior to other members of the class (including the market leading first, second and third drugs introduced). The high responder subgroup defined by a variance or variances may also exhibit a superior response to other drugs in the class (a class pharmacogenetic effect), or the superior efficacy in the genetic subgroup may be specific to the drug tested (a compound-specific pharmacogenetic effect).

In a Phase IV pharmacogenetic clinical trial, both retrospective and prospective analysis can be performed. In both cases, the key element is genetic stratification based on a variance or variances or haplotype. Phase IV trials will often have adequate sample size to test more than one pharmacogenetic hypothesis in a statistically sound way.

F. Unconventional Clinical Development

Although the above listed phases of clinical development are well-established, there are cases where strict Phase I, II, III development does not occur, for example, in the clinical development of candidate therapeutic interventions for debilitating or life threatening diseases, or for diseases where there is presently no available treatment. Some of the mechanisms established by the FDA for such studies include Treatment INDs, Fast-Track or Accelerated reviews, and Orphan Drug Status. In a clinical development program for a candidate therapeutic of this type there is a useful role for pharmacogenetic analysis, in that the candidate therapeutic may not produce a sufficient benefit in all patients to justify FDA approval, however analysis of outcome in genetic subgroups may lead to identification of a variance or variances that predict a response rate sufficient for FDA approval.

As used herein, "supplemental applications" are those in which a candidate therapeutic intervention is tested in a human clinical trial in order to gain an expanded label indication, expanding recommended use to new medical indications. In these applications, previous clinical studies of the therapeutic intervention, i.e. preclinical safety and Phase I human safety studies can be used to support the testing of the therapeutic intervention in a new indication. Pharmacogenetic analysis is also useful in the context of clinical trials to support supplemental applications. Since these are, by defininition, focused on diseases not selected for initial development the overall efficacy may not be as great as for the leading indication(s). The identification of genetic subgroups with high response rates may enable the rapid approval of supplemental applications for expanded label indications. In such instances part of the label indication may be a description of the variance or variances that define the group with superior response.

As used herein, "outcomes" or "therapeutic outcomes" describe the results and value of healthcare intervention. Outcomes can be multi-dimensional, and may include improvement of symptoms; regression of a disease, disorder, or condition; prevention of a disease or symptom; cost savings or other measures.

Pharmacoeconomics is the analysis of a therapeutic intervention in a population of patients diagnosed with a disease, disorder, or condition that includes at least one of the following studies: cost of illness study (COI); cost benefit analysis (CBA), cost minimization analysis (CMA), or cost utility analysis (CUA), or an analysis comparing the relative costs of a therapeutic intervention with one or a group of other therapeutic interventions. In each of these studies, the cost of the treatment of a disease, disorder, or condition is compared among treatment groups.

Costs have both direct (therapeutic interventions, hospitalization) and indirect (loss of productivity) components. Pharmacoeconomic factors may provide the motivation for pharmacogenetic analysis, particularly for expensive therapies that benefit only a fraction of patients. For example, interferon alpha is the only treatment that can cure hepatitis C virus infection, however viral infection is completely and permanently eliminated in less than a quarter of patients. Nearly half of patients receive virtually no benefit from alfa interferon, but may suffer significant side effects. Treatment costs are ~$10,000 per course. A pharmacogenetic test that could predict responders would save much of the cost of treating patients not able to benefit from interferon alpha therapy, and could provide the rationale for treating a population in a cost efficient manner, where treatment would otherwise be unaffordable.

As used herein, "health-related quality of life" is a measure of the impact of a disease, disorder, or condition on a patient's activities of daily living. An analysis of the health-related quality of life is often included in pharmacoeconomic studies.

As used herein, the term "stratification" refers to the partitioning of patients into groups on the basis of clinical or laboratory characteristics of the patient. "Genetic stratification" refers to the partitioning of patients or normal subjects into groups based on the presence or absence of a variance or variances in one or more genes. The stratification may be performed at the end of the trial, as part of the data analysis, or may come at the beginning of a trial, resulting in creation of distinct groups for statistical or other purposes.

G. Power analysis in pharmacogenetic clinical trials

The basic goal of power calculations in clinical trial design is to insure that trials have adequate patients and controls to fairly assess, with statistical significance, whether the candidate therapeutic intervention produces a clinically significant benefit.

Power calculations in clinical trials are related to the degree of variability of the drug response phenotypes measured and the treatment difference expected between comparison groups (e.g. between a treatment group and a control group). The smaller the variance within each group being compared, and the greater the difference in response between the two groups, the fewer patients are required to produce convincing evidence of an effect of treatment. These two factors (variance and treatment difference) determine the degree of precision required to answer a specific clinical question.

The degree of precision may be expressed in terms of the maximal acceptable standard error of a measurement, the magnitude of variation in which the 95% confidence interval must be confined or the minimal magnitude of difference in a clinical or laboratory value that must be detectable (at a statistically significant level, and with a specified power for detection) in a comparison to be performed at the end of the trial (hypothesis test). The minimal magnitude is generally set at the level that represents the minimal difference that would be considered of clinical importance.

In pharmacogenetic clinical trials there are two countervailing effects with respect to power. First, the comparison groups are reduced in size (compared to a conventional trial) due to genetic partitioning of both the treatment and control groups into two or more subgroups. However, it is reasonable to expect that variability for a trait is smaller within groups that are genetically homogeneous with respect to gene variances affecting the trait. If this is the case then power is increased as a function of the reduction in variability within (genetically defined) groups.

In general it is preferable to power a pharmacogenetic clinical trial to see an effect in the largest genetically defined subgroups. For example, for a variance with allele frequencies of 0.7 and 0.3 the common homozygote group will comprise 49% of all patients (0.7×0.7×100). It is most desirable to power the trial to observe an effect (either positive or a negative) in this group. If it is desirable to measure an effect of therapy in a small genetic group (for example, the 9% of patients homozygous for the rare allele) then genotyping should be considered as an enrollment criterion to insure a sufficient number of patients are enrolled to perform an adequately powered study.

Statistical methods for powering clinical trials are known in the art. See, for example: Shuster, J. J. (1990) *Handbook of Sample Size Guidelines for Clinical Trials.* CRC Press, Boca Raton, Fla.; Machin, D. and M. J. Campbell (1987) *Statistical Tables for the Design of Clinical Trials.* Blackwell, Oxford, UK; Donner, A. (1984) *Approaches to Sample Size Estimation in the Design of Clinical Trials—A Review. Statistics in Medicine* 3: 199–214.

H. Statistical analysis of clinical trial data

There are a variety of statistical methods for measuring the difference between two or more groups in a clinical trial. One skilled in the art will recognize that different methods are suited to different data sets. In general, there is a family of methods customarily used in clinical trials, and another family of methods customarily used in genetic epidemiological studies. Methods in quantitative and population genetics designed to measure the association betweeen genotypes and phenotypes, and to map and measure the effect of quantitative trait loci are also relevant to the task of measuring the impact of a variance on response to a treatment. Methods from any of these disciplines may be suitable for performing statistical analysis of pharmacogenetic clinical trial data, as is known to those skilled in the art.

Conventional clinical trial statistics include hypothesis testing and descriptive methods, as elaborated below. Guidance in the selection of appropriate statistical tests for a particular data set is provided in texts such as: *Biostatistics: A Foundation for Analysis in the Health Sciences,* 7th edition (Wiley Series in Probability and Mathematical Statistics, Applied Probability and statistics) by Wayne W. Daniel, John Wiley & Sons, 1998; *Bayesian Methods and Ethics in a Clinical Trial Design* (Wiley Series in Probability and Mathematical Statistics. Applied Probability Section) by J. B. Kadane (Editor), John Wiley & Sons, 1996. Examples of specific hypothesis testing and descriptive statistical procedures that may be useful in analyzing clinical trial data are listed below.

A. Hypothesis testing statistical procedures (1) One-sample procedures (binomial confidence interval, Wilcoxon signed rank test, permutation test with general scores, generation of exact permutational distributions)

(2) Two-sample procedures (t-test, Wilcoxon-Mann-Whitney test, Normal score test, Median test, Van der Waerden test, Savage test, Logrank test for censored survival data, Wilcoxon-Gehan test for censored survival data, Cochran-Armitage trend test, permutation test with general scores, generation of exact permutational distributions)

(3) R×C contingency tables (Fisher's exact test, Pearson's chi-squared test, Likelihood ratio test, Kruskal-Wallis test, Jonckheere-Terpstra test, Linear-by linear association test, McNemar's test, marginal homogeneity test for matched pairs)

(4) Stratified 2×2 contingency tables (test of homogeneity for odds ratio, test of unity for the common odds ratio, confidence interval for the common odds ratio)

(5) Stratified 2×C contingency tables (all two-sample procedures listed above with stratification, confidence intervals for the odds ratios and trend, generation of exact permutational distributions)

(6) General linear models (simple regression, multiple regression, analysis of variance—ANOVA—, analysis of covariance, response-surface models, weighted regression, polynomial regression, partial correlation, multiple analysis of variance—MANOVA—, repeated measures analysis of variance).

(7) Analysis of variance and covariance with a nested (hierarchical) structure.

(8) Designs and randomized plans for nested and crossed experiments (completely randomized design for two treatment, split-splot design, hierarchical design, incomplete block design, latin square design)

(9) Nonlinear regression models

(10) Logistic regression for unstratified or stratified data, for binary or ordinal response data, using the logit link function, the normit function or the complementary log-log function.

(11) Probit, logit, ordinal logistic and gompit regression models.

(12) Fitting parametric models to failure time data that may be right-, left-, or interval-censored. Tested distributions can include extreme value, normal and logistic distributions, and, by using a log transformation, exponential, Weibull, lognormal, loglogistic and gamma distributions.

(13) Compute non-parametric estimates of survival distribution with right-censored data and compute rank tests for association of the response variable with other variables.

B. Descriptive statistical methods

Factor analysis with rotations

Canonical correlation

Principal component analysis for quantitative variables.

Principal component analysis for qualitative data.

Hierarchical and dynamic clustering methods to create tree structure, dendrogram or phenogram.

Simple and multiple correspondence analysis using a contingency table as input or raw categorical data.

Specific instructions and computer programs for performing the above calculations can be obtained from companies such as: SAS/STAT Software, SAS Institute Inc., Cary, N.C., USA; BMDP Statistical Software, BMDP Statistical Software Inc., Los Angeles, Calif., USA; SYSTAT software, SPSS Inc., Chicago, Ill., USA; StatXact & LogXact, CYTEL Software Corporation, Cambridge, Mass., USA.

C. Statistical Genetic Methods Useful for Analysis of Pharmacogenetic Data

A wide spectrum of mathematical and statistical tools may be useful in the analysis of data produced in pharmacogenetic clinical trials, including methods employed in molecular, population, and quantitative genetics, as well as genetic epidemiology. Methods developed for plant and animal breeding may be useful as well, particularly methods relating to the genetic analysis of quantitative traits.

Analytical methods useful in the analysis of genetic variation among individuals, populations and species of various organisms are described in the following texts: *Molecular Evolution*, by W- H. Li, Sinauer Associates, Inc., 1997; *Principles of Population Genetics*, by D. L. Hartl and A. G. Clark, 1996; *Genetics and Analysis of Quantitative Traits*, By M. Lynch and B. Walsh, Sinauer Associates, Inc., *Principles of Quantitative Genetics*, by D. S. Falconer and T. F. C. Mackay, Longman, 1996; *Genetic Variation and Human Disease*, by K. M. Weiss, Cambridge University Press, 1993; *Fundamentals of Genetic Epidemiology*, by M. J. Khoury, T. H. Beaty, and B. H. Cohen, Oxford University Press, 1993; *Handbook of Genetic Linkage* by J. Terwilliger J. Ott, Johns Hopkins University Press, 1994.

The types of statistical analysis performed in different branches of genetics are outlined below as a guide to the relevant literature and publicly available software, some of which is cited.

Molecular evolutionary genetics

Patterns of nucleotide variation among individuals, families/populations and across species and genera, Alignment of sequences and description of variation/polymorphisms among the aligned sequences, amounts of similarities and dissimilarities, Measurement of molecular variation among various regions of a gene, testing of neutrality models, Rates of nucleotide changes among coding and the non-coding regions within and among populations, Construction of phylogenetic trees using methods such as neighborhood joining and maximum parsimony; estimation of ages of variances using coalescent models, Population genetics Patterns of distribution of genes among genotypes and populations. Hardy-Weinberg equilibrium, departures form the equilibrium Genotype and haplotype frequencies, levels of heterozygosities, polymorphism information contents of genes, estimation of haplotypes from genotypes; the E-M algorithm, and parsimony methods Estimation of linkage disequilibrium and recombination Hierarchical structure of populations, the F-statistics, estimation of inbreeding, selection and drift Genetic admixture/migration and mutation frequencies Spatial distribution of genotypes using spatial autocorrelation methods Kin-structured maintainance of variation and migration Quantitative genetics Phenotype as the product of the interaction between genotype and environment Additive, dominance and epistatic variance on the phenotype Effects of homozygosity, heterozygosity and developmental homeostasis Estimation of heritability: broad sense and narrow sense Determination of number of genes governing a character Determination of quantitative trait loci (QTLs) using family information or population information, and using linkage and/or association studies Determination of quantitative trait nucleotide (QTN) using a combination linkage disequilibrium methods and cladistic approaches Determination of individual causal nucleotide in the diploid or haploid state on the phenotype using the method of measured genotype approaches, and combined effects or synergistic interaction of the causal mutations on the phenotype Determination of relative importance of each of the mutations on a given phenotype using multivariate methods, such as discriminant function, principal component and step-wise regression methods Determination of direct and indirect effect of polymorphisms on a complex phenotype using path analysis (partial regression) methods Determination of the effects of specific environment on a given genotype—genotype ×environment interactions using joint regression and additive and multiplicative parameter methods.

Genetic epidemiology

Determination of sample size based on the disease and the marker frequency in the "case" and in the "control" populations Stratification of study population based on gender, ethnic, socio-economic variation Establishing a "causal relationship" between genotype and disease, using, using various association and linkage approaches—viz., case-control designs, family studies (if available), transmission disequilibrium tests etc., Linkage analysis between markers and a candidate locus using two-point and multipoint approaches.

Computer programs used for genetic analysis are: Dna SP version 3.0, by Juilo Rozas, University of Barcelona, Spain. Http://www.bio.ub.es/-Julio; Arlequin 1.1 by S. Schnieder, J-M Kueffer, D. Roessli and L. Excoffier. University of Geneva, Switzerland, http://anthropologie.unige.ch/arlequin. PAUP*4, by D. L. Swofford, Sinauer Associates, Inc., 1999. SYSTAT software, SPSS Inc., Chicago, Ill., 1998;. Linkage User's Guide, by J. Ott, Rockefeller University, Http://Linkage.rockefeller.edu/soft/linkage Guidance in the selection of appropriate genetic statistical tests for analysis of data can be obtained from texts such as: *Fundamentals of Genetic Epidemiology* (Monographs in Epidemiology and Biostatistics, Vol 22) by M. J. Khoury, B.

H. Cohen & T. H. Beaty, Oxford Univ Press, 1993; *Methods in Genetic Epidemiology* by Newton E. Morton, S. Karger Publishing, 1983; *Methods in Observational Epidemiology*, 2nd edition (Monographs in Epidemiology and Biostatistics, V. 26) by J. L. Kelsey (Editor), A. S. Whittemore & A. S. Evans, 1996; *Clinical Trials: Design, Conduct, and Analysis* (Monographs in Epidemiology and Biostatistics, Vol 8) by C. L. Meinert & S. Tonascia, 1986)

I. Retrospective clinical trials.

In general, the goal of retrospective clinical trials is to test and refine hypotheses regarding genetic factors that are associated with drug responses. The best supported hypotheses can subsequently be tested in prospective clinical trials, and data from the prospective trials will likely comprise the main basis for an application to register the drug and predictive genetic test with the appropriate regulatory body. In some cases, however, it may become acceptable to use data from retrospective trials to support regulatory filings. Exemplary strategies and criteria for stratifying patients in a retrospective clinical trial are provided below.

Clinical trials to study the effect of one gene locus on drug response

A. Stratify patients by genotype at one candidate variance in the candidate gene locus.

1. Genetic stratification of patients can be accomplished in several ways, including the following (where 'A' is the more frequent form of the variance being assessed and 'a' is the less frequent form):
    (a) AA vs. aa
    (b) AA vs. Aa vs. aa
    (c) AA vs. (Aa+aa)
    (d) (AA+Aa) vs. aa.

2. The effect of genotype on drug response phenotype may be affected by a variety of nongenetic factors. Therefore it may be beneficial to measure the effect of genetic stratification in a subgroup of the overall clinical trial population. Subgroups can be defined in a number of ways including, for example, biological, clinical, pathological or environmental criteria. For example, the predictive value of genetic stratification can be assessed in a subgroup or subgroups defined by:

a. Biological criteria:
   i. gender (males vs. females)
   ii. age (for example above 60 years of age). Two, three or more age groups may be useful for defining subgroups for the genetic analysis.
   iii. hormonal status and reproductive history, including pre- vs. post-menopausal status of women, or multiparous vs. nulliparous women
   iv. ethnic, racial or geographic origin, or surrogate markers of ethnic, racial or geographic origin. (For a description of genetic markers that serve as surrogates of racial/thnic origin see, for example: Rannala, B. and J. L. Mountain, Detecting immigration by using multilocus genotypes. *Proc Natl Acad Sci USA*, 94 (17): 9197–9201, 1997. Other surrogate markers could be used, including biochemical markers.)

b. Clinical criteria:
   i. Disease status. There are clinical grading scales for many diseases. For example, the status of Alzheimer's Disease patients is often measured by cognitive assessment scales such as the mini-mental status exam (MMSE) or the Alzheimer's Disease Assessment Scale (ADAS), which includes a cognitive component (ADAS-COG). There are also clinical assessment scales for many other diseases, including cancer.
   ii. Disease manifestations (clinical presentation).
   iii. Radiological staging criteria.

c. Pathological criteria:
   i. Histopathologic features of disease tissue, or pathological diagnosis. (For example there are many varieties of lung cancer: squamous cell carcinoma, adenocarcinoma, small cell carcinoma, bronchoalveolar carcinoma, etc., each of which may—which, in combination with genetic variation, may correlate with
   ii. Pathological stage. A variety of diseases, particularly cancer, have pathological staging schemes
   iii. Loss of heterozygosity (LOH)
   iv. Pathology studies such as measuring levels of a marker protein
   v. Laboratory studies such as hormone levels, protein levels, small molecule levels 3. Measure frequency of responders in each genetic subgroup. Subgroups may be defined in several ways.
   i. more than two age groups
   ii. reproductive status such as pre or post-menopausal 4. Stratify by haplotype at one candidate locus where the haplotype is made up of two variances, three variances or greater than three variances. Data from already completed clinical trials can be retrospectively reanalyzed. Since the questions are new, the data can be treated as if it were a prospective trial, with identified variances or haplotypes as stratification criteria or endpoints in clinically stratified data (e.g. what is the frequency of a particular variance in a response group compared to nonresponsders). Care should be taken to in studying a population in which there may be a link between drug-related genes and disease-related genes.

Retrospective pharmacogenetic trials can be conducted at each of the phases of clinical development, if sufficient data is available to correlate the physiologic effect of the candidate therapeutic intervention and the allelic variance or variances within the treatment population. In the case of a retrospective trial, the data collected from the trial can be re-analyzed by imposing the additional stratification on groups of patients by specific allelic variances that may exist in the treatment groups. Retrospective trials can be useful to ascertain whether a hypothesis that a specific variance has a significant effect on the efficacy or toxicity profile for a candidate therapeutic intervention.

A prospective clinical trial has the advantage that the trial can be designed to ensure the trial objectives can be met with statistical certainty. In these cases, power analysis, which includes the parameters of allelic variance frequency, number of treatment groups, and ability to detect positive outcomes can ensure that the trial objectives are met.

In designing a pharmacogenetic trial, retrospective analysis of Phase II or Phase III clinical data can indicate trial variables for which further analysis is beneficial. For example, surrogate endpoints, pharmacokinetic parameters, dosage, efficacy endpoints, ethnic and gender differences, and toxicological parameters may result in data that would require further analysis and re-examination through the design of an additional trial. In these cases, analysis involving statistics, genetics, clinical outcomes, and economic parameters may be considered prior to proceeding to the stage of designing any additional trials. Factors involved in the consideration of statistical significance may include Bonferroni analysis, permutation testing, with multiple testing correction resulting in a difference among the treatment groups that has occurred as a result of a chance of no greater than 20%, i.e. $p<0.20$. Factors included in determining clinical outcomes to be relevant for additional testing may include, for example, consideration of the target indication, the trial endpoints, progression of the disease, disorder, or condition during the trial study period, biochemical or pathophysiologic relevance of the candidate therapeutic intervention, and other variables that were not included or anticipated in the initial study design or clinical protocol. Factors to be included in the economic significance in determining additional testing parameters include sample size, accrual rate, number of clinical sites or institutions required, additional or other available medical or therapeutic interventions approved for human use, and additional or other available medical or therapeutic interventions concurrently or anticipated to enter human clinical testing. Further, there may be patients within the treatment categories that present data that fall outside of the average or mean values, or there may be an indication of multiple allelic loci that are involved in the responses to the candidate therapeutic intervention. In these cases, one could propose a prospective clinical trial having an objective to determine the significance of the variable or parameter and its effect on the outcome of the parent Phase II trial. In the case of a pharmacogenetic difference, i.e. a single or multiple allelic difference, a population could be selected based upon the distribution of genotypes. The candidate therapeutic intervention could then be tested in this group of volunteers to test for efficacy or toxicity. The repeat prospective study could be a Phase I limited study in which the subjects would be healthy human volunteers, or a Phase II limited efficacy study in which patients which satisfy the inclusion criteria could be enrolled. In either case, the second, confirmatory trial could then be used to systematically ensure an adequate number of patients with appropriate phenotype is enrolled in a Phase III trial.

A placebo controlled pharmacogenetics clinical trial design will be one in which target allelic variance or variances will be identified and a diagnostic test will be performed to stratify the patients based upon presence, absence, or combination thereof of these variances. In the Phase II or Phase III stage of clinical development, determination of a specific sample size of a prospective trial will be described to include factors such as expected differences between a placebo and treatment on the primary or secondary endpoints and a consideration of the allelic frequencies.

The design of a pharmacogenetics clinical trial will include a description of the allelic variance impact on the observed efficacy between the treatment groups. Using this type of design, the type of genetic and phenotypic relationship display of the efficacy response to a candidate therapeutic intervention will be analyzed. For example, a genotypically dominant allelic variance or variances will be those in which both heterozygotes and homozygotes will demonstrate a specific phenotypic efficacy response different from the homozygous recessive genotypic group. A pharmacogenetic approach is useful for clinicians and public health professionals to include or eliminate small groups of responders or non-responders from treatment in order to avoid unjustified side-effects. Further, adjustment of dosages when clear clinical difference between heterozygous and homozygous individuals may be beneficial for therapy with the candidate therapeutic intervention.

In another example, a reccesive allelic variance or variances will be those in which only the homozygote recessive for that or those variances will demonstrate a specific phenotypic efficacy response different from the heterozygotes or homozygous dominants. An extension of these examples may include allelic variance or variances organized by haplotypes from additional gene or genes.

V. Variance Identification and Use

A. Initial Identification of variances in genes

Selection of population size and composition

Prior to testing to identify the presence of sequence variances in a particular gene or genes, it is useful to understand how many individuals should be screened to provide confidence that most or nearly all pharmacogenetically relevant variances will be found. The answer depends on the frequencies of the phenotypes of interest and what assumptions we make about heterogeneity and magnitude of genetic effects. Prior to testing to identify the presence of sequence variances in a particular gene or genes, it is useful to understand how many individuals should be screened to provide confidence that most or nearly all pharmacogenetically relevant variances will be found. The answer depends on the frequencies of the phenotypes of interest and what assumptions we make about heterogeneity and magnitude of genetic effects. At the beginning we only know phenotype frequencies (e.g. responders vs. nonresponders, frequency of various side effects, etc.).

The most conservative assumption (resulting in the lowest estimate of allele frequency, and consequently the largest suggested screening population) is (i) that the phenotype (e.g. toxicity or efficacy) is multifactorial (i.e. can be caused by two or more variances or combinations of variances), (ii) that the variance of interest has a high degree of penetrance (i.e. is consistently associated with the phenotype), and (iii) that the mode of transmission is Mendelian dominant. Consider a pharmacogenetic study designed to identify predictors of efficacy for a compound that produces a 15% response rate in a nonstratified population. If half the response is sustantially attributable to a given variance, and the variance is consistently associated with a positive response (in 80% of cases) and the variance need only be present in one copy to produce a positive result then ~10% of the subjects are likely heterozygotes for the variance that produces the response. The Hardy-Weinberg equation can be used to infer an allele frequency in the range of 5% from these assumptions (given allele frequencies of 5%/95% then: 2×0.05×0.95=0.095, or 9.5% heterozygotes are expected, and 0.05×0.05=0.0025, or 0.25% homozygotes are expected. They sum to 9.5%+0.25%=9.75% likely responders, 80% of whom, or 7.6%, are likely real responders due to presence of the positive response allele. Thus about half of the 15% responders are accounted for.). From the Table it can be seen that, in order to have a 99% chance of detecting an allele present at a frequency of 5% nearly 50 subjects should be screened for variances, assuming that the variances occur in the screening population at the same frequency as they occur in the patient population. Similar analyses can be performed for other assumptions regarding likely magnitude of effect, penetrance and mode of genetic transmission.

At the beginning we only know phenotype frequencies (e.g. responders vs. nonresponders, frequency of various side effects, etc.). As an example, the occurrence of serious 5-FU/FA toxicity—e.g. toxicity requiring hospitalization is often >10%. The occurrence of life threatening toxicity is in the 1–3% range (Buroker et al. 1994). The occurrence of complete remissions is on the order of 2–8%. The lowest frequency phenotypes are thus on the order of ~2%. If we assume that (i) homogeneous genetic effects are responsible for half the phenotypes of interest and (ii) for the most part the extreme phenotypes represent recessive genotypes, then we need to detect alleles that will be present at ~10% frequency (0.1×0.1=0.01, or 1% frequency of homozygotes)

if the population is at Hardy-Weinberg equilibrium. To have a ~99% chance of identifying such alleles would require searching a population of 22 individuals (see Table below). If the major phenotypes are associated with heterozygous genotypes then we need to detect alleles present at ~0.5% frequency (2×0.005×0.995=0.00995, or ~1% frequency of heterozygotes). A 99% chance of detecting such alleles would require ~40 individuals (Table below). Given the heterogeneity of the North American population we cannot assume that all genotypes are present in Hardy-Weinberg proportions, therefore a substantial oversampling may be done to increase the chances of detecting relevant variances: For our initial screening, usually, 62 individuals of known race/ethnicity are screened for variance. Variance detection studies can be extended to outliers for the phenotypes of interest to cover the possibility that important variances were missed in the normal population screening.

TABLE 4

Number of subjects genotyped

| Allele frequencies | n = 5 | n = 10 | n = 15 | n = 20 | n = 25 | n = 30 | n = 35 | n = 50 |
|---|---|---|---|---|---|---|---|---|
| p = .99, | 9.56 | 18.21 | 26.03 | 33.10 | 39.50 | 45.28 | 50.52 | 63.40 |
| p = .97, | 26.26 | 45.62 | 59.90 | 70.43 | 78.19 | 83.92 | 88.14 | 95.24 |
| p = .95, | 40.13 | 64.15 | 78.53 | 87.15 | 92.30 | 95.39 | 97.24 | 99.65 |
| p = .93, | 51.60 | 76.58 | 88.66 | 94.51 | 97.34 | 98.71 | 99.38 | 99.93 |
| p = .9, q = | 65.13 | 87.84 | 95.76 | 98.52 | 99.48 | 99.82 | 99.94 | >99.9 |
| p = .8, q = | 89.26 | 98.84 | 99.88 | 99.99 | >99.9 | >99.9 | >99.9 | >99.9 |
| p = .7, q = | 97.17 | 99.92 | 99.99 | >99.9 | >99.9 | >99.9 | >99.9 | >99.9 |

Likelihood of Detecting Polymorphism in a Population as a Function of Allele Frequency & Number of Individuals Genotyped Table 4 above shows the probability (expressed as percent) of detecting both alleles (i.e. detecting heterozygotes) at a biallelic locus as a function of (i) the allele frequencies and (ii) the number of individuals genotyped. The chances of detecting heterozygotes increases as the frequencies of the two alleles approach 0.5 (down a column), and as the number of individuals genotyped increases (to the right along a row). The numbers in the table are given by the formula: $1-(p)^{2n}-(q)^{2n}$. Allele frequencies are designated p and q and the number of individuals tested is designated n. (Since humans are diploid, the number of alleles tested is twice the number of individuals, or 2n.)

While it is preferable that numbers of individuals, or independent sequence samples, are screened to identify variances in a gene, it is also very beneficial to identify variances using smaller numbers of individuals or sequence samples. For example, even a comparison between the sequences of two samples or individuals can reveal sequence variances between them. Preferably, 5, 10, or more samples or individuals are screened.

Source of nucleic acid samples

Nucleic acid samples, for example for use in variance identification, can be obtained from a variety of sources as known to those skilled in the art, or can be obtained from genomic or cDNA sources by known methods. For example, the Coriell Cell Repository (Camden, N.J.) maintains over 6,000 human cell cultures, mostly fibroblast and lymphoblast cell lines comprising the NIGMS Human Genetic Mutant Cell Repository. A catalog (http://locus.umdnj.edu/nigms) provides racial or ethnic identifiers for many of the cell lines. It is preferable to perform polymorphism discovery on a population that mimics the population to be evaluated in a clinical trial, both in terms of racial/ethnic/geographic background and in terms of disease status. Otherwise, it is generally preferable to include a broad population sample including, for example, (for trials in the United States): Caucasians of Northern, Central and Southern European origin, Africans or African-Americans, Hispanics or Mexicans, Chinese, Japanese, American Indian, East Indian, Arabs and Koreans.

Source of human DNA, RNA and cDNA samples

PCR based screening for DNA polymorphism can be carried out using either genomic DNA or cDNA produced from mRNA. For many genes, only cDNA sequences have been published, therefore the analysis of those genes is, at least initially, at the cDNA level since the determination of intron-exon boundaries and the isolation of flanking sequences is a laborious process. However, screening genomic DNA has the advantage that variances can be identified in promoter, intron and flanking regions. Such variances may be biologically relevant. Therefore preferably, when variance analysis of patients with outlier responses is performed, analysis of selected loci at the genomic level is also performed. Such analysis would be contingent on the availability of a genomic sequence or intron-exon boundary sequences, and would also depend on the anticipated biological importance of the gene in connection with the particular response.

When cDNA is to be analyzed it is very beneficial to establish a tissue source in which the genes of interest are expressed at sufficient levels that cDNA can be readily produced by RT-PCR. Preliminary PCR optimization efforts for 19 of the 29 genes in Table 2 reveal that all 19 can be amplified from lymphoblastoid cell mRNA. The 7 untested genes belong on the same pathways and are expected to also be PCR amplifiable.

PCR Optimization

Primers for amplifying a particular sequence can be designed by methods known to those skilled in the art, including by the use of computer programs such as the PRIMER software available from Whitehead Institute/MIT Genome Center. In some cases it is preferable to optimize the amplification process according to parameters and methods known to those skilled in the art; optimization of PCR reactions based on a limited array of temperature, buffer and primer concentration conditions is utilized. New primers are obtained if optimization fails with a particular primer set.

Variance detection using T4 endonuclease VII mismatch cleavage method

Any of a variety of different methods for detecting variances in a particular gene can be utilized, such as those described in the patents and applications cited in section A above. An exemplary method is a T4 EndoVII method. The enzyme T4 endonuclease VII (T4E7) is derived from the bacteriophage T4. T4E7 specifically cleaves heteroduplex DNA containing single base mismatches, deletions or insertions. The site of cleavage is 1 to 6 nucleotides 3' of the mismatch. This activity has been exploited to develop a general method for detecting DNA sequence variances (Youil et al. 1995; Mashal and Sklar, 1995). A quality controlled T4E7 variance detection procedure based on the T4E7 patent of R. G. H. Cotton and co-workers. (Del Tito et al., in press) is preferably utilized. T4E7 has the advantages of being rapid, inexpensive, sensitive and selective. Further, since the enzyme pinpoints the site of sequence variation, sequencing effort can be confined to a 25–30 nucleotide segment.

The major steps in identifying sequence variations in candidate genes using T4E7 are: (1) PCR amplify 400–600 bp segments from a panel of DNA samples; (2) mix a fluorescently-labeled probe DNA with the sample DNA; (3) heat and cool the samples to allow the formation of heteroduplexes; (4) add T4E7 enzyme to the samples and incubate for 30 minutes at 37° C., during which cleavage occurs at sequence variance mismatches; (5) run the samples on an ABI 377 sequencing apparatus to identify cleavage bands, which indicate the presence and location of variances in the sequence; (6) a subset of PCR fragments showing cleavage are sequenced to identify the exact location and identity of each variance.

The T4E7 Variance Imaging procedure has been used to screen particular genes. The efficiency of the T4E7 enzyme to recognize and cleave at all mismatches has been tested and reported in the literature. One group reported detection of 81 of 81 known mutations (Youil et al. 1995) while another group reported detection of 16 of 17 known mutations (Mashal and Sklar, 1995). Thus, the T4E7 method provides highly efficient variance detection.

DNA sequencing

A subset of the samples containing each unique T4E7 cleavage site is selected for sequencing. DNA sequencing can, for example, be performed on ABI 377 automated DNA sequencers using BigDye chemistry and cycle sequencing. Analysis of the sequencing runs will be limited to the 30–40 bases pinpointed by the T4E7 procedure as containing the variance. This provides the rapid identification of the altered base or bases.

In some cases, the presence of variances can be inferred from published articles which describe Restriction Fragment Length Polymorphisms (RFLP). The sequence variances or polymorphisms creating those RFLPs can be readily determined using convention techniques, for example in the following manner. If the RFLP was initially discovered by the hybridization of a cDNA, then the molecular sequence of the RFLP can be determined by restricting the cDNA probe into fragments and separately hybridizing to a Southern blot consisting of the restriction digestion with the enzyme which reveals the polymorphic site, identifying the sub-fragment which hybridizes to the polymorphic restriction fragment, obtaining a genomic clone of the gene (e.g., from commercial services such as Genome Systems (Saint Louis, Mo.) or Research Genetics (Ala.) which will provide appropriate genomic clones on receipt of appropriate primer pairs). Using the genomic clone, restrict the genomic clone with the restriction enzyme which revealed the polymorphism and isolate the fragment which contains the polymorphism, e.g., identifying by hybridization to the cDNA which detected the polymorphism. The fragment is then sequenced across the polymorphic site. A copy of the other allele can be obtained by PCT from addition samples.

Variance detection using sequence scanning

In addition to the physical methods, e.g., those described above and others known to those skilled in the art (see, e.g., Housman, U.S. Pat. No. 5,702,890; Housman et al., U.S. patent application No. 09/045,053), variances can be detected using computational methods, involving computer comparison of sequences from two or more different biological sources, which can be obtained in various ways, for example from public sequence databases. The term "variance scanning" refers to a process of identifying sequence variances using computer-based comparison and analysis of multiple representations of at least a portion of one or more genes. Computational variance detection involves a process to distinguish true variances from sequencing errors or other artifacts, and thus does not require perfectly accurate sequences. Such scanning can be performed in a variety of ways, preferably, for example, as described in Stanton et al., filed Oct. 14, 1999, Ser. No. 09/419,705, attorney docket number 246/128.

While the utilization of complete cDNA sequences is highly preferred, it is also possible to utilize genomic sequences. Such analysis may be desired where the detection of variances in or near splice sites is sought. Such sequences may represent full or partial genomic DNA sequences for a gene or genes. Also, as previously indicated, partial cDNA sequences can also be utilized although this is less preferred. As described below, the variance scanning analysis can simply utilize sequence overlap regions, even from partial sequences. Also, while the present description is provided by reference to DNA, e.g., cDNA, some sequences may be provided as RNA sequences, e.g., mRNA sequences. Such RNA sequences may be converted to the corresponding DNA sequences, or the analysis may use the RNA sequences directly.

B. Determination of Presence or Absence of Known Variances

The identification of the presence of previously identified variances in cells of an individual, usually a particular patient, can be performed by a number of different techniques as indicated in the Summary above. Such methods include methods utilizing a probe which specifically recognizes the presence of a particular nucleic acid or amino acid sequence in a sample. Common types of probes include nucleic acid hybridization probes and antibodies, for example, monoclonal antibodies, which can differentially bind to nucleic acid sequences differing in one or more variance sites or to polypeptides which differ in one or more amino acid residues as a result of the nucleic acid sequence variance or variances. Generation and use of such probes is well-known in the art and so is not described in detail herein.

Preferably, however, the presence or absence of a variance is determined using nucleotide sequencing of a short sequence spanning a previously identified variance site. This will utilize validated genotyping assays for the polymorphisms previously identified. Since both normal and tumor cell genotypes can be measured, and since tumor material will frequently only be available as paraffin embedded sections (from which RNA cannot be isolated), it will be necessary to utilize genotyping assays that will work on genomic DNA. Thus PCR reactions will be designed, optimized, and validated to accommodate the intron-exon structure of each of the genes. If the gene structure has been published (as it has for some of the listed genes), PCR primers can be designed directly. However, if the gene structure is unknown, the PCR primers may need to be moved around in order to both span the variance and avoid exon-intron boundaries. In some cases one-sided PCR methods such as bubble PCR (Ausubel et al. 1997) may be useful to obtain flanking intronic DNA for sequence analysis.

Using such amplification procedures, the standard method used to genotype normal and tumor tissues will be DNA sequencing. PCR fragments encompassing the variances will be cycle sequenced on ABI 377 automated sequencers using Big Dye chemistry C. Correlation of the Presence or Absence of Specific Variances with Differential Treatment Response Prior to establishment of a diagnostic test for use in the selection of a treatment method or elimination of a treatment method, the presence or absence of one or more specific variances in a gene or in multiple genes is correlated with a differential treatment response. (As discussed above, usually the existence of a variable response and the correlation of such a response to a particular gene is performed first.) Such a differential response can be determined using prospective and/or retrospective data. Thus, in some cases, published reports will indicate that the course of treatment will vary depending on the presence or absence of particular variances. That information can be utilized to create a diagnostic test and/or incorporated in a treatment method as an efficacy or safety determination step.

Usually, however, the effect of one or more variances is separately determined. The determination can be performed by analyzing the presence or absence of particular variances in patients who have previously been treated with a particular treatment method, and correlating the variance presence or absence with the observed course, outcome, and/or development of adverse events in those patients. This approach is useful in cases in which observation of treatment effects was clearly recorded and cell samples are available or can be obtained. Alternatively, the analysis can be performed prospectively, where the presence or absence of the variance or variances in an individual is determined and the course, outcome, and/or development of adverse events in those patients is subsequently or concurrently observed and then correlated with the variance determination.

Analysis of Haplotypes Increases Power of Genetic Analysis

In some cases, variation in activity due to a single gene or a single genetic variance in a single gene may not be sufficient to account for a clinically significant fraction of the observed variation in patient response to a treatment, e.g., a drug, there may be other factors that account for some of the variation in patient response. Drug response phenotypes may vary continuously, and such (quantitative) traits may be influenced by a number of genes (Falconer and Mackay, *Quantitative Genetics,* 1997). Although it is impossible to determine a priori the number of genes influencing a quantitative trait, potentially only one or a few loci have large effects, where a large effect is 5–20% of total variation in the phenotype (Mackay, 1995).

Having identified genetic variation in enzymes that may affect action of a specific drug, it is useful to efficiently address its relation to phenotypic variation. The sequential testing for correlation between phenotypes of interest and single nucleotide polymorphisms may be adequate to detect associations if there are major effects associated with single nucleotide changes; certainly it is useful to this type of analysis. However there is no way to know in advance whether there are major phenotypic effects associated with single nucleotide changes and, even if there are, there is no way to be sure that the salient variance has been identified by screening cDNAs. A more powerful way to address the question of genotype-phenotype correlation is to assort genotypes into haplotypes. (A haplotype is the cis arrangement of polymorphic nucleotides on a particular chromosome.) Haplotype analysis has several advantages compared to the serial analysis of individual polymorphisms at a locus with multiple polymorphic sites.

(1) Of all the possible haplotypes at a locus ($2^n$ haplotypes are theoretically possible at a locus with n binary polymorphic sites) only a small fraction will generally occur at a significant frequency in human populations. Thus, association studies of haplotypes and phenotypes will involve testing fewer hypotheses. As a result there is a smaller probability of Type I errors, that is, false inferences that a particular variant is associated with a given phenotype.

(2) The biological effect of each variance at a locus may be different both in magnitude and direction. For example, a polymorphism in the 5' UTR may affect translational efficiency, a coding sequence polymorphism may affect protein activity, a polymorphism in the 3' UTR may affect mRNA folding and half life, and so on. Further, there may be interactions between variances: two neighboring polymorphic amino acids in the same domain—say cys/arg at residue 29 and met/val at residue 166 —may, when combined in one sequence, for example, 29cys-166val, have a deleterious effect, whereas 29cys-166met, 29arg-166met and 29arg-166val proteins may be nearly equal in activity. Haplotype analysis is the best method for assessing the interaction of variances at a locus.

(3) Templeton and colleagues have developed powerful methods for assorting haplotypes and analyzing haplotype/phenotype associations (Templeton et al., 1987). Alleles which share common ancestry are arranged into a tree structure (cladogram) according to their (inferred) time of origin in a population (that is, according to the principle of parsimony). Haplotypes that are evolutionarily ancient will be at the center of the branching structure and new ones (reflecting recent mutations) will be represented at the periphery, with the links representing intermediate steps in evolution. The cladogram defines which haplotype-phenotype association tests should be performed to most efficiently exploit the available degrees of freedom, focusing attention on those comparisons most likely to define functionally different haplotypes (Haviland et al., 1995). This type of analysis has been used to define interactions between heart disease and the apolipoprotein gene cluster (Haviland et al 1995) and Alzheimer's Disease and the Apo-E locus (Templeton 1995) among other studies, using populations as small as 50 to 100 individuals. The methods of Templeton have also been applied to meaure the genetic determinants of variation in the angiotensin-I converting enzyme gene. (Keavney, B., McKenzie, C. A., Connoll, J. M. C., et al. Measured haplotype analysis of the angiotensin-I converting enzyme gene. *Human Molecular Genetics* 7: 1745–1751.)

Methods for determining haplotypes

The goal of haplotyping is to identify the common haplotypes at selected loci that have multiple sites of variance. Haplotypes are usually determined at the cDNA level. Several general approaches to identification of haplotyes can be employed. Haplotypes may also be estimated using computational methods or determined definitively using experimental approaches. Computational approachs generally include an expectation maximization (E-M) algorithm (see, for example: Excoffier and Slatkin, Mol. Biol. Evol. 1995) or a combination of Parsimony (see below) and E-M methods.

Haplotypes can be determined experimentally without requirement of a haplotyping method by genotyping samples from a set of pedigrees and observing the segregation of haplotypes. For example families collected by the Centre d'Etude du Polymorphisme Humaine (CEPH) can be used. Cell lines from these families are available from the Coriell Repository. This approach will be useful for cataloging common haplotypes and for validating methods on samples with known haplotypes. The set of haplotypes determined by pedigree analysis can be useful in computational methods, including those utilizing the E-M algorithm.

Haplotypes can also be determined directly from cDNA using the T4E7 procedure. T4E7 cleaves mismatched heteroduplex DNA at the site of the mismatch. If a heteroduplex contains only one mismatch, cleavage will result in the generation of two fragments. However, if a single heteroduplex (allele) contains two mismatches, cleavage will occur at two different sites resulting in the generation of three fragments. The appearance of a fragment whose size corresponds to the distance between the two cleavage sites is diagnostic of the two mismatches being present on the same strand (allele). Thus, T4E7 can be used to determine haplotypes in diploid cells.

An alternative method, allele specific PCR, may be used for haplotyping. The utility of allele specific PCR for haplotyping has already been established (Michalatos-Beloin et al., 1996; Chang et al. 1997). Opposing PCR primers are designed to cover two sites of variance (either adjacent sites or sites spanning one or more internal variances). Two versions of each primer are synthesized, identical to each other except for the 3' terminal nucleotide. The 3' terminal nucleotide is designed so that it will hybridize to one but not the other variant base. PCR amplification is then attempted with all four possible primer combinations in separate wells. Because Taq polymerase is very inefficient at extending 3' mismatches, the only samples which will be amplified will be the ones in which the two primers are perfectly matched for sequences on the same strand (allele). The presence or absence of PCR product allows haplotyping of diploid cell lines. At most two of four possible reactions should yield products. This procedure has been successfully applied, for example, to haplotype the DPD amino acid polymorphisms.

Parsimony methods are also useful for classifying DNA sequences, haplotypes or phenotypic characters. Parsimony principle maintains that the best explanation for the observed differences among sequences, phenotypes (individuals, species) etc., is provided by the smallest number of evolutionary changes. Alternatively, simpler hypotheses are preferable to explain a set of data or patterns, than more complicated ones, and ad hoc hypotheses should be avoided whenever possible (Molecular Systematics, Hillis et al., 1996). Parsimony methods thus operate by minimizing the number of evolutionary steps or mutations (changes from one sequence/character) required to account for a given set of data.

For example, supposing we want to obtain relationships among a set of sequences and construct a structure (tree/topology), we first count the minimum number of mutations that are required for explaining the observed evolutionary changes among a set of sequences. A structure (topology) is constructed based on this number. When once this number is obtained, another structure is tried. This process is continued for all reasonable number of structures. Finally, the structure that required the smallest number of mutational steps is chosen as the likely structure/evolutionary tree for the sequences studied.

For haplotypes identified herein, haplotypes were identified by examining genotypes from each cell line. This list of genotypes was optimized to remove variance sites/individuals with incomplete information, and the genotype from each remaining cell line was examined in turn. The number of heterozygotes in the genotype were counted, and those genotypes containing more than one heterozygote were discarded, and the rest were gathered in a list for storage and display.

D. Selection of Treatment Method Using Variance Information

1. General

Once the presence or absence of a variance or variances in a gene or genes is shown to correlate with the efficacy or safety of a treatment method, that information can be used to select an appropriate treatment method for a particular patient. In the case of a treatment which is more likely to be effective when administered to a patient who has at least one copy of a gene with a particular variance or variances (in some cases the correlation with effective treatment is for patients who are homozygous for a variance or set of variances in a gene) than in patients with a different variance or set of variances, a method of treatment is selected (and/or a method of administration) which correlates positively with the particular variance presence or absence which provides the indication of effectiveness. As indicated in the Summary, such selection can involve a variety of different choices, and the correlation can involve a variety of different types of treatments, or choices of methods of treatment. In some cases, the selection may include choices between treatments or methods of administration where more than one method is likely to be effective, or where there is a range of expected effectiveness or different expected levels of contra-indication or deleterious effects. In such cases the selection is preferably performed to select a treatment which will be as effective or more effective than other methods, while having a comparatively low level of deleterious effects. Similarly, where the selection is between method with differing levels of deleterious effects, preferably a method is selected which has low such effects but which is expected to be effective in the patient.

Alternatively, in cases where the presence or absence of the particular variance or variances is indicative that a treatment or method of administration is more likely to be ineffective or contra-indicated in a patient with that variance or variances, then such treatment or method of administration is generally eliminated for use in that patient.

2. Diagnostic Methods

Once a correlation between the presence and absence of at least one variance in a gene or genes and an indication of the effectiveness of a treatment, the determination of the presence or absence of that at least one variance provides diagnostic methods, which can be used as indicated in the Summary above to select methods of treatment, methods of administration of a treatment, methods of selecting a patient or patients for a treatment and others aspects in which the determination of the presence or absence of those variances provides useful information for selecting or designing or preparing methods or materials for medical use in the aspects of this invention. As previously stated, such variance determination or diagnostic methods can be performed in various ways as understood by those skilled in the art.

In certain variance determination methods, it is necessary or advantageous to amplify one or more nucleotide sequences in one or more of the genes identified herein. Such amplification can be performed by conventional methods, e.g., using polymerase chain reaction (PCR) amplification. Such amplification methods are well-known to those skilled in the art and will not be specifically described herein. For most applications relevant to the present invention, a sequence to be amplified includes at least one variance site, which is preferably a site or sites which provide variance information indicative of the effectiveness of a method of treatment or method of administration of a treatment, or effectiveness of a second method of treatment which reduces a deleterious effect of a first treatment method, or which enhances the effectiveness of a first method of treatment. Thus, for PCR, such amplification generally utilizes primer oligonucleotides which bind to or extent through at least one such variance site under amplification conditions.

For convenient use of the amplified sequence, e.g., for sequencing, it is beneficial that the amplified sequence be of limited length, but still long enough to allow convenient and specific amplification. Thus, preferably the amplified sequence has a length as described in the Summary.

Also, in certain variance determination, it is useful to sequence one or more portions of a gene or genes, in particular, portions of the genes identified in this disclosure. As understood by persons familiar with nucleic acid sequencing, there are a variety of effective methods. In particular, sequencing can utilize dye termination methods and mass spectrometric methods. The sequencing generally involves a nucleic acid sequence which includes a variance site as indicated above in connection with amplification. Such sequencing can directly provide determination of the presence or absence of a particular variance or set of variances, e.g., a haplotype, by inspection of the sequence (visually or by computer). Such sequencing is generally conducted on PCR amplified sequences in order to provide sufficient signal for practical or reliable sequence determination.

Likewise, in certain variance determinations, it is useful to utilize a probe or probes. As previously described, such probes can be of a variety of different types.

VI. Pharmaceutical Compositions, Including Pharmaceutical Compositions Adapted to be Preferentially Effective in Patients Having Particular Genetic Characteristics A. General The methods of the present invention, in many cases will utilize conventional pharmaceutical compositions, but will allow more advantageous and beneficial use of those compositions due to the ability to identify patients who are likely to benefit from a particular treatment or to identify patients for whom a particular treatment is less likely to be effective or for whom a particular treatment is likely to produce undesirable or intolerable effects. However, in some cases, it is advantageous to utilize compositions which are adapted to be preferentially effective in patients who possess particular genetic characteristics, i.e., in whom a particular variance or variances in one or more genes is present or absent (depending on whether the presence or the absence of the variance or variances in a patient is correlated with an increased expectation of beneficial response). Thus, for example, the presence of a particular variance or variances may indicate that a patient can beneficially receive a significantly higher dosage of a drug than a patient having a different B. Regulatory Indications and Restrictions The sale and use of drugs and the use of other treatment methods usually are subject to certain restrictions by a government regulatory agency charged with ensuring the safety and efficacy of drugs and treatment methods for medical use, and approval is based on particular indications. In the present invention it is found that variability in patient response or patient tolerance of a drug or other treatment often correlates with the presence or absence of particular variances in particular genes. Thus, it is expected that such a regulatory agency may indicate that the approved indications for use of a drug with a variance-related variable response or toleration include use only in patients in whom the drug will be effective, and/or for whom the administration of the drug will not have intolerable deleterious effects, such as excessive toxicity or unacceptable side-effects. Conversely, the drug may be given for an indication that it may be used in the treatment of a particular disease or condition where the patient has at least one copy of a particular variance, variances, or variant form of a gene. Even if the approved indications are not narrowed to such groups, the regulatory agency may suggest use limited to particular groups or excluding particular groups or may state advantages of use or exclusion of such groups or may state a warning on the use of the drug in certain groups. Consistent with such suggestions and indications, such an agency may suggest or recommend the use of a diagnostic test to identify the presence or absence of the relevant variances in the prospective patient. Such diagnostic methods are described in this description. Generally, such regulatory suggestion or indication is provided in a product insert or label, and is generally reproduced in references such as the Physician's Desk Reference (PDR). Thus, this invention also includes drugs or pharmaceutical compositions which carry such a suggestion or statement of indication or warning or suggestion for a diagnostic test, and which may also be packaged with an insert or label stating the suggestion or indication or warning or suggestion for a diagnostic test.

In accord with the possible variable treatment responses, an indication or suggestion can specify that a patient be heterozygous, or alternatively, homozygous for a particular variance or variances or variant form of a gene. Alternatively, an indication or suggestion may specify that a patient have no more than one copy, or zero copies, of a particular variance, variances, or variant form of a gene.

A regulatory indication or suggestion may concern the variances or variant forms of a gene in normal cells of a patient and/or in cells involved in the disease or condition. For example, in the case of a cancer treatment, the response of the cancer cells can depend on the form of a gene remaining in cancer cells following loss of heterozygosity affecting that gene. Thus, even though normal cells of the patient may contain a form of the gene which correlates with effective treatment response, the absence of that form in cancer cells will mean that the treatment would be less likely to be effective in that patient than in another patient who retained in cancer cells the form of the gene which correlated with effective treatment response. Those skilled in the art will understand whether the variances or gene forms in normal or disease cells are most indicative of the expected treatment response, and will generally utilize a diagnostic test with respect to the appropriate cells. Such a cell type indication or suggestion may also be contained in a regulatory statement, e.g., on a label or in a product insert.

C. Preparation and Administration of Drugs and Pharmaceutical Compositions Including Pharmaceutical Compositions Adapted to be Preferentially Effective in Patients Having Particular Genetic Characteristics A particular compound useful in this invention can be administered to a patient either by itself, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of one or more symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et. al., in *The Pharmacological Basis of Therapeutics,* 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of disorder of interest will vary with the severity of the condition to be treated and the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences,* 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The invention described herein features methods for determining the appropriate identification of a patient diagnosed with an inflammatory disease or dysfunction or immunologic disorder based on an analysis of the patient's allele status for a gene listed in Tables 1 and 3. Specifically, the presence of at least one allele indicates that a patient will respond to a candidate therapeutic intervention aimed at treating an inflammatory or immune system clinical symptoms. In a preferred approach, the patient's allele status is rapidly diagnosed using a sensitive PCR assay and a treatment protocol is rendered. The invention also provides a method for forecasting patient outcome and the suitability of the patient for entering a clinical drug trial for the testing of a candidate therapeutic intervention for an inflammatory ot immunologic disease, condition, or dysfunction.

The findings described herein indicate the predictive value of the target allele in identifying patients at risk for inflammatory or immune disease or dysfunction. In addition, because the underlying mechanism influenced by the allele status is not disease-specific, the allele status is suitable for making patient predictions for diseases not affected by the pathway as well.

The following examples, which describe exemplary techniques and experimental results, are provided for the purpose of illustrating the invention, and should not be construed as limiting.

EXAMPLES

Example 1

Asthma

I. Description of Asthma

Asthma can be an acute or a chronic condition associated with inflammation of the lower airways and variable levels of airflow obstruction. Asthma symptoms vary among individuals and may include wheezing, shortness of breadth, tightness of the chest, trouble controlling a cough, persistent cough at night, difficulty breathing during or soon after physical exertion or exercise, or waking up at night due to one of these symptoms. Episodes of these symptoms (referred to as asthma attacks, flare-ups, or exacerbations) occur when there is sufficiently severe airway constriction to render a patient almost unable or unable to breathe. Although, there can be warning signs, many attacks are sudden and unanticipated.

Individuals with asthma have inflamed airways that are supersensitive to inducers of asthma which exacerbate asthma and enhance underlying inflammation such as allergens, respiratory infections, or industrial pollutants. Provokers of asthma leading to bronchospasm include exercise or physical activities, irritants, emotions and aspirin. Asthma attacks are associated with swollen and inflamed linings of the airways, excess mucus in the airways, and bronchospasm which are reversible. In chronic asthma, there is persistent activation of resident cells (e.g. basophils, eosinophils, neutrophils) lining the airway leading to chronic inflammation which can result in irreversible changes in the airway pasages. These permanent changes are part of a remodeling process.

Recent evidence has suggested that airway inflammation is a major factor in the pathogenesis and in the severity of the disease. One theory holds that asthsma is a T helper 2 (Th2) cell-driven chronic eosinophilia mediated via dendritic and other antigen-presenting cells. The inflammatory nature of the disease is multicellular in nature, with mast cells, eosinophils, macrophages, basophils, lymphocytes, neutrophils, and epithelial cells participating and therefore immunoglobins, cytokines, chemokines, adhesion molecules, proteinases, inflammatory mediators, and growth factors are involved in various stages and interact to maintain and amplify the inflammatory response. The net result of these interactions is persistent inflammation and repair, ultimately leading to irreversible airway remodeling.

II. Current therapies for Asthma

Because asthma results from a complex combination of mediators of inflammation, most useful anti-asthma agents affect pathways for these mediators. In acute or chronic asthma, the therapeutic categories include: immunosuppressive agents including glucocorticoids, antiinflammatory agents including leukotriene receptor agonists and mast cell stabilizers (cromolyn sulfate); bronchodilators including $\beta$-adrenergic agonists, sympathomimetic agents, and xanthines; and agents to treat cough and excess mucus including expectorants and mucolytics.

Corticosteroids affect the inflammation within the airways by decreasing growth and development of mast cells, inducing apoptosis, suppressing lymphocyte generation of IL-5 and other cytokines, inhibiting some mediator release, inhibiting cytokine production, inhibiting the transcription of cytokines (for example IL-8, TNF-$\alpha$, prototypic antiviral chemokine (regulated-on-activation normal T-expressed and secreted, RANTES), and GM-CSF), and inhibiting nitric oxide synthesis.

$\beta$-Adrenergic agonists and sympathomimetics affect the pulmonary airway lining in a well-characterized mechanism of $\beta$-adrenergic receptor activation of adenylyl cyclase as well as cAMP independent mechanisms. Bronchodilation is the immediate clinical effect.

Leukotriene modifiers affect the airway by inhibition of 5-lipoxygenase, the initial enzyme of leukotriene biosynthesis, and exert their effect by decreasing leukotriene production, thereby interferring with eosinophil migration and other processes.

Corticosteroids affect the inflammation within the airways by: decreasing growth and development of mast cells, inducing apoptosis, suppressing lymphocyte generation of IL-5 and other cytokines, inhibiting some mediator release, inhibiting cytokine production, inhibiting the transcription of cytokines (for example IL-8, TNF-α, prototypic antiviral chemokine (regulated-on-activation normal T-expressed and secreted, RANTES), and GM-CSF), and inhibiting nitric oxide synthesis.

Corticosteroids in combination with long-acting β-adrenegic agonists work well as combination therapy.

Cromones are believed to act on the airway by modifying mediator release, and inhibiting mast cell degranulation.

Xanthines are believed to act on the airway in asthma by inhibiting eosinophil cell migration, and enhancing β-adrenergic pathway mediated bronchodilation via the inhibition of phosphodiesterase.

Difficult to treat or therapy-resistant asthma syndromes present a challenge to clinicians. They include difficult acute and chronic, as well as chronic severe, acute severe, therapy-resistant, difficult to control and corticosteroid-dependent asthma.

III. Limitations of Current Therapies for Asthma

Limitations Involving Efficacy

The therapies discussed above do not reverse the underlying pathological process in asthma: they merely slow or retard the progression of asthma. As thickening of the airways occurs and becomes irreversible, the therapeutic options become limited. Thus, therapies for asthma are aimed at reduction of inflammatory processes and control of symptoms starting at the earliest date (frequently in the pediatric setting).

The limitations of the adrenegic agonist compounds used for the treatment of asthma include short duration of action and ligand desensitization. Excessive use of short acting β-adrenergic agonists has been proposed to lead to loss of asthma control and consequent increases in morbidity and mortality. Long acting bronchoactive/bronchoprotective agonists acting at adrenergic receptors have supplanted short duration β-agonists.

Short-acting β-adrenergic agonists are primarily used for the relief of acute asthma symptoms. Excessive reliance on these agents is generally not advisable because 1) β-adrenergic receptors undergo a rapid desenitization and the agonist becomes an ineffective bronchodilator, and 2) repetitive high doses of short acting β-adrenergic agonists may be detrimental to to the control of asthma by potentially interfering with corticosteroid action. This desensitization occurs through a process involving G-protein receptor coupled-kinases and or cAMP dependent protein kinase or by enhanced degradation of cAMP by phosphodiesterase activity.

Glucocorticoid associated side effects include: increased appetite, weight gain, fluid retention, acne, ecchymosis, development of Cushingoid facies, hypertension, hyperkalemia, diabetes, hyperglycemia, hyperosmolar state, hyperlipidemia, hepatic steatosis, atherosclerosis, myopathy, aseptic necrosis, osteoporosis, ulcers, pancreatitis, psuedotumor cerebri, pyschosis, glaucoma, cataract formation, vascular necrosis, increased suseptibility to infection, impairment of the hypothalamus-pituitary axis, decreased thyroid hormone serum binding protiens, and impaired wound healing.

Theophylline or other phosphodiesterase inhibitors have been shown to have a narrow therapeutic window and can result in life-threatening cardiac arrythmias.

Difficult to treat asthma involves a spectrum of disease that responds suboptimally to doses of glucocorticoids. In the face of partial response to inhaled or oral steroids, higher doses are administered risking steroid associated side-effects.

The reduction of clinical symptoms of asthma following antiinflammatory therapy may only become evident after several weeks to months of therapy. The slow action of these therapies creates problems for the clinician seeking to expeditiously determine optimal therapy for an individual patient. The development of genetic tests to predict response to different agets will allow selection of optimal therapy with less of the time consuming empirical clinical decision making required presently.

Limitations Involving Toxicity or Undesired Side Effects

There are toxicities and undesired side effects associated with the above current therapies for asthma that require monitoring. Drugs used to treat asthma may cause death, disability, disease, and place a fetus at risk. The undesired side effects or toxicities are listed for each drug category as described above.

IV. Impact of Stratification Based Upon Genotype in Drug Development for Drugs, Compounds, or Candidate Therapeutic Interventions for Asthma In a recent report, it was demonstrated that the 5-lipoxygenase (5-LO) gene promoter variation among asthma patients is linked to drug response to 5-LO inhibitors (Drazen et al., Nature Genetics 22: 1999). In a clinical trial to test efficacy of a potent, selective 5-LO inhibitor (ABT-761), the trial was abruptly closed due to inordinate event rate of abnormal liver function tests. Although the projected enrollment was not reached, the interim data suggested superior efficacy regarding forced expiratory volume in the high dose relative to low dose or placebo groups. The investigators chose to stratify the high dose and placebo group of the enrolled patients based upon genotype of the 5-LO gene promoter. The 5-LO gene promoter has been found to contain 3–6 tandem repeats of the Sp 1 -binding motif. The wild-type allele was designated as 5 tandem repeats and had a frequency of 0.772 in the study population. The forced expiratory volume data indicated that heterozygous patients on high-dose active treatment had, on average, an improvement of forced expiratory volume within one week (23.3±6.0%) and was similar to the wild-type patients (18.8±3.6%). In contrast, the patients with mutant genotype had no benefit from active 5-LO inhibitor treatment (−1.2±2.9%). In Table 12, the trial outcome data is described for two periods following treatment with high dose or placebo

TABLE 14

| Patient Group | $FEV_1$, % change from baseline[a] | |
| --- | --- | --- |
| | Day 8 | Day 84 |
| Wild type, high dose | 8.2 | 18.5 |
| Mutant, high dose | 1.8 | 5 |
| Placebo | −0.7 | −1.4 |

[a]Data extrapolated from published data

Approximately 6% of asthma patients do not carry a wild-type allele at the 5-LO core promoter locus, and this data indicates that these patients would not benefit from 5-LO inhibitor drug therapy. Further, these data indicate that there is evidence 5 to reasonably identify patients, i.e. stratification based upon 5-LO genotype, to appropriately treat patients with asthma.

A recent double blind, placebo controlled crossover designed pharmacogenetic restrospective clinical trial of a β2-adrenoreceptor polymorphism was implemented to analyze the significance of β2-adrenoreceptor polymorphisms (Tan et al. Lancet 350:995–999). In vitro studies have suggested that polymorphism of the β2-adrenergic receptor may influence the desensitization induced by β2 agonists. Twenty-two moderately severe asthmatics were enrolled into a placebo-controlled, cross-over study of formeterol (a β2-adrenergic agonist). The patients were divided into groups by allelic variances: 1) at codon 16, homozygous arginine (n=4), heterozygous arginine/glycine (n=8), and homozygous glycine (n=10); and 2) at codon 27, homozygous glutamine (n=5), heterozygous glutatmine/glutamic acid (n=11), and homozygous glutamic acid (n=6). Genotypic analysis determined that individuals who were homozygous for glycine at codon 16 were also homozygous for glutamic acid at codon 27. The results were as follows:

TABLE 15

| Polymorphisms of the β2-adrenergic receptor | Degree of Brochodilator Desensitisation after Formoterol Therapy[1] | | | |
|---|---|---|---|---|
| | 6 hour $FEV_1$ | Maxim al $FEV_1$ | 6 Hour $FEF_{25-75}$ | Maxim al $FEF_{25-75}$ |
| Gly 16 (n = 10) | 80% | 48% | 103% | 73% |
| Arg 16 (n = 4) | 28% | -8% | 23% | -35% |
| Gly/Arg 16 (n = 8) | 57% | 48% | 70% | 50% |
| Glu27 (n = 6)[2] | 73% | 35% | 90% | 68% |
| Gln27 (n = 5) | 47% | 3% | 38% | -15% |
| Glu/Gln27 (n = 11) | 65% | 52% | 70% | 45% |

[1]Data extrapolated from published graphs.
[2]All individuals homozygous for Glu27 were also homozygous for Gly16.

The homozygous glycine at position 16 was associated with individuals who were prone to bronchodilator desensitization than at arginine at position 16: the mean $FEV_1$ desensitisation was 80% for Gly16 homozygotes versus 28% for the Arg16 homozygotes. Similar results were observed for the 6 hour $FEV_1$ and the FEF.

For the polymorphism at codon 27, the mean for the Glu27 homozygous individuals demonstrated greater desensitization than those who were homozygous for Gln27.

The allelic variance, glycine at position 16 appeared to dominate over the putative protective effects of the mutation of glutamic acid at position 27.

The effects of the codon 16 and 27 polymorphism in the β2-adrenoreceptor on β2-agonist desensitization, as observed in the above data, suggest that there may be an identifiable subset of patients for whom β2-adrenergic receptor desensitization occurs in the presence of long-acting or repeated use of β2-agonists.

Thus, one skilled in the art, will be able to utilize the presently described pharmacogenetic techniques to identify the allelic variances with the coding region of the β-adrenergic receptor or other receptor proteins that are similar to the β-adrenergic receptor, including but not limited to those variances for those genes listed in Tables 1 and 3 and those 7-membrane spanning receptor G-protein coupled receptors. In this way, a skilled practitioner will be able to utilize the methods, protocols, and techniques that are described in the detailed description and those known in the art to identify the gene targets, allelic variance or variances, and candidate drugs that affect these pathways. Further, one can design and implement a strategy that incorporates a diagnostic test to genotype the individual for a given allele or alleles or halpotype, grouping these candidates by genotype, and testing a β-adrenergic agonist or other candidate therapeutic product for the affect of the pharmacogenomic difference between or among the groups.

As described above, there is evidence to suggest that there are safety response differences to drug therapy in asthma which may be attributable to genotypic differences between individuals. There is provided in this invention examples of gene pathways that are implicated in the disease process or its therapy and those that potentially cause this variability. The Detailed Description above demonstrates how identification of a candidate gene or genes and gene pathways, stratification, clinical trial design, and implementation of genotyping for appropriate medical management of a given disease can be used to identify the genetic cause of variations in clinical response to therapy, new diagnostic tests, new therapeutic approaches for treating this disorder, and new pharmacuetical products or formulations for therapy. Gene pathways including, but not limited to, those that are outlined in the gene pathway Table 1, and pathway matrix Table 2 and discussed below are candidates for the genetic analysis and product development using the methods described above.

Advantages of Inclusion of Pharmacogenetic Stratification in Clinical Development of Agents for use in Asthma The advantages of a clinical research and drug development program that includes the use of polymorphic genotyping for the stratification of patients for the appropriate selection of candidate therapeutic intervention includes 1) identification of patients that may respond earlier and show signs and symptoms of clinical improvement or side effects and toxicities, 2) identification of the primary gene and relevant polymorphic variance that directly affects manifestation of asthma, 3) identification of pathophysiologic relevant variance or variances and potential therapies affecting those allelic genotypes or haplotypes, and 4) identification of allelic variances or haplotypes in genes that indirectly affects efficacy, safety or both.

By identifying subsets of asthma subjects based upon genotype that experience different responses to the administration of a drug, agent, or candidate therapeutic intervention, optimal selection may reduce level and extent of asthma damage to affected joints. Appropriate genotyping and correlation to dosing regimen, or selection of optimal therapy would be beneficial to the patient, caregivers, medical personnel, and the patient's loved ones.

Based upon these advantages, designing and performing a clinical trial, either prospective or retrospective, which includes a genotype stratification arm will incorporate analysis of clinical outcomes and genetic variation associated with those outcomes, and hypothesis testing of the statistically relevant correlation of the genotypic stratification and therapeutic benefits. If statistical relevance is detectable, these studies will be incorporated into regulatory filings. Ultimately, these clinical trial data will be considered during the approval for marketing process, as well as, incorporated into accepted medical management of asthma.

As an example of identification of the primary gene and relevant polymorphic variance that directly affects efficacy, safety, or both one could select an gene pathway as described in the Detailed Description, and determine the effect of genetic polymorphism and therapy efficacy, safety, or both within that given pathway. For example, referring to Table 2, genes involved in cytokine-mediated immune regulation, non-cytokine mediated immune regulation (including, but not excluded to, cyclophilins, corticosteroids), cell mediated inflammation involving apoptosis, adhesion and migration, protease and protease inhibitors, complement, degranulation (platelets, mast cells, neutrophils, ans eosinophils), release of inflammatory modulators (including membrane lipids, prostaglandin, platelet activating factor, leukotrienes, histamine, nitric oxide), vascularization mediators (including endothelin and vascular endothelial cell growth factor), neurotransmitters and peptide hormone inflammation modulators (including adrenergic, purinergic, cholinergic, ion channels, tachykinin, neurokinin, substance P, bradykinin, parathyroid hormone, melanocortin and adrenocorticotrophic hormones, and modulators of general cell growth pathways the optimization of therapy of by an agent can be achieved by determining whether the patient has a predisposing genotype in which the selected agents are more effective and or are more safe. In considering an optimization protocol, one could potentially predetermine the genotypic profile of these genes involved in the manifestation of the adverse effect, or those genes preeminently responsible for drug response. By embarking on the previously described gene pathway approach, it is technical feasibility to determine the relevant genes within such a targeted drug development program.

V. Description of Mechanism of Action Hypotheses for Future Drug Development

There are many potential mechanisms that may serve as targets for candidate therapeutic interventions. For example, phosphodiesterase inhibitors to PDE4; T-lymphocyte-eosinophil interactions inhibition: targeting the factors involved in the regulation of the TH2(CD+4) differentiation and/or activation by soluble factors (cytokines (IL-4, IL-5); co-stimulatory molecules (B7-2/CD86); and transcritpion factors (GATA-3, AP-1). These targets may be available to limit the TH2 cell involvement in the initiation of asthmatic inflammation.

Suppression of eosinophil adhesion with consequent inhibition of influx into the lung is a strategy to suppress asthmatic airway inflammation. Such inhibition may be mediated through inhibitors directed towards very late antigen-4 (VLA-4), monoclonal antibodies directed towards VLA-4, intracellular adhesion molecule 1 (ICAM1), and alpha 1,3-fucosyltransferase VII (an enzyme which regulates sekectin function). Furthermore, molecules may be targeted to suppress the expression of adhesion molecules (e-selectin, vascular cell-adhesion molecule 1 (VCAM-1) and ICAM1).

There are a group of chemokines that contain a cysteine-X-cysteine motif, such as IL-8 that are effectors of acute inflammatory episodes, whereas cysteine-cysteine chemokines, such as macrophage inhibitory peptide 1 (MIP-1), eotaxin, RANTES, or macrophage chemotactic peptide 1 (MCP-1) act as chronic mediators of inflammation. These molecules may be appropriate targets for inhibiting either the acute or chronic inflammatory pathway.

Cysteinyl leukotrienes have a central role in the development of chronic asthma, and antagonists (i.e., $CysLT_1$) may be able to ablate the actions of this ligand. These novel leukotriene receptor agonists may have potential for anti-inflammatory effects. Endothelin receptors may also be a target, with endothelin antagonists to specific receptor subtypes $ET_A$ or $ET_B$. Other receptors known to be involved in the inflammatory process that may be potential targets are the tachykinin NK1 receptors and selective ligands to the NK1/NK2 receptors.

Induction of cyclooxygenase and the consequent increase in prostaglandin release is associated with the development of inflammation. Antisense oligonucleotides directed against the receptor types NK-KB, major basic protein, 5-lipoxygenase, leukotriene C4(LTC4 synthetase, IL-4, IL-5, IL-8 and adenosine have been developed that are inhalable products that can directly block the expression of these mediators of the inflammatory response.

Other areas of drug target development include immunobiology of the airways i.e., TH1 and TH2 and their involvement in the immune response, synthesis of immunoglobulin, IgE, integrins, inhibition of αIL5 and αIL5 monoclonal antibody, soluble IL4 receptor, neurokinin receptor antagonist, chemokine inhibitors.

The inflammatory response is also being evaluated in terms of the effects of NO2, SO2, and ozone on the subsequent effect on airway response to these potential allergens. As well as adhesion molecule expression, cytokine production and cytokine gene transcription factors are also being evaluated.

Optimization of nonsteroidal or steroidal antiinflammatory agents, or agents aimed at a mechanism of therapy of the underlying etiology of asthma that further demonstrates the utility of selection of a potential asthma patient that has a predisposing genotype in which selective antiasthmatic or other agents, may be more effective and or have a more desirable safety profile. In considering an optimization protocol, one could potentially predetermine variance or variances within the nonsteroidal antiinflammatory pathway, steroid antiinflammatory pathway, or antiinflammatory mediated intracellular mechanism of action that is preeminently responsible for antiasthmatic drug response. By embarking on the previously described gene pathway approach, it is technically feasible to determine the relevant genes within such a targeted drug development program for asthma.

A sample of therapies approved or in development for preventing or treating the progression of asthma currently known in the art is shown in Table 16. In this table, the candidate therapeutics were sorted and listed by mechanism of action. Further, the product name, the pharmacologic mechanism of action, chemical name (if specified), and the indication is listed as well.

Pharmacogenomics studies for these drugs, as well as other agents, drugs, compounds or candidate therapeutic interventions, could be performed by: identifying genes that are involved in the the function of a drug including, but not limited to its absorption, distribution metabolism, or elimination, interaction of the drug with its target as well as potential alternative targets, the response of the cell to the binding of a drug to a target, the metabolism (including synthesis, biodistribution or elimination) of natural compounds which may alter the activity of the drug by complementary, competitive or allosteric mechanisms that potentiate or limit the effect of the drug, and genes involved in the etiology of the disease that alter its response to a particular class of therapeutic agents. It will be recognized to those skilled in the art that this broadly includes proteins involved in pharmacokinetics as well as genes involved in pharmacodynamics. This also includes genes that encode proteins homologous to the proteins believed to carry out the above functions, which are also worth evaluation as they may carry out similar functions. Together, the foregoing proteins comprise the candidate genes for affecting response of a patient to the therapeutic intervention. Using the methods described above, variances in these genes can be identified, and research and clinical studies can be performed to establish an association between a drug response or toxicity and specific variances.

Example 2

Inflammatory Bowel Disease

Description of inflammatory Bowel Disease

Inflammatory bowel disease (IBD) is a broad clinical term that includes idiopathic chronic inflammatory bowel diseases including Crohn's disease (CD) and ulcerative colitis (UC) which can be distinguished from inflammatory bowel disease of known origin including diverticulitis, radiation enteritis, colitits, drug or toxin-induced enterocolitis, or vasiculitis of the intestinal tract. UC is a term that encompasses a broad category of diffuse, continuous, and superficial inflammation of the colon, which begins within the rectum and extends proximally. The condition is limited to the colon and large intestine, with limited involvement of the small intestine. In UC, the inflammation primarily affects the mucosal process and is not transluminal within these anatomical regions. CD is characterized by focal, asymetric, transmural inflammation affecting any portion of the gastrintestinal tract, i.e. from the mouth to the anus. The focal localization and possible extent of the inflammation distinguishes UC from CD. There are currently approximately 35–100 and 10–100 CD per 100,000 Americans diagnosed with UC or CD, respectively.

Clinically, patients with UC experience variable stool consistencies from constipation to diarrhea, low-grade fever, malaise, nausea, vomiting associated with defecation, night sweats, arthalgias, dehydration, tachycardia, and symptoms of abdominal tenderness. There can be rectal bleeding, tenemus, and passage of mucopus.

Patients with Crohn's disease experience symptoms of peptic ulcer disease, nausea, vomiting, and epigastric pain. Transmural inflammation leads to fibrosis and transluminal narrowing. In some cases, the narrowing leads to signs and symptoms of intestinal obstruction including nausea, vomiting, waves of abdominal pain, and a reduced output of stool. Patients with colonic CD are likely to experience abdominal pain, cramping or localized pain, rectal bleeding, and diarrhea. Weight loss is common among CD patients due to malabsorption of nutrients and reduced food intake due to minimization of postprandial symptoms.

There are extraintestinal manifestations of inflammatory bowel disease affecting the following processes including: nutritional and metabolic abnormalities, hematologic abnormalities, skin and mucous membranes, musculoskeletal, hepatic and biliary abnormalities, renal complications, and optic complications. These complications are associated when the colon or intestinal tract is inflammed. These complications are clinically menifset as joint swelling or pain, erythema nodosum, pyoderma gangenosum, sclerosing cholangitis, conjunctivitis, or uveitis.

There is an increased risk for the development of gastrointestinal cancer in patients with IBD. In both UC and CD, there is an increased risk of adenocarcinoma of the intestine. This is not correlated to the intensity of the first attack, subsequent course, or and specific medical therapeutic approach. Therefore routine screenig for dysplasia and neoplasia is warranted.

Current Therapy of Inflammatory Bowel Disease

Strategies for the therapy of inflammatory bowel disease includes antiinflammatory agents and immunomodulation.

Antiinflammatory agents include the use of glucocorticoids and/or aminosalicylates. Glucocorticoids act by modulation of the immune response. Corticosteroids affect the inflammation within the gastrointestinal tract by decreasing growth and development of mast cells, inducing apoptosis, suppressing lymphocyte generation of IL-5 and other cytokines, inhibiting some mediator release, inhibiting cytokine production, inhibiting the transcription of cytokines (for example IL-8, TNF-$\alpha$, prototypic antiviral chemokine (regulated-on-activation normal T-expressed and secreted, RANTES), and GM-CSF), and inhibiting nitric oxide synthesis.

5-aminosalicyclic acid (5ASA) is a salicylate that is used for the treatment of IBD, is not orally active, is poorly absorbed and is inactivated by intestinal bacteria, and is delivered as a suppository or rectal suspension enema. Oral formulations can be used to deliver active drug to the lower intestine which are cogeners of 5ASA. The aminosalicylates are potent antiinflammatory agents that inhibit cyclooxygenase (COX), arate limiting enzyme in the protaglandin and leukotriene pathway.

Immunosuppressive agents are also used to modulate the inflammatory/immune response. There are four broad categories of immunosuppresive agents that have distinct mechanisms of action: inhibition of ribonucleotide synthesis which acts to inhibit the proliferation of T-cell clones (6-mercaptopurine), inhibition of folic acid which acts to inhibit T-cell and B-cell function as well as decrease IL-1 and IL-6 activity (methotrexate), inhibition of T-cell receptor stimulated transcription of lymphokine genes which act to ihibit the production of IL-2 and IL-2 receptors as well as inhibit certain cytokines (TNF-$\alpha$, IFN-$\gamma$) (cyclosporin and FK506), and inhibition of guanosine nucleotide synthesis which acts as cytostatic effects on lymphocytes (mycophenolate). Each of these catgoiies of agents have been employed for the therapy of IBD.

Recently, a chimeric monoclonal antibody was approved for use in the treatment of moderately to severely active Crohn's disease for those patients that are unresponsive to conventional therapy. This monoclonal antibody is specific for TNF-$\alpha$ and can remove TNF from the bloodstream before it reaches the site of inflammation.

Crohn's disease may progress to a level and extent in which surgical removal of the localized inflammation is warranted. Surgery has been indicated for recurrent intestianl obstruction, complicated fistulas, intractable hemorrhage, disease refractory to medical therapy, growth retardation refractory to therapies, or cancer. The surgical procedures vary from excision of a localized, diseased portion of the gastrointestinal tract to removal of large portions, i.e. the entire colon (colectomy). Surgical excision of the inflammed region or to correct complications such as blockage, perforation, abscess, or bleeding can result in a substantial relief of symptoms.

Limitations to Current Therapies for IBD

Salicylate associated side effects include dyspepsia, gastric or small bowel bleeding, ulceration, renal insufficiency, confusion, rash, headache, and hepatic toxicity. NSAIDs also reversibly inhibit platelet aggregation and prolong bleeding time.

Glucocorticoid associated side effects include increased appetite, weight gain, fluid retention, acne, ecchymosis, development of cushoid facies, hypertension, hyperkalemia, diabetes, hyperglycemia, hyperosmolar state, hyperlipidemia, hepatic steatosis, atherosclerosis, myopathy, aseptic necrosis, osteoporosis, ulcers, pancreatitis, psuedotumor cerebri, pyschosis, glaucoma, cataract formation, vascular necrosis, increased suseptibility to infection, impairment of the hypothalamus-pituitary axis, decreased thyroid hormone serum binding protiens, and impaired wound healing.

Agents involved in immunomodulation have the following undesirable side effects including antimetabolites: hepatic compromise including hepatic fibrosis, ascites, esopageal varices, cirrhosis, pneumonitis, myelosuppression; immunosuppressives: myelosuppression, (cyclosporine: renal insufiienciency anemia, hypertension.

Monoclonal antibody to TNF proteins therapies have been shown to generate a human-antimouse antibody response (HAMA). However, patients on immunosuppressive agents such as glucocorticoids and others are less likely to generate antibodies to the treatment antibody. Delayed hypersensitivty is demonstrable 2 to 4 years after initial treatment in 25% of the patients treated with the chimeric antibody. Further, there are patients that develop a serum sickness reaction which includes fever, and joint swelling that requiring hospital admission. A positive antinuclear antibody (ANA) occurred in 24–36% of the patients analyzed. Nine percent of the patients developed anti-DNA antibodies, less than 1% developed a lupus-like reaction requiring steroid therapy.

In surgical therapy of IBD, reccurring inflammation and relapse, after excision procedures occurs in 75% of the patients. Attempts have been made to include salicylate therapy after resective surgery, however, the inflammation reccurrance rate in that group was 52%.

Impact of Stratification Based Upon Genotype in Drug Development for Drugs, Compounds, or Candidate Therapeutic Interventions for Autoimmune Disease Thiopurine methyltransferase (TPMT)

The thiopurine S-methyltransferase (TPMT) is a cytosolic enzyme whose precise physiological role is unknown. This enzyme catalyzes the S-methylation of widely used immunosuppressive or cytotoxic thiopurine drugs such as 6-thioguanine, 6-mercaptopurine and azathioprine 8. The in vivo activity of this cytosolic enzyme is characterized by interindividual and interethnic variability caused by the genetic polymorphism of the TPMT gene, which was discovered, using pharmacogenetic techniques, by the existence of three major phenotypes, high (HM), intermediate (IM) and deficient (DM) methylation. As a consequence, individuals greatly differ in detoxication of thiopurine drugs to 6-methylmercaptopurine as well as the occurrence of side effects or therapeutic efficacy. Using genomic techniques, PCR-SSCP (polymerase chain reaction—single strand conformation polymorphism), Spire-Vayron de la Moureyre et al. 9 have defined the mutational and allelic spectrum of TPMT in a group of 191 Europeans. In this analysis, PCR-SSCP techniques identified allelic variances in the entire coding sequence, the exon-intron boundaries, the promoter region and the 3'-flanking region of the genes. Six mutations were detected throughout the ten exons and seven TPMT alleles were characterized. Within the promoter region, six alleles corresponding to a variable number of repeats (VNTR) were identified. The TPMT phenotype was correctly predicted by genotyping for 87% of individuals. A clear negative correlation between the total number of repeats from both alleles and the TPMT activity level was observed, indicating that VNTRs contribute to interindividual variations of TPMT activity. This VNTR polymorphism can be considered responsible for shifts to lower or higher TPMT activities observed among discordant individuals. Seven out of the nine phenotyped HMs but genotyped IMs were carrier of a total of eight VNTR repeats. This low number of repeat can account for the switch to high TMPT activities of these samples.

One in 300 patients with IBD are homozygous-deficient for TPMT. The clinical relevance for this deficiency is that TPMT is the enzyme responsible for the conversion of 6-MP to 6-MMP, and the AZA compounds to 6-TG. In TPMT deficient patients, higher levels of 6-TG and 6-MMP are then produced and are associated with significant leukopenia. In general, patients produce variable levels of 6-TG and 6-MMP as determined by their intrinsic enzyme systems. Higher 6-TG levels are correlated with good therapuetic response, but produce leukopenia. Higher 6-MMP levels correlate with hepatotoxicity and in recent studies with leukopenia.

There is evidence to suggest that there are safety response differences to drug therapy in IBD which may be attributable to genotypic differences between individuals, one example being the TPMT gene described above. There is provided in this invention examples of other gene pathways that are implicated in the disease process or its therapy and those that potentially cause this variability. The Detailed Description above demonstrates how identification of a candidate gene or genes and gene pathways, stratification, clinical trial design, and implementation of genotyping for appropriate medical management of a given disease can be used to identify the genetic cause of variations in clinical response to therapy, new diagnostic tests, new therapeutic approaches for treating this disorder, and new pharmacuetical products or formulations for therapy. Gene pathways including, but not limited to, those that are outlined in the gene pathway Table 1, and pathway matrix Table 2 and discussed below are candidates for the genetic analysis and product development using the methods described above.

Advantages of Inclusion of Pharmacogenetic Stratification in Clinical Development of Agents for use in Inflammatory Bowel Disease The advantages of a clinical research and drug development program that includes the use of polymorphic genotyping for the stratification of patients for the appropriate selection of candidate therapeutic intervention includes: 1) identification of patients that may respond earlier and show signs and symptoms of clinical improvement or side effects and toxicities, 2) identification of the primary gene and relevant polymorphic variance that directly affects manifestation of inflammatory bowel disease, 3) identification of pathophysiologic relevant variance or variances and potential therapies affecting those allelic genotypes or haplotypes, and 4) identification of allelic variances or haplotypes in genes that indirectly affects efficacy, safety or both.

Pharmacogenomics studies for these drugs, or other agent, compound, drug, or candidate therapeutic intervention, could be performed by identifying genes that are involved in the the function of a drug including, but not limited to absorption, distribution, metabolism, or elimination, the interaction of the drug with its target as well as potential alternative targets, the response of the cell to the binding of a drug to a target, the metabolism (including synthesis, biodistribution or elimination) of natural compounds which may alter the activity of the drug by complementary, competitive or allosteric mechanisms that potentiate or limit the effect of the drug, and genes involved in the etiology of the disease that alter its response to a particular class of therapeutic agents. It will be recognized to those skilled in the art that this broadly includes proteins involved in pharmacokinetics as well as genes involved in pharmacodynamics. This also includes genes that encode proteins homologous to the proteins believed to carry out the above functions are also worth evaluation as they may carry out similar functions. Together the foregoing proteins constitute the candidate genes for affecting response of a patient to the therapeutic intervention. Using the methods described above, variances in these genes can be identified, and research and clinical studies can be performed to establish an association between a drug response or toxicity and specific variances.

V. Description of Mechanism of Action Hypotheses for Future Drug Development

The majority of the hypotheses for future therapuetic interventions for inflammatory bowel disease are based upon the understanding the immunologic mechanisms that cause and perpetuate the inflammation within the gastrointestinal tract. Although the initiating event is elusive, the resulting immunologic events have been studied. All of the gastrointestinal enterocytes have immunologic function. Under physiologic conditions, these enterocytes selectively activate CD8+ nonspecific suppressor cells, in response to inflammation. In patients with IBD, these enterocytes selectively stimulate the development of CD4+ helper T cells which can respond in two ways 1) the Th1 response which involves the activation of IL-2 and IFN-g and leads to delayed hypersensitivity and cellular immunity and 2) the Th2 response which involves IL-4, IL-5, IL-6, and IL-10 and leads to antibody response and humoral immunity. Both Th1 and Th2 responses are genetically controlled and are coordinately regulated, i.e. Th1 response stimulation results in down regulation of Th2 response and vice versa. It has been demonstrated that in UC patients the Th2 response is favored and in CD patients the Th1 response is favored.

A humanized (95% human, 5% mouse) version of the chimeric antibody (75% human, 25% mouse) to TNF is currently under development. Some antiidiotypic antibodies are generated, but it doesn't appear to stimulate a delayed hypersensitivity, no stimulation of anti-DNA antibodies, or lupus-like reactions.

Mediators of the immune response including intracellular adhesion molecule (ICAM-1) inhibitors (antisense molecules or others), IL-10, IL-11 have been tested in humans. Further, and anti-CD4 monoclonal antibody which has been shown to interfere with the interaction of the CD4 molecule and the HLA class II molecules leading to an inhibition of antigen presentation has been tested.

Thalidomide (inhibitor of TNF, acceleration of the degradation of the TNF mRNA) is also under consideration.

It has been noted that individuals who smoke tobacco products have a lower incidence of IBD. Therefore, understanding the immune response and correlation with nicotinic chloinergic pathways is under investigation.

A sample of therapies approved or in development for preventing or treating the progression of IBD currently known in the art is shown in Table 17. In this table, the candidate therapeutics were sorted and listed by mechanism of action. Further, the product name, the pharmacologic mechanism of action, chemical name (if specified), and the indication is listed as well.

Example 3

Hepatitis C

Selecting Optimal Therapy for HCV Patients

Genetically Determined Variation in Response to Interferon α

Treatment of hepatitis C virus (HCV) infection with interferon α is expensive, benefits a minority of patients, and produces side effects in a significant fraction of patients. Addition of ribavirin increases efficacy, but combination therapy remains expensive and still falls well short of providing a lasting benefit to most patients. It would therefore be desirable to identify prospectively those patients likely to have a sustained response to treatment. Ideally, a diagnostic test would also predict what dose of interferon and ribavirin, administered for what length of time, will afford to each patient the best chance of a sustained response. Pre-treatment identification of patients likely to suffer serious toxic side effects would also be desirable.

The best characterized predictors of response to interferon a therapy are viral load and HCV genotype. Low viral load before therapy is predictive of a positive response. However, demonstration of decreased viral load after initiation of therapy is currently the best predictor of response to therapy. There is no consensus on the optimal time after initation of therapy for measuring viral levels with periods ranging from 2 weeks to four months have been proposed. The viral load test is not very effective at discriminating long-term responders from those patients who suffer rebound of HCV infection within 6 months after treatment. Also, the ideal test would be performed in advance of any treatment, thereby saving the considerable costs associated with even short-term therapy. In search of other predictive indices, over 100 controlled clinical studies have examined a variety of viral and host factors in responders and nonresponders. Genetic variation in both HCV and host genes has been shown to independently influence patient response to interferon α treatment. A consensus has emerged regarding the interaction of viral genotype and treatment response, however the contribution of host factors to treatment response has not been as well investigated. There are a number of promising recent findings suggesting that polymorphisms in regulators of human immune function are correlated with response to interferon α.

Viral genome variation

Comparison of sequenced HCV genomes reveals considerable variation in viral sequence, with at least 6 major types and well over a dozen minor types recognized. The geographical distribution of viral types is nonrandom, perhaps accounting for some of the apparent racial heterogeneity in the natural history of HCV infection. HCV is present in each patient as a heterogeneous population of viral quasispecies, with the degree of heterogeneity differing among patients. Despite these complexities, there are strong correlations between predominant viral type and treatment response. In general, patients with genotype 1 (especially 1b) respond poorly to interferon a, with many studies showing response rates under 10 percent. Patients with genotype 2 or 3 do well, with response rates typically greater than 40 percent. Most viral genotyping is based on a short variable segment. However, there are multiple segments of the viral genome that vary, and some studies have found that more detailed viral genotyping, for example of the 5' untranslated region, provides stronger correlations with treatment response.

Human zenome variation

A recent study suggests that there is significant variation in response to interferon α treatment among racial groups in the United States, even after controlling for effect of different HCV types. This finding suggests that host genetic variation may be an important factor in response. A number of candidate genes have recently been tested for correlation with interferon a response. The best studied genes are regulators of immune function such as IL-6, IL-10 and TNFα. One study, for example, found that patients with high expression of IL-10 (attributable to a specific haplotype) tend to respond poorly to interferon, perhaps due to impaired immune response. IL-4, IL-12 and TGF-β levels have been correlated with treatment response in some (but not all) studies. However, no genetic analysis has been performed.

Similarly, hepatic levels of interferon α–β receptor have been correlated with response to interferon, but no genetic analysis has been performed to determine whether polymorphism affects receptor levels. HLA alleles have also been correlated with response to interferon, particularly the A24-B54-DR2 haplotype. A number of other compelling candidate genes have not been investigated. For example, a recent report shows that HCV can enter cells via the low density lipoprotein receptor. If so, the well studied amino acid polymorphisms of the LDL-R should be investigated for effects on disease course and response to treatment. There are also likely to be genetic factors that influence response to ribavirin. For example, the drug must be transported across the plasma membrane and then phosphorylated before becoming a substrate for viral enzymes. The transporters and kinases responsible for these processes may be worth genetic investigation.

An optimal test for selecting treatment for HCV infection would (i) suggest the optimal therapeutic regimen (interferon alone, interferon and ribavirin, or some other combination), (ii) suggest the optimal dose and duration of treatment, (iii) predict sustained responders vs. short term responders, and (iv) predict patients likely to suffer serious adverse effects. At least three areas should be further investigated to better predict the reponse to interferon a treatment. First, it is not clear that conventional viral genotyping methods, focusing on the 5' untranslated region, capture all of the aspects of viral sequence variation that affect viral biology. Additional genetic determinants of viral pathogenicity should be investigated. Second, the human gene variants that have been associated with response need to be more thoroughly investigated, and interactions between human candidate gene alleles, as well as perhaps between human genes and viral genes, should be tested. Third, recent work suggests a number of new host proteins that may affect response to interferon, and proteins that mediate response to ribavirin have not yet been investigated. The genes encoding these proteins should be thoroughly investigated. With additional information on candidate genes available, it should be possible to construct a plan, ideally via retrospective analysis of clinical trial data, for first assesing the impact of variation in each of the candidate genes, then examining gene x gene interactions, and finally reducing the number of tests to a much smaller number for confirmatory prospective trials.

In Table 18, there a list of the candidate therapeutic interventions that in development for Hepatitis. One skilled in the art could apply, as described in the text, the methods of this invention to ascertain whether there is a gene in the inflammatory pathway that may be involved in the efficacy, safety, or toxicities of these candidate interventions.

Example 4

Method for Producing cDNA

In order to identify sequence variances in a gene by laboratory methods it is in some instances useful to produce cDNA(s) from multiple human subjects. (In other instances it may be preferable to study genomic DNA.). Methods for producing cDNA are known to those skilled in the art, as are methods for amplifying and sequencing the cDNA or portions thereof. An example of a useful cDNA production protocol is provided below. As recognized by those skilled in the art, other specific protocols can also be used.

cDNA Production

** Make sure that all tubes and pipette tips are RNase-free. (Bake them overnight at 100° C. in a vaccum oven to make them RNase-free.)

1. Add the following to a RNase-free 0.2 ml micro-amp tube and mix gently:
   24 ul water (DEPC treated)
   12 ul RNA (lug/ul)
   12 ul random hexamers(50 ng/ul)
2. Heat the mixture to 70° C. for ten minutes.
3. Incubate on ice for 1 minute.
4. Add the following:
   16 ul 5 X Synthesis Buffer
   8ul 0.1 MDTT
   4 ul 10 mM dNTP mix (10 mM each dNTP)
   4 ul SuperScript RT II enzyme
   Pipette gently to mix.
5. Incubate at 42° C. for 50 minutes.
6. Heat to 70° C. for ten minutes to kill the enzyme, then place it on ice.
7. Add 160 ul of water to the reaction so that the final volume is 240 ul.
8. Use PCR to check the quality of the cDNA. Use primer pairs that will give a ~800 base pair long piece. See "PCR Optimization" for the PCR protocol.

The following chart shows the reagent amounts for a 20 ul reaction, a 80 ul reaction, and a batch of 39 (which makes enough mix for 36) reactions:

|  | 20 ul × 1 tube | 80 ul × 1 tube | 80 ul × 39 tubes |  |
| --- | --- | --- | --- | --- |
| Water | 6 ul | 24 ul | 936 | Water |
| RNA | 3 ul | 12 ul |  | RNA |
| random hexamers | 3 ul | 12 ul | 468 | Random hexamers |
| synthesis buffer | 4 ul | 16 ul | 624 | Synthesis buffer |
| 0.1M DTT | 2 ul | 8 ul | 312 | 0.1M DTT |
| 10 mM dNTP | 1 ul | 4 ul | 156 | 10 mM dNTP |
| SSRT | 1 ul | 4 ul | 156 | SSRT |

Example 5

Method for Detecting Variances by Single Strand Conformation Polymorphism (SSCP) Analysis This example describes the SSCP technique for identification of sequence variances of genes. SSCP is usually paired with a DNA sequencing method, since the SSCP method does not provide the nucleotide identity of variances. One useful sequencing method, for example, is DNA cycle sequencing of $^{32}p$ labeled PCR products using the Femtomole DNA cycle sequencing kit from Promega (WI) and the instructions provided with the kit. Fragments are selected for DNA sequencing based on their behavior in the SSCP assay.

Single strand conformation polymorphism screening is a widely used technique for identifying an discriminating DNA fragments which differ from each other by as little as a single nucleotide. As originally developed by Orita et al. (Detection of polymorphisms of human DNA by gel electrophoresis as single-strand conformation polymorphisms. *Proc Natl Acad Sci U S A.* 86(8):2766–70, 1989), the technique was used on genomic DNA, however the same group showed that the technique works very well on PCR amplified DNA as well. In the last 10 years the technique has been used in hundreds of published papers, and modifications of the technique have been described in dozens of papers. The enduring popularity of the technique is due to (1) a high degree of sensitivity to single base differences (>90%) (2) a high degree of selectivity, measured as a low frequency of false positives, and (3) technical ease. SSCP is almost always used together with DNA sequencing because SSCP does not directly provide the sequence basis of differential fragment mobility. The basic steps of the SSCP procdure are described below.

When the intent of SSCP screening is to identify a large number of gene variances it is useful to screen a relatively large number of individuals of different racial, ethnic and/or geographic origins. For example, 32 or 48 or 96 individuals is a convenient number to screen because gel electrophoresis apparatus are available with 96 wells (Applied Biosystems Division of Perkin Elmer Corporation), allowing 3×32, 2×48 or 96 samples to be loaded per gel.

The 32 (or more) individuals screened should be representative of most of the worlds major populations. For example, an equal distribution of Africans, Europeans and Asians constitutes a reasonable screening set. One useful source of cell lines from different populations is the Coriell Cell Repository (Camden, N.J.), which sells EBV immortalized lyphoblastoid cells obtained from several thousand subjects, and includes the racial/ethnic/geographic background of cell line donors in its catalog. Alternatively, a panel of cDNAs can be isolated from any specific target population.

SSCP can be used to analyze cDNAs or genomic DNAs. For many genes cDNA analysis is preferable because for many genes the full genomic sequence of the target gene is not available, however, this circumstance will change over the next few years. To produce cDNA requires RNA. Therefore each cell lines is grown to mass culture and RNA is isolated using an acid/phenol protocol, sold in kit form as Trizol by Life Technologies (Gaithersberg, Md.). The unfractionated RNA is used to produce cDNA by the action of a modified Maloney Murine Leukemia Virus Reverse Transcriptase, purchased in kit form from Life Technologies (Superscript II kit). The reverse transcriptase is primed with random hexamer primers to initiate cDNA synthesis along the whole length of the RNAs. This proved useful later in obtaining good PCR products from the 5' ends of some genes. Alternatively, oligodT can be used to prime cDNA synthesis.

Material for SSCP analysis can be prepared by PCR amplification of the cDNA in the presence of one α $^{32}$P labeled dNTP (usually α $^{32}$P dCTP). Usually the concentration of nonradioactive dCTP is dropped from 200 uM (the standard concentration for each of the four dNTPs) to about 100 uM, and $^{32}$P dCTP is added to a concentration of about 0.1–0.3 uM. This involves adding a 0.3–1 ul (3–10 uCi) of $^{32}$P cCTP to a 10 ul PCR reaction. Radioactive nucleotides can be purchased from DuPont/New England Nuclear.

The customary practice is to amplify about 200 base pair PCR products for SSCP, however, an alternative approach is to amplify about 0.8–1.4 kb fragments and then use several cocktails of restriction endonucleases to digest those into smaller fragments of about 0.1–0.4kb, aiming to have as many fragments as possible between 0.15 and 0.3 kb. The digestion strategy has the advantage that less PCR is required, reducing both time and costs. Also, several different restriction enzyme digests can be performed on each set of samples (for example 96 cDNAs), and then each of the digests can be run separately on SSCP gels. This redundant method (where each nucleotide is surveyed in three different fragments) reduces both the false negative and false positive rates. For example: a site of variance might lie within 2 bases of the end of a fragment in one digest, and as a result not affect the conformation of that strand; the same variance, in a second or third digest, would likely lie in a location more prone to affect strand folding, and therefore be detected by SSCP.

After digestion, the radiolabelled PCR products are diluted 1:5 by adding formamide load buffer (80% formamide, 1X SSCP gel buffer) and then denatured by heating to 90%C for 10 minutes, and then allowed to renature by quickly chilling on ice. This procedure (both the dilution and the quick chilling) promotes intra- (rather than inter-) strand association and secondary structure formation. The secondary structure of the single strands influences their mobility on nondenaturing gels, presumably by influencing the number of collisions between the molecule and the gel matrix (i.e., gel sieving). Even single base differences consistently produce changes in intrastrand folding sufficient to register as mobility differences on SSCP.

The single strands were then resolved on two gels, one a 5.5% acrylamide, 0.5X TBE gel, the other an 8% acrylamide, 10% glycerol, 1X TTE gel. (Other gel recipes are known to those skilled in the art.) The use of two gels provides a greater opportunity to recognize mobility differences. Both glycerol and acrylamide concentration have been shown to influence SSCP performance. By routinely analyzing three different digests under two gel conditions (effectively 6 conditions), and by looking at both strands under all 6 conditions, one can achieve a 12-fold sampling of each base pair of cDNA. However, if the goal is to rapidly survey many genes or cDNAs then a less redundant procedure would be optimal.

Example 6

Method for Detecting Variances by T4 endonuclease VII (T4E7) mismatch cleavage method The enzyme T4 endonuclease VII is derived from the bacteriophage T4. T4 endonuclease VII is used by the bacteriophage to cleave branched DNA intermediates which form during replication so the DNA can be processed and packaged. T4 endonuclease can also recognize and cleave heteroduplex DNA containing single base mismatches as well as deletions and insertions. This activity of the T4 endonuclease VII enzyme can be exploited to detect sequence variances present in the general population.

The following are the major steps involved in identifying sequence variations in a candidate gene by T4 endonuclease VII mismatch cleavage:

1. Amplification by the polymerase chain reaction (PCR) of 400–600 bp regions of the candidate gene from a panel of DNA samples The DNA samples can either be cDNA or genomic DNA and will represent some cross section of the world population.
2. Mixing of a fluorescently labeled probe DNA with the sample DNA. Heating and cooling the mixtures causing heteroduplex formation between the probe DNA and the sample DNA.
3. Addition of T4 endonuclease VII to the heteroduplex DNA samples. T4 endonuclease will recognize and cleave at sequence variance mismatches formed in the heteroduplex DNA.
4. Electrophoresis of the cleaved fragments on an ABI sequencer to determine the site of cleavage.
5. Sequencing of a subset of PCR fragments identified by T4 endonuclease VI to contain variances to establish the specific base variation at that location.

A more detailed description of the procedure is as follows:

A candidate gene sequence is downloaded from an appropriate database. Primers for PCR amplification are designed which will result in the target sequence being divided into amplification products of between 400 and 600 bp. There will be a minimum of a 50 bp of overlap not including the primer sequences between the 5' and 3' ends of adjacent fragments to ensure the detection of variances which are located close to one of the primers.

Optimal PCR conditions for each of the primer pairs is determined experimentally. Parameters including but not limited to annealing temperature, pH, $MgCl_2$ concentration, and KCl concentration will be varied until conditions for optimal PCR amplification are established. The PCR conditions derived for each primer pair is then used to amplify a panel of DNA samples (cDNA or genomic DNA) which is chosen to best represent the various ethnic backgrounds of the world population or some designated subset of that population.

One of the DNA samples is chosen to be used as a probe. The same PCR conditions used to amplify the panel are used to amplify the probe DNA. However, a flourescently labeled nucleotide is included in the deoxy-nucleotide mix so that a percentage of the incorporated nucleotides will be fluorescently labeled.

The labeled probe is mixed with the corresponding PCR products from each of the DNA samples and then heated and cooled rapidly. This allows the formation of heteroduplexes between the probe and the PCR fragments from each of the DNA samples. T4 endonuclease VII is added directly to these reactions and allowed to incubate for 30 min. at 37 C. 10 ul of the Formamide loading buffer is added directly to each of the samples and then denatured by heating and cooling. A portion of each of these samples is electrophoresed on an ABI 377 sequencer. If there is a sequence variance between the probe DNA and the sample DNA a mismatch will be present in the heteroduplex fragment formed. The enzyme T4 endonuclease VII will recognize the mismatch and cleave at the site of the mismatch. This will result in the appearance of two peaks corresponding to the two cleavage products when run on the ABI 377 sequencer.

Fragments identified as containing sequencing variances are subsequently sequenced using conventional methods to establish the exact location and sequence variance.

Example 7

Method for Detecting Variances by DNA sequencing.

Sequencing by the Sanger dideoxy method or the Maxim Gilbert chemical cleavage method is widely used to determine the nucleotide sequence of genes. Presently, a worldwide effort is being put forward to sequence the entire human genome. The Human Genome Project as it is called has already resulted in the identification and sequencing of many new human genes. Sequencing can not only be used to identify new genes, but can also be used to identify variations between individuals in the sequence of those genes.

The following are the major steps involved in identifying sequence variations in a candidate gene by sequencing:

1. Amplification by the polymerase chain reaction (PCR) of 400–700 bp regions of the candidate gene from a panel of DNA samples The DNA samples can either be cDNA or genomic DNA and will represent some cross section of the world population.
2. Sequencing of the resulting PCR fragments using the Sanger dideoxy method. Sequencing reactions are performed using flourescently labeled dideoxy terminators and fragments are separated by electrophoresis on an ABI 377 sequencer or its equivalent.
3. Analysis of the resulting data from the ABI 377 sequencer using software programs designed to identify sequence variations between the different samples analyzed.

A more detailed description of the procedure is as follows:

A candidate gene sequence is downloaded from an appropriate database. Primers for PCR amplification are designed which will result in the target sequence being divided into amplification products of between 400 and 700 bp. There will be a minimum of a 50 bp of overlap not including the primer sequences between the 5' and 3' ends of adjacent fragments to ensure the detection of variances which are located close to one of the primers.

Optimal PCR conditions for each of the primer pairs is determined experimentally. Parameters including but not limited to annealing temperature, pH, $MgCl_2$ concentration, and KCl concentration will be varied until conditions for optimal PCR amplification are established. The PCR conditions derived for each primer pair is then used to amplify a panel of DNA samples (cDNA or genomic DNA) which is chosen to best represent the various ethnic backgrounds of the world population or some designated subset of that population.

PCR reactions are purified using the QIAquick 8 PCR purification kit (Qiagen cat# 28142) to remove nucleotides, proteins and buffers. The PCR reactions are mixed with 5 volumes of Buffer PB and applied to the wells of the QIAquick strips. The liquid is pulled through the strips by applying a vacuum. The wells are then washed two times with 1 ml of buffer PE and allowed to dry for 5 minutes under vacuum. The PCR products are eluted from the strips using 60 ul of elution buffer.

The purified PCR fragments are sequenced in both directions using the Perkin Elmer ABI Prism™ Big Dye™ terminator Cycle Sequencing Ready Reaction Kit (Cat# 4303150). The following sequencing reaction is set up: 8.0 ul Terminator Ready Reaction Mix, 6.0 ul of purified PCR fragment, 20 picomoles of primer, deionized water to 20 ul. The reactions are run through the following cycles 25 times: 96° C. for 10 second, annealing temperature for that particular PCR product for 5 seconds, 60° C. for 4 minutes.

The above sequencing reactions are ethanol precipitated directly in the PCR plate, washed with 70% ethanol, and brought up in a volume of 6 ul of formamide dye. The reactions are heated to 90° C. for 2 minutes and then quickly cooled to 4° C. 1 ul of each sequencing reaction is then loaded and run on an ABI 377 sequencer.

The output for the ABI sequencer appears as a series of peaks where each of the different nucleotides, A, C, G, and T appear as a different color. The nucleotide at each position in the sequence is determined by the most prominent peak at each location. Comparison of each of the sequencing outputs for each sample can be examined using software programs to determine the presence of a variance in the sequence. One example of heterozygote detection using sequencing with dye labeled terminators is described by Kwok et. al. (Kwok, P.-Y.; Carlson, C.; Yager, T. D., Ankener, W.,and D. A. Nickerson, Genomics 23, 138≅144, 1994). The software compares each of the normalized peaks between all the samples base by base and looks for a 40% decrease in peak height and the concomitant appearance of a new peak underneath. Possible variances flagged by the software are further analyzed visually to confirm their validity.

Example 8

Hardy-Weinberg equilibrium

Evolution is the process of change and diversification of organisms through time, and evolutionary change affects morphology, physiology and reproduction of organisms, including humans. These evolutionary changes are the result of changes in the underlying genetic or hereditary material. Evolutionary changes in a group of interbreeding individuals or Mendelian population, or simply populations, are described in terms of changes in the frequency of genotypes and their constituent alleles. Genotype frequencies for any given generation is the result of the mating among members (genotypes) of their previous generation. Thus, the expected proportion of genotypes from a random union of individuals in a given population is needed for describing the total genetic variation for a population of any species. For example, the expected number of genotypes that could form from the random union of two alleles, A and a, of a gene are AA, Aa and aa. The expected frequency of genotypes in a large, random mating population was discovered to remain constant from generation to generation; or achieve Hardy-Weinberg equilibrium, named after its discoverers. The expected genotypic frequencies of alleles A and a (AA, 2Aa, aa) are conventionally described in terms of $p^2+2pq+q^2$ in which p and q are the allele frequencies of A and a. In this equation ($p^2+2pq+q^2=1$), p is defined as the frequency of one allele and q as the frequency of another allele for a trait controlled by a pair of alleles (A and a). In other words, p equals all of the alleles in individuals who are homozygous dominant (AA) and half of the alleles in individuals who are heterozygous (Aa) for this trait. In mathematical terms, this is $p=AA+\frac{1}{2}Aa$ Likewise, q equals the other half of the alleles for the trait in the population, or $q=aa+\frac{1}{2}Aa$ Because there are only two alleles in this case, the frequency of one plus the frequency of the other must equal 100%, which is to say $p+q=1$ Alternatively, $p=1-q$ OR $q=1-p$ All possible combinations of two alleles can be expressed as:

$(p+q)^2=1$ or more simply, $p^2+2pq+q^2=1$

In this equation, if p is assumed to be dominant, then $p^2$ is the frequency of homozygous dominant (AA) individuals in a population, 2 pq is the frequency of heterozygous (Aa) individuals, and $q^2$ is the frequency of homozygous recessive (aa) individuals.

From observations of phenotypes, it is usually only possible to know the frequency of homozygous dominant or recessive individuals, because both dominant and recessives will express the distinguishable traits. However, the Hardy-Weinberg equation allows us to determine the expected frequencies of all the genotypes, if only p or q is known. Knowing p and q, it is a simple matter to plug these values into the Hardy-Weinberg equation ($p^2+2pq+q^2=1$). This then provides the frequencies of all three genotypes for the selected trait within the population. This illustration shows Hardy-Weinberg frequency distributions for the genotypes AA, Aa, and aa at all values for frequencies of the alleles, p and q. It should be noted that the proportion of heterozygotes increases as the values of p and q approach 0.5.

Linkage disequilibirum

Linkage is the tendency of genes or DNA sequences (e.g. SNPs) to be inherited together as a consequence of their physical proximity on a single chromosome. The closer together the markers are, the lower the probability that they will be separated during DNA crossing over, and hence the greater the probability that they will be inherited together. Suppose a mutational event introduces a "new" allele in the close proximity of a gene or an allele. The new allele will tend to be inherited together with the alleles present on the "ancestral," chromosome or haplotype. However, the resulting association, called linkage disequilibrium, will decline over time due to recombination. Linkage disequilibrium has been used to map disease genes. In general, both allele and haplotype frequencies differ among populations. Linkage disequilibrium is varied among the populations, being absent in some and highly significant in others.

Quantification of the relative risk of observable outcomes of a Pharmacogenetics Trial Let PlaR be the placebo response rate (0% ( PlaR ( 100%) and TntR be the treatment response rate (0% ( TntR ( 100%) of a classical clinical trial. ObsRR is defined as the relative risk between TntR and PlaR:

ObsRR=TntR/PlaR.

Suppose that in the treatment group there is a polymorphism in relation to drug metabolism such as the treatment response rate is different for each genotypic subgroup of patients. Let q be the allele a frequency of a recessive biallelic locus (e.g. SNP) and p=1−q the allele A frequency. Following Hardy-Weinberg equilibrium, the relative frequency of homozygous and heterozygous patients are as follow:

AA: p2 Aa: 2pq aa: q2 with (p2+2pq+q2)=1.

Let's define AAR, AaR, aaR as respectively the response rates of the AA, Aa and aa patients. We have the following relationship:

TntR=AAR*p2+AaR*2pq+aaR*q2.

Suppose that the aa genotypic group of patients has the lowest response rate, i.e. a response rate equal to the placebo response rate (which means that the polymorphism has no impact on natural disease evolution but only on drug action) and let's define ExpRR as the relative risk between AAR and aaR, as ExpRR=AAR /aaR.

From the previous equations, we have the following relationships:

ObsRR ( ExpRR (1/PlaR TntR/PlaR=(AAR*p2+AaR*2pq+ aaR*q2)/PlaR

The maximum of the expected relative risk, max(ExpRR), corresponding to the case of heterozygous patients having the same response rate as the placebo rate, is such that:

ObsRR =ExpRR*p2+2pq+q2⇔ExpRR=(ObsRR—2pq—q2)/p2

The minimum of the expected relative risk, min(ExpRR), corresponding to the case of heterozygous patients having the same response rate as the homozygous non-affected patients, is such that:

$$ObsRR = ExpRR^*(p2+2pq)+q2 \Leftrightarrow ExpRR = (ObsRR - q2)/(p2+2pq)$$

For example, if q=0.4, PlaR=40% and ObsRR=1.5 (i.e. TntR=60%), then 1.6 (ExpRR (2.4. This means that the best treatment response rate we can expect in a genotypic subgroup of patients in these conditions would be 95.6% instead of 60%.

This can also be expressed in terms of maximum potential gain between the observed difference in response rates (TntR—PlaR) without any pharmacogenetic hypothesis and the maximum expected difference in response rates (max(ExpRR)*PlaR—TntR) with a strong pharmacogenetic hypothesis:

$$(\max(ExpRR)^*PlaR-TntR)=[(ObsRR-2pq-q2)/p2]^* PlaR-TntR$$

$$\Leftrightarrow (\max(ExpRR)^*PlaR-TntR)=[TntR-PlaR^*(2pq+q2)-TntR^*p2]/p2$$

$$\Leftrightarrow (\max(ExpRR)^*PlaR-TntR)=[TntR^*(1-p2)\, PlaR^*(2pq+q2)]/p2$$

$$\Leftrightarrow (\max(ExpRR)^*PlaR-TntR)=[(1-p2)/p2]^* (TntR-PlaR)$$

that is for the previous example, $$(95.6\%-60\%)=[(1-0.62)/0.62]^* (60\%-40\%)=35.6\%$$

Suppose that, instead of one SNP, we have p loci of SNPs for one gene. This means that we have 2p possible haplotypes for this gene and (2p)(2p-1)/2 possible genotypes. And with 2 genes with p1 and p2 SNP loci, we have [(2p1)(2p1-1)/2]*[(2p2)(2p2-1)/2] possibilities; and so on. Examining haplotypes instead of combinations of SNPs is especially useful when there is linkage disequilibrium enough to reduce the number of combinations to test, but not complete since in this latest case one SNP would be sufficient. Yet the problem of frequency above still remains with haplotypes instead of SNPs since the frequency of a haplotype cannot be higher than the highest SNP frequency involved.

Statistical Methods to be used in Objective Analyses

The statistical significance of the differences between variance frequencies can be assessed by a Pearson chi-squared test of homogeneity of proportions with n-1 degrees of freedom. Then, in order to determine which variance(s) is(are) responsible for an eventual significance, we can consider each variance individually against the rest, up to n comparisons, each based on a 2×2 table. This should result in chi-squared tests that are individually valid, but taking the most significant of these tests is a form of multiple testing. A Bonferroni's adjustment for multiple testing will thus be made to the P-values, such as $p^*=1-(1-p)^n$.

The statistical significance of the difference between genotype frequencies associated to every variance can be assessed by a Pearson chi-squared test of homogeneity of proportions with 2 degrees of freedom, using the same Bonferroni's adjustment as above.

Testing for unequal haplotype frequencies between cases and controls can be considered in the same framework as testing for unequal variance frequencies since a single variance can be considered as a haplotype of a single locus. The relevant likelihood ratio test compares a model where two seqarate sets of haplotype frequencies apply to the cases and controls, to one where the entire sample is characterized by a single common set of haplotype frequencies. This can be performed by repeated use of a computer program (Terwilliger and Ott, 1994, Handbook of Human Linkage Analysis, Baltimore, John Hopkins University Press) to successively obtain the log-likelihood corresponding to the set of haplotpe frequency estimates on the cases ($\ln L_{case}$), on the controls ($\ln L_{control}$) and on the overall ($\ln L_{combined}$). The test statistic $2((nL_{case})+(\ln L_{control})-(\ln L_{combined}))$ is then chi-squared with r-1 degrees of freedom (where r is the number of haplotypes).

To test for potentially confounding effects or effect-modifiers, such as sex, age, etc., logistic regression can be used with case-control status as the outcome variable, and genotypes and covariates (plus possible interactions) as predictor variables.

Example 9

Exemplary Pharmacogenetic Analysis Steps

In accordance with the discussion of distribution frequencies for variances, alleles, and haplotypes, variance detection, and correlation of variances or haplotypes with treatment response variability, the points below list major items which will typically be performed in an analysis of the pharmacogenetic determination of the effects of variances in the treatment of a disease and the selection/optimization of treatment.

1) List candidate gene/genes for a known genetic disease, and assign them to the respective metabolic pathways.
2) Determine their alleles, observed and expected frequencies, and their relative distributions among various ethnic groups, gender, both in the control and in the study (case) groups.
3) Measure the relevant clinical/phenotypic (biochemical/physiological) variables of the disease.
4) If the causal variance/allele in the candidate gene is unknown, then determine linkage disequilibria among variances of the candidate gene(s).
5) Divide the regions of the candidate genes into regions of high linkage disequilibrium and low disequilibrium.
6) Develop haplotypes among variances that show strong linkage disequilibrium using the computation methods.
7) Determine the presence of rare haplotypes experimentally. Confirm if the computationally determined rare haplotypes agree with the experimentally determined haplotypes.
8) If there is a disagreement between the experimentally determined haplotypes and the computationally derived haplotypes, drop the computationally derived rare haplotypes, construct cladograms from these haplotypes using the Templeton (1987) algorithm.
9) Note regions of high recombination. Divide regions of high recombination further to see patterns of linkage disequilibria.
10) Establish association between cladograms and clinical variables using the nested analysis of variance as presented by Templeton (1995), and assign causal variance to a specific haplotype.
11) For variances in the regions of high recombination, use permutation tests for establishing associations between variances and the phenotypic variables.
12) If two or more genes are found to affect a clinical variable determine the relative contribution of each of the genes or variances in relation to the clinical variable, using step-wise regression or discriminant function or principal component analysis.
13) Determine the relative magnitudes of the effects of any of the two variances on the clinical variable due to their genetic (additive, dominant or epistasis) interaction.

14) Using the frequency of an allele or haplotypes, as well as biochemical/clinical variables determined in the in vitro or in vivo studies, determine the effect of that gene or allele on the expression of the clinical variable, according to the measured genotype approach of Boerwinkle et al (Ann. Hum. Genet 1986).
15) Stratify ethnic/ clinical populations based on the presence or absence of a given allele or a haplotype.
16) Optimize drug dosages based on the frequency of alleles and haplotypes as well as their effects using the measured genotype approach as a guide.

Example 10

Exemplary Pharmacogenetic Analysis Steps—biological function analysis

In many cases when a gene which may affect drug action is found to exhibit variances in the gene, RNA, or protein sequence, it is preferable to perform biological experiments to determine the biological impact of the variances on the structure and function of the gene or its expressed product and on drug action. Such experiments may be performed in vitro or in vivo using methods known in the art. The points below list major items which may typically be performed in an analysis of the effects of variances in the treatment of a disease and the selection/optimization of treatment using biological studies to determine the structure and function of variant forms of a gene or its expressed product.

1) List candidate gene/genes for a known genetic disease, and assign them to the respective metabolic pathways.
2) Identify variances in the gene sequence, the expressed mRNA sequence or expressed protein sequence.
3) Match the position of variances to regions of the gene, mRNA, or protein with known biological functions. For example, specific sequences in the promotor of a gene are known to be responsible for determining the level of expression of the gene; specific sequences in the mRNA are known to be involved in the processing of nuclear mRNA into cytoplasmic mRNA including splicing and polyadenylation; and certain sequences in proteins are known to direct the trafficking of proteins to specific locations within a cell and to constitute active sites of biological functions including the binding of proteins to other biological consituents or catalytic functions. Variances in sites such as these, and others known in the art, are candidates for biological effects on drug action.
4) Model the effect of the variance on mRNA or protein structure. Computational methods for predicting the structure of mRNA are known and can be used to assess whether a specific variance is likely to cause a substantial change in the structure of mRNA. Computational methods can also be used to predict the structure of peptide sequences enabling predictions to be made concerning the potential impact of the variance on protein function. Most useful are structures of proteins determined by X-ray diffraction, NMR or other methods known in the art which provide the atomic structure of the protein. Computational methods can be used to consider the effect of changing an amino acid within such a structure to determine whether such a change would disrupt the structure and/or funciton of the protein. Those skilled in the art will recognize that this analysis can be performed on crystal structures of the protein known to have a variance as well as homologous proteins expressed from different loci in the human genome, or homologous proteins from other species, or non-homologous but analogous proteins with similar functions from humans or other species.
5) Produce the gene, mRNA or protein in amounts sufficient to experimentally characterize the structure and function of the gene, mRNA or protein. It will be apparent to those skilled in the art that by comparing the activity of two genes or their products which differ by a single variance, the effect of the variance can be determined. Methods for producing genes or gene products which differ by one or more bases for the purpose of experimental analysis are known in the art.
6) Experimental methods known in the art can be used to determine whether a specific variance alters the transcription of a gene and translation into a gene product. This involves producing amounts of the gene by molecular cloning sufficient for in vitro or in vivo studies. Methods for producing genes and gene products are known in the art and include cloning of segments of genetic material in prokaryotes or eukarotic hosts, run off transcription and cell-free translation assays that can be performed in cell free extracts, transfection of DNA into cultured cells, introduction of genes into live animals or embryos by direct injection or using vehicles for gene delivery including transfection mixtures or viral vectors.
7) Experimental methods known in the art can be used to determine whether a specific variance alters the ability of a gene to be transcribed into RNA. For example, run off transcription assays can be performed in vitro or expression can be characterized in transfected cells or transgenic animals.
8) Experimental methods known in the art can be used to determine whether a specific variance alters the processing, stability, or translation of RNA into protein. For example, reticulocyte lysate assays can be used to study the production of protein in cell free systems, transfection assays can be designed to study the production of protein in cultured cells, and the production of gene products can be measured in transgenic animals.
9) Experimental methods known in the art can be used to determine whether a specific variant alters the activity of an expressed protein product. For example, protein can be producted by reticulocyte lystae systems or by introducing the gene into prokaryotic organisms such as bacteria or lowre eukaryotic organisms such as yeast or fungus), or by introducing the gene into cultured cells or transgenic animals. Protein produced in such systems can be extracted or purified and subjected to bioassays known to those in the art as measures of the nction of that particular protein. Bioassays may involve, but are not limited to, binding, inhibiton, or catalytic functions.
10) Those skilled in the art will recognize that it is sometimes preferred to perform the above experiments in the presence of a specific drug to determine whether the drug has differential effects on the activity being measured. Alternatively, studies may be performed in the presence of an analogue or metabolite of the drug.
11) Using methods described above, specific variances which alter the biological function of a gene or its gene product that could have an impact on drug action can be identified. Such variances are then studied in clinical trial populations to determine whether the presence or absence of a specific variance correlates with observed clinical outcomes such as efficacy or toxicity.

12) It will be further recognized that there may be more than one variance within a gene that is capable of altering the biological function of the gene or gene product. These variances may exhibit similar, synergistic effects, or may have opposite effects on gene function. In such cases, it is necessary to consider the haplotype of the gene, namely the combination of variances that are present within a single allele, to assess the composite function of the gene or gene product.
13) Perform clinical trials with stratification of patients based on presence or absence of a given variance, allele or haplotype of a gene. Establish associations between observed drug responses such as toxicity, efficacy, drug response, or dose toleration and the presence or absense of a specific variance, allele, or haplotype.
14) Optimize drug dosage or drug usage based on the presence of the variant.

Example 11

Stratification of patients by genotype in prospective clinical trials.

In a prospective clinical trial, patients will be stratified by genotype to determine whether the observed outcomes are different in patients having different genotypes. A critical issue is the design of such trials to assure that a sufficient number of patients are studied to observe genetic effects.

The number of patients required to achieve statistical significance in a conventional clinical trial is calculated from:

$$1.1 \; N = 2(z_\alpha + z_{2\beta})^2 / (\delta/\sigma)^2 \text{ (two tailed test)}$$

From this equation it may be inferred that the size of a genetically defined subgroup $N_i$ required to achieve statistical significance for an observed outcome associated with variance or haplotype "i" can be calculated as:

$$1.2 \; N_i = 2(z_\alpha + z2\beta)^2 / (\delta_i/\sigma_i)^2$$

If $P_i$ is the prevalence of the genotype "i" in the population, the total number of patients that need to be incorporated in a clinical trial $N_g$ to identify a population with haplotype "i" of size $N_i$ is given by:

$$1.3 \; Ng = N_i/P_i$$

It should be noted that $N_g$ describes the total number of patients that need to be genotyped in order to identify a subset of $N_i$ patients with genotype "i".

If genotyping is used as means for statistical stratification of patients, $N_g$ represents the number of patients that would need to be enrolled in a trial to achieve statistical significance for subgroup "i". If genotyping is used as a means for inclusion, it represents the number of patients that needs to be screened to identify a population of $N_i$ individuals for an appropriately powered clinical trial. Thus, $N_g$ is a critical determinant of the scope of the clinical trial as well as $N_i$.

A clinical trial can also be designed to test associations for multiple genetic subgroups "j" defined by a single allele in which case:

$$1.4 \; N_g = \max(N_{gi}) \text{ for } i = \ldots j$$

If more than one subgroup is tested, but there is no overlap in the patients contained within the subgroups, these can be considered to be independent hypotheses and no multiple testing correction should be required. If consideration of more than one subgroup constitutes multiple testing, or if individual patients are included in multiple subgroups, then statistical corrections may be required in the values of $z_\alpha$ or $Z_{2\beta}$ which would increase the number of patients required.

It should be emphasized that a clinical trial of this nature may not provide statistically significant data concerning associations with any genotype other than "i". The total number of patients that would be required in a clinical trial to test more than one genetically defined subgroup would be determined by the maximum value of $N_g$ for any single subgroup.

The power of pharmacogenomics to improve the efficiency of clinical trials arises from the fact it is possible to have $N_g < N$. The goal of pharmacogenomic analysis is to identify a genetically define subgroup in which the magnitude of the clinical response is greater and the variability in response is reduced. These observations correspond to an increase in the magnitude of the (mean) observed response $\delta$ or a decrease the degree of variability $\sigma$. Since the value of $N_i$ calculated in equation 1.2 decreases non-linearly as the square of these changes, the total number of patients $N_g$ can also decrease non-linearly, resulting in a clinical trial that requires fewer patients to achieve statistical significance. If $\delta_i$ and $\sigma_i$ are not different than $\delta$ and $\sigma$, then $N_g$ is greater than N as given by $N_g = N_i/P_i$. Values of $\delta_i$ and $\sigma_i$ that give $N_g < N$ can be calculated:

$$1.5 \; N_g < N \text{ if: } P_i > [(\delta/\sigma)^2]/[(\delta_i/\sigma_i)^2]$$

It is apparent from this analysis that $N_g$ is not uniformly less than N, even with modest improvements in the values for $\delta_i$ and $\sigma_i$.

As with a conventional clinical trial, the incorporation of an appropriate control group in the study design is critical for achieving success. In the case of a prospective clinical trial, the control group commonly is selected on the basis of the same inclusion criteria as the treatment group, but is treated with placebo or a standard therapeutic regimen rather than the investigational drug. In the case of a study with subgroups that are defined by haplotype, the ideal control group for a treatment subgroup with hapotype "i" is a placebo-treated subgroup with haplotype "i". This is often a critical control, since haplotypes which may be associated with the response to treatment may also affect the natural course of the disease.

A critical issue in considering control groups is that C for the control group placebo treated population with haplotype "i" may not be equivalent to that of the control population. If so, 1.5 may overestimate the benefits of any reduction in $\sigma_i$ in the treatment response group if there is not also a reduction in $\sigma_i$ in the control group.

If $\sigma$ of the treatment and control groups are not equivalent, $\delta$ would be still calculated as the difference in the response of the two groups, but $\sigma_i$ would be different in the two groups with values of $\sigma_0$ or $\sigma_1$ respectively. In this case, the number of patients in the genetically defined subgroup $N_i$ would be defined by:

$$2.1 \; N_i = (\sigma_i Z_\alpha + \sigma_i Z_\beta)^2 / \Delta^2$$

The total number of patients that would need to be enrolled in such a trial would be the maximum of $$2.2 \; N \text{ or } N/Pi$$

It will be apparent that such an analysis remains sensitive to increases in δ, but is less sensitive to changes in σ which are not also reflected in the control group.

Certain analysis may be performed by comparing individuals with one haplotype against the entire normal population. Such an analysis may be used to establish the selectivity of the response associated with a specific haplotype. For example, it may be desirable to establish that the response or toxicity observed in a specific subgroup is greater than that associated observed with the entire population. It may also be of interest to compare the response to treatment between two different subgroups. If σ differs between the groups, then the estimate of the number of patients that need to be enrolled in the trial should be calculated using equations 2.1 with N being the maximum of $N_i/P_i$ for the different subgroups.

Another issue in controls is the relative size of the treatment and control groups. In a prospectively designed clinical trial, which selectively incorporates patients with haplotype "i", the number of patients in the control and treatment group will be essentially equivalent. If the control group is different, or if haplotypes are used for stratification but not inclusion, statistical corrections may need to be made for having populations of different size.

Example 12

Stratification of patients by phenotype.

The identification of genetic associations in Phase II or retrospective studies can be performed by stratifying patients by phenotype and analyzing the distribution of genotypes/haplotypes in the separate populations. A particularly important aspect of this analysis is that any gene may have only a partial effect on the observed outcome, meaning that there will be an association value (A) corresponding to the fraction of patients in a phenotypically-defined subgroup who exhibit that phenotype due to a specific genotype/phenotype.

It will be recognized to those skilled in the art that the fraction of individuals who exhibit a phenotype due to any specific allele will be less than 1 (i.e. A<1). This is true for several reasons. The observed phenotype may occur by random chance. The observed phenotype may be associated with environmental influences, or the observed phenotype may be due to different genetic effects in different individuals. Furthermore, the onstruction of haplotypes and analysis of recombination may not group all alleles with pheontypically-significant variances within a single haplotype or haplotype cluster. In this case, causative variances at a single locus may be associated with more than one haplotype or haplotype cluster and the association constant A for the locus would be $A=A_1+A_2+...+A_n<1$. It is likely that many phenotypes will be associated with multiple alleles at a given locus, and it is particularly important that statistical methods be sufficiently robust to identify association with a locus even if $A_i$ is reduced by the presence of several causative alleles.

Statistical methods can be used to identify genetic effects on an observed outcome in patient groups stratified by phenotype, eg the presence or absence of the observed response. One such method entails determining the allele frequencies in two populations of patients stratified by an observed clinical outcome, for example efficacy or toxicity and performing a maximum likelihood analysis for the association between a given gene and the observed phenotype based on the allele frequencies and a range of values for A (the association constant between a specific allele and the observed outcome used to stratify patients).

This analysis is performed by comparing the observed gene frequencies in a patient population with an observed outcome to gene frequencies in a table in which the predicted frequencies of different alleles of the gene assuming different values of the association constant A for that allele. This table of predicted gene frequencies can be constructed by those skilled in the art based on the frequency of any specific allele in the normal population, the predicted inheritance of the effect (e.g. dominant or recessive) and the fraction of a subgroup with a specific outcome who would have that allele based on the association constant A.

For example, if a specific outcome was only observed in the presence of a specific allele of a gene, the expected frequency would be 1. If a specific outcome was never observed in the presence of a specific allele of a gene, the expected fequency would be 0. If there was no association between the allele and the observed outcome, the frequency of that allele among individuals with an observed outcome would be the same as in the general population. A statistical analysis can be performed to compare the observed allele frequencies with the predicted allele frequencies and determine the best fit or maximum likeihood of the association. For example, a chi square analysis will determine whether the observed outcome is statistically similar to predicted outcomes calculated for different modes of inheritance and different potential values of A. P values can then be calculated to determine the likelihood that any specific association is statistically significant. A curve can be calculated based on different values of A, and the maximal likelihood of an association determined from the peak of such a curve. Methods for chi square analysis are known to those in the art.

A multidimensional analysis can also be performed to determine whether an observed outcome is associated with more than one allele at a specific genetic locus. An example of this analysis considering the potential effects of two different alleles of a single gene is shown. It will be apparent to those skilled in the art that this analysis can be extended to n dimensions using computer programs.

This analysis can be used to determine the maximum likelihood that one or more alleles at a given locus are associated with a specific clinical outcome.

It will be apparent to those skilled in the art that critical issues in this analysis include the fidelity of the phenotypic association and identification of a control group. In particular, it may be useful to perform an identical analysis in patients receiving a placebo to eliminate other forms of bias which may contribute to statistical errors.

Other Embodiments

The invention described herein provides a method for identifying patients with a risk of developing inflammatory or immunological disease or dysfunction by determining the patients allele status for a gene listed in Tables 1 and 3 and providing a forecast of the patients ability to respond to a given drug treatment. In particular, the invention provides a method for determining, based on the presence or absence of a polymorphism, a patient's likely response to drug therapies as inflammatory or immunological disease or dysfunction. Given the predictive value of the described polymorphisms across two different classes of drug, having different mechanisms of action, the candidate polymorphism is likely to have a similar predictive value for other drugs acting through other pharmacological mechanisms. Thus, the methods of the invention may be used to determine a patient's response to other drugs including, without limitation, antihypertensives, anti-obesity, anti-hyperlipidemic, or anti-proliferative, antioxidants, or enhancers of terminal differentiation.

In addition, while determining the presence or absence of the candidate allele is a clear predictor determining the efficacy of a drug on a given patient, other allelic variants of reduced catalytic activity are envisioned as predicting drug efficacy using the methods described herein. In particular, the methods of the invention may be used to treat patients with any of the possible variances, e.g., as described in Table 3 of Stanton & Adams, U.S. application No. 09/300,747, supra.

In addition, while the methods described herein are preferably used for the treatment of human patient, non-human animals (e.g., pets and livestock) may also be treated using the methods of the invention.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims. It will be readily apparent to one skilled in the art that varying substitutions and modifications may be made to the invention disclosed herein without departing from the scope and spirit of the invention. For example, using other compounds, and/or methods of administration are all within the scope of the present invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

TABLE 1

| Class | Pathway | Function | Name | OMIM | GID | Locus |
|---|---|---|---|---|---|---|
| Immune Discrimination (Self vs Non-Self) | Antigen Presentation and Recognition | Major Histocompatibility Complex I | MHC class I HLA A/HLA-A | 1E + 05 | AF148863 | 6p21.3 |
| | | | MHC class I HLA B/HLA-B | 1E + 05 | NM_005514 | 6p21.3 |
| | | | MHC class I HLA C/HLA-C | 1E + 05 | AF168611 | 6p21.3 |
| | | | MHC class I HLA E/HLA-E | 1E + 05 | NM_005516 | 6p21.3 |
| | | | MHC class I HLA F/HLA-F | 1E + 05 | X17093 | 6p21.3 |
| | | | MHC class I HLA G/HLA-G | 1E + 05 | AH005893 | 6p21.3 |
| | | | beta-2-microglobulin/B2M | 1E + 05 | NM_004048 | 15q21-q22 |
| | | Major Histocompatibility Complex I-Related | thymocyte antigen CD1A/CD1A | 2E + 05 | AF142665 | 1q21-q23 |
| | | | thymocyte antigen CD1B/CD1B | 2E + 05 | AF142666 | 1q21-q23 |
| | | | thymocyte antigen CD1C/CD1C | 2E + 05 | AF142667 | 1q21-q23 |
| | | | thymocyte antigen CD1D/CD1D | 2E + 05 | AF142668 | 1q21-q23 |
| | | | thymocyte antigen CD1E/CD1E | 2E + 05 | AF142669 | 1q21-q23 |
| | | MHC Class I Transcription | interferon-gamma receptor 1/IFNGR1 | 1E + 05 | NM_000416 | 6q23-q24 |
| | | | interferon-gamma receptor 2/IFNGR2 | 1E + 05 | NM_005534 | 21q22.1-q22.2 |
| | | | TATA box binding protein (TBP)-associated factor, RNA polymerase II, A, 250kD/TAF2A | 3E + 05 | NM_004606 | Xq13 |
| | | | interferon regulatory factor 1/IRF1 | 1E + 05 | NM_002198 | 5q31.1 |
| | | | nuclear factor kappa-B DNA binding subunit 2/NFKB2 | 2E + 05 | NM_002502 | 10q24 |
| | | Major Histocompatibility Complex II | MHC class II HLA DR-alpha chain/HLA-DRA | 1E + 05 | X83114 | 6p21.3 |
| | | | MHC class II HLA DR-beta chain/HLA-DRB | 1E + 05 | M11161 | 6p21.3 |
| | | | MHC class II HLA DP-alpha chain/HLA-DPA | 1E + 05 | M23905 | 6p21.3 |
| | | | MHC class II HLA DP-beta chain/HLA-DPB | 1E + 05 | AH002893 | 6p21.3 |
| | | | MHC class II HLA DM-alpha chain/HLA-DMA | 1E + 05 | NM_006120 | 6p21.3 |
| | | | MHC class II HLA DM-beta chain/HLA-DMB | 1E + 05 | NM_002118 | 6p21.3 |
| | | | MHC class II HLA DQ-alpha chain/HLA-DQA | 1E + 05 | M11124 | 6p21.3 |
| | | | MCH class II HLA DQ-beta chain/HLA-DQB | ******* | M24364 | 6p21.3 |
| | | | MHC class II HLA DN-alpha chain/HLA-DNA | 1E + 05 | X02882 | 6p21.3 |
| | | | MHC class II HLA DO-beta chain/HLA-DOB | 6E + 05 | NM_002120 | 6p21.3 |
| | | | MHC class II antigen gamma chain/CD74 | 1E + 05 | K01144 | 5q32 |
| | | | antigen peptide transporter 1/MHC1/TAP1 | 2E + 05 | NM_000593 | 6p21.3 |
| | | | antigen peptide transporter 2/MHC2/TAP2 | 2E + 05 | NM_000544 | 6p21.3 |
| | | MHC Class II Transcription | interferon-gamma receptor 1/IFNGR1 | 1E + 05 | NM_000416 | 6q23-q24 |
| | | | interferon-gamma receptor 2/IFNGR2 | 1E + 05 | NM_005534 | 21q22.1-q22.2 |
| | | | regulatory factor X, 5 (influences HLA class II expression)/RFX5 | 6E + 05 | NM_000449 | 1q21.1-q21.3 |
| | | | MHC class II transactivator/MHC2TA | 6E + 05 | NM_000246 | 16p13 |
| | | | regulatory factor X-associated protein/RFXAP | 6E + 05 | NM_000538 | 13q14 |
| | | | regulatory factor X-associated ankyrin-containing protein/RFXANK | 6E + 05 | NM_003721 | 19p12 |
| | | | regulatory factor X, 2 (influences HLA class II expression)/RFX2 | 1E + 05 | ******* | 19p13.3-p13.2 |
| | | | nuclear transcription factor, X-box binding 1/NFX1 | 6E + 05 | NM_002504 | ******* |
| | | | nuclear transcription factor, Y, alpha/NFYA | 2E + 05 | NM_002505 | 6p21.3 |
| | | | nuclear transcription factor Y, beta/NFYB | 2E + 05 | NM_006166 | 12q22-q23 |
| | | T-Cell Antigen Receptor Complex | T-cell antigen receptor, alpha subunit/TCRA | 2E + 05 | Z24457 | 14q11.2 |
| | | | T-cell antigen receptor, beta subunit/TCRB | 2E + 05 | AF011643 | 7q35 |
| | | | T-cell antigen receptor, gamma subunit/TCRG | 2E + 05 | M17325 | 7p15-p14 |
| | | | T-cell antigen receptor, delta subunit/TCRD | 2E + 05 | L36384 | 14q11.2 |

TABLE 1-continued

| Class | Pathway | Function | Name | OMIM | GID | Locus |
|---|---|---|---|---|---|---|
| | | Rearrangement of T-Cell Antigen Receptor Complex | thymocyte antigen receptor complex CD3G, gamma polypeptide (TiT3 complex)/CD3G | 2E + 05 | NM_000073 | 11q23 |
| | | | thymocyte antigen receptor complex CD3D, delta polypeptide (TiT3 complex)/CD3D | 2E + 05 | NM_000732 | 11q23 |
| | | | thymocyte antigen receptor complex CD3E, epsilon polypeptide (TiT3 complex)/CD3E | 2E + 05 | NM_000733 | 11q23 |
| | | | thymocyte antigen receptor complex CD3Z, zeta polypeptide (TiT3 complex)/CD3Z | 2E + 05 | NM_000734 | 1q22-q23 |
| | | | thymocyte antigen receptor CD2 (p50), sheep red blood cell receptor/CD2 | 2E + 05 | NM_001767 | 1p13.1 |
| | | | ataxia telangiectasia mutated (includes complementation groups A, C and D)/ATM | 2E + 05 | NM_000051 | 11q22.3 |
| | | | recombination activating gene-1/RAG1 | 2E + 05 | NM_000448 | 11p13 |
| | | | recombination activating gene-2/RAG2 | 2E + 05 | M94633 | 11p13 |
| | | | interleukin 7 receptor/IL7R | 1E + 05 | NM_002185 | 5p.13 |
| | | | v-myb avian myeloblastosis viral oncogene homolog/MYB | 2E + 05 | NM_005375 | 6q22 |
| | | | core binding factor, alpha 1 subunit/CBFA1 | 6E + 05 | AH005498 | 6p21 |
| | | | core-binding factor, beta subunit/PEBP2B/CBFB | 1E + 05 | L20298 | 16q22 |
| | | | ligase I, DNA, ATP-dependent/LIG1 | 1E + 05 | NM_000234 | 19q13.2-q13.3 |
| | | | ligase IV, DNA, ATP dependent/LIG4 | 6E + 05 | NM_002312 | 13q22-q34 |
| | | | X-ray repair, complementing defect in Chinese hamster/Ku antigen, 80 kD)/KU80/XRCC5 | 2E + 05 | ****** | 2q35 |
| | | | thyroid autoantigen, 70 kD/KU70/G22P1 | 2E + 05 | NM_001469 | 22q11-q13 |
| | | | GATA binding protein 3/GATA3 | 1E + 05 | NM_002051 | 10p15 |
| | | Transcription of T-Cell Antigen Receptor Complex | long form transcription factor G-MAF/GMAF | ****** | AF055377 | ****** |
| | | | B-cell antigen CD25/interleukin 2 receptor, alpha chain/IL2RA/CD25 | 1E + 05 | 10p15-p14 | 10Op15-p14 |
| | | | interleukin 2 receptor, beta/IL2RB | 1E + 05 | NM_000878 | 22q11.2-q13 |
| | | | interleukin 2 receptor, gamma chain/IL2RG | 3E + 05 | NM_000206 | Xq13 |
| | | | transcription factor 1/hepatic nuclear factor/HNF1/albumin proximal factor/TCF1 | 1E + 05 | NM_000545 | 12q24.2 |
| | | B-Cell Antigen Receptor Complex | lymphocyte antigen CD79A/immunoglobulin-associated alpha/CD79A | 1E + 05 | NM_001783 | 19q13.2 |
| | | | lymphocyte antigen CD79B/immunoglobulin-associated beta/CD79B | 1E + 05 | L27587 | 17q23 |
| Cytokine-Mediated Immune Regulation | Interferons | Synthesis | interferon regulatory factor 1/IRF1 | 1E + 05 | NM_002198 | 5q31.1 |
| | | | interferon regulatory factor 2/IRF2 | 1E + 05 | NM_002199 | 4q35.1 |
| | | | interferon consensus sequence binding protein 1/ICSBP1 | 6E + 05 | NM_002163 | ****** |
| | | | interferon alpha 1/IFNA1 | 1E + 05 | X02956 | 9p22 |
| | | | interferon alpha 2/IFNA2 | 1E + 05 | Y11834 | 9p22 |
| | | | interferon alpha 4/IFNA4 | 1E + 05 | ****** | 9p22 |
| | | | interferon alpha 5/IFNA5 | 1E + 05 | NM_002169 | 9p22 |
| | | | interferon alpha 6/IFNA6 | 1E + 05 | ****** | 9p22 |
| | | | interferon alpha 7/IFNA7 | 1E + 05 | ****** | 9p22 |
| | | | interferon alpha 8/IFNA8 | 1E + 05 | NM_002170 | 9p22 |
| | | | interferon alpha 10/IFNA10 | 1E + 05 | NM_002171 | 9p22 |
| | | | interferon alpha 13/IFNA13 | 1E + 05 | NM_006900 | 9p22 |
| | | | interferon alpha 14/IFNA14 | 1E + 05 | NM_002172 | 9p22 |
| | | | interferon alpha 16/IFNA16 | 1E + 05 | NM_002173 | 9p22 |
| | | | interferon alpha 17/IFNA17 | 1E + 05 | ****** | 9p22 |
| | | | interferon alpha 21/IFNA21 | 1E + 05 | NM_002175 | 9p22 |
| | | | interferon beta 1/IFNB1 | 1E + 05 | NM_002176 | 9p21 |
| | | | interferon beta 3/IFNB3 | 1E + 05 | K03196 | Chr. 8 |
| | | | interferon gamma/IFNG | 1E + 05 | L07633 | 12q14 |
| | | | interferon omega 1/IFNW1 | 1E + 05 | NM_002177 | 9p21 |

TABLE 1-continued

| Class | Pathway | Function | Name | OMIM | GID | Locus |
|---|---|---|---|---|---|---|
| | | Receptors | interferon (alpha, beta and omega) receptor 1/IFNAR1 | 1E + 05 | X77722 | 21q22.1 |
| | | | interferon (alpha, beta and omega) receptor 2/IFNAR2 | 6E + 05 | NM_000874 | 21q22.1 |
| | | | interferon-gamma receptor 1/IFNGR1 | 1E + 05 | NM_000416 | 6q23–q24 |
| | | | interferon-gamma receptor 2/IFNGR2 | 1E + 05 | NM_005534 | 21q22.1-q22.2 |
| | Interleukins | Synthesis | interleukin enhancer binding factor 1/ILF1 | 1E + 05 | NM_004514 | 17q25 |
| | | | interleukin enhancer binding factor 2, 45 kD/ILF2 | 6E + 05 | NM_004515 | ****** |
| | | | interleukin enhancer binding factor 3, 90 kD/ILF3 | 6E + 05 | NM_004516 | ****** |
| | | | interleukin 1 alpha/IL-1A2 | 1E + 05 | M15330 | 3q14 |
| | | | interleukin 1 beta/IL-1B | 6E + 05 | AF043335 | 2q14 |
| | | | apoptosis-related cystein protease 1/interleukin 1-beta converting enzyme/ICE/capase 1/CASP1 | 1E + 05 | NM_001223 | 11q22.2-q22.3 |
| | | | interleukin 2/IL2 | 1E + 05 | X01586 | 4q26–q27 |
| | | | interleukin 3/IL3 | 1E + 05 | NM_000588 | 5q31.1 |
| | | | interleukin 4/IL4 | 1E + 05 | NM_000589 | 5q31.1 |
| | | | interleukin 5/IL5 | 1E + 05 | NM_000879 | 5q31.1 |
| | | | interleukin 6/IL6 | 1E + 05 | AF048692 | 7p21 |
| | | | interleukin 7/IL7 | 1E + 05 | NM_000880 | 8q12-q13 |
| | | | interleukin 8/IL8 | 1E + 05 | M26383 | 4q12-q13 |
| | | | interleukin 9/IL9 | 1E + 05 | X17543 | 5q31.1 |
| | | | interleukin 10/IL10 | 1E + 05 | M57627 | 1q31-q32 |
| | | | interleukin 11 beta/IL11B | 1E + 05 | NM_000881 | 19q13.3-q13.4 |
| | | | interleukin 12A (natural killer cell stimulatory factor 1 cytotoxic lymphocyte maturation factor 1 p35)/IL12A | 2E + 05 | NM_002187 | 3p12-q13.2 |
| | | | interleukin 12B/IL12B | 2E + 05 | NM_000440 | 5q31.1-q33.1 |
| | | | interleukin 13/IL13 | 1E + 05 | NM_002188 | 5q31 |
| | | | interleukin 15/IL15 | 6E + 05 | U14407 | 4q31 |
| | | | interleukin 16/IL16 | 6E + 05 | NM_004513 | ****** |
| | | | interleukin 17 (cytotoxic T-lymphocyte-associated serine esterase 8)/IL17 | 6E + 05 | NM_002190 | 2q31 |
| | | | interleukin 18 (interferon-gamma-inducing factor)/IL18 | 6E + 05 | NM_001562 | 11q22.2-q22.3 |
| | | Receptors | interleukin 1 receptor type 1/IL1R1 | 1E + 05 | NM_000877 | 2q12 |
| | | | interleukin 1 receptor-type 2/IL1R2 | 1E + 05 | NM_004633 | 2q12-q22 |
| | | | interleukin 1 receptor-like 2/IL1RL2 | ****** | NM_003854 | ****** |
| | | | interleukin 1 receptor accessory protein/IL1RAP | 6E + 05 | NM_002182 | 3q28 |
| | | | B-cell antigen CD25/interleukin 2 receptor, alpha chain/IL2RA/CD25 | 1E + 05 | | 10p15-p14 |
| | | | interleukin 2 receptor, beta/IL2RB | 1E + 05 | NM_000878 | 22q11.2-q13 |
| | | | interleukin 2 receptor, gamma chain/IL2RG | 3E + 05 | NM_000206 | Xq13 |
| | | | interleukin 3 alpha receptor/IL3RA | 3E + 05 | M74782 | Xp22.3 |
| | | | interleukin 4 receptor precursor/IL4R | 1E + 05 | NM_000418 | 16p12.1-p11.2 |
| | | | interleukin 5 receptor alpha/IL5RA | 1E + 05 | M96652 | 3p26-p24 |
| | | | interleukin 6 receptor/IL6R | 1E + 05 | NM_000565 | 1q21 |
| | | | interleukin 7 receptor/IL7R | 1E + 05 | NM_002185 | 5p13 |
| | | | interleukin 9 receptor/IL9R | 3E + 05 | NM_002186 | Xq28 |
| | | | interleukin 10 receptor, alpha/IL10RA | 1E + 05 | NM_001558 | 11q23.3 |
| | | | interleukin 10 receptor, beta/IL10RB | ****** | NM_000628 | ****** |
| | | | interleukin receptor 11 alpha/IL11RA | 6E + 05 | NM_004512 | 9p13 |
| | | | interleukin 12 receptor, beta 1/IL12RB1 | 6E + 05 | NM_005535 | 9p13 |

TABLE 1-continued

| Class | Pathway | Function | Name | OMIM | GID | Locus |
|---|---|---|---|---|---|---|
| | | | interleukin 12 receptor, beta 2/IL12RB2 | 6E+05 | NM_001559 | 1p31.2 |
| | | | interleukin 13 receptor, alpha 1/IL13RA1 | 3E+05 | NM_001560 | Chr.X |
| | | | interleukin 13 receptor 13 alpha 2/IL13A2 | 3E+05 | X95302 | Xq24 |
| | | | interleukin 15 receptor, alpha/IL15RA | 6E+05 | NM_002189 | 10p15-p14 |
| | | | interleukin 18 receptor 1/IL18R1 | ****** | NM_003855 | ******* |
| | | | interleukin 18 receptor accessory protein/IL18RAP | ****** | NM_003853 | ******* |
| Tumor Necrosis Factor Ligand Superfamily | | Synthesis | LPS-induced TNF-Alpha Factor/LITAF | 6E+05 | U77396 | 16p13.3-p12 |
| | | | tumor necrosis factor alpha/TNFA | 2E+05 | X01394 | 6p21.3 |
| | | | tumor necrosis factor beta/TNFB/lymphotoxin alpha/LTA | 2E+05 | NM_000595 | 6p21.3 |
| | | | tumor necrosis factor C/TNFC/lymphotoxin-beta/LTB | 6E+05 | NM_002341 | 6p21.3 |
| | | | tumor necrosis factor ligand superfamily, member 4/TNFSF4 | 6E+05 | NM_003326 | 1q25 |
| | | | tumor necrosis factor ligand superfamily, member 5/TNFSF5 | 3E+05 | NM_000074 | Xq26 |
| | | | tumor necrosis factor ligand superfamily, member 6/TNFSF6 | 1E+05 | NM_000639 | 1q23 |
| | | | B-cell antigen CD70/tumor necrosis factor ligand superfamily, member 7/TNFSF7/CD27 ligand/CD70 | 6E+05 | NM_001252 | 19p13 |
| | | | tumor necrosis factor ligand superfamily, member 8/TNFSF8 | 6E+05 | NM_001244 | 9q33 |
| | | | tumor necrosis factor ligand superfamily, member 10/TNFSF10 | 6E+05 | NM_003810 | 3q26 |
| | | | tumor necrosis factor ligand superfamily, member 11/TNFSF11 | 6E+05 | NM_003701 | 13q14 |
| | | | tumor necrosis factor ligand superfamily, member 12/TNFSF12 | 6E+05 | NM_003809 | 17p13.3 |
| | | | tumor necrosis factor ligand superfamily, member 13B/TNFSF13B | 6E+05 | NM_006573 | 13q32-q34 |
| | | | tumor necrosis factor ligand superfamily, member 15/TNFSF15 | 6E+05 | ****** | 9q33 |
| | | Receptors | tumor necrosis factor receptor superfamily, member 1A/TNFRSF1A | 2E+05 | NM_001065 | 12q13.2 |
| | | | tumor necrosis factor receptor superfamily, member 1B/TNFRSF1B | 2E+05 | NM_001066 | 1p36.3-p36.2 |
| | | | lymphotoxin beta receptor (TNFR superfamily, member 3/LTBR | 6E+05 | NM_002342 | 12p13 |
| | | | tumor necrosis factor receptor superfamily, member 4/TNFRSF4 | 6E+05 | NM_003327 | 1p36 |
| | | | B-cell antigen CD40/tumor necrosis factor receptor superfamily, member 5/CD40/TNFRSF5 | 1E+05 | NM_001250 | 20q12-q13.2 |
| | | | lymphocyte antigen CD95/tumor necrosis factor receptor superfamily, member 6/TNFRSF6/CD95 | 1E+05 | NM_000043 | 10q24.1 |
| | | | tumor necrosis factor receptor superfamily, member 6B/TNFRSF6B | 6E+05 | NM_003823 | 20q13 |
| | | | T-cell antigen CD27 tumor necrosis factor receptor superfamily, member 7/CD27/TNFRSF7 | 2E+05 | M63928 | 12p13 |
| | | | lymphocyte antigen CD30/tumor necrosis factor receptor superfamily, member 8/CD30/TNFRSF8 | 2E+05 | NM_001243 | 1p36 |
| | | | tumor necrosis factor receptor superfamily, member 9/TNFRSF9 | 6E+05 | NM_001561 | 1p36 |
| | | | tumor necrosis factor receptor superfamily, member 10A/TNFRSF10A | 6E+05 | NM_003844 | 8p21 |
| | | | tumor necrosis factor receptor superfamily, member 10B/TNFRSF10B | 6E+05 | NM_003842 | 8p22-p21 |
| | | | tumor necrosis factor receptor superfamily, member 10C/TNFRSF10C | 6E+05 | AF014794 | 8p22-p21 |
| | | | tumor necrosis factor receptor superfamily, member 10D/TNFRSF10D | 6E+05 | NM_003840 | 8p21 |
| | | | tumor necrosis factor receptor superfamily, member 11A/TNFRSF11A | 1E+05 | NM_003839 | 18q22.1 |
| | | | tumor necrosis factor receptor superfamily, member 11B/TNFRSF11B | 6E+05 | NM_002546 | 8q24 |
| | | | tumor necrosis factor receptor superfamily, member 12/TNFRSF12 | 2E+05 | NM_003790 | 1p36.3 |
| | | | tumor necrosis factor receptor superfamily, member 14/TNFRSF14 | 6E+05 | NM_003820 | 1p363-p36.2 |
| | | | tumor necrosis factor receptor superfamily, member 16/TNFRSF16 | 2E+05 | NM_002507 | 17q21-q22 |
| | | | tumor necrosis factor receptor superfamily, member 17/TNFRSF17 | 1E+05 | Z14954 | 16p13.1 |
| | | | tumor necrosis factor receptor superfamily, member 18/TNFRSF18 | 6E+05 | ****** | 1p36.3 |
| Transforming Growth Factor | | Synthesis | transforming growth factor, alpha/TGFA | 2E+05 | NM_003236 | 2p13 |
| | | | transforming growth factor, beta-1/TGFB1 | 2E+05 | M60315 | 19q13.1-q13.3 |
| | | | transforming growth factor, beta-2/TGFB2 | 2E+05 | NM_003238 | 1q41 |
| | | | transforming growth factor, beta-3/TGFB3 | 2E+05 | NM_003239 | 14a24 |
| | | | growth differentiation factor 1/GDF1 | 6E+05 | NM_001492 | 19p12 |
| | | Receptors | transforming growth factor, beta receptor I (activin A receptor type II-like kinase 53 kD)/TGFBR1 | 2E+05 | NM_004612 | 9q33-q34 |
| | | | transforming growth factor, beta receptor II (70-80 kD)/TGFBR2 | 2E+05 | NM_003242 | 3p22 |
| | | | transforming growth factor, beta receptor III (betaglycan, 300 kD)/TGFBR3 | 6E+05 | NM_003243 | 1p33-p32 |

TABLE 1-continued

| Class | Pathway | Function | Name | OMIM | GID | Locus |
|---|---|---|---|---|---|---|
| | Chemokines | Synthesis (see also signaling and transcription factors below) | small inducible cytokine subfamily A (Cys-Cys), member 1/inflammatory cytokine 1309/SCYA1 | 2E + 05 | NM_002981 | Chr. 17 |
| | | | small inducible cytokine subfamily A (Cys-Cys), member 2/monocyte chemotactic protein 1/MCP1/SGYA2) | 2E + 05 | NM_002982 | 17q11.2-q12 |
| | | | small inducible cytokine subfamily A (Cys-Cys), member 1/macrophage inflammatory protein 1A/MIP1A/SGYA3 | 2E + 05 | NM_002983 | 17q11.2-q21 |
| | | | small inducible cytokine subfamily A (Cys-Cys), member 3-like 1/LD78-beta/SCYA3L1 | 6E + 05 | D90144 | 17q11.2 |
| | | | small inducible cytokine subfamily A (Cys-Cys), member 4/macrophage inflammatory protein 1B/MIP1B/SCYA4 | 2E + 05 | NM_002984 | 17q21-q23 |
| | | | small inducible cytokine subfamily A (Cys-Cys), member 4-like/macrophage inflammatory protein 1B/MIP1B/SCYA4L | 6E + 05 | X52149 | 17q11.2 |
| | | | small inducible cytokine subfamily A (Cys-Cys), member 5/T cell specific protein p228/TCP228/SCYA5 | 2E + 05 | NM_002985 | 17q11.2-q12 |
| | | | small inducible cytokine subfamily A (Cys-Cys), member 6/SCYA6 | ******* | ******* | ******* |
| | | | small inducible cytokine subfamily A (Cys-Cys), member 7/monocyte chemotactic protein 2/MCP2/SCYA7 | 2E + 05 | AF043338 | 17q11.2-q12 |
| | | | small inducible cytokine subfamily A (Cys-Cys), member 8/monocyte chemotactic protein 2/MCP2/SCYA8 | 6E + 05 | NM_005623 | 17q11.2 |
| | | | small inducible cytokine subfamily A (Cys-Cys), member 9/10/SCYA9SCY10 | ******* | ******* | ******* |
| | | | small inducible cytokine subfamily A (Cys-Cys), member 11/eotaxin/SCYA11 | 6E + 05 | NM_002986 | 17q21.1-q21.2 |
| | | | small inducible cytokine subfamily A (Cys-Cys), member 12/SCYA12 | ******* | ******* | ******* |
| | | | small inducible cytokine subfamily A (Cys-Cys), member 13/monocyte chemotactic protein 4/MCP4/SCYA13 | 6E + 05 | NM_005408 | 17q11.2 |
| | | | small inducible cytokine subfamily A (Cys-Cys), member 14/new cc chemokine 2/NCC2/SCYA14 | 6E + 05 | NM_004590 | 17q11.2 |
| | | | small inducible cytokine subfamily A (Cys-Cys), member 15/leukotactin 1/LKN1/SCYA15 | 6E + 05 | NM_004167 | 17q11.2 |
| | | | small inducible cytokine subfamily A (Cys-Cys), member 16/new cc chemokine 4/NCC4/SCYA16 | 6E + 05 | NM_004590 | 17q11.2 |
| | | | small inducible cytokine subfamily A (Cys-Cys), member 17/thymus and activation-regulated chemokine/TARC/SCYA17 | 6E + 05 | NM_002987 | 16q13 |
| | | | small inducible cytokine subfamily A (Cys-Cys), member 18/pulmonary and activation-regulated chemokine/PARC/SCYA18 | 6E + 05 | NM_002988 | 17q11.2 |
| | | | small inducible cytokine subfamily A (Cys-Cys), member 19/macrophage inflammatory protein 3B/MIP3B/SCYA19 | 6E + 05 | NM_006274 | 9p13 |
| | | | small inducible cytokine subfamily A (Cys-Cys), member 20/macrophage inflammatory protein 3A/MIP3A/exodus 1/SCYA20 | 6E + 05 | NM_004591 | 2q33-q37 |
| | | | small inducible cytokine subfamily A (Cys-Cys), member 21/secondary lymphoid tissue chemokine/SLC/exodus 2/SCYA21 | 6E + 05 | NM_002989 | 9p13 |
| | | | small inducible cytokine subfamily A (Cys-Cys), member 22/SCYA22 | 6E + 05 | NM_002990 | 16q13 |
| | | | small inducible cytokine subfamily A (Cys-Cys), member 23/myeloid progenitor inhibitory factor 1/MPIF1/SCYA23 | 6E + 05 | NM_005064 | ******* |
| | | | small inducible cytokine subfamily A (Cys-Cys), member 24/myeloid progenitor inhibitory factor 2/MPIF2/SCYA24 | 6E + 05 | NM_002991 | 7q11.23 |
| | | | small inducible cytokine subfamily A (Cys-Cys), member 25/thymus expressed chemokine/TECK/SCYA25 | 6E + 05 | NM_005624 | 19p13.2 |
| | | | small inducible cytokine subfamily A (Cys-Cys), member 26/eotaxin 3/SCYA26 | ******* | AA716120 | Chr. 7 |
| | | | small inducible cytokine subfamily A (Cys-Cys), member 27/ALP/SCYA27 | ******* | ******* | Chr. 9 |

TABLE 1-continued

| Class | Pathway | Function | Name | OMIM | GID | Locus |
|---|---|---|---|---|---|---|
| | | | small inducible cytokine subfamily B (Cys-X-Cys), member 1/GRO2/SCYB1 | 2E + 05 | NM_001511 | 4q12-q13 |
| | | | small inducible cytokine subfamily B (Cys-X-Cys), member 2/GRO1/SCYB2 | 1E + 05 | NM_002089 | 4q12-q13 |
| | | | small inducible cytokine subfamily B (Cys-X-Cys), member 3/GRO3/SCYB3 | 1E + 05 | AA935273 | 4q12-q13 |
| | | | small inducible cytokine subfamily B (Cys-X-Cys), member 4/SCYB4/platelet factor 4/PF4 | 2E + 05 | NM_002619 | 4q12-q13 |
| | | | small inducible cytokine subfamily B (Cys-X-Cys), member 5/epithelial-derived neutrophil-activating peptide 78/SCYB5 | 6E + 05 | NM_002994 | 4q13-q21 |
| | | | small inducible cytokine subfamily B (Cys-X-Cys), member 6/granulocyte chemotactic protein 2/GCP2/SCYB6 | 1E + 05 | U83303 | 4q12-q21 |
| | | | small inducible cytokine subfamily B (Cys-X-Cys), member 7/SCYB7 | 1E + 05 | NM_002704 | 4q12-q13 |
| | | | small inducible cytokine subfamily B (Cys-X-Cys), member 8/SCYB8/interleukin 8/IL8 | 1E + 05 | M26383 | 4q12-q13 |
| | | | small inducible cytokine subfamily B (Cys-X-Cys), member 9/SCYB9 | 6E + 05 | AA037522 | 4q21 |
| | | | small inducible cytokine subfamily B (Cys-X-Cys), member 10/SCYB10 interferon (gamma) induced protein of 10 kDa/INP10 | 1E + 05 | NM_001565 | 4q21 |
| | | | small inducible cytokine subfamily B (Cys-X-Cys), member 11/SCYB11 | ******* | ******* | Chr. 4 |
| | | | small inducible cytokine subfamily B (Cys-X-Cys), member 12/SCYB12/stromal cell drived factor/SDF1 | 6E + 05 | AA361853 | 10q11.1 |
| | | | small inducible cytokine subfamily B (Cys-X-Cys), member 13/SCYB13 | ******* | ******* | ******* |
| | | | small inducible cytokine subfamily B (Cys-X-Cys), member 14/SCYB14 | 6E + 05 | AC005738 | 5q31 |
| | | | small inducible cytokine subfamily C, member 1/lymphotactin/LTN/SCYC1 | 6E + 05 | NM_002995 | 1q21-q25 |
| | | | small inducible cytokine subfamily C, member 2/SCYC2 | ******* | NM_003175 | ******* |
| | | | small inducible cytokine subfamily D (Cys-X3-Cys), member 1/fractalkine/neurotactin/NTT/NTN/SCYD1 | 6E + 05 | NM_002996 | 16q |
| | | C-Motif Chemokine Receptors | chemokine (C-C motif) receptor 1/MIP1A receptor/CCR1 | 6E + 05 | NM_001295 | 3p21 |
| | | | chemokine (C-C motif) receptor 2/MCP1 receptor/CCR2 | 6E + 5 | NM_000647 | 3p21 |
| | | | chemokine (C-C motif) receptor 3/eotaxin receptor/CCR3 | 6E + 05 | NM_001837 | 3p21.3 |
| | | | chemokine (C-C motif) receptor 4/CCR4 | ******* | NM_005508 | ******* |
| | | | chemokine (C-C motif) receptor 5/CCR5 | 6E + 05 | NM_000579 | 3p21 |
| | | | chemokine (C-C motif) receptor 6/G protein-coupled receptor 29/GPR29/CCR6 | 6E + 05 | NM_004367 | 6q27 |
| | | | chemokine (C-C motif) receptor 7/epstein-barr virus induced gene 1/EBI1/CCR7 | 6E + 05 | NM_001838 | 17q12-q21.2 |
| | | | chemokine (C-C motif) receptor 8/CCR8 | 6E + 05 | NM_005201 | 3p22 |
| | | | chemokine (C-C motif) receptor 9/chemokine-binding protein 2/CCBP2/CCR9 | 6E + 05 | NM_006641 | 3p21.3 |
| | | | chemokine (C-C motif) receptor 10/CCR10 | ******* | U94888 | ******* |
| | | | chemokine (C-X-C motif), receptor 3/G protein-coupled receptor 9/GPR9/CXCR3 | 6E + 05 | NM_001504 | 8p12-p11.2 |
| | | | chemokine (C-X-C motif), receptor 4/fusin/CXCR4 | 2E + 05 | NM_003467 | 2q21 |
| | | | chemokine (C-X-C motif), receptor 1/fractalkine receptor/CX3CR1 | 6E + 05 | NM_001337 | 3pter-p21 |
| | | | interleukin 8 receptor, alpha/IL8RA | 1E + 05 | NM_000634 | 2q35 |
| | | | interleukin 8 receptor beta/IL8RB | 1E + 05 | NM_001557 | 2q35 |
| | | | chemokine (C motif) XC receptor 1/G protein-coupled receptor 5/GPR5/CCXCR1 | 6E + 05 | NM_005283 | 3p21.3-p21.1 |
| | | | macrophage migration inhibitory factor (glycosylation-inhibiting factor)/MIF | 2E + 05 | NM_002415 | 22q11.2 |
| | | | leukemia inhibitory factor/LIF | 2E + 05 | NM_002309 | 22q12.1-q12.2 |
| | | | oncostatin M | 2E + 05 | AF129855 | 22q12.1-q12.2 |
| | | | ciliary neurotrophic factor/CNTF | 1E + 05 | NM_000614 | 11q12.2 |
| | | | epidermal growth factor/EGF | 1E + 05 | NM_001963 | 4q25 |
| | | | pre-B cell stimulating factor homologue/SDF1A | 6E + 05 | L36034 | 10q11.1 |
| | | | cardiotrophin 1 | 6E + 05 | ******* | ******* |
| Other Growth Factors | Synthesis | | mast cell growth factor/MGF | 2E + 05 | NM_003994 | 12q22 |
| | | | granulocyte-macrophage colony stimulating factor 2/CSF2 | 1E + 05 | NM_000758 | 5q21.1 |
| | | | macrophage-specific colony-stimulating factor/CSF1 | 1E + 05 | AH005300 | 1p21-p13 |
| | | | granulocyte colony stimulating factor 3/CSF3 | 1E + 05 | NM_000759 | 17q11.2-q12 |

TABLE 1-continued

| Class | Pathway | Function | Name | OMIM | GID | Locus |
|---|---|---|---|---|---|---|
| | | Receptors | epidermal growth factor receptor/EGFR | 1E + 05 | NM_005228 | 7p12.3-p12.1 |
| | | | ciliary neurotrophic factor receptor/CNTFR | 1E + 05 | NM_001842 | 9p13 |
| | | | oncostatin M receptor/OSMR | 6E + 05 | NM_003999 | ******* |
| | | | neutrophil chemotactic response receptor/gp130 | 2E + 05 | ******* | 7q22-qter |
| | | | colony stimulating factor 1 receptor/CSFR1 | 2E + 05 | U63963 | 5q33.2-q33.3 |
| | | | granulocyte-macrophage colony stimulating factor 2 receptor, alpha, low-affinity/CSF2RA | 3E + 05 | NM_006140 | Xp22.32 |
| | | | granulocyte-macrophage colony stimulating factor 2 receptor, beta/CSF2RB | 1E + 05 | U18373 | 22q12.2-q13.1 |
| | | | granulocyte-macrophage colony stimulating factor 2 receptor, alpha, Y chromasomal/CSF2RY | 4E + 05 | ******* | Yp11 |
| | | | myelocyte antigen CD105/endoglin/ENG/TGFB receptor component/CD105 | 1E + 05 | NM_000118 | 9q24.1 |
| | | | leukocyte antigen CD 97/CD97 | 6E + 05 | NM_001784 | 19p13.2 p12.12 |
| | Cytokine Response | Signaling and Transcription Factors | signal transducer and activator of transcription 1/STAT1 | 6E + 05 | ******* | 2q32.2-q32.3 |
| | | | signal transducer and activator of transcription 2 113 kD)/STAT2 | 6E + 05 | NM_005419 | ******* |
| | | | signal transducer and activator of transcription 3/STAT3 | 1E + 05 | NM_003150 | 17q21 |
| | | | signal transducer and activator of transcription 6 interleukin-4 induced/STAT 6 | 6E + 05 | NM_003153 | 12q13 |
| | | | signal transducing adaptor molecule (SH3 domain and ITAM motif) 1/STAM | 6E + 05 | NM_003473 | 10p14-p13 |
| | | | STAM-like protein containing SH3 and ITAM domains 2/STAM2 | 6E + 05 | NM_005843 | ******* |
| | | | interferon-stimulated transcription factor 3, gamma (48 kD)/ISGF3G | 1E + 05 | NM_006084 | 14q11.2 |
| | | | interferon alpha-inducible protein 27/IFI27 | 6E + 05 | NM_005532 | 14q32 |
| | | | interferon alpha-inducible protein (clone IFI-6-16)/GIP3 | 1E + 05 | NM_002038 | 1p35 |
| | | | Janus kinase 1 (protein tyrosine kinase)/JAK1 | 1E + 05 | NM_002227 | 1p31.3 |
| | | | Janus kinase 3 (protein tyrosine kinase)/JAK3 | 6E + 05 | NM_000215 | 19p13.1 |
| | | | interleukin-1 receptor-associated kinase M/IRAK-M | ******* | NM_007199 | ******* |
| | | | interleukin-1 receptor-associated kinase 1/IRAK1 | 6E + 05 | NM_001569 | Xq28 |
| | | | interleukin-1 receptor-associated kinase 1/IRAK2 | 6E + 05 | NM_001570 | ******* |
| | | | nuclear factor, interleukin 3 regulated/NFIL3 | 6E + 05 | NM_005384 | ******* |
| | | | nuclear factor of activated T-cells cytoplasmic 1/NFATC1 | 6E + 05 | NM_006162 | 18q23 |
| | | | nuclear factor of activated T-cells cytoplasmic 2/NFATC2 | 6E + 05 | NM_005655 | 20q13.2-q13.3 |
| | | | nuclear factor of activated T-cells cytoplasmic 3/NFATC3 | ******* | L41066 | 16q13-q24 |
| | | | nuclear factor of activated T-cells cytoplasmic 4/NFATC4 | 6E + 05 | L41067 | ******* |
| | | | caspase 1, apoptosis-related cysteine protease (interleukin 1, beta, convertase)/CASP1 | 1E + 05 | NM_001223 | 11q22.2-q22.3 |
| | | | TGFB inducible early growth response/TIEG | 6E + 05 | NM_005655 | ******* |
| | | | TGFB inducible early growth response 2/TIEG2 | 6E + 05 | NM_003597 | ******* |
| | | | eukaryotic translation initiation factor 3, subunit 8 (110 kD)/EIF3S8 | 6E + 05 | NM_003752 | 1p34.1 |
| | | | MAD (mothers against decapentaplegic) homolog 1/MADH1 | 6E + 05 | NM_005900 | 4q28 |
| | | | homolog of Xenopus forkhead activin signal transducer-1/FAST1 | 6E + 05 | NM_003923 | 8q24.3 |
| | | | interleukin 1 receptor accessory protein/IL1RAP | 6E + 05 | NM_002182 | 3q28 |
| | | | CCAAT/enhancer binding protein (C/EBP), delta/CEBPD | 2E + 05 | NM_005195 | 20q13.1 |
| | | | T-lymphocytes-specific interleukin 2 inhibitor/transcription factor 8/TCF8 | 2E + 05 | U12170 | 10p11.2 |
| | | | cAMP responsive element binding protein 1/CREB1 | 1E + 05 | NM_004379 | 2q32.3-q34 |
| | | | interferon-stimulated transcription factor 3, gamma (48 kD)/ISGF3G | 1E + 05 | NM_006084 | 14q11.2 |
| | | | interferon regulatory factor 3/IRF3 | 6E + 05 | NM_001571 | 19q13.3-q13.4 |
| | | | lymphocyte specific interferon regulatory factor/ LSIRF/interferon regulatory factor 4/IRF4 | 6E + 05 | U52683 | 6p25-p23 |
| | | | TNF receptor associated factor 1/TRAF1 | 6E + 05 | NM_005658 | 9q33-q34 |
| | | | TNF receptor associated factor 2/TRAF2 | 6E + 05 | U12597 | 9q34 |
| | | | TNF receptor associated factor 3/TRAF3 | 6E + 05 | NM_003300 | ******* |
| | | | TNF receptor associated factor 4/TRAF4 | 6E + 05 | NM_004295 | 17q11-q12 |
| | | | TNF receptor associated factor 5/TRAF5 | 6E + 05 | AB000509 | 1q32 |
| | | | TNF receptor associated factor 6/TRAF6 | 6E + 05 | NM_004620 | ******* |

TABLE 1-continued

| Class | Pathway | Function | Name | OMIM | GID | Locus |
|---|---|---|---|---|---|---|
| | | | TRAF family member-associated NFKB activator/TANK | 6E + 05 | NM_004180 | 2q24-q31 |
| | | | mitogen activated protein kinase PRKM1/MAPK1 | 2E + 05 | NM_002745 | 22q11.2 |
| | | | mitogen activated protein kinase PRKM3/MAPK3 | 6E + 05 | X60188 | 16p11.2 |
| | | | mitogen activated protein kinase PRKM4/MAPK4 | 2E + 05 | NM_002747 | 18q12-q21 |
| | | | mitogen activated protein kinase PRKM6/MAPK6 | 6E + 05 | NM_002748 | 17p11.2 |
| | | | mitogen activated protein kinase PRKM7/MAPK7 | 6E + 05 | NM_002749 | ****** |
| | | | mitogen activated protein kinase JNK1/PRKM8/MAPK8 | 6E + 05 | L26318 | 17p11.2 |
| | | | mitogen activated protein kinase JNK2/PRKM9/MAPK9 | 6E + 05 | U09759 | 5q35 |
| | | | mitogen activated protein kinase JNK3/PRKM10/MAPK10 | 6E + 05 | U35003 | ****** |
| | | | mitogen activated protein kinase PRKM11/MAPK11 | 6E + 05 | AF031135 | 22q13.3 |
| | | | mitogen activated protein kinase SAPK3/MAPK12 | 6E + 05 | NM_002969 | ****** |
| | | | mitogen activated protein kinase PRKM13/MAP13 | 6E + 05 | NM_002754 | 6p21.2-q21.2 |
| | | | mitogen activated protein kinase SAPK2A/MAPK14 | 6E + 05 | NM_001315 | 15q22.1 |
| | | | mitogen activated protein kinase kinase 1/MAP2K1 | 2E + 05 | NM_002755 | q22.33 |
| | | | mitogen activated protein kinase kinase 2/MAP2K2 | 6E + 05 | L11285 | ****** |
| | | | mitogen activated protein kinase kinase 3/MAP2K3 | 6E + 05 | NM_002756 | 17q11.2 |
| | | | mitogen activated protein kinase kinase 4/MAP2K4 | 6E + 05 | NM_003010 | 17p11.2 |
| | | | mitogen activated protein kinase kinase 5/MAP2K5 | 6E + 05 | NM_002757 | ****** |
| | | | mitogen activated protein kinase kinase 6/MAP2K6 | 6E + 05 | U39065 | ****** |
| | | | mitogen activated protein kinase kinase 7/MAP2K7 | 6E + 05 | NM_005043 | 17q22-q23.2 |
| | | | protein kinase C alpha/PRKCA | 2E + 05 | NM_002737 | 16p11.2 |
| | | | protein kinase C beta/PRKCB | 2E + 05 | X06318 | 3p |
| | | | protein kinase C, delta/PRKCD | 2E + 05 | NM_006254 | 19q13.4 |
| | | | protein kinase C gamma/PRKCG | 2E + 05 | ****** | 10p15 |
| | | | protein kinase C, theta/PRKCQ | 6E + 05 | NM_006257 | ****** |
| | | | protein kinase C, zeta/PRKCZ | 2E + 05 | NM_002744 | 13q13 |
| | | | casein kinase 1 alpha 1 | 6E + 05 | NM_001892 | 19p13.3 |
| | | | casein kinase 1 gamma 2 | 6E + 05 | U89896 | 17q25 |
| | | | casein kinase 1 delta | 6E + 05 | NM_001893 | 22q12-q13 |
| | | | casein kinase 1 epsilon | 6E + 05 | NM_001894 | 20p13 |
| | | | casein kinase 2 alpha 1 | 1E + 05 | J02853 | 16p13.3-p13.2 |
| | | | casein kinase 2 alpha 2 | 1E + 05 | NM_001896 | 6p21.3 |
| | | | casein kinase 2 beta | 2E + 05 | X57152 | 5q13 |
| | | | phosphatidylinositol 3-kinase, regulatory subunit, polypeptide 1 (p85, alpha)/PIK3R1 | 2E + 05 | M61906 | 19q13.2-q13.4 |
| | | | phosphatidylinositol 3-kinase, regulatory subunit, polypeptide 2 (p85, beta)/PIK3R2 | 6E + 05 | NM_005027 | ****** |
| | | | phosphatidylinositol 3-kinase, regulatory subunit, polypeptide 3 (p55, gamma)/PIK3R3 | ****** | NM_003629 | 3q26.3 |
| | | | phosphatidylinositol 3-kinase, catalytic, alpha polypeptide/PIK3CA | 2E + 05 | NM_006218 | 1p36.2 |
| | | | phosphatidylinositol 3-kinase, catalytic, beta polypeptide/PIK3CB | 6E + 05 | NM_006219 | ****** |
| | | | phosphatidylinositol 3-kinase, catalytic, delta polypeptide/PIK3CD | 6E + 05 | NM_005026 | 7p13 |
| | | | phosphatidylinositol 3-kinase, catalytic, gamma polypeptide/PIK3CG | 6E + 05 | NM_002649 | chr. 15 |
| Non-Cytokine Mediated Immune Regulation | Cyclophilins | Biosynthesis | peptidyl-prolyl isomerase A/cyclophilin A/PPIA | 1E + 05 | Y00052 | 4q31.3 |
| | | | peptidyl-prolyl isomerase B/cyclophilin B/PPIB | 1E + 05 | M60857 | ****** |
| | | | peptidyl-prolyl isomerase C/cyclophilin C/PPIC | 1E + 05 | S71018 | 6p21.1 |
| | | | peptidyl-prolyl isomerase D/cyclophilin D/PPID | 6E + 05 | NM_005038 | |
| | | | peptidyl-prolyl isomerase E/cyclophilin E/PPIE | ****** | M_006112 | |
| | | | peptidyl-prolyl isomerase like/PPIL1 | 6E + 05 | AF090992 | |

TABLE 1-continued

| Class | Pathway | Function | Name | OMIM | GID | Locus |
|---|---|---|---|---|---|---|
| | | Receptors | FK506 binding protein 1A/immunophilin/FKBP1A | 2E + 05 | NM_000801 | 20p13 |
| | | | FK506 binding protein 2/immunophilin/FKBP2 | 2E + 05 | NM_004470 | 11q13.1-q13.3 |
| | | | FK506 binding protein 4/immunophilin/FKBP4 | 6E + 05 | NM_002014 | ******* |
| | | | FK506 binding protein 5/immunophilin/FKBP5 | 6E + 05 | NM_004117 | ******* |
| | | | calcium modulating cyclophilin ligand/CAMLG | 6E + 05 | NM_001745 | 5q23 |
| | | Response | protein phosphatase 3 catalytic subunit, alpha isoform/calcineurin A/PPP3CA | 1E + 05 | M29550 | 4q21-q24 |
| | | | protein phosphatase 3 catalytic subunit, beta isoform/calcineurin B/PPP3CB | 1E + 05 | M30773 | 10q21-q22 |
| | | | protein phosphatase 3 catalytic subunit, gamma isoform/calcineurin A/PPP3CG | 1E + 05 | NM_005605 | Chr. 8 |
| | | | protein phosphatase 3 regulatory subunit B, alpha isoform/calcineurin A/PPP3R1 | 6E + 05 | ******* | 2p16-p15 |
| | | | calmodulin 1/CALM1 | 1E + 05 | AH005370 | 14q24-q31 |
| | | | calmodulin 2/CALM2 | 1E + 05 | NM_001743 | 2p21.3-p21.1 |
| | | | calmodulin 3/CALM3 | 1E + 05 | NM_005184 | 19q13.2-q13.3 |
| | Corticosteriods | Biosynthesis | cytochrome P450, subfamily XXI (steroid 21-hydroxylase)/CYP21 | 2E + 05 | M13936 | 6p21.3 |
| | | | cytochrome P450, subfamily XIB (steroid 18-beta-hydroxylase), polypeptide 2/CYP11B2 | 1E + 05 | NM_000498 | 8q21 |
| | | | cytochrome P450, subfamily XIB (steroid 11-beta-hydroxylase), polypeptide 1/CYP11B1 | 2E + 05 | NM_000497 | 8q21 |
| | | Receptors and Signaling | nuclear receptor subfamily 3, group C-member 1/NR3C1 | 1E + 05 | NM_000176 | 5q31 |
| | | | melanocortin 2 receptor/ACTH receptor/MC2R | 2E + 05 | NM_000529 | 18p11.2 |
| | | | mineralcorticoid receptor/MCR/nuclear receptor subfamily 3, group C, member 2/NR3C2 | 6E + 05 | NM_000901 | 4q31.1 |
| | | | heat shock 70 kD protein 1/HSPA1A | 1E + 05 | NM_005345 | 6p21.3 |
| | | | heat shock 70 kD protein-like 1/HSPA1L | 1E + 05 | NM_005527 | 6p21.3 |
| | | | heat shock 70 kD protein 1/HSPA1B | 6E + 05 | NM_005346 | 6p21.3 |
| | | | heat shock 90-kD protein 1, alpha subunit/HSPCA | 1E + 05 | ******* | 1q21.2-q22 |
| | | | heat shock 90-kD protein 1, beta subunit/HSPCB | 1E + 05 | J04988 | 6p12 |
| | | | FK 506-binding protein 4 (59 kD)/FKBP4 | 6E + 05 | NM_002014 | ******* |
| | | Metabolism | corticosteroid binding globulin precursor/CBG | 1E + 05 | NM_001756 | 14q32.1 |
| | | | hydroxy-D-5-steroid dehydrogenase, 3 b- and steroid D-isomerase 2/HSD3B2 | 2E + 05 | NM_000198 | 1p13.1 |
| | | | UDP glycosyltransferase 1/UGT1 | 2E + 05 | NM_001072 | Chr. 12 |
| | | | UDP glycosyltransferase family 2, member B4/UGT2B4 | 6E + 05 | NM_001073 | 4q13 |
| | | | UDP glycosyltransferase family 2, member B7/UGT2B7 | 6E + 05 | NM_001074 | 1q14 |
| | | | UDP glycosyltransferase family 2 family, polypeptide B11/UGT2B11 | 6E + 05 | NM_001073 | ******* |
| | | | UDP glycosyltransferase family 2, member B15/UGT2B15 | 6E + 05 | NM_001076 | 4q13 |
| | | | UDP glycosyltransferase family 2, member B17/UGT2B17 | 6E + 05 | NM_001077 | 1q14 |
| | | | Dehydroepiandrosterone (DHEA)-preferring sulfotransferase, family 2A, member 1/SULT2A1 | 1E + 05 | NM_003167 | 19q13.3 |
| | | | estrogen-preferring sulfotransferase/STE | 6E + 05 | NM_005420 | 4q13.1 |
| | Vitamin D | Receptors | vitamin D (125 dihydroxy vitamin D3) receptor/VDR | 6E + 05 | NM_000376 | 12q12-q14 |
| | Retinoic Acid | Receptors | Retinoic acid receptor, alpha/RARA | 2E + 05 | NM_000964 | 17q12 |
| | | | Retinoic acid receptor, beta/RARB | 2E + 05 | NM_000965 | 3p24 |
| | | | Retinoic acid receptor, gamma/RARG | 2E + 05 | M57707 | 12q13 |
| Cell-Mediated Inflammation | T-Cell Activation, Differentiation, and Proliferation (excluding genes from cytokine section above) | Receptors | T-cell antigen CD4/LEU3/CD4 | 2E + 05 | X87579 | 12pter-p12 |
| | | | T-cell antigen CD6/T-cell differentiation antigen/CD6 | 2E + 05 | NM_006725 | Chr. 11 |
| | | | lymphocyte antigen CD5/LEU1/CD5 | 2E + 05 | X04391 | 11q13 |
| | | | thymocyte antigen CD7/Tp41/CD7 | 2E + 05 | NM_006137 | 17q25.2-q25.3 |
| | | | lymphocyte antigen CD19/B-lymphocyte antigen/CD19 | 1E + 05 | X13312 | 16p11.2 |
| | | | B-lymphocyte antigen CD80 (CD28 antigen ligand 1, B7-1 antigen)/CD80 | 1E + 05 | NM_005191 | 3q21 |
| | | | CD86 antigen (CD28 antigen ligand 2, B7-2 antigen)/CD86 | 6E + 05 | NM_006889 | 3q21 |
| | | | T-cell antigen CD28 (Tp44)/CD28 | 2E + 05 | NM_006139 | 2q33-q34 |
| | | | T-cell antigen receptor, beta subunit/TCRB | 6E + 05 | NM_005420 | 7q35 |
| | | | CD3G antigen, gamma polypeptide (TIT3 complex)/CD3G | 2E + 05 | AF011643 | 11q23 |
| | | | CD3D antigen, delta polypeptide (TIT3 complex)/CD3D | 2E + 05 | NM_000732 | 11q23 |

TABLE 1-continued

| Class | Pathway | Function | Name | OMIM | GID | Locus |
|---|---|---|---|---|---|---|
| | | | CD3E antigen, epsilon polypeptide (TiT3 complex)/CD3E | 2E+05 | NM_000733 | 11q23 |
| | | | CD3Z antigen, zeta polypeptide (TiT3 complex)/CD3Z | 2E+05 | NM_000734 | 1q22-q23 |
| | | | leukocyte common antigen T200/CD45 | 2E+05 | M23492 | 1q31-q32 |
| | | | T-cell antigen CD69/p60/CD69 | 1E+05 | NM_001781 | 12p13-p12 |
| | | | lymphoblast antigen CD38/ADP-ribose cyclase/cyclic ADP-ribose hydrolase/CD38 | 1E+05 | NM_001775 | 4p15 |
| | | | lymphocyte antigen CD39/vascular ATP diphosphohydrolase/CD39 | 6E+05 | NM_001776 | 10q24 |
| | | | lymphocyte antigen CD73/5′ nucleotidase/NT5/CD73 | 1E+05 | NM_002526 | 6q14-q21 |
| | | | leukocyte antigen CD23/low-affinity receptor II for Fc portion of IgE/FCER2/CD23 | 2E+05 | NM_002002 | 19p13.3 |
| | | | macrophage antigen CD 64/high-affinity receptor IA for Fc fragment of IgG/FCGR1A | 1E+05 | Y10206 | 1q21.2-q21.3 |
| | | | lymphocye antigen CD57/LEU7/CD57 | 2E+05 | ****** | Chr. 11 |
| | | | lymphocyte function-associated antigen, type 3/LAF3/LEU7/CD58 | 2E+05 | NM_001779 | 1p13 |
| | | | lymphocyte antigen CD45/protein tyrosine phosphatase, receptor type, c polypeptide/PTPRC/CD45 | 2E+05 | NM_002838 | 1q31-q32 |
| | | | T-cell antigen receptor, gamma subunit/TCRG | 2E+05 | M17325 | 7p15-p14 |
| | | | T-cell antigen receptor, delta subunit/TCRD | 2E+5 | L36384 | 14q11.2 |
| | | | T-cell antigen CD8, alpha polypeptide (p32)/CD8A | 2E+05 | NM_001768 | 2p12 |
| | | | T-cell antigen CD8, beta polypeptide/CD8B | 2E+05 | AH003859 | 2p12 |
| | | | T-cell antigen CD28 (Tp44)/CD28 | 2E+05 | NM_006139 | 2q33-q34 |
| | | | cytotoxic T-lymphocyte-associated 4/CTLA4 | 1E+05 | L15006 | 2q33 |
| | | | T-cell antigen receptor, alpha subunit/TCRA | 2E+05 | Z24457 | 14q11.2 |
| | | | CD89 antigen/receptor for Fc fragment of IgA/FCAR/CD89 | 1E+05 | NM_002000 | 19q13.4 |
| | | | T-cell activation antigen p250/TP250 | 2E+05 | ****** | 11pter-p11.2 |
| | | Signaling | signaling lymphocytic activation molecule/SLAM | 6E+05 | NM_003037 | ******* |
| | | | T cell receptor associated protein tyrosine kinase ZAP 70/ZAP70 | 6E+05 | S69911 | 2q12 |
| | | | v-mos Moloney murine sarcoma viral oncogene homolog/MOS | 2E+05 | NM_005372 | 8q11 |
| | | | IL2-inducible T-cell kinase/ITK/T-cell tyrosine kinase EMT/EMT | 2E+05 | NM_005546 | 5q32 |
| | | | mature T-cell proliferation 1/MTCP1 | 3E+05 | Z24459 | Xq28 |
| | | | lymphocyte-specific protein tyrosine kinase/LCK | 2E+05 | NM_005356 | 1p35-p34.3 |
| | B-Cell Activation Differentiation, and Proliferation (excluding genes from cytokine section above) | Receptors | B-cell antigen CD20/B-lymphocyte differentiation antigen B1/CD20 | 1E+05 | AH003353 | 11q13 |
| | | | B-cell antigen CD72/CD72 | 1E+05 | NM_001782 | 9p |
| | | | natural resistance associated macrophage protein 1/NRAMP1/solute carrier family 11, member 1/SLC11A1 | 6E+05 | AH002806 | 2q35 |
| | | | natural resistance associated macrophage protein 2/NRAMP2/solute carrier family 11, member 1/SLC11A2 | 6E+05 | AB015355 | 12q13 |
| | | | 1-lymphocyte antigen CDW52 (CAMPATH-1 antigen)/CDW52 | 1E+05 | NM_001803 | ******* |
| | | | B-cell antigen CD22/CD22 | 1E+05 | NM_001771 | 19q13.1 |
| | | | B-cell antigen CD24/CD62 ligand/CD24 | 6E+05 | X69397 | 6q21 |
| | | | B-cell antigen CD40/tumor necrosis factor receptor superfamily, member 5/CD40/TNFRSF5 | 1E+05 | NM_001250 | 20q12-q13.2 |
| | | | leukocyte antigen CD156/disintegrin and metalloprotease domain 8/ADAM8/CD156 | 6E+05 | NM_001109 | 10q26.3 |
| | | | platelet antigen CD151/platelet-endothelial cell tetraspan antigen 3/PETA3/CD151 | 1E+05 | NM_004357 | 11p15.5 |
| | | | antigen CD32/low-affinity receptor IIA for Fc fragment of IgG/FCGR2A/CD32 | 1E+05 | NM_004001 | 1q21-q23 |
| | | | activated leucocyte cell adhesion molecule/CD6 ligand/ALGAM | 6E+05 | NM_001627 | 3q13.1-q13.2 |
| | Myeloid Progenitor Cell Differentiation and Proliferation (excluding genes from cytokine section above) | Signaling | regulator of G-protein signaling 1/RGS1 | 6E+05 | NM_002922 | 1q31 |
| | | Growth Factors | macrophage specific colony stimulating factor/GSF1 | 1E+05 | AH005300 | 1p21-p13 |
| | | | granulocyte macrophage colony stimulating factor 2/CSF2 | 1E+05 | NM_000758 | 5q31.1 |
| | | | granulocyte colony stimulating factor 3/CSF3 | 1E+05 | NM_000759 | 17q11.2-q12 |
| | | Receptors | colony stimulating factor 1 receptor/CSFR1 | 2E+05 | U63963 | 5q33.2-q33.3 |
| | | | granulocyte macrophage colony stimulating factor 2 receptor, alpha, Y chromosomal/GSF2RY | 4E+05 | ****** | Yp11 |
| | | | granulocyte macrophage colony stimulating factor 2 receptor, alpha, low-affinity/GSF2RA | 3E+05 | NM_006140 | Xp22.32 |
| | | | granulocyte macrophage colony stimulating factor 2 receptor, beta/CSI2RB | 1E+05 | U18373 | 22q12.2-q13.1 |

TABLE 1-continued

| Class | Pathway | Function | Name | OMIM | GID | Locus |
|---|---|---|---|---|---|---|
| | | Signaling | CCAAT/enhancer binding protein (C/EBP), beta/CEBPB | 2E + 05 | NM_005194 | 20q13.1 |
| | | | CCAAT/enhancer binding protein (C/EBP), epsilon/CEBPE | 6E + 05 | NM_001805 | 14q11.2 |
| | | | flt3 ligand/FMS-related tyrosine kinase 3 ligand/FLT3LG | 6E + 05 | U03858 | 19q13.3 |
| | | | FMS-related tyrosine kinase 3/FLT3 | 1E + 05 | NM_004119 | 13q12 |
| | | | myeloid differentiation primary response gene (88)/MYD88 | 6E + 05 | NM_002468 | 3p22-p21.3 |
| | Apoptosis | Apoptosis | BCL2 | 2E + 05 | M13994 | 18q21.3 |
| | (additional genes in | | BCL-X/BCLX | 6E + 05 | Z23115 | ****** |
| | Oncology) | | BCL2 associated protein/BAX | 6E + 05 | L22473 | 19q13.3-q13.4 |
| | | | BCL2-antagonist/killer 1/BAK1 | 6E + 05 | NM_001188 | 6p21.3-p21.2 |
| | | | BCL2-associated anthanogene 1/BAG1 | 6E + 05 | NM_004323 | 9p12 |
| | | | BCL2-associated anthanogene 2/BAG2 | 6E + 05 | NM_004282 | ****** |
| | | | BCL2-associated anthanogene 3/BAG3 | 6E + 05 | AF095193 | ****** |
| | | | BCL2-associated anthanogene 4/BAG4 | 6E + 05 | AF095194 | ****** |
| | | | BCL2-associated anthanogene 5/BAG5 | 6E + 05 | AF095195 | ****** |
| | | | BCL-X/BCL-2 binding protein/BAD | 6E + 05 | AF021792 | ****** |
| | | | BCL2-like 1/BCL2L1 | 6E + 05 | NM_001191 | ****** |
| | | | BCL2-like 2/BCL2L2 | 6E + 05 | NM_004050 | 14q11.2-q12 |
| | | | BCL2-like 11 (apoptosis facilitator)/BCL2L11 | 6E + 05 | NM_006538 | ****** |
| | | | BCL2-related protein A1/BCL2A1 | 6E + 05 | Y09397 | 15q24.3 |
| | | | BCL2-interacting protein harikari/HRK | 6E + 05 | NM_003806 | ****** |
| | | | Bcl-2 interacting killer/BIK | 6E + 05 | U34584 | ****** |
| | | | tumor protein p53/TP53 | 2E + 05 | X02469 | 17p13.1 |
| | | | tumor necrosis factor receptor superfamily, member 6/FAS/TNFRSF6 | 1E + 05 | NM_000043 | 10q24.1 |
| | | | nuclear factor kappa-B DNA binding subunit 1/NFKB1 | 2E + 05 | M58603 | 4q23-q24 |
| | | | nuclear factor kappa-B DNA binding subunit 2/NFKB2 | 2E + 05 | NM_002502 | 10q24 |
| | | | apoptosis-related cystein protease 1/caspase 1/CASP1 | 1E + 05 | L27475 | 11q22.2-q22.3 |
| | | | apoptosis-related cystein protease 1/caspase 1/CASP2 | 6E + 05 | ****** | 7q35 |
| | | | apoptosis-related cystein protease 1/caspase 1/CASP3 | 6E + 05 | NM_004346 | 4q35, 4q33-q35.1 |
| | | | apoptosis-related cystein protease 1/caspase 1/CASP4 | 6E + 05 | NM_004347 | 11q22.2-q22.3 |
| | | | apoptosis-related cystein protease 1/caspase 1/CASP5 | 6E + 05 | NM_004347 | 11q22.2-q22.3 |
| | | | apoptosis-related cystein protease 1/caspase 1/CASP6 | 6E + 05 | NM_001226 | 4q25-q25 |
| | | | apoptosis-related cystein protease 1/caspase 1/CASP7 | 6E + 05 | NM_001227 | 10q25.1-q25.2 |
| | | | apoptosis-related cystein protease 1/caspase 1/CASP8 | 1E + 05 | NM_001228 | 2q33-q34 |
| | | | apoptosis-related cystein protease 1/caspase 1/CASP9 | 6E + 05 | ****** | ****** |
| | | | apoptosis-related cystein protease 1/caspase 1/CASP10 | 6E + 05 | NM_001230 | 2q33-q34 |
| | | | apoptosis-related cystein protease 1/caspase 1/CASP13 | 6E + 05 | NM_003723 | ****** |
| | | | ADP ribosyltransferase (NAD+ poly (ADP ribose) polymerase)/PARP/DPRT | 2E + 05 | NM_001618 | 1q42 |
| | | | poly (ADP ribose) glycohydrolase/PARG | 6E + 05 | NM_003631 | 10q11.23 |
| | Adhesion and | Integrins | lymphocyte antigen CD11A/integrin, alpha-L/CD11A/ITGAL | 2E + 05 | NM_002209 | 16p11.2 |
| | Migration | | lymphocyte antigen CD11B/integrin, alpha-M/CD11B/ITGAM | 1E + 05 | NM_000632 | 16p11.2 |
| | | | lymphocyte antigen CD11C/integrin, alpha-X/CD11C/ITGAX | 2E + 05 | NM_000887 | 16p11.2 |
| | | | lymphocyte antigen CD11D/integrin, alpha-D/CD11D/ITGAD | 6E + 05 | NM_005353 | 16p11.2 |
| | | | antigen CD51/integrin, alpha-V/vitronectin receptor/CD51/ITGAV | 2E + 05 | NM_002210 | 2q31-q32 |
| | | | integrin, alpha 1/ITGA1 | 2E + 05 | ****** | Chr. 5 |
| | | | integrin, alpha 2/ITGA2 | 2E + 05 | NM_002203 | 5q23-q31 |
| | | | integrin, alpha 3/ITGA3 | ****** | NM_005501 | ****** |
| | | | integrin, alpha 4/ITGA4 | 2E + 05 | NM_000885 | 2q31-q32 |
| | | | integrin, alpha 5/fibronectin receptor, alpha subunit/FNRA/ITGA5 | 1E + 05 | NM_002205 | 12q1-q13 |

TABLE 1-continued

| Class | Pathway | Function | Name | OMIM | GID | Locus |
|---|---|---|---|---|---|---|
| | | | integrin, alpha 6/ITGA6 | 1E+05 | NM_000210 | Chr. 2 |
| | | | integrin, alpha 7/ITGA7 | 6E+05 | NM_002206 | 12q13 |
| | | | integrin, alpha 8/ITGA8 | 6E+05 | L36531 | ******* |
| | | | integrin, alpha 9/ITGA9 | 6E+05 | L24158 | 3p21.3 |
| | | | integrin, alpha 10/ITGA10 | 6E+05 | NM_003637 | ****** |
| | | | antigen, CD29/integrin, beta-1/CD29/ITGB1 | 1E+05 | NM_002211 | 10p11.2 |
| | | | leukocyte antigen CD18/integrin, beta chain, beta 2/CD18/ITGB2 | 6E+05 | NM_000211 | 21q22.3 |
| | | | platelet antigen CD61/integrin beta 3/CD61/ITGB3 | 2E+05 | NM_000212 | 17q21.32 |
| | | | integrin, beta 5/ITGB5 | 1E+05 | NM_002213 | ****** |
| | | | integrin, beta 6/ITGB6 | 1E+05 | NM_000888 | Chr. 2 |
| | | | integrin, beta 7/ITGB7 | 1E+05 | NM_000889 | 12q13.13 |
| | | | integrin, beta-like 1 (with EGF-like repeat domains)/ITGBL1 | 6E+05 | NM_004791 | 13q33 |
| | | | erythrocyte antigen CD47/Rh-related antigen, integrin-associated signal transducer/CD47 | 6E+05 | NM_001777 | 3q13.1-q13.2 |
| | | | integrin-linked kinase/ILK | 6E+05 | NM_004517 | 11p15.5-p15.4 |
| | | Selectins | selectin E/endothelial adhesion molecule 1/ELAM1/SELE | 1E+05 | NM_000450 | 1q23-q25 |
| | | | granulocyte antigen CD62/platelet alpha-granule membrane protein/selectin P/CD62/SELP | 2E+05 | NM_003005 | 1q23-q25 |
| | | | selectin L/lymphocyte adhesion molecule 1/LAM1/SELL | 2E+05 | NM_000655 | 1q23-q25 |
| | | Other adhesion molecules | T-cell antigen CD8, alpha polypeptide (p32)/LEU2/CD8A | 2E+05 | NM_001768 | 2p12 |
| | | | T-cell antigen CD8, beta polypeptide/CD8B | 2E+05 | AH003859 | 2p12 |
| | | | leukocyte antigen CD9/MIC3/CD9 | 1E+05 | NM_001769 | 12p13 |
| | | | activated leukocyte cell adhesion molecule/CD6 ligand/ALCAM | 6E+05 | NM_001627 | 3q13.1-q13.2 |
| | | | mucosal addressin cell adhesion molecule-1/MACAM1 | 1E+05 | NM_007164 | 19p13.3 |
| | | | platelet antigen CD151/platelet-endothelial cell tetraspan antigen 3/PETA3/CD151 | 6E+05 | NM_004357 | 11p15.5 |
| | | | leukocyte antigen CD36/thrombospondin receptor/platelet collagen receptor/CD36 | 2E+05 | NM_000072 | 7q11.2 |
| | | | leukocyte antigen CD37/CD37 | 2E+05 | NM_001774 | 19p13-q13.4 |
| | | | platelet antigen CD31/platelet-endothelial cell adhesion molecule 1/PECAM1/CD31 | 2E+05 | NM_000442 | 17q23 |
| | | | T-cell antigen CD26/dipeptidylpeptidase IV/DPP4/CD26 | 1E+05 | NM_001935 | 2q23 |
| | | | lymphocyte antigen CD44/hermes antigen/CD44 | 1E+05 | AF098641 | 11pter-p13 |
| | | | B-cell antigen CD48/B-cell activation marker/BCM1/BLAST1 | 2E+05 | NM_001778 | 1q21.3-q22 |
| | | | leukocyte antigen CD53/tetraspan antigen/CD53 | 2E+05 | AJ243474 | 1p21-p13.3 |
| | | | B-cell antigen CD54/intercellular adhesion molecule 1/ICAM1/CD54 | 1E+05 | NM_000201 | 19p13.3-p13.2 |
| | | | intercellular adhesion molecule 2/ICAM2 | 1E+05 | NM_000873 | 17q23-q25 |
| | | | intercellular adhesion molecule 3/ICAM3 | 2E+05 | NM_002162 | 19p13.3-p13.2 |
| | | | myeloid antigen CD33/p67/CD33 | 2E+05 | NM_001772 | 19q13.3-q13.4 |
| | | | granulocyte antigen CD66/biliary glycoprotein/CD66 | 1E+05 | NM_001712 | 19q13.2 |
| | | | leukocyte antigen CD81/target of antiproliferative antibody 1/TAPA1/CD81 | 2E+05 | NM_004356 | 11p |
| | | | leukocyte antigen CD82/R2/suppression of tumorigenicity 6/kangai 1/KAI1/CD82 | 6E+05 | NM_002231 | 11p11.2 |
| | | | killer cell lectin-like receptor subfamily B, member 1/KLRB1 | 6E+05 | NM_002258 | 12p13-p12 |
| | | | killer cell lectin-like receptor subfamily C, member 1/KLRC1 | 2E+05 | NM_002259 | 12p13.2-p12.3 |
| | | | killer cell lectin-like receptor subfamily C, member 2/KLRC2 | 6E+05 | NM_002260 | 12p13.2-p12.3 |
| | | | killer cell lectin-like receptor subfamily C, member 3/KLRC3 | 6E+05 | NM_002261 | 12p13.2-p12.3 |
| | | | killer cell lectin-like receptor subfamily C, member 4/KLRC4 | 6E+05 | NM_003497 | 12p13.2-p12.3 |
| | | | killer cell antigen CD94/killer cell lectin-like receptor subfamily D, member 1/KLRD1/CD94 | 6E+05 | NM_002262 | 12p13.2-p12.3 |
| | | | T-cell antigen CD99/MIC2/CD99 | 3E+05 | NM_006378 | 9q22-q31 |
| | | | leukocyte antigen CD100/semaphorin 4D/SEMA4D/CD100 | 6E+05 | NM_006378 | 9q22-q31 |
| | | | hematopoietic progenitor cell antigen CD34/CD34 | 1E+05 | AH000040 | 1q32 |
| | | | macrophage antigen CD68/macrosialin/CD68 | 2E+05 | NM_001251 | 17p13 |
| | | | cadherin 2, N-cadherin (neuronal)/CDH2 | 1E+05 | NM_001792 | 18q11.2 |
| | | | receptor for advanced glycation end products/RAGE | 6E+05 | AJ133822 | 6p21.3 |

TABLE 1-continued

| Class | Pathway | Function | Name | OMIM | GID | Locus |
|---|---|---|---|---|---|---|
| | | | leukocyte antigen CD43/sialophorin/SPN/CD43 | 2E + 05 | NM_003123 | 16p11.2 |
| | | | vascular cell adhesion molecule 1/VCAM1 | 2E + 05 | NM_001078 | 1p32-p31 |
| | | Glycosyltransferases | UDP-Gal:betaGlcNAc beta 1,4-galactosyltransferase, polypeptide 1/B4GALT1 | 1E + 05 | NM_001497 | 9p13 |
| | Glycosyltransferases | | UDP-Gal:betaGlcNAc beta 1,4-galactosyltransferase, polypeptide 2/B4GALT2 | 6E + 05 | NM_003780 | 1p33-p32 |
| | | | UDP-Gal:betaGlcNAc beta 1,4-galactosyltransferase, polypeptide 3/B4GALT3 | 6E + 05 | NM_003779 | 1q23 |
| | | | UDP-Gal:betaGlcNAc beta 1,4-galactosyltransferase, polypeptide 4/B4GALT4 | 6E + 05 | AF038662 | 3q13.3 |
| | | | UDP-Gal:betaGlcNAc beta 1,4-galactosyltransferase, polypeptide 5/B4GALT5 | 6E + 05 | NM_004776 | Chr. 11 |
| | | | UDP-Gal:betaGlcNAc beta 1,4-galactosyltransferase, polypeptide 6/B4GALT6 | 6E + 05 | AF038664 | 18q11 |
| | | | myeloid antigen CD15/fucosyltransferase 4/FUT4/CD15 | 1E + 05 | NM_002033 | 11q21 |
| | | | monocyte antigen CD87/plasminogen activator receptor, urokinase type/PLAUR/CD87 | 2E + 05 | NM_002659 | 19q13 |
| | Proteases and Inhibitors | Proteases | lymphocyte antigen CD10/membrane metalloendopeptidase/MME/CD10 | 1E + 05 | NM_000902 | 3q21-q27 |
| | | | leukocyte antigen CD13/alanyl aminopeptidase/ANPEP/CD13 | 2E + 05 | NM_001150 | 15q25-q26 |
| | | | chymase 1, mast cell/CMA1 | 1E + 05 | NM_001836 | 14q11.2 |
| | | | tryptase alpha/TPS1 | 2E + 05 | NM_003293 | Chr. 16 |
| | | | matrix metalloproteinase 1 (interstitial collagense)/MMP1 | 1E + 05 | NM_002421 | 11q22-q23 |
| | | | matrix metalloproteinase 2 (neutrophil gelatinase)/CLG4/MMP2 | 1E + 05 | AH002654 | 16q13 |
| | | | matrix metalloproteinase 3 (stomelysin 1, progelatinase)/MMP3 | 2E + 05 | NM_002422 | 11q23 |
| | | | matrix metalloproteinase 8 (neutrophil collagenase)/MMP8 | 1E + 05 | NM_002424 | 11q21-q22 |
| | | | matrix metalloproteinase 9 (gelatinase B, 92kD type IV collagenase)/MMP9 | 1E + 05 | NM_004994 | 20q11.2-q13.1 |
| | | | matrix metalloproteinase 10 (stromelysin 2)/MMP10 | 2E + 05 | NM_002425 | 11q22.3-q23 |
| | | | matrix metalloproteinase 11 (stomelysin 3)/MMP11 | 2E + 05 | NM_005940 | 22q11.2 |
| | | | matrix metalloproteinase 12 (macrophage elastase)/MMP12 | 6E + 05 | NM_002426 | 11q22.2-q22.3 |
| | | | matrix metalloproteinase 13 (collagenase 3)/MMP13 | 6E + 05 | NM_002427 | 11q22.3 |
| | | | matrix metalloproteinase 14 (membrane-inserted)/MMP14 | 6E + 05 | NM_004995 | 14q11-q12 |
| | | | matrix metalloproteinase 15 (membrane-inserted)/MMP15 | 2E + 05 | NM_002428 | 16q13-q21 |
| | | | matrix metalloproteinase 16 (membrane-inserted)/MMP16 | 6E + 05 | NM_005941 | 8q21 |
| | | | matrix metalloproteinase 17 (membrane-inserted)/MMP17 | 6E + 05 | NM_004141 | 12q24.33 |
| | | | matrix metalloproteinase 19/MMP19 | 2E + 05 | NM_002429 | 12q14 |
| | | | matrix metalloproteinase 23A/MMP23A | 6E + 05 | NM_004659 | 1p36.3 |
| | | | matrix metalloproteinase 23B/MMP23B | 6E + 05 | NM_006983 | 1p36.3 |
| | | | matrix metalloproteinase 24 (membrane-inserted)/MMP24 | ******* | NM_006690 | ******* |
| | | | tryptase beta/TPS2 | 2E + 05 | NM_003294 | Chr. 16 |
| | | Inhibitors | tissue inhibitor of metalloproteinase 1/erythroid potentiating activity/EPA/human collagenase inhibitor/HCI/TIMP1 | 3E + 05 | NM_003254 | Xp11.3-p11.23 |
| | | | secretory leukocyte protease inhibitor (antileukoproteinase)/SLP1 | 1E + 05 | NM_003064 | ******* |
| | | | mononcyte/neutrophil elastase inhibitor/ELANH2 | 1E + 05 | M93056 | 6pter-p24 |
| | | | alpha-1-microglobulin/bikunin precursor/AMBP | 2E + 05 | NM_001633 | 9q32-q33 |
| | | | alpha-2-macroglobulin/A2M | 1E + 05 | NM_000014 | 12p13.3-p12.3 |
| Cell-Mediated Pathogen Defense | Phagocytosis of Pathogens | Scavenger Receptors | leukocyte antigen CD36/thrombospondin receptor/platelet collagen receptor/CD36 | 2E + 05 | NM_000072 | 7q11.2 |
| | | | CD36 antigen (collagen type I receptor, thrombospondin receptor)-like 1/CD36L1/SRB1 | 6E + 05 | NM_005505 | Chr. 12 |
| | | | CD5 antigen-like (scavenger receptor cysteine rich family)/CD5L | 6E + 05 | NM_005894 | 1q21-q23 |
| | | | acetyl LDL receptor/scavenger receptor expressed by endothelial cells/SREC | ******* | NM_003693 | ******* |
| | | | macrophage scavenger receptor 1/MSR1 | 2E + 05 | NM_002445 | 8p22 |
| | | | macrophage scavenger receptor 1-like/MSRL1 | 6E + 05 | ******* | 8p21 |
| | | | mannose receptor, C type 1/MRC1 | 2E + 05 | NM_002438 | 10p13 |
| | | | endocytic receptor (macrophage mannose receptor family) (KIAA0709) | ******* | NM_006039 | ******* |
| | | | toll-like receptor 1/TLR1 | 6E + 05 | NM_003263 | 4p14 |
| | | | toll-like receptor 2/TLR2 | 6E + 05 | NM_003264 | 4q32 |
| | | | toll-like receptor 3/TLR3 | 6E + 05 | NM_003265 | 4q35 |

TABLE 1-continued

| Class | Pathway | Function | Name | OMIM | GID | Locus |
|---|---|---|---|---|---|---|
| | | | toll-like receptor 4/TLR4 | 6E+05 | NM_003266 | 9q32-q33 |
| | | | toll-like receptor 5/TLR5 | 6E+05 | NM_006068 | 1q41-q42 |
| | | | collectin 34 | ******* | AB002631 | ******* |
| | | | liver collectin 1/CL-L1 | 1E+05 | NM_006438 | ******* |
| | | | collectin receptor/complement component C1q receptor/C1QR | 1E+05 | ******* | 10q23.3 |
| | | | surfactant, pulmonary-associated protein D/SFTPD | 2E+05 | NM_003019 | 10q22.2-q23.1 |
| | | | surfactant, pulmonary-associated protein A1/SFTPA1 | 2E+05 | NM_005411 | 10q22.2-q23.1 |
| Defense Proteins and Peptides | Immunoglobulin Light Chains | Kappa Light Chain | immunoglobulin K light chain constant region locus/IGKC | 1E+05 | ******* | 2p12 |
| | | | immunoglobulin K light chain variable region locus/IGKV | 1E+05 | K01322 | 2p12 |
| | | | immunoglobulin K light chain joining region locus/IGKJ | 1E+05 | ******* | 2p12 |
| | | Lambda Light Chain | immunoglobulin L light chain constant region locus/IGLC1 | 1E+05 | NM_006146 | 22p11.2 |
| | | | immunoglobulin L light chainjoining region locus/IGLJ | 1E+05 | NM_006146 | 22p11.2 |
| | | | immunoglobulin L light chain variable region locus/IGLJ | 1E+05 | NM_006146 | 22p11.2 |
| | Immunoglobulin Heavy Chains | IgA Heavy Chain Constant Region | immunoglobulin A heavy chain constant region locus 1/IGHA1 | 1E+05 | ******* | 14q32.33 |
| | | IgD Heavy Chain Constant Region | immunoglobulin A heavy chain constant region locus 2/IGHA2 | 1E+05 | ******* | 14q32.33 |
| | | | immunoglobulin D heavy chain constant region locus/IGHD | 1E+05 | ******* | 14q32.33 |
| | | IgE Heavy Chain Constant Region Locus | immunoglobulin E heavy chain constant region locus/IGHE | 1E+05 | ******* | 14q32.33 |
| | | IgG Heavy Chain Constant Region Locus | immunoglobulin G heavy chain constant region locus 1/IGHG1 | 1E+05 | ******* | 14q32.33 |
| | | | immunoglobulin G heavy chain constant region locus 2/IGHG2 | 1E+05 | ******* | 14q32.33 |
| | | | immunoglobulin G heavy chain constant region locus 3/IGHG3 | 1E+05 | ******* | 14q32.33 |
| | | | immunoglobulin G heavy chain constant region locus 4/IGHG4 | 1E+05 | ******* | 14q32.33 |
| | | IgM Heavy Chain Constant Region Locus | immunoglobulin M heavy chain constant region locus/IGHM | 1E+05 | ******* | 14q32.33 |
| | | Heavy Chain Variable Region Locus | immunoglobulin heavy chain variable region locus 1/IGHV1 | 1E+05 | X92279 | 14q32.33 |
| | | | immunoglobulin heavy chain variable region locus 2/IGHV2 | 6E+05 | ******* | 16p11 |
| | | Heavy Chain Diversity Region Locus | immunoglobulin heavy chain diversity region locus 1/IGHDY1 | 1E+05 | X97051 | 14q32.33 |
| | | | immunoglobulin heavy chain diversity region locus 2/IGHDY2 | 1E+05 | L25544 | 15q11-q12 |
| | | Heavy Chain Joining Region Locus | immunoglobulin heavy chain joining region locus/IGHJY1 | 1E+05 | ******* | 14q32.33 |
| | Immunoglobulin Gene Rearrangement | Signaling | recombination activating gene 1/RAG1 | 2E+05 | NM_000448 | 11p13 |
| | | | recombination activating gene 2/RAG2 | 2E+05 | M94633 | 11p13 |
| | | | immunoglobulin kappa J region recombination signal binding protein/RBPJK/IGKJRB1 | 1E+05 | L07872 | 9p13-p12 |
| | | | Bruton agammaglobulinemia tyrosine kinase/BTK | 3E+05 | NM_000061 | Xq21.3-q22 |
| | | | interleukin 7 receptor/IL7R | 1E+05 | NM_002185 | 5p13 |
| | | | interferon-gamma receptor 1/IFNGR1 | 1E+05 | NM_000416 | 6q23-q24 |
| | | | interferon-gamma receptor 2/IFNGR2 | 1E+05 | NM_005534 | 21q22.1-q22.2 |
| | | | interleukin 4 receptor precursor/IL4R | 1E+05 | NM_000418 | 16p12.1-p11.2 |
| | | | interleukin 4 receptor precursor/IL4R | 1E+05 | NM_000418 | 16p12.1-p11.2 |
| | | Recombination | ligase 1, DNA, ATP-dependent/LIG1 | 1E+05 | NM_000234 | 19q13.2-q13.3 |
| | | | ligase IV, DNA, ATP-dependent/LIG4 | 6E+05 | NM_002312 | 13q22-q34 |
| | | | X-ray repair, complementing defect in Chinese hamster/Ku antigen, 80 kD/KU80/XRCC5 | 2E+05 | ******* | 2q35 |
| | | | thyroid autoantigen, 70 kD/KU70/G22P1 | 2E+05 | NM_001469 | 22q11-q13 |

TABLE 1-continued

| Class | Pathway | Function | Name | OMIM | GID | Locus |
|---|---|---|---|---|---|---|
| | Immunoglobulin Gene Transcription | Transcription Factors | nuclear factor kappa B DNA binding subunit 1/NFKB1 | 2E + 05 | M58603 | 4q23-q24 |
| | | | nuclear factor kappa B DNA binding subunit 2/NFKB2 | 2E + 05 | NM_002502 | 10q24 |
| | | | nuclear factor kappa B DNA subunit 3/NFKB3 | 2E + 05 | Z22949 | 11q12-q13 |
| | | | nuclear factor of kappa light chain gene enhancer in B cells, inhibitor alpha/NFKBIA | 2E + 05 | ******* | 14q13 |
| | | | nuclear factor of kappa light chain gene enhancer in B cells, inhibitor beta/NFKBIB | 6E + 05 | NM_002503 | 8p11.2 |
| | | | YY1 transcription factor/YY1 | 6E + 05 | NM_003403 | 14q |
| | | | immunoglobulin transcription factor 1/ITF1/transcription factor 3/TCF3 | 1E + 05 | ******* | 19p13.3 |
| | | | immunoglobulin transcription factor 2/ITF2/transcription factor 4/TCF4 | 6E + 05 | NM_003199 | 18q21.1 |
| | | | immunoglobulin mu binding protein 2/IGHMBP2 | 6E + 05 | NM_002180 | 11q13.2-q13.4 |
| | | | transcription factor binding to IGHM enhancer 3/TFE3 | 3E + 05 | NM_006521 | Xp11.22 |
| | | | homeobox protein OCT1/POU domain transcription factor 2, class 1/POU2F1 | 2E + 05 | NM_002697 | 1q22-q23 |
| | | | homeobox protein OCT2/POU domain transcription factor 2, class 2/POU2F2 | 2E + 05 | M22596 | Chr. 19 |
| | | | POU domain, class 2, associating factor 1/POU2AF1 | 6E + 05 | NM_006235 | 11q23.1 |
| | | | inhibitor of DNA binding 1, dominant negative helix-loop-helix protein/ID1 | 6E + 05 | NM_002165 | 20q11 |
| | | | inhibitor of DNA binding 2, dominant negative helix-loop-helix protein/ID2 | 6E + 05 | NM_002166 | 2p25 |
| | Immunoglobulin Isotype Switching | Signaling | B-cell antigen CD40/tumor necrosis factor receptor superfamily, member 5/CD40/TNFRSF5 | 1E + 05 | NM_001250 | 20q12-q13.2 |
| | | | paired box gene 5/B-cell lineage-specific activator protein/BSAP/PAX5 | 2E + 05 | ******* | 9p13 |
| | | | lymphocyte function-associated antigen, type 3/LFA3/LEU7/CD58 | 2E + 05 | NM_001779 | 1p13 |
| | | | interleukin 10 receptor, alpha/IL10RA | 1E + 05 | NM_001558 | 11q23.3 |
| | | | lymphocyte antigen CD45/protein tyrosine phosphatase, receptor type, c polypeptide/PTPRC/CD45 | 2E + 05 | NM_002838 | 1q31-q32 |
| | | | prostaglandin E receptor 1, EP1 subtype/PTGER1 | 2E + 05 | NM_000955 | 19p13.1 |
| | | | prostaglandin E receptor 2, EP2 subtype/PTGER2 | 2E + 05 | ****** | 5p13.1 |
| | | | prostaglandin E receptor 3, EP3 subtype/PTGER3 | 2E + 05 | NM_000957 | 1p31.2 |
| | | | prostaglandin E receptor 4, EP4 subtype/PTGER4 | 6E + 05 | NM_000958 | 5p13.1 |
| | | | interleukin 13 receptor, alpha 1/IL13RA1 | 3E + 05 | NM_001560 | Chr. X |
| | | | interleukin 13 receptor, alpha 2/IL13RA2 | 1E + 05 | X95302 | Xq24 |
| | | | interferon-gamma receptor 1/IFNGR1 | 1E + 05 | NM_000416 | 6q23-q24 |
| | | | interferon-gamma receptor 2/IFNGR2 | 1E + 05 | NM_005534 | 21q22.1-q22.2 |
| | | | interleukin 5 receptor alpha/IL5RA | 1E + 05 | M96652 | 3p26-p24 |
| | | | transforming growth factor, beta receptor I (activin A receptor type II-like kinase, 53kD)/TGFBR1 | 2E + 05 | NM_004612 | 9q33-q34 |
| | | | transforming growth factor, beta receptor II (70–80kD)/TGFBR2 | 2E + 05 | NM_003242 | 3p22 |
| | | | transforming growth factor, beta receptor III (betaglycan, 300kD)/TGFBR3 | 6E + 05 | NM_003243 | 1p33-p32 |
| | | Recombination | X-ray repair, complementing defect in Chinese hamster/Ku antigen, 80 kD/KU80/XRCC5 | 2E + 05 | ****** | 2q35 |
| | | | thyroid autoantigen, 70 kD/KU70/G22P1 | 2E + 05 | NM_001469 | 22q11-q13 |
| Complement | | Classical Pathway | complement component 1, R subcomponent/C1R | 2E + 05 | NM_001733 | 12p13 |
| | | | complement component 1, S subcomponent/C1S | 1E + 05 | NM_001734 | 12p13 |
| | | | complement component 1, Q subcomponent, alpha polypeptide/C1QA | 1E + 05 | ******* | 1p36.3-p34.1 |
| | | | complement component 1, Q subcomponent, beta polypeptide/C1QB | 1E + 05 | ******* | 1p36.3-p34.1 |
| | | | complement component 1, Q subcomponent, gamma polypeptide/C1QG | 1E + 05 | ******* | 1p36.3-p34.1 |
| | | | complement component 1, Q subcomponent, binding protein/C1QBP | 6E + 05 | NM_001212 | 17p13.3 |
| | | | complement component 1 inhibitor (angioedema, hereditary)/C1NH | 1E + 05 | NM_000062 | 11q11-q13.1 |
| | | | complement component 2/C2 | 2E + 05 | NM_000063 | 6p21.3 |
| | | | complement component 3/C3 | 1E + 05 | NM_000064 | 19p13.3-p13.2 |
| | | | complement component 4B/C4B | 1E + 05 | NM_000592 | 6p21.3 |
| | | | complement component 5/C5 | 1E + 05 | NM_001735 | 9q34.1 |
| | | | complement component 6/C6 | 2E + 05 | NM_000065 | 5p13 |
| | | | complement component 7/C7 | 2E + 05 | NM_000587 | 5p13 |
| | | | complement component 8, alpha polypeptide/C8A | 1E + 05 | NM_000562 | 1p32 |
| | | | complement component 8, beta polypeptide/C8B | 1E + 05 | NM_000066 | 1p32 |

TABLE 1-continued

| Class | Pathway | Function | Name | OMIM | GID | Locus |
|---|---|---|---|---|---|---|
| | | | complement component 8, gamma polypeptide/C8G | 1E + 05 | NM_000606 | 9q34.3 |
| | | | complement component 9/C9 | 1E + 05 | NM_001737 | 5p13 |
| | | | complement factor H/H factor 1/HF1 | 1E + 05 | NM_000186 | 1q32 |
| | | | I factor (complement)/IF | 2E + 05 | NM_000204 | 4q25 |
| | | | decay-accelerating factor for complement/DAF/CD55 | 1E + 05 | S72858 | 1q32 |
| | | | perforin 1/preforming protein/PRF1 | 2E + 05 | NM_005041 | 10q22 |
| | | | leukocyte antigen p18–20/protectin/CD59 | 1E + 05 | M95708 | 11p13 |
| | | | T-cell antigen CD46/membrane cofactor protein/MCP/measles virus receptor/CD46 | 1E + 05 | Y07713 | 1q32 |
| | | | erythrocyte antigen CD55/decay-accelerating factor for complement/DAF/CD55 | 1E + 05 | S72858 | 1q32 |
| | | | leukocyte antigen p18–20/protectin/CD59 | 1E + 05 | M95708 | 11p13 |
| | | | erythrocyte antigen CD35/complement receptor CR1 (receptor for components C3b/C4b)/CD35/CR1 | 1E + 05 | AH002679 | 1q32 |
| | | | complement component 3a receptor 1/C3AR1 | ****** | NM_004054 | ****** |
| | | | complement component 4-binding protein, alpha/C4BPA | 1E + 05 | NM_000715 | 1q32 |
| | | | complement component 4 binding protein, beta/C4BPB | 1E + 05 | NM_000716 | 1q32 |
| | | | complement component 5 receptor 1 (C5a ligand)/C5AR1 | 1E + 05 | NM_001736 | Chr. 19 |
| | | | antigen CD21/CD21 | ****** | X98257 | ****** |
| | | Alternative Pathway | B-factor, properdin/BF | 1E + 05 | NM_001710 | 6p21.3 |
| | | | properdin P factor, complement/PFC | 3E + 05 | NM_002621 | Xp11.4-p11.23 |
| | | | adipsin/complement factor D precursor/DF | 1E + 05 | NM_001928 | ****** |
| Acute Protection from Pathogens | | Defensins and Related Protective Proteins | defensin, alpha 1, myeloid-related sequence/DEFA1 | 1E + 05 | NM_004084 | 8p23.2-p23.1 |
| | | | defensin, alpha 3, neutrophil-specific/DEFA3 | ****** | NM_005217 | ****** |
| | | | defensin, alpha 4/corticostatin/DEFA4 | 6E + 05 | NM_001925 | Chr. 8 |
| | | | defensin, alpha 5/DEFA5 | 6E + 05 | M97925 | 8pter-p21 |
| | | | defensin, alpha 6, Paneth cell-specific/DEFA6 | 6E + 05 | NM_001926 | 8pter-p21 |
| | | | defensin, beta 1/DEFB1 | 6E + 05 | NM_005218 | 8p23.2-p23.1 |
| | | | defensin, beta 2/DEFB2 | 6E + 05 | NM_004942 | 8p23.1-p22 |
| | | | ribonuclease, RNase A family, 2/eosinophil-derived neurotoxin/EDN/RNASE2 | 6E + 05 | NM_002934 | 14q24-q31 |
| | | | ribonuclease, RNase A family, 2/eosinophil cationic protein/ECP/RNASE3 | 1E + 05 | NM_002935 | 14q24-q31 |
| | | | myeloperoxidase/MPO | 31398 | J02694 | 17q23.1 |
| | | | eosinophil peroxidase/EPX | 3E + 05 | NM_000502 | ****** |
| | | | cathelicidin antimicrobial peptide/CAMP | 1E + 05 | NM_004345 | 3p21.3 |
| | | | lysozyme/LYZ | 6E + 05 | NM_000239 | Chr. 12 |
| | | | chitinase 1/CHIT1 | 2E + 05 | NM_003465 | 1q31-q32 |
| | | | lactotransferrin/LTF | 6E + 05 | NM_002343 | 3q21-q23 |
| | | | polyadenylate binding protein/TIA1 | 2E + 05 | M77142 | 2p13 |
| | | | TIA1 cytotoxic granule-associated RNA-binding protein-like 1/TIAL1 | 6E + 05 | NM_003252 | 10q |
| | | | granulysin/NKG5 | 6E + 05 | NM_006433 | 2p12-q11 |
| | | | neutrophil azurocidin/NAZC | 2E + 05 | M96326 | 19p13.3 |
| | | | bactericidal/permeability-increasing protein precursor/BPI | 1E + 05 | NM_001725 | 20q11.23-q12 |
| | | | lipopolysaccharide-binding protein/LBP | 2E + 05 | AF105067 | 20q11.23-q12 |
| | | | monocyte antigen CD14/monocyte differentiation antigen/CD14 | 2E + 05 | NM_000591 | 5q31.1 |
| | | | proteoglycan 1, secretory granule/serglycin/PRG1 | 2E + 05 | NM_002727 | 10q22.1 |
| | | | proteoglycan 2, bone marrow/natural killer cell activator, eosinophil granule major basic protein/PRG2 | ****** | NM_002728 | ****** |
| | | | prepro-major basic protein homolog/MBPH | 1E + 05 | NM_006093 | ****** |
| | | Pentraxins | neuronal pentraxin I/NPTX1 | 6E + 05 | NM_002522 | 17q25.1-q25.2 |
| | | | neuronal pentraxin II/NPTX2 | 6E + 05 | U26662 | 7q21.3-q22.1 |
| | | | pentaxin-related gene, rapidly induced by IL-1 beta/PTX3 | 6E + 05 | NM_002852 | 3q25 |
| | | | amyloid P component, serum/APCS | 1E + 05 | NM_001639 | 1q21-q23 |
| | | | C-reative protein, pentraxin-related/CRP | 1E + 05 | X56214 | 1q21-q23 |

TABLE 1-continued

| Class | Pathway | Function | Name | OMIM | GID | Locus |
|---|---|---|---|---|---|---|
| Small Molecule Mediators of Inflammation | Degranulation of Platelets Mast Cells, Neutrophils, and Eosinophils | Receptors | mast cell IgE receptor alpha polypeptide/FCER1A | 1E + 05 | ******* | 1q23 |
| | | | mast cell IgE receptor beta polypeptide/FCER1B | 1E + 05 | NM_000139 | 11q13 |
| | | | mast cell IgE receptor beta polypeptide/FCER1G | 1E + 05 | NM_004106 | 1q23 |
| | | | granulocyte antigen CD62/platelet alpha-granule membrane protein/selectin P/CD62/SELP | 2E + 05 | NM_003005 | 1q23-a25 |
| | | | neutrophil antigen CD16/low-affinity IIIA for Fc fragment of IgG/FCGR3A/CD16 | 1E + 05 | M24853 | 19q13.3 |
| | | | prostaglandin 12 receptor/PTGIR/prostacyclin receptor | 6E + 05 | SEG_HUMIP | Chr. 19 |
| | | | formyl peptide receptor 1/FPR1 | 1E + 05 | NM_002029 | 19q13.3-q13.4 |
| | | | formyl peptide receptor-like 1/FPRL1 | 1E + 05 | NM_001462 | 19q13.3-q13.4 |
| | | | formyl peptide receptor-like 2/FPRL2 | 1E + 05 | NM_002030 | 19q13.3-q13.4 |
| | | | lipoxin A4 receptor | ******* | AF054013 | ******* |
| | | Signaling | inositol polyphosphate-5-phosphatase, 145 kD/SH2-containing inositol 5-phosphatase/SHIP/INPP5D | 6E + 05 | NM_005541 | 2q36-q37 |
| | | | v-yes-1 Yamaguchi sarcoma viral related oncogene homolog/LYN | 2E + 05 | NM_002350 | 8q13-qter |
| | | | guanine nucleotode binding protein (G protein), q polypeptide/GNAQ | 6E + 05 | NM_002072 | 9q21 |
| | | | guanine nucleotode binding protein (G protein), alpha inhibiting activity, polypeptide 2/GNA12 | 1E + 05 | NM_002070 | 3p21 |
| | Release of Membrane Lipids (common to PAF, lipoxin, leukotriene, and prostaglandin pathways) | Phospholipases | phospholipase A2 group 1LA/PLA2G2A | 2E + 05 | NM_000300 | 1p35 |
| | | | phospholipase A2 group 1B/PLA2G1B | 2E + 05 | NM_000928 | 12q23-q24.1 |
| | | | phospholipase A2 group X/PLA2G10 | 6E + 05 | NM_003561 | 16p13.1-p12 |
| | | | phospholipase A2 group 1VA/PLA2G4 | 6E + 05 | U08374 | 1q25 |
| | | | phospholipase A2 group V1/PLA2G6 | 6E + 05 | AF064594 | 22q13.1 |
| | | | phospholipase A2 group 1VC/PLA2G4C | 6E + 05 | NM_003706 | chr. 19 |
| | | | phospholipase A2 group V/PLA2G5 | 6E + 05 | NM_000929 | 1p36-p34 |
| | | | phospholipase C, beta 2/PLCB2 | 6E + 05 | NM_004573 | 15q15 |
| | | | phospholipase C, beta 3/PLCB3 | 6E + 05 | U26425 | 11q13 |
| | | | phospholipase C, beta 4/PLCB4 | 6E + 05 | NM_000933 | 20p12 |
| | | | phospholipase C, delta 1/PLCD1 | 6E + 05 | NM_006225 | 3p22-p21.3 |
| | | | phospholipase C, epsilon/PLCE | 6E + 05 | NM_006226 | 2q33 |
| | | | phospholipase C, gamma 1 (formerly subtype 148)/PLCG1 | 2E + 05 | NM_002660 | 20q12-q13.1 |
| | | | phospholipase C, gamma 2 (phosphatidylinositol specific)/PLCG2 | 6E + 05 | NM_002661 | 16q24.1 |
| | | | lysosomal acid lipase/LIPB | 3E + 05 | NM_000235 | 10q24-q25 |
| | | Annexins | lipocortin 1/annexin 1/ANXA1 | 2E + 05 | V00546 | 9q11-q22 |
| | | | lipocortin 2/annexin 2/ANXA2 | 2E + 05 | D00017 | 15q21-q22 |
| | | | lipocortin 3/annexin 3/ANXA3 | 1E + 05 | M20560 | 4q21 |
| | | | lipocortin 5/annexin 5/ANXA4 | 1E + 05 | NM_001154 | 4q26-q28 |
| | | | lipocortin 7/annexin 7/ANXA1 | 2E + 05 | NM_004034 | 10q21.1-q21.2 |
| | | Arachidonate Metabolism | arachidonate 12-lipoxygenase, 12R-type/ALOX12B | 6E + 05 | NM_001139 | 17pter-p13.1 |
| | | | arachidonate 15-lipoxygenase/ALOX15 | 2E + 05 | NM_001141 | 17p13.3 |
| | | | arachidonate 15-lipoxygenase, second type/ALOX15B | 6E + 05 | NM_001141 | ******* |
| | Prostaglandins | Biosynthesis | prostaglandin/endoperoxide synthetase 1/COX1/PTGS1 | 2E + 05 | AH001520 | 9q32-q33.3 |
| | | | prostaglandin/endoperoxide synthetase 2/COX2/PTGS2 | 6E + 05 | NM_000963 | 1q25.2-q25.3 |
| | | | thromboxane A synthase 1/TBXAS1 | 3E + 05 | EG_D34613 | 7q34 |
| | | | prostaglandin D2 synthase (hematopoietic) | 6E + 05 | ******* | ******* |
| | | | prostaglandin D2 synthase (21kD, brain)/PTGDS | 2E + 05 | M61900 | 20q13 |
| | | | prostaglandin I2 synthase/prostacyclin synthase/PTGIS | 6E + 05 | EG_D83393 | 19p13.1 |
| | | Receptors | prostaglandin E receptor 1, EP1 subtype/PTGER1 | 2E + 05 | NM_000955 | 5p13.1 |
| | | | prostaglandin E receptor 2, EP2 subtype/PTGER2 | 2E + 05 | ******* | 1p31.2 |
| | | | prostaglandin E receptor 3, EP3 subtype/PTGER3 | 2E + 05 | NM_000957 | 5p13.1 |
| | | | prostaglandin E receptor 4, EP4 subtype/PTGER4 | 2E + 05 | NM_000958 | 1p31.1 |
| | | | prostaglandin F receptor/PTGFR | 6E + 05 | L24470 | 1p31.1 |
| | | | prostaglandin F2 receptor negative regulator/PTGFRN | 6E + 05 | U26664 | 1p13.1-q21.3 |

TABLE 1-continued

| Class | Pathway | Function | Name | OMIM | GID | Locus |
|---|---|---|---|---|---|---|
| | | | prostaglandin I2 receptor/PTGIR/prostacyclin receptor | 6E + 05 | SEG_HUMIP | 19q13.3 |
| | | | solute carrier family 21 (prostaglandin transporter), member 2/SLC21A2 | 6E + 05 | NM_005630 | 3q21 |
| | | Catabolism | 15-hydroxyprostaglandin dehydrogenase/HPGD | 6E + 05 | NM_000860 | 4q34-q35 |
| | | | aldo-keto reductase family 1, member C2/AKR1C2 | 6E + 05 | NM_001353 | 10p15-p14 |
| | Platelet Activating | Biosynthesis | CDP-choline:alkylacetylglycerol cholinephosphotransferase | ******* | ******* | ******* |
| | Factor (PAF) | Receptors | platelet activating factor receptor/PTAFR | 2E + 05 | M88177 | 1p35-p34.3 |
| | | Catabolism | platelet activating factor acetylhydrolase 1/PAFAHI | 6E + 05 | NM_005084 | 6p21.2-p12 |
| | | | platelet activating factor acetylhydrolase, isoform 1B, alpha subunit/PAFAH1B1 | 6E + 05 | NM_000430 | 17p13.3 |
| | | | platelet activating factor acetylhydrolase, isoform 1B, beta subunit/PAFAH1B2 | 6E + 05 | NM_002572 | 11q23 |
| | | | platelet activating factor acetylhydrolase, isoform 1B, gamma subunit/PAFAH1B3 | 6E + 05 | NM_002573 | 19q13.1 |
| | | | platelet activating factor acetylhydrolase 2/PAFAH2 | 6E + 05 | NM_000437 | ******* |
| | Lipoxins | Biosynthesis | arachidonate 5-lipoxygenase/ALOX5 | 2E + 05 | NM_000698 | Chr. 10 |
| | | | arachidonate 5-lipoxygenase activating protein/FLAP/ALOX5 | 6E + 05 | NM_001629 | 13q12 |
| | | | arachidonate 12-lipoxygenase 12R type/ALOX12B | 6E + 05 | NM_001139 | 17pter-p13.1 |
| | | | Gamma-glutamyltranspeptidase 1/GGT1 | 2E + 05 | J04131 | 22q11.1-q11.2 |
| | | | Gamma-glutamyltranspeptidase 2/GGT2 | 1E + 05 | AH002728 | 22q11.1 |
| | | | Gamma-glutamyltransferase-like activity 1/GGTLA1 | 1E + 05 | NM_004121 | ******* |
| | | Receptors | lipoxin A4 receptor | ******* | AF054013 | ******* |
| | | Catabolism | renal microsomal dipeptidase/DPEP1 | 2E + 05 | NM_004413 | 16q24.3 |
| | Leukotrienes | Synthesis | arachidonate 5-lipoxygenase/ALOX5 | 2E + 05 | NM_000698 | Chr. 10 |
| | | | arachidonate 5-lipoxygenase-activating protein/FLAP/ALOX5AP | 6E + 05 | NM_001629 | 13q12 |
| | | | leukotriene A4 hydrolase/LTA4H (aminopeptidase) | 2E + 05 | NM_000895 | 12q22 |
| | | | leukotriene C4 synthase/LTC4S | 2E + 05 | NM_000897 | 5q35 |
| | | | Gamma-glutamyltranspeptidase 1/GGT1 | 2E + 05 | J04131 | 22q11.1-q11.2 |
| | | | Gamma-glutamyltranspeptidase 2/GGT2 | 1E + 05 | AH002728 | 22q11.1 |
| | | | Gamma-glutamyltransferase-like activity 1/GGTLA1 | 1E + 05 | NM_004121 | ******* |
| | | Receptors | cysteinyl leukotriene receptor 1/CYSLT1 | 3E + 05 | NM_006639 | Xq13-q21 |
| | | | leukotriene b4 receptor (chemokine receptor-like 1)/LTB4R | 6E + 05 | NM_000752 | 14q11.2-q12 |
| | | Catabolism | renal microsomal dipeptidase/DPEP1 | 2E + 05 | NM_004413 | 16q24.3 |
| | Histamine | Biosynthesis | Histidine Decarboxylase | 1E + 05 | M60445 | 15q21-q22 |
| | | Receptors | histmaine H1 receptor/HRH1 | 6E + 05 | NM_000861 | 3p21-p14 |
| | | | histmaine H2 receptor/HRH2 | 1E + 05 | AB023486 | ******* |
| | | | histmaine H3 receptor/HRH3 | ******* | NM_007232 | ******* |
| | | Catabolism | Histamine N-methyltransferase | 6E + 05 | D16224 | chr. 2 |
| | | | Amine oxidase (copper-containing) 2/AOC2 | 6E + 05 | D88213 | 17q21 |
| | | | Amine oxidase (copper-containing) 3/AOC3 | 6E + 05 | AF054985 | 17q21 |
| | Serotonin | Synthesis | aromatic L-Amino Acid Decarboxylase/AADC | 1E + 05 | M76180 | 7p11 |
| | | | tryptophan hydroxylase/TPH | 2E + 05 | X52836 | 11p15.3-p14 |
| | | | 14-3-3 protein ETA | 1E + 05 | X78138 | 22q12 |
| | | | 14-3-3 protein ZETA | 6E + 05 | M86400 | 2p25.2-p25.1 |
| | | | 14-3-3 protein BETA | 6E + 05 | X57346 | 20q13.1 |
| | | | 14-3-3 protein SIGMA | 6E + 05 | X57348 | ******* |
| | | Receptors | serotonin 5-HT receptors 5-HT1A, G protein-coupled | 1E + 05 | X57829 | 5q11.2-q13 |
| | | | serotonin 5-HT receptors 5-HT1B, G protein-coupled | 2E + 05 | M81590 | 6q13 |
| | | | serotonin 5-HT receptors 5-HT1C, G protein-coupled | 3E + 05 | U49516 | Xq24 |
| | | | serotonin 5-HT receptors 5-HT1D, G protein-coupled | 2E + 05 | M81590 | 1p36.3-p34.3 |
| | | | serotonin 5-HT receptors 5-HT1E, G protein-coupled | 2E + 05 | M91467 | 6q14-q15 |
| | | | serotonin 5-HT receptors 5-HT1F, G protein-coupled | 2E + 05 | L05597 | 3p12 |
| | | | serotonin 5-HT receptors 5-HT2A, G protein-coupled | 2E + 05 | D87030 | 13q14-q21 |

TABLE 1-continued

| Class | Pathway | Function | Name | OMIM | GID | Locus |
|---|---|---|---|---|---|---|
| | | | serotonin 5-HT receptors 5-HT2B, G protein-coupled | 6E + 05 | X77307 | 2q36.3-q37.1 |
| | | | serotonin 5-HT receptors 5-HT2C, G protein-coupled | 3E + 05 | U49516 | Xq24 |
| | | Uptake | serotonin transporter | 2E + 05 | X70697 | 17q11.1-q12 |
| | | Catabolism | monoamine oxidase A/MAOA | 3E + 05 | M69226 | Xp11.23 |
| | | | monoamine oxidase B/MAOB | 3E + 05 | M69177 | Xp11.23 |
| | | | serotonin N-Acetyltransferase/SNAT | 6E + 05 | U40347 | 17q25 |
| | | | tryptophan 2,3-dioxygenase/TDO2 | 2E + 05 | NM_005651 | 4q31-q32 |
| | Nitric Oxide Pathway | Synthesis | nitric oxide synthetase 1/NOS1 | 2E + 05 | AH001515 | 12q24.2-q24.31 |
| | | | nitric oxide synthetase 2A/NOS2A | 2E + 05 | X85766 | 17cen-q11.2 |
| | | | macrophage nitric oxide synthetase 2B/NOS2B | 6E + 05 | AH006623 | 17p13.1-q25 |
| | | | macrophage nitric oxide synthetase 2C/NOS2C | 6E + 05 | 600720 | 17p13.1-q25 |
| | | | nitric oxide synthetase 3/NOS3 | 2E + 05 | AH001515 | 7q36 |
| | | | chondrocyte nitric oxide synthetase 3/NOS4 | 2E + 05 | X73029 | ****** |
| | | | arginase/ARG1 | 1E + 05 | NM_000045 | ****** |
| | | | arginase/ARG2 | 1E + 05 | NM_001172 | 14q24.1-q24.3 |
| Vascularization | Endothelin | Synthesis | endothelin 1/EDN1 | 1E + 05 | NM_001955 | 6p24-p23 |
| | | | endothelin 2/EDN2 | 1E + 05 | NM_01956 | 1p34 |
| | | | endothelin 3/EDN3 | 1E + 05 | NM_000114 | 20q13.2-q13.3 |
| | | | endothelin converting enzyme 1/ECE1 | 6E + 05 | NM_001397 | 1p36.1 |
| | | Receptor | endothelin A receptor isoform delta 3/EDNRA | 1E + 05 | AF014826 | Chr. 4 |
| | | | endothelin receptor type B/EDNRB | 1E + 05 | NM_000115 | 13q22 |
| | Vascular Endothelial Growth Factor | Synthesis | vascular endothelial growth factor A/VEGFA | 2E + 05 | M32977 | 6p12 |
| | | | vascular endothelial growth factor B/VEGFB | 6E + 05 | U52819 | 11q13 |
| | | | vascular endothelial growth factor C/VEGFC | 6E + 05 | X94216 | ****** |
| | | Receptor | VEGF receptor | 2E + 05 | X61656 | 4q12 |
| Neurotransmitter and Peptide Hormone | Epinephrine and Norepinephrine | Synthesis | dopamine beta hydroxylase/DBH | 2E + 05 | Y00096 | 9q34 |
| | | | phenylethanolamine-N-methyltransferase/PNMT | 2E + 05 | NM_002686 | 17q21-q22 |
| | | | tyrosine hydroxylase/TH | 2E + 05 | X05290 | 11p15.5 |
| Inflammetory Modulation | Receptors | | alpha-1a-adrenergic receptor/ADRA1A | 1E + 05 | M76446 | Chr. 20 |
| | | | alpha-1b-adrenergic receptor/ADRA1B | 1E + 05 | L31773 | 5q33 |
| | | | alpha-1c-adrenergic receptor/ADRA1C | 1E + 05 | D25235 | 8p21 |
| | | | alpha-1d-adrenergic receptor/ADRA1D | 1E + 05 | M76446 | 20p13 |
| | | | alpha-2a-adrenergic receptor/ADRA2A | 1E + 05 | M18415 | 10q24-q26 |
| | | | alpha-2b-adrenergic receptor/ADRA2B | 1E + 05 | AF005900 | Chr. 2 |
| | | | alpha-2c-adrenergic receptor/ADRA2C | 1E + 05 | J03853 | 4q16.1 |
| | | | beta-1-adrenergic receptor/ADRB1 | 1E + 05 | M15169 | 10q24-q26 |
| | | | Beta-2-Adrenergic Receptor/ADRB2 | 1E + 05 | NM_001619 | 5q32-q34 |
| | | | beta-adrinergic receptor kinase 1/BARK1 | 1E + 05 | X57829 | 11cen-q13 |
| | | | Beta-2-Adrenergic Receptor-Like Protein G-21/ADRB2L | 1E + 05 | X70811 | 5q11.2-q13 |
| | | | Beta-3-Adrenergic Receptor/ADRB3 | 1E + 05 | X61157 | 8p12-p11.2 |
| | | | Beta-Adrenergic Receptor Kinase 1/ADRBK1 | 1E + 05 | X69117 | 11cen-q13 |
| | | Response | Beta-Adrenergic Receptor Kinase 2/ADRBK2 | 6E + 05 | NM_006202 | 22q11 |
| | | | phosphodiesterase 4A, cAMP-specific/PDE4A | 6E + 05 | NM_002600 | 19p13.2 |
| | | | phosphodiesterase 4B, cAMP-specific/PDE4B | 6E + 05 | ****** | 1p31 |
| | | | phosphodiesterase 4C, cAMP-specific/PDE4C | 6E + 05 | NM_006203 | Chr. 19 |
| | | | phosphodiesterase 4D, cAMP-specific/PDE4D | 6E + 05 | NM_006203 | 5q12 |

TABLE 1-continued

| Class | Pathway | Function | Name | OMIM | GID | Locus |
|---|---|---|---|---|---|---|
| | | | phosphodiesterase 7A, cAMP-specific/PDE7A | 2E+05 | L12052 | 8q13-q22 |
| | | | phosphodiesterase 8A, cAMP-specific/PDE8A | 6E+05 | AF056490 | ******* |
| | | | phosphodiesterase 9A, cAMP-specific/PDE9A | 6E+05 | NM_002606 | 21q22.3 |
| | | Uptake | Vesicular Amine Transporter 2/VAT2 | 2E+05 | L09118 | 10q25 |
| | | | Vesicular Amine Transporter 1/VAT1 | 2E+05 | ******* | 8p21.3 |
| | | | Solute carrier family 6, member 5/SLC6A2/NAT1/NET1 | 2E+05 | NM_001043 | 16q12.2 |
| | | Catabolism | Monoamine Oxidase A/MAOA | 3E+05 | M69226 | Xp11.23 |
| | | | Monoamine Oxidase B/MAOB | 3E+05 | M69117 | Xp11.23 |
| | | | Catechol-O-Methyltransferase/COMT | 1E+05 | M58525 | 22q11.2 |
| | Dopamine | Biosynthesis | Aromatic L-Amino Acid Decarboxylase/AADC/dopa decarboxylase | 1E+05 | M76180 | 7p11 |
| | | | Tyrosine Hydroxylase | 2E+05 | X05290 | 11p15.5 |
| | | Receptors | Dopamine Receptor D1 | 1E+05 | X58987 | 5q35.1 |
| | | | Dopamine Receptor D2/DRD2 | 1E+05 | NM_000795 | 11q23 |
| | | | Dopamine Receptor D3/DRD3 | 1E+05 | U32499 | 3q13.3 |
| | | | Dopamine Receptor D4 | 1E+05 | L12398 | 11p15.5 |
| | | | Dopamine Receptor D5 | 1E+05 | M67439 | 4p16.1-p15.3 |
| | | Reuptake | Dopamine Transporter/DAT1 | 1E+05 | L24178 | 5p15.3 |
| | | Catabolism | Dopamine Beta-Hydroxylase/monooxygenase | 2E+05 | Y00096 | 9q34 |
| | | | Catechol-O-Methyltransferase | 1E+05 | M58525 | 22q11.2 |
| | | | Monoamine Oxidases A | 3E+05 | M69226 | Xp11.23 |
| | | | Monoamine Oxidases B | 3E+05 | M69177 | Xp11.23 |
| | | | Phenol Sulfotransferase 1 | 2E+05 | L10819 | 16p12.1-p11.2 |
| | | | Phenol Sulfotransferase 2 | 6E+05 | X78282 | 16p12.1-p11.2 |
| | | | Phenol Sulfotransferase 3 | 6E+05 | L19956 | 16p11.2 |
| | Adenosine | Biosynthesis | adenylosuccinate lyase/ADSL | 1E+05 | NM_000026 | 22q13.1 |
| | | | adenylosuccinate synthetase/ADSS | 1E+05 | NM_001126 | 1cen-q12 |
| | | Receptors | Adenosine A1 Receptor, Adora1/G protein-coupled | 1E+05 | L22214 | 1q32.1 |
| | | | Adenosine A2 Receptor, Adora2a/G protein-coupled | 1E+05 | X68486 | 22q11.2 |
| | | | Adenosine A2b Receptor, Adora2b/G protein-coupled | 6E+05 | X68487 | 17p12-p11.2 |
| | | | Adenosine A3 Receptor, Adora3/G protein-coupled | 6E+05 | L20463 | 1p21-p13 |
| | | | Adenosine A2 Receptor-like/ADORA21.1 | 1E+05 | ******* | 10q25.3-q26.3 |
| | | | Purinergic Receptor P2x, Ligand-Gated Ion Channel, 1, P2rx1 | 6E+05 | NM_002558 | ******* |
| | | | Purinergic Receptor P2x, Ligand-Gated Ion Channel, 3, P2rx3 | 6E+05 | Y07683 | 11q12 |
| | | | Purinergic Receptor P2x, Ligand-Gated Ion Channel, 4, P2rx4 | 6E+05 | AF000234 | 12q24.32 |
| | | | Purinergic Receptor P2x, Ligand-Gated Ion Channel, 5, P2rx5 | 6E+05 | NM_002561 | ******* |
| | | | Purinergic Receptor P2x, Ligand-Gated Ion Channel, 7, P2rx7 | 1E+05 | ******* | 10q25.3-q26.3 |
| | | | P2Y11 purinoceptor/G protein-coupled | 6E+05 | ******* | ******* |
| | | | P2Y7 purinoceptor/leukotriene B4 receptor/G protein-coupled | 6E+05 | NM_000752 | 14q11.2-q.12 |
| | | | P2Y2 purinoceptor/G protein-coupled | 6E+05 | U07225 | 11q13.5-q14.1 |
| | | | P2Y1 purinoceptor/G protein-coupled | 6E+05 | U42029 | 3q25 |
| | | | P2Y4 pyrimidinergic receptor/G protein-coupled | 3E+05 | NM_002565 | Xq13 |
| | | | P2Y6 pyrimidinergic receptor/G protein-coupled | 6E+05 | NM_004154 | 11q13.5 |
| | | Reuptake | Solute carrier family 29 (nuceleosides), member 1/SLC29A1/ENT1 | 6E+05 | NM_004955 | 6p21.2-p21.1 |
| | | | Solute carrier family 29 (nuceleosides), member 2/SLC29A2/ENT2 | 6E+05 | X86681 | 11q13 |
| | | Catabolism | adenosine deaminase | 1E+05 | NM_000022 | 20q13.11 |
| | Acetylcholine | Biosynthesis | Choline acetyltransferase/CHAT | 1E+05 | NM_003055 | 10q11.2 |
| | | | carnitine acetyltransferase/CRAT | 6E+05 | NM_004003 | 9q34.1 |
| | | | apolipoprotein E | 1E+05 | NM_000041 | 19q13.2 |

TABLE 1-continued

| Class | Pathway | Function | Name | OMIM | GID | Locus |
|---|---|---|---|---|---|---|
| | | Receptors | Cholinergic Receptor, Muscarinic, 1; CHRM1 | 1E+05 | X15263 | 11q13 |
| | | | Cholinergic Receptor, Muscarinic, 2; CHRM2 | 1E+05 | U19800 | 7q35-q36 |
| | | | Cholinergic Receptor, Muscarinic, 3; CHRM3 | 1E+05 | U29589 | 1q41-q44 |
| | | | Cholinergic Receptor, Muscarinic, 4; CHRM4 | 1E+05 | M16405 | 11p12-p11.2 |
| | | | Cholinergic Receptor, Muscarinic, 5; CHRM5 | 1E+05 | AF026263 | 15q26 |
| | | | Nicotinic, Cholinergic receptor alpha 1 | 1E+05 | X70108 | 2q24-q32 |
| | | | Nicotinic, Cholinergic receptor alpha 2 | 1E+05 | U62431 | Chr. 8 |
| | | | Nicotinic, Cholinergic receptor alpha 3 | 1E+05 | X53559 | 15q24 |
| | | | Nicotinic, Cholinergic receptor alpha 4 | 1E+05 | U62433 | 20q13.2-q13.3 |
| | | | Nicotinic, Cholinergic receptor alpha 5 | 1E+05 | M83712 | 15q24 |
| | | | Nicotinic, Cholinergic receptor alpha 7/CHRNA7 | 1E+05 | U40583 | 15q14 |
| | | | Nicotinic, Cholinergic receptor beta 1 | 1E+05 | X14830 | 17p12-p11 |
| | | | Nicotinic, Cholinergic receptor beta 2 | 1E+05 | Y08415 | 1p21 |
| | | | Nicotinic, Cholinergic receptor beta 3 | 1E+05 | X67513 | 8p11.2 |
| | | | Nicotinic, Cholinergic receptor beta 4 | 1E+05 | X68275 | 15q24 |
| | | | Nicotinic, Cholinergic receptor epsilon polypeptide | 1E+05 | X66403 | Chr. 17 |
| | | | Nicotinic, Cholinergic receptor, muscle d | 1E+05 | X55019 | 2q33-q34 |
| | | | Nicotinic, Cholinergic receptor muscle g | 6E+05 | NM_005199 | 2q33-q34 |
| | | Reuptake | Vesicular acetylcholine transporter | 1E+05 | NM_003055 | 10q11.2 |
| | | Catabolism | Acetylcholinesterase/ACHE | 2E+05 | M55040 | 7q22 |
| | | | butyrylcholinesterase 1/serum cholinesterase 1/BCHE1 | 2E+05 | NM_000055 | 3q26.1-q26.2 |
| | | | butyrylcholinesterase 1/serum cholinesterase 2/BCHE2 | | ****** | 2q33-q35 |
| | Channels | Calcium Channels | voltage dependent calcium channel, P/Q type alpha 1A subunit/CACNA1A | 1E+05 | NM_000068 | 19p13 |
| | | | calcium channel, voltage-dependent, L type, alpha 1B subunit/CACNA1B | 6E+05 | NM_000718 | 9q34 |
| | | | calcium channel, voltage-dependent, L type, alpha 1C subunit/CACNA1C | 1E+05 | NM_000719 | 12p13.3 |
| | | | calcium channel, voltage-dependent, L type, alpha 1D subunit/CACNA1D | 1E+05 | NM_000720 | 3p14.3 |
| | | | L-type voltage dependent calcium channel alpha 1S subunit/CACNA1S | 1E+05 | NM_000069 | 1q32 |
| | | | calcium channel, voltage-dependent, beta 1 subunit/CACNB1 | 1E+05 | NM_000723 | 17q21-q22 |
| | | | voltage dependent calcium channel beta 2 subunit/CACNB2 | 6E+05 | U07139 | 10p12 |
| | | | calcium channel, voltage-dependent, alpha 2/delta subunit/CACNA2D1 | 1E+05 | Z28613 | 7q21-q22 |
| | | | calcium channel, voltage-dependent, gamma subunit/CACNG | 1E+05 | NM_000727 | 17q24 |
| | | | neuronal voltage dependent calcium channel gamma subunit/CACNG2 | 6E+05 | NM_006078 | ****** |
| | | Sodium Channels | sodium channel, nonvoltage-gated 1, beta (Liddle syndrome)/SCNN1B | 6E+05 | NM_000336 | 16p13-p12 |
| | | | sodium channel, nonvoltage-gated 1, gamma/SCNN1G | 6E+05 | NM_001039 | 16p13-p12 |
| | | Potassium Channels | cyclic nucleotide gated hyperpolarization activated potassium channel 1/HCN1 | 6E+05 | AF064876 | ****** |
| | | | cyclic nucleotide gated hyperpolarization activated potassium channel 2/HCN2 | 6E+05 | AF064877 | Chr. 17 |
| | | | potassium inwardly-rectifying channel, subfamily J, member 2 (KCNJ2) | 6E+05 | NM_000891 | 1q41 |
| | | | voltage dependent potassium channel, subfamily K, member 2/KCNK2 | 6E+05 | ****** | 2q24.1 |
| | | | G protein coupled potassium channel, subfamily J, member 3/KCNJ3/GIRK1 | 6E+05 | NM_002239 | 1q21-q23 |
| | | | G protein coupled potassium channel inward rectifier/GIRK3 | 6E+05 | ****** | 2p24 |
| | | | voltage dependent potassium channel, subfamily S, member 3/KCNK3 | 6E+05 | AF043472 | 11p15.5 |
| | | | potassium voltage-gated channel precursor, KQT-like subfamily, member 1/KCNQ1 | 2E+05 | NM_000218 | 19q13.2 |
| | | | potassium intermediate/small conductance calcium-activated channel, subfamily N, member 4/KCNN4 | 6E+05 | NM_002250 | 1p31-p22 |
| | | Chloride | chloride channel, calcium activated, family member 1/CLCA1 | 6E+05 | NM_001285 | ****** |
| | | | chloride channel, calcium activated, family member 2/CLCA2 | 6E+05 | NM_006536 | ****** |
| | | | cystic fibrosis transmembrane conductance regulator/CFTR | 6E+05 | NM_000492 | 7q31.2 |

TABLE 1-continued

| Class | Pathway | Function | Name | OMIM | GID | Locus |
|---|---|---|---|---|---|---|
| | Opioids | Biosynthesis | membrane metalloendopeptidase/MME/neutral endopeptidase | 1E + 05 | AH002677 | 3q21-q27 |
| | | | proopiomelanocortin | 2E + 05 | NM_000939 | 2p23.3 |
| | | | prepronociceptin/nociseptin/nosistatin/PNOC | 6E + 05 | ******* | 8p21 |
| | | | preproenkephalin B/prodynorphin/PDYN | 1E + 05 | NM_006211 | 20pter-p12.21 |
| | | | preproenkephalin A/proenkephalin/PENK | 1E + 05 | NM_006211 | 8q23-q24 |
| | | Receptors | Opioid Receptor, Mu-1; Oprm 1 | 6E + 05 | NM_000914 | 6q24-q25 |
| | | | Opioid Receptor, Kappa-1; Oprk 1 | 2E + 05 | U17298 | 8q11.2 |
| | | | opioid receptor-like 1/OPRL 1 | 6E + 05 | X77130 | ******* |
| | | | Opioid Receptor, Delta-1; Oprd1 | 2E + 05 | U10504 | 1p36.1-p34.3 |
| | | | Opioid Receptor, Sigma 1 | 6E + 05 | U75283 | ******* |
| | | | opioid binding cell adhesion molecule/OBCAM | 6E + 05 | ******* | Chr. 11 |
| | | | G protein-coupled receptor 7/GPR7 | 6E + 05 | U22491 | 10q11.2-q21.1 |
| | | | G protein-coupled receptor 8/GPR8 | 6E + 05 | U22492 | 20q13.3 |
| | Leptin | Biosynthesis | leptin/LEP | 2E + 05 | NM_000230 | 7q31.3 |
| | | Receptor | leptin reptor/LEPR | 6E + 05 | NM_002303 | 1p31 |
| | Cholecystokinin (CCK) | Biosynthesis | Cholecystokinin/CCK | 1E + 05 | L00354 | 3pter-p21 |
| | | Receptors | Cholecystokinin A receptor/CCKAR | 1E + 05 | L13605 | 4p15.2-p15.1 |
| | | | Cholecystokinin B receptor/CCKBR | 1E + 05 | L08112 | 11p15.5-p15.4 |
| | Tachykinin or Substance P or Neurokinin | Biosynthesis | Neurokinin A/Tachykinin 1 or 2/Substance P or K | 2E + 05 | U37529 | 7q21-q22 |
| | | | Neurokinin B/Tachykinin 3 | 2E + 05 | ******* | 12q13-q21 |
| | | Receptors | Tachykinin NK1 receptor/TACR1 | 2E + 05 | M81797 | Chr. 2 |
| | | | Tachykinin NK2 receptor/TACR2 | 2E + 05 | M57414 | 10q11-q21 |
| | | | Tachykinin NK3 receptor/TACR3 | 2E + 05 | M89473 | ******* |
| | Bradykinin | Biosynthesis | kininogen/KNG | 2E + 05 | AH002853 | 3q27 |
| | | | kallikrein 1/KLK1 | 1E + 05 | NM_000710 | 19qa13.2-q13.4 |
| | | Receptor | bradykinin receptor B1/BDKRB1G protein-coupled | 6E + 05 | NM_000710 | 14q32.1-q32.2 |
| | | | bradykinin receptor B2/BDKRB2G protein-coupled | 1E + 05 | NM_000623 | 14q32.1-q32.2 |
| | Parathyroid Hormone (PTH) | Biosynthesis | parathyroid hormone-related protein/parathyroid hormone-like hormone/PTHLH | 2E + 05 | NM_002820 | 12p12.1-p11.2 |
| | | | parathyroid hormone/PTH | 2E + 05 | NM_000315 | 11p15.3-p15.1 |
| | | Receptors | parathyroid hormone receptor 1/PTHR1 | 2E + 05 | NM_000316 | 3p22-p21.1 |
| | | | parathyroid hormone receptor 2/PTHR2 | 6E + 05 | NM_005048 | 2q33 |
| | ACTH | Biosynthesis | proopiomelanocortin | 2E + 05 | NM_000939 | 2p23.3 |
| | | Receptor | melanocortin 1 receptor (alpha melanocyte stimulating hormone receptor)/MC1R | 2E + 05 | NM_002386 | 16q24.3 |
| | | | melanocortin 2 receptor/ACTH receptor/MC2R | 2E + 05 | NM_000529 | 18p11.2 |
| | | | melanocortin 4 receptor/MC4R | 2E + 05 | NM_005912 | 18q22 |
| | | | melanocortin 5 recepto/MC5R | 6E + 05 | NM_005913 | 18p11.2 |
| General Cell Growth | Folate Metabolism | Receptors | Folate Receptor Alpha/FOLR1 | 1E + 05 | M28099 | 11q13.3-q13.5 |
| | | | Folate Receptor Beta/FOLR2 | 1E + 05 | AF000380 | 11q13.3-q13.5 |
| | | | Folate Receptor Gamma/FOLR3 | 6E + 05 | Z32564 | ******* |
| | | Transporter | Folate Transporter (SLC19A1) | 6E + 05 | U19720 | 21q22.3 |
| | | | Vitamin B12 binding protein | 3E + 05 | NM_000355 | 22q11.2-qter |
| | | Glutamination | folylpolyglutamate synthetase/FPGS | 1E + 05 | M98045 | 9cen-q34 |
| | | | gamma-glutamyl hydrolase/GGH | 6E + 05 | U55206 | ******* |

TABLE 1-continued

| Class | Pathway | Function | Name | OMIM | GID | Locus |
|---|---|---|---|---|---|---|
| | | Metabolism | Methylenetetrahydrofolate reductase/MTHFR | 2E+05 | U09806 | 1p36.3 |
| | | | Dihydrofolate reductase/DHFR | 1E+05 | J00140 | 5q11.2-q13.2 |
| | | | 5,10-methylenetetrahydrofolate dehydrogenase, 5,10-methylenetetrahydrofolate cyclohydrolase, 10-formyltetrahydrofolate synthetase/MTHFD1 | 2E+05 | NM_005956 | 14q24 |
| | | | 5,10-methenyltetrahydrofolate synthetase (5-formyltetrahydrofolate cyclo-ligase)/MTHFS | 6E+05 | NM_006441 | Chr. 15 |
| | | | phosphoribosylglycinamide formyltransferase, phosphoribosylglycinamide synthetase, phosphoribosylaminoimidazole synthetase/GART | 1E+05 | NM_000819 | 21q22.1 |
| | | | folate hydrolase 1/FOH1 | 6E+05 | NP_004467 | 11q14 |
| | | | 6-pyruvoyl tetrahydrobiopterin synthase/PTPS | 3E+05 | Q03393 | 11q22.3-q23.3 |
| | | | serine hydroxymethyltransferase 1 (soluble)/SHMT1 | 2E+05 | NM_004169 | 17p11.2 |
| | | | serine hydroxymethyltransferase 2 (mitochondrial)/SHMT2 | 1E+05 | NM_005412 | 12q13 |
| | | | Glycine aminotransferase/glycine cleavage T protein/GAT | 2E+05 | NM_000481 | 3p21.1-p21.1 |
| | | | 5-methyltetrahydrofolate-homocysteine methyltransferase/methionine synthase/MTR | 2E+05 | NM_000254 | 1q43 |
| | | | glutamate formiminotransferase/dihydrofolate synthetase | 2E+05 | ****** | ****** |
| | Purine Metabolism | | hypoxanthine-guanine phosphoribosyltransferase | 3E+05 | M31642 | Xq26-q27.2 |
| | | | adenosine phosphoribosyltransferase/APRT | 1E+05 | NM_000485 | 16q24 |
| | | | thiopurine S-methyltransferase/TPMT | 2E+05 | NM_000367 | 6p22.3 |
| | | | IMP (inosine monophosphate) dehydrogenase 1/IMPDH1 | 1E+05 | NM_000883 | 7q31.3-q32 |
| | | | IMP (inosine monophosphate) dehydrogenase 2/IMPDH2 | 1E+05 | NM_000884 | 3p21.2 |
| | | | adenylosuccinate synthetase/ADSS | 1E+05 | NM_001126 | 1cen-q12 |
| | | | adenylosuccinate lyase | 1E+05 | NM_000026 | 22q13.1 |
| | | | glycinamide ribotide formyltransferase | 1E+05 | X54199 | 21q22.1 |
| | | | urate oxidase | 2E+05 | AH003594 | 1p22 |
| | | | purine nucleoside phosphorylase | 2E+05 | NM_000270 | 14q13.1 |
| | | | xanthine oxidase | 3E+05 | NM_000379 | 2p23-p22 |
| | | | adenosine deaminase | 1E+05 | NM_000022 | 20q13.11 |
| | Cytoskeleton | Tubulin | beta tubulin/TUBB | 2E+05 | NM_001069 | 6p21.3 |
| | | | beta tubulin 2/TUBB2 | 6E+05 | NM_006088 | ******* |
| | | | beta tubulin 4/TUBB4 | 6E+05 | NM_006086 | ******* |
| | | | beta tubulin 5/TUBB5 | 6E+05 | NM_006087 | ******* |
| | | | gamma tubulin/TUBG | 2E+05 | NM_001070 | ******* |
| | Oxygen Stress | Oxygen Stress | superoxide dismutase 1/SOD1 | 1E+05 | NM_000454 | 21q22.1 |
| Oxygen Stress (additional genes in Toxicology) | | | superoxide dismutase 2, mitochondrial/SOD2 | 1E+05 | X65965 | 6q25.3 |
| | | | thioredoxin-dependent peroxide reductase/TDPX1 | 6E+05 | NM_005809 | 13q12 |
| | | | peptide methionine sulfoxide reductase/MSRA | 6E+05 | ****** | ******* |
| | | | lipoprotein, Lp(a)/LPA | 6E+05 | NM_005577 | 6q27 |
| | | | succinate dehydrogenase complex, subunit C, integral membrane protein/SDHC | 6E+05 | NM_003001 | 1q21 |
| | | | glucose-6-phosphate dehydrogenase/G6PD (mitochondrial) | 3E+05 | NM_000402 | Xq28 |
| | | | aldehyde oxidase 1/AOX1 | 6E+05 | NM_001159 | 2q33 |

TABLE 2

| | Pathway | Inflammatory Indication | | | | | | | | | | |
|---|---|---|---|---|---|---|---|---|---|---|---|---|
| | | ARTHRITIS | ASTHMA | CHRONIC OBSTRUCTIVE PULMONARY DISEASE | AUTOIMMUNE | INFAMMATORY BOWEL DISEASE | MUNOSUPRESSI | INFLAMMATION | NEPHRITIS | PSORIASIS | THEROSCLEROSI | HEPATITIS |
| Immune Discrimination (Self vs Non-Self) | Antigen Presentation and Recognition | X | | | | | X | X | | | | X |
| Cytokine-Mediated Immune Regulation | Interferences, Interleukins, TNF Ligand Superfamily, Chemokine Superfamily, and other Growth Factors | X | X | X | X | X | X | X | X | X | X | X |
| | Cyclophilins | | | | | | X | | | | | X |
| Non-Cytokine Mediated Immune Regulation | Corticosteriods | X | | | | | X | | X | | | |
| | Testosterone/DHT | | | | | | X | | | X | | |
| | Vitamin D | X | | | | | | | | X | | |
| | Rellnoic Acid | X | | | | | | | | X | | |
| Cell-Mediated Inflammation | Cell Activation, Differentiation, and Cell Activation, Differentiation, and Proliferation (excluding games from cytokine section above) | X | X | X | X | X | X | X | X | | X | X |
| | Apoptosis (additional genes in Oncology) | X | | | | | X | X | X | | | X |
| | Adhesion and Migration | X | | | X | | | X | | | X | X |
| | Glycosyltransferences | | | | | | | | | | | |
| | Profcase and Profcase Inhibitors | X | | | X | X | X | X | X | | X | X |
| | Phagocytosis of Pathogene | | | | | | X | X | | | | |
| Defense Proteins and Peptides | Immunoglobudin Heavy and Light Chains and Genes Involved in Rearrangement, isotype Switching, and Transcription | | | | | | | | | | | |
| | Complexness | | | | | | | X | | | | |
| | Acute Protection from Pathogens | | | | | | | | | | | |
| Small Molecule Mediators of Inflammation | Degranulation of Pintelets, Masi Cells, Neutrophila, and Eosinophils | | | | | | | | | | | |
| | Release of Membrane Lipids (common to PAF, leukotriene, and prostaglandin pathways) | | X | | X | | | | | | X | |
| | Prostaglandins | | | | | | | | | | | |
| | Platelet Activating Factor (PAF) | X | | | | X | | | X | | | X |
| | Lipoxins | X | | | | X | | | | | | |

TABLE 2-continued

| | | | | | | | | | | | |
|---|---|---|---|---|---|---|---|---|---|---|---|
| | Leukotrienes | | | | | | | ▓ | | | |
| | Histamine | | | | | | | | | ▓ | |
| | Serotonin | | | ▓ | | | | | ▓ | | |
| | Nitric Oxide Pathway | ▓ | | | ▓ | | ▓ | ▓ | | | |
| Vaxularization | Endothelin and Vascular Endothelial Growth Factor | ▓ | | | | ▓ | ▓ | | | | |
| | Epinophrine and Nonepinephrine Pathway | | | ▓ | | | ▓ | | ▓ | | |
| | Dopamine Pathway | ▓ | | | | | ▓ | | | | |
| | Adenosine Pathway | | | | | | ▓ | | | | |
| | Acetylcholine Pathway | | | ▓ | | | | | | | |
| Neurtracsmiller and Peptide Hormone Inflammatory Modulation | Ion Channels | | | | ▓ | | | | | | |
| | Opioids | | | | | | | | | | |
| | Leptia | | | ▓ | | | | | | | |
| | Cholsecystokinin (CCK) | ▓ | | | | | | | | | |
| | Tachykinin, Substance P, or Neurokinin Pathway | | | | | | ▓ | ▓ | | | |
| | Bradykinin | ▓ | | | | | ▓ | | | | |
| | Parathyroid Hormone (PTH) | | | | | | ▓ | | | | |
| | Metanocorfin and Adrenocorticotropic Hormone | | | ▓ | | | | | | | |
| | Fobia Metabolism | ▓ | | | | ▓ | | | | | |
| General Cell Growth | Nucleotide Metabolism | ▓ | | | | | | | ▓ | | |
| | Cytoskeleton | ▓ | | | | ▓ | | | ▓ | | |
| | Oxygen Stress (additional genes in Taxicology) | | | | | ▓ | | | ▓ | | ▓ |

TABLE 3

| Hugo | GID | OMIM ID | VGX Symbol | Description |
|---|---|---|---|---|
| | Variance Start | | Variance | |
| M32315 | M32315 | 191191 | GEN-3MW | Tumor necrosis factor receptor 2 (75 kD) |
| | 257 | 168A > G | Silent | |
| | 676 | 587T > G | M196R | |
| | 783 | 694G > A | E232K | |
| | 1663 | 1574A > G | 3' | |
| | 1668 | 1579G > T | 3' | |
| | 1690 | 1601T > C | 3' | |
| | 1862 | 1773C > A | 3' | |
| | 2624 | 2535C > T | 3' | |
| | 2898 | 2809G > A | 3' | |
| | 2970 | 2881A > G | 3' | |
| | 2977 | 2888T > G | 3' | |
| | 3120 | 3031G > A | 3' | |
| | 3236 | 3147G > A | 3' | |
| M58286 | 191190 | | GEN-3R | TUMOR NECROSIS FACTOR RECEPTOR 1 PRECURSOR |
| | 222 | 36G > A | Silent | |
| | 309 | 123T > G | D41E | |
| | 410 | 224C > T | P75L | |
| | 1887 | 1701G > A | 3' | |
| | 1941 | 1755A > G | 3' | |
| U19487 | U19487 | 176804 | GEN-4I | "PROSTAGLANDIN E2 RECEPTOR, EP2 SUBTYPE" |
| | 85 | (−72)A > G | 3' | |
| | 231 | 75A > T | Silent | |
| | 1269 | 1113C > G | 3' | |
| | 1295 | 1139C > T | 3' | |
| | 1442 | 1286A > G | 3' | |
| U70867 | U70867 | 601460 | GEN-4S | prostaglandin transporter hPGT |
| | 301 | 210G > A | Silent | |
| | 931 | 840A > G | Silent | |
| | 1069 | 978A > G | Silent | |
| | 1888 | 1797C > T | Silent | |
| | 2014 | 1923C > T | Silent | |
| | 2323 | 2232A > T | 3' | |
| | 2706 | 2615T > G | 3' | |
| | 2839 | 2748T > A | 3' | |
| | 2908 | 2817A > G | 3' | |
| | 3171 | 3080A > G | 3' | |
| | 3253 | 3162A > G | 3' | |
| | 3594 | 3503T > A | 3' | |
| X01394 | X01394 | 191160 | GEN-4Y | Tumor necrosis factor |
| | 239 | 87G > T | Silent | |
| | 931 | 779A > C | 3' | |
| | 1307 | 1155G > T | 3' | |
| | 1572 | 1420G > A | 3' | |
| Z15026 | Z15026 | None | GEN-MW9 | Tumor necrosis factor alpha, promoter and genomic |
| | 307 | 307C > T | Intron | |
| | 322 | 322G > A | Intron | |
| | 335 | 335G > C | Intron | |
| | 425 | 425G > A | Intron | |
| | 503 | 503G > A | Intron | |
| | 528 | 528G > A | Intron | |
| | 600 | 600C > A | Intron | |
| | 640 | 640C > T | Intron | |
| | 654 | 654C > T | Intron | |
| | 695 | 695G > A | Intron | |
| | 1001 | 1001C > T | Intron | |
| | 1136 | 1136C > T | Intron | |
| | 1266 | 1266C > T | Intron | |
| | 1327 | 1327A > G | Intron | |
| | 1354 | 1354C > T | Intron | |
| | 1621 | 1621C > G | Intron | |
| | 2725 | 2725T > G | 3' | |
| | 3474 | 3474T > C | Intron | |
| | 3929 | 3929T > C | Intron | |
| | 4291 | 4291C > T | Intron | |
| | 4360 | 4360C > T | Intron | |
| | 4471 | 4471G > A | Silent | |
| | 4513 | 4513C > A | Silent | |
| | 5017 | 5017C > T | Intron | |
| | 5023 | 5023C > T | Intron | |
| | 5087 | 5087C > T | Intron | |
| | 5155 | 5155C > T | Intron | |
| | 5351 | 5351T > G | Intron | |
| | 5585 | 5585G > A | Intron | |
| | 5636 | 5636G > A | Intron | |
| | 5642 | 5642T > G | Intron | |
| | 5810 | 5810G > A | Intron | |
| | 6005 | 6005A > G | Intron | |
| | 6159 | 6159C > G | Intron | |
| | 6170 | 6170G > A | Intron | |
| | 6270 | 6270A > T | Intron | |
| | 6339 | 6339T > C | Intron | |
| | 6601 | 6601G > C | Intron | |
| | 7334 | 7334G > T | Intron | |
| | 7361 | 7361T > G | Intron | |
| | 7562 | 7562G > A | Intron | |
| | 7689 | 7689C > G | Intron | |
| X52425 | X52425 | 147781 | GEN-59 | Interleukin 4 receptor |
| | 170 | (−6)C > G | 5' | |
| | 398 | 223A > G | I75V | |
| | 412 | 237C > T | Silent | |
| | 1114 | 939T > C | Silent | |
| | 1211 | 1036A > G | I346V | |
| | 1374 | 1199G > C | E4000A | |
| | 1417 | 1242G > T | Silent | |
| | 1474 | 1299T > C | Silent | |
| | 1682 | 1507T > C | S503P | |
| | 1730 | 1555C > T | Silent | |
| | 1902 | 1727A > G | Q576R | |
| | 2198 | 2023C > T | P675S | |
| | 2572 | 2397T > C | Silent | |
| | 2659 | 2484T > C | 3' | |
| | 2661 | 2486T > C | 3' | |
| | 2741 | 2566C > G | 3' | |
| | 2892 | 2717G > A | 3' | |
| | 3044 | 2869G > A | 3' | |
| | 3289 | 3114A > G | 3' | |
| | 3391 | 3216C > T | 3' | |
| | 3419 | 3244G > C | 3' | |
| M57230 | M57230 | 162820 | GEN-60 | Interleukin 6 signal transducer |
| | 697 | 442G > C | G148R | |
| | 708 | 453A > G | Silent | |
| | 927 | 672G > A | Silent | |
| | 1616 | 1361T > C | I454T | |
| | 1750 | 1495G > A | V499I | |
| D25418 | D25418 | 600022 | GEN-78 | Prostaglandin I2 (prostacyclin) receptor (IP) |
| | 250 | 159G > C | Silent | |
| | 726 | 635G > A | R212H | |
| | 1047 | 956C > G | S319W | |
| | 1075 | 984A > C | Silent | |
| | 1332 | 1241C > T | 3' | |
| | 1562 | 1471C > G | 3' | |
| IFNB1 | V00546 | 147640 | GEN-TV | Messenger RNA for human fibroblast interferon |
| | 166 | 102C > G | S34R | |
| | 217 | 153C > T | Silent | |
| | 244 | 180C > A | D60E | |
| | 292 | 228G > T | Silent | |
| | 296 | 232T > C | Silent | |
| | 521 | 457T > C | Y153H | |
| AB006537 | AB006537 | 602626 | GEN-XZ | Homo sapiens mRNA for interleukin 1 receptor accessory protein, complete cds |
| | 1217 | 1011C > A | Silent | |
| | 1514 | 1308G > A | Silent | |
| | 3150 | 2944A > G | 3' | |
| | 3156 | 2950A > G | 3' | |
| | 3293 | 3087T > C | 3' | |
| | 3318 | 3112G > A | 3' | |

TABLE 5

Current Candidate Therapeutic Interventions in Development for Arthritis.

| Product Name | Chemical Name | Action | Indication |
| --- | --- | --- | --- |
| BW 4C; BW A4C; BW 4C86 | N-(3-phenoxy-phenyl-2-propenyl)acetohydroxamic acid | 5 lipoxygenase inhibitor; chelating agent; NSAID | arthritis; psoriasis |
| tenidap; tenidap sodium; CP 66248; CP 6624842; KENIDA; ENABLE; ENABLEX; REUMATEN | (Z)-5-chloro-2,3-dihydro-3-(hydroxy-2-thienylmethylene)-2-oxo-1H-indole-1-carboxamide | 5 lipoxygenase inhibitor; COX inhibitor; NSAID | rheumatoid arthritis; arthritis |
| flobufen; VUFB 16066 | 2',4'-difluoro-alpha-methyl-gamma-oxo-[1,1'-biphenyl]-4-butanoic acid | 5 lipoxygenase inhibitor; COX inhibitor; NSAID | rheumatoid arthritis |
| ZD 2138; ICI D2138 | 6-[[3-fluoro-5-(tetrahydro-4-methoxy-2H-pyran-4-yl)phenoxy]methyl]-1-methyl-2(1H)-quinolinone | 5 lipoxygenase inhibitor; NSAID | arthritis; asthma |
| AKI 1 | unspecified | adenosine regulating agent; NSAID | inflammation; arthritis |
| AKI 2 | unspecified | adenosine regulating agent; NSAID | inflammation; arthritis |
| analben | unspecified | analgesic | rheumatoid arthritis; pain |
| drug delivery system, OSAT ibuprofen; ibuprofen sustained release | unspecified | analgesic; NSAID | pain; rheumatoid arthritis; osteoarthritis; inflammation |
| SC 107 | unspecified | analgesic; NSAID | arthritis; pain |
| samarium 153 Sm lexidronam; Sm 153-EDTMP; samarium 153-EDTMP; samarium EDTMP; CYT 424; QUADRAMET | (OC-6-21)-[[[1,2-ethanediylbis[nitrilobis(methylene)]tetrakis[phosphonato]](8-)-N,N',OP,OP', OP'',OP''']-samarate(5-)-153Sm | analgesic; NSAID; radiotherapeutic | cancer; pain; rheumatoid arthritis |
| AE 941; NEOVASTAT; NEORETNA; PSOVASCAR; ARTHROVAS | unspecified | angiogenesis inhibitor; NSAID | cancer; psoriasis; rheumatoid arthritis; eye disease; retinopathy |
| FR 111142; WF 2015A | 4,5-dihydroxy-2-hexenoic acid 5-methoxy-4-[2-methyl-3-(3-methyl-2-butenyl)oxiranyl]-1-oxaspiro[2.5]oct-6-yl ester | angiogenesis inhibitor; NSAID | cancer; rheumatoid arthritis; retinopathy |
| troponin I; cartilage derived inhibitor | unspecified | angiogenesis inhibitor; NSAID; biotechnology | cancer; rheumatoid arthritis; eye disease |
| MHC II peptidomimetic, rheumatoid arthritis | unspecified | Antagonists of MHC | rheumatoid arthritis |
| SB 226882 | 4-[4-(4-fluoropheyl)-1-(4-piperidinyl)-1H-imidazol-5-yl]-N-methyl-2-pyrimidinamine | antifungal; MAP kinase inhibitor; signal transduction inhibitor; imidazole | inflammation; asthma; rheumatoid arthritis |
| ZYN-LINKER conjugated methotrexate | unspecified | antimetabolite; NSAID | cancer; rheumatoid arthritis; psoriasis |
| TRK 530 | [[[4-(methylthio)phenyl]thio]methylene]bisphosphonic acid disodiumsalt | antioxidant; bisphosphonate | rheumatoid arthritis |
| LY 221068 | 5-[[3,5-bis(1,1-dimethylethyl)-4-hydroxyphenyl]methylene]-3-(dimethylamino)-4-thiazolidinone | antioxidant; NSAID | arthritis |
| LY 269415 | 5-[[3,5-bis(1,1-dimethylethyl)-4-hydroxyphenyl]methylene]-3-(methylamino)-4-thiazolidinone | antioxidant; NSAID | arthritis |

TABLE 5-continued

Current Candidate Therapeutic Interventions in Development for Arthritis.

| | | | |
|---|---|---|---|
| AHR 15010 | 1-[(2-methoxyphenoxy)methyl]-1,2-ethanediyl ester of sulfamic acid | carbonate dehydratase inhibitor; NSAID | arthritis |
| caspase inhibitors, Cytovia | unspecified | caspase inhibitor | neurodegeneration; myocardial infarction; rheumatoid arthritis; septic shock |
| ICE inhibitor, IDUN | unspecified | caspase inhibitor; apoptosis inhibitor; IL-1 beta converting enzyme inhibitor; immuno-suppressant | transplant rejection; septic shock; rheumatoid arthritis; inflammatory bowel disease; diabetes |
| VLA4 integrin antagonist, Cytel | unspecified | cell adhesion inhibitor; integrin antagonist; VLA 4 antagonist; NSAID | asthma; rheumatoid arthritis; multiple sclerosis |
| drug delivery system, somatomedin C; drug delivery system, insulin-like growth factor-1; somatomedin C DepoFoam; Depo IGF-1 | unspecified | cicatrizant; hormone; NSAID; growth factor | rheumatoid arthritis; osteoporosis |
| fibroblast anticollagenase; FIBAC; anticollagenase fibroblast | unspecified | cicatrizant; NSAID | arthritis; cancer; skin ulcer; arthritis |
| BB 926 | unspecified | collagenase inhibitor; matrix metalloproteinase inhibitor; proteinase inhibitor; NSAID | arthritis; eye disease |
| collagenase inhibitors, Affymax | unspecified | collagenase inhibitor; matrix metalloproteinase inhibitor; proteinase inhibitor; NSAID | arthritis; inflammation |
| collagenase inhibitors, Xenova; XR 168 series | unspecified | collagenase inhibitor; matrix metalloproteinase inhibitor; proteinase inhibitor; NSAID | rheumatoid arthritis |
| Ro 319790 | unspecified | collagenase inhibitor; matrix metalloproteinase inhibitor; proteinase inhibitor; NSAID | rheumatoid arthritis; arthritis |
| GR 129574A | (R)-N-[1-carboxy-3-(1,3-dihydro-1,3-dioxo-2H-benz[f]isoindol-2-yl)propyl]-L-leucyl-N-methyl-L-phenylalaninamide mono(trifluoroacetate) | collagenase inhibitor; matrix metalloproteinase inhibitor; proteinase inhibitor; NSAID | arthritis |
| Ro 323555; TROCADE | beta-(cyclopentylmethyl)-N-hydroxy-gamma-oxo-alfa-[(3,4,4-trimethyl-2,5-dioxo-1-imidazolidinyl)methyl]-1-piperidinebutanamide | collagenase inhibitor; matrix metalloproteinase inhibitor; proteinase inhibitor; NSAID | arthritis |

TABLE 5-continued

Current Candidate Therapeutic Interventions in Development for Arthritis.

| | | | |
|---|---|---|---|
| WY 46135 | N-[[(5-chloro-2-benzothiazolyl)thio]phenylacetyl)-L-cysteine | collagenase inhibitor; matrix metalloproteinase inhibitor; proteinase inhibitor; NSAID | arthritis |
| MAb, C5; MAb, complement C5; 5G1.1 | unspecified | complement inhibitor; monoclonal antibody; immunosuppressant; NSAID | rheumatoid arthritis; systemic lupus erythematosus |
| hyaluronic acid 6-alpha-methylprednisolone ester; HYC 141 | unspecified | corticosteroid | rheumatoid arthritis |
| MYC 2095 | unspecified | corticosteroid | arthritis |
| rimexolone; trimexolone; ORG 6216; RIMEXEL; VEXOL | (11beta,16alpha,17beta)-11-hydroxy-16,17-dime)hyl-17-(1-oxopropyl)androsta-1,4-dien-3-one | corticosteroid | rheumatoid arthritis; inflammation; eye disease |
| deflazacont; azacort; L 5458; MDL 458; AZACORTID; CALCORT; LANTADIN; DEFLAN; FLANTADIN; DEZACOR; ZAMENE; ROSILIN; DEFLAMON; PRANDIN | (11beta, 16beta)-21-(acetyloxy)-11-hydroxy-2'-methyl-5'H-pregna-1,4-die no[17,16-d]oxazole-3,20-dione | corticosteroid | rheumatoid arthritis; skin disease; asthma |
| prednisolone farnesylate; PNF 21; FARNESONE; FARNERATE GEL; FARNEZONE GEL | [11.beta.,21 (2E,6E)]-11,17-dihydroxy-21-[(3,7,11-trimethyl-1-oxo-2,6,10-dodecatrienyl)oxy]-pregna-1,4-diene-3,20-dione | corticosteroid | rheumatoid arthritis; osteoarthritis |
| ORG 6632 | 21-chloro-9alfa-fluoro-11beta-hydroxy-16alfa,17alfa-dimethylpregna-1,4-diene-3,20-dione | corticosteroid; immunosuppressant | cancer; rheumatoid arthritis |
| RU 46057 | 2-[1,2-bis(1-oxopropoxy)ethyl]-4-hydroxy-N-2-thiazolyl-8-(trifluoromethyl)-3-quinoline carboxamide | COX inhibitor; 5 lipoxygenase inhibitor; NSAID | arthritis; psoriasis |
| meloxicam; UH AC62 UH AC26XX; MOBIC MOBICOX; MOBEC, MOVALIS; MOVATEC | 4-hydroxy-2-methyl-N-(5-methyl-2-thiazolyl)-2H-1,2-benzothiazine-3-carboxamide 1,1-dioxide | COX inhibitor; analgesic; COX 2 inhibitor; NSAID | rheumatoid arthritis; inflammation, pain; osteoarthritis |
| SD 8381 | unspecified | COX inhibitor; COX 2 inhibitor; analgesic; NSAID | arthritis |
| SC 57666 | 1-(4-fluorophenyl)-2-(4-methylsulphonylphenyl)cyclopentene | COX inhibitor; COX 2 inhibitor; analgesic; NSAID | arthritis |
| valdecoxib; SC 65872 | 4-(5-methyl-3-phenyl-4-isoxazolyl)benzenesulfonamide | COX inhibitor; COX 2 inhibitor; analgesic; NSAID | arthritis; pain |
| rofecoxib; MK 966; VIOXX | 4-[4-(methylsulfonyl)phenyl]-3-phenyl-2(5H)-furanone | COX inhibitor; COX 2 inhibitor; analgesic; NSAID | inflammation; rheumatoid arthritis; osteoarthritis; pain; Alzheimer disease |
| celecoxib; SC 58635; YM 177; CELEBREX; CELEBRA | 4-[5-(4-methylphenyl)-3-(trifluoromethyl)-1H-pyrazol-1-yl]benzenesulfonamide | COX inhibitor; COX 2 inhibitor; analgesic; NSAID | arthritis; pain; cancer |
| LAS 33826 | unspecified | COX inhibitor; COX 2 inhibitor; NSAID | rheumatoid arthritis |
| pranoprofen; Y 8004; ITEOPAN; NIEFTOP; NIFLAN; CESFLAN; ELICAPRIL; MABUL; FLANIN; PRAFEN; PRANOX; DIFEN | alpha-methyl-5H[1]benzopyrano[2,3-b]pyridine-7-acetic acid | COX inhibitor; NSAID | rheumatoid arthritis; eye disease |
| lipophosphoglycan analogue | unspecified | Cytokine antagonist | atherosclerosis; arthritis; septic shock; HIV infection |

TABLE 5-continued

Current Candidate Therapeutic Interventions in Development for Arthritis.

| | | | |
|---|---|---|---|
| cytokine trap, Regeneron | unspecified | cytokine antagonist | cancer; asthma; rheumatoid arthritis; allergy |
| interleukin-12 signal transduction antagonists, Ligand | unspecified | cytokine antagonist; immunosuppressant; NSAID | autoimmune disease; transplant rejection; rheumatoid arthritis |
| RP 54745 | 4-chloro-5-(3,4-dihydro-1-methyl-2(1H)-isoquinolinyl)-3H-1,2-dithiol-3-one | cytokine antagonist; immunosuppressant; NSAID | rheumatoid arthritis; inflammatory bowel disease; psoriasis |
| interleukin-8 receptor; IL-8r | unspecified | cytokine antagonist; NSAID | psoriasis; rheumatoid arthritis; respiratory distress syndrome; septic shock |
| interleukin-8 antagonists, Warner Lambert; interleukin-8 antagonists, LeukoSite | unspecified | cytokine antagonist; NSAID | rheumatoid arthritis; psoriasis; atherosclerosis |
| anakinra; interleukin-1 receptor antagonist; IL-1ra; interleukin-1 inhibitor; ANTRIL | N2-L-methionylinterleukin 1 receptor antagonist (human isoform x reduced) | Cytokine inhibitor; immunosuppressant; NSAID | rheumatoid arthritis; inflammatory bowel disease; transplant rejection; asthma; septic shock |
| interleukin-1 receptor ligands, Affymax | unspecified | cytokine inhibitor; NSAID | arthritis; inflammation |
| SB 242235 | unspecified | cytokine inhibitor; NSAID | rheumatoid arthritis |
| IX 207887 | 10-methoxy-4H-benzo(4,5)cyclohepta(1,2-b)thiophene-4-yliden)acetic acid | cytokine inhibitor; NSAID | rheumatoid arthritis |
| ACP | 4-[bis(acetyloxy)methyl]-1,2-benzenediol, diacetate | cytokine inhibitor; NSAID | arthritis |
| interleukin-4; IL-4; SCH 39400; QUADRAKINE | unspecified | cytokine; immunostimulant; NSAID | cancer; viral infection; rheumatoid arthritis |
| interleukin-10; IL-10; cytokine synthesis inhibitory factor; CSIF; SCH 52000; TENOVIL | interleukin 10 (human clone pH15C) | cytokine; vaccine adjuvant; immunosuppressant; NSAID | autoimmune disease; inflammatory bowel disease; rheumatoid arthritis; multiple sclerosis; psoriasis; HIV infection; viral infection |
| holmium 166 chitosan; DW 166HC | unspecified | Cytotoxic agent; radiation emmision at site of injection | cancer; rheumatoid arthritis |
| CI 959 | 5-methoxy-3-(1-methylethoxy)-N-1H-tetrazol-5-yl-benzo[b]thiophene-2-carboxamide sodium salt | degranulation inhibitor; immunosuppressant; NSAID | rhinitis; inflammation; asthma; arthritis |
| trimetrexate; trimetrexate glucuronate; TMQ; NSC 249008; CI 898; NeuTrexin | 5-methyl-6-[[(3,4,5-trimethoxyphenyl)amino]methyl]-2,4-quinazolinediamine | dihydrofolate reductase inhibitor; antifolate; NSAID | cancer; psoriasis; rheumatoid arthritis; pneumocystis |
| MDAM | N-[4-[2-(2,4-diamino-6-pteridinyl)ethyl]benzoyl]-4-methylene-DL-glutamic acid | dihydrofolate reductase inhibitor; NSAID; immunosuppressant | cancer; transplant rejection; rheumatoid arthritis; asthma |
| prinomide; prinomide tromethamine; CGS 10787; CGS 10787B | alpha-cyano-1-methyl-beta-oxopyrrole-2-propionanilide with 2-amino-2-(hydroxymethyl)-1,3-propanediol | DMARD; analgesic; immunosuppressant; NSAID | inflammation; pain; rheumatoid arthritis |
| actarit; MS 932; MOVER; ORCL | 4-(acetylamino)phenylacetic acid | DMARD; immunosuppressant; NSAID | rheumatoid arthritis |
| rheumatoid arthritis therapy, Xenova; rheumatoid arthritis therapy, Suntory | unspecified | DMARD; NSAID | rheumatoid arthritis |

TABLE 5-continued

Current Candidate Therapeutic Interventions in Development for Arthritis.

| | | | |
|---|---|---|---|
| spirogermanium; NSC 192965; SPIRO-32 | 8,8-diethyl-N,N-dimethyl-2-aza-8-germaspiro[4.5]decane-2-propanamine | DMARD; NSAID | malaria; multiple sclerosis; rheumatoid arthritis; cancer |
| elastase inhibitors, Cortech | unspecified | elastase inhibitor; proteinase inhibitor; NSAID | arthritis; inflammatory bowel disease; pulmonary obstructive disease |
| free radical scavenging estrogens, Jenapharm | unspecified | estrogen; free radical scavenger; NSAID | osteoporosis; arthritis; neurological |
| TBC 2573 | unspecified | FGF antagonist; NSAID | restenosis; rheumatoid arthritis; retinopathy |
| CGP 39565 | unspecified | free radical scavenger; DMARD; NSAID | rheumatoid arthritis; arthritis |
| superoxide dismutase B, manganese complex, Mn-SOD-B | unspecified | free radical scavenger; NSAID | ischemia; arthritis |
| free radical scavengers, Strathclyde University | unspecified | free radical scavenger; NSAID | neurodegeneration; arthritis; reperfusion injury; psoriasis; stroke |
| SLH 301 | unspecified | free radical scavenger; NSAID | neurodegeneration; arthritis; reperfusion injury; psoriasis; stroke |
| sudismase; superoxide dismutase copper zinc complex; CuZnSOD; OxSODrol | N-acetylsuperoxide dismutase (human clone pS 61-10 copper-zinc subunit protein moiety reduced) | free radical scavenger; NSAID | respiratory disease; ischemia; rheumatoid arthritis; inflammation |
| superoxide dismutase manganese complex; hMNSOD | unspecified | free radical scavenger; NSAID; immunosuppressant | ischemia; rheumatoid arthritis; inflammation; reperfusion injury |
| denileukin diftitox; interleukin-2 diphtheria toxin chimeric protein; interleukin-2 fusion protein; DAB 389-IL-2; LY 335348; DAB389IL2; ONTAK | 1-388-toxin (Corneybacterium diphtheriae strain C7), N-L-methionyl-387-L-histidine-388-L-alanine-, (388.fwdarw.2')-protein with 2-133-interleukin 2 (human clone pTIL2-21a) | fusion toxin; NSAID | diabetes; HIV infection; rheumatoid arthritis; psoriasis; cancer |
| immune system modulators, Chiroscience | unspecified | gene | autoimmune disease; rheumatoid arthritis; cancer; HIV infection |
| glycosidase inhibitor, Oxford GlycoSciences | unspecified | glycosidase inhibitor; NSAID | cancer; rheumatoid arthritis |
| pentosan polysulfate sodium; SP 54; PZ 68; CARTROPHEN; LASONIL; ELMIRON; LELONG MOUSSE | (1-4)-beta-D-xylan 2,3-bis(hydrogen sulfate), sodium salt | heparinoid; vasodilator; NSAID | arthritis; angina; hyperlipidemia; rheumatoid arthritis; cancer; cystitis |
| ICE inhibitors, BASF/Parke-Davis | unspecified | IL-1 beta converting enzyme inhibitor; caspase inhibitor; NSAID | endotoxic shock; rheumatoid arthritis; Alzheimer disease |
| VE 19512 | unspecified | IL-1 beta converting enzyme inhibitor; caspase inhibitor; NSAID | rheumatoid arthritis; osteoarthritis; inflammation |
| VX 740; HMR 3480 | unspecified | IL-1 beta converting enzyme inhibitor; caspase inhibitor; NSAID | rheumatoid arthritis; osteoarthritis; inflammation |
| OM 89; OM 8980; SUBREUM; MODIMMUDAL; MUNOLIXOM | Glycoprotein-rich, endotoxin free E. Coli extract | Immunomodulation | rheumatoid arthritis |
| thiethazole | 2-[1-(1,1-dioxothiethanyl-3)benzimidazolyl-2-thio] acetic acid | immunostimulant; immunosuppressant; antioxidant | cancer; rheumatoid arthritis; infectious disease; transplant rejection |
| FCE 20696 | 6H-dibenzo[b,d]pyran-6-carboxylic acid 2-(dimethylamino)ethyl ester hydrochloride | immunostimulant; immunosuppressant, NSAID | viral infection, rheumatoid arthritis |
| IMREG 1 | unspecified | immunostimulant; NSAID; peptide | rheumatoid arthritis; HIV infection |

TABLE 5-continued

Current Candidate Therapeutic Interventions in Development for Arthritis.

| | | | |
|---|---|---|---|
| PEPTIMER | unspecified | immunosuppressant | autoimmune disease; multiple sclerosis; rheumatoid arthritis; diabetes |
| esonarimod; KE 298 | alpha-[(acetylthio)methyl]-4-methyl-gamma-oxobenzenebutanoic acid | immunosuppressant | rheumatoid arthritis |
| antisense oligonucleotide, ICAM-1; antisense oligonucleotide, intracellular adhesion molecule-1; ISIS 2302 | d[(R)-P-thio](G-C-C-C-A-A-G-C-T-G-G-C-A-T-C-C-G-T-C-A) DNA | immunosuppressant; antisense; oligonucleotide; NSAID | rheumatoid arthritis; psoriasis; inflammatory bowel disease; asthma |
| apoptosis-inducing antigen, rheumatoid arthritis | unspecified | immunosuppressant; biotechnology; apoptosis inducer; NSAID | rheumatoid arthritis |
| monocyte colony inhibitory factor-1, Human Genome Sciences | unspecified | immunosuppressant; biotechnology; chemokine | autoimmune disease; rheumatoid arthritis; systemic lupus erythematosus |
| AI 201 | unspecified | immunosuppressant; biotechnology; NSAID | rheumatoid arthritis |
| AI 202 | unspecified | immunosuppressant; biotechnology; peptide; NSAID | rheumatoid arthritis |
| autoimmune disease-specific MHC blockers, 3 Dimensional Pharmaceuticals | unspecified | immunosuppressant; DMARD; NSAID | rheumatoid arthritis; autoimmune disease |
| ZYN-LINKER conjugated superantigens | unspecified | immunosuppressant; immunostimulant; NSAID | rheumatoid arthritis; cancer |
| enlimomab; MAb, intracellular adhesion molecule-1; MAb, ICAM-1; MAb, ICAM; MAb, R65; MAb, CD54; BIRR 0001; BIRR 1 | unspecified | immunosuppressant; monoclonal antibody; NSAID | transplant rejection; autoimmune disease; rheumatoid arthritis |
| MAb, gp39; MAb, arthritis | unspecified | immunosuppressant; monoclonal antibody; NSAID | rheumatoid arthritis |
| MAb, R73; MAb, rat alpha/beta T cell receptor | unspecified | immunosuppressant; monoclonal antibody; NSAID | transplant rejection; rheumatoid arthritis |
| priliximab; MAb, humanized CD4; cM-T412; CEN 000029 CENTARA | immunoglobulin G1 (human-mouse monoclonal cm-T412 anti-human antigen CD 4), disulfide with human-mouse monoclonal cm-T412.kappa.-chain, dimer | immunosuppressant; monoclonal antibody, NSAID | multiple sclerosis; autoimmune disease; rheumatoid arthritis |
| IRA 378 | (S)-8-chloro-1,2,3,4-tetrahydro-2-(trifluoromethyl)-6-quinolineacetic acid | immunosuppressant; nitric oxide synthase inhibitor; NSAID | rheumatoid arthritis |
| BMS 188667; CTLA4Ig | unspecified | immunosuppressant; NSAID | transplant rejection; systemic lupus erythematosus; psoriasis; arthritis; allergy |
| C-Maf based therapy | unspecified | immunosuppressant; NSAID | autoimmune disease; rheumatoid arthritis |
| corticotropin releasing factor binding protein; CRF binding protein; NBI 112 | unspecified | immunosuppressant; NSAID | rheumatoid arthritis; inflammation |
| lenercept; tumor necrosis factor receptor fusion protein; TNF receptor fusion protein; Ro 452081; TENEFUS | unspecified | immunosuppressant; NSAID | rheumatoid arthritis; asthma; septic shock; multiple sclerosis |

TABLE 5-continued

Current Candidate Therapeutic Interventions in Development for Arthritis.

| | | | |
|---|---|---|---|
| autoimmune disease therapy, Molecumetics/Bristol-Myers Squibb | unspecified | immunosuppressant; NSAID | rheumatoid arthritis; multiple sclerosis; systemic lupus erythematosus |
| CD2 binding agents, Procept | unspecified | immunosuppressant; NSAID | rheumatoid arthritis |
| CT 2576 | unspecified | immunosuppressant; NSAID | HIV infection; rheumatoid arthritis |
| immunoregulators, AVANT Immunotherapeutics; immunoregulators, Repligen | unspecified | immunosuppressant; NSAID | transplant rejection; rheumatoid arthritis; asthma |
| PG 12 | unspecified | immunosuppressant; NSAID | rheumatoid arthritis; transplant rejection |
| PG 27 | unspecified | immunosuppressant; NSAID | rheumatoid arthritis; transplant rejection |
| PG 2946 | unspecified | im munosuppressant; NSAID | rheumatoid arthritis; systemic lupus erythematosus; transplant rejection |
| PG 3028 | unspecified | immunosuppressant; NSAID | rheumatoid arthritis; systemic lupus erythematosus; transplant rejection |
| PG 3113 | unspecified | immunosuppressant; NSAID | rheumatoid arthritis; systemic lupus erythematosus; transplant rejection |
| PG 94 | unspecified | immunosuppressant; NSAID | rheumatoid arthritis; transplant rejection |
| PIC 060 analogs | unspecified | immunosuppressant; NSAID | psoriasis; dermatitis; diabetes; transplant rejection; rheumatoid arthritis |
| PIC 101 | unspecified | immunosuppressant; NSAID | rheumatoid arthritis; autoimmune disease; transplant rejection |
| PIC 102 | unspecified | immunosuppressant; NSAID | rheumatoid arthritis; transplant rejection; autoimmune disease |
| PIC 231 | unspecified | immunosuppressant; NSAID | rheumatoid arthritis; transplant rejection; autoimmune disease |
| VX 10393 | unspecified | immunosuppressant; NSAID | transplant rejection; rheumatoid arthritis; psoriasis; diabetes |
| VX 10428 | unspecified | immunosuppressant; NSAID | transplant rejection; rheumatoid arthritis; psoriasis; diabetes |
| laflunimus; HR 325 | (Z)-2-cyano-3-cyclopropyl-3-hydroxy-N-[3-methyl-4-(trifluoromethyl)phenyl]-2-propenamide | immunosuppressant; NSAI D | rheumatoid arthritis; transplant rejection; psoriasis |
| SCH 24937 | 1-[6-bromo-5-chloro-3-(2-pyridinyl)-1H-indol-2-yl]-2-(methylsulfinyl)ethanone | immunosuppressant; NSAID | rheumatoid arthritis |
| KF 20444 | 10-fluoro-3-(2-fluorophenyl)-6,7-dihydro-5H-benzo[6,7]cyclohepta[1,2-b]quinoline-8-carboxylic acid | immunosuppressant; NSAID | rheumatoid arthritis |
| KB 2683 | 2-(4-methylphenyl)-4-benzothiazolol acetate | immunosuppressant; NSAID | rheumatoid arthritis; inflammation; autoimmune disease |
| CI 972 | 2,6-diamino-1,5-dihydro-7-(3-thienylmethyl)-4H-pyrrolo[3,2-d[pyrimidin-4-one monohydrochloride | immunosuppressant; NSAID | rheumatoid arthritis; cancer; psoriasis |

TABLE 5-continued

Current Candidate Therapeutic Interventions in Development for Arthritis.

| | | | |
|---|---|---|---|
| MX 68 | 2-[[[4-[2,4-diamino-6-pteridinyl]methyl]-3,4-dihydro-2H-1,4-benzothiazin-7-yl]carbonyl]amino] hexanedioic acid | immunosuppressant; NSAID | rheumatoid arthritis; systemic lupus erythematosus; autoimmune disease |
| baohuoside 1; icariside II; B-1 | 3-[(6-deoxy-alpha-L-mannopyranosyl)oxy]-5,7-dihydroxy-2-(4-methoxyphenyl)-8-(3-methyl-2-butenyl)-4H-1-benzopyran-4-one | immunosuppressant; NSAID | systemic lupus erythematosus; rheumatoid arthritis |
| CL 306293 | 3-amino-2-[1,1'-biphenyl]-4-yl-6-fluoro-4-quinolinecarboxylic acid | immunosuppressant; NSAID | arthritis; HIV infection |
| amiprilose; amiprilose hydrochloride; TH N; SM 1213; KAP 690; THERAFECTIN | 3-O-(3-(dimethylamino)propyl)-1,2-O-isopropylidene-alfa-D-glucofuranose hydrochloride | immunosuppressant; NSAID | rheumatoid arthritis; psoriasis |
| TAK 603 | 4-(3,4-dimethoxyphenyl)-6,7-dimethoxy-2-(1H-1,2,4-triazol-1-ylmethyl)-3-quinolinecarboxylic acid ethyl ester | immunosuppressant; NSAID | rheumatoid arthritis |
| mizoribine; HE 69; BREDININ | 5-hydroxy-1-beta-D-ribofuranosylimidazole-4-carboxamide | immunosuppressant; NSAID | rheumatoid arthritis; transplant rejection; kidney disease |
| TA 383 | cis-2-(4-chlorophenyl)-4,5-dihydro-4,5-diphenyl-1H-imidazole monohydrochloride | immunosuppressant; NSAID | rheumatoid arthritis |
| SKF 105685 | N,N-dimethyl-8,8-dipropyl-2-azaspiro[4,5]decane-2-propanamine dihydrochloride | immunosuppressant; NSAID | autoimmune disease; rheumatoid arthritis; HIV infection |
| AI 200; COLLORAL | trimeric (16-1059)alpha1 (II) collagen | immunosuppressant; NSAID | rheumatoid arthritis |
| atiprimod; atiprimod dimaleate; SKF 106615 | N,N-diethyl-8,8-dipropyl-2-azaspiro[4.5]decane-2-propanamine | immunosuppressant; NSAID; macrophage inhibitor | rheumatoid arthritis; autoimmune disease; psoriasis |
| cladribine; 2-CdA; NSC 105014F; RWJ 26251; LEUSTATIN; LEUSTAT; MYLINAX | 2-chloro-2'-deoxyadenosine | immunosuppressant; nucleoside analogue; NSAID | cancer; multiple sclerosis; rheumatoid arthritis |
| PP 14 | unspecified | immunosuppressant; peptide; NSAID | autoimmune disease; rheumatoid arthritis |
| ZAP inhibitors, Ariad | unspecified | immunosuppressant; protein kinase inhibitor; tyrosine kinase inhibitor; NSAID | transplant rejection; rheumatoid arthritis; inflammatory bowel disease; systemic lupus erythematosus; multiple sclerosis |
| PEGylated p75 TNFR Fc mutein | unspecified | immunosuppressant; TNF inhibitor | rheumatoid arthritis |
| leflunomide; HWA 486; ARAVA | 5-methyl-N-[4-(trifluoromethyl)phenyl]-4-isoxazolecarboxamide | immunosuppressant; tyrosine kinase inhibitor; NSAID; DMARD | rheumatoid arthritis; autoimmune disease |
| fusion protein, CD5-gelonin; CD5-gelonin T lymphocyte-targeted immunofusion protein; GENIMUNE | unspecified | immunotoxin; NSAID | rheumatoid arthritis; inflammation |
| alpha d modulator | unspecified | integrin antagonist; adhesion inhibitor; NSAID | cell diabetes; atherosclerosis; arthritis; inflammatory bowel disease; respiratory disease |
| cell adhesion inhibitors, Ligand/Sankyo | unspecified | integrin antagonist; cell adhesion inhibitor; NSAID | asthma; rheumatoid arthritis; reperfusion injury |

TABLE 5-continued

Current Candidate Therapeutic Interventions in Development for Arthritis.

| | | | |
|---|---|---|---|
| RGD-based angiogenesis antagonists | unspecified | integrin antagonist; NSAID; cell adhesion inhibitor | cancer; rheumatoid arthritis; eye disease |
| NPC 15669 | N-(9H-(2,7-dimethylfluorenyl-9-methoxy)carbonyl)-L-leucine | leukocyte mediator inhibitor; NSAID | arthritis; septic shock; inflammatory bowel disease |
| CP 105696 | (3S-trans)-1-[3-([1,1'-biphenyl)4-ylmethyl)-3,4-dihydro-4-hydroxy-2H-1-benzopyran-7-yl]cyclopentanecarboxylic acid | leukotriene B4 antagonist; leukotriene antagonist; NSAID | rheumatoid arthritis |
| SC 51146 | 7-[3-[2(cyclopropylmethyl)-3-methoxy-4-(4-thiazolyl)phenoxy]propoxy]-3,4-dihydro-8-propyl-2H-1-benzopyran-2-carboxylic acid | leukotriene B4 antagonist; leukotriene antagonist; NSAID | asthma; psoriasis; rheumatoid arthritis; inflammatory bowel disease |
| NPC 16570 | 4-[[[2-(9H-fluoren-9-yl)ethoxy]carbonyl]amino]benzoic acid | leumedin; NSAID | rheumatoid arthritis |
| NPC 17923 | 4-[[3-[(2,7-dichloro-9H-fluoren-9-yl)oxy]-1-oxopropyl]amino]benzoic acid | leumedin; NSAID | rheumatoid arthritis |
| tacrolimus; tsukubaenolide; fujimycin; FK 506; (−)-FK506; FR 900506; L 679934; PROGRAF; PROTOPIC | [3S-[3R*[E(1S*,3S*,4S*)],4S*,5R*,8S*,9E,12R*,14R*,15S*,16R*,18S*,19S*,26aR*]]-5,6,8,11,12,13,14,15,16,17,18,19,24,25,26,26a-hexadecahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c][1,4]oxaazacyclotricosine-1,7,20,21(4H,23H)-tetrone | macrolide; immunosuppressant; NSAID; antibiotic | transplant rejection; dermatitis; eye disease; rheumatoid arthritis |
| matrix metalloproteinase inhibitors, OsteoArthritis; cartilage degrading enzyme inhibitors, OsteoArthritis; CHONDROPROTECTRS | unspecified | matrix metalloproteinase inhibitor; cicatrizant; proteinase inhibitor; NSAID | arthritis; periodontal disease; skin ulcer; cancer |
| anti-arthritic matrix metalloproteinase inhibitors | unspecified | matrix metalloproteinase inhibitor; proteinase inhibitor; NSAID | rheumatoid arthritis; osteoporosis |
| CH 138 | unspecified | matrix metalloproteinase inhibitor; proteinase inhibitor; NSAID | rheumatoid arthritis |
| CH 263 | unspecified | matrix metalloproteinase inhibitor; proteinase inhibitor; NSAID | rheumatoid arthritis |
| matrix metalloproteinase inhibitor, State University of New York | unspecified | matrix metalloproteinase inhibitor; proteinase inhibitor; NSAID | periodontal disease; kidney disease; cancer; arthritis; osteoporosis |
| matrix metalloproteinase inhibitors, Bayer | unspecified | matrix metalloproteinase inhibitor; proteinase inhibitor; NSAID | rheumatoid arthritis |

TABLE 5-continued

Current Candidate Therapeutic Interventions in Development for Arthritis.

| | | | |
|---|---|---|---|
| matrix metalloproteinase inhibitors, ProScript | unspecified | matrix metalloproteinase inhibitor; proteinase inhibitor; NSAID | cancer; arthritis |
| BE 16627B | N-[N-[2-[2-(hydroxyamino)-2-oxoethyl]4-methyl-1-oxopentyl]-L-seryl)-L-valine | matrix metalloproteinase inhibitor; proteinase inhibitor; NSAID | rheumatoid arthritis |
| solimastat; BB 3644 | (2S,3R)-3-[[)1S)-2,2-dimethyl-1-(2-pyridylcarbamoyl)propyl)carbamoyl]-2-methoxy-methylhexanohydroxamic acid | matrix metalloproteinase inhibitor; TNF inhibitor; proteinase inhibitor | multiple sclerosis; rheumatoid arthritis; inflammatory bowel disease; cancer |
| bindarit; AF 2838 | 2-methyl-2-[[1-(phenylmethyl)-1H-indazol-3-yl)methoxy]-propanoic acid | MCP-1 production inhibitor (reduction of mRNA expression) | rheumatoid arthritis; nephritis |
| metalloproteinase inhibitors, Syntem | unspecified | metalloproteinase inhibitor; proteinase inhibitor; NSAID | cancer; arthritis |
| TNF alpha converting enzyme inhibitors, Immunex; TACE inhibitors, Immunex | unspecified | metalloproteinase inhibitor; proteinase inhibitor; NSAID | rheumatoid arthritis; inflammation |
| MAb, CD23; GW 353430 | unspecified | monoclonal antibody; biotechnology; NSAID | rheumatoid arthritis; asthma |
| MAb, CD4; 4162W94; BW 4162W94 | unspecified | monoclonal antibody; biotechnology; NSAID | rheumatoid arthritis |
| MAb, chimeric APO1 | unspecified | monoclonal antibody; biotechnology; NSAID | rheumatoid arthritis |
| MAb, interleukin-8; MAb, IL-8; ABX IL8 | unspecified | monoclonal antibody; biotechnology; NSAID | respiratory distress syndrome; inflammatory bowel disease; rheumatoid arthritis; inflammation; psoriasis |
| MAb, tumor necrosis factor; MAb, TNF | unspecified | monoclonal antibody; biotechnology; NSAID | inflammatory bowel disease; rheumatoid arthritis |
| MAb, Fv, cytokine; CDP 870 | unspecified | monoclonal antibody; cytokine inhibitor; immunosuppressant | rheumatoid arthritis; autoimmune disease |
| MAb, 6G5.1; MAb, autoimmune disease human, Medarex; MDX CD4 | unspecified | monoclonal antibody immunosuppressant | autoimmune disease; rheumatoid arthritis |
| MAb, T cell receptor; TM 31 | unspecified | monoclonal antibody; immunosuppressant; NSAID | rheumatoid arthritis |
| MAb, 16H5; MAb, CD4; MAb, rheumatoid arthritis; MAX 16H5 | unspecified | monoclonal antibody; NSAID | rheumatoid arthritis |
| MAb, cytokines; AGT 1 | unspecified | monoclonal antibody; NSAID | rheumatoid arthritis |
| MAb, humanized tumor necrosis factor; MAb, humanized TNF; MAb, CDP571; CDP 571; BAY 103356; B 1351 | unspecified | monoclonal antibody; NSAID | septic shock; inflammation; bacterial infection; inflammatory bowel disease; rheumatoid arthritis |
| MAb, humanized, leukemia; MAb, IgG2B; LDP 03; BW 7U; CAMPATH; CAMPATH-1H | unspecified | monoclonal antibody; NSAID | rheumatoid arthritis; cancer; multiple sclerosis; transplant rejection |
| MAb, macrophage migration inhibitory factor, Picower Institute for Medical Research | unspecified | monoclonal antibody; NSAID | arthritis; asthma |
| MAb, VLA-4, humanized; MAb, very late antigen-4, humanized | unspecified | monoclonal antibody; NSAID | inflammation; rheumatoid arthritis; asthma; diabetes |

TABLE 5-continued

Current Candidate Therapeutic Interventions in Development for Arthritis.

| | | | |
|---|---|---|---|
| clenoliximab; MAb, CD4; MAb, PRIMATIZED CD4; IDEC 151; SB 217969 | immunoglobulin G 4 (human-Macaca monoclonal CE9gamma4PE gamma4-chain anti-human antigen CD4), disulfide with human-Macaca monoclonal CE9gamma4PE kappa-chain, dimer | monoclonal antibody; NSAID | rheumatoid arthritis; psoriasis; asthma |
| infliximab; MAb, tumor necrosis factor alpha; MAb, TNF-alpha; cA2; TA 650; REMICADE; AVAKINE | immunoglobulin G, anti-(human tumour necrosis factor) (human-mouse monoclonal cA2 heavy chain), disulfide with human-mouse monoclonal cA2 light chain, dimer | monoclonal antibody; NSAID | rheumatoid arthritis; Crohn disease |
| keliximab; MAb, CD4; MAb, PRIMATIZED CD4; IDEC CE9.1; SB 210396 | immunoglobulin G1 (human-Macaca monoclonal CE9.1.gamma.1-chain anti-human antigen CD 4), disulfide with human-Macaca monoclonal CE9.1.lambda.-chain, dimer | monoclonal antibody; NSAID | rheumatoid arthritis; asthma |
| mercaptoethylguanidine MEG | (2-mercaptoethyl)-guanidine | nitric oxide synthase inhibitor; COX inhibitor; NSAID | cardiovascular disease; arthritis; colitis |
| targinine; 546C88; BW 546C88 | N5-[imino(methylamino) methyl]-L-ornithine | nitric oxide synthase inhibitor; NSAID | septic shock; arthritis; kidney disease |
| nitric oxide inhibitors, Fisons | unspecified | nitric oxide synthetase inhibitor; NSAID | stroke; rheumatoid arthritis |
| CPR 3005 | Lipid analogue | NSAID | skin disease; eye disease; asthma; rheumatoid arthritis |
| CPR 3014 | Lipid analogue | NSAID | skin disease; eye disease; asthma; rheumatoid arthritis |
| CPR 3016 | Lipid analogue | NSAID | skin disease; eye disease; asthma; rheumatoid arthritis |
| ZD 2315 | unspecified | NSAID | rheumatoid arthritis |
| collagen, human type II | unspecified | NSAID | rheumatoid arthritis |
| neutrophil degranulation inhibitor; DGI | unspecified | NSAID | asthma; rheumatoid arthritis |
| recombinant soluble Fc receptor, rheumatoid arthritis; FcgammaRII | unspecified | NSAID | rheumatoid arthritis |
| telomere modulators, Geron | unspecified | NSAID | neurodegeneration; atherosclerosis; arthritis |
| anti-inflammatory agents, Phytera/Tsumura | unspecified | NSAID | rheumatoid arthritis allergy |
| antiarthritic agent, Proteus | unspecified | NSAID | rheumatoid arthritis |
| arthritis therapy, OSI/Hoechst Marion Roussel | unspecified | NSAID | arthritis |
| arthritis therapy, Sumitomo/CombiChem | unspecified | NSAID | arthritis |
| autoimmune disease therapy, AMRAD/Kaneka | unspecified | NSAID | diabetes; rheumatoid arthritis |
| CBF BS2 | unspecified | NSAID | rheumatoid arthritis |
| drug delivery system, GEOMATRIX controlled release diclofenac; diclofenac GEOMATRIX; DICLOFENAC-UNO | unspecified | NSAID | arthritis |

TABLE 5-continued

Current Candidate Therapeutic Interventions in Development for Arthritis.

| | | | |
|---|---|---|---|
| drug delivery system, GEOMATRIX controlled release naproxen; naproxen GEOMATRIX | unspecified | NSAID | rheumatoid arthritis |
| drug delivery system, transdermal flurbiprofen; flurbiprofen transdermal | unspecified | NSAID | arthritis |
| EN 08 | unspecified | NSAID | arthritis |
| FA 31A | unspecified | NSAID | arthritis |
| gene discovery, arthritis, LifeSpan | unspecified | NSAID | rheumatoid arthritis |
| gene discovery, immune system disorders, AlphaGene | unspecified | NSAID | arthritis, asthma; allergy |
| gene discovery, inflammatory diseases, Ariad/Hoechst Marion Roussel | unspecified | NSAID | inflammation; rheumatoid arthritis |
| glucocorticoid agonists, Ligand | unspecified | NSAID | inflammation; rheumatoid arthritis; inflammatory bowel disease; asthma |
| GP 44 | unspecified | NSAID | arthritis |
| GW 92527 | unspecified | NSAID | rheumatoid arthritis |
| HP 466 | unspecified | NSAID | arthritis |
| KP 106 | unspecified | NSAID | rheumatoid arthritis |
| lipophosphoglycan analogue | unspecified | NSAID | rheumatoid arthritis; atherosclerosis; HIV infection |
| lithium gammalinolenic acid + eicosapentaenioc acid; EF 5 | unspecified | NSAID | rheumatoid arthritis |
| macrophage migration inhibitory factor inhibitors, Picower Institute for Medical Research | unspecified | NSAID | arthritis; asthma |
| NBI 116 | unspecified | NSAID | multiple sclerosis; rheumatoid arthritis |
| nitric oxide modulators, Duke University | unspecified | NSAID | hypotension; cancer; rheumatoid arthritis |
| osteoarthritis therapy, Maxia; rheumatoid arthritis therapy, Maxia | unspecified | NSAID | osteoarthritis; rheumatoid arthritis |
| PKC-RACK interaction inhibitors, Telik | unspecified | NSAID | arthritis; multiple sclerosis; asthma |
| protein discovery, rheumatoid arthritis, Oxford GlycoSciences; protein discovery, rheumatoid arthritis, Oxford University | unspecified | NSAID | rheumatoid arthritis |
| pseudopterosin | unspecified | NSAID | arthritis; asthma; psoriasis |
| rheumatoid arthritis therapy, Corixa; rheumatoid arthritis therapy, organon; RA-Anergix | unspecified | NSAID | rheumatoid arthritis |
| SC 105 | unspecified | NSAID | arthritis |
| telomerase activators, Geron | unspecified | NSAID | neurodegeneration; atherosclerosis; arthritis |
| fepradinol; DALGEN; FLEXIDOL | (I)-alpha-(((2-hydroxy-1,1-dimethyl)amino) methyl)benzyl alcohol | NSAID | rheumatoid arthritis |
| CTC 23 | (OC-6-22)-diammine[[4,4'-(1,2-ethanediyldinitrilo)bis[2-pentanonato]](2-)-N,N',O,O'cobalt(1+) chloride | NSAID | viral infection, arthritis |

TABLE 5-continued

Current Candidate Therapeutic Interventions in Development for Arthritis.

| | | | |
|---|---|---|---|
| U 91502 | [3-(1,6-dihydro-1-methyl-6-oxo-4-phenyl-2-pyrimidinyl)propylidene] bisphosphonic acid tetraethyl ester | NSAID | inflammation; arthritis |
| sulfasalazine; salazosulfapyridine; azulfide; SI 88; AZULFIDINE; SALAZOPYRIN; SLAMA | 2-hydroxy-5-[[4-[(2-pyridinylamino)sulfonyl] phenyl]azo]benzoic acid | NSAID | ulcerative colitis; rheumatoid arthritis |
| seprilose; GW 80126 | 3-O-heptyl-1,2-O-(1-methylethylidene)-alpha-D-glucofuranose | NSAID | rheumatoid arthritis |
| amtolmetin guacil; ST 679; MED 15; ARTROMED; EUFANS | N-[[1-methyl-5-(4-methylbenzoyl)-1H-pyrrol-2-yl]acetyl]glycine 2-methoxyphenyl ester | NSAID; analgesic | arthritis; rheumatoid arthritis; inflammation; pain |
| monocyte chemoattractant protein-1 antagonists | unspecified | NSAID; chemokine antagonist | rheumatoid arthritis; atherosclerosis |
| TNF alpha antagonists, Texas Biotechnology | unspecified | NSAID; cytokine antagonist; apoptosis inhibitor | rheumatoid arthritis |
| S 2474 | unspecified | NSAID; DMARD; COX inhibitor; COX 2 inhibitor; immunosuppressant | rheumatoid arthritis; autoimmune disease |
| rheumatoid arthritis therapy, Birmingham University | unspecified | NSAID; peptide | rheumatoid arthritis |
| phospholipase A2 inhibitors, La Jolla | unspecified | NSAID; phospholipase inhibitor | rheumatoid arthritis; inflammatory bowel disease; asthma |
| ZYN-LINKER conjugated yttrium 90 | unspecified | NSAID; radiotherapeutic | arthritis |
| IPL 423; IZP 96001; BISPAN | unspecified | NSAID; transcription factor regulator | arthritis |
| nalmefene; nalmetrene; JF 1; INCYSTENE; ARTHENE; FENARC; CERVENE; REVEX | 17-(cyclopropylmethyl)-4,5alpha-epoxy-6-methylenemorphinan-3,14-diol | opiate antagonist; NSAID | intoxication; alcoholism; pruritis; obesity; neurological depression; rheumatoid arthritis; cystitis; trauma |
| complement inhibitors, Lidak | unspecified | peptide; immunosuppressant; NSAID | rheumatoid arthritis; systemic lupus erythematosus; autoimmune disease; reperfusion injury; respiratory distress syndrome; transplant rejection |
| rheumatoid arthritis therapy, Peptide Therapeutics | unspecified | peptide; NSAID | rheumatoid arthritis |
| rheumatoid arthritis therapy, Peptide Therapeutics | unspecified | peptide; NSAID | rheumatoid arthritis |
| TNF peptide antagonist, Tocor | unspecified | peptide; NSAID | rheumatoid arthritis |
| TNF receptor antagonist, Peptor; TNF receptor antagonist, Teva | unspecified | peptide; NSAID | rheumatoid arthritis; multiple sclerosis |
| type II collagen analogue | unspecified | peptide; NSAID | rheumatoid arthritis |
| piclamilast; RP 73401; RPR 73401 | 3-cyclopentyloxy-N-(3,5-dichloropyridin-4-yl)-4-methoxybenzamide | phosphodiesterase inhibitor; phosphodiesterase IV inhibitor; bronchodilator; NSAID | asthma; arthritis |
| lipocortin; lipomodulin; macrocortin | unspecified | phospholipase inhibitor; NSAID | asthma; arthritis |
| phospholipase A2 inhibitors, Fisons | unspecified | phospholipase inhibitor; NSAID | asthma; rheumatoid arthritis; psoriasis; inflammatory bowel disease |

TABLE 5-continued

Current Candidate Therapeutic Interventions in Development for Arthritis.

| | | | |
|---|---|---|---|
| LM 1228 | phosphoric acid mono[2-[(decylsulfonyl)amino]octyl)mono[2-(phenylmethoxy)ethyl] ester | phospholipase inhibitor; NSAID | rheumatoid arthritis |
| verteporfin; benzoporphyrin derivative; BPD-MA; CL 318952; BPDR; VISUDYNE | trans-18-ethenyl-4,4a-dihydro-3,4-bis(methoxycarbonyl)-4a,8,14,19-tetramethyl-23H,25H-benzo[b]porphine-9,13-dipropanoic acid monomethyl ester | photosensitizer; NSAID | cancer; psoriasis; arthritis; retinopathy |
| polyclonal antibody, tumor necrosis factor alpha; immunoglobulin, TNF-alpha lysate; PASSTN F-alpha | unspecified | polyclonal antibody; immunoglobulin; NSAID | rheumatoid arthritis; inflammatory bowel disease |
| iloprost; ciloprost; ZK 36374; E 1030; SH 401; ILOMED; ENDOPROST; ILOMEDIN; AIPRO | 5-[hexahydro-5-hydroxy-4-(3-hydroxy-4-methyl-1-octen-6-ynyl)-2(1H)-pentalenylidene]pentanoic acid | prostanoid; platelet antiaggregant; vasodilator; NSAID | peripheral vascular disease; thrombosis; thrombocytopenia; rheumatoid arthritis |
| Ro 320432; Ro 32-0432 | (S)-3-[8-[(dimethylamino)methyl]-6,7,8,9-tetrahydropyrido[1,2-a]indol-10-yl]-4-(1-methyl-1H-indol-3-yl)-1H-pyrrole-2,5-dione | protein kinase inhibitor; protein kinase C inhibitor; immunosuppressant; NSAID | transplant rejection; rheumatoid arthritis |
| proteinase nexin-1 elastase variant; PN-1 elastase variant | unspecified | proteinase inhibitor; biotechnology; cicatrizant | arthritis; skin ulcer |
| K 11097 | unspecified | proteinase inhibitor; cathepsin S inhibitor; NSAID | rheumatoid arthritis |
| PS 508 | unspecified | proteinase inhibitor; matrix metalloproteinase inhibitor | arthritis; inflammatory bowel disease; periodontal disease |
| matrix metalloproteinase inhibitor | unspecified | proteinase inhibitor; matrix metalloproteinase inhibitor; NSAID | arthritis; cancer; arthritis |
| BB 2983; GI 245402 | unspecified | proteinase inhibitor; matrix metalloproteinase inhibitor; TNF inhibitor; proteinase inhibitor; NSAID | rheumatoid arthritis osteoporosis; inflammatory bowel disease |
| cysteine proteinase inhibitor, SynPhar/British Biotech | unspecified | proteinase inhibitor; NSAID | rheumatoid arthritis; osteoporosis; cancer; osteoarthritis |
| P 34081 | unspecified | proteinase inhibitor; NSAID | arthritis |
| P 35012 | unspecified | proteinase inhibitor; NSAID | arthritis |
| P 35016 | unspecified | proteinase inhibitor; NSAID | arthritis |
| WY 48989 | 4-[[2-(7-chloro-2-phenyl-2H-pyrazolo[4,3-c]quinolin-4-yl)ethyl]amino]benzonitrile | proteinase inhibitor; NSAID | arthritis |
| BABIM | bis(5-amidino-2-benzimidazo)methane | proteinase inhibitor; NSAID | arthritis |
| peldesine; BCX 34; BCX 34B | 2-amino-1,5-dihydro-7-(3-pyridinylmethyl)-4H-pyrrolo[3,2-d]pyrimidin-4-one | purine nucleoside phosphorylase inhibitor; immunosuppressant; NSAID | cancer; psoriasis; rheumatoid arthritis transplant rejection; eye disease; dermatitis; HIV infection |
| CH 799 | unspecified | purine nucleoside phosphorylase inhibitor; NSAID | rheumatoid arthritis; inflammatory bowel disease; cancer |

TABLE 5-continued

Current Candidate Therapeutic Interventions in Development for Arthritis.

| | | | |
|---|---|---|---|
| purine nucleoside phosphorylase inhibitors, Chiroscience; PNP inhibitors, Chiroscience | unspecified | purine nucleoside phosphorylase inhibitor; NSAID | cancer; psoriasis; rheumatoid arthritis; transplant rejection |
| CI 1000; PD 141955 | 2-amino-1,5-dihydro-7-(3-thienylmethyl)-4H-pyrrolo[3,2-d]pyrimidin-4-one | purine nucleoside phosphorylase inhibitor; NSAID | cancer; psoriasis; rheumatoid arthritis |
| mycophenolate mofetil; RS 61443; CellCept | (E)-6-(1,3-dihydro-4-hydroxy-6-methoxy-7-methyl-3-oxo-5-isobenzofuranyl)-4-methyl-4-hexenoic acid 2-(4-morpholinyl)ethyl ester | purine synthesis inhibitor; immunosuppressant; NSAID | transplant rejection; rheumatoid arthritis; asthma; restenosis; kidney disease; systemic lupus erythematosus |
| fenretinide; HPR, 4; 4HPR; RAHA; McN R1967 | N-(4-hydroxyphenyl)retinamide | retinoid; NSAID | rheumatoid arthritis; cancer |
| rheumatoid arthritis therapy | unspecified | SAIK immunomodulation | rheumatoid arthritis |
| SR 31747 | (Z)-N[3-chloro-4-cyclohexylphenyl)-2-propenyl]-N-ethyl-cyclohexanamine hydrochloride | sigma antagonist; immunosuppressant; NSAID | autoimmune disease; arthritis |
| stromelysin inhibitors, Affymax | unspecified | stromelysin inhibitor; proteinase inhibitor; matrix metalloproteinase inhibitor; NSAID | arthritis |
| stromelysin inhibitors, Agouron | unspecified | stromelysin inhibitor; proteinase inhibitor; matrix metalloproteinase inhibitor; NSAID | cancer; arthritis |
| drug delivery system, biodegradable micellar paclitaxel; paclitaxel micellar | unspecified | taxane; DMARD; NSAID | rheumatoid arthritis; multiple sclerosis |
| etanercept; tumor necrosis factor receptor; TNFr; TNR 001; ENBREL | unspecified | TNF inhibitor; immunosuppressant; NSAID; analgesic | rheumatoid arthritis heart failure; diabetes; pain; endometriosis; autoimmune disease |
| soluble tumor necrosis factor-a receptor type 1; sTNFR1 | unspecified | TNF inhibitor; NSAID | rheumatoid arthritis |
| CC 1080 | unspecified | TNF inhibitor; NSAID | arthritis; cancer; multiple sclerosis |
| ITF 1779 | unspecified | TNF inhibitor; NSAID | rheumatoid arthritis; psoriasis; inflammatory bowel disease |
| MNX 160 | Unspecified | TNF inhibitor; NSAID | rheumatoid arthritis diabetes; multiple sclerosis |
| thalidomide; SYNOVIR; THALOMID | N-(2,6-dioxo-3-piperidyl)phthalimide | TNF modulator; immunosuppressant | cachexia; diarrhea; leprosy; rheumatoid arthritis; transplant rejection; cancer; Crohn disease |
| CC 1069 | beta-(3,4-dimethoxyphenyl)-1,3-dihydro-1,3-dioxo-2H-isoindole-2-propanamide | TNF modulator; NSAID | cachexia; arthritis cancer |
| MHC expression inhibitors, BLSI | unspecified | transcription inhibitor; NSAID | rheumatoid arthritis; systemic lupus erythematosus |
| SC 106 | unspecified | triglyceride; NSAID | rheumatoid arthritis |
| TCR peptide, rheumatoid arthritis | unspecified | vaccine | rheumatoid arthritis |
| vaccine, arthritis; vaccine, Vbeta14 T cell receptor; AI 205; IR 205 | unspecified | vaccine | rheumatoid arthritis |
| vaccine, arthritis; vaccine, Vbeta17 T cell receptor; AI 204; IR 204 | unspecified | vaccine | rheumatoid arthritis |

TABLE 5-continued

Current Candidate Therapeutic Interventions in Development for Arthritis.

| | | | |
|---|---|---|---|
| vaccine, rheumatoid arthritis; IR 501; AI 501 | unspecified | vaccine | rheumatoid arthritis |
| non-ionic surfactant vesicles; NISV | unspecified | vaccine adjuvant; immunosuppressant | rheumatoid arthritis; asthma inflammation |
| vaccine, TNF alpha | unspecified | vaccine; cytokine antagonist | rheumatoid arthritis; Crohn disease; cachexia; asthma |
| MAb, HRF1; vaccine, rheumatoid arthritis | unspecified | vaccine; monoclonal antibody | rheumatoid arthritis |
| MHC-vaccine, rheumatoid arthritis; AGDR 4/1; Anervax; RA-Anervax | unspecified | vaccine; peptide | rheumatoid arthritis |
| VCAM antagonists, Texas Biotechnology | unspecified | vascular cell adhesion molecule inhibitor; NSAID | atherosclerosis; rheumatoid arthritis multiple sclerosis |
| TBC 609 | unspecified | vascular cell adhesion molecule inhibitor; NSAID; peptide | atherosclerosis; rheumatoid arthritis multiple sclerosis |
| TBC 772 | unspecified | vascular cell adhesion molecule inhibitor; NSAID; peptide | atherosclerosis; rheumatoid arthritis; multiple sclerosis |
| 20-epi-1,25 dihydroxyvitamin D3; MC 1288; IE | (1alpha,3beta,5Z,7E,20 S)-9,10-secocholesta-5,7,10(19)-triene-1,3,25-triol | vitamin D3 analogue; immunosuppressant | diabetes; transplant rejection; arthritis |
| ZD 7349 | unspecified | VLA 4 antagonist; integrin antagonist; NSAID; cell adhesion inhibitor | multiple sclerosis; arthritis |

TABLE 6

Current Candidate Therapeutic Interventions in Development for the Treatment of COPD

| Product Name | Chemical Name | Action | Indication |
|---|---|---|---|
| 3323W | unspecified | 5 lipoxygenase inhibitor | asthma |
| bunaprolast; U 66858 | 2-butyl-4-methoxy-1-naphthalenol acetate | 5 lipoxygenase inhibitor | asthma |
| BW B70C | N-[3-[3-(4-fluorophenoxy)phenyl]-1-methyl-2-propenyl]-N-hydroxyurea | 5 lipoxygenase inhibitor | asthma |
| CMI 977 | unspecified | 5 lipoxygenase inhibitor | asthma |
| docebenone; AA 861 | 6-(12-hydroxy-5,10-dodecadiynyl)-2,3,5-trimethyl-1,4-benzoquinone | 5 lipoxygenase inhibitor | asthma; heart failure |
| drug delivery system, controlled release zileuton; zileuton | unspecified | 5 lipoxygenase inhibitor | asthma |
| FR 110302 | 2,2-dibutyl-1,2,3,4-tetrahydro-5-(2-quinolinyl-methoxy)-1-naphthalenol | 5 lipoxygenase inhibitor | asthma |
| L 691816 | 5-[3-[1-(4-chlorobenzyl)-4-methyl-6-[(5-phenylpyridin-2-yl)methoxy]-4,5-dihydro-1H-thiopyrano[2,3,4-c,d]indol-2-yl]-2,2-dimethyl-propyl]-1H-tetrazole | 5 lipoxygenase inhibitor | asthma |
| L 739010 | 1,6-anhydro-3-C-[6-[[[7-cyano-5-(3-furanyl)-2-naphthalenyl]oxy]methyl]-2-pyridinyl]-2,4-dideoxy-beta-D-threo-hexopyranose | 5 lipoxygenase inhibitor | asthma |
| linazolast; TMK 688; YM 257 | 4-[5-[[2-[4-(diphenylmethoxy)-1-piperidinyl]-ethyl]amino]-5-oxo-1,3-pentadienyl]-2-methoxy-phenylcarbonic acid ethyl ester | 5 lipoxygenase inhibitor | asthma; rhinitis |
| PF 5901 | alpha-pentyl-3-(2-quinolinylmethoxy)benzene-methanol | 5 lipoxygenase inhibitor | asthma |
| R 85355 | Unspecified | 5 lipoxygenase inhibitor | asthma; psoriasis; inflammatory bowel disease |
| SB 202235 | (S)-N-(2,3-dihydro-6-phenylmethoxy-3-benzo-furanyl)urea | 5 lipoxygenase inhibitor | asthma |
| TZI 41127 | 4-(5-methoxy-3-methyl-1H-indol-2-yl)-2,6-dimethylphenol | 5 lipoxygenase inhibitor | asthma |
| WY 50295; WY 50295 tromet | (S)-alpha-methyl-6-(2-quinolinylmethoxy)-2-naphthaleneacetic acid | 5 lipoxygenase inhibitor | asthma; rhinitis |
| ZD 4407 | (2S-trans)-1,3-dihydro-1-methyl-5-[[4-(tetra-hydro-4-hydroxy-2-methyl-2H-pyran-4-yl)-2-thienyl]thio]-2H-indol-2-one | 5 lipoxygenase inhibitor | asthma |

TABLE 6-continued

Current Candidate Therapeutic Interventions in Development for the Treatment of COPD

| Product Name | Chemical Name | Action | Indication |
| --- | --- | --- | --- |
| CGS 25997 | (2S)-(−)-2-[[N-(aminocarbonyl)-N-hydroxy-amino]methyl]-7-(4-fluorophenoxy)-1,4-benzo-dioxan | 5 lipoxygenase inhibitor; NSAID | asthma; inflammation |
| CHF 1909 | unspecified | 5 lipoxygenase inhibitor; NSAID | inflammation; asthma |
| E 6080 | 4-[[(6-hydroxy-4,4,7-trimethyl-2-benzo-thiazolyl)amino]methyl]benzenesulfonamide monohydrochloride | 5 lipoxygenase inhibitor; NSAID | asthma; inflammation |
| GR 80907 | unspecified | 5 lipoxygenase inhibitor; NSAID | asthma; inflammation |
| L 651392 | 4-bromo-2,7-dimethoxy-3H-phenothiazin-3-one | 5 lipoxygenase inhibitor; NSAID | inflammation; bacterial infection; asthma |
| L 663536; MK 886 | 1-[(4-chlorophenyl)methyl]-3-[(1,1-dimethyl-ethyl)thio]alfa,alfa-diethyl-5-(1-methylethyl)-1H-indole-2-propanoic acid | 5 lipoxygenase inhibitor; NSAID | inflammation; asthma; psoriasis |
| L 699333 | 2-[2-[1-[(4-chlorophenyl)methyl]-4,5-dihydro-4-methyl-6-[(5-phenyl-2-pyridinyl)methoxy]-1H-thiopyrano[2,3,4-cd]indol-2-yl]ethoxy]-butanoic acid | 5 lipoxygenase inhibitor; NSAID | asthma; inflammation |
| SC 45662 | unspecified | 5 lipoxygenase inhibitor; NSAID | inflammation; asthma; psoriasis; inflammatory bowel disease |
| ZD 2138; ICI D2138 | 6-[[3-fluoro-5-(tetrahydro-4-methoxy-2H-pyran-4-yl)phenoxy]methyl]-1-methyl-2(1H)-quinolinone | 5 lipoxygenase inhibitor; NSAID | arthritis; asthma |
| ZD 7717; ICI D7717 | 7-[[3-fluoro-5-(tetrahydro-4-methoxy-2H-pyran-4-yl)phenyl]thio]-4-methyl-2H-1,4-benzoxazin-3(4H)-one | 5 lipoxygenase inhibitor; NSAID | asthma; inflammation |
| zileuton; A 64077; ZYFLO | N-(1-benzo[b]thien-2-ylethyl)-N-hydroxyurea | 5 lipoxygenase inhibitor; NSAID | inflammation; asthma |
| GW 328267 | unspecified | adenosine agonist; adenosine A2 agonist | asthma |
| midaglizole; DG 5128 | 2-[2-(4,5-dihydro-1H-imidazol-2-yl)-1-phenyl-ethyl]pyridine | alpha adrenergic antagonist; alpha2 adrenergic antagonist | asthma; diabetes |
| melanocortin receptor-1 modulators, | unspecified | analgesic; melanocortin agonist; melanocortin MC1 agonist | asthma; pain; nephritis |
| LA 351 | 5H-(1)-benzopyrano(2,3-b)-pyridin-5-one | analgesic; NSAID | inflammation; pain; asthma |
| HP 228 | N-acetyl-Nleu-Gln-His-Phe-Arg-Trp-Gly-amide | analgesic; NSAID; peptide; melanocortin agonist | pain; inflammation; asthma; cachexia |
| L 680833 | [S-(R*,S*)]-4-[[3,3-diethyl-1-[[[1-(4-methylphenyl)butyl]amino]carbonyl]-4-oxo-2-azetidinyl]oxy]benzeneacetic acid | antibiotic; elastase inhibitor; beta lactam; proteinase inhibitor | emphysema |
| anti-inflammatory macrolide analogues, | unspecified | antibiotic; macrolide | asthma; inflammation |
| SB 226882 | 4-[4-(4-fluorophenyl)-1-(4-piperidinyl)-1H-imidazol-5-yl]-N-methyl-2-pyrimidinamine | antifungal; MAP kinase inhibitor; signal trans-duction inhibitor; imidazole | inflammation; asthma; rheumatoid arthritis |
| antioxidants | unspecified | antioxidant | respiratory distress syndrome; stroke; reper-fusion injury; asthma |
| U 74389F | 21-[4-(2,6-di-1-pyrrolidinyl-4-pyrimidinyl)-1-piperazinyl]pregna-1,4,9(11)-triene-3,20-dione monomethanesulfonate | antioxidant | emphysema |
| synthetic catalytic scavenger analogues; SCS analogues | unspecified | antioxidant; free radical scavenger | stroke; trauma; atherosclerosis; neuro-degeneration; asthma |
| VANTOX | unspecified | antioxidant; NSAID | asthma; Parkinson disease; Alzheimer disease; stroke |
| Z 4003 | 2-[1-[4-(2-methylpropyl)phenyl]ethyl]-4-thiazolidine-carboxylic acid | antioxidant; NSAID | angina; inflammation; emphysema |
| antisense oligonucleotide, interleukin-5; antisense oligonucleotide, IL-5 | unspecified | antisense; oligo-nucleotide;, | asthma |
| D 2522 | unspecified | beta adrenergic agonist | asthma |
| drug delivery system, liposome terbutaline sulfate; terbutaline sulfate liposome | unspecified | beta adrenergic agonist | asthma |

TABLE 6-continued

Current Candidate Therapeutic Interventions in Development for the Treatment of COPD

| Product Name | Chemical Name | Action | Indication |
|---|---|---|---|
| nardeterol; SOM 1122 | alpha-[[[3-(1H-benzimidazol-1-yl)-1,1-dimethylpropyl]amino]methyl]-2-fluoro-4-hydroxybenzenemethanol | beta adrenergic agonist | asthma |
| procaterol; procaterol hydrochloride; OPC 2009; CI 888; MEPTIN; PRO-AIR; ONSUKIL; BRON NOVO; PROMAXOL; MASACIN; PROCADIL; PROPULUM | 2(1H)-quinolone, 8-hydroxy-5-(1-hydroxy-2-(1-methylethyl)amino)butyl)—, monohydrochloride, (R*S*) (+,−) | beta adrenergic agonist | asthma |
| RP 58802B | alpha-[[[3-(1H-benzimidazol-1-yl)-1-methylpropyl]amino]methyl]-4-hydroxy-3-methoxybenzenemethanol | beta adrenergic agonist | asthma |
| SL 2021 | unspecified | beta adrenergic agonist | asthma |
| CEDO 20433 | unspecified | beta adrenergic agonist; beta2 adrenergic agonist | asthma |
| drug delivery system, liposome salbutamol sulfate; salbutamol sulfate liposome | unspecified | beta adrenergic agonist; beta2 adrenergic agonist | asthma |
| drug delivery system, OROS oral controlled release salbutamol; salbutamol | unspecified | beta adrenergic agonist; beta2 adrenergic agonist | asthma |
| drug delivery system, PULSINCAP salbutamol; salbutamol PULSINCAP | unspecified | beta adrenergic agonist; beta2 adrenergic agonist | asthma |
| drug delivery system, salbutamol sustained release; salbutamol sustained release | unspecified | beta adrenergic agonist; beta2 adrenergic agonist | asthma |
| drug delivery system, transdermal salbutamol; salbutamol transdermal | unspecified | beta adrenergic agonist; beta2 adrenergic agonist | asthma |
| drug delivery system, transdermal salbutamol; salbutamol transdermal; albuterol transdermal | unspecified | beta adrenergic agonist; beta2 adrenergic agonist | asthma |
| drug delivery system, transdermal TheraDerm-LRS salbutamol; salbutamol TheraDerm-LRS | unspecified | beta adrenergic agonist; beta2 adrenergic agonist | asthma |
| formoterol, (R,R); (R,R)-formoterol | [R-(R*,R*)-(+,−)-N-[2-hydroxy-5-[1-hydroxy-2-[[2-(4-methoxypheny)-1-methylethyl]-amino]ethyl]phenyl]formamide | beta adrenergic agonist; beta2 adrenergic agonist | asthma |
| formoterol; eformoterol; formoterol fumarate; YM 08316; BD 40A; CGP 25827; CGP 25827A; ATOCK; FORADIL; ASMATEC; SINASFIX; LEMOTEC; OXIS | (R*,R*)-(+,−)-N-[2-hydroxy-5-[1-hydroxy-2-[[2-(4-methoxypheny)-1-methylethyl]amino]-etyl]phenyl]formamide | beta adrenergic agonist; beta2 adrenergic agonist | asthma |
| picumeterol; picumeterol fumarate; GR 114297; GR 114297 X; GR 63411 | (−)-(R)-4-amino-3,5-dichloro-alpha-[[[6-[2-(2-pyridinyl)ethoxy]hexyl]amino]methyl]benzenemethanol | beta adrenergic agonist; beta2 adrenergic agonist | asthma |
| salmeterol, (R)-; (R)-salmeterol | (R)-4-hydroxy-alpha.1-[[[6-(4-phenylbutoxy)-hexyl]amino]methyl-1,3-benzenedimethanol | beta adrenergic agonist; beta2 adrenergic agonist | asthma |
| bambuterol; BWD 2183; BAMBEC | dimethylcarbamic acid 5-[2-[(1,1-dimethyl-ethyl)-amino]-1-hydroxyethyl]-1,3-phenylene ester | beta adrenergic agonist; beta2 adrenergic agonist; bronchodilator | asthma |
| broxaterol; Z 1170; SUMMAIR | (+,−)-3-bromo-alpha-[(tert-butylamino)-methyl]-5-isoxazolemethanol | beta adrenergic agonist; beta2 adrenergic agonist; bronchodilator | asthma |
| etanterol | 5-amino-alpha-[[(p-hydroxy-alphamethylphen-ethyl)amino]methyl]-m-xylene-alpha,alpha'-diol | beta adrenergic agonist; beta2 adrenergic agonist; bronchodilator | asthma |
| LAS 32521 | unspecified | beta adrenergic agonist; beta2 adrenergic agonist; bronchodilator | asthma |
| levosalbutamol; levalbuterol; salbutamol, (R)-; (R)-salbutamol; (R)-albuterol; levalbuterol sulfate; XOPENEX | (R)-alpha'-[[(1,1-dimethylethyl)amino]methyl]-4-hydroxy-1,3-benzenedimethanol | beta adrenergic agonist; beta2 adrenergic agonist; bronchodilator | asthma |

TABLE 6-continued

Current Candidate Therapeutic Interventions in Development for the Treatment of COPD

| Product Name | Chemical Name | Action | Indication |
|---|---|---|---|
| salmeterol + fluticasone; fluticasone + salmeterol; SERETIDE; ADVAIR DISKUS; VIANI | unspecified | beta adrenergic agonist; beta2 adrenergic agonist; bronchodilator; corticosteroid | asthma |
| salmeterol; salmaterol; GR 33343X; SN 408; GR 33343G; SEREVENT | 4-hydroxy-alpha.1-[[[6-(4-phenylbutoxy)-hexyl]amino]methyl-1,3-benzenedimethanol | beta adrenergic agonist; beta2 adrenergic agonist; bronchodilator | asthma; pulmonary obstructive disease |
| TA 2005 | [R-(R*,R*)]-8-hydroxy-5-[1-hydroxy-2-[[2-(4-methoxyphenyl)-1-methylethyl]amino]ethyl]-2(1H)-quinolinone monohydrochloride | beta adrenergic agonist; beta2 adrenergic agonist; bronchodilator | asthma |
| SM 11044 | [R-(R*,S*)]-1-[3-(3,4-dihydroxypheny)-2-[[3-(4-fluorophenyl)propyl]amino]-3-hydroxy-1-oxopropyl]pyrrolidine monohydrobromide | beta adrenergic agonist; beta3 adrenergic agonist; leukotriene antagonist; leukotriene D4 antagonist | asthma |
| AR C68397AA; AR-C68397AA; ARL 68397 | 4-hydroxy-7-[2-[[2-[[3-(2-phenylethoxy)-propyl]sulfonyl]ethyl]amino]ethyl-2(3H)-benzothiazolone monohydrochloride | beta adrenergic agonist; broncholidator | asthma; pulmonary obstructive disease; rhinitis |
| drug delivery system, transdermal controlled release tulobuterol; tulobuterol transdermal; HOKUNALIN TAPE | unspecified | beta adrenergic agonist; bronchodilator | asthma |
| tulobuterol; HN 078; C 78; HSR 078A; BRELOMAX; BREMAX; ATENOS; BERACHIN; HOKUNALIN | alpha-[(tert-butylamino)methyl]-o-chlorobenzyl alcohol | beta adrenergic agonist; bronchodilator | asthma |
| drug delivery system, HALO salbutamol; salbutamol HALO | unspecified | beta2 adrenergic agonist; beta adrenergic agonist | asthma |
| allergy immunogen, migis epsilon | unspecified | , | allergy; asthma |
| allergy therapy, *E. coli* enterotoxin B subunit-antigen fusion protein | unspecified | , | rhinitis; asthma |
| DNase, second generation | unspecified | , | bronchitis; cystic fibrosis |
| emoctakin; interleukin-8 | unspecified | , | asthma |
| fusion protein, IL-10 | unspecified | , | asthma; inflammatory bowel disease |
| secretory leukocyte proteinase inhibitor, truncated; TEI 7361 | unspecified | , | respiratory distress syndrome; emphysema |
| antisense oligonucleotide, adenosine A1 receptor antisense oligonucleotide, asthma; EPI 2010; E 2010; | unspecified | ,; antisense; oligo-nucleotide; mRNA translation inhibitor | asthma |
| interleukin-4 receptor; IL-4r; | unspecified | ,; cytokine antagonist | inflammation; asthma |
| soluble interleukin-5 receptor; alpha; IL-5Ra | unspecified | ,; cytokine antagonist | asthma |
| interleukin-1 receptor; IL-1r; HJ 1306 | unspecified | ,; cytokine inhibitor; immunosuppressant | asthma |
| anakinra; interleukin-1 receptor antagonist; IL-1ra; interleukin-1 inhibitor; ANTRIL | N2-L-methionylinterleukin 1 receptor antagonist (human isoform x reduced) | ,; cytokine inhibitor; immunosuppressant; NSAID | rheumatoid arthritis; inflammatory bowel disease; transplant rejection; asthma; septic shock |
| interleukin-12; IL-12; natural killer stimulatory factor; NKSF; edodekin alfa; Ro 247472; Ro 24-7472 | unspecified | ,; cytokine; immunostimulant | asthma |
| dornase alfa; deoxyribo-nuclease; DNase; PULMOZYME | deoxyribonuclease, (human clone 18-1 protein moiety) | ,; deoxyribonuclease; enzyme | cystic fibrosis; bronchitis; pulmonary obstructive disease; systemic lupus erythematosus |
| enkephalinase | unspecified | ,; enkephalinase; enzyme | asthma; eye disease |
| platelet-activating factor acetylhydrolase; PAF-AH; SUN Y7016; PAFASE | unspecified | ,; hydrolase | respiratory distress syndrome; asthma; inflammatory bowel disease |
| IgE receptors, soluble, CorBec | unspecified | ,; immunosuppressant | asthma |

TABLE 6-continued

Current Candidate Therapeutic Interventions in Development for the Treatment of COPD

| Product Name | Chemical Name | Action | Indication |
|---|---|---|---|
| antisense oligonucleotide, ICAM-1; antisense oligonucleotide, intracellular adhesion molecule-1; ISIS 2302 | d[(R)-P-thio](G-C-C-C-A-A-G-C-T-G-G-C-A-T-C-C-G-T-C-A) DNA | ,; immunosuppressant; antisense; oligo- nucleotide; NSAID | rheumatoid arthritis; psoriasis; inflammatory bowel disease; asthma |
| lenercept; tumor necrosis factor receptor fusion protein; TNF receptor fusion protein; Ro 452081; TENEFUSE | unspecified | ,; immunosuppressant; NSAID | rheumatoid arthritis; asthma; septic shock; multiple sclerosis |
| MAb, AL 901; MAb, IgE; AL 901; CGP 51901; IGE 025A | unspecified | ,; monoclonal antibody | allergy; rhinitis; asthma |
| MAb, CD23; MAb, PRIMATIZED CD23 | unspecified | ,; monoclonal antibody | asthma; allergy; rhinitis |
| MAb, IgE; MAb, E25 | unspecified | ,; monoclonal antibody | asthma; allergy; rhinitis |
| MAb, interleukin-4; SB 240683 | unspecified | ,; monoclonal antibody | asthma |
| MAb, interleukin-5; MAb, IL-5; SCH 55700; CDP 835 | unspecified | ,; monoclonal antibody; immunosuppressant | asthma |
| clenoliximab; MAb, CD4; MAb, PRIMATIZED CD4; IDEC 151; SB 217969 | immunoglobulin G 4 (human-Macaca monoclonal CE9gamma4PE gamma4-chain anti-human antigen CD4), disulfide with human-Macaca monoclonal CE9gamma4PE kappa-chain, dimer | ,; monoclonal antibody; NSAID | rheumatoid arthritis; psoriasis; asthma |
| keliximab; MAb, CD4; MAb, PRIMATIZED CD4; IDEC CE9.1; SB 210396 | immunoglobulin G1 (human-Macaca monoclonal CE9.1.gamma.1-chain anti-human antigen CD 4), disulfide with human-Macaca monoclonal CE9.1.lambda.-chain, dimer | ,; monoclonal antibody; NSAID | rheumatoid arthritis; asthma |
| MAb, macrophage migration inhibitory factor, | unspecified | ,; monoclonal antibody; NSAID | arthritis; asthma |
| MAb, VLA-4, humanized; MAb, very late antigen-4, humanized | unspecified | ,; monoclonal antibody; NSAID | inflammation; rheumatoid arthritis; asthma; diabetes |
| neutrophil degranulation inhibitor; DGI | unspecified | ,; NSAID | asthma; rheumatoid arthritis |
| RecepTox-Fce | unspecified | ,; peptide; fusion toxin | asthma; allergy |
| lipocortin; lipomodulin; macrocortin | unspecified | ,; phospholipase inhibitor; NSAID | asthma; arthritis |
| eglin C | unspecified | ,; proteinase inhibitor | septic shock; emphysema |
| EPI-HNE-1 | unspecified | ,; proteinase inhibitor | cystic fibrosis; emphysema |
| alpha-1-antitrypsin; TgAAT; BAY 105233 | unspecified | ,; proteinase inhibitor; elastase inhibitor | emphysema; cystic fibrosis; genetic disorder |
| LEX 043 | unspecified | ,; proteinase inhibitor; serine proteinase inhibitor | inflammation; asthma |
| neutral endopeptidase; NEP | unspecified | ,; proteinase; metalloproteinase | cancer; migraine; inflammatory bowel disease; inflammation; asthma; respiratory disease |
| ribozymes, asthma | unspecified | ,; ribozyme; oligo- nucleotide | asthma |
| secretory leukocyte proteinase inhibitor; serine leukocyte proteinase inhibitor; SLPI; serine proteinase inhibitor; SPI; SLPI | unspecified | ,; serine proteinase inhibitor; proteinase inhibitor | asthma |
| vaccine, TNF alpha | unspecified | ,; vaccine; cytokine antagonist | rheumatoid arthritis; Crohn disease; cachexia; asthma |
| bradykinin2 antagonists, | unspecified | bradykinin antagonist | asthma |
| NOVA 567; NPC 567 | N2-D-arginyl-3-(trans-4-hydroxy-L-proline)-7-D-phenylalaninebradykinin | bradykinin antagonist; cicatrizant; peptide; NSAID | asthma; skin ulcer; inflammation |
| icatibant; icatibant acetate; HOE 140 | D-arginyl-L-arginyl-L-prolyl-trans-4-hydroxy-L-prolylglycyl-3-(2-thienyl)-L-alanyl-L-seryl-D-1,2,3,4-tetrahydro-3-isoquinolincarbonyl-L-(2alfa,3abeta,7abeta)-octahydro-1H-indole-2-carbonyl-L-arginine | bradykinin antagonist; NSAID | asthma; inflammation; rhinitis; osteoarthritis |
| NPC 17731 | N2-D-arginyl-3-(trans-4-hydroxy-L-proline)-7-(trans-4-propoxy-D-proline)-8-[L-(2alpha, 3abeta,7abeta)-octahydro-1H-indole-2-carboxylic acid]-bradykinin | bradykinin antagonist; NSAID | inflammation; septic shock; asthma |

TABLE 6-continued

Current Candidate Therapeutic Interventions in Development for the Treatment of COPD

| Product Name | Chemical Name | Action | Indication |
| --- | --- | --- | --- |
| FR 173657 | (E)-3-[6-(acetylamino)-3-pyridinyl]-N-[2-[[2,4-dichloro-3-[[(2-methyl-8-quinolinyl)oxy]-methyl]phenyl]methylamino]-2-oxoethyl-2-propenamide | bradykinin antagonist; NSAID; analgesic | asthma; inflammation; pain |
| dametralast; LA 2851 | 7-methylpyrazolo[1,5-a]-1,3,5-triazine-2,4-diamine | bronchodilator | asthma |
| F 3121 | 1,4-dihydro-3-amino-4-oxo-1-((3-trifluoro-methyl)phenyl)pyridazine | bronchodilator | asthma |
| HOE 058A | unspecified | bronchodilator | asthma |
| KF 15570 | imidazo(4,5-c)quinoline-4-one | bronchodilator | asthma |
| KF 17625 | 5-phenyl-(3H)-imidazo(4,5-c) (1,8)-naphythyridin-4-(5H)-one | bronchodilator | asthma |
| LM 3339 | 2-(7,8-dichloro-2,3-dihydro-3,3-dimethyl-1-benzoxepin-5-yl)pyridine 1-oxide | bronchodilator | asthma |
| PF 904 | 1-ethyl-6-methyl-1H-pyrazino[2,3-c][1,2,6]-thiadiazin-4-amine 2,2-dioxide | bronchodilator | asthma |
| RU 32210 | unspecified | bronchodilator | asthma |
| S 123701 | unspecified | bronchodilator | asthma |
| SC 109 | unspecified | bronchodilator | asthma; pulmonary fibrosis |
| SDZ MKS492 | (R)-8-[[1-(3,4-dimethoxyphenyl)-2-hydroxy-ethyl]amino]-3,7-dihydro-7-(2-methoxyethyl)-1,3-dimethyl-1H-purine-2,6-dione | bronchodilator | asthma |
| LY 150310 | 1-(1,2,3,4-tetrahydro-1-naphthalenyl)-1H-imidazole mononitrate | bronchodilator; imidazole | asthma |
| fenspiride; KSP 193; PNEUMORAL; ESPIRAN | 8-(2-phenylethyl)-1-oxa-3,8-diazaspiro[4.5]-decan-2-one | bronchodilator; NSAID | inflammation; asthma |
| Ro 251553; Ro 25-1553 | N-acetyl-His-Ser-Asp-Ala-Val-Phe-Thr-Glu-Asn-Tyr-Thr-Lys-Leu-Arg-Lys-Gln-NLeu-Ala-Ala-Lys-Lys-Tyr-Leu-Asn-Asp-Leu-Lys-Lys-Gly-Gly-Thr-amide, cyclic (25−>21)-peptide | bronchodilator; VIP agonist | asthma |
| CD 349 | 1,4-dihydro-2,6-dimethyl-4-(3-nitrophenyl)-3,5-pyridinedicarboxylic acid 2-(nitrooxy)-propyl 3-(nitrooxy)propyl ester | calcium antagonist; bronchodilator | hypertension; asthma; angina |
| RWJ 22108 | 4-(2-chloro-6-fluorophenyl_-1,4,6,7,8,9-hexa-hydro-2-methylthiepino[3,2-b]pyridine-3-carboxylic acid 5,5-dioxide 2-[methyl(phenyl-methyl)amino]ethyl ester | calcium antagonist; bronchodilator | asthma |
| MDL 27399 | N-[1-[N-[N-(4-methoxy-1,4-dioxobutyl)-L-alanyl]-L-alanyl]-L-prolyl]-L-phenylalanine methyl ester | cathepsin G inhibitor; proteinase inhibitor | emphysema |
| VLA4 integrin antagonist | unspecified | cell adhesion inhibitor; integrin antagonist; VLA 4 antagonist; NSAID | asthma; rheumatoid arthritis; multiple sclerosis |
| CCR3 inhibitors | unspecified | chemokine antagonist | asthma |
| chloride channel blocker | unspecified | chloride channel blocker | asthma; pulmonary obstructive disease |
| AQRA 721 | N-1-azabicyclo[2.2.2]oct-3-yl-6,11-dihydro-6-oxo-5H-dibenz[b,e]azepine-11-carboxamide | cholinergic antagonist; bronchodilator | asthma |
| DAC 5889; DAC 6150 | 6-oxo-3-phenyl-3-piperidinecarboxylic acid 1-azabicyclo[2.2.2]oct-3-yl ester | cholinergic antagonist; muscarinic antagonist; muscarinic M1 antagonist; broncho-dilator | asthma |
| rispenzepine; ulvenzepine; DF 594 | 6,11-dihydro-11-[(1-methyl-3-piperidinyl)-carbonyl]-5H-pyrido[2,3-b][1,5]benzodiazepin-5-one | cholinergic antagonist; muscarinic antagonist; muscarinic M1 antagonist; muscarinic M3 antagonist; anti-spasmodic; broncho-dilator | asthma; bronchitis |
| revatropate; UK 112166 | (R)-3-quinuclidyl-(2S)-2-hydroxymethyl-4-(R)-methylsulfinyl-2-phenylbutyrate | cholinergic antagonist; muscarinic M3 antagonist; muscarinic antagonist | asthma; pulmonary obstructive disease |
| chymase inhibitors, | unspecified | chymase inhibitor; NSAID | asthma; inflammation; rhinitis |
| CMI 903 | unspecified | complement inhibitor | asthma |
| anti-inflammatory cortico-steroids | unspecified | corticosteroid | psoriasis; asthma |

TABLE 6-continued

Current Candidate Therapeutic Interventions in Development for the Treatment of COPD

| Product Name | Chemical Name | Action | Indication |
|---|---|---|---|
| budesonide; budesonide propionate; S 1320; PREFERID; PULMICORT; RHINOCORT; ENTOCORT; NARICORT; INFLAMMIDE; BETACTIN; ELTAIR; HORACORT; RHINOCORT AQUA | (11beta,16alpha)-16,17-[butylidenebis(oxy)]-11,21-dihydroxypregna-1,4-diene-3,20-dione | corticosteroid | asthma; skin disease; inflammation; rhinitis; ulcerative colitis; Crohn disease |
| butixocort propionate; JO 1222 | (11beta)-11-hydroxy-17-(1-oxobutoxy)-21-[(1-oxopropyl)thio)]pregn-4-ene-3,20-dione | corticosteroid | inflammation; asthma; inflammatory bowel disease |
| CGP 13774; KSR 592 | (+)-methyl 9alpha-chloro- -6alpha-fluoro-11beta-hydroxy-16alpha-methyl-3-oxo-17alpha-propionyloxy-androsta-1,4-diene-17beta-carboxylate | corticosteroid | asthma; rhinitis |
| ciclesonide; BY 9010; BTR 15 | [11beta,16alfa(R)]-16,17-[(cyclohexylmethylene)bis(oxy)]-11-hydroxy-21-(2-methyl-1-oxopropoxy)-pregna-1,4-diene-3,20-dione | corticosteroid | asthma |
| D 5272 | unspecified | corticosteroid | asthma |
| D 5519 | unspecified | corticosteroid | asthma |
| deflazacort; azacort; L 5458; MDL 458; AZACORTID; CALCORT; LANTADIN; DEFLAN; FLANTADIN; DEZACOR; ZAMENE; ROSILIN; DEFLAMON; PRANDIN | (11beta,16beta)-21-(acetyloxy)-11-hydroxy-2'-methyl-5'H-pregna-1,4-dieno[17,16-d]oxazole-3,20-dione | corticosteroid | rheumatoid arthritis; skin disease; asthma |
| drug delivery system, corticosteroid binding globulin; corticosteroid binding globulin; ALX 25 | unspecified | corticosteroid | inflammation; asthma |
| drug delivery system, LDS microemulsion anti-asthma steroids; anti-asthma steroids LDS microemulsion | unspecified | corticosteroid | asthma |
| drug delivery system, liposome beclometasone dipropionate; beclometasone dipropionate, liposome | unspecified | corticosteroid | asthma |
| drug delivery system, liposome rofleponide; rofleponide liposome; rofleponide palmitate | [6alfa,11beta,16alfa(R)] 16,17-[butylidenebis(oxy)]6,9-difluoro-11,21-dihydroxypregn-4-ene-3,20-dione | corticosteroid | asthma; rhinitis |
| fluticasone propionate; fluticasone; CCI 18781; SN 410; SN 411MD; FLOVENT; FLIXONASE; FLIXOTIDE; FLONASE; FLUTIVATE; FLUTIDE NASAL; CUTIVATE; RONTILONA; TRIALONA; FLUNASE | (6alfa,11beta,16alfa,17alfa)-6,9-difluoro-11-hydroxy-16-methyl-3-oxo-17-(1-oxopropoxy)-androsta-1,4-diene-17-carbothioic acid, S-(fluoromethyl)ester | corticosteroid | dermatitis; rhinitis; asthma; pulmonary obstructive disease; skin disease |
| GW 215864 | unspecified | corticosteroid | asthma |
| GW 250495 | unspecified | corticosteroid | asthma |
| icometasone enbutate; icomethasone enbutate; icometasone acetate; isomethasone acetatew; CL 09 | (11.beta.,16.alphs.)-21-(acetyloxy)-9-chloro-11-hydroxy-16-methyl-17-(1-oxobutoxy)-pregna-1,4-diene-3,20-dione | corticosteroid | asthma; skin disease |
| mometasone furoate; mometasone; S 2640; SCH 32088; ELOCOM; ELOCON; FULMETA; ECURAL; ERMIL; NASONEX; ASMANEX | (11beta,16alpha)-9,21-dichloro-17-[(2-furanyl-carbonyl)oxy]-11-hydroxy-16-methyl-pregna-1,4-diene-3,20-dione | corticosteroid | dermatitis; asthma; rhinitis; psoriasis; pruritis |
| rofleponide; D 5522 | [6alfa,11beta,16alfa(R)] 16,17-[butylidenebis(oxy)]-6,9-difluoro-11,21-dihydroxypregn-4-ene-3,20-dione | corticosteroid | asthma |
| ST 126; TO 199 | unspecified | corticosteroid | asthma |
| RPR 106541 | [6alpha,11beta,16alpha(R),17beta]-16,17-[butylidenebis(oxy)]-6,9-difluoro-11-hydroxy-17-(methylthio)androst-4-en-3-one | corticosteroid; glucocorticoid | asthma |
| methylprednisolone suleptanate; U 67590A; PROMEDROL | (6alfa,11beta)-11,17-dihydroxy-6-methyl-21-[[8-[methyl(2-sulfoethyl)amino]-1,8-dioxooctyl]oxy]pregna-1,4-diene-3,20-dione monosodium salt | corticosteroid; immuno-suppressant | inflammation; asthma; anaphylactic shock; transplant rejection |

TABLE 6-continued

Current Candidate Therapeutic Interventions in Development for the Treatment of COPD

| Product Name | Chemical Name | Action | Indication |
|---|---|---|---|
| tepoxalin; RWJ 20485; ORF 20485 | 5-(4-chlorophenyl)-N-hydroxy-1-(4-methoxyphenyl)-N-methyl-1H-pyrazole-3-propanamide | COX inhibitor; 5 lipoxygenase inhibitor; NSAID | asthma; inflammation; inflammatory bowel disease |
| BAY 169996 | unspecified | cytokine antagonist | asthma |
| cytokine trap, | unspecified | cytokine antagonist | cancer; asthma; rheumatoid arthritis; allergy |
| IL-4 antagonists, Pharmacopeia; IL-4 antagonists | unspecified | cytokine antagonist | asthma |
| interleukin-4 signal transduction antagonists | unspecified | cytokine antagonist | asthma |
| interleukin-5 inhibitor | unspecified | cytokine antagonist | asthma |
| interleukin-4 receptor inhibitors | unspecified | cytokine inhibitor | asthma; diabetes |
| interleukin-1 inhibitors, | unspecified | cytokine inhibitor; NSAID | inflammation; asthma; inflammatory bowel disease |
| JTE 711 | unspecified | cytokine synthesis inhibitor | dermatitis; asthma; rhinitis |
| amlexanox; amoxanox; CHX 3673; AA 673; SOLFA; ELICS; APHTHASOL | 2-amino-7-(1-methylethyl)-5-oxo-5H-[1]-benzopyrano[2,3-b]pyridine-3-carboxylic acid | degranulation inhibitor | asthma; psoriasis; rhinitis; mucositis; conjunctivitis; allergy |
| asobamast; Z 1819 | 2-ethoxyethyl[4-(3-methyl-5-isoxazolyl)-2-thiazolyl]oxamate | degranulation inhibitor | asthma |
| azelastine; A 5610; W 2979M; E 0659; AZEPTIN; ALLERGODIL; ASTELIN; RADETHAZIN; AFLUONA; AFLUON; AZEPIT; AZECOF; AZERUNART CHOS H; BIFERTIN | 4-[(4-chlorophenyl)methyl]-2-(hexahydro-1-methyl-1H-azepin-4-yl)-1(2H)-phthalazinone | degranulation inhibitor | asthma; rhinitis; skin disease; conjunctivitis |
| BN 50601 | 2-[4-(1,1-dimethylethyl)phenyl]-2,3-dihydro-6-methyl-1H-pyrrolo[3,4-b]pyridin-7-ol | degranulation inhibitor | asthma |
| CGP 25875 | unspecified | degranulation inhibitor | asthma |
| cromoglicate lisetil; AKY 953; KY 556; N 556 | 2-[[2-(ethoxycarbonyl)-4-oxo-4H-1-benzopyran-5-yl]oxy]-1-[[[2-(ethoxycarbonyl)-4-oxo-4H-1-benzopyran-5-yl]oxy]methyl]ethyl ester, L-lysine dihydrochloride | degranulation inhibitor | asthma; rhinitis; dermatitis; allergy |
| drug delivery system, oral cromolyn sodium; cromolyn sodium oral delivery system | unspecified | degranulation inhibitor | asthma; allergy; eye disease |
| nedocromil; FPL 59002; FPL 59002KP; TILADE; TILARIN; TILAVIST; TILAD; NEDREL; DISVEN; IRTEN | 9-ethyl-6,9-dihydro-4,6-dioxo-10-propyl-4H-pyrano[3,2-g]quinoline-2,8-dicarboxylic acid | degranulation inhibitor | asthma; eye disease; skin disease; rhinitis |
| pemirolast; pemirolast potassium; BMY 26517; DE 068; BL 5617; PEMILASTON; ALLEGYSAL | 9-methyl-3-(1H-tetrazol-5-yl)-4H-pyrido[1,2-a]pyrimidin-4-one | degranulation inhibitor | asthma; conjunctivitis; rhinitis; dermatitis; restenosis |
| picumast; picumast dihydrochloride; BM 15100 | 7-[3-[4-(4-chlorobenzyl)-1-piperazinyl]-propoxy]-3,4-dimethylcoumarin | degranulation inhibitor | rhinitis; asthma |
| quinotolast; quinotolast sodium; FK 021; FR 71021; ASLOCK | 4-oxo-1-phenoxy-N-1H-tetrazol-5-yl-4H-quinolizine-3-carboxamide | degranulation inhibitor | asthma; rhinitis; dermatitis |
| sulochrin | unspecified | degranulation inhibitor | asthma |
| suplatast tosilate; IPD 1151T; MPD; IPD | dimethyl-2-[4-(3-ethoxy-2-hydroxypropoxy)-phenylcarbamoyl]ethylsulfonium-p-toluene sulfonate | degranulation inhibitor | dermatitis; asthma; allergy; rhinitis |
| tazanolast; WP 833; TAZANOL; TAZALEST | oxo[[3-(1H-tetrazol-5-yl)phenyl]amino]acetic acid, butyl ester | degranulation inhibitor | asthma; rhinitis |
| tetrazolast meglumine; tetrazolast; MDL 26024GO | 4-(1H-tetrazol-5-yl)tetrazolo[1,5-a]quinoline with 1-deoxy-1-(methylamino)-D-glucitol | degranulation inhibitor | asthma |
| CI 959 | 5-methoxy-3-(1-methylethoxy)-N-1H-tetrazol-5-yl-benzo[b]thiophene-2-carboxamide sodium salt | degranulation inhibitor; immunosuppressant; NSAID | rhinitis; inflammation; asthma; arthritis |
| AP 414 | unspecified | degranulation inhibitor; tyrosine kinase inhibitor | asthma; allergy |
| MDAM | N-[4-[2-(2,4-diamino-6-pteridinyl)ethyl]benzoyl]-4-methylene-DL-glutamic acid | dihydrofolate reductase inhibitor; NSAID; immunosuppressant | cancer; transplant rejection; rheumatoid arthritis; asthma |

TABLE 6-continued

Current Candidate Therapeutic Interventions in Development for the Treatment of COPD

| Product Name | Chemical Name | Action | Indication |
|---|---|---|---|
| ALP 231 | unspecified | elastase inhibitor; proteinase inhibitor | emphysema |
| ALP 242 | unspecified | elastase inhibitor; proteinase inhibitor | asthma; emphysema; psoriasis |
| DF 1283 | tert-butyl(7S)3-(acetoxymethyl)-7-[(N-benzyl-oxycarbonyl-L-valyl)amino]-5,5-dioxide-5-thia-1-azabicyclo[4.2.0]oct-2-8-one-2-carboxylate | elastase inhibitor; proteinase inhibitor | emphysema; cystic fibrosis; bronchitis |
| FK 706 | N-[4-[[(carboxymethyl)amino]carbonyl]-benzoyl]-L-valyl-N-[3,3,3-trifluoro-1-(1-methylethyl)-2-oxopropyl]-L-prolinamide monosodium salt | elastase inhibitor; proteinase inhibitor | emphysema |
| FR 134043 | unspecified | elastase inhibitor; proteinase inhibitor | emphysema |
| FR 901277 | unspecified | elastase inhibitor; proteinase inhibitor | emphysema |
| MDL 27324 | (S)-N-[[5-(dimethylamino)-1-naphthalenyl]-sulfonyl]-L-alanyl-L-alanyl-N-[3,3,3-trifluoro-1-(1-methylethyl)-2-oxopropyl]-L-prolinamide | elastase inhibitor, proteinase inhibitor | emphysema |
| TEI 5624 | (S)-4-[[(4-chlorophenyl)sulfonyl]amino]-5-[[5-methyl-2[(1-methylethyl)amino]-4-oxo-4H-3,1-benzoxazin-7-yl]amino]-5-oxopentanoic acid | elastase inhibitor; proteinase inhibitor | emphysema |
| TEI 6344 | (S)-6-amino-2-[[(4-chlorophenyl)sulfonyl]-amino]-N-[5-methyl-2[(1-methylethyl)amino]-4-oxo-4H-3,1-benzoxazin-7-yl]hexanamide | elastase inhibitor; proteinase inhibitor | emphysema |
| TEI 8362 | unspecified | elastase inhibitor; proteinase inhibitor | emphysema; respiratory distress syndrome |
| SR 26831 | 5-[(2-chlorophenyl)methyl]-2-(2,2-dimethyl-1-oxopropoxy)-4,5,6,7-tetrahydro-5-hydroxy-thieno[3,2-c]pyridinium | elastase inhibitor; proteinase inhibitor; NSAID | inflammation; emphysema |
| BQ 153 | cyclo(3-sulfo-D-alanyl-L-prolyl-D-valyl-L-leucyl-D-tryptophyl) | endothelin A antagonist; endothelin antagonist | asthma |
| endothelin antagonist | unspecified | endothelin antagonist | kidney disease; ischemia; inflammatory bowel disease; asthma |
| BW 443C | L-tyrosyl-D-arginylglycyl-4-nitro-L-phenyl-alanyl-L-prolinamide diacetate (salt) | enkephalinase inhibitor; analgesic | asthma; pain; cough |
| BAY x 1005 | (R)-alpha-cyclopentyl-4-(2-quinolinyl-methoxy)benzeneacetic acid | FLAP antagonist | asthma |
| VML 530; ABT 080 | unspecified | FLAP antagonist | asthma |
| VB 5122 | unspecified | free radical scavenger; xanthine oxidase inhibitor | inflammation; asthma |
| beta-glucan antagonist | unspecified | glucan antagonist | conjunctivitis; asthma; psoriasis; ulcerative colitis |
| itrocinonide | 6alfa,9-difluoro-11beta,16alfa,17-trihydroxy-3-oxoandrosta-1,4-diene-17beta-carboxylic acid, ester with ethyl(S)-1-hydroxyethyl carbonate, cyclic(R)-16,17-acetal with butyraldehyde | glucocorticoid | asthma |
| glucocorticoids, | unspecified | glucocorticoid; immuno-suppressant; NSAID | inflammation; asthma; autoimmune disease |
| methylhistamine, R-alpha; BP 2.94 | unspecified | histamine agonist; histamine H3 agonist | asthma; anxiety; gastrointestinal ulcer |
| SCH 49648 | (2S-trans)-4-(2-methyl-3-pyrrolidinyl)-1H-imidazole | histamine agonist; histamine H3 agonist | asthma; anxiety; gastrointestinal ulcer |
| SCH 50971 | (3R-trans)-4-(4-methyl-3-pyrrolidinyl)-1H-imidazole | histamine agonist; histamine H3 agonist | asthma; anxiety; gastrointestinal ulcer |
| HQL 79 | 4-(diphenylmethoxy)-1-[3-(1H-tetrazol-5-yl)-propyl]piperidine | histamine antagonist; 5HT antagonist | allergy; asthma |
| asthma therapy | unspecified | histamine antagonist; hisamine H1 antagonist | asthma |
| DF 1111301 | 1-(2-ethoxyethyl)-N,N-dimethyl-1H-benzimidazole-2-ethanamine dihydrochloride | histamine antagonist; histamine H1 antagonist | allergy; asthma |
| ebastine; LAS W090; LAS 90; EBASTEL; KESTINE; EVASTEL | 1-[4-(1,1-dimethylethyl)phenyl]-4-[4-(diphenyl-methoxy)-1-piperidinyl]-1-butanone | histamine antagonist; histamine H1 antagonist | allergy; rhinitis; asthma |
| epinastine; WAL 801; WAL 801CL; ALESION | 9,13b-dihydro-1H-dibenz[c,f]imidazo[1,5-a]-azepin-3-amine | histamine antagonist; histamine H1 antagonist | allergy; asthma; psoriasis; rhinitis |
| F 9505A | unspecified | histamine antagonist; histamine H1 antagonist | asthma |

TABLE 6-continued

Current Candidate Therapeutic Interventions in Development for the Treatment of COPD

| Product Name | Chemical Name | Action | Indication |
| --- | --- | --- | --- |
| mizolastine; SL 850324; MKC 431; MIZOLLEN; ZOLIM; MISTAMINE | 2-[[1-[1-[(4-fluorophenyl)methyl]-1H-benzimidazol-2-yl]-4-piperidinyl]methyl-amino]-4(1H)-pyrimidinone | histamine antagonist; histamine H1 antagonist | asthma; allergy; rhinitis |
| olopatadine; olopatadine hydrochloride; KW 4679; ALO 4943A; PATANOL | (Z)-11-[3-(dimethylamino)propylidene]-6,11-dihydro-dibenz[b,e]oxepin-2-acetic acid | histamine antagonist; histamine H1 antagonist | allergy; rhinitis; asthma; conjunctivitis |
| selenotifen; BN 52256 | 4,9-dihydro-4-(1-methyl-4-piperidinylidene)-10H-benzo[4,5]cyclohepta[1,2-b]selenophen-10-one | histamine antagonist; histamine H1 antagonist | eye disease; asthma; arrhythmia; rhinitis |
| ZCR 2060 | 2-[2-[4-(diphenylmethyl)-1-piperazinyl]-ethoxy]benzoic acid maleate | histamine antagonist; histamine H1 antagonist | asthma; allergy |
| FCC 13 | 3,4,10,14b-tetrahydrodibenzo[c.f]pyranzino]-1,2-a]azepine-2(1H)carboxamide | histamine antagonist; histamine H1 antagonist; 5HT antagonist | asthma |
| mequitamium iodide; LG 30435 | 1-methyl-3-(10H-phenothiazin-10-ylmethyl)-1-azoniabicyclo[2.2.2]octane iodide | histamine antagonist; histamine H1 antagonist; muscarinic antagonist; cholinergic antagonist | asthma; rhinitis |
| KY 234 | 1-[3-(4-benzhydryl-1-piperazinyl)propyl]-3-(1H-imidazol-1-ylmethyl)-1H-indole-6-carboxylic acid | histamine antagonist; histamine H1 antagonist; thromboxane synthetase inhibitor | asthma |
| pibaxizine; UCB 20028; UCB J028; J028; J 028 | [2-[2-[4-(dipenylmethylene)piperidinyl]-ethoxy]ethoxy]acetic acid | histamine antagonist; histamine H2 antagonist | irritable bowel syndrome; asthma |
| KC 11425 | 5,6-dihydro-2-methyl-8-(2-methylpropyl)-1-[2-[4-(4-methyl-2-pyridinyl)-1-piperazinyl]-ethyl]-4H-pyrrolo[3,2,1-ij]quinoline | histamine antagonist; PAF antagonist | asthma; allergy |
| KC 11404 | 4-n-butyl-5,6-dihydro-8-hydroxy-2-methyl-1-[2-[4-(4-methyl-2-pyridinyl)-1-piperazinyl]-ethyl]-4H-pyrrolo[3,2,1-ij]quinoline | histamine antagonist; PAF antagonist; 5 lipoxygenase inhibitor | asthma; allergy |
| dehydroepiandrosterone sulfate; DHEAS; PB 005 | unspecified | hormone; vaccine adjuvant; corticosteroid | inflammation; infectious disease; asthma |
| pentigetide; IgE pentapeptide human; pentapeptide DSDPR; TA 521; PENTYDE | N2-[1-N-(N-L-alpha-aspartyl-L-seryl)-L-[alpha-aspartyl]-L-prolyl]-L-arginine | immunoglobulin | conjunctivitis; asthma; rhinitis |
| SRL 172 | unspecified | immunostimulant | tuberculosis; cancer; asthma; bacterial infection; leprosy; rhinitis |
| asthma/allergy therapy, D 22557 | unspecified | immunosuppressant | asthma; allergy |
| D 7193 | unspecified | immunosuppressant | allergy; asthma |
| IgE receptor inhibitors, | unspecified | immunosuppressant | asthma |
| immunology/inflammation therapy | unspecified | immunosuppressant | asthma |
| immunosuppressant | unspecified | immunosuppressant | inflammation; auto-immune disease; asthma |
| immunosuppressants, | unspecified | immunosuppressant | asthma |
| LCB 2183 | Unspecified | immunosuppressant | autoimmune disease; asthma |
| oxeclosporin; SDZ IMM 125; IMM 125 | 2-[O-(2-hydroxyethyl)-D-serine]-cyclosporin A | immunosuppressant | rhinitis; dermatitis; asthma |
| T cell modulators, | unspecified | immunosuppressant | asthma |
| CBP 1011 | unspecified | immunosuppressant; corticosteroid | asthma; rhinitis; conjunctivitis; allergy |
| D 22558 | unspecified | immunosuppressant; cytokine inhibitor | autoimmune disease; systemic lupus erythematosus; asthma |
| immunoregulators, | unspecified | immunosuppressant; NSAID | asthma; allergy |
| phellodendrine; OB 5 | (7S-cis)-5,8,13,13a-tetrahydro-2,11-dihydroxy-3,10-dimethoxy-7-methyl-6H-dibenzo[a,g]-quinolizinium | immunosuppressant; NSAID | transplant rejection; rheumatoid arthritis; asthma |
| alphaE beta7 antagonists, | unspecified | integrin antagonist; cell adhesion inhibitor | transplant rejection; inflammation; viral infection; asthma; kidney disease |
| cell adhesion inhibitors, | unspecified | integrin antagonist; cell adhesion inhibitor; NSAID | asthma; psoriasis; inflammatory bowel disease |
| | | | asthma; rheumatoid arthritis; reperfusion injury |

TABLE 6-continued

Current Candidate Therapeutic Interventions in Development for the Treatment of COPD

| Product Name | Chemical Name | Action | Indication |
|---|---|---|---|
| TBC 1269 | 3',3'''-(1,6-hexanediyl)bis[6'-(alpha-D-manno-pyranosyloxy)-[1,1'-biphenyl]-3-acetic acid | integrin antagonist; selectin antagonist; immunosuppressant; cell adhesion inhibitor; NSAID | inflammation; asthma |
| VLA-4 antagonist, | unspecified | integrin antagonist; VLA 4 antagonist | asthma |
| VLA-4 antagonists, inflammatory diseases; BIO 1211 | N-[[4-[[[(2-methylphenyl)amino]carbonyl]-amino]phenyl]acetyl]-L-leucyl-L-alpha-aspartyl-L-valyl-L-proline | integrin antagonist; VLA 4 antagonist | asthma; multiple sclerosis |
| VLA4 antagonists | unspecified | integrin antagonist; VLA 4 antagonist; cell adhesion inhibitor | asthma; inflammatory bowel disease |
| BW A137C | N-hydroxy-N-[[4-(phenylmethoxy)phenyl]-methyl]acetamide | leukotriene antagonist | asthma |
| BW A797C | acetamide,n-hydroxy-n-(3-(5,6,7,8-tetrahydro-2-naphthalenyl)-2-propenyl)— | leukotriene antagonist | asthma |
| CL 891301 | unspecified | leukotriene antagonist | asthma |
| CS 615 | unspecified | leukotriene antagonist | asthma |
| FK 011 | unspecified | leukotriene antagonist | asthma |
| LF 60361 | unspecified | leukotriene antagonist | asthma |
| RP 12525 | unspecified | leukotriene antagonist | asthma |
| zafirlukast; 204219; ICI 204219; ACCOLATE; VANTICON | [3-[[2-[[[(2-methoxy-4-methylphenyl)sulfonyl]-amino]carbonyl]phenyl]methyl]-1-methyl-1H-indol-5-yl]carbamic acid, cyclopentyl ester | leukotriene antagonist | asthma; rhinitis |
| BIIL 284 | unspecified | leukotriene antagonist; leukotriene B4 antagonist | asthma; pulmonary obstructive disease |
| pranlukast; dolukast; ONO 1078; RS 411; ONON; ULTAIR | N-[4-oxo-2-(1H-tetrazol-5-yl)-4H-1-benzo-pyran-8-yl]-4-(4-phenylbutoxy)benzamide | leukotriene antagonist; leukotriene C4 antagonist; leukotriene D4 antagonist; leukotriene E4 antagonist | asthma; rhinitis |
| leukotriene D4 antagonists | unspecified | leukotriene antagonist; leukotriene D4 antagonist | asthma |
| LY 290154 | (E)-7-chloro-2-[2-[3-[4-(1H-tetrazol-5-yl)-1-[7-(1H-tetrazol-5-ylmethoxy)-1H-indol-1-yl]-butyl]phenyl]ethenyl]quinoline | leukotriene antagonist; leukotriene D4 antagonist | asthma |
| RG 14524 | unspecified | leukotriene antagonist; leukotriene D4 antagonist | asthma |
| RS 601 | 4-[5,5,6,6,6-pentafluoro-1-[[(4-fluorophenyl)-sulfonyl]amino]hexyl]benzenebutanoic acid | leukotriene antagonist; leukotriene D4 antagonist; thromboxane antagonist | asthma |
| YM 158; YM 57158 | N-[5-[3-[(4-chlorophenyl)sulfonyl]propyl]-2-(1H-tetrazol-5-ylmethoxy)phenyl]-3-[[4-(1,1-dimethylethyl)-2-thiazolyl]methoxy]benzamide | leukotriene antagonist; leukotriene D4 antagonist; thromboxane antagonist | asthma; rhinitis |
| ZD 3523; ICI D3523 | unspecified | leukotriene antagonist; NSAID | asthma; inflammation |
| LY 292728 | 7-carboxy-3-[3-[(5-ethyl-4'-fluoro-2-hydroxy-[1,1'-biphenyl]-4-yl)oxy]propoxy]-9-oxo-9H-xanthene-4-propanoic acid disodium salt | leukotriene B4 antagonist; leukotriene antagonist | asthma |
| ontazolast; BIRM 270 | (S)-N-[2-cyclohexyl-1-(2-pyridinyl)ethyl]-5-methyl-2-benzoxazolamine | leukotriene B4 antagonist; leukotriene antagonist | asthma |
| RP 69698 | 5-(1,1-dimethyl-5-((4,6-diphenyl-2-pyridyl)-oxy)pentyl)-1H-tetrazole | leukotriene B4 antagonist; leukotriene antagonist | asthma; emphysema |
| RG 14893 | 4-(2-(methyl(2-phenethyl)amino)-2-oxoethyl)-8-(phenylmethoxy)-2-naphthalenecarboxylic acid | leukotriene B4 antagonist; leukotriene antagonist; NSAID | asthma; inflammation |
| SC 51146 | 7-[3-[2(cyclopropylmethyl)-3-methoxy-4-(4-thiazolyl)phenoxy]propoxy]-3,4-dihydro-8-propyl-2H-1-benzopyran-2-carboxylic acid | leukotriene B4 antagonist; leukotriene antagonist; NSAID | asthma; psoriasis; rheumatoid arthritis; inflammatory bowel disease |
| BAY x 7195 | [S-(Z)]-4-[[1-(2-carboxyethyl)-4-[4-(4-phenoxybutoxy)phenyl]-2-butenyl]thio]benzoic acid | leukotriene C4 antagonist; leukotriene D4 antagonist; leukotriene antagonist | asthma |
| cinalukast; Ro 245913 | (E)-4-(3-(2-(4-cyclobutyl-2-thiazolyl)ethenyl)-phenylamino)-2,2-diethyl-4-oxobutanoic acid | leukotriene C4 antagonist; leukotriene D4 antagonist; leukotriene antagonist | asthma |

TABLE 6-continued

Current Candidate Therapeutic Interventions in Development for the Treatment of COPD

| Product Name | Chemical Name | Action | Indication |
|---|---|---|---|
| pirodomast; SCH 37224 | 4-hydroxy-1-phenyl-3-(1-pyrrolidinyl)-1,8-naphthyridin-2(1H)-one | leukotriene C4 antagonist; leukotriene D4 antagonist; leukotriene E4 antagonist; leukotriene antagonist | rhinitis; asthma |
| CGP 44044A | (1R,2S)-1-hydroxy-1-(3-trifluoromethyl-phenyl)-8-(4-acetyl-3-hydroxy-2-propyl-phenoxy)octa-3(E),5(Z)-dien-2-yl-7-thio-4-oxo-4H-1-benzopyran-2-carboxylic acid sodium salt | leukotriene D4 antagonist; leukotriene antagonist | asthma |
| DS 4574 | 6-(2-cyclohexylethyl)-[1,3,4]thiadiazolo[3,2-a]-1,2,3-triazolo[4,5-d]pyrimidin-9(1H)-one | leukotriene D4 antagonist; leukotriene antagonist | gastrointestinal ulcer; asthma |
| LY 203647 | 1-[2-hydroxy-3-propyl-4-[4-[2-[4-(1H-tetrazol-5-yl)butyl]-2H-tetrazol-5-yl]butoxy]phenyl]-ethanone | leukotriene D4 antagonist; leukotriene antagonist | hypertension; asthma |
| LY 287192 | (E)-2-[[5-[3-[2-(7-chloro-2-quinolinyl)ethenyl]-phenyl]-2H-tetrazol-2-yl]methyl]-5-fluoro-benzoic acid sodium salt | leukotriene D4 antagonist; leukotriene antagonist | asthma |
| LY 290324 | (E)-7-chloro-2-[2-[3-[[7-[2-(1H-tetrazol-5-yl)-ethyl]-1H-indol-1-yl]methyl]phenyl]ethenyl]-quinoline hydrochloride | leukotriene D4 antagonist; leukotriene antagonist | asthma |
| montelukast; montelukast sodium; MK 476; MK 0476; SINGULAIR | [R-(E)]-1-[[[1-[3-[2-(7-chloro-2-quinolinyl)-ethenyl]phenyl]-3-[2-(1-hydroxy-1-methyl-ethyl)phenyl]propyl]thio]methyl]cyclopropane-acetic acid | leukotriene D4 antagonist; leukotriene antagonist | asthma |
| NZ 107 | 4-bromo-5-[[(3-ethoxy-4-methoxyphenyl)-methyl]amino]-3(2H)-pyridazinone | leukotriene D4 antagonist; leukotriene antagonist | asthma |
| pobilukast; pobilukast edamine; SKF 104353; SKF 104353Z2; SKF 104353Q | [R-(R*,S*)]-beta-[(2-carboxyethylthio]alpha-hydroxy-2-(8-phenyloctyl)benzenepropanoic acid | leukotriene D4 antagonist; leukotriene antagonist | asthma; rhinitis |
| RG 12525 | 2-[[4-[[2-(1H-tetrazol-5-ylmethyl)phenyl]-methoxy]phenoxy]methyl]quinoline | leukotriene D4 antagonist; leukotriene antagonist | asthma |
| ritolukast; WY 48252 | 1,1,1-trifluoro-alpha-2-quinolylmethanesulfon-m-anisidide | leukotriene D4 antagonist; leukotriene antagonist | asthma |
| SKF 106203 | (S)-beta[(2-carboxyethyl)thio]-2-(8-phenyl-octyl)benzenepropanoic acid | leukotriene D4 antagonist; leukotriene antagonist | asthma |
| verlukast; MK 679; L 660711; MK 571; L 668019 | [R-(E)]-3-[[[3-[2-(7-chloro-2-quinolinyl)-ethenyl]phenyl][[3-(dimethylamino)-3-oxo-propyl]thio]methyl]thio]propanoic acid | leukotriene D4 antagonist; leukotriene antagonist | asthma |
| YM 16638 | [[5-[[3-(4-acetyl-3-hydroxy-2-propylphenoxy)-propyl]thio]-1,3,4-thiadiazol-2-yl]thio]acetic acid | leukotriene D4 antagonist; leukotriene antagonist | asthma |
| CGP 44826 | 2-ethenyloxy-N-[4-(5-cyclopentylcarbonyl-amino-1-methylindol-3-ylmetyl)-3-methoxy-benzoyl]benzenesulfonylamide | leukotriene D4 antagonist; leukotriene E4 antagonist; leukotriene antagonist | asthma |
| FPL 55712 | 7-[3-(4-acetyl-3-hydroxy-2-propylphenoxy)-2-hydroxypropoxy]-4-oxo-8-propyl-4H-1-benzopyran-2-carboxylic acid monosodium salt | leukotriene D4 antagonist; leukotriene E4 antagonist; leukotriene antagonist | asthma |
| iralukast; CGP 45715A | (1R,2S)-1-hydroxy-1-(3-trifluoromethyl-phenyl)-10-(4-acetyl-3-hydroxy-2-propyl-phenoxy)deca-3(E),5(Z)-diene-2-yl-7-thio-4-oxo-4H-1-benzopyran-2-carboxylic acid sodium salt | leukotriene D4 antagonist; leukotriene E4 antagonist; leukotriene antagonist | asthma |
| MDL 43291 | (4a.alpha,7Z,8.beta,8a.beta)-[(octahydro-2-oxo-7-tetradecylidene-2H-1-benzopyran-8-yl)-thio]acetic acid | leukotriene D4 antagonist; leukotriene E4 antagonist; leukotriene antagonist | asthma |
| sulukast; LY 170680 | 5-(3-(2(R)-(carboxyethylthio)-1(S)-hydroxy-pentadeca-3(E),5(Z)-dienyl)phenyl)-1H-tetrazole | leukotriene E4 antagonist; leukotriene D4 antagonist; leukotriene antagonist | asthma |
| BAY y 1015 | unspecified | leukotriene synthesis inhibitor | asthma |

TABLE 6-continued

Current Candidate Therapeutic Interventions in Development for the Treatment of COPD

| Product Name | Chemical Name | Action | Indication |
| --- | --- | --- | --- |
| MAb, interleukin-5; MAb, IL-5; SB 240563 | unspecified | monoclonal antibody; | asthma |
| MAbs, CCR3 | unspecified | monoclonal antibody; ,; chemokine antagonist | asthma |
| MAb, CD4; HumaT4 | unspecified | monoclonal antibody; ,; immunosuppressant | psoriasis; asthma; rheumatoid arthritis; irritable bowel syndrome; transplant rejection; allergy |
| MAb, CD23; GW 353430 | unspecified | monoclonal antibody; ,; NSAID | rheumatoid arthritis; asthma |
| J 104135 | unspecified | muscarinic antagonist; muscarinic M3 antagonist; cholinergic antagonist | urinary incontinence; pulmonary obstructive disease; asthma |
| FK 888 | trans-4-hydroxy-1-[(1-methyl-1H-indol-3-yl)-carbonyl]-L-propyl-N-methyl-3-(2-naphthalenyl)-N-(phenylmethyl)-L-alaninamide | neurokinin antagonist | asthma; migraine |
| lanepitant; LY 303870 | (R)-N-[2-acetyl[(2-methoxyphenyl)methyl]-amino]-1-(1H-indol-3-ylmethyl)ethyl]-[1,4'-bipiperidine]-1'-acetamide | neurokinin antagonist; analgesic; neurokinin 1 antagonist | asthma; pain; migraine |
| L 733060 | (2S-cis)-3-[[3,5-bis(trifluoromethyl)phenyl]-methoxy]-2-phenylpiperidine | neurokinin antagonist; analgesic; neurokinin 1 antagonist; NSAID | inflammation; pain; asthma |
| saredutant; SR 48968 | (S)-N-[4-(4-acetylamino-4-phenyl-1-piperidinyl)-2-(3,4-dichlorophenyl)butyl]-N-methyl-benzamide | neurokinin antagonist; analgesic; neurokinin 2 antagonist | asthiria; pain; urinary incontinence |
| MEN 10376 | unspecified | neurokinin antagonist; bronchodilator; neurokinin 2 antagonist | asthma; anxiety |
| CP 99994 | (2S-cis)-N-[(2-methoxyphenyl)methyl]-2-phenyl-3-piperidinamine | neurokinin antagonist; neurokinin 1 antagonist; analgesic | asthma; pain |
| nolpitantium besilate; SR 140333 | (S)1-[2-[3-(3,4-dichlorophenyl)-1-[[3-(1-methylethoxy)phenyl]acetyl]-3-piperidinyl]-ethyl]-4-phenyl-1-azoniabicyclo[2.2.2]octane | neurokinin antagonist; neurokinin 1 antagonist; NSAID | asthma; inflammation |
| NKP 608C | unspecified | neurokinin antagonist; neurokinin 1 antagonist; substance P antagonist | bronchitis |
| ZD 7944 | unspecified | neurokinin antagonist; neurokinin 2 antagonist | asthma |
| SR 144190 | (R)-4-benzoyl-2-(3,4-difluorophenyl)-2-[2-[4-[[(dimethylamino)carbonyl]amino]-4-phenyl-1-piperidinyl]ethyl]morpholine | neurokinin antagonist; neurokinin 2 antagonist; analgesic | asthma; urinary incontinence; asthma; pain |
| FK 224; FR 115224 | N-[N2-[N-[N-[N-[alfa,beta-didehydro-N-methyl-N-[N-[1-oxo-3-(2-pentylphenyl)propyl]-L-threonyl]tyrosyl]-L-leucyl]-D-phenylalanyl]-L-allothreonyl]-L-asparaginyl]-L-serine upsilon-lactone | neurokinin antagonist; neurokinin 2 antagonist; NSAID | asthma; inflammation |
| NS 2073 | unspecified | nitric oxide activator; NSAID | inflammation; glaucoma; gastrointestinal ulcer; asthma |
| NCX 1005 | (11beta,16alpha)-9-fluoro-11,17-dihydroxy-16-methyl-21-[4-(nitrooxy)-1-oxobutoxyl]pregna-1,4-diene-3,20-dione | nitric oxide donor | asthma; inflammatory bowel disease |
| andolast; CR 2039 | N-4-(5-tetrazolyl)-phenyl-4-(5-tetrazolyl)-benzamide | NSAID | asthma; inflammation; allergy |
| anti-inflammatory agent, | unspecified | NSAID | inflammation; asthma |
| bamaquimast; F 10126; L 0042 | 3-[3-[[(methylamino)carbonyl]oxy]propyl]-1-propyl-2(1H)-quinoxalinone | NSAID | asthma |
| BTS 71321 | N-[1-(4-chlorophenyl)-1-methylethyl]-1H-imidazole-1-propanamine | NSAID | asthma |
| CD40 receptor signalling pathway inhibitor, CD40 receptor signalling pathway inhibitor, | unspecified | NSAID | allergy; asthma; inflammation |
| chemokine receptor modulators | unspecified | NSAID | inflammation; asthma; atherosclerosis |
| contignasterol; IZP 94005 | (3alpha,4beta,5alpha,6alpha,7beta,14beta,22S)-22,29-epoxy-3,4,6,7,29-pentahydroxy-stigmastan-15-one | NSAID | asthma; respiratory disease |
| glucocorticoid agonists | unspecified | NSAID | inflammation; rheumatoid arthritis; inflammatory bowel disease; asthma |

TABLE 6-continued

Current Candidate Therapeutic Interventions in Development for the Treatment of COPD

| Product Name | Chemical Name | Action | Indication |
|---|---|---|---|
| interleukin modulators, | unspecified | NSAID | inflammation; asthma |
| IPL 576092 | unspecified | NSAID | asthma; respiratory disease |
| limazocic; SA 3443 | (R)-hexahydro-7,7-dimethyl-6-oxo-1,2,5-dithiazocine-4-carboxylic acid | NSAID | liver disease; inflammation; emphysema; drug overdose |
| macrophage migration inhibitory factor inhibitors | unspecified | NSAID | arthritis; asthma |
| PKC-RACK interaction inhibitors | unspecified | NSAID | arthritis; multiple sclerosis; asthma |
| PNU 142731; PNU 142731A | 1-[(2,4-di-1-pyrrolidinyl-9H-pyrimido[4,5-b]-indol9-yl)acetyl]pyrrolidine monohydrochloride | NSAID | asthma |
| pseudopterosin | unspecified | NSAID | arthritis; asthma; psoriasis |
| tioxamast; F 1865 | [[4-(4-methoxyphenyl)-2-thiazolyl]amino]-oxoacetic acid ethyl ester | NSAID | asthma; inflammation; skin disease |
| Z 1957 | ethyl N-((3-methyl-5-isoxazolyl)-2-thiazolyl) oxamate | NSAID | asthma; inflammation |
| VX 745 | unspecified | NSAID; MAP kinase inhibitor; signal transduction inhibitor | inflammation; neurological; heart failure; Crohn disease; asthma |
| NCX 1004 | unspecified | NSAID; nitric oxide donor | asthma |
| phospholipase A2 inhibitors | unspecified | NSAID; phospholipase inhibitor | rheumatoid arthritis; inflammatory bowel disease; asthma |
| INKP 300 | unspecified | NSAID; signal transduction inhibitor | asthma |
| D 7003 | unspecified | nucleoside | bronchitis |
| oligonucleotide, asthma | unspecified | oligonucleotide; ,; immunostimulant | asthma |
| sulfated oligosaccharide | unspecified | oligosaccharide | asthma |
| bepafant; WEB 2170 | 4-[[6-(2-chlorophenyl)-8,9-dihydro-1-methyl-4H,7H-cyclopenta[4,5]thieno[3,2-f][1,2,4]-triazolo[4,3-a][1,4]diazpin-8-yl]carbonyl]-morpholine | PAF antagonist | asthma; rhinitis |
| E 6123 | (S)-(+)-6-(2-chlorophenyl)-3-cyclopropane-carbonyl-8,11-dimethyl,2,3,4,5-tetrahydro-8H-pyrido(4',3':4,5)thieno(3,2-f)(1,2,4)triazolo(4,3-a)(1,4)diazepine | PAF antagonist | asthma |
| foropafant; SR 27417 | N,N-dimethyl-N'-(3-pyridinylmethyl)-N'-[4-[2,4,6-tris(1-methylethyl)phenyl)-2-thiazolyl]-1,2-ethanediamine | PAF antagonist | asthma |
| ginkgolide A,B,C; BN 52063 | (1alpha,7beta)-1,7-dihydroxyginkgolide A mixt with ginkgolide A and (1beta)-1-hydroxy-ginkgolide A | PAF antagonist | asthma; rhinitis; thrombocytopenia |
| israpafant; Y 24180; PAFNOL | 4-(2-chlorophenyl)-6,9-dimethyl-2-[2-[4-(2-methylpropyl)phenyl]ethyl]-6H-thieno[3,2-f]-[1,2,4]triazolo[4,3-a][1,4]diazepine | PAF antagonist | asthma |
| L 680573; MK 287 | (2S-trans)-2-[[3-methoxy-2-propoxy-5-[tetra-hydro-5-(3,4,5-trimethoxyphenyl)-2-furanyl]-phenyl]sulfonyl]ethanol | PAF antagonist | asthma; septic shock |
| Ro 191400 | unspecified | PAF antagonist | asthma |
| Ro 193704; Ro 19-3704 | (R)-3-[4-[2-[(methoxycarbonyl)oxy]-3-[[(octadecylamino)carbonyl]oxy]propoxy]-butyl]thiazolium iodide | PAF antagonist | asthma |
| Ro 240238; Ro 24-0238; Ro 244376 | [R-(E,E)]-5-(4-methoxyphenyl)-N-[1-methyl-4-(3-pyridinyl)butyl]-2,4-decadienamide | PAF antagonist | asthma |
| rocepafant; BN 50730 | 6-(2-chlorophenyl)-7,10-dihydro-N-(4'-methoxyphenyl)-1-methyl-4H-pyrido[4',3:4,5]-thieno[3,2-f][1,2,4]triazolo[4,3-a][1,4]-diazepine-9(8H)-carbothioamide | PAF antagonist | hypotension; cytoprotectant; asthma |
| tulopafant; RP 59227 | (+)-N-(3-benzoylphenyl)-3-(3-pyridinyl)-1H,3H-pyrrolo[1,2-c]thiazole-7-carboxamide | PAF antagonist | asthma |
| YM 461; YM 46A | 1-(3-phenylpropyl)-4-[[2-(3-pyridinyl)-4-thiazolidinyl]carbonyl]piperazine(E)-2-butenedioate(1:1) | PAF antagonist | asthma; pulmonary obstructive disease |
| SCH 37370 | 1-acetyl-4-(8-chloro-5,6-dihydro-11H-benzo-[5,6]cyclohepta[1,2-b]pyridin-11-ylidene)-piperidine | PAF antagonist; histamine antagonist; histamine H1 antagonist | asthma; rhinitis |
| CMI 392 | trans-2-[5-N'-methyl-N'-hydroxyureidyl-methyl)-3-methoxy-4-p-chlorophenylthioethoxy-phenyl]-5-(3,4,5-trimethoxyphenyl)tetrahydro-furan | PAF antagonist; leukotriene antagonist | psoriasis; dermatitis; asthma |

TABLE 6-continued

Current Candidate Therapeutic Interventions in Development for the Treatment of COPD

| Product Name | Chemical Name | Action | Indication |
|---|---|---|---|
| BN 52111 | 1-(6-((2-heptadecyl-2-methyl-1,3-dioxolan-4-yl)methoxy)-6-oxohexyl)-pyridinium bromide | PAF antagonist; NSAID | asthma; inflammation |
| BN 52115 | 1-[6-[(2-heptadecyl-2-methyl-1,3-dioxolan-4-yl)methoxy]-6-oxohexyl]quinolinium bromide | PAF antagonist; NSAID | asthma; inflammation |
| SM 10661 | cis-(+,−)-3,5-dimethyl-2-(3-pyridinyl)-4-thiazolidinone monohydrochloride | PAF antagonist; NSAID | endotoxic shock; inflammation; asthma |
| tetrahydrocarbazole | 4-(2-chlorophenyl)-9-methyl-2-[3-(1,2,3,4-tetrahydro-9H-carbazol-9-yl)-1-propynyl]-6H-thieno[3,2-f][1,2,4]triazolo[4,3-a][1,4]diazepine | PAF antagonist; NSAID | inflammation; asthma |
| tiapafant; PCA 4248 | 1,4-dihydro-2,4,6-trimethyl-3,5-pyridinedicarboxylic acid methyl 2-(phenylthio)ethyl ester | PAF antagonist; NSAID | asthma; inflammation |
| UR 10324 | 2-(2-acetyl-3,11-dioxo-4,10-dioxa-7-thia-2,12-diazanonacos-1-yl)-1-ethylpyridinium chloride | PAF antagonist; NSAID | inflammation; asthma |
| UR 12460 | 4-[[(diphenylmethyl)amino]acetyl]-alpha-(2-methyl-3-pyridinyl)-1-piperazineacetonitrile | PAF antagonist; NSAID | inflammation; asthma |
| UR 12510 | unspecified | PAF antagonist; NSAID | inflammation; asthma |
| UR 12519 | unspecified | PAF antagonist; NSAID | inflammation; asthma |
| UR 12551 | unspecified | PAF antagonist; NSAID | inflammation; asthma |
| AH 21132 | cis N-(4-(1,2,3,4,4a,10b-hexahydro-8,9-dimethoxy-2-methylbenzo(c)(1,6)naphthyridin-6-yl)phenyl)-acetamide(Z)-2-butenedioate(1:2) | PAF antagonist; phosphodiesterase inhibitor; phosphodiesterase III inhibitor; phosphodiesterase IV inhibitor; bronchodilator | asthma |
| apafant; WEB 2086; WEB 2086BS | 4-[3-[4-(2-chlorophenyl)-9-methyl-6H-thieno-[3,2-f][1,2,4]triazolo[4,3-a][1,4]diazepin-2-yl]-1-oxopropyl morpholine | PAF antagonist; platelet antiaggregant | asthma; rhinitis; pancreatitis |
| dacopafant; RP 48740 | (3R)-3-(3-pyridyl)-1H,3H-pyrrolo[1,2-c]-thiazole-7-carboxamide | PAF antagonist; platelet antiaggregant | asthma; thrombosis |
| F 1850 | unspecified | PAF antagonist; platelet antiaggregant | thrombosis; asthma |
| ginkgolide B; BN 52021 | hexacyclic trilactone | PAF antagonist; platelet antiaggregant | thrombosis; dermatitis; asthma; multiple sclerosis; septic shock |
| L 659989 | trans-(+,−)-tetrahydro-2-[3-methoxy-5-(methylsulfonyl)-4-propoxyphenyl]-5-(3,4,5-trtimethoxyphenyl)furan | PAF antagonist; platelet antiaggregant | asthma; thrombosis |
| R 74654 | 3-(6-(0-(2R,2S)-(3-heptadecylcarbamoyloxy-tetrahydropyran-2-yl)methyl)phosphonoxy)-hexylthiazolium | PAF antagonist; platelet antiaggregant | asthma; thrombosis |
| R 74717 | 3-(5-(0-(2S,3S)-(3-heptadecylcarbamoylthio-tetrahydropyran-2-yl)methyl)phosphonoxy)-pentylthiazolium | PAF antagonist; platelet antiaggregant | asthma; thrombosis |
| Ro 244736; Ro 24-4736 | 5-[3-[4-(2-chlorophenyl)-9-methyl-6H-thieno-[3,2-f][1,2,4]triazolo[4,3-a][1,4]diazepin-2-yl]-2-propynyl]-6(5H)-phenanthridinone | PAF antagonist; platelet antiaggregant | thrombosis; asthma; septic shock |
| SDZ 64412; SDZ 64-412 | 2,3-dihydro-5-[4-[2-(3,4,5-trimethoxyphenyl)-ethyl]phenyl]imidazo[2,1-a]isoquinoline monohydrochloride | PAF antagonist; platelet antiaggregant | asthma; thrombosis |
| SR 27388 | 4-[2-[[2-(dimethylamino)ethyl](3-pyridinyl-methyl)amino]-4-thiazolyl]-2,6-bis(1,1-dimethylethyl)phenol | PAF antagonist; platelet antiaggregant | thrombosis; asthma; septic shock |
| UK 74505 | 4-(2-chlorophenyl)-1,4-dihydro-6-methyl-2-[4-(2-methyl-1H-imidazo[4,5-c]pyridin-1-yl)-phenyl]-5-[(2-pyridinylamino)carbonyl-3-pyridinecarboxylic acid ethyl ester | PAF antagonist; platelet antiaggregant | thrombosis; asthma |
| UR 12670 | 4-[(2-methyl-1H-imidazo[4,5-c]pyridin-1-yl)-methyl]-1-(1-oxo-3,3-diphenylpropyl)piperidine | PAF antagonist; platelet antiaggregant | kidney disease; ischemia; asthma; pancreatitis |
| WEB 2347 | 6-(2-chlorophenyl)-8,9-dihydro-1-methyl-N,N-dipropyl-4H,7H-cyclopenta[4,5]thieno[3,2-f][1,2,4]triazolo[4,3-a][1,4]diazepine-8-carboxamide | PAF antagonist; platelet antiaggregant | asthma; anaphylactic shock; thrombosis |
| YM 264 | 1-(3-methyl-3-phenylbutyl)-4-[[2-(3-pyridinyl)-4-thiazolidinyl]carbonyl]piperazine(E)-2-butenedioate(1:1) | PAF antagonist; platelet antiaggregant | thrombosis; asthma |
| SDZ 64619 | (+,−)-2-[6-methoxy-2-(methylsulfonyl)-3,9-dioxo-4,8-dioxa-2,10-diazaoctacosan-1-yl)-1-methylpyridinium iodide | PAF antagonist; platelet antiaggregant; bronchodilator | thrombosis; asthma |

TABLE 6-continued

Current Candidate Therapeutic Interventions in Development for the Treatment of COPD

| Product Name | Chemical Name | Action | Indication |
|---|---|---|---|
| asthma therapy | unspecified | peptide | asthma |
| cathepsin S inhibitors, Peptimmune | unspecified | peptide; proteinase inhibitor; cathepsin S inhibitor | asthma |
| BY 244 | unspecified | phosphodiesterase inhibitor | asthma |
| BY 343 | unspecified | phosphodiesterase inhibitor | asthma |
| phosphodiesterase inhibitor | unspecified | phosphodiesterase inhibitor | asthma |
| roflumilast; BY 217 | 3-(cyclopropylmethoxy)-N-(3,5-dichloro-4-pyridinyl)-4-(difluoromethoxy)benzamide | phosphodiesterase inhibitor | asthma |
| KF 19514 | 1,5-dihydro-5-phenyl-4H-imidazo[4,5-c][1,8]-naphthyridin-4-one | phosphodiesterase inhibitor; bronchodilator | asthma |
| KP 885 | unspecified | phosphodiesterase inhibitor; bronchodilator | asthma |
| P 1432 | 3-(cyclopropylmethyl)xanthine | phosphodiesterase inhibitor; bronchodilator | asthma |
| WY 123641; PDA 641 | unspecified | phosphodiesterase inhibitor; bronchodilator | asthma |
| arofylline; LAS 31025 | 3-(4-chlorophenyl)-3,7-dihydro-1-propyl-1H-purine-2,6-dione | phosphodiesterase inhibitor; bronchodilator; NSAID | asthma; inflammation |
| LAS 31396 | unspecified | phosphodiesterase inhibitor; bronchodilator; NSAID | asthma; inflammation |
| tolafentrine; BY 4070 | (−)-4-(cis-1,2,3,4,4a,10b-hexahydro-8,9-dimethoxy-2-methylbenzo[c][1,6]=naphthyridin-6-yl)-p-toluenesulfonamide | phosphodiesterase inhibitor; phosphodiesterase III inhibitor; phosphodiesterase IV inhibitor; bronchodilator | asthma |
| zardaverine; B 84290 | 6-(4-(difluoromethoxy)-3-methoxyphenyl)-3(2H)-pyridazinone | phosphodiesterase inhibitor; phosphodiesterase III inhibitor; phosphodiesterase IV inhibitor; bronchodilator | asthma |
| AWD 12281 | unspecified | phosphodiesterase inhibitor; phosphodiesterase IV inhibitor | asthma |
| BAY 198004 | unspecified | phosphodiesterase inhibitor; phosphodiesterase IV inhibitor | asthma |
| CP 220629; CP 220,629 | 1-cyclopentyl-3-ethyl-1,4,5,6-tetrahydro-6-(2-methylphenyl)-7H-pyrazolo[3,4-c]pyridin-7-one | phosphodiesterase inhibitor; phosphodiesterase IV inhibitor | asthma |
| DWP 205297 | unspecified | phosphodiesterase inhibitor; phosphodiesterase IV inhibitor | asthma |
| PDE-4 inhibitors | unspecified | phosphodiesterase inhibitor; phosphodiesterase IV inhibitor | asthma |
| YM 976 | unspecified | phosphodiesterase inhibitor; phosphodiesterase IV inhibitor | asthma |
| CDP 840 | (R)-4-[2-[3-(cyclopentyloxy)-4-methoxyphenyl]-2-phenylethyl]pyridine | phosphodiesterase inhibitor; phosphodiesterase IV inhibitor; bronchodilator; NSAID | asthma; inflammation |
| filaminast; WAY PDA 641 | 1-[3-(cyclopentyloxy)-4-methoxyphenyl]-ethanone, (E)-O-(aminocarbonyl)oxime | phosphodiesterase inhibitor; phosphodiesterase IV inhibitor; bronchodilator | asthma |
| LAS 32688 | unspecified | phosphodiesterase inhibitor; phosphodiesterase IV inhibitor; bronchodilator | asthma |
| phosphodiesterase inhibitors | unspecified | phosphodiesterase inhibitor; phosphodiesterase IV inhibitor; bronchodilator | asthma |
| piclamilast; RP 73401; RPR 73401 | 3-cyclopentyloxy-N-(3,5-dichloropyridin-4-yl)-4-methoxybenzamide | phosphodiesterase inhibitor; phosphodiesterase IV inhibitor; bronchodilator; NSAID | asthma; arthritis |

TABLE 6-continued

Current Candidate Therapeutic Interventions in Development for the Treatment of COPD

| Product Name | Chemical Name | Action | Indication |
| --- | --- | --- | --- |
| SB 207499; ARIFLO | cis-4-cyano-4-[3-(cyclopentyloxy)-4-methoxy-phenyl]cyclohexanecarboxylic acid | phosphodiesterase inhibitor; phosphodiesterase IV inhibitor; bronchodilator; NSAID | asthma; pulmonary obstructive disease |
| D 4418 | N-(3,5-dichloro-4-pyridinyl)-8-methoxy-5-quinolinecarboxamide | phosphodiesterase inhibitor; phosphodiesterase IV inhibitor; immunosuppressant; bronchodilator | asthma |
| D 22888 | unspecified | phosphodiesterase inhibitor; phosphodiesterase IV inhibitor; phosphodiesterase V inhibitor; bronchodilator | asthma |
| SKF 96231 | 2-(2-propoxyphenyl)-6-purinone | phosphodiesterase inhibitor; phosphodiesterase V inhibitor; bronchodilator | asthma |
| doxofylline; ABC 12/3; DO 309; MAXIVENT; ANSIMAR | 7-(1,3-dioxolan-2-ylmethyl)-3,7-dihydro-1,3-dimethyl-1H-purine-2,6-dione | phosphodiesterase inhibitor; xanthine | asthma |
| CI 1018 | (R)-N-(3,4,6,7-tetrahydro-9-methyl-4-oxo-1-phenylpyrrolo[3,2,1-jk][1,4]benzodiazepin-3-yl)-4-pyridinecarboxamide | phosphodiesterase IV inhibitor | asthma |
| phospholipase A2 inhibitors | Unspecified | phospholipase inhibitor; NSAID | asthma; rheumatoid arthritis; psoriasis; inflammatory bowel disease |
| cyclic polyamine analogue | unspecified | polyamine analogue; NSAID | Crohn disease; asthma; inflammation |
| BIIX 1; RS 91309 | unspecified | potassium channel activator | asthma |
| BRL 55834 | (3S,4R)-3,4-dihydro-2,2-dimethyl-4-(2-oxopiperidin-1-yl)-6 pentafluoroethyl-2H-1-benzopyran-3-ol | potassium channel activator; bronchodilator | asthma |
| CL 891902 | unspecified | potassium channel activator; bronchodilator | asthma; hypertension |
| emakalim; EMD 56431 | (3S-trans)-3,4-dihydro-3-hydroxy-2,2-dimethyl-4-(2-oxo-1(2H)-pyridinyl)-2H-1-benzopyran-6-carbonitrile | potassium channel activator; bronchodilator | hypertension; heart failure; asthma; peripheral vascular disease |
| potassium channel activator | 4-[(1,6-dihydro-1-methyl-6-oxo-3-pyridazinyl)-oxy]-3,4-dihydro-3-hydroxy-2,2-dimethyl-2H-1-benzopyran-6-carbonitrile | potassium channel activator; bronchodilator | hypertension; asthma |
| Ro 316930 | 2,2-dimethyl-4-(2-pyridinyl)-2H-1-benzopyran-6-carbonitrile N4-oxide | potassium channel activator; bronchodilator | hypertension; asthma |
| RP 66471 | 1S,2R-trans-2-benzoyloxy-1-(pyrid-3-yl)-cyclohexane-(N-methyl)carbthioamide | potassium channel activator; bronchodilator | asthma |
| SCA 40 | 6-bromo-8-(methylamino)-imidazo[1,2-a]-pyrazine-2-carbonitrile | potassium channel activator; bronchodilator | hypertension; asthma |
| SDZ PCO400 | (3S-trans)-2,4-dihydro-3-hydroxy-2,2-dimethyl-4-[(3-oxo-1-cyclopenten-1-yl)oxy]-2H-1-benzopyran-6-carbonitrile | potassium channel activator; bronchodilator | asthma |
| SR 47063 | 4-(2-cyanoimino-1,2-dihydropyrid-1-yl)-6-nitro-2,2-dimethyl-2H-1-benzopyran | potassium channel activator; bronchodilator | heart ischemia; asthma |
| symakalim; EMD 57283 | 4-[(1,6-dihydro-1-methyl-6-oxo-3-pyridazinyl)-oxy]-3,4-dihydro-3-hydroxy-2,2-dimethyl-2H-1-benzopyran-6-carbonitrile | potassium channel activator; bronchodilator | hypertension; coronary artery disease; asthma |
| UR 8225 | 1,2-dihydro-4-(1,2-dihydro-2-oxo-1-pyridyl)-2,2-dimethyl-1-oxonaphthalene-6-carbonitrile | potassium channel activator; bronchodilator | hypertension; asthma; urinary incontinence |
| UR 8308 | 1,2-dihydro-2,2-dimethyl-4-(N-oxide-2-pyridyl)-1-oxonaphthalen-6-carbonitrile | potassium channel activator; bronchodilator | asthma |
| UR 8328 | 1,2-dihydro-2,2-dimethyl-4-(N-oxide-2-pyridyl)-6-pentafluoroethylnaphthalen-1-one | potassium channel activator; bronchodilator | asthma |
| YM 934 | 3,4-dihydro-2,2-dimethyl-6-nitro-4-(2-pyridinyl)-2H-1,4-benzoxazine N-oxide | potassium channel activator; bronchodilator | hypertension; asthma; urinary incontinence |
| bimakalim; EMD 52692; SR 44866 | 2,2-dimethyl-4-(2-oxo-1(2H)-pyridinyl)-2H-1-benzopyran-6-carbonitrile | potassium channel activator; vasodilator; bronchodilator | coronary artery disease; asthma; peripheral vascular disease |
| rilmakalim; HOE 234 | (3S,4R)-3-hydroxy-2,2-dimethyl-4-(3-oxo-1-pyrrolidinyl)-6-phenylsulfonylchroman hemihydrate | potassium channel activator; vasodilator; bronchodilator | asthma |

TABLE 6-continued

Current Candidate Therapeutic Interventions in Development for the Treatment of COPD

| Product Name | Chemical Name | Action | Indication |
|---|---|---|---|
| potassium channel modulators | unspecified | potassium channel modulator | cognitive defect; attention deficit disorder; depression; asthma; diabetes |
| NS 1619 | 1,3-dihydro-1-[2-hydroxy-5-(trifluoromethyl)-phenyl]-5-(trifluoromethyl)-2H-benzimidazol-2-one | potassium channel modulator; broncho-dilator | stroke; asthma |
| protein kinase activators | unspecified | protein kinase activator; protein kinase A activator | asthma; thrombosis |
| allergy therapy | unspecified | protein kinase inhibitor | allergy; asthma |
| Y 27632 | [4(R)-trans]-4-(1-aminoethyl)-N-4-pyridinyl-cyclohexane carboxamide | protein kinase inhibitor | hypertension; asthma; cancer |
| Syk inhibitors | unspecified | protein kinase inhibitor; tyrosine kinase inhibitor | asthma; allergy |
| Der p I inhibitor | unspecified | proteinase inhibitor | asthma |
| midesteine; MR 889 | 2-thiophenecarbothioic acid, S-ester with (+,−)-2-mercapto-N-(tetrahydro-2-oxo-3-thienyl)-propionamide | proteinase inhibitor | emphysema |
| alpha-1-antitrypsin | unspecified | proteinase inhibitor;, | emphysema |
| alpha-1-antitrypsin | unspecified | proteinase inhibitor;, | asthma; emphysema; cystic fibrosis; dermatitis; psoriasis |
| MDL 101146 | N-[4-(4-morpholinylcarbonyl)benzoyl]-L-valyl-N-[3,3,4,4,4-pentafluoro-1-(1-methylethyl)-2-oxobutyl]-L-prolinamide | proteinase inhibitor; neutrophil elastase inhibitor | bronchitis |
| mycophenolate mofetil; mycophenolate mofetil hydrochloride; RS 61443; RS-61443-190; | (E)-6-(1,3-dihydro-4-hydroxy-6-methoxy-7-methyl-3-oxo-5-isobenzofuranyl)-4-methyl-4-hexenoic acid 2-(4-morpholinyl)ethyl ester | purine synthesis inhibitor; immuno-suppressant; NSAID | transplant rejection; rheumatoid arthritis; asthma; restenosis; kidney disease; systemic lupus erythematosus |
| NO-SOD mimetics, NitroMed; nitrosylated superoxide dismutase mimetics | unspecified | SOD mimetic; nitric oxide donor | asthma; respiratory distress syndrome; ischemia; reperfusion injury |
| CGP 49823 | (2R-trans)-1-(3,5-dimethylbenzoyl)-2-(phenyl-methyl)-N-(4-quinolinylmethyl)-4-piperidin-amine | substance P antagonist | anxiety; asthma |
| FR 113680 | N-acetyl-L-threonyl-1-formyl-D-tryptophyl-N-methyl-N-(phenylmethyl)-L-phenylalaninamide | substance P antagonist | asthma |
| WS 9326A | unspecified | substance P antagonist | asthma |
| dapitant; RPR 100893 | [3aS-[2(R*),3aalpha,4beta,7aalpha]]-octahydro-4-(2-methoxyphenyl)-2-[2-(2-methoxyphenyl)-1-oxo-propyl]-7,7-diphenyl-1H-isoindol-4-ol | substance P antagonist; NSAID | asthma; inflammation; migraine |
| MEN 10627 | unspecified | tachykinin antagonist; antispasmodic | irritable bowel syndrome; asthma |
| nepadutant; MEN 11420 | Cyclo[3-amino-L-alanyl-L-leucyl-N-[2-(acetylamino)-2-deoxy-beta-D-glucopyranosyl]-L-asparaginyl-L-alpha-aspartyl-L-tryptophyl-L-phenylalanyl], cyclic (4->1)-peptide | tachykinin antagonist; antispasmodic | asthma; irritable bowel syndrome |
| seratrodast; serabenast; AA 2414; A 73001; ABT 001; BRONICA | (+,−)-zeta-(2,4,5-trimethyl-3,6-dioxo-1,4-cyclohexadien-1-yl)-benzeneheptanoic acid | thromboxane antagonist | asthma; rhinitis |
| SKF 88046 | N,N'-bis[7-93-chlorobenzeneaminosulfonyl)-1,2,3,4-tetrahydroisoquinolyl]disulfonylimide | thromboxane antagonist | asthma |
| domitroban; S 1452; S 145; ANBOXAN | (+,−)-[1alfa,2alfa(Z),3beta,4alfa]-7-[3-[(phenylsulfonyl)amino]bicyclo[2.2.1]hept-2-yl]-5-heptenoic acid | thromboxane antagonist; platelet antiaggregant | asthma; rhinitis; thrombosis |
| ICI 185282 | [2alfa,4alfa,5alfa(Z)]-7-[4-(2-hydroxyphenyl)-2-(trifluoromethyl)-1,3-dioxan-5-yl]-5-heptenoic acid | thromboxane antagonist; platelet antiaggregant | thrombosis; asthma |
| ICI 192605 | [2alfa,4alfa,5alfa(Z)]-6-[2-(2-chlorophenyl)-4-(2-hydroxyphenyl)-1,3-dioxan-5-yl]-4-hexenoic acid | thromboxane antagonist; platelet antiaggregant | thrombosis; asthma |
| KT 2962; KT 2-962 | 3-[4-[[(4-chlorophenyl)sulfonyl]amino]butyl]-6-(1-methylethyl)-1-azulene sulfonic acid monosodium salt | thromboxane antagonist; platelet antiaggregant | stroke; asthma; kidney disease; thrombosis |
| L 670596 | (−)-6,8-difluoro-2,3,4,9-tetrahydro-9-[[4-(methylsulfonyl)phenyl]methyl]-1H-carbazole-1-acetic acid | thromboxane antagonist; platelet antiaggregant | asthma; thrombosis |
| ON 579 | 4-(2-(4-chlorophenylsulfonylamino)ethylthio)-2,6-difluorophenoxyacetic acid | thromboxane antagonist; platelet antiaggregant | thrombosis; asthma |

TABLE 6-continued

Current Candidate Therapeutic Interventions in Development for the Treatment of COPD

| Product Name | Chemical Name | Action | Indication |
|---|---|---|---|
| ONO 8809 | [1S-[1alfa,2alfa(Z),3beta,4alfa]]-6-[3-[[[(4-bromophenyl)sulfonyl]amino]methyl]bicyclo-[2.2.1]hept-2-yl]-5-hexenoic acid decyl ester | thromboxane antagonist; platelet antiaggregant | thrombosis; asthma |
| ramatroban; BAY u 3405; EN 137774 | (R)-3-[[(4-fluorophenyl)sulfonyl]amino]-1,2,3,4-tetrahydro-9H-carbazole-9-propanoic acid | thromboxane antagonist; platelet antiaggregant | asthma; rhinitis |
| SQ 33961 | [1S-(exo,exo)]-2-[[3-[4-[[(4-cyclohexylbutyl)-amino]carbonyl]-2-oxazolyl]-7-oxabicyclo-[2.2.1]hept-2-yl]methyl]benzenepropanoic acid | thromboxane antagonist; platelet antiaggregant | thrombosis; peripheral vascular disease; asthma |
| KDI 792; FK 070; FR 12170 | [2S-[2alpha,(Z),4beta]]-6-[4-[[(4-chloro-phenyl)sulfonyl]amino]-1-(3-pyridinylmethyl)-2-pyrrolidinyl]-5-hexenoic acid | thromboxane antagonist; thromboxane synthetase inhibitor; platelet anti-aggregant | thrombosis; peripheral vascular disease; asthma |
| E 6700 | (E)-alpha-[(4-methoxy-2,5-dimethyl-3,6-dioxo-1,4-cyclohexadien-1-yl)methylene]-3-pyridine-heptanoic acid | thromboxane synthetase inhibitor | asthma |
| F 1322 | N-[2-[4-(diphenylmethoxy)-1-piperidinyl]-ethyl]-3-hydroxy-5-(3-pyridinylmethoxy)-2-naphthalenecarboxamide | thromboxane synthetase inhibitor | asthma |
| KK 505 | 2-ethyl-4-(3-pyridyl)-1(2H)-phthalazinone | thromboxane synthetase inhibitor; bronchodilator | asthma |
| KK 562 | 2-methyl-4-(5-thiazolyl)-1(2H)-phthalazinone | thromboxane synthetase inhibitor; bronchodilator | asthma |
| imitrodast; CS 518; RS 5186 | 4,5-dihydro-2-(1H-imidazol-1-ylmethyl)-benzo[b]thiophene-6-carboxylic acid sodium salt | thromboxane synthetase inhibitor; platelet anti-aggregant | asthma |
| nafagrel; DP 1904 | 5,6,7,8-tetrahydro-6-(1H-imidazol-1-ylmethyl)-2-naphthalenecarboxylic acid | thromboxane synthetase inhibitor; platelet anti-aggregant | thrombosis; angina; asthma; restenosis |
| ozagrel; ozagrel sodium; OKY 046; DOMENAN; CATACLOT; XANBON; VEGA | (E)-3-[4-(1H-imidazol-1-ylmethyl)phenyl]-2-propenoic acid | thromboxane synthetase inhibitor; platelet anti-aggregant | stroke; thrombosis; asthma; cough |
| Y 20811 | 4-(hydroxy(5-(1H-imidazol-1-yl)-2-methyl-phenyl)methyl)-3,5-dimethyl-benzoic acid, monosodium salt | thromboxane synthetase inhibitor; platelet anti-aggregant | thrombosis; asthma; stroke |
| ZT 386 | unspecified | thromboxane synthetase inhibitor; thromboxane antagonist; platelet anti-aggregant | thrombosis; asthma |
| tumor necrosis factor inhibitors | unspecified | TNF inhibitor; NSAID | inflammation; asthma; inflammatory bowel disease |
| NF-kappaB inhibitor | unspecified | transcription factor regulator; NSAID | asthma; inflammation; restenosis |
| BAY 358535; BAY 35-8535; BAY 171998; BAY 17-1998 | unspecified | tryptase inhibitor | asthma |
| BAY 443428 | unspecified | tryptase inhibitor | asthma |
| oral tryptase inhibitors, | unspecified | tryptase inhibitor | inflammatory bowel disease; asthma; psoriasis |
| tryptase inhibitors | unspecified | tryptase inhibitor | asthma |
| tryptase inhibitors | unspecified | tryptase inhibitor; NSAID | asthma; inflammation; rhinitis; inflammatory bowel disease; psoriasis |
| APC 366 | N2-[(1-hydroxy-2-naphthalenyl)carbonyl]-L-arginyl-L-prolinamide monohydrochloride | tryptase inhibitor; peptide | asthma |
| allergy/asthma therapy, | unspecified | Unspecified | asthma; allergy |
| antiasthma agent | unspecified | unspecified | asthma |
| AP 0341 | 5-amino-3-(4-chlorophenyl)-N-methyl-1H-1,2,4-triazole-1-carbothioamide | unspecified | asthma |
| APO 77 | unspecified | unspecified | asthma |
| ARL 68475; FPL 68475 | unspecified | unspecified | asthma |
| asthma therapy | unspecified | unspecified | asthma |
| asthma therapy | unspecified | unspecified | asthma |
| asthma therapy | unspecified | unspecified | asthma |
| asthma therapy | unspecified | unspecified | asthma |
| asthma therapy | unspecified | unspecified | asthma |
| asthma/allergy therapy, | unspecified | unspecified | asthma; allergy |
| batebulast; batebulast hydrochloride; NCO 650 | trans-4-guanidinomethylcyclohexanecarboxylic acid p-tert-butyl-phenyl ester hydrochloride | unspecified | asthma |
| CCR3 receptor modulators | unspecified | unspecified | asthma |
| CL 296141 | unspecified | unspecified | asthma |
| CPR 3005 | unspecified | unspecified | skin disease; eye disease; asthma; rheumatoid arthritis |

TABLE 6-continued

Current Candidate Therapeutic Interventions in Development for the Treatment of COPD

| Product Name | Chemical Name | Action | Indication |
|---|---|---|---|
| CPR 3014 | unspecified | unspecified | skin disease; eye disease; asthma; rheumatoid arthritis |
| CPR 3016 | unspecified | unspecified | skin disease; eye disease; asthma; rheumatoid arthritis |
| CPR 7011 | L-alpha-dipalmitoyl-sn-glycero-3-phosphocholine | unspecified | bronchitis; cystic fibrosis; rhinitis; asthma |
| CT 1441 | unspecified | unspecified | asthma; allergy |
| D 20783 | unspecified | unspecified | asthma; rhinitis |
| D 21247 | unspecified | unspecified | asthma; rhinitis |
| D 24241 | unspecified | unspecified | asthma; allergy |
| D 43787 | unspecified | unspecified | asthma; allergy |
| D 4396 | unspecified | unspecified | asthma |
| DF 1012 | endo-N-(8-methyl-8-azabicyclo[3.2.1]oct-3-yl)-1H-pyrrolo[2,3-b]pyridine-3-carboxamide | unspecified | cough; bronchitis |
| drug delivery system, transdermal ketotifen; ketotifen | unspecified | unspecified | asthma |
| endothelium-associated disease therapy | unspecified | unspecified | stroke; asthma |
| erdosteine; dithiosteine; RV 144; P 144; KW 9144; EDIREL; TUSSOL | [[2-oxo-2-[(tetrahydro-2-oxo-3-thienyl)amino]-ethyl]thio]acetic acid | unspecified | bronchitis |
| FPL 68164 | unspecified | unspecified | asthma |
| IgE regulators | unspecified | unspecified | asthma; allergy |
| INS 365 | unspecified | unspecified | cystic fibrosis; bronchitis; eye disease |
| ion channel modulators, | unspecified | unspecified | arrhythmia; asthma |
| KCA 757 | 4-[6-acetyl-3-[3-[(4-acetyl-3-hydroxy-2-propyl-phenyl)thio]propoxy]-2-propylphenoxy]-butanoic acid | unspecified | asthma |
| KP 136; AL 136 | 8-hexyloxy-3-(1H-tetrazol-5-yl)-2H-1-benzo-pyran-2-one | unspecified | asthma |
| KSU 2178 | unspecified | unspecified | dermatitis; asthma |
| L 0066; F 11105 | unspecified | unspecified | asthma |
| LAS 30813 | unspecified | unspecified | asthma; allergy |
| LDP 977 | unspecified | unspecified | asthma |
| mast cell activation inhibitors | unspecified | unspecified | asthma; rhinitis |
| MDL 105212 | (R)-1-[2-[3-(3,4-dichlorophenyl)-1-(3,4,5-trimethoxybenzoyl)-3-pyrrolidinyl]ethyl]-4-phenyl-4-piperidinecarboxamide | unspecified | asthma |
| NIP 502 | 4-chloro-5-[[(3-ethoxy-4-methoxyphenyl)-methyl]amino]-3(2H)-pyridazinone | unspecified | asthma |
| osthole; osthol | 7-methoxy-8-(3-methyl-2-butenyl)-2H-1-benzo-pyran-2-one | unspecified | asthma |
| repirinast; BAY u 2372; MY 5116; ROMET | isopentyl 5,6-dihydro-7,8-dimethyl-4,5-dioxo-4H-pyrano[3,2-c]quinoline-2-carboxylate | unspecified | asthma |
| SCA 8801 | 6-bromo 8-(methylamino)imidazo[1,2-a]-pyrazine-2-carbonitrile | unspecified | asthma |
| scopinast; KA 398 | 7-[3-[4-[bis(4-fluorophenyl)hydroxymethyl]-1-piperidinyl]propoxy]-6-methoxy-2H-1-benzo-pyran-2-one | unspecified | asthma; allergy |
| TA 270 | N-[1,2-dihydro-4-hydroxy-1-methyl-3-(octyl-oxy)-2-oxo-7-quinolinyl]-3-(4-hydroxy-3,5-dimethoxyphenyl)-2-propenamide | unspecified | asthma; rhinitis |
| TAK 661 | unspecified | unspecified | dermatitis; asthma |
| tetrahydrocorynanthein | 17-methoxycorynan-16-carboxylic acid methyl ester | unspecified | asthma; allergy |
| Th2 modulators | unspecified | unspecified | asthma; dermatitis |
| thymosin beta 4; Tbeta4 | Thymosin beta 4 (rat clone pROS2 precursor) | unspecified | septic shock; respiratory distress syndrome; asthma |
| TO 190 | unspecified | unspecified | asthma |
| tranilast; MK 341; AINTERU; BESSARAL; CLANIST; LIZAMONT; RIZALAST; SYNBERNIA; TEIBLOCK; RIZABEN | 2-[[3-(3,4-dimethoxyphenyl)-1-oxo-2-propenyl]amino]benzoic acid | unspecified | asthma; allergy; conjunctivitis; rhinitis; restenosis |
| U 75412E | (16alpha)-21-[4-[3-(ethylamino)-2-pyridinyl]-1-piperazinyl]-16-methylpregna-1,4,9(11)-triene-3,20-dione(2Z)-2-butenedioate(1:1) | unspecified | asthma |
| doqualast; SM 857 | 11-oxo-11H-pyrido[2,1-b]quinazoline-2-carboxylic acid | uricosuric | asthma; gout |

TABLE 6-continued

Current Candidate Therapeutic Interventions in Development for the Treatment of COPD

| Product Name | Chemical Name | Action | Indication |
| --- | --- | --- | --- |
| vaccine, asthma | unspecified | vaccine | asthma |
| vaccine, asthma, Proteus International | unspecified | vaccine | asthma |
| nonionic surfactant vesicles; NISV | unspecified | vaccine adjuvant; immunosuppressant | rheumatoid arthritis; asthma; inflammation |
| colforsin dapropate; NKH 477; ADEHL | N,N-dimethyl-beta-alanine(3R,4aS,5S,6S,6aS,-10S,10aR,10bS)-5-(acetyloxy)-3-ethenyl-dodecahydro-10,10b-dihydroxy-3,4a,7,7,10a-pentamethyl-1-oxo-1H-naphtho[2,1-b]pyran-6-yl ester | vasodilator; broncho-dilator | heart failure; asthma; musculoskeletal disorder |
| ibudilast; KC 404; KETAS; AIVYNAL; EYEVYNIL | 3-isobutyryl-2-isopropylpyrazolo-(1,5alpha)-pyridine | vasodilator; PAF antagonist | asthma; eye disease |
| VLA-4 inhibitors, Epimmune | unspecified | VLA 4 antagonist; integrin antagonist; cell adhesion inhibitor | asthma |
| isbufylline | 7-isobutyltheophylline | xanthine | asthma |
| MX 2120 | 7-(2,2 dimethyl)propyl-1-methylxanthine | xanthine | asthma |
| nestifylline; ABC 99 | 7-(1,3-dithiolan-2-ylmethyl)-3,7-dihydro-1,3-dimethyl-1H-purine-2,6-dione | xanthine | asthma |
| MPX | 3,7-dihydro-1-methyl-3-(1-methylethyl)-1H-purine-2,6-dione | xanthine; bronchodilator | asthma |

TABLE 7

Current Candidate Therapeutic Interventions in Development for the Treatment of Autoimmune Disorders

| Product Name | Chemical Name | Action | Indication |
| --- | --- | --- | --- |
| brequinar; brequinar sodium; DUP 785; NSC 368390 | 6-fluoro-2-(2'-fluoro[1,1'-biphenyl]4-yl)-3-methyl-4-quinolinecarboxylic acid | antimetabolite; immunosuppressant | cancer; autoimmune disease; transplant rejection |
| ENZYOX | unspecified | antioxidant | autoimmune disease |
| antisense oligonucleotide, autoimmune disease | unspecified | antisense; oligonucleotide immunosuppressant | autoimmune disease |
| apoptosis modulators | unspecified | apoptosis inhibitor; apoptosis inducer | cancer; autoimmune disease; neurodegeneration |
| complement inhibitor, | unspecified | complement inhibitor; proteinase inhibitor; serine proteinase inhibitor; immunosuppressant | autoimmune disease |
| interferon gamma antagonists, | unspecified | cytokine antagonist; immunosuppressant | autoimmune disease |
| interleukin-12 signal transduction antagonists | unspecified | cytokine antagonist; immunosuppressant; NSAID | autoimmune disease; transplant rejection; rheumatoid arthritis |
| uromodulin | unspecified | cytokine inhibitor; immunosuppressant | autoimmune disease |
| SelCIDs | unspecified | cytokine inhibitor; NSAID; immunosuppressant; TNF inhibitor; phosphodiesterase inhibitor; phosphodiesterase IV inhibitor | autoimmune disease; inflammation |
| interleukin-10; IL-10; cytokine synthesis inhibitory factor; CSIF; SCH 52000; TENOVIL | interleukin 10 (human clone pH15C) | cytokine; vaccine adjuvant; immunosuppressant; NSAID | autoimmune disease; inflammatory bowel disease; rheumatoid arthritis; multiple sclerosis; psoriasis; HIV infection; viral infection |
| superoxide dismutase variants; SOD | unspecified | free radical scavenger; NSAID; immunosuppressant | inflammation; autoimmune disease; reperfusion injury |

TABLE 7-continued

Current Candidate Therapeutic Interventions in Development for the Treatment of Autoimmune Disorders

| Product Name | Chemical Name | Action | Indication |
|---|---|---|---|
| interleukin-4 diphtheria toxin chimeric protein; IL-4 diphtheria toxin chimeric protein; IL-4 fusion protein | unspecified | fusion toxin; immunosuppressant | autoimmune disease; transplant rejection; cancer; HIV infection |
| glucocorticoids | unspecified | glucocorticoid; immunosuppressant; NSAID | inflammation; asthma; autoimmune disease |
| castanospermine | [1S-(1 alpha, 6 beta, 7 alpha, 8 beta, 8 abeta)]-octahydro-1,6,7,8-indolizine tetrol | glycosidase inhibitor, immunosuppressant | autoimmune disease; viral infection |
| growth and differentiation factor 3; GDF 3 | unspecified | growth factor; differentiation inducer; immunosuppressant | transplant rejection; autoimmune disease |
| MDL 28842 | (Z)-9-(5-deoxy-5-fluoro-beta-D-threo-pent-4 enofuranosyl-9H-purin-6-one | homocysteine hydrolase inhibitor; immunosuppressant | malaria; autoimmune disease |
| Hsp70 modulators, autoimmune disease | unspecified | HSP70 inhibition | autoimmune disease |
| cetraric acid | 9-(ethoxymethyl)-4-formyl-3,8-dihydroxy-1,6-dimethyl-11-oxo-11 H-dibenzo[b,e][1,4]dioxepin-7-carboxylic acid | immunostimulant | autoimmune disease |
| immunostimulants | unspecified | immunostimulant | cancer; autoimmune disease |
| lymphocyte activation inhibitors | unspecified | immunostimulant | autoimmune disease; transplant rejection |
| T cell modulators, | unspecified | immunostimulant; immunosuppressant | infectious disease; autoimmune disease |
| B7 molecules; B7-1; B7-2 | unspecified | immunosuppressant | autoimmune disease; transplant rejection |
| cholera toxin subunit B-antigen conjugate | unspecified | immunosuppressant | autoimmune disease |
| Fc receptors, soluble, | unspecified | immunosuppressant | autoimmune disease |
| interferon receptor type 1; IFNAR2 | unspecified | immunosuppressant | autoimmune disease |
| MAb, CD45RB | unspecified | immunosuppressant | transplant rejection; autoimmune disease |
| MAb, humanized B7.1 | unspecified | immunosuppressant | psoriasis; transplant rejection; autoimmune disease |
| MAb, humanized B7.2 | unspecified | immunosuppressant | psoriasis; transplant rejection; autoimmune disease |
| MEDI 507 | unspecified | immunosuppressant | autoimmune disease; transplant rejection; psoriasis |
| PEPTIMER | unspecified | immunosuppressant | autoimmune disease multiple sclerosis; rheumatoid arthritis; diabetes |
| RG 1046 | unspecified | immunosuppressant | autoimmune disease transplant rejection |
| T cell antigen receptor technology; TCAR technology | unspecified | immunosuppressant | research tool; autoimmune disease |
| autoimmune disease therapy | unspecified | immunosuppressant | autoimmune disease |
| bactobolamine | [3S-(3 alpha, 4 alpha, 4 abeta, 5 beta, 6 alpha)]-4-amino-3-(dichloromethyl)-3,4,4a,5,6,7-hexahydro-5,6,8-trihydroxy-3-methyl-1H-2-benzopyran-1-one | immunosuppressant | autoimmune disease |
| BTS 63155 | unspecified | immunosuppressant | autoimmune disease |
| calcineurin inhibitor | unspecified | immunosuppressant | autoimmune disease; neurological |

TABLE 7-continued

Current Candidate Therapeutic Interventions in Development for the Treatment of Autoimmune Disorders

| Product Name | Chemical Name | Action | Indication |
|---|---|---|---|
| CT 2544 | unspecified | immunosuppressant | autoimmune disease transplant rejection |
| drug delivery system, LDS microemulsion ciclosporin; ciclosporin LDS microemulsion | unspecified | immunosuppressant | autoimmune disease; transplant rejection |
| drug delivery system, microemulsion ciclosporin; ciclosporin microemulsion; SANDIMMUN NEORAL; SANDIMMUN OPTORAL; NEORAL; NEORAL-SANDIMMUN | unspecified | immunosuppressant | autoimmune disease; transplant rejection |
| FR 901459 | 4-L-leucine-7-L-threonine-10-L-leucine-cyclosporin A | immunosuppressant | autoimmune disease |
| FTY 720 | 2-amino-2-[2-(4-octylphenyl)ethyl]-1,3-propanediol hydrochloride | immunosuppressant | transplant rejection; autoimmune disease |
| glycophospholipid, Graves' disease | unspecified | immunosuppressant | autoimmune disease |
| immunologyinflammation therapy | unspecified | immunosuppressant | inflammation; autoimmune disease; asthma |
| immunophilins, | unspecified | immunosuppressant | autoimmune disease |
| immunoregulators, | unspecified | immunosuppressant | autoimmune disease |
| immunoregulatory colostrum isolate | unspecified | immunosuppressant | autoimmune disease |
| immunosuppressant | unspecified | immunosuppressant | autoimmune disease; transplant rejection |
| immunosuppressants, | unspecified | immunosuppressant | autoimmune disease; asthma |
| immunosuppressants | unspecified | immunosuppressant | transplant rejection; autoimmune disease |
| immunosuppressants, | unspecified | immunosuppressant | autoimmune disease; transplant rejection |
| immunosuppressants, | unspecified | immunosuppressant | autoimmune disease |
| immunosuppressants, | unspecified | immunosuppressant | autoimmune disease |
| immunosuppressants, ZAP70 | unspecified | immunosuppressant | autoimmune disease |
| interferon gamma inhibitor | unspecified | immunosuppressant | septic shock; autoimmune disease |
| interleukin-2 receptor ligand | unspecified | immunosuppressant | transplant rejection; autoimmune disease |
| ion channel modulators, | unspecified | immunosuppressant | cardiovascular disease; neurological; autoimmune disease |
| IR 1116 | Unspecified | immunosuppressant | autoimmune disease |
| leptin antagonists | unspecified | immunosuppressant | autoimmune disease; transplant rejection |
| LF 150195 | unspecified | immunosuppressant | autoimmune disease |
| LZ 8 | unspecified | immunosuppressant | autoimmune disease |
| microcolins | unspecified | immunosuppressant | autoimmune disease |
| myriocin; thermozymocidin; ISP-I | [2S-(2R*, 3S*, 4S*, 6E)]-2-amino-3,4-dihydroxy-2-(hydroxymethyl)-14-oxo-6-eicosenoic acid | immunosuppressant transplant rejection | autoimmune disease; |
| PRO 2844 | (OC-6-22)-pentaammine(4-methylpyridine)ruthenium (3+) trichloride | immunosuppressant | psoriasis; autoimmune disease; transplant rejection |
| prodigiosin 25-C; prodigiosin | 4-methoxy-5-[(5-methyl-4-pentyl-2H-pyrrol-2-ylidene)methyl]-2,2'-bi-1H-pyrrole | immunosuppressant | autoimmune disease |

TABLE 7-continued

Current Candidate Therapeutic Interventions in Development for the Treatment of Autoimmune Disorders

| Product Name | Chemical Name | Action | Indication |
|---|---|---|---|
| rapamycin analogue | unspecified | immunosuppressant | autoimmune disease |
| Rh toleragens | unspecified | immunosuppressant | autoimmune disease |
| SKF 106610 | 2-[3-(1-piperidinyl)propyl]-8,8-dipropyl-2-azaspiro[4.5]decane dihydrochloride | immunosuppressant | autoimmune disease |
| SM 8849 | 4-[1-(2-fluoro-4-biphenylyl)ethyl]-2-methylaminothiazole | immunosuppressant | autoimmune disease |
| Stat4/Stat6 blockers | unspecified | immunosuppressant | autoimmune disease; allergy |
| TOK 8801 | 5,6-dihydro-3,6,6-trimethyl-N-(2-phenylethyl)imidazo[2,1-b]thiazole-2-carboxamide | immunosuppressant | autoimmune disease |
| tresperimus; LF 80299; LF 299 | [4-[(3-aminopropyl)amino]butyl] carbamic acid 2-[[6-[(aminoiminomethyl)amino]hexyl]amino]-2-oxoethyl ester | immunosuppressant | autoimmune disease |
| VE 19613 | unspecified | immunosuppressant | autoimmune disease |
| VX 497 | unspecified | immunosuppressant | psoriasis; autoimmune disease; viral infection; hepatitis |
| XENOJECT | unspecified | immunosuppressant | cancer; autoimmune disease |
| aldose reductase inhibitors | unspecified | immunosuppressant; aldose reductase inhibitor; NSAID | autoimmune disease; allergy; inflammation |
| MAb, gp39; BMS 202448 | unspecified | immunosuppressant; biotechnology | autoimmune disease |
| monocyte colony inhibitory factor-1 | unspecified | immunosuppressant; biotechnology; chemokine | autoimmune disease; rheumatoid arthritis; systemic lupus erythematosus |
| chemokine receptor antagonists | unspecified | immunosuppressant; chemokine antagonist; cytokine antagonist | autoimmune disease |
| CBP 1011 | unspecified | immunosuppressant; corticosteroid | autoimmune disease; systemic lupus erythematosus; asthma |
| CBP 2011 | unspecified | immunosuppressant; corticosteroid | autoimmune disease; thrombocytopenia |
| CBP 2012 | unspecified | immunosuppressant; corticosteroid | autoimmune disease; thrombocytopenia |
| autoimmune disease-specific MHC blockers | unspecified | immunosuppressant; DMARD; NSAID | rheumatoid arthritis; autoimmune disease |
| Bcl-x gamma-based therapy, | unspecified | immunosuppressant; gene; apoptosis inducer | autoimmune disease |
| protein A-based immune modulator | unspecified | immunosuppressant; immunostimulant | autoimmune disease; cancer |
| signal transduction modulators | unspecified | immunosuppressant; immunostimulant; NSAID | autoimmune disease; cancer; inflammation |
| MAb, H65 humanized Fab' | unspecified | immunosuppressant; monoclonal antibody | autoimmune disease |
| MAb, human interleukin-6 receptor; MAb, human IL-6 receptor; hPM-1; MRA | unspecified | immunosuppressant; monoclonal antibody | autoimmune disease; cancer |
| MAb, UCHL1; MAb, CD45RO | unspecified | immunosuppressant; monoclonal antibody | autoimmune disease |
| MAb, CD3-immunotoxin | unspecified | immunosuppressant; monoclonal antibody; biotechnology; immunotoxin | transplant rejection; autoimmune disease |

TABLE 7-continued

Current Candidate Therapeutic Interventions in Development for the Treatment of Autoimmune Disorders

| Product Name | Chemical Name | Action | Indication |
|---|---|---|---|
| enlimomab; MAb, intracellular adhesion molecule-1; MAb, ICAM-1; MAb, ICAM; MAb, R65; MAb, CD54; BIRR 0001; BIRR 1 | unspecified | immunosuppressant; monoclonal antibody; NSAID | transplant rejection; autoimmune disease; rheumatoid arthritis |
| MAb, MHC class II; CDP 855 | unspecified | immunosuppressant; monoclonal antibody; NSAID | autoimmune disease; systemic lupus erythematosus |
| priliximab; MAb, humanized CD4; cM-T412; CEN 000029, | immunoglobulin G1 (human-mouse monoclonal cm-T412 anti-human antigen CD 4), disulfide with human-mouse monoclonal cm-T412.kappa.-chain, dimer | immunosuppressant, monoclonal antibody NSAID | multiple sclerosis; autoimmune disease rheumatoid arthritis |
| C-Maf based therapy | unspecified | immunosuppressant; NSAID | autoimmune disease; rheumatoid arthritis |
| leukocyte function associated antigen 3 T cell inhibitor protein; LFA3TIP; LFA3TIP; AMEVIVE | unspecified | immunosuppressant; NSAID | inflammation; autoimmune disease psoriasis |
| OX40-based immunotherapy | unspecified | immunosuppressant; NSAID | inflammation; autoimmune disease |
| inflammation therapy, | unspecified | immunosuppressant; NSAID | inflammatory bowe disease; inflammation; autoimmune disease |
| KB 2683 | 2-(4-methylphenyl)-4-benzothiazolol acetate | immunosuppressant; NSAID | rheumatoid arthritis; inflammation; autoimmune disease |
| MX 68 | 2-[[[4-[2,4-diamino-6-pteridinyl]methyl]-3,4-dihydro-2H-1,4-benzothiazin-7-yl]carbonyl]amino]hexan edioic acid | immunosuppressant; NSAID erythematosus; autoimmune disease | rheumatoid arthritis; systemic lupus |
| PIC 101 | unspecified | immunosuppressant; NSAID | rheumatoid arthritis; autoimmune disease; transplant rejection |
| PIC 102 | unspecified | immunosuppressant; NSAID | rheumatoid arthritis; transplant rejection; autoimmune disease |
| PIC 231 | unspecified | immunosuppressant; NSAID | rheumatoid arthritis; transplant rejection; autoimmune disease |
| SKF 105685 | N,N-dimethyl-8,8-dipropyl-2-azaspiro[4,5]decane-2-propanamine dihydrochloride | immunosuppressant; NSAID | autoimmune disease; rheumatoid arthritis; HIV infection |
| atiprimod; atiprimod dimaleate; SKF 106615 | N,N-diethyl-8,8-dipropyl-2-azaspiro[4.5]decane-2-propanamine | immunosuppressant; NSAID; macrophage inhibitor | rheumatoid arthritis; autoimmune disease; psoriasis |
| calcineurin inhibitory peptides | unspecified | immunosuppressant; peptide | autoimmune disease |
| immunosuppressant peptides | unspecified | immunosuppressant; peptide | transplant rejection; autoimmune disease |
| T cell peptide | unspecified | immunosuppressant; peptide | autoimmune disease; cancer; bacterial infection |
| PP 14 | unspecified | immunosuppressant; peptide; NSAID | autoimmune disease; rheumatoid arthritis |
| potassium channel blocker | unspecified | immunosuppressant; potassium channel blocker | autoimmune disease; allergy; inflammation |
| autoimmune disease therapy | unspecified | immunosuppressant; proteinase inhibitor | autoimmune disease |
| leflunomide; HWA 486; ARAVA | 5-methyl-N-[4-(trifluoromethyl)phenyl]-4-isoxazolecarboxamide | immunosuppressant; tyrosine kinase inhibitor; NSAID; DMARD | rheumatoid arthritis; autoimmune disease |

TABLE 7-continued

Current Candidate Therapeutic Interventions in Development for the Treatment of Autoimmune Disorders

| Product Name | Chemical Name | Action | Indication |
| --- | --- | --- | --- |
| MAb, ICAM-3; MAb, intracellular adhesion molecule-3; MAb, ICAM-R; ICM3 | unspecified | integrin antagonist; biotechnology; cell adhesion inhibitor; immunosuppressant; monoclonal antibody | autoimmune disease; psoriasis |
| MAb, L-selectin, humanized; SMART anti-L-selectin; HuDREG 200 | unspecified | integrin antagonist; biotechnology; monoclonal antibody; cell adhesion inhibitor; immunosuppressant; L selectin antagonist | trauma; respiratory distress syndrome; autoimmune disease; reperfusion injury |
| microcolin A | N-(2,4-dimethyl-1-oxooctyl)-N-methylleucyl-N-[1-[[2-[(2,5-dihydro-2-methyl-5-oxo-1H-pyrrol-1-yl)carbonyl)-4-hydroxy 1-pyrrolidinyl]carbonyl]-2-methylpropyl]-N-methylthreoninamide, 23-acetate | lipopeptide; immunosuppressant | autoimmune disease |
| sirolimus; rapamycin; NSC 226080; AY 22989; RAPAMUNE | (3S, 6R, 7E, 9R, 10R, 12R, 14S, 15E, 17E, 19E, 21S, 23S, 26R, 27R, 34aS)-9, 10, 12, 13, 14, 21, 22, 23, 24, 25, 26, 27, 32, 33, 34, 34a-hexadecahydro-9, 27-dihydroxy-3-[(1R)-2-[(1S, 3R, 4R)-4-hydroxy-3-methoxycyclohexyl)-1-methylethyl]-10, 21-dimethoxy-6, 8, 12, 14, 20, 26-hexamethyl-23, 27-epoxy-3H-pyndo[2,1-c)[1,4]oxaazacyclohentri-acontine-1, 5, 11, 28, 29(4H, 6H, 31 H)-pentone | macrolide; immunosuppressant; antibiotic | transplant rejection; autoimmune disease; restenosis |
| MAb, red blood cell D antigen; MAb, rhesus D; AM 101 | unspecified | monoclonal antibody; biotechnology; immunosuppressant | autoimmune disease |
| MAb, interleukin-12; MAb, IL-12; J695; C17.15 | unspecified | monoclonal antibody; cytokine antagonist; immunosuppressant | autoimmune disease |
| MAb, Fv, cytokine; CDP 870 | unspecified | monoclonal antibody; cytokine inhibitor; immunosuppressant | rheumatoid arthritis; autoimmune disease |
| MAb, humanized CD3; MAb, SMART CD3; HuM291 | unspecified | monoclonal antibody; immunosuppressant | transplant rejection; autoimmune disease' psoriasis |
| daclizumab; dacliximab; MAb, Tac; MAb, humanized Tac; MAb, SMART Tac; Ro 247375; ZENAPAX | immunoglobulin G1 (human-mouse monoclonal clone 1H4 gamma chain anti-human antigen Tac), disulfide with human-mouse monoctonal clone 1H4 light chain, dimer | monoclonal antibody; immunosuppressant | transplant rejection; cancer; autoimmune disease; eye disease |
| MAb, 6G5.1; MAb, autoimmune disease, human, Medarex; MDX CD4 | unspecified | monoclonal antibody; immunosuppressant | autoimmune disease rheumatoid arthritis |
| MAb, alpha-tubulin | unspecified | monoclonal antibody; immunosuppressant | cancer; autoimmune disease; diagnosis |
| MAb, autoimmune disease; MAb, MHC II | unspecified | monoclonal antibody; immunosuppressant | autoimmune disease |
| MAb, CD45RB | unspecified | monoclonal antibody; immunosuppressant | autoimmune disease; transplant rejection |

TABLE 7-continued

Current Candidate Therapeutic Interventions in Development for the Treatment of Autoimmune Disorders

| Product Name | Chemical Name | Action | Indication |
|---|---|---|---|
| MAb, Fc antagonist; MDX33 | unspecified | monoclonal antibody; immunosuppressant | autoimmune disease; thrombocytopenia |
| MAb, gp39; MAb, CD40L; IDEC 131 | unspecified | monoclonal antibody; immunosuppressant | autoimmune disease; transplant rejection; systemic lupus erythematosus |
| MAb, H57597 | unspecified | monoctonal antibody; immunosuppressant | autoimmune disease |
| MAb, inflammation therapy, | unspecified | monoclonal antibody; immunosuppressant | inflammation; autoimmune disease |
| MAb, L0-CD2a; BTI 322 | unspecified | monoclonal antibody; immunosuppressant | autoimmune disease; transplant rejection |
| MAb, MHC II-CD4; 14-CD4 | unspecified | monoclonal antibody; immunosuppressant | autoimmune disease; graft versus host disease |
| MAb, migis-mIgG; Mab, B cell | unspecified immunosuppressant | monoclonal antibody; | autoimmune disease |
| MAb, RhCA 61-76; MAb, anti-AChR alpha subunit; TCM 240 | unspecified immunosuppressant | monoclonal antibody; | autoimmune disease |
| MAbs, B cells; migis | unspecified | monoclonal antibody; immunosuppressant | autoimmune disease; cancer |
| MAb, MHC class II | unspecified | monoclonal antibody; immunosuppressant; NSAID | autoimmune disease; transplant rejection; graft versus host disease; cancer |
| S 2474 | unspecified | NSAID; DMARD; COX inhibitor; COX 2 inhibitor; immunosuppressant | rheumatoid arthritis; autoimmune disease |
| immunosuppressive, ANUTECH | unspecified | peptide; immunosuppressant | autoimmune disease |
| inflammation therapy, BTG; autoimmune disease therapy, BTG | unspecified | peptide; immunosuppressant | inflammation; autoimmune disease |
| complement inhibitors, | unspecified | peptide; immunosuppressant; NSAID | rheumatoid arthritis; systemic lupus erythematosus; autoimmune disease; reperfusion injury; respiratory distress syndrome; transplant rejection |
| polyclonal antibody, idiopathic thrombocytopenia purpura; polyclonal antibody, ITP; MelGAM | unspecified | polyclonal antibody; immunoglobulin | autoimmune disease |
| polyclonal antibody, immune thrombocytopenia purpura; polyclonal antibody, ITP; Rho(D) immune globulin; WinRho SD; WinRho SDF | unspecified | polyclonal antibody; immunosuppressant; immunoglobulin | autoimmune disease; HIV infection |
| ANK 102 | Unspecified | polysaccharide; | autoimmune disease immunosuppressant |
| cathepsin S inhibitors, | unspecified | proteinase inhibitor; cathepsin S inhibitor; NSAID; immunosuppressant | inflammation; autoimmune disease |
| SR 31747 | (Z)-N[3-chloro-4-cyclohexylphenyl)-2-propenyl]-N-ethyl-cyclohexanamine hydrochloride | sigma antagonist; immunosuppressant; NSAID | autoimmune disease; arthritis |
| signal transduction inhibitor, SUGEN/ArQule | unspecified | signal transduction inhibitor; immunosuppressant | cancer; diabetes; neurological; autoimmune disease |
| SP 100030 | Unspecified | signal transduction inhibitor; NSAID; immunosuppressant | inflammation autoimmune disease |

TABLE 7-continued

Current Candidate Therapeutic Interventions in Development for the Treatment of Autoimmune Disorders

| Product Name | Chemical Name | Action | Indication |
| --- | --- | --- | --- |
| tumor necrosis factor binding protein; TBP-1; TBP | unspecified | TNF inhibitor; immunosuppressant | autoimmune disease; reperfusion injury; inflammation; septic shock |
| etanercept; tumor necrosis factor receptor; TNFr; TNR 001; | unspecified | TNF inhibitor; immunosuppressant; NSAID; analgesic | rheumatoid arthritis; heart failure; diabetes; pain; endometriosis; autoimmune disease |
| transcription factor inhibitors | unspecified | transcription factor regulator | inflammation, autoimmune disease |
| NF-kappaB inhibitor | unspecified | transcription factor regulator; NSAID | inflammation; ischemia; cancer; autoimmune disease |
| AP-1 inhibitor, JNK inhibitor | unspecified | transcription factor regulator; NSAID; immunosuppressant | inflammation; autoimmune disease; cancer |
| SC 114 | unspecified | triglyceride; immunosuppressant | autoimmune disease; transplant rejection |
| AP 251 | unspecified | tyrosine kinase inhibitor; immunosuppressant | autoimmune disease |
| p56 lck inhibitors | unspecified | tyrosine kinase inhibitor; immunosuppressant | autoimmune disease |
| ZAP70 inhibitors | unspecified | tyrosine kinase inhibitor; immunosuppressant | autoimmune disease |
| Tolerogen, autoimmune disease | unspecified | unspecified | autoimmune disease |
| Vaccine, gene-based, autoimmune disease | unspecified | vaccine; gene therapy | autoimmune disease; inflammation |
| vaccine, gene-based, autoimmune disease; | unspecified | vaccine; gene therapy; immunosuppressant | autoimmune disease |

TABLE 8

Current Candidate Therapeutic Interventions in Development for the Treatment of Systemic Lupus Erythematosus

| Product Name | Chemical Name | Action | Indication |
| --- | --- | --- | --- |
| prasterone; dehydroepiandrosterone; DHEA; GL 701; NBI 106; PB 007; ASTENILE; DEANDROS; DIANDRON | (3beta)-3-hydroxyandrost-5-en-17-one | androgen; vaccine adjuvant; hormone replacement therapy; corticosteroid | systemic lupus erythematosus; hormone deficiency; Alzheimer disease; reperfusion injury; ischemia |
| Fasdelta ™ | unspecified | apoptosis inhibitor | HIV infection |
| MAb, C5; MAb, complement C5; 5G1.1 | unspecified | complement inhibitor; monoclonal antibody; immunosuppressant; NSAID | rheumatoid arthritis; systemic lupus erythematosus |
| RP 54745 | 4-chloro-5-(3,4-dihydro-1-methyl-2(1H)-isoquinolinyl)-3H-1,2-dithiol-3-one | cytokine antagonist; immunosuppressant; NSAID | rheumatoid arthritis; inflammatory bowel disease; psoriasis |
| interleukin-1 receptor; IL-1r; HJ 1306 | unspecified | cytokine inhibitor; immunosuppressant | asthma |
| SelCIDs | unspecified | cytokine inhibitor; NSAID; immunosuppressant; TNF inhibitor; phosphodiesterase inhibitor; phosphodiesterase IV inhibitor | autoimmune disease; inflammation |
| dornase alfa; deoxyribonuclease; DNase; PULMOZYME | deoxyribonuclease (human clone 18-1 protein moiety) | deoxyribonuclease; enzyme | cystic fibrosis; bronchitis; pulmonary obstructive disease; systemic lupus erythematosus |

TABLE 8-continued

Current Candidate Therapeutic Interventions in Development for the Treatment of Systemic Lupus Erythematosus

| Product Name | Chemical Name | Action | Indication |
|---|---|---|---|
| actarit; MS 932; MOVER; ORCL | 4-(acetylamino)phenylacetic acid | DMARD; immunosuppressant; NSAID | rheumatoid arthritis |
| gene therapy, transforming growth factor beta | unspecified | gene therapy; NSAID | rheumatoid arthritis |
| glucocorticoids, Ligand | unspecified | glucocorticoid; immunosuppressant; NSAID | inflammation; asthma; autoimmune disease |
| gallium nitrate; NSC 15200; CALSTAT; GANITE | gallium nitrate nonahydrate | hypocalcemic; nitric oxide synthase inhibitor | hypercalcemia; cancer |
| geclosporin; ciclosporin G; cyclosporin G; ciclosporin, (NVA)2-; cyclosporin, (NVA)2-; OG 37325 | 7-L-norvaline cyclosporin A | immunostimulant | transplant rejection |
| recombinant alpha3 collagen chain; BST 3003 | unspecified | immunosuppressant | kidney disease; systemic lupus erythematosus |
| drug delivery system microemulsion ciclosporin; ciclosporin microemulsion; SANDIMMUN NEORAL; SANDIMMUN OPTORAL; NEORAL; NEORAL-SANDIMMUN | unspecified | immunosuppressant | autoimmune disease transplant rejection |
| fluasterone | unspecified | immunosuppressant | cancer; diabetes; systemic lupus erythematosus |
| immunosuppressant | unspecified | immunosuppressant | autoimmune disease; transplant rejection |
| LJP 394 | unspecified | immunosuppressant | systemic lupus erythematosus |
| VX 497 | unspecified | immunosuppressant | psoriasis; autoimmune disease; viral infection; hepatitis |
| SM 8849 | 4-[1-(2-fluoro-4-biphenylyl)ethyl]-2-methylaminothiazole | immunosuppressant | autoimmune disease |
| monocyte colony inhibitory factor-1 | unspecified | immunosuppressant; biotechnology; chemokine | autoimmune disease; rheumatoid arthritis; systemic lupus erythematosus |
| CBP 1011 | unspecified | immunosuppressant; corticosteroid | autoimmune disease; systemic lupus erythematosus; asthma |
| MAb, MHC class II; CDP 855 | unspecified | immunosuppressant; monoclonal antibody; NSAID | autoimmune disease systemic lupus erythematosus |
| BMS 188667; CTLA4Ig | unspecified | immunosuppressant; NSAID | transplant rejection; systemic lupus erythematosus; psoriasis; arthritis; allergy |
| MAb, CD40 ligand; 5C8; ANTOVA | unspecified | immunosuppressant; NSAID | inflammation; systemic lupus erythematosus; multiple sclerosis |
| autoimmune disease therapy | unspecified | immunosuppressant; NSAID | rheumatoid arthritis; multiple sclerosis; systemic lupus erythematosus |
| PG 2946 | unspecified | immunosuppressant; NSAID | rheumatoid arthritis; systemic lupus erythematosus; transplant rejection |
| PG 3028 | unspecified | immunosuppressant; NSAID | rheumatoid arthritis; systemic lupus erythematosus; transplant rejection |

TABLE 8-continued

Current Candidate Therapeutic Interventions in Development for the Treatment of Systemic Lupus Erythematosus

| Product Name | Chemical Name | Action | Indication |
| --- | --- | --- | --- |
| PG 3113 | unspecified | immunosuppressant; NSAID | rheumatoid arthritis; systemic lupus erythematosus; transplant rejection |
| MX 68 | 2-[[[4-[2,4-diamino-6-pteridinyl]methyl]-3,4-dihydro-2H-1,4-benzothiazin-7-yl]carbonyl]amino]hexanedioic acid | immunosuppressant; NSAID | rheumatoid arthritis; systemic lupus erythematosus; autoimmune disease |
| baohuoside 1; icariside II; B-1 | 3-[(6-deoxy-alpha-L-mannopyranosyl)oxy]-5,7-dihydroxy-2-(4-methoxyphenyl)-8-(3-methyl-2-butenyl)-4H-1-benzopyran-4-one | immunosuppressant; NSAID | systemic lupus erythematosus; rheumatoid arthritis |
| SKF 105685 | N,N-dimethyl-8,8-dipropyl-2-azaspiro[4,5]decane-2-propanamine dihydrochloride | immunosuppressant; NSAID | autoimmune disease; rheumatoid arthritis; HIV infection |
| ZAP inhibitors | unspecified | immunosuppressant; protein kinase inhibitor; tyrosine kinase inhibitor; NSAID | transplant rejection; rheumatoid arthritis; inflammatory bowel disease; systemic lupus erythematosus; multiple sclerosis |
| sirolimus; rapamycin; NSC 226080; AY 22989; RAPAMUNE | (3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29(4H,6H,31H)-pentone | macrolide; immunosuppressant; antibiotic | transplant rejection; autoimmune disease; restenosis |
| bindarit; AF 2838 | 2-methyl-2-[[1-(phenylmethyl)-1H-indazol-3-yl]methoxy]-propanoic acid | MCP-1 production inhibition; mRNA expression inhibition | rheumatoid arthritis; nephritis |
| MAb, 1C7; passive immunotherapy, systemic lupus erythrematosus | unspecified | monoclonal antibody; immunosuppressant | systemic lupus erythematosus |
| MAb, Fc antagonist; MDX 33 | unspecified | monoclonal antibody; immunosuppressant | autoimmune disease; thrombocytopenia |
| MAb, gamma interferon humanized; SMART anti-gamma interferon | unspecified | monoclonal antibody, immunosuppressant | systemic lupus erythematosus; multiple sclerosis |
| MAb, gp39; MAb, CD40L; IDEC 131 | unspecified | monoclonal antibody; immunosuppressant | autoimmune disease; transplant rejection; systemic lupus erythematosus |
| MAb, H57597 | unspecified | monoclonal antibody; immunosuppressant | autoimmune disease |
| MAb, interleukin-10; MAb, IL-10 | unspecified | monoclonal antibody; immunosuppressant | systemic lupus erythematosus |
| MAb, migis-mIgG; Mab, B cell | unspecified | monoclonal antibody; immunosuppressant | autoimmune disease |
| MAbs, B cells; migis | unspecified | monoclonal antibody; immunosuppressant | autoimmune disease; cancer |

TABLE 8-continued

Current Candidate Therapeutic Interventions in Development for the Treatment of Systemic Lupus Erythematosus

| Product Name | Chemical Name | Action | Indication |
| --- | --- | --- | --- |
| zolimomab aritox; MAb, H65 RTA; MAb, bone marrow-ricin A conjugate; CD5-T lymphocyte immunotoxin; MAb, CD5; XMMLY H65 RTA; XOMAZYME H65; XOMAZYME CD5+; ORTHOZYME CD5+; CD5 Plus | unspecified | monoclonal antibody; immunotoxin; immunosuppressant | transplant rejection |
| MAb, cytokines; AGT 1 | unspecified | monoclonal antibody; NSAID | rheumatoid arthritis |
| MAb, VLA-4, humanized; MAb, very late antigen-4, humanized | unspecified | monoclonal antibody; NSAID | inflammation; rheumatoid arthritis; asthma; diabetes |
| MAb, B7; MAb, PRIMATIZED B7; IDEC 114 | unspecified | monoclonal antibody; NSAID; immunosuppressant | systemic lupus erythematosus; inflammation; transplant rejection; psoriasis |
| MER W8020 | Unspecified | peptide; analgesic; NSAID | inflammation; pain |
| inflammation therapy, autoimmune disease therapy | unspecified | peptide; immunosuppressant | inflammation; autoimmune disease |
| complement inhibitors | unspecified | peptide; immunosuppressant; NSAID | rheumatoid arthritis; systemic lupus erythematosus; autoimmune disease; reperfusion injury; respiratory distress syndrome; transplant rejection |
| polyclonal antibodies, HIV, anti-70K | unspecified | polyclonal antibody; immunoglobulin | HIV infection |
| nafamostat; nafamostat mesylate; nafamostat mesilate; FUT 175; FUTHAN TORII; FUTHAN BANYU | 6-amidino-2-naphthyl p-guanidinobenzoate | proteinase inhibitor; platelet antiaggregant | thrombosis; pancreatitis; allergy; anaphylactic shock |
| mycophenolate mofetil; RS 61443 | (E)-6-(1,3-dihydro-4-hydroxy-6-methoxy-7-methyl-3-oxo-5-isobenzofuranyl)-4-methyl-4-hexenoic acid 2-(4-morpholinyl)ethyl ester | purine synthesis inhibitor; immunosuppressant; NSAID | transplant rejection; rheumatoid arthritis; asthma; restenosis; kidney disease; systemic lupus erythematosus |
| rolafagrel; FCE 22178 | 5,6-dihydro-7-(1H-imidazol-1-yl)-2-naphthalenecarboxylic acid | thromboxane synthetase inhibitor; platelet antiaggregant | thrombosis; kidney disease |
| thalidomide; SYNOVIR; THALOMID | N-(2,6-dioxo-3-piperidyl)phthalimide | TNF modulator; immunosuppressant | cachexia; diarrhea; leprosy; rheumatoid arthritis; transplant rejection; cancer; Crohn disease |
| MHC expression inhibitors, BLSI | unspecified | transcription inhibitor; NSAID | rheumatoid arthritis; systemic lupus erythematosus |
| AP 251 | unspecified | tyrosine kinase inhibitor; immunosuppressant | autoimmune disease |
| vaccine, systemic lupus erythematosus | unspecified | vaccine | systemic lupus erythematosus |
| MAb, 3E10; vaccine, nephritis | unspecified | vaccine; monoclonal antibody | nephritis |

TABLE 9

Current Candidate Therapeutic Interventions in Development for Immunnosuppression

| Product Name | Chemical Name | Action | Indication |
| --- | --- | --- | --- |
| depsidomycin; antibiotic MI 951-65F2 | N-[docosahydro-7-methyl-14-(1-methylethyl)-11,23-bis(2-methylpropyl)-5,9,12,15,21,24-hexaoxo-7H,17H-dipyridazino[6,1-c:6',1'-i][1,4,7,10,13,16]oxapentaazacyclononadecin-8-yl]-2-(formylamino)-3-methylpentanamide | antibiotic; immunosuppressant; peptide | bacterial infection |
| brequinar; brequinar sodium; DUP 785; NSC 368390 | 6-fluoro-2-(2'-fluoro[1,1'-biphenyl-4-yl)-3-methyl-4-quinolinecarboxylic acid | antimetabolite; immunosuppressant | cancer; autoimmune disease; transplant rejection |
| antisense oligonucleotide, interleukin-1; antisense oligonucleotide, IL-1 | unspecified | antisense; immunosuppressant; oligonucleotide; NSAID | inflammation |
| antisense oligonucleotide, NF-kappaB p65 subunit | unspecified | antisense; oligonucleotide; biotechnology; immunosuppressant | Crohn disease |
| antisense oligonucleotide, autoimmune disease | unspecified | antisense; oligonucleotide; immunosuppressant | autoimmune disease |
| antisense oligonucleotide, graft versus host disease | unspecified | antisense; oligonucleotide; immunosuppressant; apoptosis inducer | transplant rejection |
| apoptosis inhibitors, Oxford Asymmetry/LXR Biotechnology | unspecified | apoptosis inducer | cancer; cardiac therapy; transplant rejection; gastrointestinal disorder |
| L-selectin antagonist, NeXstar | unspecified | aptamer; oligonucleotide; integrin antagonist; L selectin antagonist; immunosuppressant; cell adhesion inhibitor; NSAID | inflammation |
| P-selectin antagonist, NeXstar | unspecified | aptamer; oligonucleotide; integrin antagonist; P selectin antagonist; immunosuppressant; cell adhesion inhibitor; NSAID | inflammation |
| gene therapy, tumor necrosis factor receptor | unspecified | biotechnology; gene therapy; TNF inhibitor; immunosuppressant; NSAID | rheumatoid arthritis |
| growth and differentiation factor 3; GDF 3 | unspecified | biotechnology; growth factor; differentiation inducer; immunosuppressant | transplant rejection; autoimmune disease |
| growth and differentiation factor-1; GDF-1 | unspecified | biotechnology; growth factor; neurotrophic factor | neurodegeneration |
| MAb, human interleukin-6 receptor; MAb, human IL-6 receptor; hPM-1; MRA | unspecified | biotechnology; immunosuppressant; monoclonal antibody | autoimmune disease; cancer |
| LFA-1 alpha subunit; leukocyte function associated antigen-1 alpha subunit; leukocyte cell surface adhesion receptor molecule | unspecified | biotechnology; nosuppressant; NSAID | inflammation |
| enlimomab; MAb, intracellular adhesion molecule-1; MAb, ICAM-1; MAb, ICAM; MAb, R65; MAb, CD54; BIRR 0001; BIRR 1 | unspecified | biotechnology;; monoclonal antibody; NSAID | transplant rejection; autoimmune disease; rheumatoid arthritis |

TABLE 9-continued

Current Candidate Therapeutic Interventions in Development for Immunnosuppression

| Product Name | Chemical Name | Action | Indication |
|---|---|---|---|
| OX40-based immunotherapy, Cantab | unspecified | biotechnology;; NSAID | inflammation; autoimmune disease |
| casein kinase inhibitors, ICOS | unspecified | casein kinase inhibitor; immunosuppressant; NSAID | inflammation; cancer |
| ICE inhibitor, IDUN | unspecified | caspase inhibitor; apoptosis inhibitor; IL-1 beta converting enzyme inhibitor; immunosuppressant | transplant rejection; septic shock; rheumatoid arthritis; inflammatory bowel disease; diabetes |
| cell therapy, FCRx | unspecified | cell therapy; immunosuppressant | transplant rejection |
| MAb, C5; MAb, complement C5; 5G1.1 | unspecified | complement inhibitor; monoclonal antibody; immunosuppressant; NSAID | rheumatoid arthritis; systemic lupus erythematosus |
| complement inhibitor, BioCryst/3 Dimensional Pharmaceuticals | unspecified | complement inhibitor; proteinase inhibitor; serine proteinase inhibitor; immunosuppressant | autoimmune disease |
| methylprednisolone suleptanate; U 67590A; PROMEDROL | (6alfa,11beta)-11,17-dihydroxy-6-methyl-21-[[8-[methyl(2-sulfoethyl)amino]-1,8-dioxooctyl]oxy]pregna-1,4-diene-3,20-dione monosodium salt | corticosteroid; immunosuppressant | inflammation; asthma; anaphylactic shock; transplant rejection |
| ORG 6632 | 21-chloro-9alfa-fluoro-11beta-hydroxy-16alfa,17alfa-dimethylpregna-1,4-diene-3,20-dione | corticosteroid; immunosuppressant | cancer; rheumatoid arthritis |
| gene therapy, soluble TNF receptor; gene therapy, corneal transplant rejection | unspecified | cytokine antagonist | transplant rejection |
| interferon gamma antagonists, Pharmacopeia; interferon gamma antagonists, Regeneron | unspecified | cytokine antagonist; immunosuppressant | autoimmune disease |
| interleukin-12 signal transduction antagonists, Ligand | unspecified | cytokine antagonist; immunosuppressant; NSAID | autoimmune disease; transplant rejection; rheumatoid arthritis |
| RP 54745 | 4-chloro-5-(3,4-dihydro-1-methyl-2(1H)-isoquinolinyl)-3H-1,2-dithiol-3-one | cytokine antagonist; immunosuppressant; NSAID | rheumatoid arthritis; inflammatory bowel disease; psoriasis |
| interleukin-8 receptor; IL-8r | unspecified | cytokine antagonist; NSAID; immunosuppressant | allergy; inflammation; transplant rejection |
| interleukin-1 receptor; IL-1r; HJ 1306 | unspecified | cytokine inhibitor; immunosuppressant | asthma |
| uromodulin | unspecified | cytokine inhibitor; immunosuppressant | autoimmune disease |
| anakinra; interleukin-1 receptor antagonist; IL-1ra; interleukin-1 inhibitor; ANTRIL | N2-L-methionylinterleukin 1 receptor antagonist (human isoform x reduced) | cytokine inhibitor; immunosuppressant; NSAID | rheumatoid arthritis; inflammatory bowel disease; transplant rejection; asthma; septic shock |
| interleukin-7 receptor; IL-7r | unspecified | cytokine inhibitor; NSAID; immunosuppressant | allergy; inflammation; transplant rejection |
| SelCIDs | unspecified | cytokine inhibitor; NSAID; immunosuppressant; TNF inhibitor; phosphodiesterase inhibitor; phosphodiesterase IV inhibitor | autoimmune disease; inflammation |

TABLE 9-continued

Current Candidate Therapeutic Interventions in Development for Immunnosuppression

| Product Name | Chemical Name | Action | Indication |
| --- | --- | --- | --- |
| interleukin-10; IL-10; cytokine synthesis inhibitory factor; CSIF; SCH 52000; TENOVIL | interleukin 10 (human clone pH15C) | cytokine; vaccine adjuvant; immunosuppressant; NSAID | autoimmune disease; inflammatory bowel disease; rheumatoid arthritis; multiple sclerosis; psoriasis; HIV infection; viral infection |
| CI 959 | 5-methoxy-3-(1-methylethoxy)-N-1H-tetrazol-5-yl-benzo[b]thiophene-2-carboxamide sodium salt | degranulation inhibitor; immunosuppressant NSAID | rhinitis; inflammation; asthma; arthritis |
| MDAM | N-[4-[2-(2,4-diamino-6-pteridinyl)ethyl]benzoyl]-4-methylene-DL-glutamic acid | dihydrofolate reductase inhibitor; NSAID; immunosuppressant | cancer; transplant rejection; rheumatoid arthritis; asthma |
| prinomide; prinomide tromethamine; CGS 10787; CGS 10787B | alpha-cyano-1-methyl-beta-oxopyrrole-2-propionanilide with 2-amino-2-(hydroxymethyl)-1,3-propanediol | DMARD; analgesic; immunosuppressant; NSAID | inflammation; pain; rheumatoid arthritis |
| actarit; MS 932; MOVER; ORCL | 4-(acetylamino)phenylacetic acid | DMARD; immunosuppressant; NSAID | rheumatoid arthritis |
| superoxide dismutase manganese complex; hMNSOD | unspecified | free radical scavenger; NSAID; immunosuppressant | ischemia; rheumatoid arthritis; inflammation; reperfusion injury |
| superoxide dismutase variants; SOD | unspecified | free radical scavenger; NSAID; immunosuppressant | inflammation; autoimmune disease; reperfusion injury |
| interleukin-4 diphtheria toxin chimeric protein; IL-4 diphtheria toxin chimeric protein; IL-4 fusion protein | unspecified | fusion toxin; immunosuppressant | autoimmune disease; transplant rejection; cancer; HIV infection |
| gene therapy, transplant rejection | unspecified | gene therapy; biotechnology; immunosuppressant | transplant rejection |
| gene cytokines therapy | unspecified | gene therapy; cytokine; immunosuppressant | autoimmune disease; rheumatoid arthritis; diabetes; multiple sclerosis |
| gene expression regulation technology, | unspecified | gene therapy; genomics; immunosuppressant | delivery system; drug design technology; graft versus host disease; transplant rejection |
| herpes simplex thymidine kinase; gene therapy, HS-tk | unspecified | gene therapy; immunosuppressant | transplant rejection |
| herpes simplex thymidine kinase; gene therapy, HS tk; gene therapy, graft versus host disease | unspecified | gene therapy; immunosuppressant | transplant rejection |
| glucocorticoids, Hoechst Marion Roussel | unspecified | glucocorticoid; immunosuppressant; NSAID | inflammation |
| glucocorticoids, Ligand | unspecified | glucocorticoid; immunosuppressant; NSAID | inflammation; asthma; autoimmune disease |
| castanospermine | [1S-(1alpha,6beta,7alpha,8beta,8abeta)]-octahydro-1,6,7,8-indolizine tetrol | glycosidase inhibitor; immunosuppressant | autoimmune disease; viral infection |
| MDL 28842 | (Z)-9-(5-deoxy-5-fluoro-beta-D-threo-pent-4enofuranosyl-9H-purin-6-one | homocysteine hydrolase inhibitor; immunosuppressant | malaria; autoimmune disease |

TABLE 9-continued

Current Candidate Therapeutic Interventions in Development for Immunnosuppression

| Product Name | Chemical Name | Action | Indication |
|---|---|---|---|
| lymphocyte activation inhibitors, Celltech | unspecified | immunostimulant | autoimmune disease transplant rejection |
| geclosporin; ciclosporin G; cyclosporin G; ciclosporin, (NVA)2-; cyclosporin, (NVA)2-; OG 37325 | 7-L-norvaline cyclosporin A | immunostimulant | transplant rejection |
| RM 06 | N-[N-[[[5-(1,6-dihydro-6-oxo-9H-purin-9-yl)pentyl]oxy]carbonyl]-L-leucyl]-L-methionine | immunostimulant | cancer; transplant rejection |
| T cell modulators, ArQule; T cell modulators, T Cell Sciences | unspecified | immunostimulant; immunosuppressant | infectious disease; autoimmune disease |
| thiethazole | 2-[1-(1,1-dioxothiethanyl-3)benzimidazolyl-2-thio] acetic acid | immunostimulant; immunosuppressant; antioxidant | cancer; rheumatoid arthritis; infectious disease; transplant rejection |
| FCE 20696 | 6H-dibenzo[b,d]pyran-6-carboxylic acid 2-(dimethylamino)ethyl ester hydrochloride | immunostimulant; immunosuppressant; NSAID | viral infection; rheumatoid arthritis |
| thymidine kinase; gene therapy, HS-tk | unspecified | immunosuppressant | transplant rejection; eye disease |
| Al 101 | unspecified | immunosuppressant | multiple sclerosis |
| Al 301 | unspecified | immunosuppressant | eye disease |
| B7 molecules; B7-1; B7-2 | unspecified | immunosuppressant | autoimmune disease; transplant rejection |
| cholera toxin subunit B-antigen conjugate | unspecified | immunosuppressant | autoimmune disease |
| Fc receptors, soluble, InKine | unspecified | immunosuppressant | autoimmune disease |
| galaptin L-14-1; immunomodulatory lectin-1; IML-1 | unspecified | immunosuppressant | transplant rejection; multiple sclerosis |
| IgE receptors, soluble, CorBec | unspecified | immunosuppressant | asthma |
| interferon receptor type 1; IFNAR2 | unspecified | immunosuppressant | autoimmune disease |
| MAb, CD45RB | unspecified | immunosuppressant | transplant rejection; autoimmune disease |
| MAb, humanized B7.1 | unspecified | immunosuppressant | psoriasis; transplant rejection; autoimmune disease |
| MAb, humanized B7.2 | unspecified | immunosuppressant | psoriasis; transplant rejection; autoimmune disease |
| MEDI 507 | unspecified | immunosuppressant | autoimmune disease; transplant rejection; psoriasis |
| OX40-IgG fusion protein | unspecified | immunosuppressant | inflammatory bowel disease |
| PEPTIMER | unspecified | immunosuppressant | autoimmune disease; multiple sclerosis; rheumatoid arthritis; diabetes |
| recombinant alpha3 collagen chain; BST 3002 | unspecified | immunosuppressant | kidney disease |
| recombinant alpha3 collagen chain; BST 3003 | unspecified | immunosuppressant | kidney disease; systemic lupus erythematosus |
| RG 1046 | unspecified | immunosuppressant | autoimmune disease; transplant rejection |
| T cell antigen receptor technology; TCAR technology | unspecified | immunosuppressant | research tool; autoimmune disease |
| AI 100; MYLORAL | unspecified | immunosuppressant | multiple sclerosis |
| AI 102 | unspecified | immunosuppressant | multiple sclerosis |
| AI 300 | unspecified | immunosuppressant | eye disease |
| asthma/allergy therapy, Rigel | unspecified | immunosuppressant | asthma; allergy |

TABLE 9-continued

Current Candidate Therapeutic Interventions in Development for Immunnosuppression

| Product Name | Chemical Name | Action | Indication |
| --- | --- | --- | --- |
| autoimmune disease therapy, Genome Pharmaceuticals | unspecified | immunosuppressant | autoimmune disease |
| BCH 1200 | unspecified | immunosuppressant | HIV infection |
| BTS 63155 | unspecified | immunosuppressant | autoimmune disease |
| calcineurin inhibitor, Agouron | unspecified | immunosuppressant | autoimmune disease; neurological |
| CI 0694; SULFASIM | unspecified | immunosuppressant | HIV infection |
| CT 2544 | unspecified | immunosuppressant | autoimmune disease; transplant rejection |
| CT 3578 | unspecified | immunosuppressant | transplant rejection |
| cytomuline | unspecified | immunosuppressant | transplant rejection |
| D 22557 | unspecified | immunosuppressant | allergy; asthma |
| D 7193 | unspecified | immunosuppressant | asthma |
| D5; PM 92114 | unspecified | immunosuppressant | cancer |
| drug delivery system, CYTOPORTER ciclosporin | unspecified | immunosuppressant | transplant rejection |
| drug delivery system, HILT, ciclosporin; ciclosporin, HILT, psoriasis; CYCLOPS | unspecified | immunosuppressant | psoriasis |
| drug delivery system, LDS microemulsion ciclosporin; ciclosporin LDS microemulsion | unspecified | immunosuppressant | autoimmune disease transplant rejection |
| drug delivery system liposome ciclosporin; ciclosporin liposome | unspecified | immunosuppressant | transplant rejection |
| drug delivery system, liposome ciclosporin; ciclosporin liposome; LipoSPOR | unspecified | immunosuppressant | psoriasis |
| drug delivery system, microemulsion ciclosporin; ciclosporin microemulsion; SANDIMMUN NEORAL; SANDIMMUN OPTORAL; NEORAL; NEORAL-SANDIMMUN | unspecified | immunosuppressant | autoimmune disease; transplant rejection |
| fluasterone | unspecified | immunosuppressant | cancer; diabetes; systemic lupus erythematosus |
| gene discovery, autoimmune disease, deCODE genetics | unspecified | immunosuppressant | autoimmune disease |
| gliotoxin | unspecified | immunosuppressant | transplant rejection |
| glycophospholipid, Graves' disease, City of Hope | unspecified | immunosuppressant | autoimmune disease |
| IgE receptor inhibitors, InKine | unspecified | immunosuppressant | asthma |
| immunology/inflammation therapy, Rigel | unspecified | immunosuppressant | inflammation; autoimmune disease; asthma |
| immunophilins, Vertex; immunophilins, Chugai | unspecified | immunosuppressant | autoimmune disease |
| immunoregulators, T Cell Sciences; immunoregulators, MYCOsearch | unspecified | immunosuppressant | autoimmune disease |
| immunoregulatory colostrum isolate | unspecified | immunosuppressant | autoimmune disease |
| immunosuppressant, Hollis Eden | unspecified | immunosuppressant | autoimmune disease; transplant rejection |
| immunosuppressant, Rhone-Poulenc Rorer | unspecified | immunosuppressant | asthma |
| immunosuppressants, Agouron | unspecified | immunosuppressant | autoimmune disease; asthma |
| immunosuppressants, AstraZeneca; immunosuppressants, University of California | unspecified | immunosuppressant | transplant rejection; autoimmune disease |

TABLE 9-continued

Current Candidate Therapeutic Interventions in Development for Immunnosuppression

| Product Name | Chemical Name | Action | Indication |
|---|---|---|---|
| immunosuppressants, Kinetix | Unspecified | immunosuppressant | autoimmune disease; transplant rejection |
| immunosuppressants, Millennium | unspecified | immunosuppressant | autoimmune disease |
| immunosuppressants, Nanodesign | unspecified | immunosuppressant | autoimmune disease |
| immunosuppressants, ZAP70, Roche; immunosuppressants, ZAP70, BioFocus | unspecified | immunosuppressant | autoimmune disease |
| insulin-dependent diabetes therapy, Procept | unspecified | immunosuppressant | diabetes |
| interferon gamma inhibitor, PharmaGenics | unspecified | immunosuppressant | septic shock; autoimmune disease |
| interleukin-2 receptor ligand, Affymax | unspecified | immunosuppressant | transplant rejection; autoimmune disease |
| ion channel modulators, ArQule; ion channel modulators, ICAgen | unspecified | immunosuppressant | cardiovascular disease; neurological; autoimmune disease |
| leptin antagonists, Imperial College | unspecified | immunosuppressant | autoimmune disease; transplant rejection |
| LF 150195 | unspecified | immunosuppressant | autoimmune disease |
| LJP 394 | unspecified | immunosuppressant | systemic lupus erythematosus |
| LJP 920 | unspecified | immunosuppressant | transplant rejection |
| LZ 8 | unspecified | immunosuppressant | autoimmune disease |
| microcolins | unspecified | immunosuppressant | autoimmune disease |
| NE 501 | unspecified | immunosuppressant | transplant rejection |
| promedulan; TERICIMUS | unspecified | immunosuppressant | cancer |
| rapamycin analogue, Reading University | unspecified | immunosuppressant | autoimmune disease |
| Rh toleragens | unspecified | immunosuppressant | autoimmune disease |
| RWJ 60475 | unspecified | immunosuppressant | transplant rejection |
| spiperone analogues, Arcturus | unspecified | immunosuppressant | skin disease |
| Stat4/Stat6 blockers, Tularik | unspecified | immunosuppressant | autoimmune disease; allergy |
| T cell modulators, Fisons | unspecified | immunosuppressant | asthma; rhinitis; conjunctivitis; allergy |
| VE 19613 | unspecified | immunosuppressant | autoimmune disease |
| VX 10367 | unspecified | immunosuppressant | transplant rejection |
| VX 497 | unspecified | immunosuppressant | psoriasis; autoimmune disease; viral infection; hepatitis |
| Xe 9 | unspecified | immunosuppressant | transplant rejection |
| XENOJECT | unspecified | immunosuppressant | cancer; autoimmune disease |
| ZAP 70 modulators, Pharmacopeia | unspecified | immunosuppressant | transplant rejection |
| oxamisole; PR 879317A | (+,−)-2,3,5,6,7,8-hexahydro-8,8-dimethoxy-2-phenyl-imidazo(1,2-a)-pyridine | immunosuppressant | viral infection |
| gusperimus; gusperimus hydrochloride; deoxyspergualin, 15-; desoxyspergualin; DSG; NKT 01; NSC 356894; BMS 181173; BMY 42215-1; SPANIDIN; SUPANIDIN | (+,−)-7-[(aminoiminomethyl)amino]-N-[2-[[4-[(3-aminopropyl)amino]butyl]amino]-1-hydroxy-2-oxoethyl]heptanamide | immunosuppressant | transplant rejection; multiple sclerosis; cancer |
| FR 901483 | (2 alpha, 5 beta, 6 beta, 7 beta, 8 beta, 10a beta)-octahydro-5-[(4-methoxyphenyl)methyl]-2-(methylamino)-1H-7,10a-methanopyrrolo[1,2-a]azocine-6,8-diol, 8-(dihydrogen phosphate) | immunosuppressant | transplant rejection |

TABLE 9-continued

Current Candidate Therapeutic Interventions in Development for Immunnosuppression

| Product Name | Chemical Name | Action | Indication |
|---|---|---|---|
| PRO 1556 | (OC-6-11)-hexakis(1H-imidazole-kappaN3)ruthenium(2+) dichloride | immunosuppressant | transplant rejection |
| PRO 2844 | (OC-6-22)-pentaammine(4-methylpyridine)ruthenium(3+)trichloride | immunosuppressant | psoriasis; autoimmune disease; transplant rejection |
| myriocin; thermozymocidin; ISP-I | [2S-(2R*,3S*,4S*,6E)]-2-amino-3,4-dihydroxy-2-(hydroxymethyl)-14-oxo-6-eicosenoic acid | immunosuppressant | autoimmune disease; transplant rejection |
| bactobolamine | [3S-(3alpha,4alpha,4abeta,5beta,6alpha)]-4-amino-3-(dichloromethyl)-3,4,4a,5,6,7-hexahydro-5,6,8-trihydroxy-3-methyl-1H-2-benzopyran-1-one | immunosuppressant | autoimmune disease |
| discodermolide | [3S-[3alfa,4beta,5beta,6alfa(2R*,3Z,5R*,6R*,7S*,8Z,11R*,12S*,13S*,14S*,15R*,16E)]]-6-[14-[(aminocarbonyl)oxy]-2,6,12-trihydroxy-5,7,9,11,13,15-hexamethyl-3,8,16,18-nonadecatetraenyl]tetrahydro-4-hydroxy-3,5-dimethyl-2H-pyran-2-one | immunosuppressant | transplant rejection |
| tresperimus; LF 80299; LF 299 | [4-[(3-aminopropyl)amino]butyl]carbamic acid 2-[[6-[(aminoiminomethyl)amino]hexyl]amino]-2-oxoethyl ester | immunosuppressant | autoimmune disease |
| SKF 106610 | 2-[3-(1-piperidinyl)propyl]-8,8-dipropyl-2-azaspiro[4,5]decane dihydrochloride | immunosuppressant | autoimmune disease |
| oxeclosporin; SDZ IMM 125; IMM 125 | 2-[O-(2-hydroxyethyl)-D-serine]-cyclosporin A | immunosuppressant | asthma |
| FTY 720 | 2-amino-2-[2-(4-octylphenyl)ethyl]-1,3-propanediol hydrochloride | immunosuppressant | transplant rejection; autoimmune disease |
| HMR 1715 | 2-cyano-3-hydroxy-N-[4-(trifluoromethyl)phenyl]-6-heptynamide | immunosuppressant | transplant rejection |
| SM 8849 | 4-[1-(2-fluoro-4-biphenylyl)ethyl]-2-methylaminothiazole | immunosuppressant | autoimmune disease |
| SDZ RAD | 42-O-(2-hydroxyethyl)rapamycin | immunosuppressant | transplant rejection |
| dinaline; GOE 1734; NSC 328786; AAPBA | 4-amino-N-(2-aminophenyl)benzamide | immunosuppressant | cancer |
| FR 901459 | 4-L-leucine-7-L-threonine-10-L-leucine-cyclosporin A | immunosuppressant | autoimmune disease |
| prodigiosin 25-C; prodigiosin | 4-methoxy-5-[(5-methyl-4-pentyl-2H-pyrrol-2-ylidene)methyl]-2,2'-bi-1H-pyrrole | immunosuppressant | autoimmune disease |
| TOK 8801 | 5,6-dihydro-3,6,6-trimethyl-N-(2-phenylethyl)imidazo[2,1-b]thiazole-2-carboxamide | immunosuppressant | autoimmune disease |

TABLE 9-continued

Current Candidate Therapeutic Interventions in Development for Immunosuppression

| Product Name | Chemical Name | Action | Indication |
| --- | --- | --- | --- |
| esonarimod; KE 298 | alpha-[(acetylthio)methyl]-4-methyl-gamma-oxobenzenebutanoic acid | immunosuppressant | rheumatoid arthritis |
| HMR 1279 | alpha-cyano-N-(4-cyanophenyl)-beta-oxocyclopropanepropan amide | immunosuppressant | transplant rejection |
| dehydrodidemnin B; DDB | N-[1-(1,2-dioxopropyl)-L-prolyl]didemnin A | immunosuppressant | viral infection; cancer |
| YM 13650 | propanedioic acid mono(3-imidazo[2,1-b]benzothiazol-2-ylphenyl) ester | immunosuppressant | transplant rejection |
| IR 1116 | Unspecified | immunosuppressant | autoimmune disease |
| LCB 2183 | Unspecified | immunosuppressant | rhinitis; dermatitis; asthma |
| aldose reductase inhibitors, Washington Research Foundation | unspecified | immunosuppressant; aldose reductase inhibitor; NSAID | autoimmune disease; allergy; inflammation |
| rapamycin analogues | unspecified | immunosuppressant; antifungal | transplant rejection; mycosis |
| antisense oligonucleotide, ICAM-1; antisense oligonucleotide, intracellular adhesion molecule-1; ISIS 2302 | d[(R)-P-thio](G-C-C-C-A-A-G-C-T-G-G-C-A-T-C-C-G-T-C-A) DNA | immunosuppressant; antisense; oligonucleotide; NSAID | rheumatoid arthritis; psoriasis; inflammatory bowel disease; asthma |
| antibody-mediated stroke inhibitor | unspecified | immunosuppressant; biotechnology | gynecological; stroke; thrombosis; myocardial infarction |
| lymphocyte activation gene 3 protein; LAG 3 protein | unspecified | immunosuppressant; biotechnology | transplant rejection; multiple sclerosis |
| MAb, gp39; BMS 202448 | unspecified | immunosuppressant; biotechnology | autoimmune disease |
| MAb, interleukin-2 receptor; MAb, IL-2R | unspecified | immunosuppressant; biotechnology | transplant rejection |
| apoptosis-inducing antigen, diabetes; IG 2; IG2 | unspecified | immunosuppressant; biotechnology; apoptosis inducer | diabetes |
| MP 4 | unspecified | immunosuppressant; biotechnology; apoptosis inducer | multiple sclerosis |
| apoptosis-inducing antigen, rheumatoid arthritis | unspecified | immunosuppressant; biotechnology; apoptosis inducer; NSAID | rheumatoid arthritis |
| monocyte colony inhibitory factor-1, Human Genome Sciences | unspecified | immunosuppressant; biotechnology; chemokine | autoimmune disease; rheumatoid arthritis; systemic lupus erythematosus |
| AI 401 | unspecified | immunosuppressant; biotechnology; hormone | diabetes |
| AI 201 | unspecified | immunosuppressant; biotechnology; NSAID | rheumatoid arthritis |
| AI 402 | unspecified | immunosuppressant; biotechnology; peptide | diabetes |
| AI 502 | unspecified | immunosuppressant; biotechnology; peptide | transplant rejection |
| ATP 012; TP 12 | unspecified | immunosuppressant; biotechnology; peptide | multiple sclerosis |
| AI 202 | unspecified | immunosuppressant; biotechnology; peptide; NSAID | rheumatoid arthritis |
| chemokine receptor antagonists, ICOS | unspecified | immunosuppressant; chemokine antagonist; cytokine antagonist | autoimmune disease |
| soluble complement receptor type 1; sCR1; TP 10; TP 10HD; BRL 55730; YM 55730 | unspecified | immunosuppressant; complement inhibitor | respiratory distress syndrome; heart ischemia; transplant rejection |

TABLE 9-continued

Current Candidate Therapeutic Interventions in Development for Immunnosuppression

| Product Name | Chemical Name | Action | Indication |
|---|---|---|---|
| CBP 1011 | unspecified | immunosuppressant; corticosteroid | autoimmune disease; systemic lupus erythematosus; asthma |
| CBP 2011 | unspecified | immunosuppressant; corticosteroid | autoimmune disease; thrombocytopenia |
| CBP 2012 | unspecified | immunosuppressant; corticosteroid | autoimmune disease; thrombocytopenia |
| D 22558 | unspecified | immunosuppressant; cytokine inhibitor | asthma; allergy |
| autoimmune disease-specific MHC blockers, 3 Dimensional Pharmaceuticals | unspecified | immunosuppressant; DMARD; NSAID | rheumatoid arthritis; autoimmune disease |
| Bcl-x gamma-based therapy, Boston Life Sciences; autoimmune disease therapy, Boston Life Sciences | unspecified | immunosuppressant; gene; apoptosis inducer | autoimmune disease |
| polyclonal antibody, rabbit antithymocyte; immunoglobulin, rabbit antithymocyte; rabbit antithymocyte immunoglobulin; THYMOGLOBULIN | unspecified | immunosuppressant; immunoglobulin; polyclonal antibody | transplant rejection; aplastic anemia |
| protein A-based immune modulator | unspecified | immunosuppressant; immunostimulant | autoimmune disease; cancer |
| ZYN-LINKER conjugated superantigens | unspecified | immunosuppressant; immunostimulant; NSAID | rheumatoid arthritis; cancer |
| signal transduction modulators, National Jewish Center for Immunology and Respiratory Medicine | unspecified | immunosuppressant; immunostimulant; NSAID | autoimmune disease; cancer; inflammation |
| SDZ 281240 | unspecified | immunosuppressant; macrolide; antibiotic | psoriasis |
| MAb, 33B3.1; MAb, anti-interleukin-2 receptor | unspecified | immunosuppressant; monoclonal antibody | transplant rejection |
| MAb, B7.1; MAb, M24; M 24 | unspecified | immunosuppressant; monoclonal antibody | transplant rejection |
| MAb, CD3 humanized | unspecified | immunosuppressant; monoclonal antibody | transplant rejection |
| MAb, H65 humanized Fab' | unspecified | immunosuppressant; monoclonal antibody | autoimmune disease |
| MAb, T10B9; T10B9.1A-31; MEDI 500 | unspecified | immunosuppressant; monoclonal antibody | transplant rejection |
| MAb, UCHL1; MAb, CD45RO | unspecified | immunosuppressant; monoclonal antibody | autoimmune disease |
| MAbs, organ transplantation; TOLERIMAB | unspecified | immunosuppressant, monoclonal antibody | transplant rejection |
| inolimomab; MAb, IL-2 receptor CD25; MAb, interleukin-2 receptor CD25; BT 563; LEUKOTAC | immunoglobulin G 1 (mouse monoclonal B-B10.gamma.-chain anti-human interleukin 2 receptor.alpha.-chain), disulfide with mouse monoclonal B-B10.kappa.-chain, dimer | immunosuppressant; monoclonal antibody | transplant rejection |
| MAb, BC3 | unspecified | immunosuppressant; monoclonal antibody; biotechnology | transplant rejection |
| MAb, CD3-immunotoxin | unspecified | immunosuppressant; monoclonal antibody; biotechnology; immunotoxin | transplant rejection; autoimmune disease |
| MAb, gp39; MAb, arthritis | unspecified | immunosuppressant; monoclonal antibody; NSAID | rheumatoid arthritis |

TABLE 9-continued

Current Candidate Therapeutic Interventions in Development for Immunnosuppression

| Product Name | Chemical Name | Action | Indication |
| --- | --- | --- | --- |
| MAb, MHC class II; CDP 855 | unspecified | immunosuppressant; monoclonal antibody; NSAID | autoimmune disease; systemic lupus erythematosus |
| MAb, R73; MAb, rat alpha/beta T cell receptor | unspecified | immunosuppressant; monoclonal antibody; NSAID | transplant rejection; rheumatoid arthritis |
| priliximab; MAb, humanized CD4; cM-T412; CEN 000029; CENTARA | immunoglobulin G1 (human-mouse monoclonal cm-T412 anti-human antigen CD 4), disulfide with human-mouse monoclonal cm-T412.kappa.-chain, dimer | immunosuppressant; monoclonal antibody; NSAID | multiple sclerosis; autoimmune disease; rheumatoid arthritis |
| IRA 378 | (S)-8-chloro-1,2,3,4-tetrahydro-2-(trifluoromethyl)-6-quinolineacetic acid | immunosuppressant; nitric oxide synthase inhibitor; NSAID | rheumatoid arthritis |
| BMS 188667; CTLA4Ig | unspecified | immunosuppressant; NSAID | transplant rejection; systemic lupus erythematosus; psoriasis; arthritis; allergy |
| C-Maf based therapy | unspecified | immunosuppressant; NSAID | autoimmune disease; rheumatoid arthritis |
| corticotropin releasing factor binding protein; CRF binding protein; NBI 112 | unspecified | immunosuppressant; NSAID | rheumatoid arthritis; inflammation |
| E 21R | unspecified | immunosuppressant; NSAID | cancer; inflammation; allergy |
| lenercept; tumor necrosis factor receptor fusion protein; TNF receptor fusion protein; Ro 452081; TENEFUSE | unspecified | immunosuppressant; NSAID | rheumatoid arthritis; asthma; septic shock; multiple sclerosis |
| leukocyte function associated antigen 3 T cell inhibitor protein; LFA3TIP; LFA3TIP; AMEVIVE | unspecified | immunosuppressant; NSAID | inflammation; autoimmune disease; psoriasis |
| MAb, CD40 ligand; 5C8; ANTOVA | unspecified | immunosuppressant; NSAID | inflammation; systemic lupus erythematosus; multiple sclerosis |
| autoimmune disease therapy, Molecumetics/Bristol-Myers Squibb | unspecified | immunosuppressant; NSAID | rheumatoid arthritis; multiple sclerosis; systemic lupus erythematosus |
| BN 58705 | unspecified | immunosuppressant; NSAID | septic shock; inflammation |
| BW 91Y78 | unspecified | immunosuppressant; NSAID | inflammation |
| CD2 binding agents, Procept | unspecified | immunosuppressant; NSAID | rheumatoid arthritis |
| CD4 inhibitors, Procept; CD4 inhibitors, Novartis | unspecified | immunosuppressant; NSAID | inflammation |
| CT 2576 | unspecified | immunosuppressant; NSAID | HIV infection; rheumatoid arthritis |
| immunoregulators, AVANT Immunotherapeutics; immunoregulators, Repligen | unspecified | immunosuppressant; NSAID | transplant rejection; rheumatoid arthritis; asthma |
| inflammation therapy, Genzyme/LeukoSite | unspecified | immunosuppressant; NSAID | inflammatory bowel disease; inflammation; autoimmune disease |
| PG 12 | unspecified | immunosuppressant; NSAID | rheumatoid arthritis; transplant rejection |
| PG 27 | unspecified | immunosuppressant; NSAID | rheumatoid arthritis; transplant rejection |
| PG 2946 | unspecified | immunosuppressant; NSAID | rheumatoid arthritis; systemic lupus erythematosus; transplant rejection |

TABLE 9-continued

Current Candidate Therapeutic Interventions in Development for Immunnosuppression

| Product Name | Chemical Name | Action | Indication |
| --- | --- | --- | --- |
| PG 3028 | unspecified | immunosuppressant; NSAID | rheumatoid arthritis; systemic lupus erythematosus; transplant rejection |
| PG 3113 | unspecified | immunosuppressant; NSAID | rheumatoid arthritis; systemic lupus erythematosus; transplant rejection |
| PG 94 | unspecified | immunosuppressant; NSAID | rheumatoid arthritis; transplant rejection |
| PIC 060 analogs | unspecified | immunosuppressant; NSAID | psoriasis; dermatitis; diabetes; transplant rejection; rheumatoid arthritis |
| PIC 101 | unspecified | immunosuppressant; NSAID | rheumatoid arthritis; autoimmune disease; transplant rejection |
| PIC 102 | unspecified | immunosuppressant; NSAID | rheumatoid arthritis; transplant rejection; autoimmune disease |
| PIC 231 | unspecified | immunosuppressant; NSAID | rheumatoid arthritis; transplant rejection; autoimmune disease |
| Ro 236457 | unspecified | immunosuppressant; NSAID | inflammation |
| VX 10393 | Unspecified | immunosuppressant; NSAID | transplant rejection; rheumatoid arthritis; psoriasis; diabetes |
| VX 10428 | unspecified | immunosuppressant; NSAID | transplant rejection; rheumatoid arthritis; psoriasis; diabetes |
| phellodendrine; OB 5 | (7S-cis)-5,8,13,13a-tetrahydro-2,11-dihydroxy-3,10-dimethoxy-7-methyl-6H-dibenzo[a,g]quinoliziniu m | immunosuppressant; NSAID | transplant rejection; inflammation; viral infection; asthma; kidney disease |
| TEI 1338 | (E)-N-(2-methoxycarbonylphenyl)-8-(2-naphthyl)-5,6-trans-5,6-methano-7-octenamide | immunosuppressant; NSAID | allergy; inflammation |
| laflunimus; HR 325 | (Z)-2-cyano-3-cyclopropyl-3-hydroxy-N-[3-methyl-4-(trifluoromethyl)phenyl]-2-propenamide | immunosuppressant; NSAID | rheumatoid arthritis; transplant rejection; psoriasis |
| TEI 3332 | [(6,7-dihydroxy-2-naphthalenyl)thio]acetic acid methyl ester | immunosuppressant; NSAID | allergy; inflammation |
| SCH 24937 | 1-[6-bromo-5-chloro-3-(2-pyridinyl)-1H-indol-2-yl]-2-(methylsulfinyl)ethanon e | immunosuppressant; NSAID | rheumatoid arthritis |
| KF 20444 | 10-fluoro-3-(2-fluorophenyl)-6,7-dihydro-5H-benzo[6,7]cyclohepta[1,2-b]quinoline-8-carboxylic acid | immunosuppressant; NSAID | rheumatoid arthritis |
| KB 2683 | 2-(4-methylphenyl)-4-benzothiazolol acetate | immunosuppressant; NSAID | rheumatoid arthritis; inflammation; autoimmune disease |
| CI 972 | 2,6-diamino-1,5-dihydro-7-(3-thienylmethyl)-4H-pyrrolo[3,2-d]pyrimidin-4-one monohydrochloride | immunosuppressant; NSAID | rheumatoid arthritis; cancer; psoriasis |

TABLE 9-continued

Current Candidate Therapeutic Interventions in Development for Immunnosuppression

| Product Name | Chemical Name | Action | Indication |
|---|---|---|---|
| MX 68 | 2-[[[4-[2,4-diamino-6-pteridinyl]methyl]-3,4-dihydro-2H-1,4-benzothiazin-7-yl]carbonyl]amino]hexanedioic acid | immunosuppressant; NSAID | rheumatoid arthritis; systemic lupus erythematosus; autoimmune disease |
| albifylline; HWA 138 | 3,7-dihydro-1-(5-hydroxy-5-methylhexyl)-3-methyl-1H-purine-2,6-dione | immunosuppressant; NSAID | septic shock; inflammation |
| baohuoside 1; icariside II; B-1 | 3-[(6-deoxy-alpha-L-mannopyranosyl)oxy]-5,7-dihydroxy-2-(4-methoxyphenyl)-8-(3-methyl-2-butenyl)-4H-1-benzopyran-4-one | immunosuppressant; NSAID | systemic lupus erythematosus; rheumatoid arthritis |
| CL 306293 | 3-amino-2-[1,1'-biphenyl]-4-yl-6-fluoro-4-quinolinecarboxylic acid | immunosuppressant; NSAID | arthritis; HIV infection |
| amiprilose; amiprilose hydrochloride; THN; SM 1213; KAP 690; THERAFECTIN | 3-O-(3-(dimethylamino)propyl)-1,2-O-isopropylidene-alfa-D-glucofuranose hydrochloride | immunosuppressant; NSAID | rheumatoid arthritis; psoriasis |
| TAK 603 | 4-(3,4-dimethoxyphenyl)-6,7-dimethoxy-2-(1H-1,2,4-triazol-1-ylmethyl)-3-quinolinecarboxylic acid ethyl ester | immunosuppressant; NSAID | rheumatoid arthritis |
| mizoribine; HE 69; BREDININ | 5-hydroxy-1-beta-D-ribofuranosylimidazole-4-carboxamide | immunosuppressant; NSAID | rheumatoid arthritis; transplant rejection; kidney disease |
| TA 383 | cis-2-(4-chlorophenyl)-4,5-dihydro-4,5-diphenyl-1H-imidazole monohydrochloride | immunosuppressant; NSAID | rheumatoid arthritis |
| SKF 105685 | N,N-dimethyl-8,8-dipropyl-2-azaspiro[4,5]decane-2-propanamine dihydrochloride | immunosuppressant; NSAID | autoimmune disease; rheumatoid arthritis; HIV infection |
| AI 200; COLLORAL | trimeric (16-1059)alpha1 (II) collagen | immunosuppressant; NSAID | rheumatoid arthritis |
| atiprimod; atiprimod dimaleate; SKF 106615 | N,N-diethyl-8,8-dipropyl-2-azaspiro[4.5]decane-2-propanamine | immunosuppressant; NSAID; macrophage inhibitor | rheumatoid arthritis; autoimmune disease; psoriasis |
| celastrol | unspecified | immunosuppressant; NSAID; terpene | inflammation |
| CD45 inhibitors, Ontogen | unspecified | immunosuppressant; NSAID; tyrosine phosphatase inhibitor | transplant rejection; inflammation |
| cladribine; 2-CdA; NSC 105014F; RWJ 26251; LEUSTATIN; LEUSTAT; MYLINAX | 2-chloro-2'-deoxyadenosine | immunosuppressant; nucleoside analogue; NSAID | cancer; multiple sclerosis; rheumatoid arthritis |
| calcineurin inhibitory peptides, Oregon Health Sciences University | unspecified | immunosuppressant; peptide | autoimmune disease |
| human leukocyte antigen-derived protein; HLA-derived protein; ALLOTRAP 2702 | unspecified | immunosuppressant; peptide | transplant rejection |
| immunosuppressant peptides, SangStat; immunosuppressant peptides, Syntem | unspecified | immunosuppressant; peptide | transplant rejection; autoimmune disease |
| T cell peptide, University of Illinois | unspecified | immunosuppressant; peptide | autoimmune disease; cancer; bacterial infection |
| PP 14 | unspecified | immunosuppressant; peptide; NSAID | autoimmune disease; rheumatoid arthritis |

TABLE 9-continued

Current Candidate Therapeutic Interventions in Development for Immunnosuppression

| Product Name | Chemical Name | Action | Indication |
|---|---|---|---|
| potassium channel blocker, Merck & Co | unspecified | immunosuppressant; potassium channel blocker | autoimmune disease; allergy; inflammation |
| ZAP inhibitors, Ariad | unspecified | immunosuppressant; protein kinase inhibitor; tyrosine kinase inhibitor; NSAID | transplant rejection; rheumatoid arthritis; inflammatory bowel disease; systemic lupus erythematosus; multiple sclerosis |
| autoimmune disease therapy, Peptimmune | unspecified | immunosuppressant; proteinase inhibitor | autoimmune disease |
| PEGylated p75 TNFR Fc mutein | unspecified | immunosuppressant; TNF inhibitor | rheumatoid arthritis |
| leflunomide; HWA 486; ARAVA | 5-methyl-N-[4-(trifluoromethyl)phenyl]-4-isoxazolecarboxamide | immunosuppressant; tyrosine kinase inhibitor; NSAID; DMARD | rheumatoid arthritis; autoimmune disease |
| alpha4 beta7 antagonists, LeukoSite/Warner Lambert | unspecified | integrin antagonist; alpha4 beta7 integrin antagonist; cell adhesion inhibitor | Crohn disease; inflammatory bowel disease |
| CDP 850 | unspecified | integrin antagonist; biotechnology; cell adhesion inhibitor; immunosuppressant; monoclonal antibody; E selectin antagonist | cancer |
| MAb, ICAM-3; MAb, intracellular adhesion molecule-3; MAb, ICAM-R; ICM3 | unspecified | integrin antagonist; biotechnology; cell adhesion inhibitor; immunosuppressant; monoclonal antibody | autoimmune disease; psoriasis |
| MAb, B11; MAb, E-selectin; MAb, endothelium leukocyte adhesion molecule | unspecified | integrin antagonist; biotechnology; immunosuppressant; monoclonal antibody; E selectin antagonist; cell adhesion inhibitor; NSAID | inflammation |
| MAb, L-selectin, humanized; SMART anti-L-selectin; HuDREG 200 | unspecified | integrin antagonist; biotechnology; monoclonal antibody; cell adhesion inhibitor; immunosuppressant; L selectin antagonist | trauma; respiratory distress syndrome; autoimmune disease; reperfusion injury |
| GM 1676 | unspecified | integrin antagonist; cell adhesion inhibitor immunosuppressant; NSAID | inflammation |
| selectin antagonists, Oxford GlycoSciences | unspecified | integrin antagonist; P selectin antagonist; immunosuppressant; cell adhesion inhibitor; NSAID | inflammation |
| low molecular weight selectin inhibitors, kanebo/Ontogen | Unspecified | integrin antagonist; selectin antagonist; immunosuppressant; cell adhesion inhibitor; NSAID | inflammation; allergy |
| TBC 427 | unspecified | integrin antagonist; selectin antagonist; immunosuppressant; cell adhesion inhibitor | ischemia; psoriasis; respiratory distress syndrome; transplant rejection; reperfusion injury |
| TBC 1269 | 3',3'''-(1,6-hexanediyl)bis[6'-(alpha-D-mannopyranosyloxy)-[1,1'-biphenyl]-3-acetic acid | integrin antagonist; selectin antagonist; immunosuppressant; cell adhesion inhibitor; NSAID | inflammation; asthma |
| interferon, modified, Tanox | unspecified | interferon; biotechnology; immunosuppressant | cancer |

TABLE 9-continued

Current Candidate Therapeutic Interventions in Development for Immunnosuppression

| Product Name | Chemical Name | Action | Indication |
| --- | --- | --- | --- |
| microcolin A | N-(2,4-dimethyl-1-oxooctyl)-N-methylleucyl-N-[1-[[2-[(2,5-dihydro-2-methyl-5-oxo-1H-pyrrol-1-yl)carbonyl]-4-hydroxy-1-pyrrolidinyl]carbonyl]-2-methylpropyl]-N-methylthreoninamide, 23-acetate | lipopeptide; immunosuppressant | autoimmune disease |
| drug delivery system, NanoCrystal sirolimus; sirolimus NanoCrystal | unspecified | macrolide; antibiotic; immunosuppressant | transplant rejection |
| sirolimus; rapamycin; NSC 226080; AY 22989; RAPAMUNE | (3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29(4H,6H,31H)-pentone | macrolide; immunosuppressant; antibiotic | transplant rejection; autoimmune disease; restenosis |
| tacrolimus; tsukubaenolide; fujimycin; FK 506; (−)-FK 506; FR 900506; L 679934; PROGRAF; PROTOPIC | [3S-[3R*[E(1S*,3S*,4S*)],4S*,5R*,8S*,9E,12R*,14R*,15S*,16R*,18S*,19S*,26aR*]]-5,6,8,11,12,13,14,15,16,17,18,19,24,25,26,26a-hexadecahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c][1,4]oxaazacyclotricosine-1,7,20,21(4H,23H)-tetrone | macrolide; immunosuppressant; NSAID; antibiotic | transplant rejection; dermatitis; eye disease; rheumatoid arthritis |
| MAb, red blood cell D antigen; MAb, rhesus D; AM 101 | unspecified | monoclonal antibody; biotechnology; immunosuppressant | autoimmune disease |
| MAb, interleukin-12; MAb, IL-12; J695; C17.15 | unspecified | monoclonal antibody; cytokine antagonist; immunosuppressant | autoimmune disease |
| MAb, Fv, cytokine; CDP 870 | unspecified | monoclonal antibody; cytokine inhibitor; immunosuppressant | rheumatoid arthritis; autoimmune disease |
| MAb 2E1; MAb, effector cell proteinase receptor-1 | unspecified | monoclonal antibody; immunosuppressant | transplant rejection |
| MAb, 1C7; passive immunotherapy, systemic lupus erythrematosus | unspecified | monoclonal antibody; immunosuppressant | systemic lupus erythematosus |
| MAb, 6G5.1; MAb, autoimmune disease, human, Medarex; MDX CD4 | unspecified | monoclonal antibody; immunosuppressant | autoimmune disease; rheumatoid arthritis |
| MAb, alpha-tubulin | unspecified | monoclonal antibody; immunosuppressant | cancer; autoimmune disease; diagnosis |

TABLE 9-continued

Current Candidate Therapeutic Interventions in Development for Immunnosuppression

| Product Name | Chemical Name | Action | Indication |
| --- | --- | --- | --- |
| MAb, autoimmune disease; MAb, MHC II | unspecified | monoclonal antibody; immunosuppressant | autoimmune disease |
| MAb, BMA 031 | unspecified | monoclonal antibody; immunosuppressant | transplant rejection |
| MAb, CD11a; hu 1124 | unspecified | monoclonal antibody; immunosuppressant | psoriasis; transplant rejection |
| MAb, CD45; LM CD45 | unspecified | monoclonal antibody; immunosuppressant | transplant rejection |
| MAb, CD45RB | unspecified | monoclonal antibody; immunosuppressant | autoimmune disease; transplant rejection |
| MAb, CD7; SDZ CHH 380 | unspecified | monoclonal antibody; immunosuppressant | transplant rejection |
| MAb, Fc antagonist; MDX 33 | unspecified | monoclonal antibody; immunosuppressant | autoimmune disease; thrombocytopenia |
| MAb, gamma interferon, humanized; SMART anti-gamma interferon | unspecified | monoclonal antibody; immunosuppressant | systemic lupus erythematosus; multiple sclerosis |
| MAb, gp39; MAb, CD40L; IDEC 131 | unspecified | monoclonal antibody; immunosuppressant | autoimmune disease; transplant rejection; systemic lupus erythematosus |
| MAb, H57597 | unspecified | monoclonal antibody; immunosuppressant | autoimmune disease |
| MAb, humanized CD3; MAb, SMART CD3; HuM291 | unspecified | monoclonal antibody; immunosuppressant | transplant rejection; autoimmune disease; psoriasis |
| MAb, inflammation therapy, LeukoSite/MorphoSys | unspecified | monoclonal antibody; immunosuppressant | inflammation; autoimmune disease |
| MAb, interleukin-10; MAb, IL-10 | unspecified | monoclonal antibody; immunosuppressant | systemic lupus erythematosus |
| MAb, interleukin-5; MAb, IL-5; SCH 55700; CDP 835 | unspecified | monoclonal antibody; immunosuppressant | asthma |
| MAb, L0-CD2a; BTI 322 | unspecified | monoclonal antibody; immunosuppressant | autoimmune disease; transplant rejection |
| MAb, major histocompatibility complex I; F(ab')2, MHC I | unspecified | monoclonal antibody; immunosuppressant | transplant rejection |
| MAb, MHC II-CD4; 14-CD4 | unspecified | monoclonal antibody; immunosuppressant | autoimmune disease; graft versus host disease |
| MAb, MHCII-CD8 | unspecified | monoclonal antibody; immunosuppressant | transplant rejection; graft versus host disease |
| MAb, migis-mIgG; Mab, B cell | unspecified | monoclonal antibody; immunosuppressant | autoimmune disease |
| MAb, RhCA 61–76; MAb, anti-AChR alpha subunit; TCM 240 | unspecified | monoclonal antibody; immunosuppressant | autoimmune disease |
| MAb, T cell antigen receptor; ATM 027; TM 27 | unspecified | monoclonal antibody; immunosuppressant | multiple sclerosis |
| MAb, T cell antigen receptor; TM 29 | unspecified | monoclonal antibody; immunosuppressant | cancer; Crohn disease |
| MAb, transplant rejection; CBL1; ABX CBL | unspecified | monoclonal antibody; immunosuppressant | transplant rejection |
| MAbs, B cells; migis | unspecified | monoclonal antibody; immunosuppressant | autoimmune disease; cancer |
| daclizumab; dacliximab; MAb, Tac; MAb, humanized Tac; MAb, SMART Tac; Ro 247375; ZENAPAX | immunoglobulin G1 (human-mouse monoclonal clone 1H4 gamma chain anti-human antigen Tac), disulfide with human-mouse monoclonal clone 1H4 light chain, dimer | monoclonal antibody; immunosuppressant | transplant rejection; cancer; autoimmune disease; eye disease |

TABLE 9-continued

Current Candidate Therapeutic Interventions in Development for Immunnosuppression

| Product Name | Chemical Name | Action | Indication |
| --- | --- | --- | --- |
| odulimomab; MAb, LFA-1 alpha subunit | immunoglobulin G1, anti-(human CD11 (antigen).alpha.-chain)(mouse monoclonal 25.3.gamma.1-chain), disulfide with mouse monoclonal 25.3 light chain, dimer | monoclonal antibody; immunosuppressant | transplant rejection |
| basiliximab; SDZ CHI621; CHI 621; SIMULECT | Immunoglobulin G1, anti-(human interleukin 2 receptor) (human-mouse monoclonal CHI621.gamma.1-chain),disulfide with human-mouse monoclonal CHI621 light chain, dimer | monoclonal antibody; immunosuppressant | transplant rejection |
| MAb, CD6 blocked ricin; MAb, T12-bR; ONCOLYSIN CD6 | unspecified | monoclonal antibody; immunosuppressant; immunotoxin | transplant rejection |
| MAb, MHC class II | unspecified | monoclonal antibody; immunosuppressant; NSAID | autoimmune disease; transplant rejection; graft versus host disease; cancer |
| MAb, T cell receptor; TM 31 | unspecified | monoclonal antibody; immunosuppressant; NSAID | rheumatoid arthritis |
| MAb, CD5-momordin; immunotoxin CD5-momordin; ITF 1532 | unspecified | monoclonal antibody; immunotoxin; immunosuppressant | cancer; transplant rejection |
| zolimomab aritox; MAb, H65 RTA; MAb, bone marrow-ricin A conjugate; CD5-T lymphocyte immunotoxin; MAb, CD5; XMMLY H65 RTA; XOMAZYME H65; XOMAZYME CD5+; ORTHOZYME CD5+; CD5 Plus | unspecified | monoclonal antibody; immunotoxin; immunosuppressant | transplant rejection |
| MAb, humanized, leukemia; MAb, IgG2B; LDP 03; BW 7U; CAMPATH; CAMPATH-1H | unspecified | monoclonal antibody; NSAID | rheumatoid arthritis; cancer; multiple sclerosis; transplant rejection |
| MAb, B7; MAb, PRIMATIZED B7; IDEC 114 | unspecified | monoclonal antibody; NSAID; immunosuppressant | systemic lupus erythematosus; inflammation; transplant rejection; psoriasis |
| neuroimmunophilins, KOSAN | unspecified | neurotrophic factor | neurodegeneration |
| NOX 100 | unspecified | nitric oxide scavenger | diabetes; cancer; trauma; transplant rejection; septic shock; cardiovascular disease |
| NOX 51 | unspecified | nitric oxide scavenger | diabetes; cancer; cardiovascular disease; transplant rejection; septic shock |
| NOX 101 | Unspecified | nitric oxide scavenger | stroke; diabetes; cancer; trauma; transplant rejection; septic shock; cardiovascular disease |
| S 2474 | unspecified | NSAID; DMARD; COX inhibitor; COX 2 inhibitor; immunosuppressant | rheumatoid arthritis; autoimmune disease |

TABLE 9-continued

Current Candidate Therapeutic Interventions in Development for Immunnosuppression

| Product Name | Chemical Name | Action | Indication |
|---|---|---|---|
| immune system modulators, OSI | unspecified | NSAID; immunosuppressant | inflammation |
| NE 0501 | unspecified | oligosaccharide | transplant rejection |
| opioid antagonists, NIH | unspecified | opiate antagonist; peptide; immunosuppressant | addiction; alcoholism; obesity; transplant rejection |
| recombinant PSGL 1, Genetics Institute; PSGL 1 | unspecified | P selectin antagonist; E selectin antagonist; L selectin antagonist; selectin antagonist; NSAID | inflammation; transplant rejection; ischemia; reperfusion injury |
| AH 21132 | cis N-(4-(1,2,3,4,4a,10b-hexahydro-8,9-dimethoxy-2-methylbenzo(c)(1,6)naphthyridin-6-yl)phenyl)-acetamide (Z)-2-butenedioate (1:2) | PAF antagonist; phosphodiesterase inhibitor; phosphodiesterase III inhibitor; phosphodiesterase IV inhibitor; bronchodilator | asthma |
| immunosuppressive, ANUTECH | unspecified | peptide; immunosuppressant | autoimmune disease |
| inflammation therapy, BTG; autoimmune disease therapy, BTG | unspecified | peptide; immunosuppressant | inflammation; autoimmune disease |
| rD-mPGPtide | unspecified | peptide; immunosuppressant | transplant rejection; multiple sclerosis |
| transplantation therapy, SangStat | unspecified | peptide; immunosuppressant | transplant rejection |
| CD4 peptide antagonist, Tocor | unspecified | peptide; immunosuppressant; NSAID | inflammation |
| complement inhibitors, Lidak | unspecified | peptide; immunosuppressant; NSAID | rheumatoid arthritis; systemic lupus erythematosus; autoimmune disease; reperfusion injury; respiratory distress syndrome; transplant rejection |
| D 4418 | unspecified | phosphodiesterase inhibitor; phosphodiesterase IV inhibitor; immunosuppressant; bronchodilator | asthma |
| B669 | 3-(cyclohexylimino)-3,5-dihydro-N,5-diphenyl-2-phenazinamine | phospholipase activator; immunosuppressant; NSAID | inflammation |
| polyclonal antibody, tumor necrosis factor alpha; polyclonal antibody, TNFalpha; CytoTAb | unspecified | polyclonal antibody; immunoglobulin; immunosuppressant | septic shock; malaria; restenosis; Crohn disease; graft versus host disease |
| polyclonal antibody, immune thrombocytopenic purpura; polyclonal antibody, ITP; Rho(D) immune globulin; WinRho SD; WinRho SDF | unspecified | polyclonal antibody; immunosuppressant; immunoglobulin | autoimmune disease; HIV infection |
| polysaccharide A immunomodulator | unspecified | polysaccharide; immunosuppressant | surgery |
| ANK 102 | Unspecified | polysaccharide; immunosuppressant | autoimmune disease |
| SPC 100270 | unspecified | protein kinase inhibitor; protein kinase C inhibitor; immunosuppressant | ischemia; transplant rejection; reperfusion injury |

TABLE 9-continued

Current Candidate Therapeutic Interventions in Development for Immunnosuppression

| Product Name | Chemical Name | Action | Indication |
| --- | --- | --- | --- |
| Ro 320432; Ro 32-0432 | (S)-3-[8-[(dimethylamino)methyl]-6,7,8,9-tetrahydropyrido[1,2-a]indol-10-yl]4-(1-methyl-1H-indol-3-yl)-1H-pyrrole-2,5-dione | protein kinase inhibitor; protein kinase C inhibitor; immunosuppressant; NSAID | transplant rejection; rheumatoid arthritis |
| MLR 52; (+)-MLR-52 | [9S-(9alfa,10beta,11alfa,12alfa,13alfa)]-2,3,10,11,12,13-hexahydro-11,12-dihydroxy-10-methoxy-9-methyl-9,13-epoxy-1H,9H-diindolo[1,2,3-gh:3',2',1'-1m]pyrrolo[3,4-j][1,7]benzodiazonin-1-one | protein kinase inhibitor; protein kinase C inhibitor; immunosuppressant | cancer |
| cathepsin S inhibitors, Axys/Rhone-Poulenc Rorer | unspecified | proteinase inhibitor; cathepsin S inhibitor; NSAID; immunosuppressant | inflammation; autoimmune disease |
| aloxistatin; rexostatine; EP 4S3; E 64d; E 64; EST | [S-[2alfa,3beta(R*)]]-3-[[[3-methyl-1-[[(3-methylbutyl)amino]carbonyl]butyl]amino]carbonyl]oxiranecarboxylic acid ethyl ester | proteinase inhibitor; immunosuppressant | muscular dystrophy |
| peldesine; BCX 34; BCX 34B | 2-amino-1,5-dihydro-7-(3-pyridinylmethyl)-4H-pyrrolo[3,2-d]pyrimidin-4-one | purine nucleoside phosphorylase inhibitor; immunosuppressant; NSAID | cancer; psoriasis; rheumatoid anthritis; transplant rejection; eye disease; dermatitis; HIV infection |
| purine nucleoside phosphorylase inhibitors, Chiroscience; PNP inhibitors, Chiroscience | unspecified | purine nucleoside phosphorylase inhibitor; NSAID | cancer; psoriasis; rheumatoid arthritis; transplant rejection |
| mycophenolate mofetil; RS 61443; CellCept | (E)-6-(1,3-dihydro-4-hydroxy-6-methoxy-7-methyl-3-oxo-5-isobenzofuranyl)-4-methyl-4-hexenoic acid 2-(4-morpholinyl)ethyl ester | purine synthesis inhibitor; immunosuppressant; NSAID | transplant rejection; rheumatoid anthritis; asthma; restenosis; kidney disease; systemic lupus erythematosus |
| ribozymes, organ transplantation | unspecified | ribozyme; oligonucleotide; immunosuppressant | transplant rejection |
| SR 31747 | (Z)-N[3-chloro-4-cyclohexylphenyl)-2-propenyl]-N-ethyl-cyclohexanamine hydrochloride | sigma antagonist; immunosuppressant; NSAID | autoimmune disease; arthritis |
| signal transduction inhibitor, SUGEN/ArQule | unspecified | signal transduction inhibitor; immunosuppressant | cancer; diabetes; neurological; autoimmune disease |
| SP 100030 | Unspecified | signal transduction inhibitor; NSAID; immunosuppressant | inflammation; autoimmune disease |
| ABT 281; A 86281 | unspecified | Tacrolimus-like; no immunosupression | psoriasis |
| CGS 12970 | 3-methyl-2-(3-pyridinyl)-1H-indole-1-octanoic acid | thromboxane synthase inhibitor; immunosuppressant | transplant rejection |
| pirmagrel; CGS 13080 | imidazo(1,5-a)pyridine-5-hexanoic acid | thromboxane synthetase inhibitor; immunosuppressant | transplant rejection |
| tumor necrosis factor binding protein; TBP-1; TBP | unspecified | TNF inhibitor; immunosuppressant | autoimmune disease; reperfusion injury; inflammation; septic shock |

TABLE 9-continued

Current Candidate Therapeutic Interventions in Development for Immunnosuppression

| Product Name | Chemical Name | Action | Indication |
|---|---|---|---|
| etanercept; tumor necrosis factor receptor; TNFr; TNR 001; ENBREL | unspecified | TNF inhibitor; immunosuppressant; NSAID; analgesic | rheumatoid arthritis; heart failure; diabetes; pain; endometriosis; autoimmune disease |
| thalidomide; SYNOVIR; THALOMID | N-(2,6-dioxo-3-piperidyl)phthalimide | TNF modulator; immunosuppressant | cachexia; diarrhea; leprosy; rheumatoid arthritis; transplant rejection; cancer; Crohn disease |
| thalidomide; NSC 66847 | N-(2,6-dioxo-3-piperidyl)phthalimide | TNF modulator; immunosuppressant | HIV infection; Crohn disease; multiple sclerosis; Alzheimer disease; transplant rejection |
| AP-1 inhibitor, Signal; JNK inhibitor, Signal | unspecified | transcription factor regulator; NSAID; immunosuppressant | inflammation; autoimmune disease; cancer |
| SC 114 | unspecified | triglyceride; immunosuppressant | autoimmune disease; transplant rejection |
| AP 251 | unspecified | tyrosine kinase inhibitor; immunosuppressant | autoimmune disease |
| p56 Ick inhibitors, Celltech | unspecified | tyrosine kinase inhibitor; immunosuppressant | autoimmune disease |
| ZAP70 inhibitors, Celltech | unspecified | tyrosine kinase inhibitor; immunosuppressant | autoimmune disease |
| immunosuppressant, Xcyte Therapies | unspecified | Unspecified | psoriasis |
| LSL 90202 | L-lysine monoeicosapentaenoate (1:1) | unspecified | kidney disease |
| non-ionic surfactant vesicles; NISV | unspecified | vaccine adjuvant; immunosuppressant | rheumatoid arthritis; asthma; inflammation |
| vaccine, gene-based, autoimmune disease GENEVAX | unspecified | vaccine; gene therapy; immunosuppressant | autoimmune disease |
| 20-epi-1,25 dihydroxyvitamin D3; MC 1288; IE | (1alpha,3beta,5Z,7E,20 S)-9,10-secocholesta-5,7,10(19)-triene-1,3,25-triol | vitamin D3 analogue; immunosuppressant | diabetes; transplant rejection; arthritis |

TABLE 10

Current Candidate Therapeutic Interventions in Development for the Treatment of Transplant Rejection

| Product Name | Chemical Name | Action | Indication |
|---|---|---|---|
| brequinar; brequinar sodium; DUP 785; NSC 368390 | 6-fluoro-2-(2'-fluoro[1,1'-biphenyl]-4-yl)-3-methyl-4-quinolinecarboxylic acid | antimetabolite; immunosuppressant | cancer; autoimmune disease; transplant rejection |
| antisense oligonucleotide, graft versus host disease | unspecified | antisense oligonucleotide; immunosuppressant; apoptosis inducer | transplant rejection |
| apoptosis inhibitors | unspecified | apoptosis inducer | cancer; cardiac therapy; transplant rejection; gastrointestinal disorder |
| ICE inhibitor, IDUN | unspecified | caspase inhibitor; apoptosis inhibitor; IL-1 beta converting enzyme inhibitor; immunosuppressant | transplant rejection; septic shock; rheumatoid arthritis; inflammatory bowel disease; diabetes |
| APT 070; APT 070C; APT070C | unspecified | complement inhibitor; immunosuppressant; NSAID | rheumatoid arthritis; transplant rejection |
| methylprednisolone suleptanate; U 67590A; PROMEDROL | (6alfa,11beta)-11,17-dihydroxy-6-methyl-21-[[8-[methyl(2-sulfoethyl)amino]-1,8-dioxooctyl]oxy]pregna-1,4-diene-3,20-dione monosodium salt | corticosteroid; immunosuppressant | inflammation; asthma; anaphylactic shock; transplant rejection |

TABLE 10-continued

Current Candidate Therapeutic Interventions in Development for the Treatment of Transplant Rejection

| Product Name | Chemical Name | Action | Indication |
| --- | --- | --- | --- |
| gene therapy, soluble TNF receptor; gene therapy, corneal transplant rejection | unspecified | cytokine antagonist | transplant rejection |
| interleukin-12 signal transduction antagonists, Ligand | unspecified | cytokine antagonist; immunosuppressant; NSAID | autoimmune disease; transplant rejection; rheumatoid arthritis |
| interleukin-8 receptor; IL-8r | unspecified | cytokine antagonist; NSAID; immunosuppressant | allergy; inflammation; transplant rejection |
| anakinra; interleukin-1 receptor antagonist; IL-1ra; interleukin-1 inhibitor; ANTRIL | N2-L-methionylinterleukin 1 receptor antagonist (human isoform x reduced) | cytokine inhibitor; immunosuppressant; NSAID | rheumatoid arthritis; inflammatory bowel disease; transplant rejection; asthma; septic shock |
| interleukin-7 receptor; IL-7r | unspecified | cytokine inhibitor; NSAID; immunosuppressant | allergy; inflammation; transplant rejection |
| MDAM | N-[4-[2-(2,4-diamino-6-pteridinyl)ethyl]benzoyl]-4-methylene-DL-glutamic acid | dihydrofolate reductase inhibitor; NSAID; immunosuppressant | cancer; transplant rejection; rheumatoid arthritis; asthma |
| interleukin-4 diphtheria toxin chimeric protein; IL-4 diphtheria toxin chimeric protein; IL-4 fusion protein | unspecified | fusion toxin; immunosuppressant | autoimmune disease; transplant rejection; cancer; HIV infection |
| growth and differentiation factor 3; GDF 3 | unspecified | growth factor; differentiation inducer; immunosuppressant | transplant rejection; autoimmune disease |
| lymphocyte activation inhibitors, Celltech | unspecified | immunostimulant | autoimmune disease; transplant rejection |
| geclosporin; ciclosporin G; cyclosporin G; ciclosporin, (NVA)2-; cyclosporin, (NVA)2-; OG 37325 | 7-L-norvaline cyclosporin A | immunostimulant | transplant rejection |
| RM 06 | N-[N-[[[5-(1,6-dihydro-6-oxo-9H-purin-9-yl)pentyl]oxy]carbonyl]-L-leucyl]-L-methionine | immunostimulant | cancer; transplant rejection |
| thiethazole | 2-[1-(1,1-dioxothiethanyl-3)benzimidazolyl-2-thio]acetic acid | immunostimulant; immunosuppressant; antioxidant | cancer; rheumatoid arthritis; infectious disease; transplant rejection |
| T-cell modulators | unspecified | immunosuppressant | transplant rejection |
| B7 molecules; B7-1; B7-2 | unspecified | immunosuppressant | autoimmune disease; transplant rejection |
| galaptin L-14-1; immunomodulatory lectin-1; IML-1 | unspecified | immunosuppressant | transplant rejection; multiple sclerosis |
| MAb, CD45RB | unspecified | immunosuppressant | transplant rejection; autoimmune disease |
| MAb, humanized B7.1 | unspecified | immunosuppressant | psoriasis; transplant rejection; autoimmune disease |
| MAb, humanized B7.2 | unspecified | immunosuppressant | psoriasis; transplant rejection; autoimmune disease |
| MEDI 507 | unspecified | immunosuppressant | autoimmune disease; transplant rejection; psoriasis |
| RG 1046 | unspecified | immunosuppressant | autoimmune disease; transplant rejection |
| CT 2544 | unspecified | immunosuppressant | autoimmune disease; transplant rejection |
| CT 3578 | unspecified | immunosuppressant | transplant rejection |
| cytomuline | unspecified | immunosuppressant | transplant rejection |
| drug delivery system, CYTOPORTER ciclosporin | unspecified | immunosuppressant | transplant rejection |

TABLE 10-continued

Current Candidate Therapeutic Interventions in Development for the Treatment of Transplant Rejection

| Product Name | Chemical Name | Action | Indication |
| --- | --- | --- | --- |
| drug delivery system, LDS microemulsion ciclosporin; ciclosporin LDS microemulsion | unspecified | immunosuppressant | autoimmune disease; transplant rejection |
| drug delivery system, liposome ciclosporin, ciclosporin liposome | unspecified | immunosuppressant | transplant rejection |
| drug delivery system, microemulsion ciclosporin; ciclosporin microemulsion; SANDIMMUN NEORAL; SANDIMMUN OPTORAL; NEORAL; NEORAL-SANDIMMUN | unspecified | immunosuppressant | autoimmune disease; transplant rejection |
| gliotoxin | unspecified | immunosuppressant | transplant rejection |
| immunosuppressant, Hollis Eden | unspecified | immunosuppressant | autoimmune disease; transplant rejection |
| immunosuppressants, AstraZeneca; immunosuppressants, University of California | unspecified | immunosuppressant | transplant rejection; autoimmune disease |
| immunosuppressants, Fujisawa/Hoechst Marion Roussel | unspecified | immunosuppressant | transplant rejection |
| immunosuppressants, Kinetix | unspecified | immunosuppressant | autoimmune disease; transplant rejection |
| interleukin-2 receptor ligand, Affymax | unspecified | immunosuppressant | transplant rejection; autoimmune disease |
| ISAtx 247 | unspecified | immunosuppressant | transplant rejection |
| leptin antagonists, Imperial College | unspecified | immunosuppressant | autoimmune disease; transplant rejection |
| LJP 920 | unspecified | immunosuppressant | transplant rejection |
| NE 501 | unspecified | immunosuppressant | transplant rejection |
| RWJ 60475 | unspecified | immunosuppressant | transplant rejection |
| VX 10367 | unspecified | immunosuppressant | transplant rejection |
| Xe 9 | unspecified | immunosuppressant | transplant rejection |
| ZAP 70 modulators, Pharmacopeia | unspecified | immunosuppressant | transplant rejection |
| gusperimus; gusperimus hydrochloride; deoxyspergualin, 15-; desoxyspergualin; DSG; NKT 01; NSC 356894; BMS 181173; BMY 42215-1; SPANIDIN; SUPANIDIN | (+,-)-7[(aminoiminomethyl)amino]-N-[2-[[4-[(3-aminopropyl)amino]butyl]amino]-1-hydroxy-2-oxoethyl]heptanamide | immunosuppressant | transplant rejection; multiple sclerosis; cancer |
| FR 901483 | (2 alpha,5 beta, 6 beta, 7 beta, 8 beta, 10a beta)-octahydro-5-[(4-methoxyphenyl)methyl]-2-(methylamino)-1H-7,10a-methanopyrrolo[1,2-a]azocine-6,8-diol,8-(dihydrogen phosphate) | immunosuppressant | transplant rejection |
| PRO 1556 | (OC-6-11)-hexakis(1H-imidazole-kappaN3)ruthenium(2+) dichloride | immunosuppressant | transplant rejection |
| PRO 2844 | (OC-6-22)-pentaammine(4-methylpyridine)rutheniu m(3+) trichloride | immunosuppressant | psoriasis; autoimmune disease; transplant rejection |
| myriocin; thermozymocidin; ISP-I | [2S-(2R*,3S*,4S*,6E)]-2-amino-3,4-dihydroxy-2-(hydroxymethyl)-14-oxo-6-eicosenoic acid | immunosuppressant | autoimmune disease; transplant rejection |

TABLE 10-continued

Current Candidate Therapeutic Interventions in Development for the Treatment of Transplant Rejection

| Product Name | Chemical Name | Action | Indication |
| --- | --- | --- | --- |
| discodermolide | [3S-[3alfa,4beta,5beta,6alfa(2R*,3Z,5R*,6R*,7S*,8Z,11R*,12S*,13S*,14S*,15R*,16E)]]-6-[14-[(aminocarbonyl)oxy]-2,6,12-trihydroxy-5,7,9,11,13,15-hexamethyl-3,8,16,18-nonadecatetraenyl]tetrahydro-4-hydroxy-3,5-dimethyl-2H-pyran-2-one | immunosuppressant | transplant rejection |
| FTY 720 | 2-amino-2-[2-(4-octylphenyl)ethyl]-1,3-propanediol hydrochloride | immunosuppressant | transplant rejection; autoimmune disease |
| HMR 1715 | 2-cyano-3-hydroxy-N-[4-(trifluoromethyl)phenyl]-6-heptynamide | immunosuppressant | transplant rejection |
| RAD 001; SDZ RAD | 42-O-(2-hydroxyethyl)rapamycin | immunosuppressant | transplant rejection |
| HMR 1279 | alpha-cyano-N-(4-cyanophenyl)-beta-oxocyclopropanepropanamide | immunosuppressant | transplant rejection |
| YM 13650 | propanedioic acid, mono(3-imidazo[2,1-b]benzothiazol-2-ylphenyl)ester | immunosuppressant | transplant rejection |
| rapamycin analogues | unspecified | immunosuppressant; antifungal | transplant rejection; mycosis |
| lymphocyte activation gene 3 protein; LAG 3 protein | unspecified | immunosuppressant; biotechnology | transplant rejection; multiple sclerosis |
| MAb, interleukin-2 receptor; MAb, IL-2R | unspecified | immunosuppressant; biotechnology | transplant rejection |
| AI 502 | unspecified | immunosuppressant; biotechnology; peptide | transplant rejection |
| soluble complement receptor type 1; sCR1; TP 10; TP 10HD; BRL 55730; YM 55730 | unspecified | immunosuppressant; complement inhibitor | respiratory distress syndrome; heart ischemia; transplant rejection |
| polyclonal antibody, rabbit antithymocyte; immunoglobulin, rabbit antithymocyte; rabbit antithymocyte immunoglobulin; THYMOGLOBULIN | unspecified | immunosuppressant; immunoglobulin; polyclonal antibody | transplant rejection; aplastic anemia |
| MAb, 33B3.1; MAb, anti-interleukin-2 receptor | unspecified | immunosuppressant; monoclonal antibody | transplant rejection |
| MAb, B7.1; MAb, M24; M 24 | unspecified | immunosuppressant; monoclonal antibody | transplant rejection |
| MAb, CD3 humanized | unspecified | immunosuppressant; monoclonal antibody | transplant rejection |
| MAb, T10B9; T10B9.1A-31; MEDI 500 | unspecified | immunosuppressant; monoclonal antibody | transplant rejection |
| MAbs, organ transplantation; TOLERIMAB | unspecified | immunosuppressant; monoclonal antibody | transplant rejection |
| inolimomab; MAb, IL-2 receptor CD25; MAb, interleukin-2 receptor CD25; BT 563; LEUKOTAC | immunoglobulin G 1 (mouse monoclonal B-B10.gamma.-chain anti-human interleukin 2 receptor.alpha.-chain), disulfide with mouse monoclonal B-B10.kappa.-chain, dimer | immunosuppressant; monoclonal antibody | transplant rejection |

TABLE 10-continued

Current Candidate Therapeutic Interventions in Development for the Treatment of Transplant Rejection

| Product Name | Chemical Name | Action | Indication |
|---|---|---|---|
| MAb, BC3 | unspecified | immunosuppressant; monoclonal antibody; biotechnology | transplant rejection |
| MAb, CD3-immunotoxin | unspecified | immunosuppressant; monoclonal antibody; biotechnology; immunotoxin | transplant rejection; autoimmune disease |
| enlimomab; MAb, intracellular adhesion molecule-1; MAb, ICAM-1; MAb, ICAM; MAb, R65; MAb, CD54; BIRR 0001; BIRR 1 | unspecified | immunosuppressant; monoclonal antibody; NSAID | transplant rejection; autoimmune disease; rheumatoid arthritis |
| MAb, R73; MAb, rat alpha/beta T cell receptor | unspecified | immunosuppressant; monoclonal antibody; NSAID | transplant rejection; rheumatoid arthritis |
| BMS 188667; CTLA4Ig | unspecified | immunosuppressant; NSAID | transplant rejection; systemic lupus erythematosus; psoriasis; arthritis; allergy |
| immunoregulators, AVANT Immunotherapeutics; immunoregulators, Repligen | unspecified | immunosuppressant; NSAID | transplant rejection; rheumatoid arthritis; asthma |
| PG 12 | unspecified | immunosuppressant; NSAID | rheumatoid arthritis; transplant rejection |
| PG 27 | unspecified | immunosuppressant; NSAID | rheumatoid arthritis; transplant rejection |
| PG 2946 | unspecified | immunosuppressant; NSAID | rheumatoid arthritis; systemic lupus erythematosus; transplant rejection |
| PG 3028 | unspecified | immunosuppressant; NSAID | rheumatoid arthritis; systemic lupus erythematosus; transplant rejection |
| PG 3113 | Unspecified | immunosuppressant; NSAID | rheumatoid arthritis; systemic lupus erythematosus; transplant rejection |
| PG 94 | unspecified | immunosuppressant; NSAID | rheumatoid arthritis; transplant rejection |
| PIC 060 analogs | unspecified | immunosuppressant; NSAID | psoriasis; dermatitis; diabetes; transplant rejection; rheumatoid arthritis |
| PIC 101 | unspecified | immunosuppressant; NSAID | rheumatoid arthritis; autoimmune disease; transplant rejection |
| PIC 102 | unspecified | immunosuppressant; NSAID | rheumatoid arthritis; transplant rejection; autoimmune disease |
| PIC 231 | unspecified | immunosuppressant; NSAID | rheumatoid arthritis; transplant rejection; autoimmune disease |
| VX 10393 | unspecified | immunosuppressant; NSAID | transplant rejection; rheumatoid arthritis; psoriasis; diabetes |
| VX 10428 | unspecified | immunosuppressant; NSAID | transplant rejection; rheumatoid arthritis; psoriasis; diabetes |
| phellodendrine; OB 5 | (7S-cis)-5,8,13,13a-tetrahydro-2,11-dihydroxy-3,10-dimethoxy-7-methyl-6H-dibenzo[a,g]quinoliziniu m | immunosuppressant; NSAID | transplant rejection; inflammation; viral infection; asthma; kidney disease |
| laflunimus; HR 325 | (Z)-2-cyano-3-cyclopropyl-3-hydroxy-N-[3-methyl-4-(trifluoromethyl)phenyl]-2-propenamide | immunosuppressant; NSAID | rheumatoid arthritis; transplant rejection; psoriasis |

TABLE 10-continued

Current Candidate Therapeutic Interventions in Development for the Treatment of Transplant Rejection

| Product Name | Chemical Name | Action | Indication |
|---|---|---|---|
| mizoribine; HE 69; BREDININ | 5-hydroxy-1-beta-D-ribofuranosylimidazole-4-carboxamide | immunosuppressant; NSAID | rheumatoid arthritis; transplant rejection; kidney disease |
| CD45 inhibitors, Ontogen | unspecified | immunosuppressant; NSAID; tyrosine phosphatase inhibitor | transplant rejection; inflammation |
| human leukocyte antigen-derived protein; HLA-derived protein; ALLOTRAP 2702 | unspecified | immunosuppressant; peptide | transplant rejection |
| immunosuppressant peptides, Sangstat; immunosuppressant peptides, Syntem | unspecified | immunosuppressant; peptide | transplant rejection; autoimmune disease |
| ZAP inhibitors, Ariad | unspecified | immunosuppressant; protein kinase inhibitor; tyrosine kinase inhibitor; NSAID | transplant rejection; rheumatoid arthritis; inflammatory bowel disease; systemic lupus erythematosus; multiple sclerosis |
| TBC 427 | unspecified | integrin antagonist; selectin antagonist; immunosuppressant; cell adhesion inhibitor | ischemia; psoriasis; respiratory distress syndrome; transplant rejection; reperfusion injury |
| drug delivery system, NanoCrystal sirolimus; sirolimus NanoCrystal | unspecified | macrolide; antibiotic; immunosuppressant | transplant rejection |
| sirolimus; rapamycin; NSC 226080; AY 22989; RAPAMUNE | (3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29(4H,6H,31H)-pentone | macrolide; immunosuppressant; antibiotic | transplant rejection; autoimmune disease; restenosis |
| tacrolimus; tsukubaenolide; fujimycin; FK 506; (−)-FK 506; FR 900506; L 679934; PROGRAF; PROTOPIC | [3S-[3R*[E(1S*,3S*,4S*)],4S*,5R*,8S*,9E,12R*,14R*,15S*,16R*,18S*,19S*,26aR*]]5,6,8,11,12,13,14,15,16,17,18,19,24,25,26,26a-hexadecahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-c][1,4]oxaazacyclotricosine-1,7,20,21(4H,23H)-tetrone | macrolide; immunosuppressant; NSAID; antibiotic | transplant rejection; dermatitis; eye disease; rheumatoid arthritis |
| MAb 2E1; MAb, effector cell proteinase receptor-1 | unspecified | monoclonal antibody; immunosuppressant | transplant rejection |
| MAb, 64G12; Mab, interferon receptor type-1; 64G12 | unspecified | monoclonal antibody; immunosuppressant | autoimmune disease; transplant rejection |
| MAb, BMA 031 | unspecified | monoclonal antibody; immunosuppressant | transplant rejection |

TABLE 10-continued

Current Candidate Therapeutic Interventions in Development for the Treatment of Transplant Rejection

| Product Name | Chemical Name | Action | Indication |
| --- | --- | --- | --- |
| MAb, CD11a; hu 1124 | unspecified | monoclonal antibody; immunosuppressant | psoriasis; transplant rejection |
| MAb, CD45; LM CD45 | unspecified | monoclonal antibody; immunosuppressant | transplant rejection |
| MAb, CD45RB | unspecified | monoclonal antibody; immunosuppressant | autoimmune disease; transplant rejection |
| MAb, CD7; SDZ CHH 380 | unspecified | monoclonal antibody; immunosuppressant | transplant rejection |
| MAb, gp39; MAb, CD40L; IDEC 131 | unspecified | monoclonal antibody; immunosuppressant | autoimmune disease; transplant rejection; systemic lupus erythematosus |
| MAb, humanized CD3; MAb, SMART CD3; HuM291 | unspecified | monoclonal antibody; immunosuppressant | transplant rejection; autoimmune disease; psoriasis |
| MAb, L0-CD2a; BTI 322 | unspecified | monoclonal antibody; immunosuppressant | autoimmune disease; transplant rejection |
| MAb, major histocompatibility complex I; F(ab')2, MHC I | unspecified | monoclonal antibody; immunosuppressant | transplant rejection |
| MAb, MHCII-CD8 | unspecified | monoclonal antibody; immunosuppressant | transplant rejection; graft versus host disease |
| MAb, transplant rejection; CBL1; ABX CBL | unspecified | monoclonal antibody; immunosuppressant | transplant rejection |
| MAb, CD4; HumaT4 | unspecified | monoclonal antibody; immunosuppressant | psoriasis; asthma; rheumatoid arthritis; irritable bowel syndrome; transplant rejection; allergy |
| daclizumab; dacliximab; MAb, Tac; MAb, humanized Tac; MAb, SMART Tac; Ro 247375; ZENAPAX | immunoglobulin G1 (human-mouse monoclonal clone 1H4 gamma chain anti-human antigen Tac), disulfide with human-mouse monoclonal clone 1H4 light chain, dimer | monoclonal antibody; immunosuppressant | transplant rejection; cancer; autoimmune disease; eye disease |
| odulimomab; MAb, LFA-1 alpha subunit; ANTILFA | immunoglobulin G1, anti-(human CD11 (antigen).alpha-chain)(mouse monoclonal 25.3.gamma.1-chain), disulfide with mouse monoclonal 25.3 light chain, dimer | monoclonal antibody; immunosuppressant | transplant rejection |
| basiliximab; SDZ CHI621; CHI 621; SIMULECT | Immunoglobulin G1, anti-(human interleukin 2 receptor) (human-mouse monoclonal CHI621.gamma.1-chain),disulfide with human-mouse mo noclonal CHI621 light chain, dimer | monoclonal antibody; immunosuppressant | transplant rejection |
| MAb, CD6 blocked ricin; MAb, T12-bR; ONCOLYSIN CD6 | unspecified | monoclonal antibody; immunosuppressant; immunotoxin | transplant rejection |
| MAb, MHC class II | unspecified | monoclonal antibody; immunosuppressant; NSAID | autoimmune disease; transplant rejection; graft versus host disease; cancer |
| MAb, CD5-momordin; immunotoxin CD5-momordin; ITF 1532 | unspecified | monoclonal antibody; immunotoxin; immunosuppressant | cancer; transplant rejection |

TABLE 10-continued

Current Candidate Therapeutic Interventions in Development for the Treatment of Transplant Rejection

| Product Name | Chemical Name | Action | Indication |
| --- | --- | --- | --- |
| zolimomab aritox; MAb, H65 RTA; MAb, bone marrow-ricin A conjugate; CD5-T lymphocyte immunotoxin; MAb, CD5; XMMLY H65 RTA; XOMAZYME H65; XOMAZYME CD5+; ORTHOZYME CD5+; CD5 Plus | unspecified | monoclonal antibody; immunotoxin; immunosuppressant | transplant rejection |
| MAb, humanized, leukemia; MAb, IgG2B; LDP 03; BW 7U; CAMPATH; CAMPATH-1H | unspecified | monoclonal antibody; NSAID | rheumatoid arthritis; cancer, multiple sclerosis; transplant rejection |
| MAb, B7; MAb, PRIMATIZED B7; IDEC 114 | unspecified | monoclonal antibody; NSAID; immunosuppressant | systemic lupus erythematosus; inflammation; transplant rejection; psoriasis |
| NOX 100 | unspecified | nitric oxide scavenger | diabetes; cancer; trauma; transplant rejection; septic shock; hemorrhagic shock |
| NOX 51 | unspecified | nitric oxide scavenger | diabetes; cancer; hemorrhagic shock; transplant rejection; septic shock |
| NOX 101 | Unspecified | nitric oxide scavenger | stroke; diabetes; cancer; trauma; transplant rejection; septic shock; hemorrhagic shock |
| NE 0501 | unspecified | oligosaccharide | transplant rejection |
| opioid antagonists, NIH | unspecified | opiate antagonist; peptide; immunosuppressant | drug addiction; alcoholism; obesity; transplant rejection |
| recombinant PSGL 1, Genetics Institute; PSGL 1 | unspecified | P selectin antagonist; E selectin antagonist; L selectin antagonist; selectin antagonist; NSAID | inflammation; transplant rejection; ischemia; reperfusion injury |
| rD-mPGPtide | unspecified | peptide; immunosuppressant | transplant rejection; multiple sclerosis |
| transplantation therapy, SangStat | unspecified | peptide; immunosuppressant | transplant rejection |
| complement inhibitors, Lidak | unspecified | peptide; immunosuppressant; NSAID | rheumatoid arthritis; systemic lupus erythematosus; autoimmune disease; reperfusion injury; respiratory distress syndrome; transplant rejection |
| SPC 100270 | unspecified | protein kinase inhibitor; protein kinase C inhibitor; immunosuppressant | ischemia; transplant rejection; reperfusion injury |
| Ro 320432; Ro 32-0432 | (S)-3-[8-[(dimethylamino)methyl]-6,7,8,9-tetrahydropyrido[1,2-a]indol-10-yl]-4-(1-methyl-1H-indol-3-yl)-1H-pyrrole-2,5-dione | protein kinase inhibitor; protein kinase C inhibitor; immunosuppressant; NSAID | transplant rejection; rheumatoid arthritis |
| peldesine; BCX 34; BCX 34B | 2-amino-1,5-dihydro-7-(3-pyridinylmethyl)-4H-pyrrolo[3,2-d]pyrimidin-4-one | purine nucleoside phosphorylase inhibitor; immunosuppressant; NSAID | cancer; psoriasis; rheumatoid arthritis; transplant rejection; eye disease; dermatitis; HIV infection |

TABLE 10-continued

Current Candidate Therapeutic Interventions in Development for the Treatment of Transplant Rejection

| Product Name | Chemical Name | Action | Indication |
|---|---|---|---|
| purine nucleoside phosphorylase inhibitors, Chiroscience; PNP inhibitors, Chiroscience | unspecified | purine nucleoside phosphorylase inhibitor; NSAID | cancer; psoriasis; rheumatoid arthritis; transplant rejection |
| mycophenolate mofetil; mycophenolate mofetil hydrochloride; RS 61443; RS-61443-190; CellCept | (E)-6-(1,3-dihydro-4-hydroxy-6-methoxy-7-methyl-3-oxo-5-isobenzofuranyl)-4-methyl-4-hexenoic acid 2-(4-morpholinyl)ethyl ester | purine synthesis inhibitor; immunosuppressant; NSAID | transplant rejection; rheumatoid arthritis; asthma; restenosis; kidney disease; systemic lupus erythematosus |
| ribozymes, organ transplantation | unspecified | ribozyme; oligonucleotide; immunosuppressant | transplant rejection |
| CGS 12970 | 3-methyl-2-(3-pyridinyl)-1H-indole-1-octanoic acid | thromboxane synthase inhibitor; immunosuppressant | transplant rejection |
| pirmagrel; CGS 13080 | imidazo(1,5-a)pyridine-5-hexanoic acid | thromboxane synthetase inhibitor; immunosuppressant | transplant rejection |
| thalidomide; SYNOVIR; THALOMID | N-(2,6-dioxo-3-piperidyl)phthalimide | TNF modulator; immunosuppressant | cachexia; diarrhea; leprosy; rheumatoid arthritis; transplant rejection; cancer; Crohn disease |
| thalidomide; NSC 66847 | N-(2,6-dioxo-3-piperidyl)phthalimide | TNF modulator; immunosuppressant | HIV infection; Crohn disease; multiple sclerosis; Alzheimer disease; transplant rejection |
| SC 114 | unspecified | triglyceride; immunosuppressant | autoimmune disease; transplant rejection |
| 20-epi-1,25 dihydroxyvitamin D3; MC 1288; IE | (1alpha,3beta,5Z,7E,20 S)-9,10-secocholesta-5,7,10(19)-triene-1,3,25-triol | vitamin D3 analogue; immunosuppressant | diabetes; transplant rejection; arthritis |

TABLE 11

Current Candidate Therapeutic Interventions in Development for the Treatment of Pain Related to Inflammation

| Product Name | Chemical Name | Action | Indication |
|---|---|---|---|
| anti-inflammatory | 4,5-dihydro-3-(1-pyrrolyl)-1-(3-trifluoromethylphenyl)-1H pyrazole | 15 lipoxygenase, cyclooxygenase, and thromboxane synthetase inhibitor | inflammation |
| CO 1828 | 4-methoxy-2-(3-phenyl-2-propynyl)phenol | 5 lipoxygenase and cyclooxygenase inhibitor | inflammation |
| darbufelone; CI 1004 | (Z)-2-amino-5-[(3,5-bis(1,1-dimethylethyl)-4-hydroxyphenyl]methylene]-4(5H)-thiazolone | 5 lipoxygenase inhibitor; COX inhibitor; COX 2 inhibitor; NSAID | inflammation |
| P 8892 | 2-[2-(ethylhydroxyamino)ethyl] dibenz[b,e]oxepin-11(6H)-one | 5 lipoxygenase inhibitor; COX inhibitor; NSAID | inflammation |
| CI 986 | 2-hydroxy-N,N,N-trimethylethanaminium salt with 5-[3,5-bis(1,1-dimethylethyl)-4-hydroxyphenyl]-1,3,4-thiadiazole-2(3H)-thione (1:1) | 5 lipoxygenase inhibitor; COX inhibitor; NSAID | inflammation |
| P 8977 | 3-(6,11-dihydro-11-oxo-dibenz[b,e]oxepin-2-yl)-N-methylpropanamide | 5 lipoxygenase inhibitor; COX inhibitor; NSAID | inflammation |

TABLE 11-continued

Current Candidate Therapeutic Interventions in Development for the Treatment of
Pain Related to Inflammation

| Product Name | Chemical Name | Action | Indication |
|---|---|---|---|
| CI 987 | 5-[[3,5-bis(1,1-dimethylethyl)-4-hydroxyphenyl]methylene]-2,4-thiazolidinedione | 5 lipoxygenase inhibitor; COX inhibitor; NSAID | inflammation |
| BIL 226XX | unspecified | 5 lipoxygenase inhibitor; NSAID | inflammation |
| CGS 23885 | unspecified | 5 lipoxygenase inhibitor; NSAID | psoriasis; inflammation |
| CGS 24891 | unspecified | 5 lipoxygenase inhibitor; NSAID | inflammation |
| CHF 1909 | unspecified | 5 lipoxygenase inhibitor; NSAID | inflammation; asthma |
| GR 80907 | unspecified | 5 lipoxygenase inhibitor; NSAID | asthma; inflammation |
| lagunamycin | unspecified | 5 lipoxygenase inhibitor; NSAID | inflammation |
| SC 45662 | unspecified | 5 lipoxygenase inhibitor; NSAID | inflammation; asthma; psoriasis; inflammatory bowel disease |
| DUP 654 | (2-phenylmethyl)-1-naphthalenol | 5 lipoxygenase inhibitor; NSAID | psoriasis; inflammation |
| CGS 25997 | (2S)-(−)-2-[[N-(aminocarbonyl)-N-hydroxyamino]methyl]-7-(4-fluorophenoxy)-1,4-benzodioxan | 5 lipoxygenase inhibitor; NSAID | asthma; inflammation |
| A 121798 | (E)-1-methyl-6-[[[3-(tetrahydro-4-methoxy-2-methyl-2H-pyran-4-yl)-2-propenyl]oxy]methyl]-2(1H)-quinolinone | 5 lipoxygenase inhibitor; NSAID | inflammation |
| enofelast; BIL 239X | (E)-4-[2-(4-fluorophenyl)ethenyl]-2,6-dimethylphenol | 5 lipoxygenase inhibitor; NSAID | inflammation |
| T 0757; T 757 | (E)-N-(4-hydroxy-3,5-dimethylphenyl)-3,7-dimethyl-2,6-octadienamide | 5 lipoxygenase inhibitor; NSAID | inflammation |
| L 663536; MK 886 | 1-[(4-chlorophenyl)methyl]-3-[(1,1-dimethylethyl)thio]-alfa, alfa-diethyl-5-(1-methylethyl)-1H-indole-2-propanoic acid | 5 lipoxygenase inhibitor; NSAID | inflammation; asthma; psoriasis |
| SCH 40120 | 10-(3-chlorophenyl)-6,8,9,10-tetrahydrobenzo[b][1,8]naphthyridin-5(7H)-one | 5 lipoxygenase inhibitor; NSAID | inflammation; psoriasis |
| ICI 211965 | 2-[1-methoxy-1-[3-(2-naphthalenylmethoxy)phenyl]propyl]thiazole | 5 lipoxygenase inhibitor; NSAID | inflammation |
| L 699333 | 2-[2-[1-[(4-chlorophenyl)methyl]-4,5-dihydro-4-methyl-6-[(5-phenyl-2-pyridinyl)methoxy]-1H-thiopyrano[2,3,4-cd]indol-2-yl]ethoxy]butanoic acid | 5 lipoxygenase inhibitor; NSAID | asthma; inflammation |
| carbazomycin C | 3,6-dimethoxy-1,2-dimethyl-9H-carbozol-4-ol | 5 lipoxygenase inhibitor; NSAID | inflammation |
| carbazomycin B | 3-methoxy-1,2-dimethyl-9H-carbazol-4-ol | 5 lipoxygenase inhibitor; NSAID | inflammation |
| E 6080 | 4-[[(6-hydroxy-4,4,7-trimethyl-2-benzothiazolyl)amino]methyl]benzenesulfonamide monohydrochloride | 5 lipoxygenase inhibitor; NSAID | asthma; inflammation |
| L 651392 | 4-bromo-2,7-dimethoxy-3H-phenothiazin-3-one | 5 lipoxygenase inhibitor; NSAID | inflammation; bacterial infection; asthma |

TABLE 11-continued

Current Candidate Therapeutic Interventions in Development for the Treatment of
Pain Related to Inflammation

| Product Name | Chemical Name | Action | Indication |
| --- | --- | --- | --- |
| ZD 7717; ICI D7717 | 7-[[3-fluoro-5-(tetrahydro-4-methoxy-2H-pyran-4-yl)phenyl]thio]-4-methyl-2H-1,4-benzoxazin-3(4H)-one | 5 lipoxygenase inhibitor; NSAID | asthma; inflammation |
| zileuton; A 64077; ABBOTT 64077; ZYFLO | N-(1-benzo[b]thien-2-ylethyl)-N-hydroxyurea | 5 lipoxygenase inhibitor; NSAID | inflammation; asthma |
| T 0799; T 799 | N-(4-hydroxy-3,5-dimethylphenyl)-3-thiophenecarboxamide | 5 lipoxygenase inhibitor; NSAID | inflammation |
| A 69412 | N-[1-(3-furanyl)ethyl]-N-hydroxyurea | 5 lipoxygenase inhibitor; NSAID | inflammation |
| A 78773; A 79175 | N-[3-[5-(4-fluorophenoxy)-2-furanyl]-1-methyl-2-propynyl]-N-hydroxyurea | 5 lipoxygenase inhibitor, NSAID | allergy; inflammation |
| atreleuton; atreluton; ABT 761; A 85761.0; ABT 85761 | N-[3-[5-[(4-fluorophenyl)methyl]-2-thienyl]-1-methyl-2-propynyl]-N-hydroxy-urea | 5 lipoxygenase inhibitor; NSAID | inflammation |
| A 72694; ABT72694 | N-2,2-dimethyl-3((1-(4-chlorophenylmethyl)-3-(1,1-dimethylethylthio)-5-(1-methylethyl)indol-2-yl))-propyl-n-hydrourea | 5 lipoxygenase inhibitor; NSAID | inflammation |
| lipoxygenase inhibitor | N-hydroxy-N-[1-(2-phenyl-5-benzofuranyl)ethyl]urea | 5 lipoxygenase inhibitor; NSAID | inflammation |
| lurosetron; lurosetron mesylate; GR 87442; GR 87442N; GR 87442X | 6-fluoro-2,3,4,5-tetrahydro-5-methyl-2-[(5-methylimidazol-4-yl)methyl]-1H-pyndo[4,3-b]indol-1-one | 5HT antagonist; 5HT3 antagonist; NSAID | inflammation; emesis |
| AAL 13 | 2-[4-(3-chloropropyl)-1-piperazinyl]quinoline | 5HT reuptake inhibitor; analgesic; NSAID | inflammation; pain |
| AKI 1 | unspecified | adenosine regulating agent; NSAID | inflammation; arthritis |
| AKI 2 | unspecified | adenosine regulating agent; NSAID | inflammation; arthritis |
| GP 1515 | 1-(5-amino-5-deoxy-beta-D-ribofuranosyl)-3-bromo-1H-pyrazolo[3,4-d]pyrimidin-4-amine | adenosine regulating agent; NSAID | inflammation |
| drug delivery system, hydrogel diclofenac; diclofenac hydrogel; DICLOFENAC HYCORE-R | unspecified | analgesic; NSAID | pain; inflammation |
| drug delivery system, OSAT diclofenac; diclofenac sustained release | unspecified | analgesic; NSAID | pain; inflammation |
| drug delivery system, OSAT ibuprofen; ibuprofen sustained release | unspecified | analgesic; NSAID | pain; rheumatoid arthritis; osteoarthritis; inflammation |
| drug delivery system, sustained release microsphere flurbiprofen; flurbiprofen, sustained release | unspecified | analgesic; NSAID | pain; inflammation |
| TZI 41078 | unspecified | analgesic; NSAID | inflammation; pain |
| RP 67580 | (3aR-cis)-octahydro-2-[1-imino-2-(2-methoxyphenyl)ethyl]-7,7-diphenyl-4H-isoindol-4-one | analgesic; NSAID | pain; inflammation |

TABLE 11-continued

Current Candidate Therapeutic Interventions in Development for the Treatment of Pain Related to Inflammation

| Product Name | Chemical Name | Action | Indication |
|---|---|---|---|
| HU 239 | (6aR-trans)-3-(1,1-dimethylheptyl)-6a,7,10,10a-tetrahydro-1-hydroxy-6,6-dimethyl-6H-dibenzo[b,d]pyran-9-carboxylic acid | analgesic; NSAID | inflammation; pain |
| proglumetacin; protacine; CR 604; IMPETIN; PROXIL; PROXATIL; AFLOXAN; TOLINDOL; BRUXEL; MIRIDACIN | 1-(4-chlorobenzoyl)-5-methoxy-2-methyl-1H-indole-3-acetic acid 2-[4-[3-[[4-(benzoylamino)-5-(dipropylamino)-1,5-dioxopentyl]oxy]propyl]-1-piperazinyl]ethyl ester, | analgesic; NSAID | inflammation; pain |
| FA 401 | 1-(4-fluorobenzoyl)-5-methoxy-2-methyl-1H-indole-3-acetic acid carboxymethyl ester | analgesic; NSAID | pain; inflammation |
| BN 50370 | 1,3-dihydro-3,6-dimethyl-7-hydroxy-furo(3,4)pyridine hydrochloride | analgesic; NSAID | inflammation; pain |
| flurbiprofen axetil; LFP 83; ROPION; LIPFEN | 2-fluoro-alpha-methyl-(1,1'-biphenyl)-4-acetic acid, 1-(acetyloxy)ethyl ester | analgesic; NSAID | pain; inflammation |
| analgesic | 3-methyl-5-oxobenzo(b)thieno(2,3-d)thiazolo(3,2-a)pyrimidine-2-carboxylic acid ethyl ester | analgesic; NSAID | pain; inflammation; gastrointestinal ulcer |
| DTA | 4'-methyl-[1,1':3',1"-terphenyl]-5'-acetic acid | analgesic; NSAID | inflammation; pain |
| diaveridine; EGIS 5645 | 5-[(3,4-dimethoxyphenyl)methyl]-2,4-pyrimidinediamine | analgesic; NSAID | inflammation; pain |
| LA 351 | 5H-(1)-benzopyrano(2,3-b)pyridin-5-one | analgesic; NSAID | inflammation; pain; asthma |
| M 5011; T 3788 | alpha-2-[4-(3-methyl-thienyl)phenyl]propionic acid | analgesic; NSAID | inflammation; pain |
| 2-halopyridines | unspecified | analgesic; NSAID | inflammation; pain; insomnia |
| HCT 3012 | unspecified | analgesic; NSAID; nitric oxide donor | pain; inflammation |
| HP 228 | N-acetyl-Nleu—Gln—His—Phe—Arg—Trp—Gly-amide | analgesic; NSAID; peptide; melanocortin agonist | pain; inflammation; asthma; cachexia |
| heparanase inhibitors | unspecified | angiogenesis inhibitor; NSAID | cancer; inflammation |
| XMP 300 | unspecified | angiogenesis inhibitor; peptide | inflammation; cancer |
| AGN 190383 | 4-[1-(acetyloxy)tridecyl]-5-hydroxy-2(5H)-furanone | Antagonist prior to 5 lipoxygenase and cyclooxygenase | inflammation |
| loteprednol + tobramycin; tobramycin + loteprednol | unspecified | antibiotic | inflammation; bacterial infection |
| anti-inflammatory macrolide analogues, KOSAN | unspecified | antibiotic; macrolide | asthma; inflammation |
| drug delivery system, ATRIGEL sustained release sanguinarine chloride; sanguinarine chloride ATRIGEL | unspecified | antibiotic; NSAID; antifungal | bacterial infection; mycosis; inflammation; periodontal disease |
| SB 226882 | 4-[4-(4-fluorophenyl)-1-(4-piperidinyl)-1H-imidazol-5-yl]-N-methyl-2-pyrimidinamine | antifungal; MAP kinase inhibitor; signal transduction inhibitor; imidazole | inflammation; asthma; rheumatoid arthritis |

TABLE 11-continued

Current Candidate Therapeutic Interventions in Development for the Treatment of Pain Related to Inflammation

| Product Name | Chemical Name | Action | Indication |
|---|---|---|---|
| aminoimidazole carboxamide ribonucleotide formyltransferase inhibitors, AICART inhibitors | unspecified | antifungal; ribonucleotide formyltransferase inhibitor; NSAID; imidazole | cancer; inflammation |
| drug delivery system, anti-inflammatory; | intraocular biodegradable polymer | anti-inflammatory intraocular | inflammation |
| ibuprofen piconol; U 75630; BE 100; OU 75630; STADERM; VESICUM | alpha-methyl-4-(2-methylpropyl)benzeneacetic acid 2-pyridinylmethyl ester | Antiinflammatory with ibuprofen mechanism, topical cream | inflammation |
| EN 07 | Medicinal herbal extract | Antiinflammatory; dermatologic antiinflammatory | inflammation |
| nitroxide antioxidant | unspecified | antioxidant; free radical scavenger; NSAID | respiratory distress syndrome; inflammation; cancer; reperfusion injury |
| antioxidants | unspecified | antioxidant; NSAID | inflammation; atherosclerosis |
| antioxidants | unspecified | antioxidant; NSAID | skin disease; inflammation; cancer |
| naphterpin; CL 190Y2 | (4aS-cis)-3,4a,5,12b-tetrahydro-8,10-dihydroxy-2,5,5,9-tetramethyl-4H-benzo[d]naphtho[2,3-b]pyran-7,12-dione | antioxidant; NSAID | diabetes cardiovascular disease, cancer; inflammation |
| boldine | (S)-5,6,6a,7-tetrahydro-1,10-dimethoxy-6-methyl-4H-dibenzo[de,g]quinoline-2,9-diol | antioxidant; NSAID | inflammation |
| AD 0261 | 2-[[3-[4-[bis(4-fluorophenyl)methyl]-1-piperazinyl]propyl]amino]-4-methylphenol | antioxidant; NSAID | inflammation; allergy; skin disease |
| Z 4003 | 2-[1-[4-(2-methylpropyl)phenyl]ethyl]-4-thiazolidinecarboxylic acid | antioxidant; NSAID | angina; inflammation; emphysema |
| antisense oligonucleotide, IL-1 receptor(type 1) | unspecified | antisense; biotechnology; oligonucleotide; NSAID | inflammation |
| antisense oligonucleotide, interleukin-1; antisense oligonucleotide, IL-1 | unspecified | antisense; immunosuppressant; oligonucleotide; NSAID | inflammation |
| antisense oligonucleotide, B7-1 | unspecified | antisense; oligonucleotide; biotechnology; NSAID | inflammation |
| antisense oligonucleotide, B7-2 | unspecified | antisense; oligonucleotide; biotechnology; NSAID | inflammation |
| antisense oligonucleotide, ELAM; ISIS 4730 | unspecified | antisense; oligonucleotide; NSAID | inflammation |
| antisense oligonucleotide, PECAM-1 | unspecified | antisense; oligonucleotide; NSAID | inflammation |
| antisense oligonucleotides, VCAM-1 | unspecified | antisense; oligonucleotide; NSAID | inflammation |
| drug delivery system, antisense oligonucleotide, ICAM-1; antisense oligonucleotide, ICAM-1 delivery system; Oligo TCS | unspecified | antisense; oligonucleotide; NSAID | inflammation |

TABLE 11-continued

Current Candidate Therapeutic Interventions in Development for the Treatment of Pain Related to Inflammation

| Product Name | Chemical Name | Action | Indication |
| --- | --- | --- | --- |
| drug delivery system, oral, antisense oligonucleotide, TNF-alpha; antisense oligonucleotide, TNF-alpha delivery system | unspecified | antisense; oligonucleotide; NSAID | inflammation |
| anti-inflammatory aptamers | unspecified | aptamer; NSAID | inflammation |
| L-selectin antagonist | unspecified | aptamer; oligonucleotide; integrin antagonist; L selectin antagonist; immunosuppressant; cell adhesion inhibitor; NSAID | inflammation |
| P-selectin antagonist | unspecified | aptamer; oligonucleotide; integrin antagonist; P selectin antagonist; immunosuppressant; cell adhesion inhibitor; NSAID | inflammation |
| neutrophil elastase inhibitor, NeXstar | unspecified | aptamer; oligonucleotide; NSAID; elastase inhibitor; proteinase inhibitor | inflammation; respiratory disease |
| bradykinin antagonists | unspecified | bradykinin antagonist; analgesic; NSAID | pain; inflammation; septic shock |
| NOVA 567; NPC 567 | N2-D-arginyl-3-(trans-4-hydroxy-L-proline)-7-D-phenylalaninebradykinin | bradykinin antagonist; cicatrizant; peptide; NSAID | asthma; skin ulcer; inflammation |
| bradykinin antagonist/mu agonist | unspecified | bradykinin antagonist; mu agonist; opiate agonist; analgesic; NSAID | inflammation; pain; migraine |
| CP 0880; CP 880 | N-[[3-[[1-oxo-3-[4-[(1-oxopropyl)phenylamino]-1-(2-phenylethyl)-3-piperidinyl]propyl]amino]phenyl]acetyl]-beta-alanyl-D-arginyl-L-arginyl-L-prolyl-(4R)-4-hydroxy-L-prolylglycyl-3-(2-thienyl)-L-alanyl-L-seryl-(3R)-1,2,3,4-tetrahydro-3-isoquinolinecarbonyl-N-cyclohexylglycyl-L-arginine | bradykinin antagonist; mu agonist; opiate agonist; analgesic; NSAID | inflammation; pain |
| CP 0364 | unspecified | bradykinin antagonist; NSAID | hypertension; inflammation |
| CP 0494 | unspecified | bradykinin antagonist; NSAID | septic shock; inflammation |
| FR 172357 | unspecified | bradykinin antagonist; NSAID | inflammation |
| non-peptide bradykinin antagonist | unspecified | bradykinin antagonist; NSAID | inflammation |
| icatibant; icatibant acetate; HOE 140 | D-arginyl-L-arginyl-L-prolyl-trans-4-hydroxy-L-prolylglycyl-3-(2-thienyl)-L-alanyl-L-seryl-D-1,2,3,4-tetrahydro-3-isoquinolincarbonyl-L-(2 alfa, 3 abeta, 7 abeta)-octahydro-1H-indole-2-carbonyl-L-arginine | bradykinin antagonist NSAID | asthma, inflammation; rhinitis, osteoarthritis |
| NPC 17731 | N2-D-arginyl-3-(trans-4-hydroxy-L-proline)-7-(trans-4-propoxy-D-proline)-8-[L-(2 alpha, 3 abeta, 7 abeta)-octahydro-1H-indole-2-carboxylic acid]-bradykinin | bradykinin antagonist; NSAID | inflammation; septic shock; asthma |

TABLE 11-continued

Current Candidate Therapeutic Interventions in Development for the Treatment of Pain Related to Inflammation

| Product Name | Chemical Name | Action | Indication |
|---|---|---|---|
| FR 173657 | (E)-3-[6-(acetylamino)-3-pyridinyl]-N-[2-[[2,4-dichloro-3-[[(2-methyl-8-quinolinyl)oxy]methyl]phenyl]methylamino]-2-oxoethyl-2-propenamide | bradykinin antagonist; NSAID; analgesic | asthma; inflammation; pain |
| CP 9430 | unspecified | bradykinin antagonist; NSAID; peptide | inflammation |
| CP 0597 | D-arginyl-L-arginyl-L-prolyl-(4R)-4-hydroxy-L-prolylglycyl-3-(2-thienyl)-L-alanyl-L-seryl-(3R)-1,2,3,4-tetrahydro-3-isoquinolinecarbonyl-N-cyclohexylglycyl-L-arginine | bradykinin antagonist; NSAID; peptide | inflammation |
| fenspiride; KSP 193; PNEUMORAL; ESPIRAN | 8-(2-phenylethyl)-1-oxa-3,8-diazaspiro[4.5]decan-2-one | bronchodilator; NSAID | inflammation; asthma |
| C5A antagonists, | unspecified | C5A antagonists | inflammation |
| SKF 96365 | 1-[2-(4-methoxyphenyl)-2-[3-(4-methoxyphenyl)propoxy]ethyl]-1H-imidazole | calcium antagonist; NSAID | inflammation |
| NE 28345 | (Z)-4-hydroxy-3-methoxy-N-9-octadecenylbenzeneacetamide | capsaicin analogue; NSAID | inflammation |
| casein kinase inhibitors | unspecified | casein kinase inhibitor; immunosuppressant; NSAID | inflammation; cancer |
| CD11b/CD18 inhibitors, Corvas; CORLEUKIN | unspecified | CD11b/CD18 receptor inhibitor; NSAID | inflammation |
| atrinositol; PP 56 | D-myo-inositol 1,2,6-tris(dihydrogen phosphate) | chelating agent; NSAID | inflammation; hyperlipidemia |
| chemoattractant antagonists | unspecified | chemokine antagonist | inflammation |
| chemokine antagonists | unspecified | chemokine antagonist | inflammation |
| CHEMOTIDES | unspecified | chemokine antagonist; NSAID | inflammation |
| chymase inhibitors, Axys | unspecified | chymase inhibitor; NSAID | asthma; inflammation; rhinitis |
| MDS 004 | unspecified | cicatrizant; NSAID | skin ulcer; inflammation |
| malotilate; NND 105; NKK 105; DA 3857; KANTEC; KANTECS; TRACTAL | 1,3-dithiol-2-ylidenepropanedioic acid bis(1-methylethyl) ester | cicatrizant; NSAID | liver disease; inflammation; skin ulcer |
| collagenase inhibitors | unspecified | collagenase inhibitor; matrix metalloproteinase inhibitor; proteinase inhibitor; NSAID | arthritis; inflammation |
| complement factor inhibitors | unspecified | Complement factor inhibitors | inflammation; respiratory distress syndrome |
| CMI CAB2 | unspecified | complement inhibitor; biotechnology; NSAID | inflammation; respiratory distress syndrome |
| inflammation therapy, complement regulatory protein | unspecified | complement inhibitor; biotechnology; NSAID | inflammation |
| MAb, C5 single chain; MAb, complement C5; 5G1.1-SC | unspecified | complement inhibitor; monoclonal antibody; NSAID | inflammation; myocardial infarction; stroke; ischemia |
| sCRlsLex; TP 20 | unspecified | complement inhibitor; neutrophil adhesion inhibitor; NSAID | respiratory distress syndrome; inflammation |
| TP 16 | unspecified | complement inhibitor; NSAID | inflammation |
| kallikrein inhibitors | unspecified | complement inhibitor; NSAID | inflammation |

TABLE 11-continued

Current Candidate Therapeutic Interventions in Development for the Treatment of Pain Related to Inflammation

| Product Name | Chemical Name | Action | Indication |
| --- | --- | --- | --- |
| TK 9C | unspecified | complement inhibitor; NSAID | inflammation |
| CSK 802 | unspecified | corticosteroid | inflammation |
| DM V; DM 5 | unspecified | corticosteroid | inflammation |
| ORG 7258 | unspecified | corticosteroid | inflammation |
| P16CM analogues | unspecified | corticosteroid | inflammation |
| butixocort propionate; JO 1222 | (11 beta)-11-hydroxy-17-(1-oxobutoxy)-21-[(1-oxopropyl)thio]pregn-4-ene-3,20-dione | corticosteroid | inflammation; asthma; inflammatory bowel disease |
| budesonide; budesonide propionate S 1320; PREFERID; PULMICORT; RHINOCORT; ENTOCORT; NARICORT; INFLAMMIDE; BETACTIN; ELTAIR; HORACORT; RHINOCORT AQUA | (11 beta, 16 alpha)-16,17-[butylidenebis(oxy)]-11,21-dihydroxypregna-1,4-diene-3,20-dione | corticosteroid | asthma skin disease; inflammation, rhinitis; ulcerativecolitis; Crohn disease |
| rimexolone; trimexolone; ORG 6216; RIMEXEL; VEXOL | (11 beta, 16 alpha, 17 beta)-11-hydroxy-16,17-dimethyl-17-(1-oxopropyl)androsta-1,4-dien-3-one | corticosteroid | rheumatoid arthritis inflammation; eye disease |
| prednisolone analogue | (11 beta, 16 beta)-11,21-dihydroxy-3,20-dioxo-4'H-pregna-1,4-dieno[16,17-d]isoxazole-3'-carboxylic acid | corticosteroid | inflammation |
| amelometasone; TS 410; CS 830; REONA | (11 beta, 16 beta)-9-fluoro-11-hydroxy-21-methoxy-16-methyl-17-(1-oxopropoxy)pregna-1,4-diene-3,20-dione | corticosteroid | inflammation |
| tipredane; SQ 27239 | (11 beta, 17 alfa)-17-(ethylthio)-9-fluoro-11-hydroxy-17-(methylthio)androsta-1,4-diene-3-one | corticosteroid | inflammation; psoriasis |
| clobetasone butyrate; clobetasone; DE 049; CCI 5537; GR 2/1214; SN 203; CLOBETRON; EUMOVATE; EUMOVATE N KINDABATE; KINDALONE; BUTIDEX | (16 beta)-21-chloro-9-fluoro-16-methyl-17-(1-oxobutoxy)pregna-1,4-diene-3,11,20-trione | corticosteroid | eye disease; inflammation |
| 16-epiestriol; epiestriol | (16 beta, 17.beta)estra-1,3,5(10)-triene-3,16,17-triol | corticosteroid | inflammation |
| ulobetasol propionate; halobetasol propionate; CGP 14458; BMY 30056; ULTRAVATE | (6 alfa, 11 beta, 16 beta)-21-chloro-6,9-difluoro-11-hydroxy-16-methyl-17-(1-oxopropoxy)-pregna-1,4-diene-3,20-dione | corticosteroid | skin disease; inflammation; psoriasis |
| methylprednisolone aceponate; MPA; SH 440; ZK 91588; ADVANTAN | (6 alpha, 11 beta)-21-(acetyloxy)-11-hydroxy-6-methyl-17-(1-oxopropoxy)pregna-1,4-diene-3,20-dione | corticosteroid | inflammation |
| P16CM | 16 alpha-methoxycarbonylprednisolone | corticosteroid | inflammation |
| halopredone; THS 20; THS 201; F2; HALOART; HALOART S | 17 alfa, 21-diacetoxy-2-bromo-6 beta, 9 alfa-difluoro-11 beta-hydroxy-1,4-pregnadiene-3,20-dione | corticosteroid | inflammation |

TABLE 11-continued

Current Candidate Therapeutic Interventions in Development for the Treatment of
Pain Related to Inflammation

| Product Name | Chemical Name | Action | Indication |
|---|---|---|---|
| prednisolone analogue | 21-(acetyloxy)-11-hydroxy-3,20-dioxo-4'H-pregna-1,4-dieno[16,17-d]isoxazole-3'-carboxylic acid ethyl ester | corticosteroid | inflammation |
| compound 3Ae | 21-ethylthio-6 alpha, 9 alpha-difluoro-11 beta-hydroxy-16 alpha, 17 alpha-iso-propylidenedioxy-1,4-pregnadiene-3,20-dione | corticosteroid | inflammation; skin disease |
| methylprednisolone suleptanate; U 67590A; PROMEDROL | (6 alfa, 11 beta)-11,17-dihydroxyl-methyl-21-[[8-[methyl(2-sulfoethyl)amino]-1,8-dioxooctyl]oxy]pregna-1,4-diene-3,20-dione monosodium salt | corticosteroid; immunosuppressant | inflammation; asthma; anaphylactic shock; transplant rejection |
| BIL 93BS; BIL 0093BS | unspecified | COX inhibitor; 5 lipoxygenase inhibitor; NSAID | inflammation |
| anti-inflammatory | 1,2-dihydro-1-oxo-N-2-thiazolylpyrrolo[3,2,1-kl]phenothiazine-2-carboxamide | COX inhibitor; 5 lipoxygenase inhibitor; NSAID | inflammation |
| E 5110 | 3-[[3,5-bis-(1,1-dimethylethyl)4-hydroxyphenyl)methylene]-1-methoxy-2-pyrrolidinone | COX inhibitor; 5 lipoxygenase inhibitor; NSAID | inflammation |
| tepoxalin; RWJ 20485; ORF 20485 | 5-(4-chlorophenyl)-N-hydroxy-1-(4-methoxyphenyl)-N-methyl-1H-pyrazole-3-propanamide | COX inhibitor; 5 lipoxygenase inhibitor; NSAID | asthma; inflammation; inflammatory bowel disease |
| LY 178002 | 5-[[3,5-bis(1,1-dimethylethyl)[4-hydroxyphenyl]methylene]-4-thiazolidinone | COX inhibitor; 5 lipoxygenase inhibitor; NSAID | inflammation; ischemia |
| ML 3000 | 6-(4-chlorophenyl)-2,3-dihydro-2,2-dimethyl-7-phenyl-1H-pyrrolizine-5-acetic acid | COX inhibitor; 5 lipoxygenase inhibitor; NSAID | inflammation |
| meloxicam; UH AC62; UH AC26XX; MOBIC; MOBICOX; MOBEC; MOVALIS; MOVATEC | 4-hydroxy-2-methyl-N-(5-methyl-2-thiazolyl)-2H-1,2-benzothiazine-3-carboxamide 1,1-dioxide | COX inhibitor; analgesic; COX 2 inhibitor; NSAID | rheumatoid arthritis; inflammation; pain; osteoarthritis |
| D 1367 | unspecified | COX inhibitor; analgesic; NSAID | pain; inflammation |
| AHR 10037 | 2-amino-3-(4-chlorobenzoyl)benzene acetamide | COX inhibitor; analgesic; NSAID | inflammation; pain |
| T 614 | N-[3-(formylamino)-4-oxo-6-phenoxy-4H-1-benzopyran-7-yl]-methanesulfonamide | COX inhibitor; analgesic; NSAID; DMARD | inflammation; pain |
| cyclooxygenase inhibitor, Oxis | unspecified | COX inhibitor; antioxidant; NSAID | inflammation |
| BF 389; biofor 389 | 4-[[3,5-bis(1,1-dimethylethyl)-4-hydroxyphenyl]methylene] dihydro-2-methyl-2H-1,2-oxazin-3(4H)-one | COX inhibitor; COX 2 inhibitor; 5 lipoxygenase inhibitor; NSAID | inflammation |
| RWJ 63556 | N-[5-[(4-fluorophenoxy)-2-thienyl]methansulfonamide | COX inhibitor; COX 2 inhibitor; 5 lipoxygenase inhibitor; NSAID | inflammation |
| CT 3 | unspecified | COX inhibitor; COX 2 inhibitor; analgesic; NSAID | pain; inflammation |
| L 748731 | unspecified | COX inhibitor; COX 2 inhibitor; analgesic; NSAID | inflammation |

TABLE 11-continued

Current Candidate Therapeutic Interventions in Development for the Treatment of Pain Related to Inflammation

| Product Name | Chemical Name | Action | Indication |
|---|---|---|---|
| MK 663 | unspecified | COX inhibitor; COX 2 inhibitor; analgesic; NSAID | inflammation; pain |
| JTE 522 | 4-(4-cyclohexyl-2-methyl-5-oxazolyl)-2-fluorobenzenesulfonamide | COX inhibitor; COX 2 inhibitor; analgesic; NSAID | inflammation; pain |
| rofecoxib; MK 966; VIOXX | 4-[4-(methylsulfonyl)phenyl]-3-phenyl-2(5H)-furanone | COX inhibitor; COX 2 inhibitor; analgesic; NSAID | inflammation; rheumatoid arthritis; osteoarthritis; pain; Alzheimer disease |
| NS 398 | N-[2-(cyclohexyloxy)-4-nitrophenyl]methanesulfonamide | COX inhibitor; COX 2 inhibitor; analgesic; NSAID | inflammation; pain |
| L 745337 | N-[6-[(2,4-difluorophenyl)thio]-2,3-dihydro-1-oxo-1H-inden-5-yl]methanesulfonamide | COX inhibitor; COX 2 inhibitor; analgesic; NSAID | pain; inflammation |
| L 752860 | unspecified | COX inhibitor; COX 2 inhibitor; analgesic; NSAID | inflammation; pain |
| COX 2 inhibitors | unspecified | COX inhibitor; COX 2 inhibitor; NSAID | inflammation |
| L 761066 | (R)-1-[(4-bromophenyl)methyl]-5-methoxy-beta,2-dimethyl-1H-indole-3-butanoic acid | COX inhibitor; COX 2 inhibitor; NSAID | inflammation |
| L 768277 | 5-[4-(methylsulfonyl)phenyl]-6-phenylthiazolo[3,2-b][1,2,4]triazole | COX inhibitor; COX 2 inhibitor; NSAID | inflammation |
| BIRL 790 | 6-chloro-4-[(1-methylethyl)sulfonyl]-2-(phenylmethyl)-1,3(2H,4H)-isoquinolinedione | COX inhibitor; COX 2 inhibitor; NSAID | inflammation |
| COX 2 inhibitors | unspecified | COX inhibitor; COX 2 inhibitor; NSAID; analgesic | inflammation; osteoarthritis; pain |
| CGP 31081 | unspecified | COX inhibitor; NSAID | inflammation |
| lornoxicam; chlortenoxicam; Ro 139297; TS 110; CTX; SAFEM; XEFO; LORCAM | 6-chloro-4-hydroxy-2-methyl-N-2-pyridinyl-2H-thieno[2,3-e]-1,2-thiazine-3-carboxamide 1,1-dioxide | COX inhibitor; NSAID; analgesic | inflammation; pain |
| COX 2 inhibitors, SALVAT | unspecified | COX inhibitor; NSAID; COX 2 inhibitor | inflammation |
| trifenagrel; BW 325U | 2-[2-(4,5-diphenyl-1H-imidazole-2-yl)phenoxy]-N,N-dimethylethanamine | COX inhibitor; platelet antiaggregant; NSAID | inflammation; thrombosis |
| nimesulide; R 805; NIM 03, MESULID; AULIN; NIMED; AINEX; NISULID; ESKAFLAM; SCAFLAN; OXETIAN; ANTIFLOXIL; ARLAGIN | N-(4-nitro-2-phenoxyphenyl)methanesulfonamide | COX inhibitor; prostaglandin synthetase inhibitor; COX2 inhibitor; NSAID | inflammation |
| interleukin-4 receptor; IL-4r; NUVANCE | unspecified | cylokine antagonist | inflammation; asthma |
| DoB 0041 | unspecified | cylokine antagonist; biotechnology; NSAID | inflammation |
| DoB 0039 | unspecified | cylokine antagonist; NSAID | inflammation |
| interleukin-1 antagonist; IRAP | unspecified | cylokine antagonist; NSAID | inflammation |
| interferon antagonists, interferon antagonists | unspecified | cylokine antagonist; NSAID | inflammation |
| interleukin-1 antagonist | unspecified | cylokine antagonist; NSAID | inflammation |
| interleukin-6 antagonist | unspecified | cylokine antagonist; NSAID | cachexia; inflammation |

TABLE 11-continued

Current Candidate Therapeutic Interventions in Development for the Treatment of Pain Related to Inflammation

| Product Name | Chemical Name | Action | Indication |
|---|---|---|---|
| interleukin-8 receptor; IL-8r | unspecified | cylokine antagonist; NSAID; immunosuppressant | allergy; inflammation; transplant rejection |
| E 5090 | (Z)-3-[4-(acetyloxy)-5-ethyl-3-methoxy-1-naphthalenyl]-2-methyl-2-propenoic acid | cylokine inhibitor; analgesic; NSAID | inflammation; pain |
| interleukin-B inactivating proteinase; CT 8 | unspecified | cylokine inhibitor; biotechnology; NSAID | respiratory disease; inflammation |
| interleukin-1 inhibitor; IL-1 inhibitor; SEPTANIL | unspecified | cylokine inhibitor; NSAID | inflammation; septic shock |
| CGP 47969A | unspecified | cylokine inhibitor; NSAID | inflammation |
| immunomodulatory cylokine modulator | unspecified | cylokine inhibitor; NSAID | inflammation |
| interleukin-1 inhibitors | unspecified | cylokine inhibitor; NSAID | inflammation; asthma; inflammatory bowel disease |
| interleukin-1 receptor ligands | unspecified | cylokine inhibitor; NSAID | arthritis; inflammation |
| interleukin-8 inhibitors | unspecified | cylokine inhibitor; NSAID | inflammation; cardiovascular disease |
| interleukin-7 receptor; IL-7r | unspecified | cylokine inhibitor; NSAID; immunosuppressant | allergy; inflammation; transplant rejection |
| SeICIDs | unspecified | cylokine inhibitor; NSAID; immunosuppressant; TNF inhibitor; phosphodiesterase inhibitor; phosphodiesterase IV inhibitor | autoimmune disease; inflammation |
| cylokine regulators | unspecified | cylokine synthesis inhibitor; NSAID | inflammation; pigmentation disorder |
| JTE 607 | unspecified | cylokine synthesis inhibitor; NSAID | inflammation |
| SKF 104351 | 2-(4-fluorophenyl)-6,7-dihydro-3-(4-pyridinyl)-5H-pyrrolo[1,2-a]imidazole | cylokine synthesis inhibitor; NSAID | inflammation |
| SKF 86002 | 6-(4-fluorophenyl)-2,3-dihydro-5-(4-pyridinyl)imidazo[2,1-b]thiazole | cylokine synthesis inhibitor; NSAID | inflammation |
| SKF 105809 | 6,7-dihydro-2-[4-(methylsulfinyl)phenyl]-3-(4-pyridinyl)-5H-pyrrolo[1,2-a]imidazole | cylokine synthesis inhibitor; NSAID | inflammation |
| BMY 30094 | N-hydroxybenzenenonanamide | cylokine synthesis inhibitor; NSAID | inflammation; psoriasis |
| CI 959 | 5-methoxy-3-(1-methylethoxy)-N-1H-tetrazol-5-yl-benzo[b]thiophene-2-carboxamide sodium salt | degranulation inhibitor, immunosuppressant NSAID | rhinitis, inflammation; asthma, arthritis |
| eclazolast; RG 2871; REV 2871; RHC 2871 | 2-ethoxyethyl-5-chloro-2-benzoxazolecarboxylate | degranulation inhibitor; NSAID | inflammation |
| prinomide; prinomide tromethamine; CGS 10787; CGS 10787B | alpha-cyano-1-methyl-beta-oxopyrrole-2-propionanilide with 2-amino-2-(hydroxymethyl)-1,3-propanediol | DMARD; analgesic; immunosuppressant; NSAID | inflammation; pain; rheumatoid arthritis |
| LY 243062 | D-1-isopropyl-6-n-propyl-8-beta-methylthiomethylergoline | dopamine agonist; dopamine D2 agonist; NSAID | inflammation |
| MAb, E-selectin | unspecified | E selectin antagonist; monoclonal antibody; NSAID | inflammation |

TABLE 11-continued

Current Candidate Therapeutic Interventions in Development for the Treatment of Pain Related to Inflammation

| Product Name | Chemical Name | Action | Indication |
| --- | --- | --- | --- |
| neutrophil elastase/matrix metalloproteinase inhibitor | unspecified | elastase inhibitor; matrix metalloproteinase inhibitor; proteinase inhibitor; NSAID | inflammation |
| SR 26831 | 5-[(2-chlorophenyl)methyl]-2-(2,2-dimethyl-1-oxopropoxy)4,5,6,7-tetrahydro-5-hydroxythieno[3,2-c]pyridinium | elastase inhibitor; proteinase inhibitor; NSAID | inflammation; emphysema |
| superoxide dismutase manganese complex; Mn-SOD | unspecified | free radical scavenger; NSAID | respiratory disease; inflammation |
| superoxide dismutase, modified; SI 3501 | unspecified | free radical scavenger; NSAID | inflammation |
| sudismase; superoxide dismutase copper zinc complex; CuZnSOD; O x SODrol | N-acetylsuperoxide dismutase (human clone pS 61-10 copper-zinc subunit protein moiety reduced) | free radical scavenger; NSAID | respiratory disease; ischemia; rheumatoid arthritis; inflammation |
| OPC 15161; NF 1616904 | 6-(1H-indol-3-ylmethyl)-5-methoxy-3-(2-methylpropyl)-2-(1H)-pyrazinone, 4-oxide | free radical scavenger; NSAID | inflammation; kidney disease |
| superoxide dismutase manganese complex; hMNSOD | unspecified | free radical scavenger; NSAID; immunosuppressant | ischemia; rheumatoid arthritis; inflammation; reperfusion injury |
| superoxide dismutase variants; SOD | unspecified | free radical scavenger; NSAID; immunosuppressant | inflammation; autoimmune disease; reperfusion injury |
| VB 5122 | unspecified | free radical scavenger; xanthine oxidase inhibitor | inflammation; asthma |
| mipragoside; AGF 44 | [R-[R*,S*-(E)]]-N-[1-[[[O-[N-acetyl-1-(1-methylethyl)-alfa-neuraminosyl]-(2-3)-O-[O-beta-D-galactopyranosyl-(1-3)-2-(acetylamino)-2-deoxy-beta-D-galactopyranosyl-(1-4)-O-beta-D-galactopyranosyl-(1-4)-beta-D-glucopyranosyl]oxy]methyl]-2-hydroxy-3-heptadecenyl]octadecanamide | ganglioside analogue; analgesic; NSAID | inflammation; pain |
| gene therapy, glucocorticomimetic receptor; gene therapy, asthma | unspecified | gene therapy; NSAID | inflammation; asthma |
| inflammatory disease therapy, IL-1 Hy273 | unspecified | gene; biotechnology | inflammation |
| genetic suppressor elements, inflammation | unspecified | Genetic suppression of inflammation | inflammation |
| glucocorticoids | unspecified | glucocorticoid; immunosuppressant; NSAID | inflammation |
| glucocorticoids | unspecified | glucocorticoid; immunosuppressant; NSAID | inflammation; asthma; autoimmune disease |
| loteprednol etabonate; loteprednol; P 5604; HGP 1; CDDD 5604; LOTEMAX; ALREX; LENOXIN | (11 beta, 17 alpha)-17-[(ethoxycarbonyl)oxy]-11-hydroxy-3-oxoandrosta-1,4-diene-17-carboxylic acid chloromethyl ester | glucocorticoid; NSAID | inflammation; conjunctivitis; rhinitis |

TABLE 11-continued

Current Candidate Therapeutic Interventions in Development for the Treatment of Pain Related to Inflammation

| Product Name | Chemical Name | Action | Indication |
|---|---|---|---|
| MY 1250 | 5,6-dihydro-7,8-dimethyl-4,5-dioxo-4H-pyrano[3,2-c]quinoline-2-carboxylic acid | histamine antagonist; histamine H1 antagonist; NSAID | inflammation; allergy |
| CP 331; CP 6 | 1-(4-chlorobenzoyl)-5-methoxy-2-methyl-1H-indole-3-acetic acid 2-[[2-oxo-2-[[3-[3-(1-piperidinylmethyl)phenoxy]propyl]amino]ethyl]o]ethyl ester | histamine antagonist; histamine H2 antagonist; analgesic; NSAID | inflammation; pain |
| dehydroepiandrosterone sulfate; DHEAS; PB 005 | unspecified | hormone; vaccine adjuvant; corticosteroid | inflammation; infectious disease; asthma |
| ICE inhibitors | unspecified | IL-1 beta converting enzyme inhibitor; caspase inhibitor; NSAID | inflammation |
| interleukin-1 beta converting enzyme inhibitors, ICE inhibitors | unspecified | IL-1 beta converting enzyme inhibitor; caspase inhibitor; NSAID | inflammation |
| interleukin-1 converting enzyme inhibitor; ICE-1 inhibitor | unspecified | IL-1 beta converting enzyme inhibitor; caspase inhibitor; NSAID | inflammation; inflammatory bowel disease |
| VE 19512 | unspecified | IL-1 beta converting enzyme inhibitor; caspase inhibitor; NSAID | rheumatoid arthritis; osteoarthritis; inflammation |
| VX 740; HMR 3480 | unspecified | IL-1 beta converting enzyme inhibitor; caspase inhibitor; NSAID | rheumatoid arthritis; osteoarthritis; inflammation |
| GYKI 66114 | N-(ethoxycarbonyl)-L-alanyl-L-tyrosyl-L-valyl-N-[(1S)-2-carboxy-1-formylethyl]-L-alaninamide | IL-1 beta converting enzyme inhibitor; caspase inhibitor; NSAID; peptide | inflammation |
| GYKI 66115 | N-(ethoxycarbonyl)-L-alanyl-L-tyrosyl-L-valyl-N-[(1S)-2-carboxy-1-formylethyl]glycinamide | IL-1 beta converting enzyme inhibitor; caspase inhibitor; NSAID; peptide | inflammation |
| clotrimazole + mometasone; mometasone + clotrimazole; SCH 458 | unspecified | imidazole; corticosteroid; antifungal | mycosis; inflammation |
| anti-inflammatory agents | Unspecified bacterial proteins | Immunomodulation | inflammation |
| acemannan; CARN 1000; CARN 750; CARRASYN; ALIMINASE; VORALEX; CARRAVEX | (1->4), (1->6)-alpha-D-galacto-beta-D-mannan acetate | immunostimulant; cicatrizant | inflammatory bowel disease; skin ulcer; inflammation; cancer |
| immunology/inflammation therapy, Rigel | unspecified | immunosuppressant | inflammation; autoimmune disease; asthma |
| aldose reductase inhibitors | unspecified | immunosuppressant; aldose reductase inhibitor; NSAID | autoimmune disease; allergy; inflammation |
| signal transduction modulators | unspecified | immunosuppressant; immunostimulant; NSAID | autoimmune disease; cancer; inflammation |
| corticotropin releasing factor binding protein; CRF binding protein; NBI 112 | unspecified | immunosuppressant; NSAID | rheumatoid arthritis; inflammation |
| E 21R | unspecified | immunosuppressant; NSAID | cancer; inflammation; allergy |
| leukocyte function associated antigen 3 T cell inhibitor protein; LFA3TIP; LFA3TIP; AMEVIVE | unspecified | immunosuppressant; NSAID | inflammation; autoimmune disease; psoriasis |

TABLE 11-continued

Current Candidate Therapeutic Interventions in Development for the Treatment of Pain Related to Inflammation

| Product Name | Chemical Name | Action | Indication |
| --- | --- | --- | --- |
| LFA-1 alpha subunit; leukocyte function associated antigen-1 alpha subunit; leukocyte cell surface adhesion receptor molecule | unspecified | immunosuppressant; NSAID | inflammation |
| MAb, CD40 ligand; 5C8; ANTOVA | unspecified | immunosuppressant; NSAID | inflammation; systemic lupus erylhematosus; multiple sclerosis |
| OX40-based immunotherapy, Cantab | unspecified | immunosuppressant; NSAID | inflammation; autoimmune disease |
| BN 58705 | unspecified | immunosuppressant; NSAID | septic shock; inflammation |
| BW 91Y78 | unspecified | immunosuppressant; NSAID | inflammation |
| CD4 inhibitors | unspecified | immunosuppressant; NSAID | inflammation |
| inflammation therapy | unspecified | immunosuppressant; NSAID | inflammatory bowel disease; inflammation; autoimmune disease |
| Ro 236457 | unspecified | immunosuppressant; NSAID | inflammation |
| phellodendrine; OB 5 | (7S-cis)-5,8,13,13a-tetrahydro-2,11-dihydroxy-3,10-dimethoxy-7-methyl-6H-dibenzo[a,g]quinolizinium | immunosuppressant; NSAID | transplant rejection; inflammation; viral infection; asthma; kidney disease |
| TEI 1338 | (E)-N-(2-methoxycarbonylphenyl)-8-(2-naphthyl)-5,6-trans-5,6-methano-7-octenamide | immunosuppressant; NSAID | allergy; inflammation |
| TEI 3332 | [(6,7-dihydroxy-2-naphthalenyl)thio]acetic acid methyl ester | immunosuppressant; NSAID | allergy; inflammation |
| KB 2683 | 2-(4-methylphenyl)-4-benzothiazolol acetate | immunosuppressant; NSAID | rheumatoid arthritis; inflammation; autoimmune disease |
| albifylline; HWA 138 | 3,7-dihydro-1-(5-hydroxy-5-methylhexyl)-3-methyl-1H-purine-2,6-dione | immunosuppressant; NSAID | septic shock; inflammation |
| celastrol | unspecified | immunosuppressant; NSAID; terpene | inflammation |
| CD45 inhibitors | unspecified | immunosuppressant; NSAID; tyrosine phosphatase inhibitor | transplant rejection; inflammation |
| potassium channel blocker | unspecified | immunosuppressant potassium channel blocker | autoimmune disease; allergy, inflammation |
| fusion protein, CD5-gelonin; CD5-gelonin T lymphocyte-targeted immunofusion protein; GENIMUNE | unspecified | immunotoxin; NSAID | rheumatoid arthritis; inflammation |
| MAb, B11; MAb, E-selectin; MAb, endothelium leukocyte adhesion molecule | unspecified | integrin antagonist; biotechnology; immunosuppressant; monoclonal antibody; E selectin antagonist; cell adhesion inhibitor; NSAID | inflammation |
| MAb, selectin; CY 1788; CY 1787 | unspecified | integrin antagonist; biotechnology; monoclonal antibody; E selectin antagonist; cell adhesion inhibitor; NSAID | inflammation; septic shock; rhinitis |
| MAb, L-selectin, human | unspecified | integrin antagonist; biotechnology; monoclonal antibody; L selectin antagonist; cell adhesion inhibitor; NSAID | inflammation anaphylactic shock |

TABLE 11-continued

Current Candidate Therapeutic Interventions in Development for the Treatment of Pain Related to Inflammation

| Product Name | Chemical Name | Action | Indication |
|---|---|---|---|
| GM 1676 | unspecified | integrin antagonist; cell adhesion inhibitor; immunosuppressant; NSAID | inflammation |
| neutrophil inhibitory factor; NIF; CORLEUKIN NIF | unspecified | integrin antagonist; cell adhesion inhibitor; NSAID | reperfusion injury; inflammation; stroke |
| anti-inflammatory agents | unspecified | integrin antagonist; cell adhesion inhibitor; NSAID | inflammation; cancer |
| cell adhesion antagonist,cell adhesion antagonist, | unspecified | integrin antagonist; cell adhesion inhibitor; NSAID | inflammation |
| cell adhesion inhibitor | unspecified | integrin antagonist; cell adhesion inhibitor; NSAID | inflammation; allergy |
| cell adhesion inhibitor | unspecified | integrin antagonist; cell adhesion inhibitor; NSAID | cancer; inflammation |
| drug delivery system, STEALTH cell adhesion inhibitors | unspecified | integrin antagonist; cell adhesion inhibitor; NSAID | cancer; inflammation |
| E-selectin inhibitors | unspecified | integrin antagonist; cell adhesion inhibitor; NSAID | inflammation |
| GM 1606 | unspecified | integrin antagonist; cell adhesion inhibitor; NSAID | inflammation |
| GM 1925 | unspecified | integrin antagonist; cell adhesion inhibitor; NSAID | inflammation |
| GM 1986 | unspecified | integrin antagonist; cell adhesion inhibitor; NSAID | inflammation |
| GM 1998 | unspecified | integer antagonist; cell adhesion inhibitor; NSAID | inflammation; respiratory distress syndrome; heart ischemia; reperfusion injury |
| GM 2296 | unspecified | integrin antagonist; cell adhesion inhibitor; NSAID | inflammation; respiratory distress syndrome |
| GM 7050 | unspecified | integrin antagonist; cell adhesion inhibitor; NSAID | inflammation; cancer |
| VCAM-1 inhibitors | unspecified | integrin antagonist; cell adhesion inhibitor; NSAID | inflammation |
| cell adhesion inhibitors | unspecified | integrin antagonist; cell adhesion inhibitor selectin antagonist; NSAID | inflammation |
| L-selectin inhibitors | unspecified | integrin antagonist; L selectin antagonist; cell adhesion inhibitor NSAID | inflammation |
| NE 1704 | unspecified | integrin antagonist; oligosaccharide; E selectin antagonist; cell adhesion inhibitor; NSAID | inflammation |
| P-selectin inhibitors | unspecified | integrin antagonist; P selectin antagonist; cell adhesion inhibitor; NSAID | inflammation |
| selectin antagonists | unspecified | integrin antagonist; P selectin antagonist; immunosuppressant; cell adhesion inhibitor; NSAID | inflammation |

TABLE 11-continued

Current Candidate Therapeutic Interventions in Development for the Treatment of Pain Related to Inflammation

| Product Name | Chemical Name | Action | Indication |
|---|---|---|---|
| CEN 100 | unspecified | integrin antagonist; peptide; P selectin antagonist; cell adhesion inhibitor; NSAID | ischemia; inflammation; repenfusion injury |
| low molecular weight selectin inhibitors | unspecified | integrin antagonist; selectin antagonist; immunosuppressant; cell adhesion inhibitor; NSAID | inflammation; allergy |
| TBC 1269 | 3',3'''-(1,6-hexanediyl)bis[6-(alpha-D-mannopyranosyloxy)-[1,1'-biphenyl]-3-acetic acid | integrin antagonist; selectin antagonist; immunosuppressant, cell adhesion inhibitor; NSAID | inflammation; asthma |
| EPI KAL2 | unspecified | kallikrein inhibitor; biotechnology | inflammation |
| PKSI 527 | [1(S)-trans]-4-[[2-[[[4-(aminomethyl)cyclohexyl]carbonyl)amino]-1-oxo-3-phenylpropyl]amino]benzene-acetic acid monohydrochloride | kallikrein inhibitor; NSAID | septic shock; inflammation; thrombosis |
| leukocyte adhesion inhibitors | unspecified | leukocyte adhesion inhibitor; NSAID | inflammation; cardiac therapy |
| moxilubant; CGS 25019; CGS 25019C | 4-[5-[4-(aminoiminomethyl)phenoxy]pentyl]oxy]-3-methoxy-N,N-bis(1-methylethyl)benzamide | leukotriene antagonist; leukotriene B4 antagonist; NSAID | inflammation |
| ZD 3523; ICI D3523 | unspecified | leukotriene antagonist; NSAID | asthma; inflammation |
| RP 66153 | unspecified | leukotriene B4 antagonist; leukotriene antagonist; NSAID | inflammation |
| WF 11605 | (1S,1R,4a5,6aR,8R,9R,10aS, 12aS)-9-acetoxy-2-((R)-1,2dimethylpropyl)-8-(beta-D-glucopyranosyl)oxy-1,2,3,4,4a,5,6,6a,7,8,9,10,10a,11,12,12a-hexadecahydro-2,4a,7,7,10a,12a,hexa methyl-3-oxochrysene-1-carboxylic acid | leukotriene B4 antagonist; leukotriene antagonist; NSAID | hepatitis; inflammation; psoriasis |
| SB 201993 | (E)-3-[[[[6-(2-carboxyethenyl)-5-[[8-(4-methoxyphenyl)octyl]oxy]-2-pyridinyl]methyl)thio]methyl]benzoic acid | leukotriene B4 antagonist; leukotriene antagonist; NSAID | psoriasis; inflammation |
| SB 201146 | (E)-3-[6-[[(3-aminophenyl)sulfinyl]methyl]-3-[[8-(4-methoxyphenyl)octyl]oxy]-2-pyridinyl]-2-propenoic acid | leukotriene B4 antagonist; leukotriene antagonist; NSAID | inflammation |
| ticolubant; SB 209247 | (E)-3-[6-[[2,6-dichlorophenyl)thio]methyl]-3-(2-phenylethoxy)-2-pyridinyl]-2-propenoic acid | leukotriene B4 antagonist; leukotriene antagonist; NSAID | inflammation; psoriasis |
| LY 255283 | 1-[5-ethyl-2-hydroxy-4-[[6-methyl-6-(1H-tetrazol-5-yl)heptyl]oxy]phenyl]ethanone | leukotriene B4 antagonist; leukotriene antagonist; NSAID | inflammation |

TABLE 11-continued

Current Candidate Therapeutic Interventions in Development for the Treatment of Pain Related to Inflammation

| Product Name | Chemical Name | Action | Indication |
|---|---|---|---|
| PF 10042 | 1-[5-hydroxy-5-[8-(1-hydroxy-2-phenylethyl)-2-dibenzofuranyl]-1-oxopentyl]pyrrolidine | leukotriene B4 antagonist; leukotriene antagonist; NSAID | inflammation |
| RP 64966 | 2-((4-(5-(3-phenylpropyl)-2-thienyl)butyl)oxy)acetic acid (sodium salt) | leukotriene B4 antagonist; leukotriene antagonist; NSAID | inflammation; psoriasis; inflammatory bowel disease |
| RG 14893 | 4-(2-(methyl(2-phenethyl)amino)-2-oxoethyl)-8-(phenylmethoxy)-2-naphthalenecarboxylic acid | leukotriene B4 antagonist; leukotriene antagonist; NSAID | asthma; inflammation |
| LY 213024 | 5-(3-carboxybenzoyl)-2-(decyloxy)benzenepropanoic acid | leukotriene B4 antagonist; leukotriene antagonist; NSAID | inflammation |
| SC 50605 | 7-[3-[2(cyclopropylmethyl)-3-methoxy-4-(4-thiazolyl)phenoxy]propoxy]-3,4-dihydro-8-propyl-2H-1-benzopyran-2-carboxylic acid | leukotriene B4 antagonist; leukotriene antagonist; NSAID | psoriasis; inflammation |
| LY 264086 | 7-carboxy-3-(decyloxy)-9-oxo-9H-xanthene-4-propanoic acid | leukotriene B4 antagonist; leukotriene antagonist; NSAID | inflammation |
| LY 210073 | Unspecified | leukotriene B4 antagonist; leukotriene antagonist; NSAID | inflammation |
| WAY 121006 trom | 3-fluoro-4'-(2-quinolinylmethoxy)-[1,1'-biphenyl]-4-acetic acid | leukotriene B4 antagonist; leukotriene D4 antagonist; leukotriene antagonist; NSAID | inflammation |
| macrophage chemotaxin inhibitor | unspecified | macrophage inhibitor; NSAID | inflammation; cardiovascular disease |
| S 3304 | unspecified | matrix metalloproteinase inhibitor; proteinase inhibitor | cancer; inflammation |
| CH 104 | unspecified | matrix metalloproteinase inhibitor; proteinase inhibitor; NSAID | cancer inflammation |
| CH 715 | unspecified | matrix metalloproteinase inhibitor; proteinase inhibitor; NSAID | cancer; inflammation |
| PI 88 | unspecified | matrix metalloproteinase inhibitor; proteinase inhibitor; NSAID | inflammation; cancer |
| PGE 2946979 | 3-[(hydroxyamino)carbonyl]-4-[(4-methoxyphenyl)sulfonyl]-1-piperazinecarboxylic acid phenylmethyl ester | metalloproteinase inhibitor; proteinase inhibitor | inflammation; cancer |
| TNF alpha converting enzyme inhibitors, TACE inhibitors | unspecified | metalloproteinase inhibitor; proteinase inhibitor; NSAID | rheumatoid arthritis; inflammation |
| MAb, inflammation | unspecified | monoclonal antibody | inflammation |
| MAb, interleukin-8; MAb, IL-8; ABX 1L8 | unspecified | monoclonal antibody; biotechnology; NSAID | respiratory distress syndrome; inflammatory bowel disease; rheumatoid arthritis; inflammation; psoriasis |
| MAb, inflammation therapy, LeukoSite/MorphoSys | unspecified | monoclonal antibody; immunosuppressant | inflammation; autoimmune disease |
| MAb, cadherin | unspecified | monoclonal antibody; NSAID | inflammation |

TABLE 11-continued

Current Candidate Therapeutic Interventions in Development for the Treatment of Pain Related to Inflammation

| Product Name | Chemical Name | Action | Indication |
|---|---|---|---|
| MAb, CD11a | unspecified | monoclonal antibody; NSAID | inflammation |
| MAb, CD11b; MAb, m60,1; m60.1; LY 303932 | unspecified | monoclonal antibody; NSAID | inflammation; heart ischemia; reperfusion injury |
| MAb, CD11b | unspecified | monoclonal antibody; NSAID | inflammation |
| MAb, CD18 | unspecified | monoclonal antibody; NSAID | inflammation |
| MAb, CD18, humanized; SMART anti-CD18 | unspecified | monoclonal antibody; NSAID | inflammation |
| MAb, humanized tumor necrosis factor; MAb, humanized TNF; MAb, CDP571; CDP 571; BAY 103356; B 1351 | unspecified | monoclonal antibody; NSAID | septic shock; inflammation; bacterial infection; inflammatory bowel disease; rheumatoid arthritis |
| MAb, interferon alfa; MAb, IFN-alfa | unspecified | monoclonal antibody; NSAID | inflammation |
| MAb, interleukin-8, Medarex | unspecified | monoclonal antibody; NSAID | inflammation |
| MAb, T cells; MAb, rheumatoid arthritis | unspecified | monoclonal antibody; NSAID | inflammation |
| MAb, tumor necrosis factor-alpha, human; D2E7; LU 200,134 | unspecified | monoclonal antibody, NSAID | inflammation |
| MAb, VLA-4, humanized; MAb, very late antigen-4, humanized | unspecified | monoclonal antibody; NSAID | inflammation rheumatoid arthritis; asthma; diabetes |
| MAb, monocyte chemoattractant protein-1 receptor; MAbs, MCP-1 receptor | unspecified | monoclonal antibody; NSAID; chemokine antagonist | inflammation |
| MAb, B7; MAb, PRIMATIZED B7; IDEC 114 | unspecified | monoclonal antibody; NSAID; immunosuppressant | systemic lupus erylhematosus; inflammation; transplant rejection; psoriasis |
| leishmania lipophosphoglycan | leishmania lipophosphoglycan | Monocyle recruitment blockade | inflammation; restenosis |
| antisense oligonucleotide, interleukin-1 beta; antisense oligonucleotide, IL-1 beta | unspecified | mRNA translation inhibitor; antisense; oligonucleotide | inflammation |
| L 733060 | (2S-cis)-3-[[3,5-bis(trifluoromethyl)phenyl]methoxy]-2-phenylpiperidine | neurokinin antagonist; analgesic; neurokinin 1 antagonist; NSAID | inflammation; pain; asthma |
| CP 96345 | (2S,3S)-cis-2-(diphenylmethyl)-N-[(2-methoxyphenyl)methyl]-1-azabicyclo[2.2.2]octan-3-amine | neurokinin antagonist; analgesic; neurokinin 1 antagonist; NSAID; substance P antagonist | inflammation; pruritis; pain |
| neurokinin antagonists | unspecified | neurokinin antagonist; analgesic; NSAID | pain; inflammation |
| nolpitantium besilate; SR 140333 | (S) 1-[2-[3-(3,4-dichlorophenyl)-1-[[3-(1-methylethoxy)phenyl]ac e tyl]-3-piperidinyl]ethyl]-4-phenyl-1-azoniabicyclo[2.2.2]octane | neurokinin antagonist; NSAID neurokinin 1 antagonist; | asthma; inflammation |
| L 737488 | (S)-N-[4-[3,5-bis(trifluoromethyl)phenyl)-1-(1H-indol-3-ylmethyl)-2-oxobutyl]-1-azabicyclo[2.2.2]octane-4-carboxamide monohydrochloride | neurokinin antagonist; neurokinin 1 antagonist; NSAID | inflammation |

TABLE 11-continued

Current Candidate Therapeutic Interventions in Development for the Treatment of Pain Related to Inflammation

| Product Name | Chemical Name | Action | Indication |
|---|---|---|---|
| FK 224; FR 115224 | N-[N2-[N-[N-[N-[alfa, beta-didehydro-N-methyl-N-[N-[1-oxo-3-(2-pentylphenyl)propyl]-L-threonyl]tyrosyl]-L-leucyl]-D-phenylalanyl]-L-allothreonyl]-L-asparaginyl]-L-serine upsilon-lactone | neurokinin antagonist neurokinin 2 antagonist, NSAID | asthma, inflammation |
| NS 2073 | unspecified | nitric oxide activator; NSAID | inflammation; glaucoma; gastrointestinal ulcer; asthma |
| NS 2028 | unspecified | nitric oxide inhibitor; NSAID | inflammation |
| NOS inhibitor | unspecified | nitric oxide synthase inhibitor; NSAID | neurological; inflammation |
| inflammatory disease therapy, | unspecified | NSAID | inflammation |
| compinact A | unspecified | NSAID | inflammation |
| compinact C | unspecified | NSAID | inflammation |
| GELIN | unspecified | NSAID | inflammation |
| TSG 6 | unspecified | NSAID | inflammation |
| acute inflammation therapy | unspecified | NSAID | inflammation |
| adenosine kinase inhibitors, inflammation | unspecified | NSAID | inflammation |
| anchoring protein modulators | unspecified | NSAID | inflammation |
| anti-inflammatory agent | unspecified | NSAID | inflammation; asthma |
| anti-inflammatory agents | unspecified | NSAID | inflammation |
| anti-inflammatory agents | unspecified | NSAID | inflammation |
| anti-inflammatory agents | unspecified | NSAID | inflammation |
| anti-inflammatory agents | unspecified | NSAID | inflammation |
| anti-inflammatory agents | unspecified | NSAID | inflammation |
| anti-inflammatory, Pharmacopeia; anti-inflammatory | unspecified | NSAID | inflammation |
| anti-inflammatory, anti-inflammatory | unspecified | NSAID | inflammation |
| anti-inflammatory, transcription factors | unspecified | NSAID | inflammation |
| anti-inflammatory | unspecified | NSAID | inflammation |
| APC 1024 | unspecified | NSAID | inflammation |
| APC 1070 | unspecified | NSAID | inflammation |
| APC 1132 | unspecified | NSAID | inflammation |
| APC 1134 | unspecified | NSAID | inflammation |
| APC 1390 | unspecified | NSAID | inflammation |
| bradykinin receptor modulators, Pharmacopeia | unspecified | NSAID | inflammation |
| C5a inhibitors | unspecified | NSAID | inflammation; cardiovascular disease |
| CD40 receptor signalling pathway inhibitor; CD40 receptor signalling pathway inhibitor | unspecified | NSAID | allergy; asthma; inflammation |
| cell adhesion molecules intracellular inhibitors | unspecified | NSAID | cancer; inflammation |
| chemokine receptor modulators | unspecified | NSAID | inflammation; asthma; atherosclerosis |
| CPH 82; REUMACON; COMIHOG | unspecified | NSAID | inflammation; Alzheimer disease |
| D 20207 | unspecified | NSAID | inflammation; respiratory disease |

TABLE 11-continued

Current Candidate Therapeutic Interventions in Development for the Treatment of Pain Related to Inflammation

| Product Name | Chemical Name | Action | Indication |
| --- | --- | --- | --- |
| diclofenac digoil; F 5402M | unspecified | NSAID | inflammation |
| drug delivery system, diclofenac; diclofenac PULSINCAP | unspecified | NSAID | inflammation |
| drug delivery system, DIFFUCAP diclofenac; diclofenac DIFFUCAP; DICLOMAX | unspecified | NSAID | inflammation |
| drug delivery system, diclofenac; diclofenac; ISV 205 | unspecified | NSAID | glaucoma; inflammation |
| drug delivery system, GEOMATRIX controlled release ketoprofen; ketoprofen GEOMATRIX | unspecified | NSAID | inflammation |
| drug delivery system, NSAIDs; ENTEROTEC | unspecified | NSAID | inflammation |
| drug delivery system, submicron emulsion diclofenac; diclofenac SME | unspecified | NSAID | inflammation |
| drug discovery | unspecified | NSAID | inflammation; diabetes; cardiovascular disease neurological; cancer; infectious disease |
| EN 03 | unspecified | NSAID | inflammation |
| G-protein antagonist | unspecified | NSAID | inflammation; cardiovascular disease; neurological |
| G-protein therapy | unspecified | NSAID | inflammation; cardiovascular disease; cancer |
| gene discovery, inflammatory diseases | unspecified | NSAID | inflammation; rheumatoid arthritis |
| gene discovery, oxidative stress pathways | unspecified | NSAID | neurological; inflammation |
| glucocorticoid agonists | unspecified | NSAID | inflammation; rheumatoid arthritis; inflammatory bowel disease; asthma |
| GM 7072 | unspecified | NSAID | inflammation |
| ICAM-1 inhibitors, intracellular adhesion molecule-1 inhibitors | unspecified | NSAID | inflammation |
| ICR 18 | unspecified | NSAID | inflammation |
| IL-8 receptor modulators | unspecified | NSAID | inflammation |
| inflammatory disease therapy | unspecified | NSAID | inflammation |
| interleukin modulators | unspecified | NSAID | inflammation; asthma |
| interleukin-8 receptor antagonists | unspecified | NSAID | inflammation |
| IPL 576; IZP 94005 | unspecified | NSAID | psoriasis; allergy; inflammation |
| kinase modulators | unspecified | NSAID | cancer; inflammation |
| leucomyzin | unspecified | NSAID | inflammation hyperlipidemia |
| LG 21101 | unspecified | NSAID | inflammation; multiple sclerosis |
| major histocompatibility complex II, ligand, MHC II ligand | unspecified | NSAID | allergy; inflammation |
| MN 10021 | unspecified | NSAID | inflammation |
| p38 kinase modulators | unspecified | NSAID | inflammation |
| PG CC8 | unspecified | NSAID | eye disease; inflammation |
| phosphosugar anti-inflammatory agent | unspecified | NSAID | inflammation |
| sialophorin chimeric molecules | unspecified | NSAID | inflammation |

TABLE 11-continued

Current Candidate Therapeutic Interventions in Development for the Treatment of Pain Related to Inflammation

| Product Name | Chemical Name | Action | Indication |
|---|---|---|---|
| signal transduction modulators | unspecified | NSAID | cancer; inflammation; neurological |
| SR 129 | unspecified | NSAID | inflammation |
| SR 318B; SR 318 | unspecified | NSAID | inflammation |
| synthetic glycosaminoglycans | unspecified | NSAID | inflammation; cancer; neuropathy |
| TNF alpha proteinase inhibitor; TAPI | unspecified | NSAID | inflammation |
| white blood cell migration inhibitors | unspecified | NSAID | inflammation; multiple sclerosis |
| ketoprofen, (R)-; (R)-ketoprofen | (R)-3-benzoyl-alpha-methylbenzeneacetic acid | NSAID | inflammation |
| limazocic; SA 3443 | (R)-hexahydro-7,7-dimethyl-6-oxo-1,2,5-dithiazocine-4-carboxylic acid | NSAID | liver disease; inflammation; emphysema; intoxication |
| dexketoprofen; ketoprofen, (S)-; (S)-ketoprofen | (S)-3-benzoyl-alpha-methylbenzeneacetic acid | NSAID | inflammation |
| tioxamast; F 1865 | [[4-(4-methoxyphenyl)-2-thiazolyl]amino]oxoacetic acid ethyl ester | NSAID | asthma; inflammation; skin disease |
| U 91502 | [3-(1,6-dihydro-1-methyl-6-oxo-4-phenyl-2-pyrimidinyl)propylidene]bisphosphonic acid tetraethyl ester | NSAID | inflammation; arthritis |
| AO 1535 | [R*[R*,S*-(E)]]-N-[1-[(beta-D-galactopyranosyfoxy)methyl]-2-hydroxy-3-heptadecenyl]-3-pyridinecarboxamide | NSAID | skin disease; inflammation |
| DUP 983 | 1-(4-(4-pyridyl)phenyl)-1-(4-fluorophenyl)-2-imidazolyl-1-ethanol | NSAID | inflammation |
| acemetacin; TV 1322; TVX 1322; K 708; BAY F 4975; ANAGEL; FLAMARION; MOSTANOL; OLDAN; RANTUDIL; RANTUDAL; RUCATEN; SPORTIX; TILUR | 1-(4-chlorbenzoyl)-5-methoxy-2-methylindole-3-acetic acid ester with glycolic acid | NSAID | inflammation |
| tropesin; indometacin tropine ester; tropine indometacinate; VUFB 12018; REPANIDAL | 1-(4-chlorobenzoyl)-5-methoxy-2-methyl-1H-indole-3-acetic acid 2-carboxy-2-phenylethyl ester | NSAID | inflammation |
| indometacin farnesil; indomethacin farnesyl; IM-F; E 0710; E 710; INFREE | 1-(4-chlorobenzoyl)-5-methoxy-2-methyl-1H-indole-3-acetic acid, 3,7,11-trimethyl-2,6,10-dodecatrienyl ester | NSAID | inflammation |
| anti-inflammatory | 1-(4-chlorophenyl)-1,3-dihydro-3,3-dimethyl-2H-pyrrolo(2,3-b)pyridine-2-one | NSAID | inflammation |
| tebufelone; NE 11740 | 1-[3,5-bis(1,1-dimethylethyl)-4-hydroxyphenyl]-5-hexyn-1-one | NSAID | inflammation |
| bermoprofen; AD 1590; DIBENON | 10,11-dihydro-alfa,8-dimethyl-11-oxodibenz[b,f]oxepin-2 acetic acid | NSAID | inflammation |
| zaltoprofen; CN 100; ZC 102; SOLETON; PEON | 10,11-dihydro-alpha-methyl-10-oxodibenzo[b,f]thiepin-2-acetic acid | NSAID | inflammation; respiratory disease |

TABLE 11-continued

Current Candidate Therapeutic Interventions in Development for the Treatment of Pain Related to Inflammation

| Product Name | Chemical Name | Action | Indication |
|---|---|---|---|
| YT 1 | 2-phenyl-4(1H)-quinolone | NSAID | inflammation |
| lonazolac; SNK 874; ARTHROAKUT; IRRITREN | 3-(4-chlorophenyl)-1-phenyl-1H-pyrazole-4-acetic acid | NSAID | inflammation |
| HWA 131 | 3-[3,5-bis(1,1-dimethylethyl)4-hydroxyphenyl]-7H-thiazolol-[3,2-b][1,2,4]triazin-7-one | NSAID | inflammation |
| KF 18280 | 3-benzyl-5-phenyl-3H-imidazo(4,5-c)(1,8)naphthyrin-4(5H)-one | NSAID | inflammation |
| piroxicam cinnamate; SPA A510; SPA S510; CINNOXICAM; SINARTROL | 3-phenyl-propenoic acid, 2-methyl-3-[(2-pyridinylamino)-carbonyl]-2H-1,2-benzothiazin-4-yl ester, S,S-dioxide | NSAID | inflammation |
| eltenac; B 78820 | 4-(2,6-dichloroanilino)-3-thiopheneacetic acid | NSAID | inflammation |
| oxaprozin; WY 21743; DAYPRO; ACTIRIN; DURAPRO; DURAPROX; DAXPROZIN | 4,5-diphenyl-2-oxazolepropanoic acid | NSAID | inflammation |
| anti-inflammatory | 4-[(2-aminoethyl)amino]-1-(2-thienyl)-1-butanone | NSAID | inflammation |
| ximoprofen; XIFAM | 4-[3-(hydroxyimino)cyclohexyl]-alpha methylbenzeneacetic acid | NSAID | inflammation |
| FK 3311 | 4'acetyl-2'-[2,4-difluorophenoxy]methane sulfonanilide | NSAID | inflammation |
| tenoxicam; Ro 12 0068; LIMAN; MITROTIL; TILCOTIL | 4-hydroxy-2-methyl-N-2-pyridyl-2H-thieno[2,3-e]-1,2-thiazine-3-carboxamide 1,1-dioxide | NSAID | inflammation |
| anti-inflammatory | 4-propylthio-o-anisidine | NSAID | inflammation |
| DUP 697 | 5-bromo-2-(4-fluorophenyl)-3-[4-(methylsulfonyl)phenyl)4-[(4-]thiophene | NSAID | inflammation |
| PD 144795 | 5-methoxy-3-(1-methylethoxy)-benzo[b]thiophene-2-carboxamide 1-oxide | NSAID | inflammation |
| droxicam; E 3128; OMBOLAN; FERPAN; DROGELON; PRECAM; DROBENAM; DROXAR | 5-methyl-3-(2-pyridyl)-2H,5H-1,3-oxazino[5,6-c][1,2]benzothiazine-2,4(3H)-dione-6,6-dioxide | NSAID | inflammation |
| decasilate | 8-(2-phenylethyl)-1-oxa-diazaspiro[4.5]decan-2-one compound with 2-thiophenecarboxylic acid (1:1) | NSAID | allergy; inflammation |
| ibuprofen guaiacol; methoxybutropate; metoxybutropate; AF 2259; BENFLOGIN; BELEP | alpha-methyl-4-(2-methylpropyl)benzeneacetic acid 2-methoxyphenyl ester | NSAID | inflammation |
| ampiroxicam; CP 65703; FLUCAM; NACYL | ethyl 1-[[2-methyl-3-[(2-pyridinylamino)carbonyl]-2H-1,2-benzothiazin-4-yl]oxy] ethyl ester S,S-dioxide carbonic acid | NSAID | inflammation |

TABLE 11-continued

Current Candidate Therapeutic Interventions in Development for the Treatment of Pain Related to Inflammation

| Product Name | Chemical Name | Action | Indication |
| --- | --- | --- | --- |
| Z 1957 | ethyl N-((3-methyl-5-isoxazolyl)-2-thiazolyl)oxamate | NSAID | asthma; inflammation |
| adelmidrol; LG 21301 | N,N'-bis(2-hydroxyethyl)nonanediamide | NSAID | inflammation; acne |
| andolast; CR 2039 | NA-(5-tetrazolyl)-phenyl-4-(5-tetrazolyl)-benzamide | NSAID allergy | asthma; inflammation; |
| salnacedin; G 201; SCY | N-acetyl-L-cysteine 2-hydroxybenzoate | NSAID disease | inflammation; skin |
| diclofenac potassium; CGP 45840B; CATAFLAM; CATAFLAN; DICLOFEN; VOLTAREN | potassium (o-(2,6-dichloroanilino)-phenyl)acetate | NSAID | inflammation; migraine; surgery |
| glucocorticoid receptor agonists, | unspecified | NSAID, glucocorticoid agonists | inflammation |
| CHF 2003 | unspecified | NSAID; analgesic | pain; inflammation |
| drug delivery system, HIT diclofenac; diclofenac HIT; HYAL AT2101; HYAL CT1101; HYAL AV2201; HYAL AT1201; HYANALGESE; HYANALGESE-D; SOLARASE; ORALEASE | unspecified | NSAID; analgesic | pain; cancer; inflammation; skin disease; mucositis |
| drug delivery system, HIT ibuprofen; ibuprofen HIT; HYAL AT2102 | unspecified | NSAID; analgesic | inflammation; pain |
| drug delivery system, HIT piroxicam; piroxicam HIT; HYAL AT2103 | unspecified | NSAID; analgesic | inflammation; pain |
| drug delivery system, IPDAS ketoprofen; ketoprofen IPDAS; KETELAN | unspecified | NSAID; analgesic | inflammation; pain |
| drug delivery system, naproxen; naproxen, sustained refease; IPDAS naproxen; NAPROLEN; NAPRELAN | unspecified | NSAID; analgesic | inflammation; pain |
| drug delivery system, oral transmucosal piroxicam; piroxicam oral transmucosal | unspecified | NSAID; analgesic | inflammation; pain |
| drug delivery system, transdermal diclofenac | unspecified | NSAID; analgesic | pain; inflammation |
| drug delivery system, transdermal fenoprofen; fenoprofen transdermal | unspecified | NSAID; analgesic | pain; inflammation |
| drug delivery system, transdermal flurbiprofen | unspecified | NSAID; analgesic | pain; inflammation |
| drug delivery system, transdermal ketoprofen | unspecified | NSAID; analgesic | inflammation; pain |
| drug delivery system, transdermal piroxicam; piroxicam transdermal | unspecified | NSAID; analgesic | pain; inflammation |
| polyunsaturated fatty acids, PUFA | unspecified | NSAID; analgesic | inflammation; pain |
| tilnoprofen arbamel; Y 23023 | (+/−)-alpha-2-methyl-5H-[1]benzopyran[2,3-b]pyridine-7-acetic acid, 2-(dimethylamino)-2-oxoethyl ester | NSAID; analgesic | inflammation; pain |

TABLE 11-continued

Current Candidate Therapeutic Interventions in Development for the Treatment of Pain Related to Inflammation

| Product Name | Chemical Name | Action | Indication |
|---|---|---|---|
| dexketoprofen trometamol; LM 1158.TRIS; D 1158; ENANTYUM; QUIRALAM; KETESSE | (S)-3-benzoyl-alpha-methylbenzeneacetic acid cpd with 2-amino-2-(hydroxymethyl)-1,3-propanediol (1:1) | NSAID; analgesic | pain; inflammation |
| florifenine; FI 2522 | 2-(1-pyrrolidinyl)ethyl-N-[7-(trifluoromethyl)-4-quinolyl]anthranilate | NSAID; analgesic | inflammation; pain |
| aceclofenac; YT 919 AIRTAL; GERBIN, FALCOL; BRISTAFLAM; PRESERVEX; BIOFENAC; BARRACAN | 2-[(2,6-dichlorophenyl)amino]benzeneacetic acid, carboxymethyl ester | NSAID; analgesic | pain, inflammation |
| bromfenac; bromfenac sodium; AHR 10282; DURACT | 2-amino-3-(4-bromobenzoyl)benzene acetic acid | NSAID; analgesic | inflammation; pain |
| mofezolac; N 22; DISOPAIN | 3,4-bis(4-methoxyphenyl)-5-isoxazoleacetic acid | NSAID; analgesic | inflammation; pain |
| nabumetone; BRL 14777; RELIFEN; RELIFEX; LISTRAN; PRODAG; BALMOX; NABUMETON; RELAFEN | 4-(6-methoxy-2-naphthyl)-2-butanone | NSAID; analgesic | pain; inflammation |
| piroxicam betadex; piroxicam cyclodextrin; CHF 1194; BREXIN; BREXINE; BREXIDOL; CYCLADOL; BREXICAM; BREXINIL | 4-hydroxy-2-methyl-N-(2-pyridinyl)-2H-1,2-benzothiazine-3-carboxamide 1,1-dioxide compound with beta-cyclodextrin | NSAID; analgesic | pain; inflammation |
| HAI 105 | 6,11-dihydro-2-methoxy-alpha-methyl-11-oxodibenz[b,e]oxepin-3-acetic acid | NSAID; analgesic | pain; inflammation |
| tifurac; RS 82917; RS 82917030 | 7-[4-(methylthio)benzoyl]-5-benzofuranacetic acid | NSAID; analgesic | inflammation; pain |
| pelubiprofen; CS 670; RS 2131 | alpha-methyl-4-[(2-oxocyclohexylidene)methyl]benzeneacetic acid | NSAID; analgesic | inflammation; pain |
| HN 3392 | N-(4-(4-methoxyphenyl)-5-phenylthiazolyl) | NSAID; analgesic | inflammation; pain |
| amtolmetin guacil; ST 679; MED 15; ARTROMED; EUFANS | N-[[1-methyl-5-(4-methylbenzoyl)-1H-pyrrol-2-yl]acetyl]glycine 2-methoxyphenyl ester | NSAID; analgesic | arthritis; rheumatoid arthritis; inflammation; pain |
| flosulide; ZK 38997; CGP 28238; CGS 28238; SH 459 | N-[6-(2,4-difluorophenoxy)-2,3-dihydro-1-oxo-1H-inden-5-yl]methanesulfonamide | NSAID; analgesic | inflammation; pain |
| olvanil; oluvanil; NE 19550 | N-vanillyloleamide | NSAID; analgesic | pain; inflammation; viral infection |
| AF 150 | N,N,-dimethyl-N-[2-[2-[4-(2-methylpropyl)phenyl]-1-oxopropoxy]ethyl]-1-octanaminium bromide | NSAID; antibacterial | bacterial infection; inflammation |
| PS 519 | unspecified | NSAID; anti-ischemic; proteinase inhibitor | inflammation stroke |
| apoptosis modulators | unspecified | NSAID; apoptosis inhibitor; apoptosis inducer; caspase inhibitor | cancer neuropathy; inflammation |
| CCR1 antagonists | unspecified | NSAID; chemokine antagonist | inflammation |
| CCR5 antagonists | unspecified | NSAID; chemokine antagonist | HIV infection; inflammation |

TABLE 11-continued

Current Candidate Therapeutic Interventions in Development for the Treatment of Pain Related to Inflammation

| Product Name | Chemical Name | Action | Indication |
| --- | --- | --- | --- |
| CXCR3 antagonists | unspecified | NSAID; chemokine antagonist | inflammation |
| neurotactin blockers | unspecified | NSAID; chemokine antagonist; gene | multiple sclerosis; inflammation |
| complement C3a receptor modulators | unspecified | NSAID; complement inhibitor | inflammation |
| etodolac; RAK 591; AY 24236; NIH 9918; RAK 593; RAK 592; HYPEN; LODINE; ULTRADOL; ARFLOGIN; TEDOLAN; ETANAL; ANTILAK; EDINE; LODIO; OSTELUC | 1,8-diethyl-1,3,4,9-tetrahydropyrano]3,4-b]indole-1-acetic acid | NSAID; COX inhibitor; COX 2 inhibitor | inflammation |
| immune system modulators, | unspecified | NSAID; immunosuppressant | inflammation |
| MKK3 modulators | unspecified | NSAID; MAP kinase inhibitor; signal transduction inhibitor | inflammation |
| MKK4 modulators | unspecified | NSAID; MAP kinase inhibitor; signal transduction inhibitor | inflammation; neurodegeneration |
| VX 745 | unspecified | NSAID; MAP kinase inhibitor; signal transduction inhibitor | inflammation; neurological; heart failure; Crohn disease; asthma |
| isalsteine; TF 914 | (+,−)-N-(2-((2-methyl-4-oxo-1,3-benzodioxan-2-yl)thio)propionyl)glycine | NSAID; mucolylic | respiratory disease; inflammation |
| NCX 284 | unspecified | NSAID; nitric oxide donor | inflammation |
| nitrosylated nonsteroidal anti-inflammatory agent; NO-NSAIDs | unspecified | NSAID; nitric oxide donor | inflammation |
| ITF 1697 | Unspecified | NSAID; peptide | septic shock; inflammation; heart ischemia; inflammatory bowel disease |
| misoprostol + diclofenac; diclofenac + misoprostol; ARTHROTEC | unspecified | NSAID; prostaglandin | inflammation |
| proteasome inhibitors, inflammation | unspecified | NSAID; transcription factor regulator | inflammation; cancer |
| recombinant PSGL 1, PSGL 1 | unspecified | P selectin antagonist; E selectin antagonist; L selectin antagonist; selectin antagonist; NSAID | inflammation; transplant rejection; ischemia; reperfusion injury |
| BN 54068 | unspecified | PAF antagonist; NSAID | inflammation |
| UR 12510 | unspecified | PAF antagonist; NSAID | inflammation; asthma |
| UR 12519 | unspecified | PAF antagonist; NSAID | inflammation; asthma |
| UR 12551 | unspecified | PAF antagonist; NSAID | inflammation; asthma |
| BN 52111 | 1-(6-((2-heptadecyl-2-methyl-1,3-dioxotan-4-yl)methoxy)-6-oxohexyl)-pyridinium bromide | PAF antagonist; NSAID | asthma; inflammation |
| tiapafant; PCA 4248 | 1,4-dihydro-2,4,6-trimethyl-3,5-pyridinedicarboxylic acid methyl 2-(phenylthio)ethyl ester | PAF antagonist; NSAID | asthma; inflammation |
| BN 52115 | 1-[6-[(2-heptadecyl-2-methyl-1,3-dioxotan-4-yl)methoxy]-6-oxohexyl]quinolinium bromide | PAF antagonist; NSAID | asthma; inflammation |
| UR 10324 | 2-(2-acetyl-3,11-dioxo-4,10-dioxa-7-thia-2,12-diazanonacos-1-yl)-1-ethylpyridinium chloride | PAF antagonist; NSAID | inflammation; asthma |

TABLE 11-continued

Current Candidate Therapeutic Interventions in Development for the Treatment of Pain Related to Inflammation

| Product Name | Chemical Name | Action | Indication |
| --- | --- | --- | --- |
| tetrahydrocarbazole | 4-(2-chlorophenyl)-9-methyl-2-[3-(1,2,3,4-tetrahydro-9H-carbazol-9-yl)-1-propynyl]-6H-thieno[3,2-f][1,2,4]triazolo[4,3-a][1,4]diazepine | PAF antagonist; NSAID | inflammation; asthma |
| UR 12460 | 4-[[(diphenylmethyl)amino]acetyl]-alpha-(2-methyl-3-pyridinyl)-1-piperazineacetonitrile | PAF antagonist; NSAID | inflammation; asthma |
| SM 10661 | cis-(+,−)-3,5-dimethyl-2-(3-pyridinyl)-4-thiazolidinone monohydrochloride | PAF antagonist; NSAID | endotoxic shock; inflammation; asthma |
| CV 6209 | 2-(2-acetyl-6-methoxy-3,9-dioxo-4,8-dioxa-2,10-diazaoctacos-1-yl)-1-ethylpyridinium chloride | PAF antagonist; antiaggregant; NSAID | platelet thrombosis; inflammation |
| UR 11353 | 2-[[acetyl[[[tetrahydro-5-(octadecyloxy)-3-furanyl]methoxy]carbonyl]amino]methyl]-1-ethylpyridinium chloride | PAF antagonist; platelet antiaggregant; NSAID | thrombosis; inflammation |
| urokinase receptor antagonists | unspecified | peptide | cancer, inflammation |
| MER W8020 | Unspecified | peptide; analgesic, NSAID | inflammation; pain |
| inflammation therapy, autoimmune disease therapy, | Unspecified | peptide; immunosuppressant | inflammation; autoimmune disease |
| CD4 peptide antagonist, | unspecified | peptide; immunosuppressant; NSAID | inflammation |
| cylochrome b558 derived peptide, anti-inflammatory peptide | unspecified | peptide; NSAID | inflammation |
| CEN 294 | unspecified | peptide; NSAID | inflammation; ischemia; reperfusion injury |
| corticotropin releasing factor analogue, CRF analogue | unspecified | peptide; NSAID | inflammation |
| inflammation therapy | unspecified | peptide; NSAID | inflammation |
| mystixins | unspecified | peptide; NSAID | inflammation |
| LAS 31396 | unspecified | phosphodiesterase inhibitor; bronchodilator; NSAID | asthma; inflammation |
| arofylline; LAS 31025 | 3-(4-chlorophenyl)-3,7-dihydro-1-propyl-1H-purine-2,6-dione | phosphodiesterase inhibitor; bronchodilator; NSAID | asthma; inflammation |
| CDP 840 | (R)-4-[2-[3-(cyclopentyloxy)-4-methoxyphenyl]-2-phenylethyl]pyridine | phosphodiesterase inhibitor; phosphodiesterase IV inhibitor; bronchodilator; NSAID | asthma; inflammation |
| phosphodiesterase IV inhibitor | unspecified | phosphodiesterase inhibitor; phosphodiesterase IV inhibitor; NSAID | inflammation |
| B669 | 3-(cyclohexylimino)-3,5-dihydro-N5-diphenyl-2-phenazinamine | phospholipase activator; immunosuppressant; NSAID | inflammation |
| phospholipase C inhibitors | unspecified | phospholipase inhibitor; NSAID | inflammation |
| WAY 121520 | 1-[(4-chlorophenyl)methyl]-2-methyl-5-(2-quinolinylmethoxy)-1H-indole-3-acetic acid | phospholipase inhibitor; NSAID | inflammation |

TABLE 11-continued

Current Candidate Therapeutic Interventions in Development for the Treatment of Pain Related to Inflammation

| Product Name | Chemical Name | Action | Indication |
|---|---|---|---|
| BMS 188184 | 3-[(1Z,2Z)-3-carboxy-2-methyl-1-[(5,6,7,8-tetrahydro-5,5,8,8-tetramethyl-2-anthracenyl)methylene]-2-propenyl]benzoic acid | phospholipase inhibitor; NSAID | psoriasis; dermatitis; inflammation |
| YM 26734 | 4-(3,5-didodecanoyl-2,4,6-trihydroxyphenyl)-7-hydroxy-2-(4-hydroxyphenyl)chroman | phospholipase inhibitor; NSAID | inflammation |
| YM 265671; YM 26567-1 | trans-(+)-1-[3-[3,4-dihydro-7-hydroxy-2-(4-hydroxyphenyl)-2H-1-benzopyran-4-yl]-2,4,6-trihydroxyphenyl]-1-dodecanone | phospholipase inhibitor; NSAID | inflammation |
| U 73122 | 1-[6-[[(17 beta)-3-methoxyestra-1,3,5(10)-trien-17-yl]amino]hexyl] | phospholipase inhibitor; platelet antiaggregant; NSAID | inflammation; thrombosis |
| plasminogen activator inhibitor; PAI-2 | unspecified | plasminogen activator inhibitor; cicatrizant | cancer; inflammation; skin ulcer |
| drug delivery system, MICROPUMP oral controlled release aspirin; aspirin MICROPUMP; ASACARD | unspecified | platelet antiaggregant; thromboxane synthetase inhibitor; analgesic; NSAID | thrombosis; pain; inflammation |
| cyctic polyamine analogue | unspecified | polyamine analogue; NSAID | Crohn disease; asthma; inflammation |
| anti-inflammatory agents | unspecified | protein kinase inhibitor; cylokine inhibitor; TNF inhibitor | inflammation |
| Ro 318830 | unspecified | protein kinase inhibitor; protein kinase C inhibitor; NSAID | inflammation |
| SPC 100840 | unspecified | protein kinase inhibitor; protein kinase C inhibitor; NSAID | ischemia; psoriasis; cancer; inflammation reperfusion injury |
| UCN 01; UCN 1; KW 2401 | (3 alfa, 9 beta,10 alfa, 11 alfa, 13 beta)-(+)-2,3,10,11,12,13-hexahydro-3-hydroxy-10-methoxy-9-methyl-11-(methylamino)-9,13-epoxy-1H,9H-diindolo[1,2,3-gh:3',2',1'-lm]pyrrolo[3,4-j][1,7]benzodiazonin-1-one | protein kinase inhibitor; protein kinase C inhibitor; NSAID | cancer; inflammation; allergy |
| batanol; (−)-batanol; azepinostatin; ophiocordin | (3R-trans)-4-(2-carboxy-6-hydroxybenzoyl)-3,5-dihydroxybenzoic acid 1-[hexahydro-3-[(4-hydroxybenzoyl)amino]-1H-azepin-4-yl]ester | protein kinase inhibitor; protein kinase C inhibitor; NSAID | cancer; inflammation; psoriasis |
| GF 109203X; Go 6850 | 3-[1-[3-(dimethylamino)propyl]-1H-indol-3-yl]-4-(1H-indol-3-yl)-1H-pyrrole-2,5-dione | protein kinase inhibitor; protein kinase C inhibitor; NSAID | inflammation |
| LEX 028 | unspecified | proteinase inhibitor; cathepsin G inhibitor; NSAID | inflammation |
| cathepsin S inhibitors | unspecified | proteinase inhibitor; cathepsin S inhibitor; NSAID; immunosuppressant | inflammation; autoimmune disease |
| APC 1403 | unspecified | proteinase inhibitor; NSAID | inflammation |
| LEX 026 | unspecified | proteinase inhibitor; serine proteinase inhibitor | thrombosis; inflammation |

TABLE 11-continued

Current Candidate Therapeutic Interventions in Development for the Treatment of Pain Related to Inflammation

| Product Name | Chemical Name | Action | Indication |
| --- | --- | --- | --- |
| LEX 043 | unspecified | proteinase inhibitor; serine proteinase inhibitor | inflammation; asthma |
| BCX 1170 | unspecified | proteinase inhibitor; serine proteinase inhibitor; complement inhibitor; NSAID | cardiovascular disease; inflammation |
| neutral endopeptidase; NEP | unspecified | proteinase; metalloproteinase | cancer; migraine; inflammatory bowel disease; inflammation; asthma; respiratory disease |
| anti-inflammatory | unspecified | rac inhibitor; RAS inhibitor; signal transduction inhibitor; NSAID | inflammation |
| secretory cell inhibitors, CAMR | unspecified | secretory cell inhibitors | allergy; inflammation; respiratory disease |
| BCX 1470 | unspecified | serine proteinase inhibitor; complement inhibitor; NSAID; proteinase inhibitor | cardiovascular disease; inflammation |
| complement inhibitors | unspecified | serine proteinase inhibitor; NSAID; complement inhibitor; proteinase inhibitor | inflammation; myocardial infarction; reperfusion injury; respiratory distress syndrome |
| p-38-2 inhibitor | unspecified | signal transduction inhibitor; NSAID | inflammation; ischemia |
| SP 100030 | Unspecified | signal transduction inhibitor; NSAID; immunosuppressant | inflammation; autoimmune disease |
| dapitant; RPR 100893 | [3aS-[2(R*),3 aalpha, 4 beta, 7 a alpha]]-octahydro-4-(2-methoxyphenyl)-2-[2-(2-methoxyphenyl)-1-oxopropyl]-7,7-diphenyl-1H-isoindol-4-ol | substance P antagonist; NSAID | asthma; inflammation; migraine |
| screening technology, cox-2 gene suppression | unspecified | target based screening; biotechnology | drug design technology; inflammation; cancer |
| TGF beta antagonists; transforming growth factor beta antagonists | unspecified | TGF beta antagonist; cicatrizant | cancer; viral infection; inflammation; skin ulcer |
| thrombospondin inhibitor | unspecified | thrombospondin inhibitor; peptide; NSAID | inflammation; cancer; sickle cell anemia |
| tumor necrosis factor binding protein; TBP-1; TBP | unspecified | TNF inhibitor; immunosuppressant | autoimmune disease; reperfusion injury; inflammation; septic shock |
| tumor necrosis factor binding protein; TNFbp | unspecified | TNF inhibitor; NSAID | septic shock; inflammation |
| tumor necrosis factor inhibitors | unspecified | TNF inhibitor; NSAID | inflammation; asthma; inflammatory bowel disease |
| tumor necrosis factor receptor inhibitors | unspecified | TNF inhibitor; NSAID | septic shock; inflammation |
| A 802715 | 3,7-dihydro-1-(5-hydroxy-5-methylhexyl)-3-methyl-7-propyl-1H-purine-2,6-dione | TNF inhibitor; NSAID | inflammation; septic shock |
| peptide T, natural; peptide T | N-[N-[N2-[N-[N-[N-(N-L-alanyl-L-seryl)-L threonyl]-L-threonyl]-L-threonyl]-L-asparaginyl]-L-tyrosyl]-L-threonine | TNF inhibitor; peptide; NSAID | HIV infection; psoriasis; inflammation |
| transcription factor inhibitors | unspecified | transcription factor regulator | inflammation; autoimmune disease |
| NF-kappaB inhibitor | unspecified | transcription factor regulator; NSAID | asthma; inflammation restenosis |
| NF-kappaB inhibitor | unspecified | transcription factor regulator; NSAID | inflammation; ischemia; cancer; autoimmune disease |

TABLE 11-continued

Current Candidate Therapeutic Interventions in Development for the Treatment of Pain Related to Inflammation

| Product Name | Chemical Name | Action | Indication |
|---|---|---|---|
| AP-1 inhibitor; JNK inhibitor | unspecified | transcription factor regulator; NSAID; immunosuppressant | inflammation; autoimmune disease; cancer |
| ademetionine; FO 1561; GUMBARAL; DONAMET; TRANSMETIL; CERITAN; ERGEN; TWIN; SAMY R | (3S)-5'-[(3-amino-3-carboxypropyl)methylsulfonio]-5'-deoxyadenosine hydroxide inner salt | transmethylator; NSAID | inflammation; cognitive defect; cholestasis |
| tryptase inhibitors | unspecified | tryptase inhibitor; NSAID | asthma; inflammation rhinitis; inflammatory bowel disease; psoriasis |
| UBC inhibitors; ubiquitin conjugating enzyme inhibitors | unspecified | ubiquitin conjugating enzyme inhibitor; NSAID | cancer; inflammation |
| non-ionic surfactant vesicles; NISV | unspecified | vaccine adjuvant; immunosuppressant | rheumatoid arthritis; asthma; inflammation |
| vaccine, gene-based, autoimmune disease | unspecified | vaccine; gene therapy | autoimmune disease; inflammation |

TABLE 12

Current Candidate Therapeutic Interventions in Development for the Treatment of Psoriasis

| Product Name | Chemical Name | Action | Indication |
|---|---|---|---|
| masoprocol; CHX 100; ACTINEX | (R*,S*)-4,4'-(2,3-dimethyl-1,4-butanediyl)bis-1,2-benzenediol | 5 lipoxygenase inhibitor | skin disease; cancer; psoriasis |
| WY 47288 | 2-[(1-naphthalenyloxy)methyl] quinoline | 5 lipoxygenase inhibitor | psoriasis |
| enazadrem; enazadrem phosphate; CP 70490; CP 7049009 | 4,6-dimethyl-2-[(6-phenylhexyl)amino]-5-pyrimidinol | 5 lipoxygenase inhibitor | psoriasis |
| Ionapalene; RS 43179 | 6-chloro-2,3-dimethoxy-1,4-naphthalenediol diacetate | 5 lipoxygenase inhibitor | psoriasis |
| R 85355 | Unspecified | 5 lipoxygenase inhibitor | asthma; psoriasis; inflammatory bowel disease |
| BW 4C; BW A4C; BW 4C86 | N-(3-phenoxy-phenyl-2-propenyl)acetohydroxamic acid | 5 lipoxygenase inhibitor; chelating agent; NSAID | arthritis; psoriasis |
| CGS 23885 | unspecified | 5 lipoxygenase inhibitor; NSAID | psoriasis; inflammation |
| SC 45662 | unspecified | 5 lipoxygenase inhibitor; NSAID | inflammation; asthma; psoriasis; inflammatory bowel disease |
| DUP 654 | (2-phenylmethyl)-1-naphthalenol | 5 lipoxygenase inhibitor; NSAID | psoriasis; inflammation |
| L 663536; MK 886 | 1-[(4-chlorophenyl)methyl]-3-[(1,1-dimethylethyl)thio]-alfa,alfa-diethyl-5-(1-methylethyl)-1H-indole-2-propanoic acid | 5 lipoxygenase inhibitor; NSAID | inflammation; asthma; psoriasis |
| SCH 40120 | 10-(3-chlorophenyl)-6,8,9,10-tetrahydrobenzo[b][1,8]naphthyridin-5(7H)-one | 5 lipoxygenase inhibitor; NSAID | inflammation; psoriasis |
| AE 941; NEOVASTAT; NEORETNA; PSOVASCAR; ARTHROVAS | unspecified | angiogenesis inhibitor; NSAID | cancer; psoriasis; rheumatoid arthritis; eye disease; retinopathy |

TABLE 12-continued

Current Candidate Therapeutic Interventions in Development for the Treatment of Psoriasis

| Product Name | Chemical Name | Action | Indication |
|---|---|---|---|
| glycopine; glucosaminylmuramyl dipeptide; GMDP; LICOPID; LIKOPID | N2-[N-[N-acetyl-4-O-[2-(acetylamino)-2-deoxy-beta-D-glucopyranosyl]muramoyl]-L-alanyl]-D-alpha-glutamine | antibiotic; vaccine adjuvant; immunostimulant; glycopeptide | psoriasis; cancer; leukopenia; septic shock; infectious disease; eye disease |
| liarozole; liarozole hydrochloride; liarozole fumarate; R 75251; R 85246; LIAZAL | 5-[(3-chlorophenyl)-1H-imidazol-1-ylmethyl]-1H-benzimidazole | antifungal; androgen synthesis inhibitor; imidazole | cancer; psoriasis |
| taxoids | unspecified | Antihyperproliferative agent | psoriasis |
| drug delivery system, psoriasis therapy, P 37 | unspecified | Antikeratinocyte activity | psoriasis |
| drug delivery system, fluorouracil; fluorouracil Therapeutic implant; MPI 5003 | unspecified | antimetabolite | cancer; psoriasis; viral infection |
| drug delivery system, topical methotrexate; methotrexate topical | unspecified | antimetabolite | psoriasis |
| ZYN-LINKER conjugated methotrexate | unspecified | antimetabolite; NSAID | cancer; rheumatoid arthritis; psoriasis |
| drug delivery system, stabilized lipid dithranol; dithranol stabilized lipid; MICANOL | unspecified | Antimitotic | psoriasis |
| TV 2801 | Anthralin derivative | antimitotic | psoriasis |
| TV 2802 | Anthralin derivative | antimitotic | psoriasis |
| trimethylangelicin; TMA; 4,4',6-trimethyiangelicin; 4,6,4'-trimethylangelicin | 4,6,9-trimethyl-2H-furo[2,3-h]-1-benzopyran-2-one | Antiporiiferative agent | psoriasis |
| topical antiproliferative agents | unspecified | antiproliferative agent | psoriasis |
| SDZ LAP977 | 5-[2-(2,5-dimethoxyphenyl)ethyl)-2-hydroxybenzoic acid methyl ester | antiproliferative agent | psoriasis |
| maxacalcitol; 22-oxacalcitriol; oxacalcitriol; OCT; MC 1275 | [1S-[1alfa(R*),3abeta,4E(1S*,3R*,5Z) 7aalfa]]-4-methylene-5-[2-octahydro-1-[1-(3-hydroxy-3-methylbutoxy)ethyl]-7a-methyl-4H-inden-4-yliden]ethylidene)-1,3-cyclohexanediol | antiproliferative agent; vitamin D3 analogue | hyperparathyroidism; psoriasis |
| drug delivery system NOVASOME topical anthralin; anthralin, topical NOVASOME | unspecified | Antitimitotic; DNA syntesis inhibition; topical agent | psoriasis |
| E2F inhibitors | unspecified | apoptosis inducer; antiproliferative agent | cancer; psoriasis; viral infection; restenosis |
| iroplact; platelet factor 4; PF4; endostatin B; REPLISTATIN | unspecified | biotechnology | heparin neutralization; psoriasis; HIV infection; cancer; diabetes |
| senescence derived inhibitor 1; Sdi 1 | unspecified | biotechnology; cyciln dependent kinase inhibitor | cancer; psoriasis; eye disease; cancer |
| sonermin; tumor necrosis factor; TNF; PAC 4D | 3-157-tumor necrosis factor (human) | biotechnology; cytokine | cancer; psoriasis |
| interleukin-8 receptor IL-8r | unspecified | biotechnology; cytokine antagonist; NSAID | psoriasis; rheumatoid arthritis; respiratory distress syndrome; septic shock |
| interleukin-10; IL-10; cytokine synthesis inhibitory factor; CSIF; SCH 52000; TENOVIL | interleukin 10 (human clone pH15C) | biotechnology; cytokine; vaccine adjuvant; immunosuppressant; NSAID | autoimmune disease; inflammatory bowel disease; rheumatoid arthritis; multiple sclerosis; psoriasis; HIV infection; viral infection |

TABLE 12-continued

Current Candidate Therapeutic Interventions in Development for the Treatment of Psoriasis

| Product Name | Chemical Name | Action | Indication |
|---|---|---|---|
| epidermal growth factor diphtheria toxin chimeric protein; EGF diphtheria toxin chimeric protein; EGF fusion protein; DAB 389-EGF; DAB 389-EGF | unspecified | biotechnology; fusion toxin | cancer; restenosis; psoriasis |
| denileukin diftitox; interleukin-2 diphtheria toxin chimeric protein; interleukin-2 fusion protein; DAB 389-IL-2; LY 335348; DAB3891L2; ONTAK | 1-388-toxin (Corneybacterium diphtheriae strain C7), N-L-methionyl-387-L-histidine-388-L-alanine-, (388.fwdarw.2')-protein with 2-133-interleukin 2 (human clone pTIL2-21a) | biotechnology; fusion toxin; NSAID | diabetes; HIV infection; rheumatoid arthritis; psoriasis; cancer |
| polyethylene glycol transforming growth factor beta2; PEG-TGF beta2; transforming growth factor beta2 macrogol | unspecified | biotechnology; growth factor | osteoporosis; psoriasis; eye disease |
| MAb, humanized B7.1 | unspecified | biotechnology; immunosuppressant | psoriasis; transplant rejection; autoimmune disease |
| MAb, humanized B7.2 | unspecified | biotechnology; immunosuppressant | psoriasis; transplant rejection; autoimmune disease |
| MEDI 507 | unspecified | biotechnology; immunosuppressant | autoimmune disease; transplant rejection; psoriasis |
| antisense oligonucleotide, ICAM-1; antisense oligonucleotide, intracellular adhesion molecuie-1; ISIS 2302 | d[(R)-P-thio](G-C-C-C-A-A-G-C-T-G-G-C-A-T-C-C-G-T-C-A) DNA | biotechnology; immunosuppressant; antisense; oligonucleotide; NSAID | rheumatoid arthritis; psoriasis; inflammatory bowel disease; asthma |
| BMS 188667; CTLA4lg | unspecified | biotechnology; immunosuppressant; NSAID | transplant rejection; systemic lupus erythematosus; psoriasis; arthritis; allergy |
| leukocyte function associated antigen 3 T cell inhibitor protein, LFA3TIP; LFA3TIP; AMEVIVE | unspecified | biotechnology; immunosuppressant; NSAID | inflammation; autoimmune disease; psoriasis |
| MAb, CD11a; hu 1124 | unspecified | biotechnology; monoclonal antibody; immunosuppressant | psoriasis; transplant rejection |
| MAb, humanized CD3; MAb, SMART CD3; HuM291 | unspecified | biotechnology; monoclonal antibody; immunosuppressant | transplant rejection; autoimmune disease; psoriasis |
| clenoliximab; MAb, CD4; MAb, PRIMATIZED CD4; IDEC 151; SB 217969 | immunoglobulin G 4 (human-Macaca monoclonal CE9gamma4PE gamma4-chain anti-human antigen CD4), disulfide with human-Macaca monoclonal CE9gamma4PE kappa-chain, dimer | biotechnology; monoclonal antibody; NSAID | rheumatoid arthritis; psoriasis; asthma |
| MAb, B7; MAb, PRIMATIZED B7; IDEC 114 | unspecified | biotechnology; monoclonal antibody; NSAID; immunosuppressant | systemic lupus erythematosus; inflammation; transplant rejection; psoriasis |
| MAb, idiotypic GD2; vaccine, cancer; cancer vaccine | unspecified | biotechnology; monoclonal antibody; vaccine | cancer; psoriasis |
| oligonucleotides, psoriasis | unspecified | biotechnology; oligonucteotide | psoriasis |

TABLE 12-continued

Current Candidate Therapeutic Interventions in Development for the Treatment of Psoriasis

| Product Name | Chemical Name | Action | Indication |
| --- | --- | --- | --- |
| oligonucleotides, | unspecified | biotechnology; oligonucleotide; ribozyme | cancer; psoriasis |
| vaccine, psoriasis; vaccine, T cell receptor; IR 502 | unspecified | biotechnology; vaccine | psoriasis |
| CDF inhibitor | unspecified | CDF inhibition; inhibition of cdc25C | cancer; psoriasis |
| SPC 101210 | unspecified | ceramide | psoriasis |
| SPC 103600 | unspecified | ceramide regulator | psoriasis |
| differentiation-inducing compounds | unspecified | Control of cell differentiation | cancer; psoriasis; restenosis |
| AGN 191743 | unspecified | corticosteroid | psoriasis |
| anti-inflammatory corticosteroids | unspecified | corticosteroid | psoriasis; asthma |
| auranofin + betamethasone dipropionate; betamethasone dipropionate + auranofin | unspecified | corticosteroid | psoriasis |
| drug delivery system, betamethasone ViaFoam mousse; betamethasone ViaFoam mousse; BETAMOUSSE; LUXIQ | unspecified | corticosteroid | psoriasis, dermatitis |
| drug delivery system, clobetasol ViaFoam mousse; clobetasol ViaFoam mousse; OLUX | unspecified | corticosteroid | psoriasis |
| drug detivery system, liposome clobetasol; clobetasol tiposome; LipoFORT | unspecified | corticosteroid | psoriasis |
| drug delivery system, topical DermaStick betamethasone dipropionate; betamethasone proprionate DermaStick; DermaStick | unspecified | corticosteroid | psoriasis |
| mometasone furoate + salicylic acid; COMBISOR | unspecified | corticosteroid | psoriasis |
| prednicarbate; HOE 777; S 770777; DERMATOP; PREDNITOP | (11beta)-17-[(ethoxycarbonyl)oxy]-11-hydroxy-21-(1-oxopropoxy)-pregna-1,4-diene-3,20-dione | corticosteroid | psoriasis |
| mometasone furoate; mometasone; S 2640; SCH 32088; ELOCOM; ELOCON; FULMETA; ECURAL; ERMIL; NASONEX; ASMANEX | (11beta,16alpha)-9,21-dichloro-17-[(2-furanylcarbonyl)oxy]-11-hydroxy-16-methyl-pregna-1,4-diene-3,20-dione | corticosteroid | dermatitis; asthma; rhinitis; psoriasis; pruritis |
| tipredane; SQ 27239 | (11beta,17alfa)-17-(ethylthio)-9-fluoro-11-hydroxy-17-(methylthio)androsta-1,4-diene-3-one | corticosteroid | inflammation; psoriasis |
| ulobetasol propionate; halobetasol propionate; CGP 14458; BMY 30056; ULTRAVATE | (6alfa,11beta,16beta)-21-chloro-6,9-difluoro-11-hydroxy-16-methyl-17-(1-oxopropoxy)-pregna-1,4-diene-3,20-dione | corticosteroid | skin disease; inflammation; psoriasis |
| FPL 62064 | N-(4-methoxyphenyl)-1-phenyl-1H-pyrazole-3-amine | COX Inhibitor; 5 lipoxygenase inhibitor | inflammatory bowel disease; psoriasis |

TABLE 12-continued

Current Candidate Therapeutic Interventions in Development for the Treatment of Psoriasis

| Product Name | Chemical Name | Action | Indication |
| --- | --- | --- | --- |
| RU 46057 | 2-[1,2-bis(1-oxopropoxy)ethyl]4-hydroxy-N-2-thiazolyl-8-(trifluo romethyl)-3-quinolinecarboxamide | COX inhibitor; 5 lipoxygenase inhibitor; NSAID | arthritis; psoriasis |
| RP 54745 | 4-chloro-5-(3,4-dihydro-1-methyl-2(1H)-isoquinolinyl)-3H-1,2-dithoil-3-one | cylokine antagonist; immunosuppressant; NSAID | rheumatoid arthritis; inflammatory bowel disease; psoriasis |
| interleukin-8 antagonists | unspecified | cytokine antagonist; NSAID | rheumatoid arthritis; psoriasis; atherosclerosis |
| ETH 615 | 4-[[[(3-fluorophenyl)methyl][4-(2-quinolinylmethoxy)phenyl]-amino]methylbenzoic acid | cylokine synthesis inhibitor | psoriasis |
| BMY 30094 | N-hydroxybenzenenonanamide | cylokine synthesis inhibitor; NSAID | inflammation; psoriasis |
| amlexanox; amoxanox; CHX 3673; AA 673; SOLFA; ELICS; APHTHASOL | 2-amino-7-(1-methylethyl)-5-oxo-5H-[1]-benzopyrano[2,3-b]pyridine-3-carboxylic acid | degranulation inhibitor | asthma; psoriasis; rhinitis; mucositis; conjunctivitis; allergy |
| alitretinoin; LGD 1057; LG 1057; LGN 1057; ALRT 1057; NSC 659772; PANRETIN | 9-cis-retinoic acid | differentiation inducer; retinoid agonist; RAR agonist; RXR agonist | cancer; psoriasis |
| psoriasis therapy | unspecified | dihydrofolate reductase inhibitor | psoriasis |
| dihydrofolate reductase inhibitor, psoriasis | unspecified | dihydrofolate reductase inhibitor; antifolate | psoriasis |
| trimetrexate; trimetrexate glucuronate; TMQ; NSC 249008; Cl 898 | 5-methyl-6-[[(3,4,5-trimethoxyphenyl)amino]-methyl]-2,4-quinazotinediamine | dihydrofolate reductase inhibitor; antifolate; NSAID | cancer; psoriasis; rheumatoid arthritis; pneumocystis |
| drug delivery system, methotrexate; methotrexate delivery system; G 301 | unspecified | Dihyrofolic acid reductase inhibition cytotoxic | psoriasis |
| drug delivery system, topical methotrexate; methotrexate, topical; CHX 150 | unspecified | Dihyrofolic acid reductase inhibition; cytotoxic | psoriasis |
| psoriasis therapy | unspecified | EGF receptor inhibitor | psoriasis |
| ALP 242 | unspecified | elastase inhibitor; proteinase inhibitor | asthma; emphysema; psoriasis |
| efomycines | unspecified | Endothelium mediated antiadhesive properties | psoriasis |
| psoriasis enzyme therapy | unspecified | enzyme | psoriasis |
| fibroblast growth factor antagonist | unspecified | FGF antagonist; angiogenesis inhibitor | cancer; retinopathy; psoriasis |
| free radical scavengers | unspecified | free radical scavenger; NSAID | neurodegeneration; arthritis; reperfusion injury; psoriasis; stroke |
| SLH 301 | unspecified | free radical scavenger; NSAID | neurodegeneration; arthritis; reperfusion injury; psoriasis; stroke |
| beta-glucan antagonist | unspecified | glucan antagonist | conjunctivitis; asthma; psoriasis; ulcerative colitis |
| SU 5271 | unspecified | growth factor modulator; signal transduction inhibitor; EGF receptor inhibitor | psoriasis |
| epinastine; WAL 801; WAL 801CL; ALESION | 9,13b-dihydro-1H-dibenz[c,f]imidazo[1,5-a]-azepin-3-amine | histamine antagonist; histamine H1 antagonist | allergy; asthma; psoriasis; rhinitis |

TABLE 12-continued

Current Candidate Therapeutic Interventions in Development for the Treatment of Psoriasis

| Product Name | Chemical Name | Action | Indication |
|---|---|---|---|
| psoriasis therapy | unspecified | Immunomodulation | psoriasis |
| drug delivery system, HILT, ciclosporin; ciclosporin, HILT, psoriasis; CYCLOPS | unspecified | immunosuppressant | psoriasis |
| drug delivery system, liposome ciclosporin; ciclosporin tiposome; LipoSPOR | unspecified | immunosuppressant | psoriasis |
| VX 497 | unspecified | immunosuppressant | psoriasis; autoimmune disease; viral infection; hepatitis |
| PRO 2844 | (OC-6-22)-pentaammine(4-methylpyridine)ruthenium m(3+) trichloride | immunosuppressant | psoriasis; autoimmune disease; transplant rejection |
| SDZ 281240 | unspecified | immunosuppressant; macrolide; antibiotic | psoriasis |
| PIC 060 analogs | unspecified | immunosuppressant; NSAID | psoriasis; dermatitis diabetes; transplant rejection; rheumatoid arthritis |
| VX 10393 | unspecified | immunosuppressant; NSAID | transplant rejection; rheumatoid arthritis; psoriasis; diabetes |
| VX 10428 | unspecified | immunosuppressant; NSAID | transplant rejection; rheumatoid arthritis; psoriasis; diabetes |
| laflunimus; HR 325 | (Z)-2-cyano-3-cyclopropyl-3-hydroxy-N-[3-methyl-4-(trifluoromethyl)phenyl]-2-propenamide | immunosuppressant; NSAID | rheumatoid arthritis; transplant rejection psoriasis |
| CI 972 | 2,6-diamino-1,5-dihydro-7-(3-thienylmethyl)-4H-pyrrolo[3,2-d]pyrimidin-4-one monohydrochloride | immunosuppressant; NSAID | rheumatoid arthritis; cancer; psoriasis |
| amiprilose; amiprilose hydrochloride; THN; SM 1213; KAP 690; THERAFECTIN | 3-O-(3-(dimethylamino)propyl)-1,2-O-isopropylidene-alfa-D-glucofuranose hydrochloride | immunosuppressant; NSAID | rheumatoid arthritis; psoriasis |
| atiprimod; atiprimod dimaleate, SKF 106615 | N,N-diethyl-8,8-dipropyl-2-azaspiro[4.5]decane-2-propanamine | immunosuppressant; NSAID; macrophage inhibitor | rheumatoid arthritis; autoimmune disease; psoriasis |
| ABT 281; A 86281 | unspecified | Immunosuppression like tacrolimus; ao systemic side effects | psoriasis |
| MAb, ICAM-3; MAb, intracellular adhesion molecule-3; MAb, ICAM-R; ICM3 | unspecified | integrin antagonist; biotechnology; cell adhesion inhibitor; immunosuppressant; monoclonal antibody | autoimmune disease; psoriasis |
| alphaE beta7 antagonists | unspecified | integrin antagonist; cell adhesion inhibitor | asthma; psoriasis; inflammatory bowel disease |
| TBC 427 | unspecified | integrin antagonist; selectin antagonist; immunosuppressant; cell adhesion inhibitor | ischemia; psoriasis; respiratory distress syndrome; transplant rejection; reperfusion injury |
| SCHAL 3 | unspecified | Ion transport modulation | skin disease; cancer; psoriasis |
| antiproliferative agents | unspecified | Ion transport modulation; antiproliferative | Cancer; psoriasis |
| sumarotene; Ro 149706 | (E)-1,2,3,4-tetrahydro-1,1,4,4-tetramethyl-6-[1-methyl-2-[4-(methylsulfonyl)phenyl)-ethenyl]naphthalene | keratolylic | psoriasis |

TABLE 12-continued

Current Candidate Therapeutic Interventions in Development for the Treatment of Psoriasis

| Product Name | Chemical Name | Action | Indication |
|---|---|---|---|
| VML 262 | unspecified | Leukotriene B4 antagonist | psoriasis |
| SC 52798 | (+)-7-[3-[2-(cyclopropylmethyl)-3-methoxy-4-(4-thiazolyl)phenoxy]propoxy]-3,4-dihydro-8-propyl-2H-1-benzopyran-2-carboxylic acid | leukotriene B4 antagonist; leukotriene antagonist | psoriasis; ulcerative colitis |
| SC 53228; (+)-SC 51146 | (S)-7-[3-[2-(cyclopropylmethyl)-3-methoxy-4-[(methylamino)carbonyl]phenoxy]propoxy]-3,4-dihydro-8-propyl-2H-1-benzopyran-2-propanoic acid | leukotriene B4 antagonist; leukotriene antagonist | psoriasis |
| LY 293111; VML 295 | 2-[3-[3-[(5-ethyl-4'-fluoro-2-hydroxy[1,1'-biphenyl]-4-yl)oxy]propoxy]2-propylphenoxy)-benzoic acid | leukotriene B4 antagonist; leukotriene antagonist | psoriasis |
| SM 15178 | 3-[[[2-[[[2-ethyl-4-(1-oxoethyl)-5-hydroxyphenyl]oxy]methyl]-pyridin-6-yl]carbonyl]ethylamino]propanoic acid | leukotriene B4 antagonist; leukotriene antagonist | psoriasis; inflammatory bowel disease |
| SC 41930 | 7-[3-(-4-acetyl-3-methoxy-2-propylphenoxy)propoxy]-3,4-dihydro-8-propyl-2H-1-benzopyran-2-carboxylic acid | leukotriene B4 antagonist; leukotriene antagonist | psoriasis |
| WF 11605 | (1S,1R,4aS,6aR,8R,9R,10aS,12aS)-9-acetoxy-2-((R)-1,2dimethylpropyl)-8-(beta-D-glucopyranosyl)oxy-1,2,3,4,4a,5,6,6a,7,8,9,10,10a,11,12,12a-hexadecahydro-2,4a,7,7,10a,12a,hexa methyl-3-oxochrysene-1-carboxylic acid | leukotriene B4 antagonist; leukotriene antagonist; NSAID | hepatitis; inflammation; psoriasis |
| SB 201993 | (E)-3-[[[[6-(2-carboxyethenyl)-5-[[8-(4-methoxyphenyl)octyl]oxy]-2-pyridinyl]-methyl]thio]methyl]benzoic acid | leukotriene B4 antagonist; leukotriene antagonist; NSAID | psoriasis; inflammation |
| ticolubant; SB 209247 | (E)-3-[6-[[2,6-dichlorophenyl)thio]methyl]-3-(2-phenylethoxy)-2-pyridinyl]-2-propenoic acid | leukotriene B4 antagonist; leukotriene antagonist; NSAID | inflammation; psoriasis |
| RP 64966 | 2-((4-(5-(3-phenylpropyl)-2-thienyl)butyl)oxy)acetic acid (sodium salt) | leukotriene B4 antagonist; leukotriene antagonist; NSAID | inflammation; psoriasis; inflammatory bowel disease |
| SC 50605 | 7-[3-[2(cyclopropylmethyl)-3-methoxy-4-(4-thiazolyl)phenoxy]propoxy]-3,4-dihydro-8-propyl-2H-1-benzopyran-2-carboxylic acid | leukotriene B4 antagonist; leukotriene antagonist; NSAID | psoriasis; inflammation |

TABLE 12-continued

Current Candidate Therapeutic Interventions in Development for the Treatment of Psoriasis

| Product Name | Chemical Name | Action | Indication |
|---|---|---|---|
| SC 51146 | 7-[3-[2(cyclopropylmethyl)-3-methoxy-4-(4-thiazolyl)phenoxy]propoxy]-3,4-dihydro-8-propyl-2H-1-benzopyran-2-carboxylic acid | leukotriene B4 antagonist; leukotriene antagonist; NSAID | asthma psoriasis; rheumatoid arthritis; inflammatory bowel disease |
| immunosuppressant | Monoclonal antiobody | Monocloanl antibody to complement | psoriasis |
| MAb, interleukin-8; MAb, IL-8; ABX IL8 | unspecified | monoclonal antibody; biotechnology; NSAID | respiratory distress syndrome; inflammatory bowel disease; rheumatoid arthritis; inflammation; psoriasis |
| IPL 400; SORTAC | unspecified | NSAID | psoriasis |
| IPL 576; IZP 94005 | unspecified | NSAID | psoriasis; allergy; inflammation |
| pseudopterosin | unspecified | NSAID | arthritis; asthma; psoriasis |
| 2-CdAP | 2-chloro-2'-deoxy-5'-adenylic acid disodium salt | nucleoside analogue | psoriasis |
| CMI 392 | trans-2-[5-(N'-methyl-N'-hydroxyureidylmethyl)-3-methoxy-4-p-chlorophenylthio-ethoxyphenyl]-5-(3,4,5-trimethoxyphenyl)tetrahydrofuran | PAF antagonist; leukotriene antagonist | psoriasis; dermatitis; asthma |
| drug delivery system, SEPA peptide T; peptide T SEPA | unspecified | peptide; TNF inhibitor | psoriasis |
| transglutaminase inhibitor | unspecified | peptide; transglutaminase inhibitor | psoriasis; Alzheimer disease |
| IC 351; GF 196960; GG 960 | unspecified | phosphodiesterase inhibitor, phosphodiesterase V inhibitor | heart failure; angina; sexual dysfunction; psoriasis |
| BMS 181162 | (Z,E,Z,E)-3-[1-(2-carboxy-1-methylethenyl)-4-methyl-6-(2,6,6-trimethyl-1-cyclohexen-1-yl)-1,3,5-hexatrienyl]benzoic acid | phospholipase inhibitor | psoriasis; dermatitis |
| phospholipase A2 inhibitors | unspecified | phospholipase inhibitor; NSAID | asthma; rheumatoid arthritis; psoriasis; inflammatory bowel disease |
| BMS 188184 | 3-[(1Z,2Z)-3-carboxy-2-methyl-1-[(5,6,7,8-tetrahydro-5,5,8,8,-tetramethyl-2-anthracenyl)methylene]-2-propenyl]benzoic acid | phospholipase inhibitor; NSAID | psoriasis; dermatitis; inflammation |
| bergapten; 5-methoxypsoralen; 5-MOP; GERALEN; PSORADERM 5; GEROXALEN | unspecified | photosensitizer | psoriasis |
| hypericin; VIMRxyn; CYCLO-WERROL; CYCLOSAN | 1,3,4,6,8,13-hexahydroxy-10,11-dimethylphenanthro[1,10,9,8-opqra]perylene-7,14-dione | photosensitizer | psoriasis; cancer |
| aminolevulinic acid, photodynamic therapy; 5-ALA PDT; LEVULAN | unspecified | photosensitizer; contrast medium | psoriasis; skin disease; endometriosis; cancer; diagnosis |

TABLE 12-continued

Current Candidate Therapeutic Interventions in Development for the Treatment of Psoriasis

| Product Name | Chemical Name | Action | Indication |
| --- | --- | --- | --- |
| verteporfin; benzoporphyrin derivative; BPD-MA; CL 318952; BPDR; VISUDYNE | trans-18-ethenyl-4,4a-dihydro-3,4-bis(methoxycarbonyl)-4a,8,14,19-tetramethyl-23H,25H-benzo[b]porphine-9,13-dipropanoic acid monomethyl ester | photosensitizer; NSAID | cancer; psoriasis; arthritis; retinopathy |
| diethylhomospermine; DEHOP; DE 444 | N,N'-bis[4-(ethylamino)butyl]-1,4-butanediamine | polyamine analogue | diarrhea; hypertension; cancer; psoriasis; ulcerative colitis |
| diethylnorspermine; DENSPM; CI 1006; DE 333 | N1,N11-diethylnorspermine | polyamine analogue | cancer; psoriasis; Alzheimer disease |
| protein kinase C inhibitor, microalgal | unspecified | protein kinase inhibitor; protein kinase C inhibitor | cancer; psoriasis |
| safingol; safingol hydrochloride; SPC 100270; mSPC 100271; KYNAC; KYNACYTE | (2S,3S)-2-amino-1,3-octadecanediol | protein kinase inhibitor; protein kinase C inhibitor | psoriasis; dermatitis cancer |
| CPR 1006 | 4-hydroxy-7-(1H-imidazol-1-yl)-N,N,N-trimethyl-3,5,9-trioxa-4-phosphaheptacosan-1-aminium, 4-oxide, inner salt | protein kinase inhibitor; protein kinase C inhibitor; ether lipid | psoriasis |
| SPC 100840 | unspecified | protein kinase inhibitor; protein kinase C inhibitor; NSAID | ischemia; psoriasis; cancer; inflammation; reperfusion injury |
| balanol; (−)-balanol; azepinostatin; ophiocordin | (3R-trans)-4-(2-carboxy-6-hydroxybenzoyl)-3,5-dihydroxybenzoic acid 1-[hexahydro-3-[(4-hydroxybenzoyl)amino]-1H-azepin-4-yl]ester | protein kinase inhibitor; protein kinase C inhibitor; NSAID | cancer; inflammation; psoriasis |
| alpha-1-antitrypsin | unspecified | proteinase inhibitor; biotechnology | asthma, emphysema; cystic fibrosis; dermatitis; psoriasis |
| peldesine; BCX 34; BCX 34B | 2-amino-1,5-dihydro-7-(3-pyridinylmethyl)-4H-pyrrolo[3,2-d]pyrimidin-4-one | purine nucleoside phosphorylase inhibitor; immunosuppressant; NSAID | cancer; psoriasis, rheumatoid arthritis; transplant rejection; eye disease; dermatitis; HIV infection |
| purine nucleoside phosphorylase inhibitors, PNP inhibitors, Chiroscience | unspecified | purine nucleoside phosphorylase inhibitor; NSAID | cancer; psoriasis; rheumatoid arthritis; transplant rejection |
| CI 1000; PD 141955 | 2-amino-1,5-dihydro-7-(3-thienylmethyl)-4H-pyrrolo[3,2-d]pyrimidin-4-one | purine nucleoside phosphorylase inhibitor; NSAID | cancer; psoriasis; rheumatoid arthritis |
| cancer therapy, retinoids | unspecified | retinoid | cancer; psoriasis |
| retinoids | unspecified | retinoid | psoriasis; acne |
| acitretin; etretin; etretinate free acid; Ro 101670; Ro 101670000; NEOTIGASON; SORIATANE | (all-E)-9-(4-methoxy-2,3,6-trimethylphenyl)-3,7-dimethyl-2,4,6,8-nonatetraenoic acid | retinoid | psoriasis |
| tazarotene; AGN 190168; ZORAC; TAZORAC | 6-[(3,4-dihydro-4,4-dimethyl-2H-1-benzothiopyran-6-yl)ethynyl]-3-pyridinecarboxylic acid ethyl ester | retinoid | acne; cancer; psoriasis |
| tamibarotene; AM 80 | 4-[[(5,6,7,8-tetrahydro-5,5,8,8-tetramethyl-2-naphthalenyl)amino]carbonyl]benzoic acid | retinoid agonist | psoriasis; cancer |

TABLE 12-continued

Current Candidate Therapeutic Interventions in Development for the Treatment of Psoriasis

| Product Name | Chemical Name | Action | Indication |
| --- | --- | --- | --- |
| AM 580 | 4-[[(5,6,7,8-tetrahydro-5,5,8,8-tetramethyl-2-naphthalenyl)carbonyl]amino]benzoic acid | retinoid agonist | psoriasis; cancer |
| ER 38925 | 4-[5-(4,7-dimethyl-2-benzofuranyl)-1H-pyrrol-2-yl]benzoic acid | retinoid agonist; RARalpha agonist | cancer; psoriasis |
| ER 65250 | 4-[5-(7-ethyl-4-methyl-2-benzofuranyl)-1H-pyrrol-2-yl]benzoic acid | retinoid agonist; RARalpha agonist | cancer; psoriasis |
| ER 69029 | 4-[5-[7-fluoro-4-(trifluoromethyl)-2-benzofuranyl]-1H-pyrrol-2-yl]benzoic acid | retinoid agonist; RARalpha agonist | cancer; psoriasis |
| bexarotene; LGD 1069; LG 100069; LG 1069; LDG 1069; TARGRETIN | 4-[1-(3,5,5,8,8-pentamethyl-5,6,7,8-tetrahydro-2-naphthenyl)-1-ethenyl]-benzoic acid | retinoid agonist; retinoid; differentiation inducer; RXR agonist | cancer; diabetes; psoriasis; skin disease |
| AGN 4310; ALRT 4310 | unspecified | retinoid antagonist | psoriasis; cancer |
| ALRT 1109 | unspecified | retinoid antagonist; RAR antagonist | psoriasis |
| lanreotide; BIM 23014; DC 13116; BIM 23014C; BN 52030; SOMATULINE; ANGIOPEPTIN; DERMOPEPTIN; IPSTYL | 3-(2-naphthalenyl)-D-alanyl-L-cysteinyl-L-tyrosyl-D-tryptophyl-L-lysyl-L-valyl-L-cysteinyl-L-threoninamide cyclic (2,7)-disulfide | somatostatin analogue | cancer; acromegaly; retinopathy; diabetes; psoriasis; restenosis |
| octreotide; octreotide acetate; SMS; SMS 201995; SMS 201995ac; SMS 995; SANDOSTATIN; SANDOSTATINE; SANDOSTATINA; LONGASTATINA; SAMILSTATINA | [R-(R*,R*)]-D-phenylalanyl-L-cysteinyl-L-phenylalanyl-D-tryptophyl-L-lysyl-L-threonyl-N-[2-hydroxy-1-(hydroxymethyl)propyl]-L-cysteinamide cyclic (2-7)-disulfide | somatostatin analogue; analgesic | Alzheimer disease; cancer; viral infection; psoriasis; diarrhea; diabetes; pain; acromegaly |
| AG 85 | 1-[[4-[[(1,4-dihydro-2-methyl-4-oxo-6-quinazolinyl)methyl]-2-propynylamino]phenyl]sulfonyl]-1H-indole | thymidylate synthase inhibitor | psoriasis |
| ITF 1779 | unspecified | TNF inhibitor; NSAID | rheumatoid arthritis; psoriasis; inflammatory bowel disease |
| peptide T, natural; peptide T | N-[N-[N2-[N-[N-[N-(N-L-alanyl-L-seryl)-L-threonyl]-L-threonyl]-L-threonyl]-L-asparaginyl]-L-tyrosyl]-L-threonine | TNF inhibitor; peptide; NSAID | HIV infection; psoriasis; inflammation |
| APC 2059 | unspecified | tryptase inhibitor | inflammatory bowel disease; psoriasis |
| oral tryptase inhibitors | unspecified | tryptase inhibitor | inflammatory bowel disease; asthma; psoriasis |
| tryptase inhibitors | unspecified | tryptase inhibitor; NSAID | asthma; inflammation; rhinitis; inflammatoy bowel disease; psoriasis |
| tyrphostins | unspecified | tyrphostin | psoriasis; cancer; atherosclerosis; septic shock |
| AG 555 | (2E)-2-cyano-3-(3,4-dihydroxyphenyl)-N-(3-phenylpropyl)-2-propenamide | tyrphostin | psoriasis; cancer; atherosclerosis |
| AG 213; RG 50964; tyrphostin AG 213; RG 50864 (no stereo) | (E)-2-cyano-3-(3,4-dihydroxyphenyl)-2-propenethioamide | tyrphostin | psoriasis; cancer; atherosclerosis |
| CHX 108 | unspecified | Unspecified | psoriasis |
| P 53 | unspecified | Unspecified | psoriasis; pruritis |
| SM 10193 | unspecified | Unspecified | psoriasis |
| T 511 | Azelaic acid analogue | unspecified | psoriasis |

TABLE 12-continued

Current Candidate Therapeutic Interventions in Development for the Treatment of Psoriasis

| Product Name | Chemical Name | Action | Indication |
|---|---|---|---|
| vaccine, PVAC, psoriasis; psoriasis vaccine | unspecified | vaccine | psoriasis |
| CPR 2005 | unspecified | vitamin D analogue | psoriasis |
| drug delivery system, vitamin D derivatives | unspecified | vitamin D analogue | psoriasis |
| SH 597 | unspecified | vitamin D analogue | psoriasis |
| calcipotriol; calcipotriene; MC 903, BMS 181161; DAIVONEX; DOVONEX; PSORCUTAN | (1alfa,3beta,5Z,7E,22E, 24S)-24-cyclopropyl-9,10-secochola-5,7,10(19),22-tetraene-1,3,24-triol | vitamin D analogue | psoriasis |
| EL 715 | unspecified | vitamin D2 analogue | psoriasis; osteoporosis; osteodystrophy |
| 1-alpha-D-hydroxycholecalciferol | unspecified | vitamin D3 analogue | psoriasis |
| drug delivery system, polymer, ST 630; ST 630 polymer | unspecified | vitamin D3 analogue | psoriasis |
| tacalcitol; 1alpha,24(R)-dihydrocholecalciferol; 1,24(R)-dihydroxyvitamin D3; TV 02; BONALFA; CURATODERM | (+)-(5Z,7E,24R)9,10-secocholesta-5,7,10(19)-triene-1alpha,3beta,24-triol | vitamin D3 analogue | psoriasis |
| falecalcitriol; flocalcitriol; ST 630; FULSTAN; HORNEL | (1alfa,3beta,5Z,7E)-26,26,26,27,27,27-hexafluoro-9,10-secocholesta-5,7,10(19)-triene-1,3,25-triol | vitamin D3 analogue | osteoporosis; kidney disease; hyperparathyroidism; psoriasis |
| solverol; PRI 1901 | (1R,3S,5Z)4-methylene-5-[(2E)-[(1R,3aS,7aR)-octahydro-1-[(1R,5E)-7-hydroxy-1,7-dimethyl-5-octenyl]-7a-methyl-4H-inden-4-ylidene]ethylidene]-1,3-cyclohexanediol | vitamin D3 analogue; differentiation inducer | cancer; psoriasis |

TABLE 13

Current Candidate Therapeutic Interventions in Development for the Treatment of Athersclerosis

| Product Name | Chemical Name | Action | Indication |
|---|---|---|---|
| AGR 529 | N-(4-amino-4-oxobutyl) adenosine hydrochloride | A1 fat cell receptor antagonist | hypertension; hyperlipidemia |
| AGR 540 | N-(4-amino-4-oxobutyl) adenosine 2',3',5'-tripropanoate | A1 fat cell receptor antagonist; AGR 529 prodrug | hypertension; hyperlipidemia |
| ACAT inhibitor | unspecified | ACAT inhibitor | hyperlipidemia |
| BW 2164U90; BW 2164 | unspecified | ACAT inhibitor | hyperlipidemia |
| FR 129169 | unspecified | ACAT inhibitor | hyperlipidemia |
| NTE 122 | unspecified | ACAT inhibitor | hyperlipidemia; atherosclerosis |
| SKF 98016 | unspecified | ACAT inhibitor | hyperlipidemia |
| terpendole C | unspecified | ACAT inhibitor | hyperlipidemia |
| terpendole D | unspecified | ACAT inhibitor | hyperlipidemia |
| CP 113818 | (S)-(2)-(hexylthio)-N-[6-methyl-2,4-bis(methylthio)-3-pyridinyl]decanamide | ACAT inhibitor | hyperlipidemia |
| CP 105191 | (S)-(2)-(hexylthio)-N-[6-(methylthio)-5-quinolinyl]decanamide | ACAT inhibitor | hyperlipidemia |
| CI 999 | [[2,6-bis(1-methylethyl)phenoxy] sulfonyl]carbamic acid 2,6-bis(1-methylethyl) phenyl ester sodium salt | ACAT inhibitor | hyperlipidemia |

TABLE 13-continued

Current Candidate Therapeutic Interventions in Development for the Treatment of Athersclerosis

| Product Name | Chemical Name | Action | Indication |
|---|---|---|---|
| gypsetin | [5aR-(5aalpha,7aalpha,8abeta, 13abeta, 15aalpha, 16aalpha)]-5a,13a-bis(1,1-dimethyl-2-propenyl)-5a,8,8a,13,13a,15a,16a-octahydro-8a,16a-dihydroxypyrazino[1",2": 1,5;4",5": 1',5']dipyrrolo[2,3-b:2',3'-b']diindole-7,15(5H,7aH)-dione | ACAT inhibitor | hyperlipidemia |
| YM 750 | 1-cycloheptyl-1-(9H-fluoren-2-ylmethyl)-3-(2,4,6-trimethylphenyl) urea | ACAT inhibitor | hyperlipidemia |
| CI 976 | 2,2-dimethyl-N-(2,4,6-trimethoxyphenyl)dodecanamide | ACAT inhibitor | hyperlipidemia |
| AS 183 | 2,4-dimethyl-2-hydroxy-5-(1,3,5,7-tetramethyl-nonyl)-3(2H)-fluronone | ACAT inhibitor | hyperlipidemia |
| RP 64477 | 3-(4-decylcloxybenzamido)-4-methylthio-N-methylthio-N-butylbenzamide | ACAT inhibitor | hyperlipidemia |
| P 06139 | 4-[3-[(4,5-diphenyl-1H-imidazol-2-yl)thio]-2-hydroxypropoxy]-benzoic acid 2-methylpropyl ester | ACAT inhibitor | hyperlipidemia |
| lateritin | 4-methyl-6-(1-methylethyl)-3-phenylmethyl-1,4-perhydrooxazine-2,5-dione | ACAT inhibitor | hyperlipidemia |
| eldacimibe; WAY 125147; ACA 147; ANA 147; WAY-ACA 147 | 5-[[[3,5-bis(1,1-dimethyl-ethyl)-4-hydroxyphenyl]amino][[4-(2,2-dimethylpropyl)phenyl]methyl]hexylamino]methylene]-2,2-dimethyl-1,3-dioxane-4,6-dione | ACAT inhibitor | hyperlipidemia |
| U 73482 | 7,7'-[1,2-ethanediylbis(4,1-piperidinediylmethylene)]-bis[4,9-dimethoxy-5H-furo[3,2-g][1]benzopyran-5-one | ACAT inhibitor | hyperlipidemia |
| lecimibide; DUP 128 | N'-(2,4-difluorophenyl)-N-[5-(4,5-diphenyl-1H-imidazol-2-ylthio)pentyl]-N-heptylurea | ACAT inhibitor | hyperlipidemia |
| HL 004; TS 962 | N-(2,6-diisopropylphenyl)-2-(tetradecylthio)acetamide | ACAT inhibitor | atherosclerosis; hyperlipidemia |
| YM 17E | N,N"-[1,3-phenylenebis(methylene)]bis[N-cycloheptyl-N'-[4-(dimethylamino)phenyl]urea dihydrochloride | ACAT inhibitor | hyperlipidemia |
| F 1394 | N-[(2,2,5,5-tetramethyl-1,3-dioxan-4-yl)carbonyl]-beta-alanine, 2-[[[2,2-dimethylpropyl)nonylamino]carbonyl]aminocyclohexyl ester | ACAT inhibitor | atherosclerosis; hyperlipidemia |
| avasimibe; CI 1011; PD 148515; AVASIMIBE | N-[[2,6-bis(1-methylethyl)phenoxy]sulfonyl]-2,4,6-tris(1-methylethyl)benzeneacetamide | ACAT inhibitor | hyperlipidemia |
| KW 3033 | N-[2,6-bis(1-methylethyl)phenyl]-2-bromo-6,11-dihydrodibenz[b,e]oxepin-11-carboxamide | ACAT inhibitor | hyperlipidemia |
| PD 129337 | N-[2,6-bis(1-methylethyl)phenyl]-N'-phenylcyclopentyl)methyl]urea | ACAT inhibitor | hyperlipidemia |
| PD 1323012; PD 132301-2 | N-[2,6-bis(1-methylethyl)phenyl]-N'-[[1-[4-(dimethylamino)phenyl]cyclopentyl]methyl]urea monohydrochloride | ACAT inhibitor | hyperlipidemia |
| TMP 153 | N-[4-(2-chlorophenyl)-6,7-dimethyl-3-quinolinyl]-N'-(2,4-difluorophenyl)urea | ACAT inhibitor | hyperlipidemia |
| ACAT inhibitor | N-butyl-N'-(2,4-dimethylphenyl)-N-(phenylmethyl)urea | ACAT inhibitor | hyperlipidemia |
| E 5324 | N-butyl-N'-[2-[3-(5-ethyl-4-phenyl-1H-imidazol-1-yl)propoxy]-6-methyl-phenyl]-urea | ACAT inhibitor | hyperlipidemia |
| BW 447C88 | N-heptyl-N'-(2(4-(2,2-dimethylpropyl)phenyl)ethyl)phenyl)urea | ACAT inhibitor | hyperlipidemia |
| ACAT inhibitors | unspecified | ACAT inhibitor; imidazole | hyperlipidemia |
| beauvericin | 1,7,13-trioxa-4,10,16-triazacyclooctadecane cyclic peptide derivative | ACAT inhibitor; peptide | bacterial infection; hyperlipidemia |
| RPR 100579 | unspecified | adenosine agonist | hypertension; heart failure; hyperlipidemia |
| SDZ WAG994; SDZ WAG 994 | N-cyclohexyl-2'-O-methyladenosine | adenosine agonist; adenosine A1 agonist | heart failure; hyperlipidemia |
| SNAP 5150 | N-[3-(4,4-diphenyl-1-piperidinyl)propyl]-1,4-dihydro-2,6-dimethyl-4-(4-nitrophenyl)-3,5-pyridinecarboxamide | alpha adrenergic antagonist; alpha 1 adrenergic antagonist | benign prostate hypertrophy; hyperlipidemia; hypertension |
| colestilan; colestimide; MCI 196; BMS 180543; CHOLEBINE | 1H-imidazole-2-methyl polymer with (chloromethyl)oxirane | anion exchange resin | hyperlipidemia |

TABLE 13-continued

Current Candidate Therapeutic Interventions in Development for the Treatment of Athersclerosis

| Product Name | Chemical Name | Action | Indication |
|---|---|---|---|
| LY 335124 | unspecified | antiestrogen; estrogen agonist | hyperlipidemia |
| raloxifene; keoxifene; LY 139481; LY 156758; EVISTA | [6-hydroxy-2-(4-hydroxyphenyl)benzo[b]thien-3-yl][4-[2-(1-piperidinyl)ethoxy]phenyl]methanone | antiestrogen; estrogen agonist | osteoporosis; hyperlipidemia; myocardial infarction; cancer |
| atpenin B | [S][(R*,S*)]-3-(2,4-dimethyl-1-oxohexyl)-4-hydroxy-5,6-dimethoxy-2(1H)-pyridinone | antifungal | hyperlipidemia; mycosis |
| probucol; DH 581; DE 3872; LORELCO; PANAVIR; SINLESTAL | 4,4'-isopropylidenedithio-bis-2,6-di-t-butylphenol | antioxidant | HIV infection; hyperlipidemia; restenosis |
| L 551369 | N,N'-diphenyl-phenylenediamine | antioxidant | hyperlipidemia |
| CK 3363; CK 3368 | unspecified | bile acid sequestrant | hyperlipidemia |
| GT 102279 | unspecified | bile acid sequestrant | hyperlipidemia |
| ICI 245991 | unspecified | bile acid sequestrant | hyperlipidemia |
| SKF 97426 | unspecified | bile acid sequestrant | hyperlipidemia |
| KF 17828 | 2-bromo-N-(2,6-diisopropylphenyl)-6,11-dihydrodibenz(b,e)oxepin-11-carboxamide | bile acid sequestrant | hyperlipidemia |
| colesevelam hydrochloride; GT 31-104HB; GT 31-104; CholestaGel | N,N,N-trimethyl-6-(2-propenylamino)-1-hexanaminium chloride polymer with (chloromethyl)oxirane, 2-propen-1-amine and N-2-propenyl-1-decanamine hydrochloride | bile acid sequestrant | hyperlipidemia |
| CP 88488 | N-[2-hydroxy-3-(trimethylammonio)propyl] chitosan chloride | bile acid sequestrant | hyperlipidemia |
| DMP 504 | Unspecified | bile acid sequestrant | hyperlipidemia |
| macrophage colony stimulating factor; M-CSF; MACROLIN | unspecified | biotechnology; growth factor; hematopoietic factor; immunostimulant; cicatrizant; antifungal | mycosis; hyperlipidemia; skin ulcer; bacterial infection |
| BN 50394 | unspecified | calcium antagonist | hyperlipidemia; hypertension |
| anipamil; LU 42668 | alpha-dodecyl-3-methoxy-alpha-[3-[[2-(3-methoxyphenyl)ethyl]methylamino]propyl]benzeneacetonitrile | calcium antagonist | hyperlipidemia |
| monatepil; monatepil maleate; monasedin maleate; AJ 2615; AD 2615 | (+,-)-N-(6,11-dihydrodibenzo[b,e]thiepin-11-yl)-4-(4-fluorophenyl)-1-piperazinebutanamide | calcium antagonist; alpha adrenergic antagonist; alpha 1 adrenergic antagonist | hypertension; angina; hyperlipidemia |
| BAY 194798 | unspecified | CETP inhibitor | atherosclerosis; hyperlipidemia |
| BNP 9010 | unspecified | CETP inhibitor | hyperlipidemia |
| cholesteryl ester transfer protein inhibitor, CETP inhibitor | unspecified | CETP inhibitor | hyperlipidemia |
| JTT 705 | unspecified | CETP inhibitor | hyperlipidemia |
| atrinositol; PP 56 | D-myo-inositol 1,2,6-tris(dihydrogen phosphate) | chelating agent; NSAID | inflammation; hyperlipidemia |
| NIP 200 | 3,5-dimethyl-4,6-diphenyl-tetrahydro-2H-1,3,5-thiadiazine-2-thione | Cholesterol 7-alpha hydoxylase inhibitor | hyperlipidemia |
| tiqueside; beta-tigogenin cellobioside; CP 88818 | (3beta,5alpha,25R)-spirostan-3-yl-4-O-beta-D-glucopyranosyl-beta-D-glucopyranoside | cholesterol absorption inhibitor | hyperlipidemia |
| SCH 48461 | (3R-trans)-1,4-bis(4-methoxyphenyl)-3-(3-phenylpropyl)-2-azetidinone | cholesterol absorption inhibitor | hyperlipidemia |
| CVT 1 | unspecified | cholesterol absorption inhibitor; polysaccharide sulfate | hyperlipidemia |
| CEB 925 | unspecified | cholesterol hydrolase inhibitor | hyperlipidemia |
| WAY 121751 | unspecified | cholesterol hydrolase inhibitor | hyperlipidemia |
| WAY 121898 | unspecified | cholesterol hydrolase inhibitor | hyperlipidemia |
| policosanol; ATEROMIXOL | unspecified | Cholesterol lowering | hyperlipidemia |
| fatty acids, microalgal | unspecified | Cholesterol lowering agent | hyperlipidemia; Parkinson disease; Alzheimer disease; eye disease |

TABLE 13-continued

Current Candidate Therapeutic Interventions in Development for the Treatment of Athersclerosis

| Product Name | Chemical Name | Action | Indication |
|---|---|---|---|
| hyperlipidemia therapy | unspecified | Cholesterol reduction | hyperlipidemia |
| MC 031 | unspecified | cholesterol synthesis inhibitor | hyperlipidemia |
| MC 032 | unspecified | cholesterol synthesis inhibitor | hyperlipidemia |
| MC 033 | unspecified | cholesterol synthesis inhibitor | hyperlipidemia |
| MC 034 | unspecified | cholesterol synthesis inhibitor | hyperlipidemia |
| SQ 34919 | unspecified | cholesterol synthesis inhibitor | hyperlipidemia |
| azalanstat; azalanstat dihydrochloride; RS 21607; RS 21607-197 | (2S-cis)-4-[[[2-[2-(4-chlorophenyl)ethyl]-2-(1H-imidazol-1-ylmethyl)-1,3-dioxolan-4-yl]methyl]thio]benzenamine | cholesterol synthesis inhibitor | hyperlipidemia |
| lifibrol; K 12148 | 4-[4-[4-(1,1-dimethylethyl)phenyl]-2-hydroxybutoxy]benzoic acid | cholesterol synthesis inhibitor | hyperlipidemia |
| MEDICA 16 | beta, beta-tetramethyl hexadecanedioic acid | cholesterol synthesis inhibitor | hyperlipidemia |
| MDL 28815 | N-[(1,5,9)-trimethyldecyl]-4alpha, 10dimethyl-8-aza-trans-decal-3beta-ol | cholesterol synthesis inhibitor | hyperlipidemia |
| acipimox; K 9321; OLBETAM; OLBEMOX; ACIPIMOX; NEDIOS | 5-methylpyrazinecarboxylic acid 4-oxide | Cyclic AMP inhibition; hormone sensitive lipase inhibitor | hyperlipidemia |
| AHL 157 | unspecified | fibrate | hyperlipidemia |
| drug delivery system, gemfibrozil; gemfibrozil sustained release; LOPID PUSH-PILL OROS | unspecified | fibrate | hyperlipidemia |
| drug delivery system, gemfibrozil; gemfibrozil sustained release; LOPID SR | unspecified | fibrate | hyperlipidemia |
| ciprofibrate; WIN 35833; LIPANOR; HYPERLIPEN; MODALIM; ESTAPROL | 2-(p-(2,2-dichlorocyclopropyl)phenoxy)-2-methylpropionic acid | fibrate | hyperlipidemia |
| fenofibrate; fenofibrato; procetofene; LF 178; LIPANTHYL; LIPANTIL; LIPIDIL; LIPSIN; NORMALIP; BISTEROL; NORMOLIP; PROMERAL; LIPCOR; TRICOR | 2-[4-(4-chlorobenzoyl)phenoxy]-2-methylpropanoic acid 1-methylethyl ester | fibrate | hyperlipidemia |
| gemfibrozil; CI 719; CS 719; LOPID; ZILOP; IPOLIPID; MARISTON; DELIPID; SCANTIPID | 5-(2,5-dimethylphenoxy)-2,2-dimethylpentanoic acid | fibrate | hyperlipidemia |
| F 2875 | [2'-chloro-4-(1,1')-biphenyl]methyl-1-(imidazolyl)acetate | free radical scavenger | hyperlipidemia |
| cilmostim; macrophage colony stimulating factor; M-CSF; MACSTIM | unspecified | growth factor; hematopoietic factor; immunostimulant | hyperlipidemia; bacterial infection; cancer |

TABLE 13-continued

Current Candidate Therapeutic Interventions in Development for the Treatment of Athersclerosis

| Product Name | Chemical Name | Action | Indication |
|---|---|---|---|
| high-density lipoproteins | HDL synthetic particles | HDL stimulation | hyperlipidemia; atherosclerosis |
| BRL 39924A | 1-[3-[[(3alfa,5beta)-3-hydroxy-24-oxocholan-24-yl]amino]propyl]-1,4,4-trimethylpiperazinium diiodide | HDL stimulator | hyperlipidemia |
| supersulfated low molecular weight heparin; ssLMWH | unspecified | heparinoid | thrombosis; hyperlipidemia |
| pentosan polysulfate sodium; SP 54; PZ 68; CARTROPHEN; LASONIL; ELMIRON; LELONG MOUSSE | (1-4)-beta-D-xylan 2,3-bis(hydrogen sulfate), sodium salt | heparinoid; vasodilator; NSAID | arthritis; angina; hyperlipidemia; rheumatold arthritis; cancer; cystitis |
| BAY 102987 | unspecified | HMG CoA reductase inhibitor | hyperlipidemia |
| BAY w 9533 | unspecified | HMG CoA reductase inhibitor | hyperlipidemia |
| BB 476 | unspecified | HMG CoA reductase inhibitor | hyperlipidemia |
| BMS 180436 | unspecified | HMG CoA reductase inhibitor | hyperlipidemia |
| BMY 22566 | unspecified | HMG CoA reductase inhibitor | hyperlipidemia |
| DMP 565 | unspecified | HMG CoA reductase inhibitor | hyperlipidemia |
| GR 95030 | unspecified | HMG CoA reductase inhibitor | hyperlipidemia |
| S 853758A | unspecified | HMG CoA reductase inhibitor | hyperlipidemia |
| S 861006A | unspecified | HMG CoA reductase inhibitor | hyperlipidemia |
| ZD 4522; S 4522; VISACOR | unspecified | HMG CoA reductase inhibitor | hyperlipidemia |
| glenvastatin; HR 780; HOE 780 | (E)-6(S)-2-[4-(fluorophenyl)-2-(2-methylethyl)-6-phenylpyridin-3-yl]ethenyl]-4(R)-hydroxy-3,4,5,6-tetrahydro-2H-pyran-2-one | HMG CoA reductase inhibitor | hyperlipidemia |
| lovastatin; mevinolin; monakolin K; MK 803; MSD 803; MB 530B; L 154803; MEVACOR; MEVLOR; LOVACOL; HIPOVASTIN; DISLIPIN; LOVASTEROL; LINCIL | (S)-2-methylbutyric acid, 8-ester with (4R,6R)-6-[2-[(1S,2S,6R,8S,8aR)-1,2,6,7,8,8a-hexahydro-8-hydroxy-2,6-dimethyl-1-naphthyl]ethyl]tetrahydro-4-hydroxy-2H-pyran-2-one | HMG CoA reductase inhibitor | hyperlipidemia; cancer |
| SQ 33600 | (S)-4-[[[1-(4-fluorophenyl)-3-(1-methylethyl)-1H-indol-2-yl]ethynyl]hydroxyphosphinyl]-3-hydroxybutanoic acid | HMG CoA reductase inhibitor | hyperlipidemia |
| U 88156 | [1alpha(E),4beta]-3-[2-(4-hydroxy-1-methylcyclohexyl)ethenyl]-alpha,alpha-dimethylbenzenepentanol | HMG CoA reductase inhibitor | hyperlipidemia |
| pravastatin; eptastatin; epastatin; CS 514; SQ 31000; RMS 431; LIPOSTAT; MEVALOTIN; PRAVACHOL, PRAVASTATIN; SELECTIN; LIPREVIL; PREVACOL; PRAVASIN; APLACTIN; BRISTACOL | [1S-[1alfa(betaS*,deltaS*),2alfa,6alfa,8beta(R*),8aalfa]]-1,2,6,7,8,8a-hexahydro-beta,delta,6-trihydroxy-2-methyl-8-(2-methyl-1-oxobutoxy)-1-naphthaleneheptanoic acid | HMG CoA reductase inhibitor | hyperlipidemia; myocardial infarction |
| L 669262 | [1S-[1alfa,7beta,8beta(2S*,45*),8abeta]] 1,2,6,7,8,8a-hexahydro-3,7-dimethyl-6-oxo-8-[2-(tetrahydro-4-hydroxy-6-oxo-2H-pyran-2-yl)ethyl]-1-naphthalenyl ester of 2,2-dimethylbutanoic acid | HMG CoA reductase inhibitor | hyperlipidemia |

TABLE 13-continued

Current Candidate Therapeutic Interventions in Development for the Treatment of Athersclerosis

| Product Name | Chemical Name | Action | Indication |
|---|---|---|---|
| RP 61969 | [2S-[2alfa(E),4beta]]-4-(4-fluorophenyl)-2-(1-methylethyl)-3-[2-(tetrahydro-4-hydroxy-6-oxo-2H-pyran-2-yl)ethenyl]-1(2H)-isoquinolinone | HMG CoA reductase inhibitor | hyperlipidemia |
| dalvastatin; RG 12561 | [4alfa,6beta(E)]-(+,−)-6-[2-2-(4-fluoro-3-methylphenyl)-4,4,6,6-tetramethyl-1-cyclohexen-1-yl]ethenyl]tetrahydro-4-hydroxy-2H-pyran-2-one | HMG CoA reductase inhibitor | hyperlipidemia |
| nisbastatin; NK 104 | [4R-[4alpha,6beta(E)]]-6-[2-[2-cyclopropyl-4-(4-fluorophenyl)-3-quinolinyl]ethenyl] tetrahydro-4-hydroxy-2H-pyran-2-one | HMG CoA reductase inhibitor | hyperlipidemia |
| atorvastatin; atorvastatin calcium; CI 981; PD 1342 98; YM 548; LIPITOR; SORTIS | [R-(R*,R*)]-2-(4-fluorophenyl)-beta,delta-dihydroxy-5-(1-methylethyl)-3-phenyl-4-[(phenylamino)carbonyl]-1H-pyrrole-1-heptanoic acid | HMG CoA reductase inhibitor | hyperlipidemia |
| CP 83101 | [R*,S*-(E)]-(+,−)-3,5-dihydroxy-9,9-diphenyl-6,8-nonadienoic acid methyl ester | HMG CoA reductase inhibitor | hyperlipidemia |
| fluvastatin; fluindostatin; XU 62320; LESCOL; LOCOL; LOCHOL; FRACTAL | [R*,S*-(E)]-(+,−)-7-[3-(4-fluorophenyl)-1-(1-methylethyl)-1H-indol-2-yl]-3,5-dihydroxy-6-heptenoic acid | HMG CoA reductase inhibitor | hyperlipidemia |
| BMS 180431; BMS 18043109; BMY 21950 | [R*,S*-(E)]-(+,−)-9,9-bis(4-fluorophenyl)-3,5-dihydroxy-8-(1-methyl-1H-tetrazol-5-yl)-6,8-nonadienoic acid | HMG CoA reductase inhibitor | hyperlipidemia |
| cerivastatin; rivastatin; BAY w 6228; LIPOBAY; BAYCOL; LIPOSTEROL; CERVASTA; VASLIP; SELTA; CERTA | [S-[R*,S*-(E)]]-7-[4-(4-fluorophenyl)-5-(methoxymethyl)-2,6-bis(1-methylethyl)-3-pyridinyl]-3,5-dihydroxy-6-heptenoic acid | HMG CoA reductase inhibitor | hyperlipidemia |
| simvastatin analogue | 2,2-dimethylbutanoic acid octahydro-3,7-dimethyl-4-hydroxy-8-(2-(tetrahydro-4-hydroxy-6-oxo-2H-pyran-2yl)ethyl)-1-naphthaleny ester | HMG CoA reductase inhibitor | hyperlipidemia |
| pannorin | 4,8,10-trihydroxy-5-methyl-2H-naphtho[1,2-b]pyran-2-one | HMG CoA reductase inhibitor | hyperlipidemia |
| simvastatin analogue; L 679336 | 6(R)-(2-(8(S)-(2,2-dimethylbutyryl)oxy)-2(S),6(R)-dimethyl-5(R)-hydroxy-1,2,3,4,4a(R),5,6,7,8,8a(R)-decahydronaphthyl-1(S))ethyl)-4-(R)-hydroxy-3,4,5,6-tetrahydro-2H-pyran-2-one | HMG CoA reductase inhibitor | hyperlipidemia |
| hypolipemic AMMCA | 6-amino-1,2-dihydro-5-methyl-2-thioxo-4-pyrimidinecarboxylic acid | HMG CoA reductase inhibitor | hyperlipidemia |
| BAY x 2678 | unspecified | HMG CoA reductase inhibitor; cholesterol synthesis inhibitor | hyperlipidemia |
| simvastatin; epistatin; synvinolin; velostatin; MK 733; L 654; L 644128; 590328; ZOCOR; DENAN; MEDIPO; SIMOVIL; COLEDIS | 2,2-dimethylbutanoic acid[1S-[1alfa,3alfa,7beta,8beta(2S*,4S*)8abeta]] 1,2,3,7,8,8a-hexahydro-3,7-dimethyl-8-[2-(tetrahydro-4-hydroxy-6-oxo-2H-pyran-2-yl)ethyl]-1-naphthalenyl ester | HMG CoA reductase inhibitor; osteoanagenetic | hyperlipidemia; osteoporosis |
| A 1233; 1233 A | unspecified | HMG CoA synthase inhibitor | hyperlipidemia |
| L 659699; F 244 | [2R-[2alfa(2E,4E,7R*),3beta]]-11-[3-(hydroxymethyl)-4-oxo-2-oxetanyl]-3,5,7-trimethyl-2,4-undecadienoic acid | HMG CoA synthase inhibitor | hyperlipidemia |

TABLE 13-continued

Current Candidate Therapeutic Interventions in Development for the Treatment of Athersclerosis

| Product Name | Chemical Name | Action | Indication |
|---|---|---|---|
| CHOLESS inhibitor of mevalonate incorporation into cholesterol; IMIC | unspecified unspecified | immunostimulant inhibitor of mevalonate incorporation into cholesterol | hyperlipidemia cancer; hyperlipidemia |
| DRF 2725 | unspecified | insulin sensitizer | diabetes; hyperlipidemia |
| englitazone; englitazone sodium; CP 68722; CP 72466; CP 72467; CP 724672 | (−)-5-[[(2R)-2-benzyl-6-chromanyl]methyl]-2,4-thiazolidinedione | insulin sensitizer | diabetes; hyperlipidemia |
| TA 1801 | ethyl 2-(4-chlorophenyl)-5-(2-furyl)-4-oxazoleacetate | Intestinal cholesterol absorption inhibitor | hyperlipidemia |
| AJ 814 | unspecified | Intestinal lipid absorption inhibitor | hyperlipidemia |
| LF 70165c | N-methyl-N,N-bis(2-hydroxyethyl)-N-[3-[(3beta,5alpha,25R)-spirostan-3-yloxy]propyl]ammonium chloride | Intestinal lipid absorption inhibitor | hyperlipidemia |
| hypolipidemic, Sam Il | unspecified | LDL lowering agent | hypertipidemia |
| S 12340 | 8-[3-[3,5-bis(1,1-dimethylethyl)-4-hydroxyphenyl]thio]propyl]-1-oxa-3,8-diazaspiro[4.5]decan-2-one | LDL peroxidation inhibition | hyperlipidemia |
| LY 295427 | (3A,4A,5A)-4-(2-propenylcholestan-3-ol | LDL receptor upregulator | hyperlipidemia |
| BAY 139952 | unspecified | LDL reduction | hyperlipidemia |
| CGP 26214 | unspecified | LDL regulator | hyperlipidemia; atherosclerosis |
| E 5050 | 4-(2,6-dimethylheptyl)-N-(2-hydroxyethyl)-beta-methyl-benzenepropanamide | LDL uptake stimulator | hyperlipidemia |
| crilvastatin; PMD 387 | 5-oxo-proline,(+,−)-cis-3,3,5-trimethyicyclohexyl ester | LDL-cholesterol stimulate uptake; potent ACAT inhibition | hyperlipidemia |
| FL 386 | trans-1-[4-(2-methylpropyl)cyclohexyl]-2-[(phenylsulfonyl)oxy]ethanone | lipase inhibitor | hyperlipidemia |
| K 85; OMACOR | Omega 3 fatty acids | Lipid lowering | hyperlipidemia; restenosis |
| apolipoprotein E | unspecified | lipid, cholesterol, triglyceride lowering agent | hyperlipidemia |
| pro-apolipoprotein AI | unspecified | lipid, cholesterol, triglyceride lowering agent | hyperlipidemia |
| yeast-derived dietary fiber; FIBBRCEL; CHOLESTRAN; CHOLAZOL | unspecified | lipid, chotesterol, triglyceride lowering agent | hyperlipidemia |
| NO 1886 | [[4-[[4-bromo-2-cyanophenyl)amino]carbonyl]phenyl]methyl]-phosphonic acid, diethyl ether | lipoprotein lipase activator | hyperlipidemia |
| imanixil; HOE 402 | 4-amino-2-(4,4-dimethyl-2-oxo-1-imidazolidinyl)-alpha,alpha,alapha-trifluoro-5-pyrimidinecarboxy-m-tolidide | lipoprotein regulator | hyperlipidemia |
| BMS 212122 | unspecified | microsomal transfer protein inhibitor | hyperlipidemia |
| GW 328713; GR 328713 | unspecified | microsomal transfer protein inhibitor | hyperlipidemia |
| JTT 722 | unspecified | microsomal transfer protein inhibitor | hyperlipidemia; obesity |
| BMS 201038 | Unspecified | microsomal transfer protein inhibitor | hyperlipidemia |
| MAb, LDL and Fc; bispecific antibody, low density lipoprotein | unspecified | monoclonal antibody | hyperlipidemia |
| drug delivery system, sustained release niacin; niacin sustained release; NIASPAN | unspecified | Niacin sustained release | hyperlipidemia |

TABLE 13-continued

Current Candidate Therapeutic Interventions in Development for the Treatment of Athersclerosis

| Product Name | Chemical Name | Action | Indication |
|---|---|---|---|
| leucomyzin | unspecified | NSAID | inflammation; hyperlipidemia |
| orlistat; orlipastat; tetra-hydrolipistatin; THL; Ro 180647; XENICAL | N-formyl-L-leucine [2S-[2alpha(R*),3beta]]-1-[(3-hexyl-4-oxo-2-oxetanyl)methyl] dodecyl ester | pancreatic lipase inhibitor | obesity; hyperlipidemia; diabetes |
| LA 230 | unspecified | peptide | hypertension; hyperlipidemia |
| ethyl eicosa-pentaenoate; ethyl icosa-pentate; EPA-E; MND 21; EPADEL | ethyl all-cis-5,8,11,14,17-eicosapentaenoate | platelet antiaggregant | thrombosis; hyperlipidemia |
| AL 0671 | (1S-endo)-N-(6-amino-3-pyridinyl)-N'-bicyclo[2.2.1]hept-2-yl-N''-cyanoguanidine | potassium channel activator | hyperlipidemia; hypertension |
| MDL 29311 | 4,4'-(methylenebis[thio])bis(2,6-bis[1,1-dimethylethyl)phenol | Probucol analogue antioxidant; LDL inhibitor | diabetes; hyperlipidemia |
| BMY 42393 | 2-[3-[2-(4,5-diphenyl-2-oxazolyl)ethyl)phenoxy]acetic acid | prostaglandin agonist; platelet antiaggregant | hyperlipidemia; thrombosis |
| KB 5246 | 6-fluoro-5-(4-methyl-1-piperazinyl)-8-oxo-3H,8H-4-oxa-1-thia-9b-azacyclopenta[cd]phenalene-9-carboxylic acid monohydrochloride | quinolone; antibiotic | cancer; pruritis; hypertension; HIV infection; gastrointestinal ulcer; hyperlipidemia; bacterial infection |
| BIBX 245 | unspecified | Squalene cyclase inhibitor | hyperlipidemia |
| NB 598 | (E)-3-([3,3'-bithiophen]-5-ylmethoxy)-N-(6,6-dimethyl-2-hepten-4-ynyl)-N-ethyl-benzenemethanamine | squalene epoxidase inhibitor | hyperlipidemia |
| RPR 107393 | 3-hydroxy-3-[4-(quinolin-6-yl)phenyl]-1-azabicyclo[2-2-2]octane dihydrochloride | squalene synthase inhibitor | hyperlipidemia |
| RPR 101821 | trans-2-[4-(benzoxazol-2-yl)-phenylmethoxy]amino cyclohexane HCl | squalene synthase inhibitor | hyperlipidemia |
| GR 105155 | unspecified | squalene synthetase inhibitor | hyperlipidemia |
| squalestatins | unspecified | squalene synthetase inhibitor | hyperlipidemia |
| squalestatin 1; zaragozic acid A; L 694599 | [5(2E,4S,6S),7S]-2,7-anhydro-3,4-di-C-carboxy-8,9,10,12,13-pentadeoxy-10-methylene-12-(phenylmethyl)-L-erythro-L-glycero-D-altro-7-trideculo-7,4-furanosonic acid 11-acetate 5-(4,6-dimethyl-2-octenoate) | squalene synthetase inhibitor | hyperlipidemia |
| BMS 188494 | 2,2-dimethylpropanoic acid [[4-(3-phenoxyphenyl)-1-sulfobutyl]phosphinylidene] bis(oxymethylene)ester | squalene synthetase inhibitor | hyperlipidemia |
| thyroid hormone receptor beta agonist, thyroid hormone receptor beta agonist | unspecified | thyroid hormone agonist | obesity; hyperlipidemia |
| transcription factor regulators, antihyper-cholesterolemia | unspecified | transcription factor regulator | hyperlipidemia |
| antiatherosclerotic agents | unspecified | Unspecified lipid, cholesterol, triglyceride lowering agent | atherosclerosis; hyperlipidemia |
| BOF 6721 | unspecified | Unspecified lipid, cholesterol, triglyceride lowering agent | hyperlipidemia |
| BOF 6766 | unspecified | Unspecified lipid, cholesterol, triglyceride lowering agent | hyperlipidemia |
| CDRI 80574 | unspecified | Unspecified lipid, cholesterol, triglyceride lowering agent | hyperlipidemia |
| CR 2083 | unspecified | Unspecified lipid, cholesterol, triglyceride lowering agent | hyperlipidemia |
| diabetes therapy | unspecified | Unspecified lipid, cholesterol, triglyceride lowering agent | diabetes; obesity; hyperlipidemia |
| FCP 3P1 | unspecified | Unspecified lipid, cholesterol, triglyceride lowering agent | atherosclerosis; hyperlipidemia |
| N 1197 | unspecified | Unspecified lipid, cholesterol, triglyceride lowering agent | hyperlipidemia |
| SRI 62320; SRI 6230 | unspecified | Unspecified lipid, cholesterol, triglyceride lowering agent | hyperlipidemia |

TABLE 13-continued

Current Candidate Therapeutic Interventions in Development for the Treatment of Athersclerosis

| Product Name | Chemical Name | Action | Indication |
|---|---|---|---|
| CGS 23425 | [[4-[4-hydroxy-3-(1-methylethyl)phenoxy]-3,5-dimethylphenyl]amino]oxoacetic acid | Unspecified lipid, cholesterol, triglyceride lowering agent | hyperlipidemia |
| compound 10 | 2-acetylthio-3-[4-(phenylthio)benzoyl]propionic acid | Unspecified lipid, cholesterol, triglyceride lowering agent | hyperlipidemia |
| F 2833 | 2'-chloro-alpha,alpha-dimethyl-[1,1'-biphenyl]-4-methanol | Unspecified lipid, cholesterol, triglyceride lowering agent | hyperlipidemia |
| LM 1554 | 2-chloromethyl-5,6,7,8-tetrahydro-benzo(b)thieno(2,3-d)pyrimidin-4(3H)-one | Unspecified lipid, cholesterol, triglyceride lowering agent | hyperlipidemia |
| RP 54275 | 2-n-octadecylindole-5-carboxylic acid | Unspecified lipid, cholesterol, triglyceride lowering agent | hyperlipidemia |
| xenalipin; BW 207U; BW 207 | 4'-(trifluoromethyl)-2-biphenylcarboxylic acid | Unspecified lipid, cholesterol, triglyceride lowering agent | hyperlipidemia |
| acifran; AY 25712; REDUCTOL | 4,5-dihydro-5-methyl-4-oxo-5-phenyl-2-furancarboxylic acid | Unspecified lipid, cholesterol, triglyceride lowering agent | hyperlipidemia |
| P 06103 | 4-[3-[(6-amino-9-beta-D-ribofuranosyl-9H-purin-8-yl)thio]-2-oxopropoxy]-benzoic acid 2-methylpropyl ester | Unspecified lipid, cholesterol, triglyceride lowering agent | hyperlipidemia |
| MKC 121 | 4-tridecylpyrrole-2-carboxylic acid | Unspecified lipid, cholesterol, triglyceride lowering agent | hyperlipidemia |
| P 0654 | 8-[3-[4-(2-methylpropyloxycarbonyl)phenoxy]-2-(R)-hydroxypropyl]adenosine | Unspecified lipid, cholesterol, triglyceride lowering agent | hyperlipidemia |
| hypolipemic | 8-O,N-dipivaloyl-3-(N'-(2,4,6-trimethylbenzyl)-N-piperazinyl)rifamycin S | Unspecified lipid, cholesterol, triglyceride lowering agent | hyperlipidemia |
| CGS 24565 | N,15-didehydro-11,15-dideoxo-1-deoxy-1,15-epoxy-11-hydroxy-4-O-methyl-3-[4-[(2,4,6-trimethylphenyl)methyl]-1-piperazinyl]rifamycin 8-(2,2-dimethylpropanoate) | Unspecified lipid, cholesterol, triglyceride lowering agent | hyperlipidemia |
| CGP 43371 | N,15-didehydro-15-deoxo-1-deoxy-1,15-epoxy-3-[4-[(2,4,6-trimethylphenyl)methyl]-1-piperazinyl]rifamycin 8-(2,2-dimethylpropanoate) | Unspecified lipid, cholesterol, triglyceride lowering agent | hyperlipidemia |
| LS 2904 | Unspecified | Unspecified lipid, cholesterol, triglyceride lowering agent | hyperlipidemia |
| NIP 261 | unspecified | VLDL catabolism stimulator; HDL synthesis stimulator | hyperlipidemia |
| S 2E | (S)-(+)-4-[[1-[4-(1,1-dimethylethyl)phenyl]-5-oxo-3-pyrrolidinyl]methoxy]benzoic acid | VLDL formation inhibitor | hyperlipidemia; atherosclerosis |

TABLE 16

Current Candidate Therapeutic Interventions in Development for the Treatment of Asthma

| Product Name | Chemical Name | Action | Indication |
|---|---|---|---|
| 3323W | unspecified | 5 lipoxygenase inhibitor | asthma |
| CMI 977 | Unspecified | 5 lipoxygenase inhibitor | asthma |
| ZD 4407 | (2S-trans)-1,3-dihydro-1-methyl-5-[[4-(tetrahydro-4-hydroxy-2-methyl-2H-pyran-4-yl)-2-thienyl]thio]-2H-indol-2-one | 5 lipoxygenase inhibitor | asthma |
| WY 50295; WY 50295 tromet | (S)-alpha-methyl-6-(2-quinolinylmethoxy)-2-naphthaleneacetic acid | 5 lipoxygenase inhibitor | asthma; rhinitis |
| SB 202235 | (S)—N-(2,3-dihydro-6-phenylmethoxy-3-benzofuranyl)urea | 5 lipoxygenase inhibitor | asthma |
| L 739010 | 1,6-anhydro-3-C-[6-[[[7-cyano-5-(3-furanyl)-2-naphthalenyl]oxy]methyl]-2-pyridinyl]-2,4-dideoxy-beta-D-threo-hexopyranose | 5 lipoxygenase inhibitor | asthma |
| FR 110302 | 2,2-dibutyl-1,2,3,4-tetrahydro-5-(2-quinolinylmethoxy)-1-naphthalenol | 5 lipoxygenase inhibitor | asthma |
| bunaprolast; U 66858 | 2-butyl-4-methoxy-1-naphthalenol acetate | 5 lipoxygenase inhibitor | asthma |

TABLE 16-continued

Current Candidate Therapeutic Interventions in Development for the Treatment of Asthma

| Product Name | Chemical Name | Action | Indication |
| --- | --- | --- | --- |
| TZI 41127 | 4-(5-methoxy-3-methyl-1H-indol-2-yl)-2,6-dimethylphenol | 5 lipoxygenase inhibitor | asthma |
| linazolast; TMK 688; YM 257 | 4-[5-[[2-[4-(diphenylmethoxy)-1-piperidinyl]ethyl]amino]-5-oxo-1,3-pentadienyl]-2-methoxyphenylcarbonic acid ethyl ester | 5 lipoxygenase inhibitor | asthma; rhinitis |
| L 691816 | 5-[3-[1-(4-chlorobenzyl)-4-methyl-6-[(5-phenylpyridin-2-yl)methoxy]-4,5-dihydro-1H-thiopyrano[2,3,4-c,d]indol-2-yl]-2,2-dimethylpropyl]-1H-tetrazole | 5 lipoxygenase inhibitor | asthma |
| docebenone; AA 861 | 6-(12-hydroxy-5,10 dodecadiynyl)-2,3,5-trimethyl-1,4-benzoquinone | 5 lipoxygenase inhibitor | asthma; heart failure |
| PF 5901 | alpha-pentyl-3-(2-quinolinylmethoxy)-benzenemethanol | 5 lipoxygenase inhibitor | asthma |
| BW B70C | N-[3-[3-(4-fluorophenoxy)phenyl]-1-methyl-2-propenyl]-N-hydroxyurea | 5 lipoxygenase inhibitor | asthma |
| R 85355 | Unspecified | 5 lipoxygenase inhibitor | asthma; psoriasis; inflammatory bowel disease |
| CHF 1909 | Unspecified | 5 lipoxygenase inhibitor; NSAID | inflammation; asthma |
| GR 80907 | Unspecified | 5 lipoxygenase inhibitor; NSAID | asthma; inflammation |
| SC 45662 | Unspecified | 5 lipoxygenase inhibitor; NSAID | inflammation; asthma; psoriasis; inflammatory bowel disease |
| CGS 25997 | (2S)-(−)-2-[[N-(aminocarbonyl)-N-hydroxyamino]methyl]-7-(4-fluorophenoxy)-1,4-benzodioxan | 5 lipoxygenase inhibitor; NSAID | asthma; inflammation |
| L 663536; MK 886 | 1-[(4-chlorophenyl)methyl)-3-[(1,1-dimethylethyl)thio]-alfa,alfa-diethyl-5-(1-methylethyl)-1H-indole-2-propanoic acid | 5 lipoxygenase inhibitor; NSAID | inflammation; asthma; psoriasis |
| L 699333 | 2-[2-[1-[(4-chlorophenyl)methyl]-4,5-dihydro-4-methyl-6-[(5-phenyl-2-pyridinyl)methoxy]-1H-thiopyrano[2,3,4-cd]indol-2-yl]ethoxy]butanoic acid | 5 lipoxygenase inhibitor; NSAID | asthma; inflammation |
| E 6080 | 4-[[(6-hydroxy-4,4,7-trimethyl-2-benzothiazolyl)amino]methyl]benzene-sulfonamide monohydrochloride | 5 lipoxygenase inhibitor; NSAID | asthma; inflammation |
| L 651392 | 4-bromo-2,7-methoxy-3H-phenothiazin-3-one | 5 lipoxygenase inhibitor; NSAID | inflammation; bacterial infection; asthma |
| ZD 2138; ICI D2138 | 6-[[3-fluoro-5-(tetrahydro-4-methoxy-2H-pyran-4-yl)phenoxy]methyl]-1-methyl-2(1H)-quinolinone | 5 lipoxygenase inhibitor; NSAID | arthritis; asthma |

TABLE 16-continued

Current Candidate Therapeutic Interventions in Development for the Treatment of Asthma

| Product Name | Chemical Name | Action | Indication |
|---|---|---|---|
| ZD 7717; ICI D7717 | 7-[[3-fluoro-5-(tetrahydro-4-methoxy-2H-pyran-4-yl)phenyl]thio]-4-methyl-2H-1,4-benzoxazin-3(4H)-one | 5 lipoxygenase inhibitor; NSAID | asthma; inflammation |
| zileuton; A 64077; ABBOTT 64077; ZYFLO | N-(1-benzo[b]thien-2-ylethyl)-N-hydroxyurea | 5 lipoxygenase inhibitor; NSAID | inflammation; asthma |
| TA 270 | N-[1,2-dihydro-4-hydroxy-1-methyl-3-(octyloxy)-2-oxo-7-quinolinyl]-3-(4-hydroxy-3,5-dimethoxyphenyl)-2-propenamide | 5-lipoxygenase inhibitor; | asthma, rhinitis |
| GW 328267 | Unspecified | adenosine antagonist; adenosine A2 antagonist | asthma |
| midaglizole; DG 5128 | 2-[2-(4,5-dihydro-1H-imidazol-2-yl)-1-phenylethyl]pyridine | alpha adrenergic antagonist; alpha2 adrenergic antagonist | asthma; diabetes |
| melanocortin receptor-1 modulators, Trega Biosciences | Unspecified | analgesic; melanocortin agonist; melanocortin MC1 agonist | asthma; pain; nephritis |
| LA 351 | 5H-(1)-benzopyrano(2,3-b)pyridin-5-one | analgesic; NSAID | inflammation; pain; asthma |
| HP 228 | N-acetyl-Nleu-Gln-His-Phe-Arg-Trp-Gly-amide | analgesic; NSAID; peptide; melanocortin agonist | pain; inflammation; asthma; cachexia |
| anti-inflammatory macrolide analogues, KOSAN | Unspecified | antibiotic; macrolide | asthma; inflammation |
| SB 226882 | 4-[4-(4-fluorophenyl)-1-(4-piperidinyl)-1H-imidazol-5-yl)-N-methyl-2-pyrimidinamine | antifungal; MAP kinase inhibitor; signal transduction inhibitor; imidazole | inflammation; asthma; rheumatoid arthritis |
| U 75412E | (16alpha)-21-[4-[3-(ethylamino)-2-pyridinyl]-1-piperazinyl]-16-methylpregna-1,4,9(11)-triene-3,20-dione (2Z)-2-butenedioate (1:1) | Antigen induced bronchopulmonary eosinophilia inhibition, no glucocorticoid activity | asthma |
| CPR 3005 | Lipid analogue | Antiinflammatory | skin disease; eye disease; asthma; rheumatoid arthritis |
| CPR 3014 | Lipid analogue | Antiinflammatory | skin disease; eye disease; asthma; rheumatoid arthritis |
| CT 1441 | Unspecified | Antiinflammatory | asthma; allergy |
| CPR 3016 | Lipid analogue | antiinflammtory | skin disease; eye disease; asthma; rheumatoid arthritis |
| synthetic catalytic scavenger analogues; SCS analogues | Unspecified | antioxidant; free radical scavenger | stroke; trauma; atherosclerosis; neurodegeneration; asthma |
| VANTOX | Unspecified | antioxidant; NSAID | asthma; Parkinson disease; Alzheimer disease; stroke |
| antisense oligonucleotide, interleukin-5; antisense oligonucleotide, IL-5 | Unspecified | antisense; oligonucleotide; biotechnology | asthma |
| D 2522 | Unspecified | beta adrenergic agonist | asthma |
| SL 2021 | Unspecified | beta adrenergic agonist | asthma |
| procaterol; procaterol hydrochloride; OPC 2009; Cl 888; MEPTIN; PRO-AIR; ONSUKIL; BRON NOVO; PROMAXOL; MASACIN; PROCADIL; PROPULUM | 2(1H)-quinolone, 8-hydroxy-5-(1-hydroxy-2-(1-methylethyl)amino)butyl)-, monohydrochloride, (R*S*)(+,-) | beta adrenergic agonist | asthma |

TABLE 16-continued

Current Candidate Therapeutic Interventions in Development for the Treatment of Asthma

| Product Name | Chemical Name | Action | Indication |
| --- | --- | --- | --- |
| nardeterol; SOM 1122 | alpha-[[[3-(1H-benzimidazol-1-yl)-1,1-dimethylpropyl)a-mino]methyl]-2-fluoro-4-hydroxy-benzenemethanol | beta adrenergic agonist | asthma |
| RP 58802B | alpha-[[[3-(1H-benzimidazol-1-yl)-1-methylpropyl]a-mino]methyl]-4-hydroxy-3-methoxy-benzenemethanol | beta adrenergic agonist | asthma |
| CEDO 20433 | Unspecified | beta adrenergic agonist; beta2 adrenergic agonist | asthma |
| picumeterol; picumeterol fumarate; GR 114297; GR 114297 X; GR 63411 | (−)-(R)-4-amino-3,5-dichloro-alpha-[[[6-[2-(2-pyridinyl)ethoxy]hexyl]a-mino]methyl]benzene-methanol | beta adrenergic agonist; beta2 adrenergic agonist | asthma |
| salmeterol, (R)-; (R)-salmeterol | (R)A-hydroxy-alpha.1-[[[6-(4-phenylbutoxy)hexyl]a-mino]methyl-1,3-benzenedimethanol | beta adrenergic agonist; beta2 adrenergic agonist | asthma |
| formoterol; eformoterol; formoterol fumarate; YM 08316; BD 40A; CGP 25827; CGP 25827A; ATOCK; FORADIL; ASMATEC; SINASFIX; LEMOTEC; OXIS | (R*,R*)-(+,−)-N-[2-hydroxy-5-[1-hydroxy-2-[[2-(4-methoxypheny)-1-methylethyl]amino]ethyl]phenyl]formamide | beta adrenergic agonist; beta2 adrenergic agonist | asthma |
| formoterol, (R,R); (R,R)-formoterol | [R-(R*,R*)-(+,−)-N-[2-hydroxy-5-[1-hydroxy-2-[[2-(4-methoxypheny)-1-methylethyl]a-mino]ethyl]phenyl]formamide | beta adrenergic agonist; beta2 adrenergic agonist | asthma |
| LAS 32521 | Unspecified | beta adrenergic agonist; beta2 adrenergic agonist; bronchodilator | asthma |
| salmeterol + fluticasone; fluticasone + salmeterol; SERETIDE; ADVAIR DISKUS | Unspecified | beta adrenergic agonist; beta2 adrenergic agonist; bronchodilator; corticosteroid | asthma |
| broxaterol; Z 1170; SUMMAIR | (+,−)-3-bromo-alpha-[(tert-butylamino)methyl]-5-isoxazolemethanol | beta adrenergic agonist; beta2 adrenergic agonist; bronchodilator | asthma |
| levosalbutamol; levalbuterol; salbutamol, (R)-; (R)-salbutamol; (R)-albuterol; levalbuterol sulfate; XOPENEX | (R)-alpha'-[[(1,1-dimethylethyl)a-mino]methyl]-4-hydroxy-1,3-benzenedimethanol | beta adrenergic agonist; beta2 adrenergic agonist; bronchodilator | asthma |
| TA 2005 | [R-(R*,R*)]-8-hydroxy-5-[1-hydroxy-2-[[2-(4-methoxyphenyl)-1-methylethyl]amino]ethyl]-2(1H)-quinolinone monohydrochloride | beta adrenergic agonist; beta2 adrenergic agonist; bronchodilator | asthma |
| salmeterol; salmaterol; GR 33343X; SN 408; GR 33343G; SEREVENT | 4-hydroxy-alpha.1-[[[6-(4-phenylbutoxy)hexyl]ami-no]methyl-1,3-benzenedimethanol | beta adrenergic agonist; beta2 adrenergic agonist; bronchodilator | asthma; pulmonary obstructive disease |
| etanterol | 5-amino-alpha-[[(p-hydroxy-alpha-methylphenethyl)amino]methyl]-m-xylene-alpha,alpha'-diol | beta adrenergic agonist; beta2 adrenergic agonist; bronchodilator | asthma |

TABLE 16-continued

Current Candidate Therapeutic Interventions in Development for the Treatment of Asthma

| Product Name | Chemical Name | Action | Indication |
|---|---|---|---|
| bambuterol; BWD 2183; BAMBEC | dimethylcarbamic acid 5-[2-[(1,1-dimethylethyl)amino]-1-hydroxyethyl]-1,3-phenylene ester | beta adrenergic agonist; beta2 adrenergic agonist; bronchodilator | asthma |
| SM 11044 | [R-(R*,S*)]-1-[3-(3,4-dihydroxypheny)-2-[[3-(4-fluorophenyl)propyl]amino]-3-hydroxy-1-oxopropyl]pyrrolidine monohydrobromide | beta adrenergic agonist; beta3 adrenergic agonist; leukotriene antagonist; leukotriene D4 antagonist | asthma |
| AR C68397AA; AR-C68397AA; ARL 68397 | 4-hydroxy-7-[2-[[2-[[3-(2-phenylethoxy)propyl]sulfonyl]ethyl]amino]ethyl-2(3H)-benzothiazolone monohydrochloride | beta adrenergic agonist; bronchodilator | asthma; pulmonary obstructive disease; rhinitis |
| tulobuterol; HN 078; C 78; HSR 078A; BRELOMAX; BREMAX; ATENOS; BERACHIN; HOKUNALIN | alpha-[(tert-butylamino)methyl]-o-chlorobenzyl alcohol | beta adrenergic agonist; bronchodilator | asthma |
| allergy immunogen, migis epsilon, Tanox | Unspecified | Immunomodulation | allergy; asthma |
| allergy therapy, *E coli* enterotoxin B subunit-antigen fusion protein | Unspecified | Immunomodulation | rhinitis, asthma |
| emoctakin; interleukin-8 | Unspecified | Immunomodulation | asthma |
| fusion protein, IL-10 | Unspecified | Immunomodulation | asthma; inflammatory bowel disease |
| antisense oligonucleotide, adenosine A1 receptor; antisense oligonucleotide, asthma; EPI 2010; E 2010; EpiGenRx | Unspecified | antisense; oligonucleotide; mRNA translation inhibitor | asthma |
| interleukin-4 receptor; IL-4r; NUVANCE | Unspecified | cytokine antagonist | inflammation; asthma |
| soluble interleukin-5 receptor alpha; IL-5Ra | Unspecified | cytokine antagonist | asthma |
| interleukin-1 receptor; IL-1r; HJ 1306 | Unspecified immunosuppressant | cytokine inhibitor; | asthma |
| anakinra; interleukin-1 receptor antagonist; IL-1ra; interleukin-1 inhibitor; ANTRIL | N2-L-methionylinterleukin 1 receptor antagonist (human isoform x reduced) | cytokine inhibitor; immunosuppressant; NSAID | rheumatoid arthritis; inflammatory bowel disease; transplant rejection; asthma; septic shock |
| interleukin-12; IL-12; natural killer stimulatory factor; NKSF; edodekin alfa; Ro 247472; Ro 24-7472 | Unspecified | cytokine; immunostimulant | asthma |
| enkephalinase | Unspecified | enkephalinase; enzyme | asthma; ophthalmogical |
| platelet-activating factor acetylhydrolase; PAF-AH; SUN Y7016; PAFASE | Unspecified | hydrolase | respiratory distress syndrome; asthma; inflammatory bowel disease |
| IgE receptors, soluble, CorBec | Unspecified | immunosuppressant | asthma |
| antisense oligonucleotide, ICAM-1; antisense oligonucleotide, intracellular adhesion molecule-1; ISIS 2302 | d[(R)-P-thio](G-C-C-C-A-A-G-C-T-G-G-C-A-T-C-C-G-T-C-A) DNA | immunosuppressant; antisense; oligonucleotide; NSAID | rheumatoid arthritis; psoriasis; inflammatory bowel disease; asthma |
| lenercept; tumor necrosis factor receptor fusion protein; TNF receptor fusion protein; Ro 452081; TENEFUSE | Unspecified | immunosuppressant; NSAID | rheumatoid arthritis; asthma; septic shock; multiple sclerosis |
| MAb, AL 901; MAb, IgE; AL 901; CGP 51901 IGE 025A | Unspecified | monoclonal antibody | allergy; rhinitis; asthma |

TABLE 16-continued

Current Candidate Therapeutic Interventions in Development for the Treatment of Asthma

| Product Name | Chemical Name | Action | Indication |
| --- | --- | --- | --- |
| MAb, CD23; MAb, PRIMATIZED CD23 | Unspecified | monoclonal antibody | asthma; allergy; rhinitis |
| MAb, IgE; MAb, E25 | Unspecified | monoclonal antibody | asthma; allergy; rhinitis |
| MAb, interleukin-4; SB 240683 | Unspecified | monoclonal antibody | asthma |
| MAb, interleukin-5; MAb, IL-5; SCH 55700; CDP 835 | Unspecified | monoclonal antibody; immunosuppressant | asthma |
| MAb, macrophage migration inhibitory factor, Picower Institute for Medical Research | Unspecified | monoctonal antibody; NSAID | arthritis; asthma |
| MAb, VLA-4, humanized; MAb, very late antigen-4, humanized | Unspecified | monoclonal antibody; NSAID | inflammation; rheumatoid arthritis; asthma; diabetes |
| clenoliximab; MAb, CD4; MAb, PRIMATIZED CD4; IDEC 151; SB 217969 | immunoglobutin G 4 (human-Macaca monoclonal CE9gamma4PE gamma4-chain anti-human antigen CD4), disulfide with human-Macaca monoclonal CE9gamma4PE kappa-chain, dimer | monoclonal antibody; NSAID | rheumatoid arthritis; psoriasis; asthma |
| keliximab; MAb, CD4; MAb, PRIMATIZED CD4; IDEC CE9.1; SB 210396 | immunoglobulin G1 (human-Macaca monoclonal CE9.1.gamma.1-chain anti-human antigen CD 4), disulfide with human-Macaca monoclonal CE9.1.lambda.-chain, dimer | monoclonal antibody; NSAID | rheumatoid arthritis asthma |
| neutrophil degranulation inhibitor; DGI | Unspecified | NSAID | asthma; rheumatoid arthritis |
| RecepTox-Fce | Unspecified | peptide; fusion toxin | asthma; allergy |
| lipocortin; lipomodulin; macrocortin | Unspecified | phospholipase inhibitor; NSAID | asthma; arthritis |
| LEX 043 | Unspecified | proteinase inhibitor; serine proteinase inhibitor | inflammation; asthma |
| neutral endopeptidase; NEP | Unspecified | proteinase; metalloproteinase | cancer; migraine; inftammatory bowel disease; inflammation; asthma; respiratory disease |
| ribozymes, asthma | Unspecified | ribozyme; oligonucleotide | asthma |
| secretory leukocyte proteinase inhibitor; serine leukocyte proteinase inhibitor; SLPI; serine proteinase inhibitor; SPI; SLPI | Unspecified | serine proteinase inhibitor; proteinase inhibitor | asthma |
| vaccine, TNF alpha | Unspecified | Immunomudulation, vaccine; cytokine antagonist | rheumatoid arthritis; Crohn disease; cachexia; asthma |
| bradykinin2 antagonists Neurogen | Unspecified | bradykinin antagonist | asthma |
| NOVA 567; NPC 567 | N2-D-arginyl-3-(trans-4-hydroxy-L-proline)-7-D-phenylalaninebradykinin | bradykinin antagonist; cicatrizant; peptide; NSAID | asthma; skin ulcer; inflammation |
| icatibant; icatibant acetate; HOE 140 | D-arginyl-L-arginyl-L-prolyl-trans-4-hydroxy-L-prolylglycyl-3-(2-thienyl)-L-alanyl-L-seryl-D-1,2,3,4-tetrahydro-3-isoquinolincarbonyl-L-(2alfa,3abeta,7abeta)-octahydro-1H-indole-2-carbonyl-L-arginine | bradykinin antagonist; NSAID | asthma; inflammation; rhinitis; osteoarthritis |

TABLE 16-continued

Current Candidate Therapeutic Interventions in Development for the Treatment of Asthma

| Product Name | Chemical Name | Action | Indication |
|---|---|---|---|
| NPC 17731 | N2-D-arginyl-3-(trans-4-hydroxy-L-proline)-7-(trans-4-propoxy-D-proline)-8-[L-(2alpha,3abeta,7abeta)-octahydro-1H-indole-2-carboxylic acid]-bradykinin | bradykinin antagonist; NSAID | inflammation; septic shock; asthma |
| FR 173657 | (E)-3-[6-(acetylamino)-3-pyridinyl]-N-[2-[[2,4-dichloro-3-[[(2-methyl-8-quinolinyl)oxy]methyl]phenyl]methylamino]-2-oxoethyl-2-propenamide | bradykinin antagonist; NSAID; analgesic | asthma; inflammation; pain |
| HOE 058A | Unspecified | bronchodilator | asthma |
| RU 32210 | Unspecified | bronchodilator | asthma |
| S 123701 | Unspecified | bronchodilator | asthma |
| SC 109 | Unspecified | bronchodilator | asthma; pulmonary fibrosis |
| SDZ MKS492 | (R)-8-[[1-(3,4-dimethoxyphenyl)-2-hydroxyethyl]amino]-3,7-dihydro-7-(2-methoxyethyl)-1,3-dimethyl-1H-purine-2,6-dione | bronchodilator | asthma |
| F 3121 | 1,4-dihydro-3-amino-4-oxo-1-((3-trifluoromethyl)phenyl)pyridazine | bronchodilator | asthma |
| PF 904 | 1-ethyl-methyl-1H-pyrazino[2,3-c][1,2,6]thiadiazin-4-amine 2,2-dioxide | bronchodilator | asthma |
| LM 3339 | 2-(7,8-dichloro-2,3-dihydro-3,3-dimethyl-1-benzoxepin-5-yl)pyridine 1-oxide | bronchodilator | asthma |
| KF 17625 | 5-phenyl-(3H)-imidazo(4,5-c) (1,8)-naphthyridin[-4-(5H)-one | bronchodilator | asthma |
| dametralast; LA 2851 | 7-methylpyrazolo[1,5-a]-1,3,5-triazine-2,4-diamine | bronchodilator | asthma |
| KF 15570 | imidazo(4,5-c)quinoline-4-one | bronchodilator | asthma |
| LY 150310 | 1-(1,2,3,4-tetrahydro-1-naphthalenyl)-1H-imidazole mononitrate | bronchodilator; imidazole | asthma |
| fenspiride; KSP 193; PNEUMORAL; ESPIRAN | 8-(2-phenylethyl)-1-oxa-3,8-diazaspiro[4.5]decan-2-one | bronchodilator; NSAID | inflammation; asthma |
| Ro 251553; Ro 25-1553 | N-acetyl-His-Ser-Asp-Ala-Val-Phe-Thr-Glu-Asn-Tyr-Thr-Lys-Leu-Arg-Lys-Gln-NLeu-Ala-Ala-Lys-Lys-Tyr-Leu-Asn-Asp-Leu-Lys-Lys-Gly-Gly-Thr-amide, cyclic (25->21)-peptide | bronchodilator; VIP agonist | asthma |
| CD 349 | 1,4-dihydro-2,6-dimethyl-4-(3-nitrophenyl)-3,5-pyridinedicarboxylic acid 2-(nitrooxy)propyl 3-(nitrooxy)propyl ester | calcium antagonist; bronchodilator | hypertension; asthma; angina |

TABLE 16-continued

Current Candidate Therapeutic Interventions in Development for the Treatment of Asthma

| Product Name | Chemical Name | Action | Indication |
|---|---|---|---|
| RWJ 22108 | 4-(2-chloro-6-fluorophenyl_-1,4,6,7,8,9-hexahydro-2-methylthiepino[3,2-b]pyridine-3-carboxylic acid 5,5-dioxide 2-[methyl(phenylmethyl)amino)ethyl ester | calcium antagonist; bronchodilator | asthma |
| IgE regulators | Unspecified | CD23 increase expression and production | asthma; allergy |
| VLA4 integrin antagonist, Cytel | Unspecified | cell adhesion inhibitor; integrin antagonist; VLA 4 antagonist; NSAID | asthma; rheumatoid arthritis; multiple sclerosis |
| CCR3 inhibitors | Unspecified | chemokine antagonist | asthma |
| CCR3 receptor modulators, | Unspecified | Chemokine receptor, CCR3 modulator | asthma |
| chloride channel blocker, Bayer | Unspecified | chloride channel blocker | asthma; pulmonary obstructive disease |
| AQRA 721 | N-1-azabicyclo[2.2.2]oct-3-yl-6,11-dihydro-6-oxo-5H-dibenz[b,e]azepine-11-carboxamide | cholinergic antagonist; bronchodilator | asthma |
| tiotropium bromide; BA 679BR | (1-alpha 2beta,4beta,5alpha,7beta)-7-[(hydroxydi-(2-thienyl)acetyl)oxy]-9,9-dimethyl-3-oxa-9-azoniatricyclo[3.3.1.02,4]nonane bromide | cholinergic antagonist; muscarinic antagonist; muscarinic M1 antagonist; muscarinic M3 antagonist; bronchodilator | asthma |
| rispenzepine; ulvenzepine; DF 594 | 6,11-dihydro-11-[(1-methyl-3-piperidinyl)carbonyl])-5H-pyrido[2,3-b][1,5]benzodiazepin-5-one | cholinergic antagonist; muscarinic antagonist; muscarinic M1 antagonist; muscarinic M3 antagonist; antispasmodic; bronchodilator | asthma; bronchitis |
| DAC 5889; DAC 6150 | 6-oxo-3-phenyl-3-piperidinecarboxylic acid 1-azabicyclo[2.2.2]oct-3-yl ester | cholinergic antagonist; muscarinic antagonist; muscarinic M1 antagonist; bronchodilator | asthma |
| revatropate; UK 112166 | (R)-3-quinuclidyl-(2S)-2-hydroxymethyl-4-(R)-methytsulfinyl-2-phenylbutyrate | cholinergic antagonist; muscarinic M3 antagonist; muscarinic antagonist | asthma; pulmonary obstructive disease |
| chymase inhibitors, Axys | Unspecified | chymase inhibitor; NSAID | asthma; inflammation; rhinitis |
| CMI 903 | Unspecified | complement inhibitor | asthma |
| anti-inflammatory corticosteroids, A&M University | Unspecified | corticosteroid | psoriasis; asthma |
| D 5272 | Unspecified | corticosteroid | asthma |
| D 5519 | Unspecified | corticosteroid | asthma |
| GW 215864 | Unspecified | corticosteroid | asthma |
| GW 250495 | Unspecified | corticosteroid | asthma |
| ST 126; TO 199 | Unspecified | corticosteroid | asthma |
| CGP 13774; KSR 592 | (+)-methyl 9alpha-chloro- -6alpha-fluoro-11beta-hydroxy-16alpha-methyl-3-oxo-17alpha-propionyloxy-androsta-1,4-diene-17beta-carboxylate | corticosteroid | asthma; rhinitis |
| icometasone enbutate; icomethasone enbutate; icomethasone acetate; isomethasone acetatew; CL 09 | (11.beta., 16.alphs.)-21-(acetyloxy)-9-chloro-11-hydroxy-16-methyl-17-(1-oxobutoxy)pregna-1,4-diene-3,20-dione | corticosteroid | asthma; skin disease |
| butixocort propionate; JO 1222 | (11beta)-11-hydroxy-17-(1-oxobutoxy)-21-[(1-oxopropyl)thio)]pregn-4-ene-3,20-dione | corticosteroid | inflammation; asthma; inflammatory bowel disease |

TABLE 16-continued

Current Candidate Therapeutic Interventions in Development for the Treatment of Asthma

| Product Name | Chemical Name | Action | Indication |
|---|---|---|---|
| budesonide; budesonide propionate; S 1320; PREFERID; PULMICORT; RHINOCORT; ENTOCORT; NARICORT; INFLAMMIDE; BETACTIN; ELTAIR; HORACORT; RHINOCORT AQUA | (11beta, 16alpha)-16,17-[butylidenebis(oxy)]-11,21-dihydroxypregna-1,4-diene-3,20-dione | corticosteroid | asthma; skin disease; inflammation; rhinitis; ulcerative colitis; Crohn disease |
| mometasone furoate; mometasone; S 2640; SCH 32088; ELOCOM; ELOCON; FULMETA; ECURAL; ERMIL; NASONEX; ASMANEX | (11beta, 16alpha)-9,21-dichloro-17-[(2-furanylcarbonyl)oxy]-11-hydroxy-16-methyl-pregna-1,4-diene-3,20-dione | corticosteroid | dermatitis; asthma; rhinitis; psoriasis; pruritis |
| deflazacort; azacort; L 5458; MDL 458; AZACORTID; CALCORT; LANTADIN; DEFLAN; FLANTADIN; DEZACOR; ZAMENE; ROSILIN; DEFLAMON; PRANDIN | (11beta,16beta)-21-(acetytoxy)-11-hydroxy-2'-methyl-5'H-pregna-1,4-die no[17,16-d]oxazole-3,20-dione | corticosteroid | rheumatoid arthritis; skin disease; asthma |
| fluticasone propionate; fluticasone; CCI 18781; SN 410; SN 411MD; FLOVENT; FLIXONASE; FLIXOTIDE; FLONASE; FLUTIVATE; FLUTIDE NASAL; CUTIVATE; RONTILONA; TRIALONA; FLUNASE | (6alfa,11beta,16alfa,17alfa)-6,9-difluoro-11-hydroxy-16-methyl-3-oxo-17-(1-oxopropoxy)-androsta-1,4-diene-17-carbothioic acid, S-(fluoromethyl) ester | corticosteroid | dermatitis; rhinitis; asthma; pulmonary obstructive disease; skin disease |
| ciclesonide; BY 9010 | [11beta,16alfa (R)]-16,17-[(cyclohexylmethylene)bis(oxy)]-11-hydroxy-21-(2-methyl-1-oxopropoxy)-pregna-1,4-diene-3,20-dione | corticosteroid | asthma |
| drug delivery system, liposome rofleponide; rofleponide liposome; rofleponide palmitate | [6alfa,11beta,16alfa(R)] 16,17-[butytidenebis(oxy))6,9-difluoro-11,21-dihydroxypregn-4-ene-3,20-dione | corticosteroid | asthma; rhinitis |
| rofleponide; D 5522 | [6alfa,11beta,16alfa(R)] 16,17-[butylidenebis(oxy)]6,9-difluoro-11,21-dihydroxypregn-4-ene-3,20-dione | corticosteroid | asthma |
| RPR 106541 | [6alpha,11 beta,16alpha (R),17beta]-16,17-[butylidenebis(oxy)]-6,9-difluoro-11-hydroxy-17-(methylthio)androst-4-en-3-one | corticosteroid; glucocorticoid | asthma |
| methylprednisolone suleptanate; U 67590A; PROMEDROL | (6alfa,11beta)-11,17-dihydroxy-6-methyl-21-[[8-[methyl(2-sulfoethyl)amino]-1,8-dioxooctyl]oxy]pregna-1,4-diene-3,20-dione monosodium salt | corticosteroid; immunosuppressant transplant rejection | inflammation; asthma; anaphylactic shock; |
| tepoxalin; RWJ 20485; ORF 20485 | 5-(4-chlorophenyl)-N-hydroxy-1-(4-methoxyphenyl)-N-methyl-1H-pyrazole-3-propanamide | COX inhibitor; 5 lipoxygenase inhibitor; NSAID | asthma; inflammation; inflammatory bowel disease |

TABLE 16-continued

Current Candidate Therapeutic Interventions in Development for the Treatment of Asthma

| Product Name | Chemical Name | Action | Indication |
| --- | --- | --- | --- |
| BAY 169996 | Unspecified | cytokine antagonist | asthma |
| cytokine trap, Regeneron | Unspecified | cytokine antagonist | cancer; asthma; rheumatoid arthritis; allergy |
| IL-4 antagonists, Pharmacopeia; IL-4 antagonists, Regeneron | Unspecified | cytokine antagonist | asthma |
| interleukin-4 signal transduction antagonists, Ligand | Unspecified | cytokine antagonist | asthma |
| interleukin-4 receptor inhibitors, Affymax | Unspecified | cytokine inhibitor | asthma; diabetes |
| interleukin-1 inhibitors, Selectide | Unspecified | cytokine inhibitor; NSAID | inflammation; asthma; inflammatory bowel disease |
| JTE 711 | Unspecified | cytokine synthesis inhibitor | dermatitis; asthma; rhinitis |
| repirinast; BAY u 2372; MY 5116; ROMET | isopentyl 5,6-dihydro-7,8-dimethyl-4,5-dioxo-4H-pyrano[3,2-c)quinoline-2-carboxylate | Degranulation inhibitor | asthma |
| CGP 25875 | Unspecified | degranulation inhibitor | asthma |
| sulochrin | Unspecified | degranulation inhibitor | asthma |
| cromoglicate lisetil; AKY 953; KY 556; N 556 | 2-[[2-(ethoxycarbonyl)-4-oxo-4H-1-benzopyran-5-yl)oxy]-1-[[[2-(ethoxycarbonyl)-4-oxo-4H-1-benzopyran-5-yl)oxy)methyl]ethyl ester, L-lysine dihydrochloride | degranulation inhibitor | asthma; rhinitis; dermatitis; allergy |
| BN 50601 | 2-[4-(1,1-dimethylethyl)phenyl]-2,3-dihydro-6-methyl-1H-pyrrolo[3,4-b]pyridin-7-ol | degranulation inhibitor | asthma |
| amlexanox; amoxanox; CHX 3673; AA 673; SOLFA; ELICS; APHTHASOL | 2-amino-7-(1-methylethyl)-5-oxo-5H-[1]-benzopyrano[2,3-b]pyridine-3-carboxylic acid | degranulation inhibitor | asthma; psoriasis; rhinitis; mucositis; conjunctivitis; allergy |
| asobamast; Z 1819 | 2-ethoxyethyl[4-(3-methyl-5-isoxazolyl)-2-thiazolyl]oxamate | degranulation inhibitor | asthma |
| tetrazolast meglumine; tetrazolast; MDL 26024GO | 4-(1H-tetrazol-5-yl)tetrazolo(1,5-a]quinoline with 1-deoxy-1-(methylamino)-D-glucitol | degranulation inhibitor | asthma |
| azelastine; A 5610; W 2979M; E 0659; AZEPTIN; ALLERGODIL; ASTELIN; RADETHAZIN; AFLUONA; AFLUON; AZEPIT; AZECOF; AZERUNART CHOS H; BIFERTIN | 4-[(4-chlorophenyl)methyl)-2-(hexahydro-1-methyl-1H-azepin-4-yt)-1(2H)-phthalazinone | degranulation inhibitor | asthma; rhinitis; skin disease; conjunctivitis |
| quinotolast; quinotolast sodium; FK 021; FR 71021; ASLOCK | 4-oxo-1-phenoxy-N-1H-tetrazol-5-yl-4H-quinolizine-3-carboxamide | degranulation inhibitor | asthma; rhinitis; dermatitis |
| picumast; picumast dihydrochloride; BM 15100 | 7-[3-[4-(4-chlorobenzyl)-1-piperazinyl]propoxy]-3,4-dimethylcoumarin | degranulation inhibitor | rhinitis; asthma |
| nedocromil; FPL 59002; FPL 59002KP; TILADE; TILARIN; TILAVIST; TILAD; NEDREL; DISVEN; IRTEN | 9-ethyl-6,9-dihydro-4,6-dioxo-10-propyl-4H-pyrano[3,2-g]quinoline-2,8-dicarboxylic acid | degranulation inhibitor | asthma; eye disease; skin disease; rhinitis |

TABLE 16-continued

Current Candidate Therapeutic Interventions in Development for the Treatment of Asthma

| Product Name | Chemical Name | Action | Indication |
|---|---|---|---|
| pemirotast; pemirolast potassium; BMY 26517; DE 068; BL 5617; PEMILASTON; ALLEGYSAL | 9-methyl-3-(1H-tetrazol-5-yl)-4H-pyrido[1,2-a]pyrimidin-4-one | degranulation inhibitor | asthma; conjunctivitis; rhinitis; dermatitis; restenosis |
| suplatast tositate; IPD 1151T; MPD; IPD | dimethyl-2-[4-(3-ethoxy-2-hydroxypropoxy)phenyl-carbamoyl]ethylsulfonium-p-toluene sulfonate | degranulation inhibitor | dermatitis; asthma; allergy; rhinitis |
| tazanolast; WP 833; TAZANOL; TAZALEST | oxo[[3-(1H-tetrazol-5-yl)phenyl]amino)acetic acid, butyl ester | degranulation inhibitor | asthma; rhinitis |
| Cl 959 | 5-methoxy-3-(1-methylethoxy)-N-1H-tetrazol-5-yl-benzo[b]thiophene-2-carboxamide sodium salt | degranulation inhibitor; immunosuppressant; NSAID | rhinitis; inflammation; asthma; arthritis |
| AP 414 | Unspecified | degranulation inhibitor; tyrosine kinase inhibitor | asthma; allergy |
| MDAM | N-[4-[2-(2,4-diamino-6-pteridinyl)ethyl]benzoyl]-4-methylene-DL-glutamic acid | dihydrofolate reductase inhibitor; NSAID, immunosuppressant | cancer; transplant rejection; rheumatoid arthritis; asthma |
| ALP 242 | Unspecified | elastase inhibitor; proteinase inhibitor | asthma; emphysema; psoriasis |
| BQ 153 | cyclo(3-sulfo-D-alanyl-L-prolyl-D-valyl-L-leucyl-D-tryptophyl) | endothelin A antagonist; endothelin antagonist | asthma |
| endothelin antagonist | Unspecified | endothelin antagonist | kidney disease; ischemia; inflammatory bowel disease; asthma |
| BW 443C | L-tyrosyl-D-arginylglycyl-4-nitro-L-phenylalanyl-L-prolinamide diacetate (salt) | enkephatinase inhibitor; analgesic | asthma; pain; cough |
| KCA 757 | 4-[6-acetyl-3-[3-[(4-acetyl-3-hydroxy-2-propylphenyl)thio]propoxy]-2-propylphenoxy]butanoic acid | Eosinophil inhibitory activity | asthma |
| VML 530; ABT 080 | Unspecified | FLAP antagonist | asthma |
| BAY x 1005 | (R)-alpha-cyclopentyl-4-(2-quinolinylmethoxy)benzeneacetic acid | FLAP antagonist | asthma |
| VB 5122 | Unspecified | free radical scavenger; xanthine oxidase inhibitor | inflammation; asthma |
| beta-glucan antagonist | Unspecified | glucan antagonist | conjunctivitis; asthma; psoriasis; ulcerative colitis |
| itrocinonide | 6alfa,9-difluoro-11beta,16alfa,17-trihydroxy-3-oxoandrosta-1,4-diene-17beta-carboxylic acid, ester with ethyl(S)-1-hydroxyethyl carbonate, cyclic(R)-16,17-acetal with butyraldehyde | glucocorticoid | asthma |
| glucocorticoids, Ligand | Unspecified | glucocorticoid; immunosuppressant; NSAID | inflammation; asthma; autoimmune disease |
| L 0066; F 11105 | Unspecified | GM-CSF inhibitor | asthma |
| methylhistamine, R-alpha; BP 2.94 | Unspecified | histamine agonist; histamine H3 agonist | asthma; anxiety; gastrointestinal ulcer |
| SCH 49648 | (2S-trans)-4-(2-methyl-3-pyrrolidinyl)-1H-imidazole | histamine agonist; histamine H3 agonist | asthma; anxiety; gastrointestinal ulcer |

TABLE 16-continued

Current Candidate Therapeutic Interventions in Development for the Treatment of Asthma

| Product Name | Chemical Name | Action | Indication |
|---|---|---|---|
| SCH 50971 | (3R-trans)-4-(4-methyl-3-pyrrolidinyl)-1H-imidazole | histamine agonist; histamine H3 agonist | asthma; anxiety; gastrointestinal ulcer |
| HQL 79 | Unspecified | histamine antagonist, 5HT antagonist | allergy, asthma |
| asthma therapy, Esteve | Unspecified | histamine antagonist, histamine H1 antagonist | asthma |
| F 9505A | Unspecified | histamine antagonist; histamine H1 antagonist | asthma |
| olopatadine; olopatadine hydrochloride; KW 4679; ALO 4943A; PATANOL | (Z)-11-[3-(dimethylamino)propylidene]-6,11-dihydro-dibenz[b,e]oxepin-2-acetic acid | histamine antagonist; histamine H1 antagonist | allergy; rhinitis; asthma; conjunctivitis |
| DF 1111301 | 1-(2-ethoxyethyl)-N,N-dimethyl-1H-benzimidazole-2-ethanamine dihydrochloride | histamine antagonist; histamine H1 antagonist | allergy; asthma |
| ebastine; LASW090; LAS 90; EBASTEL; KESTINE; EVASTEL | 1-[4-(1,1-dimethylethyl)phenyl]-4-[4-(diphenylmethoxy)-1-piperidinyl]-1-butanone | histamine antagonist; histamine H1 antagonist | allergy; rhinitis; asthma |
| mizolastine; SL 850324; MKC 431; MIZOLLEN; ZOLIM; MISTAMINE | 2-[[1-[1-[(4-fluorophenyl)methyl]-1H-benzimidazol-2-yl)-4-piperidinyl]methylamino]4(1H)-pyrimidinone | histamine antagonist; histamine H1 antagonist | asthma; allergy; rhinitis |
| ZCR 2060 | 2-[2-[4-(diphenylmethyl)-1-piperazinyl]ethoxy]benzoic acid maleate | histamine antagonist; histamine H1 antagonist | asthma; allergy |
| selenotifen; BN 52256 | 4,9-dihydro-4-(1-methyl-4-piperidinylidene)-10H-benzo[4,5]cyclohepta[1,2-b]selenophen-10-one | histamine antagonist; histamine H1 antagonist | eye disease; asthma; arrhythmia; rhinitis |
| epinastine; WAL 801; WAL 801CL; ALESION | 9,13b-dihydro-1H-dibenz[c,f]imidazo[1,5-a]azepin-3-amine | histamine antagonist; histamine H1 antagonist | allergy; asthma; psoriasis; rhinitis |
| FCC 13 | 3,4,10,14b-tetrahydrodibenzo[c.f]pyranzino]1,2-a]azepine-2(1H)carboxamide | histamine antagonist; histamine H1 antagonist; 5HT antagonist | asthma |
| mequitamium iodide; LG 30435 | 1-methyl-3-(10H-phenothiazin-10-ylmethyl)-1-azoniabicyclo[2.2.2]octane iodide | histamine antagonist; histamine H1 antagonist; muscarinic antagonist; cholinergic antagonist | asthma; rhinitis |
| KY 234 | 1-[3-(4-benzhydryl-1-piperazinyl)propyl]-3-(1H-imidazol-1-ylmethyl)-1H-indole-6-carboxylic acid | histamine antagonist; histamine H1 antagonist; thromboxane synthetase inhibitor | asthma |
| pibaxizine; UCB 20028; UCB J028; J028 | [2-[2-[4-(dipenylmethylene)piperidinyl)ethoxy)ethoxy)acetic acid | histamine antagonist; histamine H2 antagonist | irritable bowel syndrome; asthma |
| KC 11425 | 5,6-dihydro-2-methyl-8-(2-methylpropyl)-1-[2-[4-(4-methyl-2-pyridinyl)-1-piperazinyl)ethyl]-4H-pyrrolo[3,2,1-ij]quinoline | histamine antagonist; PAF antagonist | asthma; allergy |
| KC 11404 | 4-n-butyl-5,6-dihydro-8-hydroxy-2-methyl-1-[2[4-(4-methyl-2-pyridinyl)-1-piperazinyl]ethyl]-4H-pyrrolo[3,2,1-ij]quinoline | histamine antagonist; PAF antagonist: 5 lipoxygenase inhibitor | asthma; allergy |
| batebulast; batebulast hydrochloride; NCO 650 | trans-4-guanidinomethylcyclohexanecarboxylic acid p-tert-butyl-phenyl ester hydrochloride | Histamine release inhibitor | asthma |

TABLE 16-continued

Current Candidate Therapeutic Interventions in Development for the Treatment of Asthma

| Product Name | Chemical Name | Action | Indication |
|---|---|---|---|
| dehydroepiandrosterone sulfate; DHEAS; PB 005 | Unspecified | hormone; vaccine adjuvant; corticosteroid | inflammation; infectious disease; asthma |
| pentigetide; IgE pentapeptide human; pentapeptide DSDPR; TA 521; PENTYDE | N2-[1-N-(N-L-alpha-aspartyl-L-seryl)-L-[alpha-aspartyl]-L-prolyl]-L-arginine | immunoglobulin | conjunctivitis; asthma; rhinitis |
| CL 296141 | Unspecified | Immunomodulation | asthma |
| SRL 172 | Unspecified | immunostimulant | tuberculosis; cancer; asthma; bacterial infection; leprosy; rhinitis |
| asthma/allergy therapy, Rigel | Unspecified | immunosuppressant | asthma; allergy |
| D 22557 | Unspecified | immunosuppressant | allergy; asthma |
| D 7193 | Unspecified | immunosuppressant | asthma |
| IgE receptor inhibitors, InKine | Unspecified | immunosuppressant | asthma |
| immunology/inflammation therapy, Rigel | Unspecified | immunosuppressant | inflammation; autoimmune disease; asthma |
| immunosuppressant, Rhone-Poulenc Rorer | Unspecified | immunosuppressant | asthma |
| immunosuppressants, Agouron | Unspecified | immunosuppressant | autoimmune disease; asthma |
| T cell modulators, Fisons | Unspecified | immunosuppressant | asthma; rhinitis; conjunctivitis; allergy |
| oxeclosporin; SDZ IMM 125; IMM 125 | 2-[O-(2-hydroxyethyl)-D-serine]-cyclosporin A | immunosuppressant | asthma |
| LCB 2183 | Unspecified | immunosuppressant | rhinitis; dermatitis; asthma |
| CBP 1011 | Unspecified | immunosuppressant; corticosteroid | autoimmune disease; systemic lupus erythematosus; asthma |
| D 22558 | Unspecified | immunosuppressant; cytokine inhibitor | asthma; allergy |
| immunoregulators, AVANT Immunotherapeutics; immunoregulators, Repligen | Unspecified | immunosuppressant; NSAID | transplant rejection; rheumatoid arthritis; asthma |
| phellodendrine; OB 5 | (7S-cis)-5,8,13,13a-tetrahydro-2,11-dihyrdoxy-3,10-dimethoxy-7-methyl-6H-dibenzo[a,g]quinolizinium | immunosuppressant; NSAID | transplant rejection; inflammation; viral infection; asthma; kidney disease |
| antiasthma agent, s | Unspecified | Inflammatory mediator blockade, | asthma |
| alphaE beta 7 antagonists, LeukoSite/Warner Lambert | Unspecified | integrin antagonist; cell adhesion inhibitor | asthma; psoriasis; inflammatory bowel disease |
| cell adhesion inhibitors, Ligand/Sankyo | Unspecified | integrin antagonist; cell adhesion inhibitor; NSAID | asthma; rheumatoid arthritis; reperfusion injury |
| TBC 1269 | 3'3'''-(1,6-hexanediyl)bis[6'-(alpha-D-mannopyranosyloxy)-[1,1'-biphenyl]-3-acetic acid | integrin antagonist; selectin antagonist; immunosuppressant; cell adhesion inhibitor; NSAID | inflammation; asthma |
| VLA-4 antagonist, Merck/Biogen | Unspecified | integrin antagonist; VLA 4 antagonist | asthma |
| VLA-4 antagonists, inflammatory diseased; BIO 1211 | N-[[4-[[[(2-methylphenyl)amino]carbonyl]amino]phenyl]acetyl]-L-leucyl-L-alpha-aspartyl-L-valyl-L-proline | integrin antagonist; VLA 4 antagonist | asthma; multiple sclerosis |
| VLA4 antagonists, Celltech Therapeutics | Unspecified | integrin antagonist; VLA 4 antagonist; cell adhesion inhibitor | asthma; inflammatory bowel disease |
| CL891301 | Unspecified | leukotriene antagonist | asthma |
| CS 615 | Unspecified | leukotriene antagonist | asthma |
| FK 011 | Unspecified | leukotriene antagonist | asthma |

TABLE 16-continued

Current Candidate Therapeutic Interventions in Development for the Treatment of Asthma

| Product Name | Chemical Name | Action | Indication |
| --- | --- | --- | --- |
| LF 60361 | Unspecified | leukotriene antagonist | asthma |
| RP 12525 | Unspecified | leukotriene antagonist | asthma |
| zafirlukast; Zeneca 204219; ICI 204219; ACCOLATE; VANTICON | [3-[[2-methoxy-4-[[[(2-methylphenyl)sulfonyl]a-mino]carbonyl]phenyl]meth-yl]-1-methyl-1H-indol-5-yl]carbamic acid, cyclopentyl ester | leukotriene antagonist | asthma; rhinitis |
| BW A797C | acetamide,n-hydroxy-n-(3-(5,6,7,8-tetrahydro-2-naphthalenyl)-2-propenyl)- | leikotriene antagonist | asthma |
| BW A137C | N-hydroxy-N-[[4-(phenylmethoxy)phenyl]methyl]acetamide | leukotriene antagonist | asthma |
| BIIL 284 | Unspecified | leukotriene antagonist; leukotriene B4 antagonist | asthma; pulmonary obstructive disease |
| pranlukast; dulokast ONO 1078; RS 411; ONON; ULTAIR | N-[4-oxo-2-(1H-tetrazol-5-yl)-4H-1-benzopyran-8-yl]-4-(4-phenylbutoxy)benzamide | leukotriene antagonist; leukotriene C4 antagonist; leukotriene D4 antagonist; leukotriene E4 antagonist | asthma; rhinitis |
| leukotriene D4 antagonists, Pfizer | Unspecified | leukotriene antagonist; leukotriene D4 antagonist | asthma |
| RG 14524 | Unspecified | leukotriene antagonist; leukotriene D4 antagonist | asthma |
| LY 290154 | (E)-7-chloro-2-[2-[3-[4-(1H-tetrazol-5-yl)-1-[7-(1H-tetrazol-5-ylmethoxy)-1H-indol-1-yl]butyl]phenyl]ethenyl]quinoline | leukotriene antagonist; leukotriene D4 antagonist | asthma |
| RS 601 | 4-[5,5,6,6,6-pentafluoro-1-[[(4-fluorophenyl)sulfonyl]a-mino]hexyl]benzenebutanoic acid | leukotriene antagonist; leukotriene D4 antagonist; thromboxane antagonist | asthma |
| YM 158; YM 57158 | N-[5-[3-[(4-chlorophenyl)sulfonyl]propyl]-2-(1H-tetrazol-5-ylmethoxy)phenyl]-3-[[4-(1,1-dimethylethyl)-2-thiazolyl]methoxy]-benzamide | leukotriene antagonist; leukotriene D4 antagonist; thromboxane antagonist | asthma; rhinitis |
| ZD 3523; ICI D3523 | Unspecified | leukotriene antagonist; NSAID | asthma; inflammation |
| ontazolast; BIRM 270 | (S)-N-[2-cyclohexyl-1-(2-pyridinyl)ethyl]-5-methyl-2-benzoxazolamine | leukotriene B4 antagonist; leukotriene antagonist | asthma |
| RP 69698 | 5-(1,1-dimethyl-5-((4,6-diphenyl-2-pyridyl)oxy)pentyl)-1H-tetrazole | leukotriene B4 antagonist; leukotriene antagonist | asthma; emphysema |
| LY 292728 | 7-carboxy-3-[3-[(5-ethyl-4'-fluoro-2-hydroxy[1,1'-biphenyl]-4-yl)oxy]propoxy]-9-oxo-9H-xanthene-4-propanoic acid disodium salt | leukotriene B4 antagonist; leukotriene antagonist | asthma |
| RG 14893 | 4-(2-(methyl(2-phenethyl)amino)-2-oxoethyl)-8-(phenylmethoxy)-2-naphthalenecarboxylic acid | leukotriene B4 antagonist; leukotriene antagonist; NSAID | asthma; inflammation |

TABLE 16-continued

Current Candidate Therapeutic Interventions in Development for the Treatment of Asthma

| Product Name | Chemical Name | Action | Indication |
|---|---|---|---|
| SC 51146 | 7-[3-[2(cyclopropylmethyl)-3-methoxy-4-(4-thiazolyl)phenoxy]pro-poxy]-3,4-dihydro-8-propyl-2H-1-benzopyran-2-carboxylic acid | leukotriene B4 antagonist; leukotriene antagonist; NSAID | asthma; psoriasis; rheumatoid arthritis; inflammatory bowel disease |
| cinalukast; Ro 245913 | (E)-4-(3-(2-(4-cyclobutyl-2-thiazolyl)ethenyl)phenyl amino)-2,2-diethyl-4-oxobutanoic acid | leukotriene C4 antagonist; leukotriene D4 antagonist; leukotriene antagonist | asthma |
| BAY x 7195 | [S-(Z)]-4-[[1-(2-carboxyethyl)-4-[4-(4-phenoxybutoxy)phenyl]-2-butenyl]thio]benzoic acid | leukotriene C4 antagonist; leukotriene D4 antagonist; leukotriene antagonist | asthma |
| pirodomast; SCH 37224 | 4-hydroxy-1-phenyl-3-(1-pyrrolidinyl)-1,8-naphthyridin-2(1H)-one | leukotriene C4 antagonist; leukotriene D4 antagonist; leukotriene E4 antagonist; leukotriene antagonist | rhinitis; asthma |
| CGP 44044A | (1R,2S)-1-hydroxy-1-(3-trifluoromethyl-phenyl)-8-(4-acetyl-3-hydroxy-2-propy-phenoxy)-octa-3(E),5(Z)-dien-2-yl-7-thio-4-oxo-4H-1-benzopyran-2-carboxylic acid sodium salt | leukotriene D4 antagonist; leukotriene antagonist | asthma |
| LY 287192 | (E)-2-[[5-[3-[2-(7-chloro-2-quinolinyl)ethenyl]phenyl]-2H-tetrazol-2-yl]methyl]-5-fluorobenzoic acid sodium salt | leukotriene D4 antagonist; leukotriene antagonist | asthma |
| LY 290324 | (E)-7-chloro-2-[2-[3-[[7-[2-(1H-tetrazol-5-yl)ethyl]-1H-indol-1-yl]methyl]phenyl]ethenyl] quinoline hydrochloride | leukotriene D4 antagonist; leukotriene antagonist | asthma |
| SKF 106203 | (S)-beta[(2-carboxyethyl)thio]-2-(8-phenyloctyl)benzene-panoic acid | leukotriene D4 antagonist; leukotriene antagonist | asthma |
| YM 16638 | [[5-[[3-(4-acetyl-3-hydroxy-2-propylphenoxy)propyl]thio]-1,3,4-thiadiazol-2-yl]thio]acetic acid | leukotriene D4 antagonist; leukotriene antagonist | asthma |
| montelukast; montelukast sodium; MK 476; MK 0476; SINGULAIR | [R-(E)]-1-[[[1-[3-[2-(7-chloro-2-quinolinyl)ethenyl]phenyl]-3-[2-(1-hydroxy-1-methylethyl)phenyl]propyl]thio]methyl]-cyclopropaneacetic acid | leukotriene D4 antagonist; leukotriene antagonist | asthma |
| verlukast; MK 679; L 660711; MK 571; L 668019 | [R-(E)]-3-[[[3-[2-(7-chloro-2-quinolinyl)ethenyl]phen-yl][[3-(dimethylamino)-3-oxopropyl]thio]methyl]thio] propanoic acid | leukotriene D4 antagonist; leukotriene antagonist | asthma |
| pobilukast; pobilukast edamine; SKF 104353; SKF 104353Z2; SKF 104353Q | [R-(R*,S*)]-beta-[(2-carboxyethylthio]-alpha-hydroxy-2-(8-phenyloctyl)benzene-propanoic acid | leukotriene D4 antagonist; leukotriene antagonist | asthma; rhinitis |
| ritolukast; WY 48252 | 1,1,1-trifluoro-alpha-2-quinolylmethanesulfon-m-anisidide | leukotriene D4 antagonist; leukotriene antagonist | asthma |

TABLE 16-continued

Current Candidate Therapeutic Interventions in Development for the Treatment of Asthma

| Product Name | Chemical Name | Action | Indication |
| --- | --- | --- | --- |
| LY 203647 | 1-[hydroxy-3-propyl-4-[4-[2-[4-(1H-tetrazol-5-yl)butyl]-2H-tetrazol-5-yl]butoxy]phenyl]ethanone | leukotriene D4 antagonist; leukotriene antagonist | hypertension; asthma |
| RG 12525 | 2-[[4-[[2-(1H-tetrazol-5-ylmethyl)phenyl)methoxy]phenoxy]methyl]quinoline | leukotriene D4 antagonist; leukotriene antagonist | asthma |
| NZ 107 | 4-bromo-5-[[(3-ethoxy-4-methoxyphenyl)methyl]amino]-3(2H)-pyridazinone | leukotriene D4 antagonist; leukotriene antagonist | asthma |
| DS 4574 | 6-(2-cyclohexylethyl)-[1,3,4]thizdiazolo[3,2,-a]-1,2,3-triazolo[4,5-d]pyrimidin-9(1H)-one | leukotriene D4 antagonist; leukotriene antagonist | gastrointestinal ulcer; asthma |
| iralukast; CGP 45715A | (1R,2S)-1-hydroxy-1-(3-trifluoromethylphenyl)-10-(4-acetyl-3-hydroxy-2-propyl-phenoxy)-deca-3(E), 5(Z)-diene-2-yl-7-thio-4-oxo-4H-1-benzopyran-2-carboxylic acid sodium salt | leukotriene D4 antagonist; leuktriene E4 antagonist; leukotriene antagonist | asthma |
| MDL 43291 | (4a.alpha,7Z,8.beta,8a.beta)-[(octahydro-2-oxo-7-tetradecylidene-2H-1-benzopyran-8-yl)thio]acetic acid | leukotriene D4 antagonist; leukotriene E4 antagonist; leukotriene antagonist | asthma |
| CGP 44826 | 2-ethenyloxy-N-[4-(5-cyclopentyl-carbonylamino-1-methylindol-3-ylmetyl)-3-methoxy-benzoyl]benzenesulfonyl-amide | leukotriene D4 antagonist; leukotriene E4 antagonist; leukotriene antagonist | asthma |
| FPL 55712 | 7-[3-(4-acetyl-3-hydroxy-2-propylphenoxy)-2-hydroxypropoxy]-4-oxo-8-propyl-4H-1-benzopyran-2-carboxylic acid monosodium salt | leukotriene D4 antagonist; leukotriene E4 antagonist; leukotriene antagonist | asthma |
| sulukast; LY 170680 | 5-(3-(2(R)-(carboxyethylthio)-1(S)-hydroxypentadeca-3(E),5(Z)-dienyl)phenyl)-1H-tetrazole | leukotriene E4 antagonist; leukotriene D4 antagonist; leukotriene antagonist | asthma |
| LDP 977 | Unspecified | Leukotriene inhibitor | asthma |
| BAY y 1015 | Unspecified | leukotriene syntheses inhibitor | asthma |
| CPR 7011 | L-alpha-dipalmitoyl-sn-glycero-3-phosphocholine | Lung surfactant | bronchitis; cystic fibrosis; rhinitis; asthma |
| mast cell activation inhibitors, AstraZeneca | Unspecified | Mast call degranulation inhibition | asthma; rhinitis |
| MAb, interleukin-5; MAb, IL-5; SB 240563 | Unspecified | monoclonal antibody; biotechnology | asthma |
| MAbs, CCR3 | Unspecified | monoclonal antibody; biotechnology; chemokine antagonist | asthma |
| MAb, CD23; GW 353430 | Unspecified | monoclonal antibody; biotechnology; NSAID | rheumatoid arthritis; asthma |
| FK 888 | trans-4-hydroxy-1-[(1-methyl-1H-indol-3-yl)carbonyl]-L-proyl-N-methyl-3-(2-naphthalenyl)-N-(phenylmethyl)-L-alaninamide | neurokinin antagonist | asthma; migraine |

TABLE 16-continued

Current Candidate Therapeutic Interventions in Development for the Treatment of Asthma

| Product Name | Chemical Name | Action | Indication |
| --- | --- | --- | --- |
| lanepitant; LY 303870 | (R)-N-[2-acetyl[(2-methoxyphenyl)methyl]amino]-1-(1H-indol-3-ylmethyl)ethyl]-[1,4'-bipiperidine]-1'-acetamide | neurokinin antagonist; analgesic; neurokinin 1 antagonist | asthma; pain; migraine |
| L733060 | (2S-cis)-3-[[3,5-bis(trifluoromethyl)phenyl]methoxy]-2-phenylpiperidine | neurokinin antagonist; analgesic; neurokinin 1 antagonist; NSAID | inflammation; pain; asthma |
| saredutant; SR 48968 | (S)—N-[4-(4-acetylamino-4-phenyl-1-piperidinyl)-2-(3,4-dichlorophenyl)butyl]-N-methyl-benzamide | neurokinin antagonist; analgesic; neurokinin 2 antagonist | asthma; pain; urinary incontinence |
| MEN 10376 | Unspecified | neurokinin antagonist; bronchodilator; neurokinin 2 antagonist | asthma; anxiety |
| CP 99994 | (2S-cis)-N-[(2-methoxyphenyl)methyl]-2-phenyl-3-piperidinamine | neurokinin antagonist; neurokinin 1 antagonist; analgesic | asthma; pain |
| nolpitantium besilate; SR 140333 | (S) 1-[2-[3-(3,4-dichlorophenyl)-1-[[3-(1-methylethoxy)phenyl]acetyl]-3-piperidinyl]ethyl]-4-phenyl-1-azoniabicyclo[2.2.2]octane | neurokinin antagonist; neurokinin 1 antagonist; NSAID | asthma; inflammation |
| ZD 7944 | Unspecified | neurokinin antagonist; neurokinin 2 antagonist | asthma |
| SR 144190 | (R)-4-benzoyl-2-(3,4-difluorophenyl)-2-[2-[4-[[(dimethylamino)carbonyl]amino]-4-phenyl-1-piperidinyl]ethyl]morpholine | neurokinin antagonist; neurokinin 2 antagonist; analgesic | asthma; urinary incontinence; asthma; pain |
| FK 224; FR 115224 | N—[N2—[N—[N—[N-[alfa,beta-didehydro-N-methyl-N—[N-[1-oxo-3-(2-pentylphenyl)-propyl]-L-threonyl]tyrosyl]-L-leucyl]-D-phenylalanyl]-L-allothreonyl]-L-asparaginyl]-L-serine upsilon-lactone | neurokinin antagonist; neurokinin 2 antagonist; NSAID | asthma; inflammation |
| NS 2073 | Unspecified | nitric oxide activator; NSAID | inflammation; glaucoma; gastrointestinal ulcer; asthma |
| NCX 1005 | (11beta,16alpha)-9-fluoro-11,17-dihydroxy-16-methyl-21-[4-(nitrooxy)-1-oxobutoxyl]pregna-1,4-diene-3,20-dione | nitric oxide donor | asthma; inflammatory bowel disease |
| D 21247 | Unspecified | Non-steroid respiratory antiinflammatory agent | asthma; rhinitis |
| D 24241 | Unspecified | Non-steroid respiratory antiinflammatory agent | asthma; allergy |
| D 43787 | Unspecified | Non-steroid respiratory antiinflammatory agent | asthma; allergy |
| FPL 68164 | Unspecified | Non-steroid respiratory antiinflammatory agent | asthma |
| SU 2178 | Unspecified | Non-steroid respiratory antiinflammatory agent | dermatitis; asthma |
| LAS 30813 | Unspecified | Non-steroid respiratory antiinflammatory agent | asthma; allergy |
| CI 1018 | (R)-N-(3,4,6,7-tetrahydro-9-methyl-4-oxo-1-phenylpyrrolo[3,2,1-jk][1,4]benzodiazepin-3-yl)-4-pyridinecarboxamide | Non-steroid respiratory antiinflammatory agent | asthma |

TABLE 16-continued

Current Candidate Therapeutic Interventions in Development for the Treatment of Asthma

| Product Name | Chemical Name | Action | Indication |
|---|---|---|---|
| tetrahydrocorynanthein | 17-methoxycorynan-16-carboxylic acid methyl ester | Non-steroid respiratory antiinflammatory agent | asthma; allergy |
| tranilast; MK 341; AINTERU; BESSARAL; CLANIST; LIZAMONT; RIZALAST; SYNBERNIA; TEIBLOCK; RIZABEN | 2-[[3-(3,4-dimethoxyphenyl)-1-oxo-2-propenyl]amino]benzoic acid | Non-steroid respiratory antiinflammatory agent | asthma; allergy; conjunctivitis; rhinitis; restenosis |
| NIP 502 | 4-chloro-5-[[(3-ethoxy-4-methoxyphenyl)methyl)amino]-3(2H)-pyridazinone | Non-steroid respiratory antiinflammatory agent | asthma |
| AP 0341 | 5-amino-3-(4-chlorophenyl)-N-methyl-1H-1,2,4-triazole-1-carbothioamide | Non-steroid respiratory antiinflammatory agent | asthma |
| SCA 8801 | 6-bromo 8-(methylamino)-imidazo[1,2-a]pyrazine-2-carbonitrile | Non-steroid respiratory antiinflammatory agent | asthma |
| scopinast; KA 398 | 7-[3-[4-[bis(4-fluorophenyl)hydroxy-methoxyl]-1-piperidinyl]propxy]-6-methoxy-2H-1-benzopyran-2-one | Non-steroid respiratory antiinflammatory agent | asthma; allergy |
| KP 136; AL 136 | 8-hexyloxy-3-(1H-tetrazol-5-yl)-2H-1-benzopyran-2-one | Non-steroid respiratory antiinflammatory agent | asthma |
| anti-inflammatory agent, North Carolina University | Unspecified | NSAID | inflammation; asthma |
| CD40 receptor signalling pathway inhibitor, Axiom Biotechnologies; CD40 receptor signalling pathway inhibitor, Zaiya | Unspecified | NSAID | allergy; asthma; inflammation |
| chemokine receptor modulators, Pharmacopeia | Unspecified | NSAID | inflammation; asthma; atheroclerosis |
| gene discovery, immune system disorders, AlphaGene | Unspecified | NSAID | arthritis; asthma; allergy |
| glucocorticoid agonists, Ligand | Unspecified | NSAID | inflammation; rheumatoid arthritis; inflammatory bowel disease; asthma |
| interleukin modulators, Receptron | Unspecified | NSAID | inflammation; asthma |
| IPL | Unspecified | NSAID | asthma; respiratory disease |
| macrophage migration inhibitory factor inhibitors, Picower Institute for Medical Research | Unspecified | NSAID | arthritis; asthma |
| PKC-RACK interaction inhibitors, Telik | Unspecified | NSAID | arthritis; multiple sclerosis; asthma |
| pseudopterosin | Unspecified | NSAID | arthritis; asthma; psoriasis |
| contignasterol | (3alpha,4beta,5alpha,6alpha,7beta,14beta,22S)-22,29-epoxy-3,4,6,7,29-pentahydroxystigmastan-15-one | NSAID | asthma; respiratory disease |
| tioxamast; F 1865 | [[4-(4-methoxyphenyl)-2-thiazolyl]amino]oxoacetic acid ethyl ester | NSAID | asthma; inflammation; skin disease |
| PNU 142731; PNU 142731A | 1-[(2,4-di-1-pyrrolidinyl-9H-pyrimido[4,5-b]indol-9-yl)acetyl]pyrrolidone mono hydrochloride | NSAID | asthma |

TABLE 16-continued

Current Candidate Therapeutic Interventions in Development for the Treatment of Asthma

| Product Name | Chemical Name | Action | Indication |
|---|---|---|---|
| bamaquimast; F 10126; L 0042 | 3-[3-[[(methylamino)carbonyl]oxy]propyl]-1-propyl-2(1H)-quinoxalinone | NSAID | asthma |
| Z 1957 | ethyl N((3-methyl-5-isoxazolyl)-2-thiazolyl) oxamate | NSAID | asthma; inflammation |
| BTS 71321 | N-[1-(4-chlorophenyl)-1-methylethyl]-1H-imidazole-1-propanamine | NSAID | asthma |
| andolast; CR 2039 | N-4-(5-tetrazolyl)-phenyl-4-(5-tetrazolyl)-benzamide | NSAID | asthma; inflammation; allergy |
| VX 745 | Unspecified | NSAID; MAP kinase inhibitor; signal transduction inhibitor | inflammation; neurological; heart failure; Crohn disease; asthma |
| NCX 1004 | Unspecified | NSAID; nitric oxide donor | asthma |
| phospholipase A2 inhibitors, La Jolla | Unspecified | NSAID; phospholipase inhibitor | rehumatoid arthritis; inflammatory bowel disease; asthma |
| INKP 300 | Unspecified | NSAID; signal transduction inhibitor | asthma |
| oligonucleotide, asthma | Unspecified | oligonucleotide; biotechnology; immunostimulant | asthma |
| sulfated oligosaccharide, Progen | Unspecified | oligosaccharide | asthma |
| Ro 191400 | Unspecified | PAF antagonist | asthma |
| tulopafant; RP 59227 | (+)-N-(3-benzoylphenyl)-3-(3-pyridinyl)-1H,3H-pyrrolo[1,2-c]thizaole-7-carboxamide | PAF antagonist | asthma |
| ginkgolide A,B,C; BN 52063 | (1alpha,7beta)1-7-dihydroxyginkgolide A mixt with ginkgolide A and (1beta)-1-hydroxyginkgolide A | PAF antagonist | asthma; rhinitis; thrombocytopenia |
| L 680573; MK 287 | (2S-trans)-2-[[3-methoxy-2-propoxy-5-[tetrahydro-5-(3,4,5-trimethoxyphenyl)-2-furanyl]phenyl]sulfonyl] ethanol | PAF antagonist | asthma; septic shock |
| Ro 193704; Ro 19-3704 | (R)-3-[4-[2-[(methoxycarbonyl)oxy]-3-[[(octadecylamino)carbonyl]oxy]propoxy]butyl]thiazolium iodide | PAF antagonist | asthma |
| E 6123 | (S)-(+)-6-(2-chlorophenyl)-3-cyclopropanecarbonyl-8,11-dimethyl,2,3,4,5-tetrahydro-8H-pyrido(4',3';4,5)thieno(3,2-f)(1,2,4)triazolo(4,3-a)(1,4)diazepine | PAF antagonist | asthma |
| Ro 240238; Ro 24-0238; Ro 244376 | [R-(E,E)]-5-(4-methoxyphenyl)-N-[1-methyl-4-(3-pyridinyl)butyl]-2,4-decadienamide | PAF antagonist | asthma |
| YM 461; YM 46A | 1-(3-phenylpropyl)-4-[[2-(3-pyridinyl)-4-thiazolidinyl]carbonyl]piperazine (E)-2-butenedioate (1:1) | PAF antagonist | asthma; pulmonary obstructive disease |

TABLE 16-continued

Current Candidate Therapeutic Interventions in Development for the Treatment of Asthma

| Product Name | Chemical Name | Action | Indication |
| --- | --- | --- | --- |
| israpafant; Y 24180; PAFNOL | 4-(2-chlorophenyl)-6,9-dimethyl-2-[2-[4-(2-methylpropyl)phenyl]ethyl]-6H-thieno[3,2-f][1,2,4]triazolo[4,3-a][1,4]diazepine | PAF antagonist | asthma |
| bepafant; WEB 2170 | 4-[[6-(2-chlorophenyl)-8,9-dihydro-1-methyl-4H,7H-cyclopenta[4,5]thieno[3,2-f][1,2,4]triazolo[4,3-a][1,4]diazpine-8-yl]carbonyl]morpholine | PAF antagonist | asthma; rhinitis |
| rocepafant; BN 50730 | 6-(2-chlorophenyl)-7,10-dihydro-N-(4-methoxyphenyl)-1-methyl-4H-pyrido[4',3':4,5]thieno[3,2-f][1,2,4,triazolo[4,3-a][1,4]diazepine-9(8H)-carbothioamide | PAF antagonist | hypotension; cytoprotectant; asthma |
| foropafant; SR 27417 | N,N-dimethyl-N'-(3-pyridinylmethyl)-N'-[4-[2,4,6-tris(1-methylethyl)phenyl)-2-thiazolyl]1,2-ethanediamine | PAF antagonist | asthma |
| SCH 37370 | 1-acetyl-4-(8-chloro-5,6-dihycro-IIH-benzo[5,6]cyclohepta[1,2-b]pyridin-II-ylidene)piperidine | PAF antagonist; histamine antagonist; histamine H1 antagonist | asthma; rhinitis |
| CMI 392 | trans-2-[5-(N'-methyl-N'-hydroxyureidylmethyl)-3-methoxy-4-p-chlorophenylthio-ethoxyphenyl]-5-(3,4,5-trimethoxypehnyl)tetra-hydrofuran | PAF antagonist; leukotriene antagonist | psoriasis; dermatitis; asthma |
| UR 12510 | Unspecified | PAF antagonist; NSAID | inflammation; asthma |
| UR 12519 | Unspecified | PAF antagonist; NSAID | inflammation; asthma |
| UR 12551 | Unspecified | PAF antagonist; NSAID | inflammation; asthma |
| BN 52111 | 1-(6-((2-heptadecyl-2-methyl-1,3-dioxolan-4-yl)methoxy)-6-oxohexyl)-pyridinium bromide | PAF antagonist; NSAID | asthma; inflammation |
| tiapafant; PCA 4248 | 1,4-dihydro-2,4,6-trimethyl-3,5-pyridinedicarboxylic acid methyl 2-(phenylthio)ethyl ester | PAF antagonist; NSAID | asthma; inflammation |
| BN 52115 | 1-[6-[(2-heptadecyl-2-methyl-1,3-dioxolan-4-yl)methoxy]-6-oxohexyl]quinolinium bromide | PAF antagonist; NSAID | asthma; inflammation |
| UR 10324 | 2-(2-acetyl-3,11-dioxo-4,10-dioxa-7-thia-2,12-diazanonacos-1-yl)-1-ethylpyridinium chloride | PAF antagonist; NSAID | inflammation; asthma |
| tetrahydrocarbazole | 4-(2-chlorophenyl)-9-methyl-2-[3-(1,2,3,4-tetrahydro-9H-carbazol-9-yl)-1-propynyl]-6H-thieno[3,2-f][1,2,4]triazolo[4,3-a][1,4]diazepine | PAF antagonist; NSAID | inflammation; asthma |
| UR 12460 | 4-[[(diphenylmethyl)amino]acetyl]-alpha-(2-methyl-3-pyridinyl)-1-piperazineacetonitrile | PAF antagonist; NSAID | inflammation; asthma |

TABLE 16-continued

Current Candidate Therapeutic Interventions in Development for the Treatment of Asthma

| Product Name | Chemical Name | Action | Indication |
|---|---|---|---|
| SM 10661 | cis-(+,−)-3,5-dimethyl-2-(3-pyridinyl)-4-thiazolidinone monohydrochloride | PAF antagonist; NSAID | endotoxic shock; inflammation; asthma |
| AH 21132 | cis N-(4-(1,2,3,4,4a,10b-hexahydro-8,9-dimethosy-2-methylbenzo(c)(1,6)naphthyridin-6-yl)phenyl)-acetamide (Z)-2-buetendioate (1:2) | PAF antagonist; phosphodiesterase inhibitor; phosphodiesterase III inhibitor; phosphodiesterase IV inhibitor; bronchodilator | asthma |
| F 1850 | Unspecified | PAF antagonist; platelet antiaggregant | thrombosis; asthma |
| dacopafant; RP 48740 | (3R)-3-(3-pyridyl)-1H,3H-pyrrolo[1,2-c]thiazole-7-carboxamide | PAF antagonist; platelet antiaggregant | asthma; thrombosis |
| YM 264 | 1-(3-methyl-3-phenylbutyl)-4-[[2-(3-pyridinyl)-4-thiazolidinyl]carbonyl] piperazine (E)-2-butenedioate (1:1) | PAF antagonist; platelet antiaggregant | thrombosis; asthma |
| SDZ 64412; SDZ 64-412 | 2,3-dihydro-5-[4-[2-(3,4,5-trimethoxyphenyl)ethyl]phenyl]imidazo[2,1-a]isoquinoline monohydrochloride | PAF antagonist; platelet antiaggregant | asthma; thrombosis |
| R 74717 | 3-(5-(0-(2S,3S)-(3-heptadecylcarbamoyl-thiotetrahydropyran-2-yl)methyl)phosphonoxy)pentyl thiazolium | PAF antagonist; platelet antiaggregant | asthma; thrombosis |
| R 74654 | 3-(6-(0-(2R,2S)-(3-heptadecylcarbamoyloxy-tetrahydropyran-2-yl)methyl)phosphonoxy)hexyl-thiazolium | PAF antagonist; platelet antiaggregant | asthma; thrombosis |
| UK 74505 | 4-(2-chlorophenyl)-1,4-dihydro-6-methyl-2-[4-(2-methyl-1H-imidazo[4,5-c]pyridin-1-yl)phenyl]-5-[(2-pyridinylamino)carbonyl]-3-pyridinecarboxylic acid ethyl ester | PAF antagonist; platelet antiaggregant | thrombosis; asthma |
| UR 12670 | 4-[(2-methyl-1H-imidazo[4,5-c] pyridin-1-yl)methyl]-1-(1-oxo-3,3-diphenylpropyl)-piperidine | PAF antagonist; platelet antiaggregant | kidney disease; ischemia; asthma; pancreatitis |
| SR 27388 | 4-[2-[[2-(dimethylamino)ethyl](3-pyridinylmethyl)amino]-4-thiazolyl]-2,6-bis(1,1-dimethylethyl)phenol | PAF antagonist; platelet antiaggregant | thrombosis; asthma; septic shock |
| apafant; WEB 2086; WEB 2086BS | 4-[3-[4-(2-chlorophenyl)-9-methyl-6H-thieno[3,2-f][1,2,4]triazolo [4,3-a][1,4]diazepin-2-yl]-1-oxopropyl morpholine | PAF antagonist; platelet antiaggregant | asthma; rhinitis; pancreatitis |
| Ro 244736; Ro 24-4736 | 5-[3-[4-(2-chlorophenyl)-9-methyl-6H-thieno[3,2-f][1,2,4]triazolo [4,3-a][1,4]diazepin-2-yl]-2-propynyl]-6(5H)-phenanthridinone | PAF antagonist; platelet antiaggregant | thrombosis; asthma; septic shock |

TABLE 16-continued

Current Candidate Therapeutic Interventions in Development for the Treatment of Asthma

| Product Name | Chemical Name | Action | Indication |
|---|---|---|---|
| WEB 2347 | 6-(2-chlorophenyl)-8,9-dihydro-1-methyl-N,N-dipropyl-4H,7H-cyclopenta[4,5]thieno[3,2-f][1,2,4]triazolo[4,3-a][1,4]diazepine-8-carboxamide | PAF antagonist; platelet antiaggregant | asthma; anaphylactic shock; thrombosis |
| ginkgolide B; BN 52021 | hexacyclic trilactone | PAF antagonist; platelet antiaggregant | thrombosis; dermatitis; asthma; multiple sclerosis; septic shock |
| L 659989 | trans-(+,−)-tetrahydro-2-[3-methoxy-5-(methylsulfonyl)-4-propoxyphenyl]-5-(3,4,5-trtimethoxyphenyl)furan | PAF antagonist; platelet antiaggregant | asthma; thrombosis |
| SDZ 64619 | (+,−)-2-[6-methoxy-2-(methylsulfonyl)-3,9-dioxo-4,8-dioxa-2,10-diazaoctacosan-1-yl)-1-methylpyridinium iodide | PAF antagonist; platelet antiaggregant; bronchodilator | thrombosis; asthma |
| asthma therapy, Peptide Therapeutics | Unspecified | peptide | asthma |
| cathepsin S inhibitors, Peptimmune | Unspecified | peptide; proteinase inhibitor; cathepsin S inhibitor | asthma |
| BY 217 | Unspecified | phosphodiesterase inhibitor | asthma |
| phosphodiesterase inhibitor, Rhone-Poulenc Rorer | Unspecified | phosphodiesterase inhibitor | asthma |
| KP 885 | Unspecified | phosphodiesterase inhibitor; bronchodilator | asthma |
| WY 123641; PDA 641 | Unspecified | phosphodiesterase inhibitor; bronchodilator | asthma |
| KF 19514 | 1,5-dihydro-5-phenyl-4H-imidazo]4,5-c][1,8]naphthyridin-4-one | phosphodiesterase inhibitor; bronchodilaotr | asthma |
| P 1432 | 3-(cyclopropylmethyl)-xanthine | phosphodiesterase inhibitor; bronchodilator | asthma |
| LAS 31396 | Unspecified | phosphodiesterase inhibitor; bronchodilator; NSAID | asthma; inflammation |
| arofylline; LAS 31025 | 3-(4-chlorophenyl)-3,7-dihydro-1-propyl-1H-purine-2,6-dione | phosphodiesterase inhibitor; bronchodilator; NSAID | asthma; inflammation |
| tolafentrine; BY 4070 | (−)-4-(cis-1,2,3,4,4a,10b-hexahydro-8,9-dimethoxy-2-methylbenzo[c][1,6]=naphthyridin-6-yl)-p-toluenesulfonamide | phosphodiesterase inhibitor; phosphodiesterase III inhibitor; phosphodiesterase IV inhibitor; bronchodilator | asthma |
| zardaverine; B 84290 | 6-(4-(difluoromethoxy)-3-methoxyphenyl)-3(2H)-pyridazinone | phosphodiesterase inhibitor; phosphodiesterase III inhibitor; phosphodiesterase IV inhibitor; bronchodilator | asthma |
| AWD 12281 | Unspecified | phosphodiesterase inhibitor; phosphodiesterase IV inhibitor | asthma |
| BAY 198004 | Unspecified | phosphodiesterase inhibitor; phosphodiesterase IV inhibitor | asthma |
| DWP 205297 | Unspecified | phosphodiesterase inhibitor; phosphodiesterase IV inhibitor | asthma |

TABLE 16-continued

Current Candidate Therapeutic Interventions in Development for the Treatment of Asthma

| Product Name | Chemical Name | Action | Indication |
|---|---|---|---|
| PDE-4 inhibitors, Zambon | Unspecified | phosphodiesterase inhibitor; phosphodiesterase IV inhibitor | asthma |
| YM 976 | Unspecified | phosphodiesterase inhibitor; phosphodiesterase IV inhibitor | asthma |
| CP 220629; CP 220,629 | 1-cyclopentyl-3-ethyl-1,4,5,6-tetrahydro-6-(2-methylphenyl)-7H-pyrazolo[3,4-c]pyridin-7-one | phosphodiesterase inhibitor phosphodiesterase IV inhibitor | asthma |
| LAS 32688 | Unspecified | phosphodiesterase inhibitor; phosphodiesterase IV inhibitor; bronchodilator | asthma |
| phosphodiesterase inhibitors, Celltech/Merck & Co | Unspecified | phosphodiesterase inhibitor; phosphodiesterase IV inhibitor; bronchodilator | asthma |
| CDP 840 | (R)-4-[2-[3-(cyclopentyloxy)-4-methoxyphenyl]-2-phenylethyl]pyridine | phosphodiesterase inhibitor; phosphodiesterase IV inhibitor; bronchodilator NSAID | asthma; inflammation |
| filaminast; WAY PDA 641 | 1-[3-(cyclopentyloxy)-4-methoxyphenyl]ethanone, (E)-O-(aminocarbonyl)oxime | phosphodiesterase inhibitor; phosphodiesterase IV inhibitor; bronchodilator | asthma |
| piclamilast; RP 73401; RPR 73401 | 3-cyclopentyloxy-N-(3,5-dichloropyridin-4-yl)-4-methoxybenzamide | phosphodiesterase inhibitor; phosphodiesterase IV inhibitor; bronchodilator NSAID | asthma; arthritis |
| SB 207499; ARIFLO | cis-4-cyano-4-[3-(cyclopentyloxy)-4-methoxyphenyl]cyclo-hexanecarboxylic acid | phosphodiesterase inhibitor; phosphodiesterase IV inhibitor; bronchodilator NSAID | asthma; pulmonary obstructive disease |
| D 4418 | Unspecified | phosphodiesterase inhibitor; phosphodiesterase IV inhibitor; immunosuppressant; bronchodilator | asthma |
| D 22888 | Unspecified | phosphodiesterase inhibitor; phosphodiesterase IV inhibitor phosphodiesterase V inhibitor; bronchodilator | asthma |
| SKF 96321 | 2-(2-propoxyphenyl)-6-purinone | phosphodiesterase inhibitor; phosphodiesterase V inhibitor; bronchodilator | asthma |
| doxofylline; ABC 12/3; DO 309; MAXIVENT; ANSIMAR | 7-(1,3-dioxolan-2-ylmethyl)-3,7-dihydro-1,3-dimethyl-1H-purine-2,6-dione | phosphodiesterase inhibitor; xanthine | asthma |
| phospholipase A2 inhibitors, Fisons | Unspecified | phospholipase inhibitor; NSAID | asthma; rheumatoid arthritis; psoriasis; inflammatory bowel disease |
| cyclic polyamine analogue, SunPharm | Unspecified | polyamine analogue; NSAID | Crohn disease; asthma; inflammation |
| thymosin beta 4; Tbeta 4 | Thymosin beta 4 (rat clone pROS2 precursor) | Polymerization of G-actin to F-actin controlling agent | septic shock; respiratory distress syndrome; asthma |
| BIIX 1; RS 91309 | Unspecified | potassium channel activator | asthma |
| CL 891902 | Unspecified | potassium channel activator; bronchodilator | asthma; hypertension |

TABLE 16-continued

Current Candidate Therapeutic Interventions in Development for the Treatment of Asthma

| Product Name | Chemical Name | Action | Indication |
|---|---|---|---|
| BRL 55834 | (3S,4R)-3,4-dihydro-2,2-dimethyl-4-(2-oxopiperidin-1-yl)-6 pentafluoroethyl-2H-1-benzopyran-3-ol | potassium channel activator; bronchodilator | asthma |
| SDZ PCO400 | (3S-trans)-2,4-dihydro-3-hydroxy-2,2-dimethyl-4-[(3-oxo-1-cyclopenten-1-yl)oxy]-2H-1-benzopyran-6-carbonitrile | potassium channel activator; bronchodilator | asthma |
| emakalim; EMD 56431 | (3S-trans)-3,4-dihydro-3-hydroxy-2,2-dimethyl-4-(2-oxo-1(2H)-pyridinyl)-2H-1-benzopyran-6-carbonitrile | potassium channel activator; bronchodilator | hypertension; heart failure; asthma; peripheral vascular disease |
| UR 8308 | 1,2-dihydro-2,2-dimethyl-4-(N-oxide-2-pyridyl)-1-oxonaphthalen-6-carbonitrile | potassium channel activator; bronchodilator | asthma |
| UR 8328 | 1,2-dihydro-2,2-dimethyl-4-(N-oxide-2-pyridyl)-6-pentafluoroethylnaphthalen-1-one | potassium channel activator; bronchodilator | athma |
| UR 8225 | 1,2-dihydro-4-(1,2-dihydro-2-oxo-1-pyridyl)-2,2-dimethyl-1-oxonaphthalene-6-carbonitrile | potassium channel activator; bronchodilator | hypertension; asthma; urinary incontinence |
| RP 66471 | 1S,2R-trans-2-benzoyloxy-1-(pyrid-3-yl)cyclohexane-(N-methyl)-carbthioamide | potassium channel activator; bronchodilator | asthma |
| Ro 316930 | 2,2-dimethyl-4-(2-pyridinyl)-2H-1-benzopyran-6-carbonitrile N4-oxide | potassium channel activator; bronchodilator | hypertension; asthma |
| YM 934 | 3,4-dihydro-2,2-dimethyl-6-nitro-4-(2-pyridinyl)-2H-1,4-benzoxazine N-oxide | potassium channel activator; bronchodilator | hypertension; asthma; urinary incontinence |
| SR 47063 | 4-(2-cyanoimino-1,2-dihydropyrid-1-yl)-6-nitro-2,2-dimethyl-2H-1-benzopyran | potassium channel activator; bronchodilator | heart ischemia; asthma |
| potassium channel activator, Merck KGaA | 4-[(1,6-dihydro-1-methyl-6-oxo-3-pyridazinyl)oxy]-3,4-dihydro-3-hydroxy-2,2-dimethyl-2H-1-benzopyran-6-carbonitrile | potassium channel activator; bronchodilator | hypertension; asthma |
| symakalim; EMD 57283 | 4-[(1,6-dihydro-1-methyl-6-oxo-3-pyridazinyl)oxy]-3,4-dihydro-3-hydroxy-2,2-dimethyl-2H-1-benzopyran-6-carbonitrile | potassium channel activator; bronchodilator | hypertension; coronary artery disease; asthma |
| SCA 40 | 6-bromo-8-(methylamino)-imidazo[1,2-a]pyrazine-2-carbonitrile | potassium channel activator; bronchodilator | hypertension; asthma |
| rilmakalim; HOE 234 | (3S,4R)-3-hydroxy-2,2-dimethyl-4-(3-oxo-1-pyrrolidinyl)-6-phenylsulfonylchroman hemihydrate | potassium channel activator; vasodilator; bronchodilator | asthma |
| bimakalim; EMD 52692 SR 44866 | 2,2-dimethyl-4-(2-oso-1(2H)-pyridinyl)-2H-1-benzopyran-6-carbonitrile | potassium channel activator; vasodilator; bornchodilator | coronary artery disease; asthma; peripheral vascular disease |

TABLE 16-continued

Current Candidate Therapeutic Interventions in Development for the Treatment of Asthma

| Product Name | Chemical Name | Action | Indication |
|---|---|---|---|
| potassium channel modulators, Phytera/NeuroSearch | Unspecified | potassium channel modulator | cognitive defect; attention deficit disorder; depression; asthma; diabetes |
| NS 1619 | 1,3-dihydro-1-[2-hydroxy-5-(trifluoromethyl)phenyl]-5-(trifluoromethyl)-2H-benzimidazol-2-one | potassium channel modulator; bronchodilator | stroke asthma |
| protein kinase activators, SmithKline Beecham | Unspecified | protein kinase activator; protein kinase A activator | asthma; thrombosis |
| allergy therapy, Kinetix | Unspecified | protein kinase inhibitor | allergy; asthma |
| Y 27632 | [4(R)-trans]-4-(1-aminoethyl)-N-4-pyridinylcyclohexanecarboxamide | protein kinase inhibitor | hypertension; asthma; cancer |
| Syk inhibitors, Ariad | Unspecified | protein kinase inhibitor tyrosine kinase inhibitor | asthma; allergy |
| Der p I inhibitor, Peptide Therapeutics | Unspecified | proteinase inhibitor | asthma |
| alpha-1-antitrypsin | Unspecified | proteinase inhibitor; biotechnology | asthma; emphysema; cystic fibrosis; dermatitis; psoriasis |
| mycophenolate mofetil; RS 61443; CellCept | (E)-6-(1,3-dihydro-4-hydroxy-6-methoxy-7-methyl-3-oxo-5-isobenzofuranyl)-4-methyl-4-hexenoic acid 2-(4-morpholinyl)ethyl ester | purine syntheses inhibitor; immunosuppressant; NSAID | transplant rejection; rheumatoid arthritis; asthma; restenosis; kidney disease; systemic lupus erythematosus |
| asthma therapy, SAIK, | Unspecified | SAIK immunomodulation | asthma |
| NO-SOD mimetics, NitroMed; nitrosylated superoxide dismutase mimetics, NitroMed | Unspecified | SOD mimetic; nitric oxide donor | asthma; respiratory distress syndrome; ischemia; reperfusion injury |
| WS 9326A | Unspecified | substance P antagonist | asthma |
| CGP 49823 | (2R-trans)-1-(3,5-dimethylbenzoyl)-2-(phenylmethyl)-N-(4-quinolinylmethyl-4-piperidinamine | substance P antagonist | anxiety; asthma |
| FR 113680 | N-acetyl-L-threonyl-1-formyl-D-tryptophyl-N-methyl-N-(phenylmethyl)-L-phenylalaninamide | substance P antagonist | asthma |
| dapitant; RPR 100893 | [3aS-[2(R*),3aalpha,4beta,7a alpha]]-octahydro-4-(2-methoxyphenyl)-2-[2-(2-methoxyphenyl)-1-oxopropyl]-7,7-diphenyl-1H-isoindol-4-ol | substance P antagonist; NSAID | asthma; inflammation; migraine |
| MEN 10627 | Unspecified | tachykinin antagonist; antispasmodic | irritable bowel syndrome; asthma |
| nepadutant; MEN 11420 | Cyclo[3-amino-L-alanyl-L-leucyl-N-[2-(acetylamino)-2-deoxy-beta-D-glucopyranosyl]-L-asparaginyl-L-alpha-aspartyl-L-tryptophyl-L-phenylalanyl], cyclic (4->1)-peptide | tachykinin antagonist; antispasmodic | asthma; irritable bowel syndrome |
| Th2 modulators, AstraZeneca | Unspecified | Th2 modulation | asthma; dermatitis |
| seratrodast; serabenast; AA 2414; A 73001; ABT 001; BRONICA | (+,-)-zeta-(2,4,5-trimethyl-3,6-dioxo-1,4-cyclohexadien-1-yl)-benzeneheptanoic acid | thromboxane antagonist | asthma; rhinitis |

TABLE 16-continued

Current Candidate Therapeutic Interventions in Development for the Treatment of Asthma

| Product Name | Chemical Name | Action | Indication |
| --- | --- | --- | --- |
| SKF 88046 | N,N'-bis[7-93-chlorobenzene aminosulfonyl)-1,2,3,4-tetrahydroisoquinolyl]di-sulfonylimide | thromboxane antagonist | asthma |
| L 670596 | (−)-6,8-difluoro-2,3,4,9-tetrahydro-9-[[4-(methylsulfonyl)phenyl]methyl]-1H-carbazole-1-acetic acid | thromboxane antagonist; platelet antiaggregant | asthma; thrombosis |
| domitroban; S 1452; S 145; ANBOXAN | (+,−)-[1alfa,2lfa(Z),3beta,4alfa]-7-[3-[(phenylfulfonyl)amino]bicyclo[2.2.1]hept-2-yl]-5-heptenoic acid | thromboxane antagonist; platelet antiaggregant | asthma; rhinitis; thrombosis |
| ramatroba; BAY u 3405; EN 137774 | (R)-3-[[(4-fluorophenyl)sulfonyl]amino]-1,2,3,4-tetrahydro-9H-carbazole-9-propanoic acid | thromboxane antagonist; platelet antiaggregant | asthma; rhinitis |
| SQ 33961 | [1S-(exo,exo)]-2-[[3-[4-[[(4-cyclohexylbutyl)amino]carbonyl]-2-oxazolyl]-7-oxabicyclo[2.2.1]hept-2-yl]methyl]benzenepropanoic acid | thromboxane antagonist; platelet antiaggregant | thrombosis; peripheral vascular disease; asthma |
| ONO 8809 | [1S-[1alfa,2alfa(Z),3beta,4alfa]]-6-[3-[[[(4-bromophenyl)dulfonyl]amino]methyl]bicyclo[2.2.1]hept-2-yl]-5-hexenoic acid decyl ester | thromboxane antagonist; platelet antiaggregant | thrombosis; asthma |
| ICI 192605 | [2alfa,4alfa,5alfa(Z)]-6-[2-(2-chlorophenyl)-4-(2-hydroxyphenyl)-1,3-dioxan-5-yl]-4-hexenoic acid | thromboxane antagonist; platelet antiaggregant | thrombosis; asthma |
| ICI 185282 | [2alfa,4alfa,5alfa(Z)]-7-[4-(2-hydroxyphenyl)-2-(trifluoromethyl)-1,3-dioxan-5-yl]-5-heptenoic acid | thromboxane antagonist; platelet antiaggregant | thombosis; asthma |
| KT 2962; KT 2-962 | 3-[4-[[(4-chlorophenyl)sulfonyl]amino]butyl]-6-(1-methylethyl)-1-azulene sulfonic acid monosodium salt | thromboxane antagonist; platelet antiaggregant | stroke; asthma; kidney disease; thrombosis |
| ON 579 | 4-(2-(4-chlorophenylsulfonyl-amino)ethylthio)-2,6-difluorophenoxyacteic acid | thromboxane antagonist; platelet antiaggregant | thrombosis; asthma |
| KDI 792; FK 070; FR 12170 | [2S-[2alpha,(Z),4beta]]-6-[4-[[(4-chlorophenyl)dulfonyl]amino]-1-(3-pyridinylmethyl)-2-pyrrolidinyl]-5-hexenoic acid | thromboxane antagonist; thromboxane synthetase inhibitor; platelet antiaggregant | thrombosis; peripheral vascular disease; asthma |
| E 6700 | (E)-alpha-[(4-methoxy-2,5-dimethyl-3,6-dioxo-1,4-cyclohexadien-1-yl)methylene]-3-pyridineheptanoic acid | thromboxane synthetase inhibitor | asthma |
| F 1322 | N-[2-[4-(diphenylmethoxy)-1-piperidinyl]ethyl]-3-hydroxy-5-(3-pyridinylmethoxy)-2-naphthalenecarboxamide | thromboxane synthetase inhibitor | asthma |

TABLE 16-continued

Current Candidate Therapeutic Interventions in Development for the Treatment of Asthma

| Product Name | Chemical Name | Action | Indication |
| --- | --- | --- | --- |
| KK 505 | 2-ethyl-4-(3-pyridyl)-1(2H)-phthalazinone | thromboxane synthetase inhibitor; bronchodilator | asthma |
| KK 562 | 2-methyl-4-(5-thiazolyl)-1(2H)-phthalazinone | thromboxane synthetase inhibitor; bronchodilator | asthma |
| ozagrel; ozagrel sodium; OKY 046; DOMENAN; CATACLOT; XANBON; VEGA | (E)-3-[4-(1H-imidazol-1-ylmethyl)phenyl]-2-propenoic acid | thromboxane synthetase inhibitor; platelet antiaggregant | stroke; thrombosis; asthma; cough |
| Y 20811 | 4-(hydroxy(5-(1H-imidazol-1-yl)-2-methylphenyl)methyl)-3,5-dimethyl-benzoic acid, monosodium salt | thromboxane synthetase inhibitor; platelet antiaggregant | thrombosis; asthma; stroke |
| imitrodast; CS 518; RS 5186 | 4,5-dihydro-2-(1H-imidazol-1-ylmethyl)-benzo[b]thiophene-6-carboxylic acid sodium salt | thromboxane synthetase inhibitor; platelet antiaggregant | asthma |
| nafagrel; DP 1904 | 5,6,7,8-tetrahydro-6-(1H-imidazol-1-ylmethyl)-2-naphthalenecarboxylic acid | thromboxane synthetase inhibitor; platelet antiaggregant | thrombosis; angina; asthma; restenosis |
| ZT 386 | Unspecified | thromboxane synthetase inhibitor; thromboxane antagonist; platelet antiaggregant | thrombosis; asthma |
| tumor necrosis factor inhibitors, Selectide | Unspecified | TNF inhibitor; NSAID | inflammation; asthma; inflammatory bowel disease |
| NF-kappaB inhibitor, Molecumetics | Unspecified | transcription factor regulator; NSAID | asthma, inflammation; restenosis |
| asthma therapy, Proteus | Unspecified | tryptase inhibitor | asthma |
| BAY 358535; BAY 35-8535; BAY 171998; BAY 17-1998 | Unspecified | tryptase inhibitor | asthma |
| BAY 443428 | Unspecified | tryptase inhibitor | asthma |
| oral tryptase inhibitors, Molecumetics | Unspecified | tryptase inhibitor | inflammatory bowel disease; asthma; psoriasis |
| tryptase inhibitors, Axys | Unspecified | tryptase inhibitor; NSAID | asthma; inflammation; rhinitis; inflammatory bowel disease; psoriasis |
| APC 366 | N2-[(1-hydroxy-2-naphthalenyl)carbonyl]-L-arginyl-L-prolinamide monohydrochloride | tryptase inhibitor; peptide | asthma |
| allergy/asthma therapy, | Unspecified | Tyrosine kinase stimulator; blocks IgE asthma | asthma; allergy |
| APO 77 | Unspecified | | |
| ARL 68475; FPL 68475 | Unspecified | Unspecified | asthma |
| asthma/allergy therapy, | Purified plant extracts | Unspecified | asthma; allergy |
| TO 190 | Unspecified | Unspecified | asthma |
| MDL 105212 | (R)-1-[2-[3-(3,4-dichlorophenyl)-1-(3,4,5-trimethoxybenzoyl)-3-pyrrolidinyl]ethyl-4-phenyl-4-piperidinecarboxamide | Unspecified | asthma |
| doqualast; SM 857 | 11-oxo-11H-pyrido[2,1-b]quinazoline-2-carboxylic acid | uricosuric | asthma; gout |
| vaccine, asthma | Unspecified | vaccine | asthma |
| non-ionic surfactant vesicles; NISV | Unspecified | vaccine adjuvant; immunosuppressant | rheumatoid arthritis; asthma; inflammation |
| colforsin dapropate; NKH 477; ADEHL | 6-[3-(dimethylamino)pro-pionyl]forskolin | vasodilator; bronchodilator | heart failure; asthma; musculoskeletal disorder |

TABLE 16-continued

Current Candidate Therapeutic Interventions in Development for the Treatment of Asthma

| Product Name | Chemical Name | Action | Indication |
| --- | --- | --- | --- |
| ibudilast; KC 404; KETAS; AIVYNAL; EYEVYNIL | 3-isobutyryl-2-isopropylpyrazolo-(1,5alpha)-pyridine | vasodilator; PAF antagonist | asthma; eye disease |
| VLA-4 inhibitors, Cytel | Unspecified | VLA 4 antagonist; integrin antagonist; cell adhesion inhibitor | asthma |
| nestifylline; ABC 99 | 7-(1,3-dithiolan-2-ylmethyl)-3,7-dihydro-1,3-dimethyl-1H-purine-2,6-dione | xanthine | asthma |
| MX 2120 | 7-(2,2 dimethyl)propyl-1-methylxanthine | xanthine | asthma |
| isbufylline | 7-isobutyltheophylline | xanthine | asthma |
| MPX | 3,7-dihydro-1-methyl-3-(1-methylethyl)-1H-purine-2,6-dione | xanthine; bronchodilator | asthma |

TABLE 17

Current Candidate Therapeutic Interventions for the Treatment of Inflammatory Bowel Disease

| Product Name | Chemical Name | Action | Indication |
| --- | --- | --- | --- |
| E 3040 | 5,7-dimethyl-2-(methylamino)-4-(3-pyridinylmethyl)-6-benzothiazolol | 5 lipoxygenase inhibitor; thromboxane synthase inhibitor | ulcerative colitis |
| FPL 64170 | unspecified | Antiinflammatory | ulcerative colitis |
| antisense oligonucleotide, NF-kappaB p65 subunit | unspecified | antisense; oligonucleotide; immunosuppressant | Crohn disease |
| balazipone; OR 1364 | 3-(2-acetyl-3-oxo-1-butenyl)benzonitrile | chemoprotectant; cytoprotectant | Crohn disease; ulcerative colitis |
| sucralfate; ANTEPSIN; CARAFATE; KEAL; TUNALMIN; ULCAR; ULCERLMIN; ULCERIM; ULCOGENT; ULSANIC | sucrose octakis(hydrogen sulfate), aluminum complex | chemoprotectant; cyloprotectant | gastrointestinal ulcer; ulcerative colitis |
| CR 1795 | (R)-5-(dipentylamino)-4-[(2-naphthalenylcarbonyl)a-mino-5-oxo-pentanoic acid | cholecystokinin antagonist | ulcerative colitis; pancreatitis |
| budesonide; budesonide propionate; S 1320; PREFERID; PULMICORT; RHINOCORT; ENTOCORT; NARICORT; INFLAMMIDE; BETACTIN; ELTAIR; HORACORT; RHINOCORT AQUA | (11beta,16alpha)-16,17-[butylidenebis(oxy)]-11,21-dihydroxypregna-1,4-diene-3,20-dione | corticosteroid | asthma; skin disease; inflammation; rhinitis; ulcerative colitis; Crohn disease |
| FPL 62064 | N-(4-methoxyphenyl)-1-phenyl-1H-pyrazole-3-amine | COX inhibitor; 5 lipoxygenase inhibitor | inflammatory bowel disease; psoriasis |
| CRF1 partial agonist, | unspecified | CRF1 receptor agonist | Alzheimer disease; Crohn disease |
| CDC 801 | unspecified | cytokine inhibitor; TNF inhibitor; phosphodiesterase inhibitor; phosphodiesterase IV inhibitor | Crohn disease |
| oprelvekin; interleukin-11; IL-11; YM 294; NEUMEGA | unspecified | cytokine; immunostimulant | cancer; HIV infection; mucositis; Crohn disease |

TABLE 17-continued

Current Candidate Therapeutic Interventions for the Treatment of Inflammatory Bowel Disease

| Product Name | Chemical Name | Action | Indication |
|---|---|---|---|
| interleukin-10; IL-10; cylokine synthesis inhibitory factor; CSIF; SCH 52000; TENOVIL | interleukin 10 (human clone pH15C) | cytokine; vaccine adjuvant; immunosuppressant; NSAID | autoimmune disease; inflammatory bowel disease; rheumatoid arthritis; multiple sclerosis; psoriasis; HIV infection; viral infection |
| IxC 1-62/47 | unspecified | enzyme | kidney disease; inflammatory bowel disease; Crohn disease |
| interleukin-2 diphtheria toxin chimeric protein; interleukin-2 fusion toxin; IL-2 fusion toxin; DAB 486-IL-2; D-IL-2 | unspecified | fusion toxin; NSAID | diabetes; HIV infection; rheumatoid arthritis; cancer |
| WILD 20 | [R-[R*,S*-(E)]]-2-amino 3-hydroxy-4-eicosenyl-O-beta-D-galactopyranosyl-(1->3)-O-2-amino-2-deoxy-beta-D-galactopyranosyl-(1->4)-O-[alpha-neuraminosyl-(2->3)]-O-beta-D-galactopyranosyl-(1->4)-beta-D-glucopyranoside | ganglioside | inflammatory bowel disease |
| beta-glucan antagonist | unspecified | glucan antagonist | conjunctivius; asthma; psoriasis; ulcerative colitis |
| heparin binding epidermal growth factor-like factor; HB-EGF | unspecified | growth factor | respiratory distress syndrome; ulcerative colitis |
| glucagon-like peptide-2; GLP-2 | unspecified | growth factor; peptide; hormone | inflammatory bowel disease |
| ALX 0600 | unspecified | hormone; peptide | gastrointestinal disorder |
| interleukin-1 beta converting enzyme inhibitors, | unspecified | IL-1 beta converting enzyme inhibitor; caspase inhibitor; NSAID | inflammation |
| VX 740; HMR 3480 | unspecified | IL-1 beta converting enzyme inhibitor; caspase inhibitor; NSAID | rheumatoid arthritis; osteoarthritis; inflammation |
| antisense oligonucleotide, ICAM-1; antisense oligonucleotide, intracellular adhesion molecule-1; ISIS 2302 | d[(R)-P-thio](G-C-C-C-A-A-G-C-T-G-G-C-A-T-C-C-G-T-C-A) DNA | immunosuppressant; antisense; oligonucteotide; NSAID | rheumatoid arthritis; psoriasis; inflammatory bowel disease; asthma |
| leukocyle function associated antigen 3 T cell inhibitor protein; LFA3TIP; LFA3TIP; AMEVIVE | unspecified | immunosuppressant; NSAID | inflammation; autoimmune disease; psoriasis |
| atpha4 beta7 antagonists, | unspecified | integrin antagonist; alpha4 beta7 integrin antagonist; cell adhesion inhibitor | Crohn disease; inflammatory bowel disease |
| interferon alfa-2b; IFN alfa-2b; SCH 30500, YM 1490; INTRON A; CIBIAN; VIRAFERON | unspecified | interferon; cylokine immunostimulant | cancer; viral infection |
| secretory cell inhibitors, CAMR | Clostridium botulinum toxin extract | Intracellular trafficking blockade | allergy; inflammation; respiratory disease |
| SC 52798 | (+)-7-[3-[2-(cyclopropylmethyl)-3-methoxy-4-(4-thiazolyl)phenoxy]propoxy)-3,4-dihydro-8-propyl-2H-1-benzopyran-2-carboxylic acid | leukotriene B4 antagonist; leukotriene antagonist | psoriasis; ulcerative colitis |

TABLE 17-continued

Current Candidate Therapeutic Interventions for the Treatment of Inflammatory Bowel Disease

| Product Name | Chemical Name | Action | Indication |
| --- | --- | --- | --- |
| ONO 4057; LB 457 | (E)-2-(4-carboxybutoxy)-6-[[6-(4-methoxyphenyl)-5-hexenyl]oxy]benzenepropanoic acid | leukotriene B4 antagonist; leukotriene antagonist | ulcerative colitis |
| MAb, tumor necrosis factor; MAb, TNF; SMA TNF | unspecified | monoclonal antibody | Crohn disease; cancer; septic shock |
| MAb, IBD1; MAb, inflammatory bowel disease; LM IBD1 | unspecified | monoclonal antibody | Crohn disease |
| MAb, interleukin-12; MAb, IL-12 | unspecified | monoclonal antibody | Crohn disease; ulcerative colitis |
| nerelimomab; MAb, TNF; MAb, tumor necrosis factor; BAY x 1351 | immunoglobulin G1 (mouse monoclonal BAY x 1351.gamma.1-chain anti-human tumour necrosis factor.alpha.), disulfide with mouse monoclonal BAY x 1351 tight chain, dimer | monoclonal antibody | Crohn disease |
| MAb, T cell antigen receptor; TM 29 | unspecified | monoclonal antibody; immunosuppressant | cancer; Crohn disease |
| MAb, alpha4 beta7 integrin/mucosal adressin interaction; 86.2(96.1; LDP 02 | unspecified | monoclonal antibody; integrin antagonist; alpha4 beta7 integrin antagonist; cell adhesion inhibitor | Crohn disease; inflammatory bowel disease |
| MAb, humanized tumor necrosis factor; MAb, humanized TNF; MAb, CDP571; CDP 571; BAY 103356; B 1351 | unspecified | monoclonal antibody; NSAID infection; inflammatory | septic shock; inflammation; bacterial bowel disease; rheumatoid arthritis |
| MAb, VLA-4, humanized; MAb, very late antigen-4, humanized | unspecified | monoclonal antibody; NSAID | inflammation; rheumatoid arthritis; asthma; diabetes |
| infliximab; MAb, tumor necrosis factor alpha MAb, TNF-alpha; cA2; TA 650; REMICADE; AVAKINE | immunoglobulin G, anti-(human tumour necrosis factor) (human-mouse monoclonal cA2 heavy chain), disulfide with human-mouse monoclonal cA2 light chain, dimer | monoclonal antibody NSAID | rheumatoid arthritis; Crohn disease |
| ruthenium nitric oxide (NO) scavengers, | unspecified | nitric oxide scavenger | inflammatory bowel disease; cardiac therapy |
| sulfasalazine; salazosulfapyridine; azulfide; SI 88; AZULFIDINE; SALAZOPYRIN; SLAMA | 2-hydroxy-5-[[4-[(2-pyridinylamino)sulfonyl]phenyl]azo]benzoic acid | NSAID | ulcerative colitis; rheumatoid arthritis |
| P 54 | unspecified | NSAID; analgesic | osteoarthritis; Crohn disease; cancer |
| VX 745 | unspecified | NSAID; MAP kinase inhibitor; signal transduction inhibitor | inflammation, neurological; heart failure; Crohn disease; asthma |
| MAb, tumor necrosis factor-alpha, human; D2E7; LU 200134 | unspecified | onal antibody; NSAID | inflammation |
| MAb, alpha4beta1 integrin; AN 100226; ANTEGREN | unspecified | onoclonal antibody | multiple sclerosis; Crohn disease; ulcerative colitis |

TABLE 17-continued

Current Candidate Therapeutic Interventions for the Treatment of Inflammatory Bowel Disease

| Product Name | Chemical Name | Action | Indication |
|---|---|---|---|
| setipafant; BN 50727 | 6-(2-chlorophenyl)-7,10-dihydro-N-(4-methoxyphenyl)-1-methyl-4H-pyrido[4',3':4,5]thieno[3,2-f][1,2,4]triazolo[4,3-a][1,4]diazepine-9(8H)-carboxamide | PAF antagonist | gastrointestinal ulcer; cyloprotectant |
| pentapeptide | unspecified | peptide | inflammatory bowel disease |
| booly protection compound 15; BPC 15 | HOOC-val-leu-gly-ala-asp-asp-ala-pro-lys-gly-pro-pro-pro-glu-gly-NH2 | peptide | Crohn disease; ulcerative colitis |
| diethyldihydroxy-homospermine; | DEHOHO | polyamine analogue | ulcerative colitis |
| diethylhomospermine; DEHOP; DE 444 | N,N'-bis[4-(ethylamino)butyl]-1,4-butanediamine | polyamine analogue | diarrhea; hypertension; cancer; psoriasis; ulcerative colitis |
| cyclic polyamine analogue, SunPharm | unspecified | polyamine analogue; NSAID | Crohn disease; asthma; inflammation |
| polyclonal antibody, tumor necrosis factor alpha; polyclonal antibody, TNFalpha; CyloTAb | unspecified | polyclonal antibody; immunoglobulin; immunosuppressant | septic shock; malaria; restenosis; Crohn disease; graft versus host disease |
| polyclonal antibody, tumor necrosis factor alpha; immunoglobulin TNF-alpha lysate; PASSTNF-alpha | unspecified | polyclonal antibody; immunoglobulin; NSAID | rheumatoid arthritis; inflammatory bowel disease |
| ridogrel; R 68070 | (E)-5-[[[3-pyridinyl[3-(trifluoromethyl)phenyl]methylene]amino]oxy]pentanoic acid | thromboxane synthetase inhibitor; platelet antiaggregant | ulcerative colitis; Crohn disease |
| etanercept; tumor necrosis factor receptor; TNFr; TNR 001; ENBREL | unspecified | TNF inhibitor; immunosuppressant; NSAID; analgesic | rheumatoid arthritis; heart failure; diabetes; pain; endometriosis; autoimmune disease |
| thalidomide; SYNOVIR; THALOMID | N-(2,6-dioxo-3-piperidyl)phthalimide | TNF modulator; immunosuppressant | cachexia; diarrhea; leprosy; rheumatoid arthritis; transplant rejection; cancer; Crohn disease |
| thalidomide; NSC 66847 | N-(2,6-dioxo-3-piperidyl)phthalimide | TNF modulator; immunosuppressant | HIV infection; Crohn disease; multiple sclerosis; Alzheimer disease; transplant rejection |
| AZM 091 | unspecified | Undisclosed | ulcerative colitis |
| colitis therapy | Strath-1, strath-2 | Undisclosed | ulcerative colitis |
| CPR 2015 | unspecified | Undisclosed | ulcerative colitis |
| ulcerative colitis therapy, LecTec | unspecified | Undisclosed | ulcerative colitis |
| tazofelone; LY 213829 | (+,-)-5-[[3,5-bis(1,1-dimethylethyl)-4-hydroxyphenyl]methyl]-4-thiazolidinone | Undisclosed | inflammatory bowel disease |
| mesalazine; mesalamine; fisalamine; 5-ASA; N 5-ASA; SALOFALK; ASACOL; ROWASA; PENTASA; LIXACOL | 5-amino-2-hydroxybenzoic acid | Undisclosed | inflammatory bowel disease |
| vaccine, TNF alpha | unspecified | vaccine; cylokine antagonist | rheumatoid arthritis; Crohn disease; cachexia; asthma |

TABLE 18

Current Candidate Therapeutic Interventions in Development for the Treatment of Hepatitis

| Product Name | Chemical Name | Action | Indication |
|---|---|---|---|
| NP 77A | Plantain isolate | Antiviral | viral infection; hepatitis |
| hepatitis C therapy | unspecified | Epsilon RNA and 5'UTR binding | hepatitis |
| gene therapy, hepatitis B | unspecified | Hepatitis gene therapy | hepatitis |
| MAXAMINE | unspecified | histamine agonist; histamine H2 agonist | cancer; viral infection; hepatitis |
| VX 497 | unspecified | immunosuppressant | psoriasis; autoimmune disease; viral infection; hepatitis |
| gene therapy, interferon alpha-2b; gene therapy, viral infection | unspecified | interferon gene therapy | hepatitis |
| tuvirumab; MAb, human hepatitis B; OST 577; PE 11; OSTAVIR | unspecified | monoclonal antibody | hepatitis |
| MAbs, hepatitis B; HBV-AB | unspecified | monoclonal antibody | hepatitis |
| oligonucleotides, hepatitis B virus | unspecified | oligonucleotide | hepatitis |
| gene therapy, hepatitis B ribozyme; ribozyme, hepatitis B | unspecified | oligonucleotide; ribozyme gene therapy; | hepatitis |
| polyclonal antibody, hepatitis B; hepatitis B immunoglobulin; H-BIG; NABI-HB | unspecified | polyclonal antibody; immunoglobulin | hepatitis |
| AM 86 | unspecified | reverse transcriptase inhibitor | viral infection; hepatitis |
| lamivudine; BCH 189; GR 103665; GR 109714X; GG 714; 3TC; EPIVIR; ZEFFIX; EPIVIR-HBV; HEPTODIN; HEPTOVIR | (2R-cis)4-amino-1-[2-(hydroxymethyl)-1,3-oxathiolan-5-yl]-2(1H)-pyrimidinone | reverse transcriptase inhibitor; nucleoside analogue; antimetabolite | viral infection; hepatitis; HIV infection |
| adefovir dipivoxil; bis POM PMEA; GS 840; PREVEON | [[[2-(6-amino-9H-purin-9-yl)ethoxy]methyl]phos-phinylidene]bis(oxym-ethyl-ene)-2,2-dimethylpropanoic acid | reverse transcriptase inhibitor; nucleotide analogue | viral infection; HIV infection; hepatitis |
| ribozymes, hepatitis C; HEPTAZYME | unspecified | ribozyme; oligonucleotide | hepatitis |
| gene therapy, ribozyme, hepatitis C; ribozyme, hepatitis C | unspecified | Ribozyme; oligonucleotide gene therapy | hepatitis |
| gene therapy, hepatitis B, GenSet; ribozyme, hepatitis B, GenSet | unspecified | ribozyme; oligonucleotide gene therapy; | viral infection; hepatitis |
| tucaresol; BWA 589C; BW 589C80; BW 589C; 589C | 4-[(2-formyl-3-hydroxyphenoxy)methyl]benzoic acid | RNA helicase | sickle cell anemia; viral infection; HIV infection; cancer; hepatitis |
| AM 188 | unspecified | undisclosed | viral infection; hepatitis |
| VP 31593 | unspecified | Unspecified | hepatitis |
| vaccine, hepatitis A; hepatitis A vaccine | unspecified | vaccine | hepatitis |
| vaccine, hepatitis B; hepatitis B vaccine; Hepa-gene 3; HEPAGENE | unspecified | vaccine | hepatitis |
| vaccine, hepatitis C; hepatitis C vaccine | unspecified | vaccine | hepatitis |
| vaccine, hepatitis C | unspecified | vaccine | hepatitis |

What is claimed is:

1. An isolated nucleic acid molecular comprising 15 to 500 contiguous nucleotides of SEQ ID NO:1 (tumor necrosis factor receptor 2) including a nucleotide selected from the group consisting of:
   (a) nucleotide 694 of SEQ ID NO:1 wherein G is replaced by A;
   (b) nucleotide 1574 of SEQ ID NO:1 wherein A is replaced by G;
   (c) nucleotide 1579 of SEQ ID NO:1 wherein G is replaced by T;
   (d) nucleotide 1773 of SEQ ID NO:1 wherein C is replaced by A;
   (e) nucleotide 2535 of SEQ ID NO:1 wherein C is replaced by T;
   (f) nucleotide 2809 of SEQ ID NO:1 wherein G is replaced by A;
   (g) nucleotide 2881 of SEQ ID NO:1 wherein A is replaced by G; and
   (h) nucleotide 3031 of SEQ ID NO:1 wherein G is replaced by A.

2. The isolated nucleic acid molecular of claim 1, wherein the isolated nucleic acid molecule comprises fewer than 200 nucleotides of SEQ ID NO:1.

3. The isolated nucleic acid molecule of claim 1, wherein the isolated nucleic acid molecule comprises fewer than 100 contiguous nucleotides of SEQ ID NO:1.

4. The isolated nucleic acid molecule of claim 1, wherein the isolated nucleic acid molecule comprises fewer than 100 nucleotides.

5. The isolated nucleic acid molecule of claim 1, wherein the isolated nucleic acid molecule is DNA.

6. The isolated nucleic acid molecule of claim 1, wherein the isolated nucleic acid molecule comprises DNA and at least one nucleic acid analog.

7. The isolated nucleic acid molecule of claim 1, wherein the isolated nucleic acid comprises peptide nucleic acid (PNA).

8. The isolated nucleic acid molecule of claim 1, further comprising a detectable label.

9. The isolated nucleic acid of claim 8, wherein said detectable label is a fluorescent label.

10. The isolated nucleic acid molecule of claim 1 wherein the nucleic acid molecule includes at least two nucleotides selected from the group consisting of:

(a) nucleotide 694 of SEQ ID NO:1 wherein G is replaced by A;

(b) nucleotide 1574 of SEQ ID NO:1 wherein A is replaced by G;

(c) nucleotide 1579 of SEQ ID NO:1 wherein G is replaced by T;

(d) nucleotide 1773 of SEQ ID NO:1 wherein C is replaced by A;

(e) nucleotide 2535 of SEQ ID NO:1 wherein C is replaced by T;

(f) nucleotide 2809 of SEQ ID NO:1 wherein G is replaced by A;

(g) nucleotide 2881 of SEQ ID NO:1 wherein A is replaced by G; and (h) nucleotide 3031 of SEQ ID NO:1 wherein G is replaced by A.

* * * * *